US010231383B2

(12) United States Patent
Mitchum et al.

(10) Patent No.: US 10,231,383 B2
(45) Date of Patent: Mar. 19, 2019

(54) NEMATODE RESISTANT CROPS

(75) Inventors: Melissa G. Mitchum, Columbia, MO (US); Amy Replogle, Columbia, MO (US); Jianying Wang, Columbia, MO (US); Xiaohong Wang, Washington, DC (US); Shiyan Chen, Ithaca, NY (US); Ping Lang, Ithaca, NY (US); Eric L. Davis, Raleigh, NC (US); Thomas J. Baum, Ames, IA (US); Richard S. Hussey, Athens, GA (US)

(73) Assignees: The Curators of the University of Missouri, Columbia, MO (US); Cornell University, Ithaca, NY (US); North Carolina State University, Raleigh, NC (US); Iowa State University Research Foundation, Inc., Ames, IA (US); University of Georgia Research Foundation, Inc., Athens, GA (US); The United States of America, as represented by the Secretary of Agriculture, Washington, DC (US)

( * ) Notice: Subject to any disclaimer, the term of this patent is extended or adjusted under 35 U.S.C. 154(b) by 143 days.

(21) Appl. No.: 13/814,591

(22) PCT Filed: Jul. 13, 2011

(86) PCT No.: PCT/US2011/043882
§ 371 (c)(1),
(2), (4) Date: Aug. 22, 2013

(87) PCT Pub. No.: WO2012/018489
PCT Pub. Date: Feb. 9, 2012

(65) Prior Publication Data

US 2013/0326736 A1 Dec. 5, 2013

Related U.S. Application Data

(60) Provisional application No. 61/371,619, filed on Aug. 6, 2010.

(51) Int. Cl.
*A01D 91/00* (2006.01)
*C07K 14/415* (2006.01)
*C12N 15/82* (2006.01)

(52) U.S. Cl.
CPC ............ *A01D 91/00* (2013.01); *C07K 14/415* (2013.01); *C12N 15/8285* (2013.01); *Y02A 40/164* (2018.01)

(58) Field of Classification Search
None
See application file for complete search history.

(56) References Cited

U.S. PATENT DOCUMENTS

| | | | | |
|---|---|---|---|---|
| 8,569,578 | B1 * | 10/2013 | Wang | C12N 15/113 435/320.1 |
| 2002/0092041 | A1 | 7/2002 | Ronald et al. | |
| 2003/0005491 | A1 | 1/2003 | Hauge et al. | |
| 2004/0067506 | A1 * | 4/2004 | Scheres et al. | 435/6 |
| 2006/0080749 | A1 | 4/2006 | Hussey et al. | |
| 2006/0162019 | A1 | 7/2006 | Palva et al. | |
| 2009/0012029 | A1 | 1/2009 | Hussey et al. | |
| 2009/0019601 | A1 | 1/2009 | Kovalic | |
| 2009/0077687 | A1 | 3/2009 | Hussey et al. | |
| 2009/0241218 | A1 * | 9/2009 | Frankard et al. | 800/278 |
| 2010/0186129 | A1 | 7/2010 | Hussey et al. | |
| 2010/0192257 | A1 | 7/2010 | Jones et al. | |
| 2010/0281572 | A1 | 11/2010 | Hussey et al. | |
| 2012/0192315 | A1 | 7/2012 | Lightfoot | |
| 2013/0326736 | A1 | 12/2013 | Mitchum et al. | |
| 2013/0333061 | A1 * | 12/2013 | Wu | C07K 14/415 800/260 |
| 2014/0298537 | A1 | 10/2014 | Mitchum et al. | |

OTHER PUBLICATIONS

Urwin et al (Enhanced transgenic plant resistance to nematodes by dual proteinase inhibitor constructs. Planta 204: 472-479, 1998).*
Friedberg (Automated protein function prediction—the genomic challenge. Brief. Bioinformatics. 7: 225-242, 2006).*
Davis et al. Nematodes. Sophisticated Parasites of Legumes. Plant Physiology, Apr. 2005, vol. 137, pp. 1182-1188.*
Bakhetia et al. qPCR Analysis and RNAi Define Pharyngeal Gland Cell-Expressed Genes of Heterodera glycines Required for Initial Interactions with the Host. 2007. Mal. Plant Microb Interact. 20: 306-312, 2007.*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Senthil-Kumar et al (Caveat of RNAi in Plants: The Off-Target Effect. RNAi and Plant Gene Function Analysis, Methods in Molecular Biology 744, Springer Science+Business Media, LLC. P13-25, 2011.*

(Continued)

*Primary Examiner* — Medina A Ibrahim
*Assistant Examiner* — Wayne Zhong
(74) *Attorney, Agent, or Firm* — Thompson Coburn LLP; J. Wendy Davis

(57) ABSTRACT

Methods of inhibiting plant parasitic nematodes, methods of obtaining transgenic plants useful for inhibiting such nematodes, and transgenic plants that are resistant to plant parasitic nematodes through inhibition of plant nematode CLAVATA3/ESR (CLE) peptide receptor genes are provided. Methods for expressing genes at plant parasitic nematode feeding sites with plant nematode CLE peptide receptor gene promoters are also provided, along with nematode CLE peptide receptor gene promoters that are useful for expressing genes in nematode feeding sites as well as transgenic plants and nematode resistant transgenic plants comprising the promoters.

16 Claims, 19 Drawing Sheets

Specification includes a Sequence Listing.

(56) References Cited

OTHER PUBLICATIONS

Wang et al. Short communication. A parasitism gene from a plant-parasitic nematode with function similar to CLAVATA3/ESR (CLE) of *Arabidopsis thaliana*. Molecular Plant Pathology. 6:187-191, 2005.*

Mitchum et al (Diverse and conserved roles of CLE peptides. Current Opinion in Plant Biology 2008, 11:75-81. Available online Dec. 19, 2007).*

Wang et al (A parasitism gene from a plant-parasitic nematode with function similar to CLAVATA3/ESR (CLE) of *Arabidopsis thaliana*. Molecular Plant Pathology. 6:187-191, 2005).*

Hirakawa et al., "Non-Cell-Autonomous Control of Vascular Stem Cell Fate by a CLE Peptide/Receptor System", Proceedings of the National Academy of Sciences, Sep. 2008, pp. 15208-15213, vol. 105, No. 39.

Davis et al., "Nematodes. Sophisticated Parasites of Legumes", Plant Physiology, Apr. 2005, pp. 1182-1188, vol. 137.

Wang et al., "CLE Peptide Signaling During Plant Development", Protoplasma, 2009, pp. 33-43, vol. 240.

EMBL Accession No. AK244255, Glycine max cDNA, Nov. 19, 2008, downloaded from the Internet Sep. 21, 2012 <http://www.ebi.ac.uk/Tools/dbfetch?db=embl&id=AK244255&f . . . >, p. 1-2.

Liu, "Dissertation entitled: Molecular Characterization of Soybean Resistance to Soybean Cyst Nematode", Ph.D Dissertation, Dec. 2009, p. 5.

Liu et al., "Soybean Cyst Nematode Resistance in Soybean is Independent of the Rhg4 Locus LRR-RLK Gene", Functional Integrated Genomics, 2011, pp. 539-549, vol. 11.

Shpak et al., "Dominant-Negative Receptor Uncovers Redundancy in the *Arabidopsis* ERECTA Leucine-Rich Repeat Receptor-Like Kinase Signaling Pathway that Regulates Organ Shape", The Plant Cell, May 2003, pp. 1095-1110, vol. 15 No. 5.

Ithal et al., "Developmental Transcript Profiling of Cyst Nematode Feeding Cells in Soybean Roots", Molecular Plant-Microbe Interactions, May 2007, pp. 510-525, vol. 20 No. 5.

Bakhetia et al., "QPCR Analysis and RNAi Define Pharyngeal Gland Cell-Expressed Genes of Heterodera Glycines Required for Initial Interactions with the Host", Molecular Plant-Microbe Interactions, Mar. 2007, pp. 306-312, vol. 20 No. 3.

Bleckmann et al., "Stem Cell Signaling in *Arabidopsis* Requires CRN to Localize CLV2 to the Plasma Membrane", Plant Physiology, Jan. 2010, pp. 166-176, vol. 152 No. 1.

Davis et al., "Getting to the Roots of Parasitism by Nematodes", Trends in Parasitology, Mar. 2004, pp. 134-141, vol. 20 No. 3.

Davis et al., "Parasitism Proteins in Nematode-Plant Interactions", Current Opinion in Plant Biology, Aug. 2008, pp. 360-366, vol. 11 Issue 4.

Deyoung et al., "The CLAVATA1-Related BAM1, BAM2 and BAM3 Receptor Kinase-Like Proteins are Required for Meristem Function in *Arabidopsis*", The Plant Journal: For Cell and Molecular Biology, Jan. 2006, pp. 1-16, vol. 45 No. 1.

Gao et al., "The Parasitome of the Phytonematode Heterodera Glycines", Molecular Plant-Microbe Interactions, Aug. 2003, pp. 720-726, vol. 16 No. 8.

Lu et al., "Structural and Functional Diversity of CLAVATA3/ESR (CLE)-Like Genes from the Potato Cyst Nematode Globodera Rostochiensis", Molecular Plant-Microbe Interactions, Sep. 2009, pp. 1128-1142, vol. 22 No. 9.

Mitchum et al., "The Promoter of the *Arabidopsis thaliana* Cel1 Endo-1, 4-Beta Glucanase Gene is Differentially Expressed in Plant Feeding Cells Induced by Root-Knot and Cyst Nematodes", Molecular Plant Pathology, May 1, 2004, pp. 175-181, vol. 5 No. 3.

Muller et al., "The Receptor Kinase of CORYNE of *Arabidopsis* Transmits the Stem Cell-Limiting Signal CLAVATA3 Independently of CLAVATA1", The Plant Cell, Apr. 2008, pp. 934-946, vol. 20 No. 4.

Patel et al., "Similarity and Functional Analyses of Expressed Parasitism Genes in Heterodera Schachtii and Heterodera Glycines", Journal of Nematology, Dec. 2008, pp. 299-310, vol. 40 No. 4.

Shiu et al., "Plant Receptor-Like Kinase Gene Family: Diversity, Function, and Signaling", Science's STKE: Signal Transduction Knowledge Environment, Dec. 18, 2001, pp. re22, vol. 2001 Issue 113.

Wang et al., "Dual Roles for the Variable Domain in Protein Trafficking and Host-Specific Recognition of Heterodera Glycines CLE Effector Proteins", The New Phytologist, Sep. 2010, pp. 1003-1017, vol. 187 No. 4.

Wang et al., "Identification of Potential Host Plant Mimics of CLAVATA3/ESR (CLE)-Like Peptides from the Plant-Parasitic Nematode Heterodera Schachtii", Molecular Plant Pathology, Feb. 2011, pp. 177-186, vol. 12 No. 2.

Wang et al., "Signal Peptide-Selection of cDNA Cloned Directly from the Esophageal Gland Cells of the Soybean Cyst Nematode Heterodera Glycines", Molecular Plant Microbe Interactions, Apr. 2001, pp. 536-544, vol. 14 No. 4.

Wang et al., "A Parasitism Gene from a Plant-Parasitic Nematode with Function Similar to CLAVATA3/ESR (CLE) of *Arabidopsis thaliana*", Molecular Plant Pathology, Mar. 2005, pp. 187-191, vol. 6 No. 2.

Wang et al., "The Tobacco Cel7 Gene Promoter is Auxin-Responsive and Locally Induced in Nematode Feeding Sites of Heterologous Plants", Molecular Plant Pathology, Jul. 2007, pp. 423-436, vol. 8 No. 4.

Whitford et al., "Plant CLE Peptides From Two Distinct Functional Classes Synergistically Induce Division of Vascular Cells", Proceeding of the National Academy of Science of the United States of America, Nov. 25, 2008, pp. 18625-18630, vol. 105 No. 47.

Zhu et al., "Analysis of Interactions Among the CLAVATA3 Receptors Reveals a Direct Interaction Between CLAVATA2 and CORYNE in *Arabidopsis*", The Plant Journal: For Cell and Molecular Biology, pp. 223-233, vol. 61 No. 2.

Hussey, "Go Where the Science Leads You", Annual Review of Phytopathology, 2010, pp. 1-19, vol. 48.

Durbak et al., "CLAVATA signaling pathway receptors of *Arabidopsis* Regulate Cell Proliferation in Fruit Organ Formation as Well as in Meristems", Genetics, Jun. 24, 2011.

Replogle et al., "Abstract Perception of CLE Peptides in *Arabidopsis* During Cyst Nematode Pathogenesis", 2009 APS Annual Meeting, Aug. 1-5, 2009, Portland, Oregon.

Jeong et al., "The *Arabidopsis* CLAVATA2 Gene Encodes a Receptor-Like Protein Required for the Stability of the CLAVATA1 Receptor-Like Kinase", The Plant Cell, Oct. 1999, pp. 1925-1934, vol. 11 No. 10.

Mitchum et al., "Diverse and Conserved Roles of CLE Peptides", Current Opinion in Plant Biology, Feb. 2008, pp. 75-81, vol. 11 Issue 1.

Chen et al., "In Planta Processing and Glycosylation of a Nematode CLAVATA3/Endosperm Surrounding Region-Like Effector and Its Interaction with a Host CLAVATA2-Like Receptor to Promote Parasitism", Plant Physiology, Jan. 2015, pp. 262-272, vol. 167.

Guo et al., "Enhanced Resistance to Soybean Cyst Nematode Heterodera Glycines in Transgenic Soybean by Silencing Putative CLE Receptors", Plant Biotechnology Journal, 2015, pp. 1-10.

Replogle et al., "Synergistic Interaction of CLAVATA1, CLAVATA2, and Receptor-Like Protein Kinase 2 in Cyst Nematode Parasitism of *Arabidopsis*", Molecular Plant-Microbe Interactions Journal, 2013, pp. 87-96, vol. 26, No. 1.

Guo et al., "CLAVATA2 Forms a Distinct CLE-Binding Receptor Complex Regulating *Arabidopsis* Stem Cell Specification", The Plant Journal, Sep. 2010, pp. 889-900, vol. 63, No. 6.

Kim et al., "*Arabidopsis* WRKY38 and WRKY62 Transcription Factors Interact with Histone Deacetylase 19 in Basal Defense", The Plant Cell, Sep. 2008, pp. 2357-2371, vol. 20.

Kayes et al., "CLAVATA2, a Regulator of Meristem and Organ Development in *Arabidopsis*", Development, 1998, pp. 3843-3851, vol. 125.

Replogle et al., "Nematode CLE Signaling in *Arabidopsis* Requires CLAVATA2 and CORYNE", The Plant Journal, 2011, pp. 430-440, vol. 65.

(56) References Cited

OTHER PUBLICATIONS

Kinoshita et al., "RPK2 is an Essential Receptor-like Kinase that Transmits the CLV3 Signal in *Arabidopsis*," Development, 2010, pp. 3911-3920, vol. 137.

* cited by examiner

CLV1:GUS

NEMATODE RESISTANT CROPS

CROSS REFERENCE TO RELATED APPLICATIONS

This application is a National Stage application of International Patent Application No PCT/US2011/043882, filed Jul. 13, 2011 and incorporated herein by reference in its entirety, and claims the benefit under 35 USC § 119(e) of U.S. Provisional Application Ser. No, 61/371,619, filed Aug 6, 2010, which is incorporated herein by reference in its entirety.

STATEMENT REGARDING GOVERNMENTAL SUPPORT

This invention was made with Government support under Grant Numbers 2007-35607-17790, 2008-34113-19420, 2009-35302-05304, 2005-35604-15434, and 2008-35302-18824, all awarded by the USDA-NRI. The government has certain rights to this invention.

INCORPORATION OF SEQUENCE LISTING

The sequence listing that is contained in the file named "52553_111240_ST25.txt ", which is 312,382 bytes in size (measured in operating system MS-Windows), created on Feb. 4, 2013, is filed herewith by electronic submission and incorporated herein by reference in its entirety.

BACKGROUND

Obligate biotrophs are pathogens that establish intimate parasitic relationships with the host that they infect. Often times these relationships involve some kind of modification or reprogramming of the host cell(s) to accommodate the pathogen's subsequent growth and development. Plant-parasitic nematodes are obligate biotrophs that mainly attack the roots of plants and cause over $100 billion in crop damage annually (Sasser and Freckman, 1987). The most economically important plant-parasitic nematodes include the cyst forming nematodes of *Heterodera* and *Globodera* spp. These sedentary endoparasitic nematodes form intimate parasitic relationships with their hosts by penetrating the root as motile juveniles and migrating intracellularly until they reach the root vasculature where they select a single cell to initiate a feeding site. The initial syncytial cell undergoes developmental changes to re-differentiate into a syncytium to support subsequent nematode growth and development in later sedentary stages (Davis et al., 2004). The syncytium forms when neighboring cells fuse as a result of partial cell wall degradation (Endo, 1964), creating a permanent feeding cell that shares characteristics with plant cell types including meristematic cells, endosperm cells, transfer cells, and developing xylem (Mitchum et al., 2008). It has been proposed that the development and maintenance of the syncytium is dependent on the secretory effector proteins originating in the esophageal gland cells and delivered into the host root through the stylet of plant-parasitic nematodes (Davis et al., 2008). Recently, the cyst nematode secreted CLAVATA3/ESR(CLE)-like effector proteins have been shown to act as ligand mimics of plant CLE peptides, and are required for successful nematode infection (Wang et al., 2005; Patel et al., 2008; Lu et al., 2009; Wang et al., 2010a; Wang et al., 2010b).

Plant CLEs are small peptide ligands involved in regulating a population of specialized cells, called stem cells, which allow postembryonic organogenesis to occur (Simon and Stahl 2006). These stem cell pools can be found in the shoot apical meristem (SAM), the root apical meristem (RAM), and the vascular cambium. Whether or not these stems cells remain in an undifferentiated state or differentiate into new plant tissues is tightly controlled by CLE signaling pathways. In *Arabidopsis*, the population of stem cells which resides in the organizing center (OC) of the SAM is maintained by the expression of the transcription factor WUSCHEL (WUS) (Laux et al., 1996). Differentiation of those stems cells is promoted when the ligand-receptor pair of CLAVATA3 (CLV3), a small extracellular peptide ligand in the CLE family (Fletcher et al., 1999; Rojo et al., 2002), binds to CLV1 (Ogawa et al., 2008), a leucine-rich-repeat receptor like kinase (LRR-RLK) and downregulates WUS. Previous models have suggested that CLV1 forms a receptor complex with the LRR-receptor like protein (RLP) CLV2 (Clark et al., 1993; Kayes and Clark, 1998; Jeong et al., 1999; Trotochaud et al., 1999). More recently, it has been suggested that CLV1 acts in parallel or together with the heterodimer receptor complex of CLV2 and CORYNE (CRN) (Miwa et al., 2008; Muller, 2008; Bleckmann et al., 2010; Zhu et al., 2010). In comparison to the SAM, much less is known about the regulation of the stem cells in the RAM. The quiescent center (QC) is the equivalent to the OC in the SAM. However, there are significant differences between the OC and the QC. In contrast to the OC, the cells surrounding the QC are maintained as stem cells. In addition, stem cells are differentiated in both proximal and distal directions. This indicates that there is a signaling ligand involved in cell-cell communication to maintain the cells surrounding the QC as stem cells, and a signal to promote differentiation (Sarkar et al., 2007; Stahl et al., 2009). Previous reports have identified that the WUS-related homeobox 5 (WOX5) transcription factor is expressed in the QC of the RAM and is required to maintain the distal stem cell pool (Sarkar et al., 2007). Recently it has been shown that CLE40, the closest homolog to CLV3, is expressed in the columella cells and regulates expression of WOX5 (Stahl et al., 2009). The WOX5/CLE40 signaling pathway appears to only control the distal stem cell pool, indicating that other CLE signaling pathways may exist to control the proximal stem cell pool. Consistent with these observations, a number of *Arabidopsis* CLEs are expressed in roots (Sharma et al., 2003), and when some of these CLEs are overexpressed they have been shown to cause premature termination of the primary root meristem (Fiers et al., 2004; Strabala et al., 2006; Meng et al., 2010). In addition, the short root phenotype has been shown to be dependent on CLV2 and CRN perception (Casamitjana-Martinez et al., 2003; Fiers et al., 2005; Miwa et al., 2008; Meng et al., 2010). Taken together this indicates that a CLV-like and CLE-controlled signaling pathway can act in the root.

CLE-like genes from nematodes have been reported in the soybean cyst nematode (SCN, *H. glycines*) (Wang et al., 2005; Wang et al., 2010a), the beet cyst nematode (BCN, *H. schachtii*) (Patel et al., 2008; Wang et al., 2010b), and the potato cyst nematode (PCN, *G. rostochiensis*) (Lu et al., 2009). BCN CLEs have been detected in the dorsal gland ampulla indicating they are likely secreted from the stylet into host cells (Patel et al., 2008). More recently, SCN CLEs have been shown to be secreted directly to the syncytial cytoplasm where the variable domain is thought to redirect the nematode CLE peptides to the apoplast (Wang et al., 2010a). These findings suggest that when delivered to the apoplast, nematode CLEs would be available to interact with extracellular receptors to function as ligand mimics of plant CLE signaling pathways. Overexpression studies have shown that nematode CLEs can trigger plant CLE signaling pathways (Wang et al., 2005; Lu et al., 2009; Wang et al., 2010a; Wang et al., 2010b), but the identity of the receptors and downstream signaling pathways that are activated to initiate developmental cascades required for the re-differentiation of root cells to form syncytia, are currently unknown.

US Patent Applications 20090077687 and 20090012029, identified nematode parasitism (effector) genes and described potential mechanisms to disrupt their expression and the function of their products to inhibit nematode parasitism of plants.

SUMMARY OF INVENTION

This invention provides for methods of inhibiting plant parasitic nematodes, methods of obtaining transgenic plants useful for inhibiting such nematodes, methods for expressing genes at plant parasitic nematode feeding sites, and transgenic plants that are resistant to plant parasitic nematodes. Also provided are promoters including, but not limited to a BAM1 promoter, that are useful for expressing genes in nematode feeding sites as well as transgenic plants and nematode resistant transgenic plants comprising the same. It is anticipated that the BAM1 and other promoters provided herewith can in certain embodiments be operably linked to genes that provide for inhibition of plant parasitic nematodes when introduced into transgenic plants and for plants that display such inhibition. Such genes that provide for inhibition of plant parasitic nematodes that can be used with the promoters provided herewith are disclosed in US Patent Application 20090012029, which is specifically incorporated herein by reference in its entirety.

In certain embodiments, a method for inhibiting plant parasitic nematode damage to a plant comprising growing a plant comprising a mutation or a transgene that provides for inhibition of at least one endogenous plant gene encoding a receptor for a nematode CLE peptide in the presence of plant parasitic nematodes is provided. In certain embodiments of these methods, the plant gene encoding a receptor for a nematode CLE peptide is selected from the group consisting of a CLV1-like gene, a CLAVATA2-like (CLV2-like) gene, a BAM1-like gene, a BAM2-like gene, a CRN-like gene, a ACR4-like gene, an ER-like gene, and an ERL2-like gene. In certain embodiments of these methods, CLV1-like gene, said CLV2-like gene, BAM1-like gene, a BAM2-like gene, a CRN-like gene, a ACR4-like gene, an ER-like gene, or an ERL2-like gene is an ortholog of a corresponding *Arabidopsis*, soybean, or potato CLV1, CLV2, BAM1, BAM2, CRN, ACR4, ER, or ERL2 gene. In certain embodiments of these methods, the methods can further comprise the step of harvesting a product of said plant. In certain embodiments of these methods, the harvested product is a leaf, stem, flower, seed, root, or tuber. In certain embodiments of these methods, the yield and/or quality of said product is increased relative to a control plant that is grown in presence of plant parasitic nematodes and that lacks said mutation or said transgene that provides for inhibition of at least one endogenous plant gene encoding a receptor for a nematode CLE peptide. In certain embodiments of these methods, the transgene comprises: i) an siRNA directed against said plant gene; ii) an artificial microRNA targeting said plant gene; iii) a dominant negative form of said plant gene; iv) an antisense or sense form of said plant gene; or v) a genomic insertion that disrupts said plant gene.

In certain embodiments, a method for obtaining a transgenic plant that exhibits resistance to a plant parasitic nematode comprising the steps of: a) introducing a transgene that provides for inhibition of at least one endogenous plant gene encoding a receptor for a nematode CLE peptide into a plant cell or a transgene that provides for inhibition of at least one CLV1-like, a CLV2-like, a BAM1-like, a BAM2-like, a CRN-like, a ACR4-like, an ER-like, and/or an ERL2-like gene; and b) selecting a transgenic plant obtained from said plant cell, wherein said selected transgenic plant comprises said transgene and exhibits resistance to a plant nematode is provided. In certain embodiments of these methods, CLV1-like gene, said CLV2-like gene, BAM1-like gene, a BAM2-like gene, a CRN-like gene, a ACR4-like gene, an ER-like gene, or an ERL2-like gene is an ortholog of a corresponding *Arabidopsis*, soybean, or potato CLV1, CLV2, BAM1, BAM2, CRN, ACR4, ER, or ERL2 gene.

In certain embodiments, a method for obtaining a transgenic plant expressing a gene product at a plant parasitic nematode feeding site, comprising the steps of: a) introducing a transgene wherein a CRN, CLV, or BAM promoter is operably linked to a gene encoding said gene product into a plant cell; and, b) selecting a transgenic plant obtained from said plant cell, wherein said selected transgenic plant comprises said transgene and exhibits expression of said gene product at said nematode feeding site is provided. In certain embodiments of these methods, the gene product is inhibitory to the plant parasitic nematode. In certain embodiments of these methods, the inhibitory gene product is a siRNA directed against a plant parasitic nematode gene. In certain embodiments of these aforementioned methods, an ACR4, BAM1, BAM2, CLV1, CLV2, CRN, ER, or ERL2 promoter is operably linked to a gene encoding the gene product. In certain embodiments of these aforementioned methods, an ACR4, BAM1, BAM2, CLV1, CLV2, CRN, ER, or ERL2 promoter is operably linked to a gene product that is inhibitory to a plant parasitic nematode. In certain embodiments of these methods, the inhibitory gene product is an amiRNA directed against a plant parasitic nematode gene.

In certain embodiments of any of the aforementioned methods of inhibiting plant parasitic nematode damage, obtaining a transgenic plant that exhibits resistance to a plant parasitic nematode, or obtaining a transgenic plant expressing a gene product at a plant parasitic nematode feeding site, the plant nematode is a cyst nematode. In certain embodiments of these methods, the cyst nematode is a *Heterodera* or *Globodera* spp. In certain embodiments of these methods, the *Heterodera* spp. is *H. avenae, H. bifenestra, H cajani. H. carotae, H. ciceri, H. cruciferae, H. cynodontis, H. cyperi, H. davert, H. elachista, H. fii, H. galeopsidis, H. goettingiana, H. graminis, H. hordecalis, H. humuli, H. iri, H. latipons, H. lespedeza, H. leucilyma, H. Iongicaudata, H. mani, H. maydis, H. medicaginis, H. oryzae, H. oryzicola, H. sacchari, H. salixophila, H. schachtii, H. sorghii, H. trifoii, H. urticae, H. vigna*, or *H. zeae*. In certain embodiments of these methods, the *Globodera* spp. is *G. achilleae, G. artemisiae, G. hypolysi, G. leptonepia, G. mali, G. pallida, G. rostochiensis, G. tabacum*, or *G. zeylandica.*

In certain embodiments of any of the aforementioned methods of inhibiting plant parasitic nematode damage, obtaining a transgenic plant that exhibits resistance to a plant parasitic nematode, or obtaining a transgenic plant expressing a gene product at a plant parasitic nematode feeding site, the plant is a monocot or dicot plant, or is selected from the group consisting of a tobacco, cereal, sugar beet, cotton, fruit, fiber, oilseed, potato, rice, corn, soybean, vegetable, and wheat plant.

In certain embodiments of any of the aforementioned methods of inhibiting plant parasitic nematode damage or obtaining a transgenic plant that exhibits resistance to a plant parasitic nematode, the endogenous plant gene encoding a receptor for a nematode CLE is a potato StCLV1, StCLV2, StBAM1, StBAM2, StCRN, StACR4, StER, or StERL2 gene and the plant is a potato plant. In certain embodiments of these methods, the plant parasitic nematode is *G. rostochiensis* or *G. pallida.*

In certain embodiments of any of the aforementioned methods of inhibiting plant parasitic nematode damage or obtaining a transgenic plant that exhibits resistance to a plant parasitic nematode, the endogenous plant gene encoding a receptor for a nematode CLE is selected from the group consisting of soybean genes provided in Table 3 of Example 2 and said plant is a soybean plant. In certain embodiments of any of the aforementioned methods of inhibiting plant parasitic nematode damage, the plant parasitic nematode is *Heterodera glycines* or *H. schachtii.*

In certain embodiments, a plant parasitic nematode resistant transgenic plant comprising a transgene that provides for inhibition of at least one endogenous plant gene encoding a receptor for a nematode CLE peptide is provided. In certain embodiments, the transgene comprises: i) an siRNA directed against said plant gene; ii) an artificial microRNA targeting said plant gene; iii) a dominant negative form of said plant gene; iv) an antisense or sense form of said plant gene; or v) a genomic insertion that disrupts said plant gene. In certain embodiments of any of the aforementioned transgenic plants, the endogenous plant gene encoding a receptor for a nematode CLE is selected from the group consisting of soybean genes of provided in Table 3 of Example 2 and the plant is a soybean plant. In certain embodiments of any of the aforementioned transgenic plants, the endogenous plant gene encoding a receptor for a nematode CLE is a potato StCLV1, StCLV2, StBAM1, StBAM2, StCRN, StACR4, StER, or StERL2 gene and the plant is a potato plant.

In certain embodiments, a plant parasitic nematode resistant transgenic plant comprising a transgene wherein a CRN, CLV, or BAM promoter is operably linked to a gene encoding a gene product that is inhibitory to a plant parasitic nematode is provided. In certain embodiments, the gene product is an siRNA directed against a plant parasitic nematode gene. In certain embodiments of any of the aforementioned plants, the CRN, CLV, or BAM promoter is the CRN1, CLV2, or BAM1 promoter sequence provided in Example 3. In certain embodiments of these aforementioned methods, an ACR4, BAM1, BAM2, CLV1, CLV2, CRN, ER, or ERL2 promoter is operably linked to a gene product that is inhibitory to a plant parasitic nematode. In certain embodiments, the gene product is a siRNA or an amiRNA directed against a plant parasitic nematode gene.

In certain embodiments, a recombinant DNA construct comprising a BAM1 promoter that is operably linked to a heterologous gene, wherein said BAM1 promoter comprises any one of: i) the BAM1 promoter sequence provided in Example 3; ii) a promoter that has at least 70%, 85%, 90%, 95%, or 99% sequence identity to the BAM1 promoter sequence provided in Example 3; or ii) a promoter comprising a deletion of about up to about 10, 50, 100, 200, 500, 700, 1000, or 1500 nucleotides of the 5' nucleotides of the BAM1 promoter sequence provided in Example 3 is provided. In certain embodiments, the BAM promoter is operably linked to a gene encoding a gene product that is inhibitory to a plant parasitic nematode.

DESCRIPTIONS OF THE FIGURES

Figure Legends

FIG. 1. Effect of cyst nematode CLE peptides on receptor mutants.

(*a*) Average root length wild-type (Ler), clv2-1, and crn-1 seedlings grown for 9 days on media with or without the synthetic nematode dodecapeptide CLE motif Data represent the mean±SE, n=10. (*b*)-(*d*) Representative roots tips of seedlings grown on media with or without synthetic CLE peptides for 10 days and visualized with differential interference microscopy. (*b*) No peptide, (*c*) Sensitive to peptide, and (*d*) Resistant to peptide. (Scale bar, 50 μm).

FIG. 2. CRN:GUS expression during nematode infection. (*a*)-(*c*) GUS expression in uninfected *Arabidopsis* root tips (*a*), middle of the root (*b*), and older part of the root towards the hypocotyl (*c*). (*d*)-(*g*) CRN:GUS expression in response to *H. schachtii*; early parasitic J2 (*d*), late parasitic J2 (*e*), J3 parasitic (*f*), J4 parasitic (*g*). Abbreviations: nematode, N; Syn, Syncytium. (Scale bar, 50 μm).

FIG. 3. Confocal images of CLV2:H2B-mCherry expression during nematode infection. (*a*) J2 parasitic with DIC. (*b*) J2 parasitic with mCherry fluorescence. (*c*) J3 parasitic with DIC. (*d*) J3 parasitic with mCherry fluorescence. Abbreviations: nematode, N; Syn, Syncytium. (Scale bars, 50 μm).

FIG. 4. Effect of clv2-1 and crn-1 mutant alleles on *H. schachtii* infection.

(*a*) J4 females were counted at 14 dpi and adult females were counted at 30 dpi. Data represent mean±SE, n=35 for Ler, 32 for crn-1, 34 for clv2-1, and 29 for crn-1 clv2-1. Data are representative of three independent experiments.

(*b*) Seedlings were grown on vertical square plates for 10 days and inoculated with 10 J2s/root. At 14 dpi, syncytia that fed only one nematode and appeared translucent were microscopically examined and their area was determined. Data represent mean±SE, n=11 for Ler and crn-1, 14 for clv2-1, and 12 for crn-1 clv2-1.

Asterisks indicate statistically significant differences compared to Ler by Student's t test (P<0.05)

FIG. 5. Response of wild-type (Utr) and sol2-1 seedlings to the synthetic 12-aa nematode CLE peptide. Average root length wild-type (Utr) and sol2-1 seedlings grown for 9 days on media with or without the synthetic nematode dodecapeptide CLE motif. Data represent the mean ±SE, n =10.

FIG. 6. Confocal images of nematode autofluorescence in wild-type roots (a and b). Feeding site induced by a parasitic J2. (a) DIC image. (b) mCherry fluorescence. Abbreviations: nematode, N; Syn, Syncytium. (Scale bar 50 μm).

FIG. 7. Effect of sol2-1 mutant allele on *Heterodera schachtii* infection. (a). J4 females were counted at 14dpi and adult females were counted at 30 dpi. Data represent mean ±SE, n =36. Asterisks indicate statistically significant differences compared to Ler by Student's t test (P <0.0001). Effect of sol2-1 mutant allele on size of syncytia (b). Seedlings were grown on vertical square plates for 10 days and inoculated with 10 ppJ2s/root. At 14 dpi, syncytia that fed only one nematode and appeared translucent were microscopically examined and their area was determined. Data represent mean ±SE, n =11 for Utr and n =9 for sol2-1. Asterisks indicate statistically significant differences compared to Ler by Student's t test (P <0.05).

FIG. 8. Effect of *Heterodera glycines* (HgCle) and *Heterodera schachtii* (HsCLE) nematode CLE peptides on receptor mutants. Seedlings were grown for 9 days on media with or without the synthetic nematode dodecapeptide CLE motif. Data represent the mean ±SE, n =10.(A) Average root length of wild-type (Ler), clv2-1, and crn-1. (B) Average root length of wild-type (Col-0,) bam3-2, bam2, and bam1-3. (C) Average root length of wild-type (Utr) and sol2-1.

FIG. 9. Effect of *Globodera rostochiensis* (GrCLE) nematode CLE peptides on receptor mutants. Seedlings were grown for 9 days on media with or without the synthetic nematode dodecapeptide CLE motif. Data represent the mean ±SE, n =10. Average root length of wild-type (Col-0) bam1-2, bam1-4, erl2-1, and clv2-1.

FIG. 10. Effect of receptor mutant alleles on *H. schachtii* infection. J4 females were counted at 14dpi and adult females were counted at 30 dpi. Asterisks indicate statistically significant differences compared to wild-type by Student's t test (P <0.05). Data represent mean ±SE, Similar results were obtained from two additional biological replicates.

FIG. 11. CRN:GUS expression during nematode infection. (A-C) CRN: :GUS expression in uninfected Arabidopsis root tips (A), middle of the root (B), and older part of the root towards the hypocotyl (C). (D-G) CRN: :GUS expression in nematode-infected roots; (D) early J2p, (E) late J2p, (F) J3 and (G) J4 females. Abbreviations: nematode, N; Syn, Syncytium.

FIG. 12. CLV2:GUS expression during nematode infection. (A-D) Confocal section of a nematode induced feeding site 4 dpi (A-B) and 8 dpi (A-B) expressing CLV2:H2B-mCherry. Abbreviations: nematode, N; Syn, Syncytium.

FIG. 13. BAM1:GUS expression in Arabidopsis in response to nematode infection. (A) Uninfected root tip. (B-D) GUS expression in nematode infected roots; (B) Early parasitic J2, (C) Parasitic J3, and (D) Parasitic J4.

FIG. 14 Differential expression of candidate potato CLE receptor genes in *G. rostochiensis*-infected potato roots.

FIG. 15. Effect of crn-1, clv2-6, bam1-3 mutant alleles and combinations thereof on *H. schachtii* infection in *Arabidopsis.*

Figure 19:
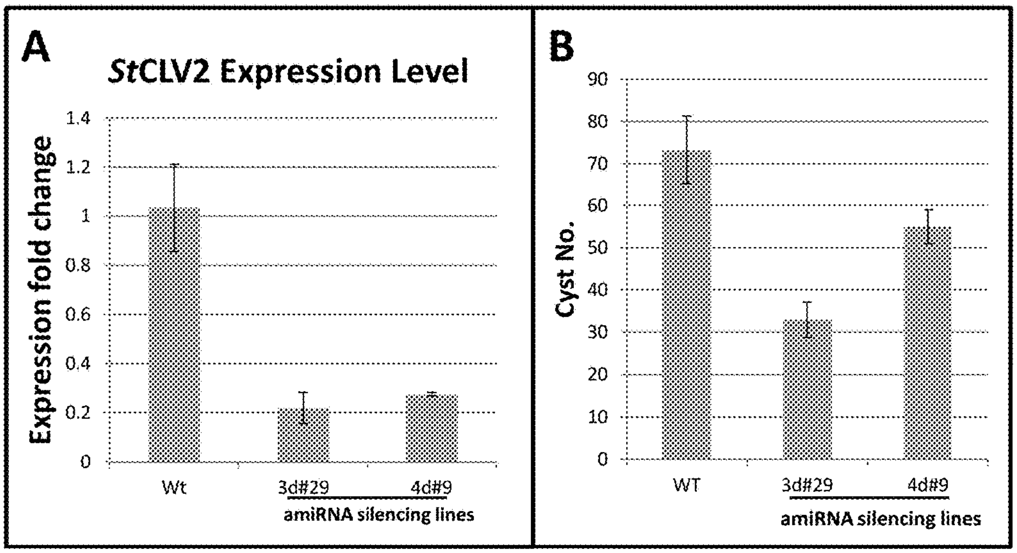

FIG. 19 A shows expression levels of the endogenous StCLV2 gene in transgenic potato plants expressing an artificial miRNA (amiRNA) directed against the StCLV2 gene (3d#29 and 4d#9) and wild type (Wt) control plants that lack the amiRNA.

FIG. 19 B shows the number of *G. rostochiensis* cysts in transgenic potato plants expressing an artificial miRNA (amiRNA) directed against the StCLV2 gene (3d#29 and 4d#9) and wild type (Wt) control plants that lack the amiRNA.

DESCRIPTION OF THE INVENTION

We describe the use of synthetic CLE peptides, nematode CLE overexpression lines, promoter-reporter lines, and nematode infection assays of receptor mutants to investigate a role for CLV2 and CRN in nematode CLE signaling. Our results indicate that the CLV2/CRN signaling pathway is required for successful nematode infection and syncytium development.

Plant-parasitic cyst nematodes secrete CLAVATA3 (CLV3)/ESR(CLE)-like effector proteins. These proteins have been shown to act as ligand mimics of plant CLE peptides and are required for successful nematode infection; however, the receptors for nematode CLE-like peptides have not been identified. Here we demonstrate that CLV2 and CORYNE (CRN), members of the receptor kinase family, are required for nematode CLE signaling. Exogenous peptide assays and overexpression of nematode CLEs in *Arabidopsis* showed that CLV2 and CRN are required for nematode CLE perception. In addition, promoter-reporter assays showed that both receptors are expressed in nematode-induced syncytia. Lastly, infection assays with receptor mutants revealed a decrease in both nematode infection and syncytia size. Taken together, our results indicate that nematode CLE perception by CLV2 and CRN is not only required for successful nematode infection, but is also involved in the formation or maintenance of nematode-induced syncytia.

Plant Nematode CLE Receptor Genes that can be Used to Obtain Nematode Resistant Plants and Methods of Use A variety of plant nematode CLE peptide receptor genes (hereinafter referred to as "PNCLEPRG") that provide for inhibition of plant parasitic nematode infections are provided herewith, along with associated methods of use, and plants comprising transgenes or mutations wherein expression of the PNCLEPRG are inhibited. Reduced expression of the PNCLEPRG in plants inhibits infection of the plants by nematodes. Such reductions in nematode infection result in improved plant yield and plant product quality.

Reductions in expression of the endogenous PNCLEPRG can be effected by any method that at least provides for reductions in the amount or activity of the PNCLEPRG at the site of nematode infection in the plant. Such sites of infection are commonly the plant roots, but can also comprise other plant parts such as tubers.

In certain embodiments, inhibition of PNCLEPRG expression in a plant can be effected by transgenes. Such transgenes include, but are not limited to, transgenes that: i) produce an siRNA directed against the PNCLEPRG; ii) produce an artificial microRNA targeting the PNCLEPRG; iii) produce a dominant negative form of the protein product of the PNCLEPRG; iv) produce an antisense or sense form of the PNCLEPRG; or v) comprise a genomic insertion that disrupts the endogenous PNCLEPRG.

Exemplary vector systems that can provide for production of siRNA in plants include, but are not limited to, vectors disclosed by Dafny-Yelin, et al. (Plant Physiology, 2007, Vol. 145, pp. 1272-1281), Wesley et al. 2001, Plant J. 27: 581-590, and Miki and Shimamoto, (2004) Plant Physiol 138: 1903-1913. Vectors for producing an siRNA are also described in U.S. Pat. No. 6,635,805, incorporated herein by reference in its entirety.

Exemplary vector systems that can provide for production of artificial miRNA in plants include, but are not limited to, vectors disclosed by Warthmann et al. (2008) PLoS ONE 3(3): e1829. doi:10.1371/journal.pone.0001829; and Alvarez et al. (2006) Plant Cell 18: 1134-1151. Vectors for effecting efficient inhibition of endogenous plant genes by expression of hairpin RNAs are also disclosed in U.S. Patent Application Nos. 20050164394, 20050160490, and 20040231016, each of which is incorporated herein by reference in their entirety. Exemplary dominant negative mutations that can provide for inhibition endogenous PNCLEPRG include, but are not limited, mutations modeled after dominant negative mutations in other Leucine Rich Repeat-Receptor Like Kinase (LRR-RLK) proteins.

In one embodiment, the dominant negative mutation can comprise a deletion or other loss-of-function mutation in the kinase domain. Such mutations have been disclosed for plant LRR-RLK proteins (Shpak et al., Plant Cell, Vol. 15, 1095-1110, 2003). Methods of identifying transgene insertions into specific genomic loci have also been disclosed. T-DNA of *Agrobacterium* is also an insertional mutagen that can be used as an agent to reduce expression of an endogenous PNCLEPRG. T-DNA mutagenesis has been described in *Arabidopsis* (Krysan et al., Plant Cell, 1999, 1: 2283-2290) and rice (Jeon et al., Plant J. June 2000; 22(6):561-70). Transposons such as those in the Ac/Ds (Activator-Disassociation) family and the Enhancer-inhibitor system can also be used to effect mutagenesis of an endogenous PNCLEPRG. Transposon mutagenesis schemes have been described (Speulman et al. Plant Cell, Vol. 11, 1853-1866, October 1999; Das, L., and Martienssen, R, 1995, Plant Cell 7:287-294).

Plants wherein expression of the endogenous PNCLEPRG is inhibited by a mutation and the use of such plants is also provided. Methods of identifying plants comprising mutations in PNCLEPRG include, but are not limited to, "TILLING" (Targeting Induced Local Lesions in Genomes). The TILLING technique comprises the induction of mutations across the genome followed by the identification and isolation of plants with mutations in desired genes (McCallum, *Plant Physiology*, 2000, Vol. 123, pp. 439-44).

PNCLEPRG target genes useful in the methods and plants of this invention include, but are not limited to, the ACR4, CLV1, CLV2, CRN, BAM1, BAM2, ER, and ERL2 genes of *Arabidopsis* and the orthologous ACR4, CLV1, CLV2, CRN, BAM1, BAM2, ER, and ERL2 genes of crop and ornamental plants subject to nematode infestation. Such orthologous genes are referred to herein as "ACR4-like, CLV1-like, CLV2-like, CRN-like, BAM1-like, BAM2-like, ER-like, and ERL2-like" genes. As used herein, the terms "orthologous" and "-like" (when appended to a gene) thus refer to genes that at least have a similar role in plant nematode CLE peptide signal transduction in their respective plant species of origin. In certain embodiments, the PNCLEPRG target genes are obtained from a plant that is a monocot or dicot plant, or that is a crop plant such as a tobacco, cereal, sugar beet, cotton, fruit, fiber, oilseed, potato, rice, corn, soybean, vegetable, and wheat plant. Exemplary vegetable plants include, but are not limited to, carrot, pepper, cucurbit, and tomato plants.

In certain embodiments, the PNCLEPRG target genes are derived from the plant that will be used (i.e. protected from nematode infection). However, a PNCLEPRG of a given plant specie can be used in a distinct plant species when it has sufficient homology to the orthologous PNCLEPRG of a distinct plant species. In this context, "sufficient homology" is that amount of homology necessary to provide for transgene-mediated inhibition of the orthologous gene. For certain transgene-mediated gene inhibition methods, a PNCLEPRG sequence of about is 23 nucleotides or longer with least 80%, 85%, 90%, 95%, 98%, 99% or 100% identity to the target orthologous sequence can be used. In certain embodiments, a hairpin RNA may comprise a 5' sequence of roughly 19-24 nucleotides of sense strand target gene sequence with 100% identity followed by a spacer nucleotide of about 8-10 nucleotides followed by a sequence of roughly 19-24 nucleotides of antisense sequence that is capable of base pairing with the preceding sense strand sequence. In certain embodiments, a 19-24 base region of a PNCLEPRG that exhibits 100% identity over 19-24 nucleotides to an orthologous PNCLEPRG can also be used to inhibit that orthologous gene.

In certain embodiments, an *Arabidopsis* PNCLEPRG can be used to obtain nematode resistant plants, where the plants are *Arabidopsis* or other plants that comprise orthologous PNCLEPRGs that can be inhibited by the *Arabidopsis* PNCLEPRG. *Arabidopsis* PNCLEPRG include, but are not limited to, the ACR4, CLV1, CLV2, CRN, BAM1, BAM2, ER, and ERL2 can in certain embodiments be used to control plant parasitic nematode infections of cruciferous plants that include, but are not limited to, arugula, cauliflower, cabbage, cress, bok choy, broccoli, radish, canola, turnip, watercress, and the like.

In certain embodiments, a potato PNCLEPRG can be used to obtain nematode resistant plants, where the plants are potato plants or other plants that comprise orthologous PNCLEPRGs that can be inhibited by the potato PNCLEPRG. Potato PNCLEPRG provided herein include, but are not limited to, stCRN (SEQ ID NO:6), stBAM1 (SEQ ID NO:7), stBAM2 (SEQ ID NO:8), stER (SEQ ID NO:9), stCLV1 (SEQ ID NO:10), stCLV2 (SEQ ID NO:11), stACR4 (SEQ ID NO:12), and stERL2 (SEQ ID NO:13). Also provided herewith are related sequences with at least 70%, 80%, 85%, 90%, 95%, 97%, 98%, or 99% identity to stCRN (SEQ ID NO:6), stBAM1 (SEQ ID NO:7), stBAM2 (SEQ ID NO:8), stER (SEQ ID NO:9), stCLV1 (SEQ ID NO:10), stCLV2 (SEQ ID NO:11), stACR4 (SEQ ID NO:12), and stERL2 (SEQ ID NO:13) as well as methods of using such sequences to control plant nematodes.

In certain embodiments, the use of such potato PNCLEPRGs and related sequences to control plant nematode, and particularly, plant cyst nematode infections, in solanaceous plants including, but not limited to, eggplant, tobacco, potato, and tomato is provided. In certain embodiments, the use of such potato PNCLEPRGs and related sequences to control *Globedera* sp. infections of potato plants is provided. In any of the aforementioned embodiments, inhibition of the plant PNCLEPRG can be limited to inhibition in roots or limited to inhibition at the site of nematode infection by use of root-specific and/or nematode inducible promoters, respectively.

In certain embodiments, a soybean PNCLEPRG can be used to obtain nematode resistant plants, where the plants are soybean plants or other plants that comprise orthologous PNCLEPRGs that can be inhibited by the soybean PNCLEPRG. Soybean PNCLEPRG provided herein include, but are not limited to, soybean CRN (SEQ ID NO:44, 45, 47, and 48), BAM1 (SEQ ID NO:23, 24, 26, 27), BAM2 (SEQ ID NO:29, 30, 32, 33), CLV1 (SEQ ID NO:38, 39, 41, 42), and CLV2 (SEQ ID NO:35, 36, 50, 51) orthologs. Also provided herewith are related sequences with at least 70%, 80%, 85%, 90%, 95%, 97%, 98%, or 99% identity to soybean CRN (SEQ ID NO:44, 45, 47, 48), BAM1 (SEQ ID NO:23, 24, 26, 27), BAM2 (SEQ ID NO:29, 30, 32, 33), CLV1 (SEQ ID NO:38, 39, 41, 42), and CLV2 (SEQ ID NO: 35, 36, 50, 51) orthologs as well as methods of using such sequences to control plant nematodes. In certain embodiments, the use of such soybean PNCLEPRGs and related sequences to control plant nematodes, and particularly, plant cyst nematode infections, in leguminous plants including, but not limited to, alfalfa, clover, peas, beans, lentils, lupins, mesquite, carob, soybean, and peanuts, is provided. In certain embodiments, the use of such soybean PNCLEPRGs and related sequences to control *Heterodera glycine* infections of soybean plants is provided. In any of the aforementioned embodiments, inhibition of the plant PNCLEPRG can be limited to inhibition in roots or limited to inhibition at the site of nematode infection by use of root-specific and/or nematode inducible promoters, respectively.

In certain embodiments of the invention, combinations of two or more a plant PNCLEPRG are inhibited in a plant to provide resistance to plant parasitic nematode infections. Plants wherein combinations of two or more PNCLEPRG selected from the group of CRN, BAM1, BAM2, ER, CLV1, CLV2, ACR4, and ERL2 genes or orthologs thereof are inhibited can be used to provide resistance to plant parasitic nematode infections. In certain embodiments, a plant CLV2-like and a plant BAM1-like gene are both inhibited in parallel to reduce nematode infections in the plant. In certain embodiments of the invention, a plant CRN-1-like and a plant BAM1-like gene are both inhibited in parallel to reduce nematode infections in the plant. In certain embodiments, combinations of two or more of a soybean CRN (SEQ ID NO:44, 45, 47, and 48), BAM1 (SEQ ID NO:23, 24, 26, 27), BAM2 (SEQ ID NO:29, 30, 32), CLV1 (SEQ ID NO:38, 39, 41, 42), and CLV2 (SEQ ID NO:35, 36, 50, 51) orthologs or a related sequence are inhibited in a soybean or other plant to provide resistance to plant parasitic nematode infections. In certain embodiments, combinations of two or more of a potato stCRN (SEQ ID NO:6), stBAM1 (SEQ ID NO:7), stBAM2 (SEQ ID NO:8), stER (SEQ ID NO:9), stCLV1 (SEQ ID NO:10), stCLV2 (SEQ ID NO:11), stACR4 (SEQ ID NO:12), and stERL2 (SEQ ID NO:13) are inhibited in a potato or other plant to provide resistance to plant parasitic nematode infections. In any of the aforementioned embodiments, inhibition of the plant PNCLEPRG can be limited to inhibition in roots or limited to inhibition at the site of nematode infection by use of root-specific and/or nematode inducible promoters, respectively.

In addition to nematode resistant plants, the instant invention also provides for parts of those plants and plant cells. Plant parts provided herein include, but are not limited to, seeds, tubers, roots, leaves, stalks, lint, and the like. Also provided herein are processed products of the nematode resistant plants. Such processed plant products include, but are not limited to, a ground meal, a feed, a cake, and the like. In certain embodiments, such processed product would comprise a detectable amount of a transgene used to inhibit the PNCLEPRG.

Promoters from Plant Nematode CLE Receptor Genes and Methods of Use

Promoters from PNCLEPRG and recombinant DNA constructs providing such promoters that are useful for expressing genes of interest in plant cells where the nematodes feed are provided. Such promoters are particularly useful for expressing nucleic acid and/or protein sequences that are inhibitory to plant parasitic nematodes. Particular advantages of the promoters include, but are not limited to, providing for expression of the operably linked nucleic acid sequences at nematode feeding sites within the plant while limiting expression of the gene in other parts of the plant where such expression is not required or desired. As used herein in the context of a promoter, the term "operably linked" means that a promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the protein desired.

A variety of recombinant DNA molecules comprising promoters of the invention that are operably linked to heterologous genes or nucleic acids of interest are provided. Heterologous genes or nucleic acids that provide for inhibition of plant parasitic nematodes can be operably linked to the PNCLEPRG promoters. In certain embodiments, the heterologous genes or nucleic acids of interest provide for inhibition of a plant parasitic nematode gene or function. Such plant parasitic nematode genes or functions include, but are not limited to, nematode genes that are essential or required for nematode viability or nematode genes involved in any aspect of plant host parasitism. In certain embodiments, the promoters are used to drive expression of heterologous genes or nucleic acids that are inhibitory to nematode genes disclosed in US Patent Application publication US20090012029, which discloses inhibitory nucleic acid specific for one or more cyst nematode esophageal gland cell proteins and which is incorporated herein by reference in its entirety.

In certain embodiments, the promoters are used to drive expression of genes or nucleic acids that inhibit formation and/or maintenance of the plant cells of the nematode feeding site. In certain embodiments, the promoters are thus used to: i) drive expression of heterologous genes or nucleic acids that are inhibitory to endogenous plant genes involved in formation and/or maintenance of the plant cells of the nematode feeding site; and/or, ii) drive expression of heterologous genes that comprise endogenous plant genes that are downregulated during the formation and/or maintenance of the plant cells of the nematode feeding site. Endogenous plant genes involved in formation and/or maintenance of the plant cells of the nematode feeding site that include, but are not limited to, genes involved in the cell wall architectural modifications during feeding site formation/maintenance, genes involved in sugar or carbohydrate, metal ion, and amino acid transport, and genes involved in plant phytohormone signaling and biosynthesis. A variety of soybean plant genes suitable for use with the promoters of the invention are disclosed in Ithal et al., Molec. Plant. Microb. Interact. Vol. 20, No. 5, 2007, pp. 510-525, incorporated herein by reference in its entirety. PNCLEPRG promoters useful in the methods and plants of this invention include, but are not limited to, the ACR4, CLV1, CLV2, CRN, BAM1, BAM2, ER, and ERL2 promoters of *Arabidopsis* and the orthologous ACR4, CLV1, CLV2, CRN, BAM1, BAM2, ER, and ERL2 promoters of crop and ornamental plants subject to nematode infestation. Such orthologous promoters are referred to herein as "ACR4-like, CLV1-like, CLV2-like, CRN-like, BAM1-like, BAM2-like, ER-like, and ERL2-like" promoters. As used herein, the terms "orthologous" and "-like" (when appended to a promoter) thus refer to promoters that at least have a similar role or expression pattern in plant nematode CLE peptide signal transduction in their respective plant species of origin. In certain embodiments, the PNCLEPRG promoters are obtained from a plant that is a monocot or dicot plant, or that is a crop plant such as a tobacco, cereal, sugar beet, cotton, fruit, fiber, oilseed, potato, rice, corn, soybean, vegetable, and wheat plant. Exemplary vegetable plants include, but are not limited to, carrot, pepper, cucurbit, and tomato plants.

In certain embodiments, a recombinant DNA construct comprising a PNCLEPRG promoter that is operably linked to a heterologous gene, or a plant, plant cell, plant part, or processed plant product comprising the same, is provided. In certain embodiments, the PNCLEPRG promoter comprises any one of: i) a potato ACR4 promoter (SEQ ID NO:15), an *Arabidopsis* (SEQ ID NO:14), potato (SEQ ID NO:16), or soybean (SEQ ID NO: 38 or 41) CLV1 promoter; ii) an *Arabidopsis* (SEQ ID NO:4), potato (SEQ ID NO:17), or soybean (SEQ ID NO:35 or 50) CLV2 promoter; iii) an *Arabidopsis* (SEQ ID NO:5), potato (SEQ ID NO:18), or soybean (SEQ ID NO: 44 or 47) CRN promoter; iv) an *Arabidopsis* (SEQ ID NO:3), potato (SEQ ID NO:19), or soybean (SEQ ID NO: 23 or 26) BAM1 promoter; v) a potato (SEQ ID 20), or soybean (SEQ ID NO: 29 or 32) BAM2 promoter; vi) a potato ER promoter (SEQ ID NO:21); vii) or a potato ERL2 promoter (SEQ ID NO:22). Also provided are recombinant DNA constructs comprising a variant PNCLEPRG promoter that has at least 70%, 85%, 90%, 95%, or 99% sequence identity to any one of: i) a potato ACR4 promoter (SEQ ID NO:15), an *Arabidopsis* (SEQ ID NO:14), potato (SEQ ID NO:16), or soybean (SEQ ID NO: 38 or 41) CLV1 promoter; ii) an *Arabidopsis* (SEQ ID NO:4), potato (SEQ ID NO:17), or soybean (SEQ ID NO:35 or 50) CLV2 promoter; iii) an *Arabidopsis* (SEQ ID NO:5), potato (SEQ ID NO:18), or soybean (SEQ ID NO: 44 or 47) CRN promoter; iv) an *Arabidopsis* (SEQ ID NO:3), potato (SEQ ID NO:19), or soybean (SEQ ID NO: 23 or 26) BAM1 promoter; v) a potato (SEQ ID 20), or soybean (SEQ ID NO: 29 or 32) BAM2 promoter; vi) a potato ER promoter (SEQ ID NO:21); vii) or a potato ERL2 promoter (SEQ ID NO:22).

In certain embodiments, recombinant DNA constructs comprising a PNCLEPRG promoter comprising a deletion of about up to about 10, 50, 100, 200, 500, 700, 1000, or 1500 nucleotides of the 5' nucleotides of any one of: i) a potato ACR4 promoter (SEQ ID NO:15), an *Arabidopsis* (SEQ ID NO:14), potato (SEQ ID NO:16), or soybean (SEQ ID NO: 38 or 41) CLV1 promoter; ii) an *Arabidopsis* (SEQ ID NO:4), potato (SEQ ID NO:17), or soybean (SEQ ID NO:35 or 50) CLV2 promoter; iii) an *Arabidopsis* (SEQ ID NO:5), potato (SEQ ID NO:18), or soybean (SEQ ID NO: 44 or 47) CRN promoter; iv) an *Arabidopsis* (SEQ ID NO:3), potato (SEQ ID NO:19), or soybean (SEQ ID NO: 23 or 26) BAM1 promoter; v) a potato (SEQ ID 20), or soybean (SEQ ID NO: 29 or 32) BAM2 promoter; vi) a potato ER promoter (SEQ ID NO:21); vii) or a potato ERL2 promoter (SEQ ID NO:22) is provided. Those skilled in the art will appreciate that promoter and 5'UT regions of PNCLEPRG provided herewith as genomic sequences in association with the coding regions can be dissociated from those coding regions and operably linked to heterologous nucleic acids or genes by transcriptional or translational fusions. In certain embodiments, the soybean PNCLEPRG promoters and 5'UT of Table 5 (SEQ ID NO: 23, 26, 29, 32, 35, 38, 41, 44, 47, and 50) thus comprise the nucleic acid sequences located 5' to the start codon of those genomic sequences.

In certain embodiments, variants of any of the aforementioned PNCLEPRG promoters comprising at least about 300, 500, 800, 900, 1,000, 1,500, 2,500, or 3,000 nucleotides of the nucleic acid sequence located 5' to the start codon or located 5' to mRNA 5' cap site of the endogenous gene associated with said promoter are provided. Also provided are recombinant DNA constructs wherein any of the aforementioned promoters is operably linked to a gene encoding a gene product that is inhibitory to a plant parasitic nematode.

In addition to nematode resistant plants comprising the recombinant DNA constructs of the aforementioned PNCLEPRG promoters, the instant invention also provides for parts of those plants and plant cells. Plant parts provided herein include, but are not limited to, seeds, tubers, roots, leaves, stalks, lint, and the like. Also provided herein are processed products of the nematode resistant plants. Such processed products include, but are not limited to, a ground meal, a feed, a cake, and the like.

In certain embodiments, such processed product would comprise a detectable amount of a recombinant DNA comprising a PNCLEPRG promoter that is operably linked to a heterologous gene.

EXAMPLES

The disclosed embodiments are merely representative of the invention, which may be embodied in various forms. Thus, specific structural and functional details disclosed herein are not to be interpreted as limiting.

Example 1

Experimental Procedures

Peptide Assays

*Arabidopsis* seeds were sterilized using the chlorine gas method (Wang et al., 2010b). Sterilized seeds were germinated on vertical plates in a growth chamber at 22° C. under long-day conditions (16 h light/8 h dark) containing synthetic peptides (Sigma-Genosys) as previously described (Wang et al., 2010b). The clv2-1 mutant in the Ler background (Koornneef et al., 1983) was obtained from the *Arabidopsis* Biological Resource Center. The crn-1 mutant in the Ler background (Muller, 2008) and the sol2-1 mutant in the Utr background (Miwa et al., 2008) have been described previously. The HgCLEp, HsCLE1p, and HsCLE2p peptides used in this study were as described (Wang et al., 2010b). Two days after germination, root length was marked each day for nine days. Plates were scanned using an Epson Perfection V200 PHOTO scanner and total root length was determined using Scion Image. Primary root tips of *Arabidopsis* were mounted on glass slides and visualized with an Olympus Vanox AHBT3 microscope equipped with Nomarski optics.

Overexpression in Mutant Backgrounds

The CLE gene sequences from the soybean cyst nematode ($HgCLE2^{\Delta SP}$) and the beet cyst nematode (HsCLE1 and HsCLE2) used to generate the overexpression constructs were previously described (Wang et al., 2010a; Wang et al., 2010b). Constructs were transformed into the mutant backgrounds using the *Arabidopsis* floral dip method (Clough and Bent, 1998). Seeds from primary *Arabidopsis* transformants (T1) were selected on 0.5×MS media [MS basal nutrients salts (Caisson Laboratories), 2% sucrose, 0.8% Type A agar (Sigma), pH 5.7] containing 50 μg/mL timentin (GlaxoSmithKline) to control *Agrobacterium* contamination, and 50 μg/mL kanamycin and grown under the same conditions as above. Seedlings resistant to kanamycin were transplanted to soil seven days after germination. Two weeks after transplanting to soil the shoot phenotypes were observed.

Promoter-Reporter Lines

CRN:GUS has been previously described and characterized (Muller et al., 2008). To generate CLV2:H2B-mCherry, vector pMDC99 (Curtis and Grossniklaus, 2003) was modified by introducing the CDS of chimeric construct mCherry-H2B at the 3' site of the gateway cassette using the unique Pad restriction site to give pAB149. To analyze the expression of CLV2 1252 bp of the 5' region and 9 bp of the CDS was amplified using the primers AB_CLV2_Pro_F (5' CACCAGACACAAAGCCCTTTCCATTGTC 3'; SEQ ID NO:1) and AB_CLV2_Pro_R (5' CTTTATCATAGCTCA-GAGGA 3'; SEQ ID NO:2) to give a CACC-TOPO containing amplicon, which was cloned into pENTR/D-TOPO (Invitrogen™). This entry clone was used in a LR reaction with pAB149 to give pAB183 (CLV2:H2B-mCherry). Expression of CLV2 under the control of the endogenous promoter, using 1252 bp of the CLV2 5' region was sufficient to rescue the clv2-1 mutant in all isolated lines (N=20).

Nematode Infection of Promoter-Reporter Lines

The beet cyst nematode (BCN) *Heterodera schachtii* was propagated on greenhouse-grown sugar beets (*Beta vulgaris* cv Monohi). BCN eggs were isolated and hatched as previously described (Mitchum et al., 2004). After 2 days, second stage juveniles (J2) were collected and surfaced sterilized according to Wang et al. (2007) except 0.004% mercuric chloride, 0.004% sodium azide, and 0.002% Triton X-100 were used. Sterilized seeds were grown on modified Knop's medium (Brunschwig Chemie) (Sijmons et al., 1991). Ten days after germination seedlings were inoculated with 20 sterilized J2/root.

Histochemical β-Glucuronidase (GUS) Assays

At the indicated timepoints, freshly excised CRN:GUS tissues were infiltrated with GUS substrate buffer (0.5 mM 5-bromo-4chloro-3-indolyl glucuronide, 100 mM Tris, pH 7.0, 50 mM NaCl, 0.06% Triton X-100, 3 mM potassium ferricyanide) and incubated overnight at 37° C. (Jefferson et al., 1987). Stained roots were placed in glass Petri dishes and visualized with a Nikon Eclipse TS 100 inverted microscope.

Confocal Microscopy

CLV2:H2B-mCherry seed was sterilized, grown, and inoculated with nematodes as described above. At the indicated timepoints, infected roots were mounted on glass slides and visualized with a 510 META confocal scanning microscope (Carl Zeiss, Thornwood, N.Y., USA) excited at 543 nm.

Infection Assay with Receptor Mutants

Sterilized receptor mutants were plated in 12-well Falcon tissue culture plates (BD Biosciences) containing modified Knop's medium with 0.8% Daishin agar in a randomized block design. Plants were grown at 24° C. with a 12 hour photoperiod. Fourteen days after germination, seedlings were inoculated with 200 surface-sterilized BCN J2. J4 females were counted at 14 days post-inoculation (dpi) and adult females were counted at 30 dpi. The average values were calculated and significant differences were determined by using Student's t test ($P<0.05$). To measure syncytia size, receptor mutants were germinated on modified Knop's medium in vertical square plates and inoculated at 10 days after germination with 10 surface-sterilized BCN J2. At 14 dpi, syncytia that were transparent and only fed upon by only one nematode were visualized with a Nikon Eclipse TS 100 inverted microscope. Area of syncytia was measured using Adobe Photoshop CS5 and significant differences were determined by using Student's t test ($P<0.05$).

Results

CLV2 and CRN are Required for Nematode CLE Perception

Figure 5:
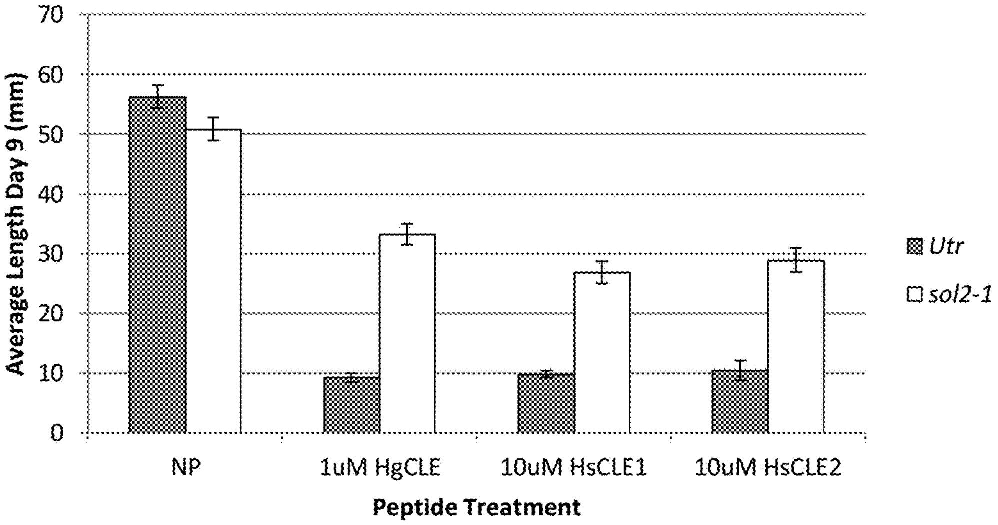

We have previously shown that exogenously applied 12-aa peptides corresponding to the CLE motifs of the SCN (HgCLEs) and the BCN (HsCLEs) CLEs can function as plant CLE peptide mimics causing termination of the primary root meristem in a concentration dependent manner (Wang et al., 2010b). In *Arabidopsis*, it has been shown that the short root phenotype caused by overexpression or exogenous application of some plant CLE peptides is dependent on CLV2 signaling (Fiers et al., 2005; Miwa et al., 2008; Muller, 2008; Meng et al., 2010). More recent evidence indicates that CLV2 forms a complex with CRN and can transmit the signal from CLV3 binding in a CLV1-independent manner (Miwa et al., 2008; Muller, 2008; Bleckmann et al., 2010; Zhu et al., 2010). To determine whether or not CLV2 and CRN might play a role in cyst nematode CLE perception we screened the *Arabidopsis* clv2-1 null mutant and the crn-1 amorphic allele for resistance to the HgCLE, HsCLE1, and HsCLE2 12-aa peptides. Seeds were grown on vertical plates in the absence of exogenous peptide or in the presence of 1 μM HgCLE or 10 μM of the HsCLEs and roots were measured 9 days after germination. Wild-type seedlings (Landsberg erecta [Ler]) had significantly shorter roots when grown on plates with any of the CLE peptides in comparison to the no peptide control (FIG. 1*a*). In contrast, clv2-1 and crn-1 root growth was relatively unimpaired in the presence of the different CLE peptides (FIG. 1*a*). The same observation was made with sol2-1, another mutant allele of CRN (Miwa et al., 2008) (FIG. 5). Previous reports have indicated that the short root phenotype can be attributed to a decrease in the number of meristematic cells (Fiers et al., 2005). Using Nomarski optics we confirmed that clv2-1 and crn-1 were insensitive to peptide application resulting in root meristems that were indistinguishable from the no peptide control (FIG. 1*b-d*).

Nematode CLEs function in planta through a CLV2- and CRN-dependent pathway Overexpression of HgCLE2, HsCLE1, and HsCLE2 in wild-type *Arabidopsis* has been shown to cause wus-like phenotypes similar to other plant CLEs (Strabala et al., 2006; Meng et al., 2010; Wang et al., 2005; Wang et al., 2010a; Wang et al., 2010b). If CLV2 and/or CRN are involved in nematode CLE perception then we would expect the phenotypes to be diminished or abolished when overexpressed in clv2-1 and/or crn-1. Each of the nematode CLE genes was cloned into an overexpression vector and transformed into the mutant backgrounds. Transgenic seedlings in the T1 generation were screened and characterized in soil. In contrast to the overexpression phenotypes seen in wild-type *Arabidopsis* where a high percentage of wus-like phenotypes were observed (Wang et al., 2010a; Wang et al., 2010b), no wus¬ -like phenotypes were observed when HgCLE2, HsCLE 1, and HsCLE2 were overexpressed in clv2-1 or crn-1 (Table 1). These results demonstrate that mutations in CRN and CLV2 suppress nematode CLE overexpression phenotypes.

TABLE 1

Summary of nematode CLE overexpression phenotypes in clv2-1 and crn-1.

| | | T1 Shoot Phenotypes | | |
|---|---|---|---|---|
| Background | Construct | wus-like (%) | WT (%) | Total T1 (#) |
| clv2-1 | HgCLE2 | 0 | 100 | 96 |
| | HsCLE1 | 0 | 100 | 67 |
| | HsCLE2 | 0 | 100 | 28 |
| crn-1 | HgCLE2 | 0 | 100 | 85 |
| | HsCLE1 | 0 | 100 | 41 |
| | HsCLE2 | 0 | 100 | 37 |

Spatial and temporal relationship between CLV2, CRN, and nematode feeding sites Cyst nematodes enter the root near the zone of elongation, migrate through root cortical cells using their stylet to puncture through cell walls, and begin feeding from a single cell near the vascular cylinder. Once cyst nematodes initiate a feeding site the dorsal esophageal gland cell becomes active and the secreted CLE peptides are delivered to the host root cells (Wang et al., 2010a). In order for CLV2 and CRN to be able to perceive the nematode CLE as a ligand mimic they must be expressed in the correct spatial and temporal context.

Figure 2:
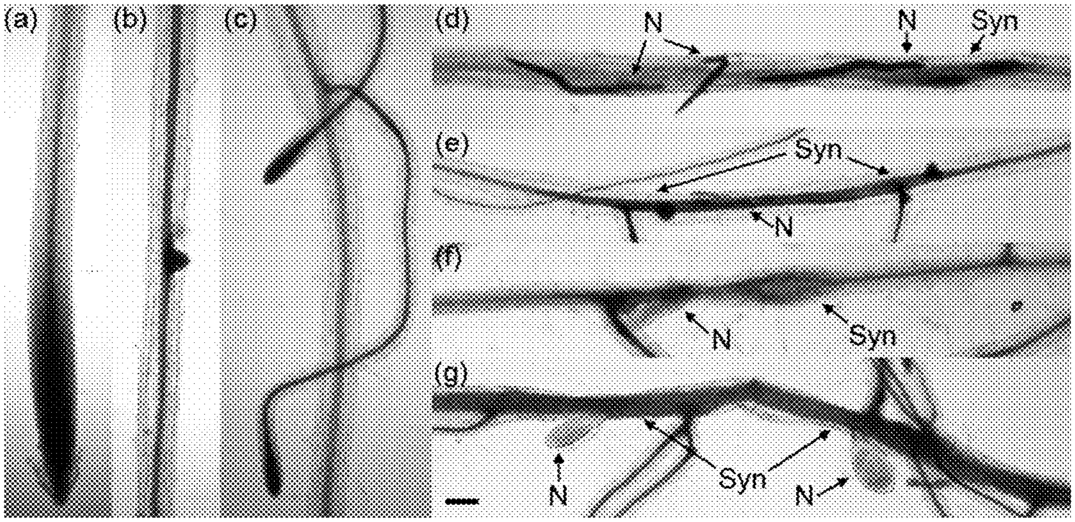

Using a CRN:GUS transgene in *Arabidopsis*, CRN expression was previously shown to be expressed throughout the root including the vasculature where the nematode initiates feeding (FIG. 2*a-c*; Muller et al., 2008). To confirm whether CRN is expressed in nematode feeding sites, transgenic *Arabidopsis* seedlings expressing CRN:GUS were infected with BCN and monitored during nematode development. GUS expression was detected in feeding sites as soon as early second-stage juveniles (J2) began to feed. (FIG. 2*d*). GUS expression reached its peak once nematodes reached late J2 parasitic stages, but remained detectable in the feeding sites of third stage juvenile (J3) parasitic nematodes (FIGS. 2*e* and *f*). By the time the nematodes reached the fourth stage juvenile (J4) life stage, GUS expression was either weak or absent in feeding sites (FIG. 2*g*).

Figure 3:
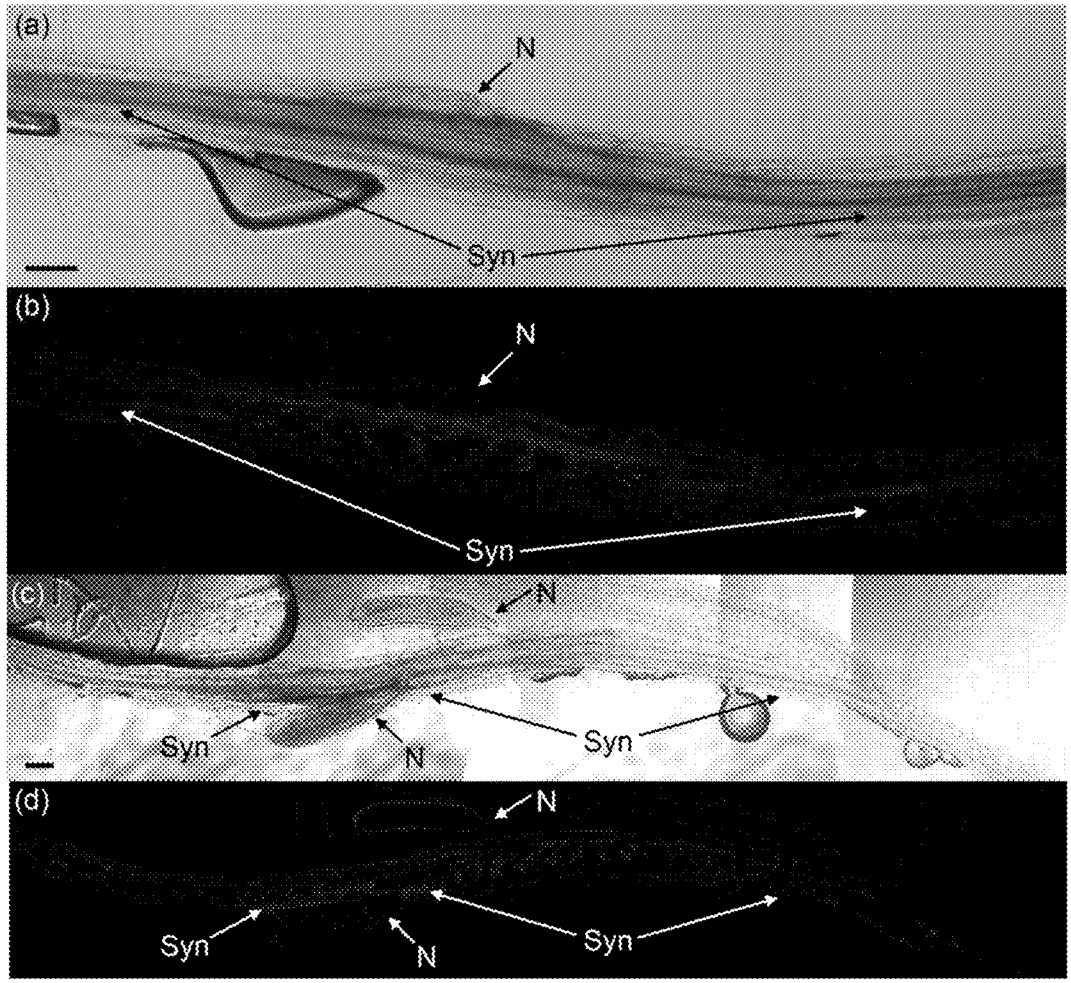

Similar to CRN, CLV2 is expressed in many different vegetative tissues (Jeong et al., 1999). However little is known about the expression pattern of CLV2 in roots. To visualize CLV2 expression in roots and nematode feeding sites, mCherry was fused to the C-terminus of the *Arabidopsis* Histone 2B (H2B) gene and placed under the transcriptional control of the CLV2 promoter. The H2B protein has been shown to be a valid marker for chromatin organization in plant nuclei and has been used to describe development of the syncytial endosperm in *Arabidopsis* (Boisnard-Lorig et al., 2001). In uninfected roots, CLV2:H2B-mCherry fluorescence was detected throughout the root vasculature with the strongest expression detected in lateral root primordia and the zone of elongation extending down to the root apical meristem (A. Bleckmann and R. Simon, unpublished). Upon nematode infection, increased expression of CLV2:H2B-mCherry fluorescence was detected in the nuclei of syncytia fed upon by parasitic J2s (FIG. 3*a-b*). At the J3 life stage CLV2:H2B-mCherry continued to be specifically expressed within feeding sites (FIG. 3*c-d*). No fluorescence was detected in nuclei of syncytia fed upon by parasitic J2s in wild-type plants (FIG. 6*a-b*).

Mutant alleles of CLV2 and CRN cause a reduction in nematode infection and defects in syncytial size.

By using an RNAi approach targeting nematode CLE genes, previous reports have shown that nematode CLE peptides are important for successful infection of host plants roots (Bakhetia et al., 2007; Patel et al., 2008). To determine if nematode CLE perception by CLV2 or CRN is required, root infection assays with nematodes were performed on the clv2-1 and crn-1 single mutants, and the crn-1 clv2-1 double mutant. According to Muller et al. (2008), crn-1 clv2-1 is morphologically indistinguishable from either of the single mutants, indicating that they act in the same pathway. The mutant alleles and the wild-type Ler were randomized in 12-well plates and grown on modified Knop's medium.

Figure 4:
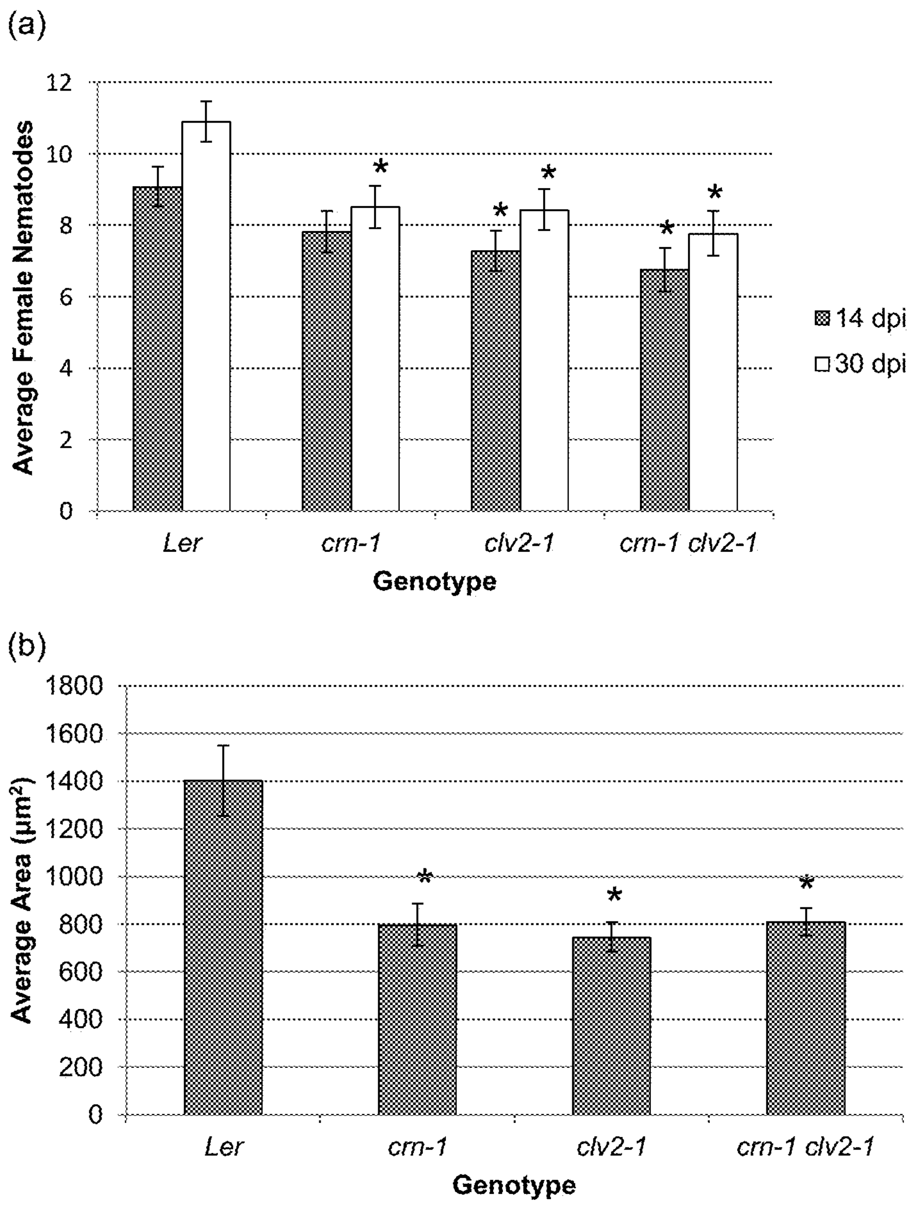

Two weeks after germination seedlings were inoculated with infective J2s. J4 females were counted at 14 days post-inoculation (dpi) and adult females were counted at 30 dpi. Both the single and double mutants showed a statistically significant reduction in nematode infection with the exception of crn-1 at 14 dpi (FIG. 4*a*). At 30 dpi nematode infection was reduced by approximately 25% in all receptor mutants tested. A similar reduction in nematode infection across all mutant lines supports the hypothesis that CLV2 and CRN are acting in the same signaling pathway. Using sol2-1, we observed a 40% reduction in nematode infection (FIG. 7*a*). Since the establishment of a feeding site is required for nematode development and reproduction, the above observations motivated us to determine if there were any defects in syncytial size between the receptor mutants and wild-type.

The mutant alleles and the wild-type Ler were grown on vertical square plates and inoculated with infective J2s. At 14 dpi, syncytia that were transparent and fed upon by only one nematode were measured. The average area of wild-type (Ler) syncytia was 1402±147 μm2 (FIG. 4*b*). In contrast, the syncytia of the receptor mutant alleles were reduced by approximately 40%. The average area of crn-1, clv2-1, and crn-1 clv2-1 was 797±89 μm2, 745±61 μm2, and 808±57 μm2, respectively (FIG. 4*b*). The same reduction in syncytia size was seen in the sol2-1 mutant allele (FIG. 7*b*).

Nematode CLE genes have been found to be upregulated in the dorsal esophageal gland cell at the onset of parasitism and remain on through the adult female life stage. CLE genes are turned off in adult males that are no longer feeding (Wang et al., 2005; Patel et al., 2008; Lu et al., 2009; Wang et al., 2010a). In SCN and BCN, immunolocalization studies have localized nematode CLEs along the dorsal gland extension and in the ampulla at the base of the nematode stylet indicating they are secreted into host plant roots via the stylet (Wang et al., 2005; Patel et al., 2008; Wang et al., 2010a). Consistent with these results an immunofluorescence study found that SCN CLEs are secreted directly into host plant root cytoplasm (Wang et al., 2010a). The variable domain of SCN CLEs is then able to redirect the proteins into the apoplast where they can act as plant CLE ligand mimics by interacting with extracellular membrane bound plant CLE receptors. However, thus far, host plant receptors that perceive nematode CLE signals have not been identified.

Many studies have used synthetic CLE peptides to help determine the roles that plant CLE peptides play in plant growth and development. Previous studies have shown that nematode CLE peptides cause root growth phenotypes similar to other plant CLEs (Lu et al., 2009; Wang et al., 2010a; Wang et al., 2010b). Other studies have also shown that these peptide screens can identify receptors that may be involved in certain CLE signaling pathways by utilizing receptor mutants (Fiers et al., 2005; Stahl et al., 2009; Meng et al., 2010).

To identify potential nematode CLE receptors we tested plant CLE receptors implicated in CLE signaling in the RAM for a role in nematode CLE perception. In the root, exogenous peptide assays and overexpression studies have shown that CLV2 is required for proper proximal meristem function (Stahl et al., 2009; Meng et al., 2010).

Figure 1:
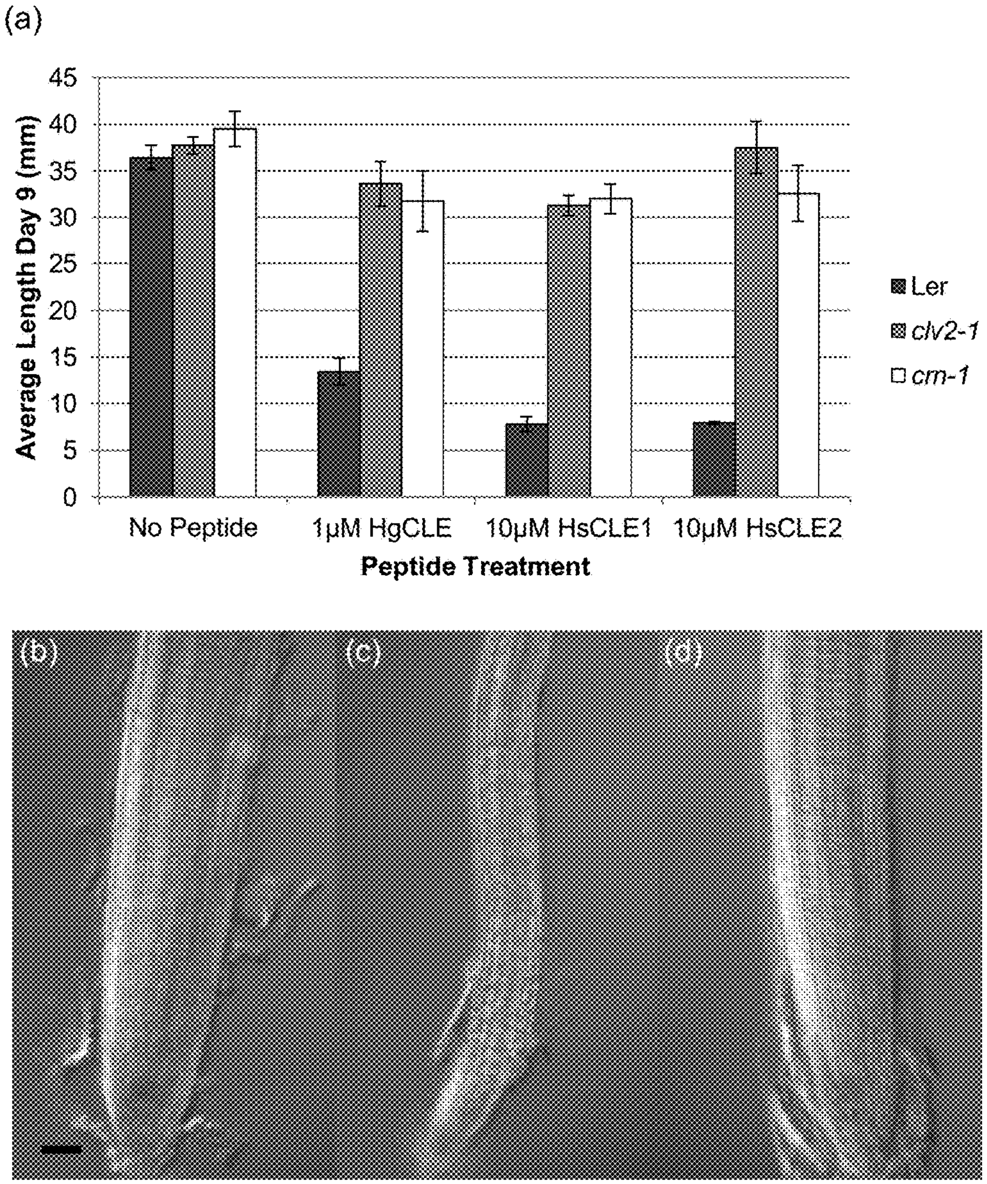

It has also been shown that a new member of the receptor kinase family, CRN, forms a heterodimer with CLV2 and is required for proper localization of the CLV2/CRN complex to the plasma membrane (Bleckmann et al., 2010; Zhu et al., 2010). In *Arabidopsis*, CRN has been found to be widely expressed in both shoot and root tissues suggesting dual roles in shoot and root development (Muller et al., 2008). CLV2 has been found to be expressed in shoot tissues (Jeong et al., 1999), but less is known about its expression in the root. In this paper we screened a null mutant allele of CLV2 and an amorphic mutant allele of CRN for resistance to the nematode CLE peptides. Both clv2-1 and crn-1 were resistant to HgCLEp, HsCLE1p, and HsCLE2p (FIGS. 1 and 5). Similar to synthetic peptide assays, overexpression of HgCLE, HsCLE1, and HsCLE2 in the clv2-1 and crn-1 mutant backgrounds abolished the wus-like phenotypes seen when the nematode CLEs are overexpressed in wild-type backgrounds (Wang et al., 2005; Wang et al., 2010a; Wang et al., 2010b). Taken together, the peptide assays and overexpression data indicate that CLV2 and CRN are required for nematode CLE perception.

In order to serve as a receptor complex for nematode CLE peptides, CLV2 and CRN would most likely need to be expressed in feeding cell initials as well as the developing feeding sites. With the use of promoter-reporter lines we confirmed that both CLV2 and CRN were expressed in nematode-induced feeding sites (FIGS. 2 and 3), consistent with a role in nematode CLE perception. It is also possible that nematode CLE receptors are expressed in the cells adjacent to the expanding syncytium. As the nematode CLEs are redirected to the host root apoplast, extracellular receptors of the adjacent cells that are primed for incorporation could trigger plant CLE signaling pathways needed to fully form the syncytium. In the future it will be interesting to more precisely localize the CLV2 and CRN proteins within syncytia using immunofluorescence techniques. This will aid in determining whether or not these nematode CLE receptors are expressed within the cell wall openings that occur during syncytium formation or if they are expressed on the outer plasma membrane of the syncytium and/or adjacent cells.

Previous reports have demonstrated that SCN and BCN CLEs are important for nematode parasitism by showing a reduction in nematode infection after knocking down CLE expression in the worm using RNAi approaches (Bakhetia et al., 2007; Patel et al., 2008). To directly test for a role of CLV2/CRN in nematode CLE perception we performed infection assays on the receptor mutants.

Figure 6:
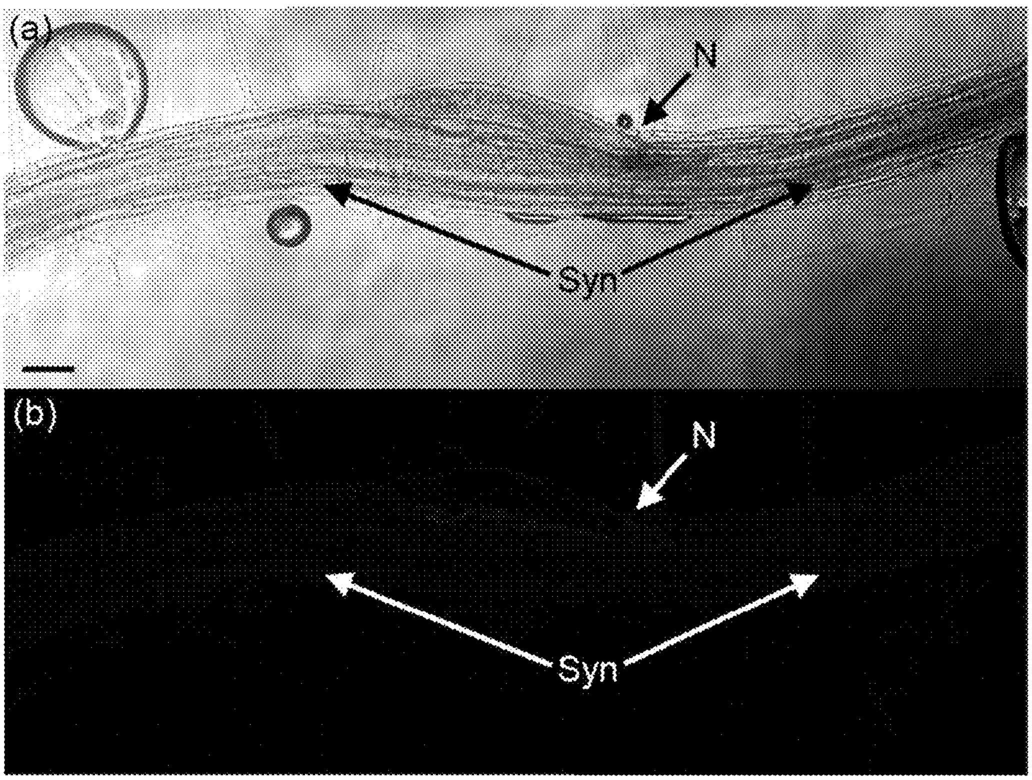
Figure 7:
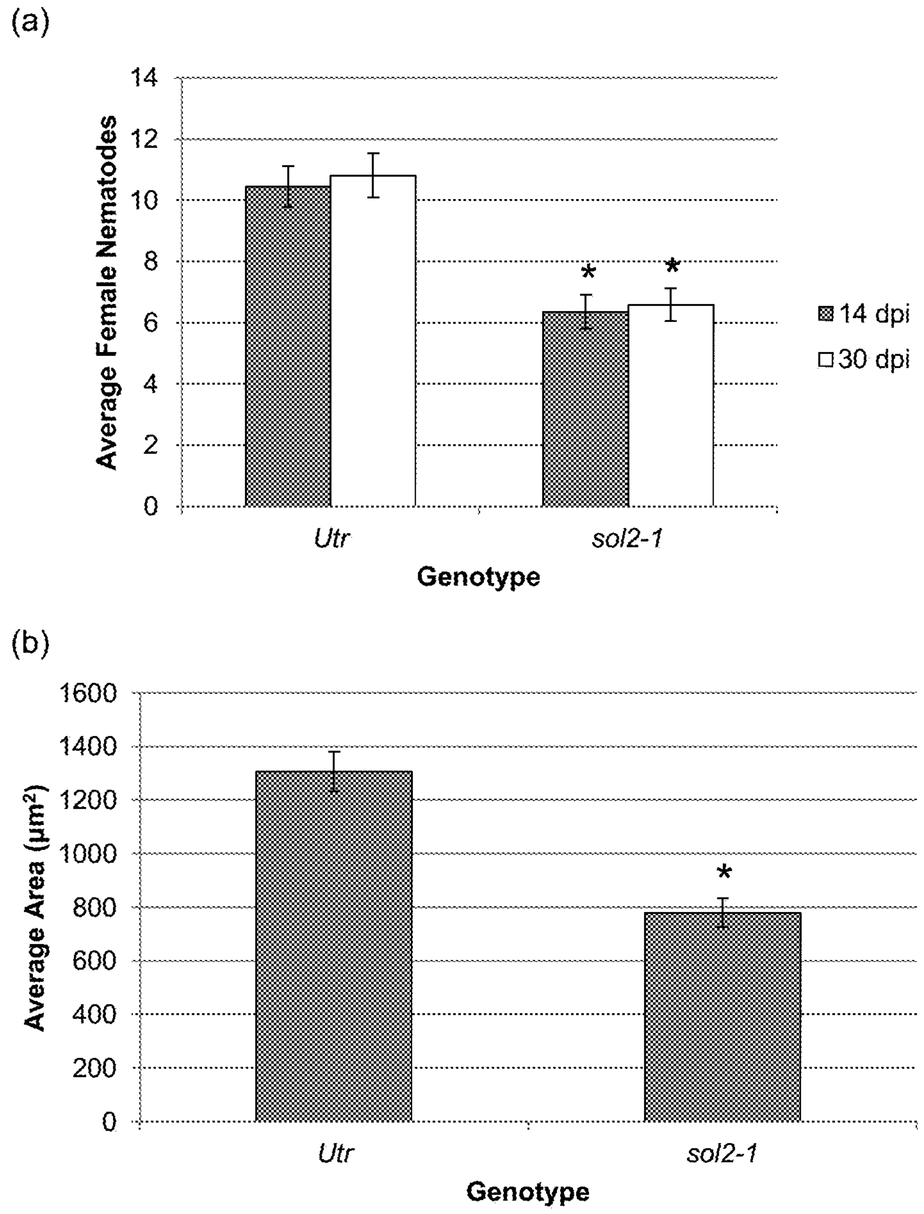

We showed that a reduction in nematode infection occurs on the receptor mutants (FIGS. 4*a* and 6). Concurrently, we also saw a reduction in syncytium size in the receptor mutants (FIGS. 4*b* and 7). The fact that we saw a similar reduction in both nematode infection and syncytia size in both the single and double mutants is consistent with genetic and biochemical data that CLV2 and CRN are acting in the same pathway (Muller et al., 2008; Bleckmann et al., 2010; Zhu et al., 2010). These data indicate that not only is nematode CLE perception by CLV2 and CRN important for successful nematode infection, but demonstrates that CLE signaling also plays a role feeding cell formation.

The involvement of CRN in nematode CLE signaling also opens up the interesting possibility that nematode CLE signaling may be directly or indirectly suppressing host plant defense responses. It has been reported that in root tips of sol2-1, another mutant allele of CRN, plant disease resistance-related and stress responsive genes were upregulated (Miwa et al., 2008). Therefore, when nematode CLEs are secreted they could activate the CLV2/CRN signaling pathway leading to a suppression of plant disease resistance-related and plant stress responsive genes. One might speculate that the main target for nematode CLEs is a signaling pathway which allows developmental programming of root cells for syncytium formation to occur and that suppression of plant defense responses is just an added benefit to the nematode. Alternatively, the nematode may require suppression of plant defense responses through plant CLE signaling in order for the syncytium to form properly. Further studies will need to be performed to investigate this possibility.

Several possibilities exist for why we only see a partial reduction in nematode numbers and syncytia size in the clv2-1 and crn-1 mutant backgrounds. First, besides CLEs, nematodes secrete many different effectors that likely play an important role in feeding cell formation (Wang et al., 2001; Gao et al., 2003).

For example, when BCN CLEs were targeted with RNAi a similar partial reduction in nematode infection was observed (Patel et al., 2008), either as a consequence of limited reductions in transcript levels or an indication that the other effectors still active in the nematode allow infection to proceed. A second possibility for the partial reduction in the receptor mutants is that there could be multiple nematode CLE receptors. So far, the nematode CLEs reported belong to gene families (Lu et al., 2009; Wang et al., 2010a; Wang et al., 2010b). In addition, PCN CLEs have multiple CLE motifs that may be simultaneously processed to release different CLE peptides (Lu et al., 2009). This leaves the possibility that nematode CLE peptides may activate multiple plant CLE signaling pathways concurrently to function in an antagonistic or synergistic fashion as reported for plant CLEs (Whitford et al., 2008). The current plant CLV3 signaling pathway in the shoot indicates that there are parallel signaling pathways. Genetic evidence indicates that CLV1 acts in a separate pathway from the CLV2/CRN pathway (Muller et al., 2008). In support of the genetic data, recent reports using luciferase complementation assays and FRET analysis have shown that CLV1 forms a homodimer and that CLV2 and CRN form a heterodimer without CLV3 stimulation (Bleckmann et al., 2010; Zhu et al., 2010).

These reports also found evidence for CLV1 interacting with the CLV2/CRN complex leading to the possibility that different signaling pathways could be activated depending on which receptor in the complex interacts with the CLE ligand (Bleckmann et al., 2010; Zhu et al., 2010). Thus it is possible that in the crn-1 clv2-1 double mutants, nematodes are still able to signal through other receptors in the roots. Unlike CLV2, which has a broad expression pattern in plants, CLV1 expression is thought to be restricted to the center of the SAM and its function is thought to be confined to stem cell specification in the shoot (Clark et al., 1997; Fletcher et al., 1999). Therefore, in order to utilize CLV1 as a receptor, nematodes would have to activate CLV1 expression in the roots. Recently, CLV1-related Barely Any Meristem (BAM) 1 and BAM2 have been shown to act redundantly in the SAM and are widely expressed throughout the plant, including root tissues (DeYoung et al., 2006; Deyoung and Clark, 2008). We have found that bam1 is also resistant to exogenous application of synthetic nematode CLE peptides (A. Replogle, S. Chen, X. Wang and M. G. Mitchum, unpublished data). Moreover, there are over 200 LRR-RLKs in *Arabidopsis* and only a few receptor-CLE ligand pairs have been identified (Shiu and Bleecker, 2001). Thus, further studies using a combination of mutants will need to be performed to investigate the possible involvement of other host plant receptors in nematode CLE signaling.

It is shown here that nematode CLE signaling through the CLV2/CRN receptor complex is important for proper syncytium formation and ultimately successful nematode infection. These findings open the door for identifying the downstream signaling components regulated by CLV2/CRN to uncover the role nematode CLE signaling plays in syncytium formation.

References

Bakhetia, M., Urwin, P. E. and Atkinson, H. J. (2007) qPCR analysis and RNAi define pharyngeal gland cell-expressed genes of *Heterodera glycines* required for initial interactions with the host. *Mol. Plant Microbe Interact.* 20, 306-312.

Bleckmann, A., Weidtkamp-Peters, S., Seidel, C. A. and Simon, R. (2010) Stem cell signaling in *Arabidopsis* requires CRN to localize CLV2 to the plasma membrane. *Plant Physiol.* 152, 166-176.

Boisnard-Lorig, C., Colon-Carmona, A., Bauch, M., Hodge, S., Doerner, P., Bancharel, E., Dumas, C., Haseloff, J. and Berger, F. (2001) Dynamic analyses of the expression of the HISTONE::YFP fusion protein in *Arabidopsis* show that syncytial endosperm is divided in mitotic domains. *Plant Cell,* 13, 495-509.

Casamitjana-Martinez, E., Hofhuis, H. F., Xu, J., Liu, C. M., Heidstra, R. and Scheres, B. (2003) Root-specific CLE19 overexpression and the sol1/2 suppressors implicate a CLV-like pathway in the control of *Arabidopsis* root meristem maintenance. *Curr. Biol.* 13, 1435-1441.

Clark, S. E., Running, M. P. and Meyerowitz, E. M. (1993) CLAVATA1, a regulator of meristem and flower development in *Arabidopsis. Development,* 119, 397-418.

Clark, S. E., Williams, R. W. and Meyerowitz, E. M. (1997) The CLAVATA1 gene encodes a putative receptor kinase that controls shoot and floral meristem size in *Arabidopsis. Cell,* 89, 575-585.

Clough, S. J. and Bent, A. F. (1998) Floral dip: a simplified method for *Agrobacterium*-mediated transformation of *Arabidopsis thaliana. Plant J.* 16, 735-743.

Curtis, M. D. and Grossniklaus, U. (2003) A gateway cloning vector set for high-throughput functional analysis of genes in planta. *Plant Physiol.* 133, 462-469.

Davis, E. L., Hussey, R. S, and Baum, T. J. (2004) Getting to the roots of parasitism by nematodes. *Trends Parasitol.* 20, 134-141.

Davis, E. L., Hussey, R. S., Mitchum, M. G. and Baum, T. J. (2008) Parasitism proteins in nematode-plant interactions. *Curr. Opin. Plant Biol.* 11, 360-366.

DeYoung, B. J., Bickle, K. L., Schrage, K. J., Muskett, P., Patel, K. and Clark, S. E. (2006) The CLAVATA1-related BAM1, BAM2 and BAM3 receptor kinase-like proteins are required for meristem function in *Arabidopsis. Plant J.* 45, 1-16.

Deyoung, B. J. and Clark, S. E. (2008) BAM receptors regulate stem cell specification and organ development through complex interactions with CLAVATA signaling. *Genetics,* 180, 895-904.

Endo, B. Y. (1964) Penetration and development of *Heterodera glycines* in soybean roots and related anatomical changes. *Phytopathology,* 54, 79-88.

Fiers, M., Hause, G., Boutilier, K., Casamitjana-Martinez, E., Weijers, D., Offring a, R., van der Geest, L., van Lookeren Campagne, M. and Liu, C. M. (2004) Mis-expression of the CLV3/ESR-like gene CLE19 in *Arabidopsis* leads to a consumption of root meristem. *Gene,* 327, 37-49.

Fiers, M., Golemiec, E., Xu, J., van der Geest, L., Heidstra, R., Stiekema, W. and Liu, C. M. (2005) The 14-amino acid CLV3, CLE19, and CLE40 peptides trigger consumption of the root meristem in *Arabidopsis* through a CLAVATA2-dependent pathway. *Plant Cell,* 17, 2542-2553.

Fletcher, L. C., Brand, U., Running, M. P., Simon, R. and Meyerowitz, E. M. (1999) Signaling of cell fate decisions by CLAVATA3 in *Arabidopsis* shoot meristems. *Science,* 283, 1911-1914.

Gao, B., Allen, R., Maier, T., Davis, E. L., Baum, T. J. and Hussey, R. S. (2003) The parasitome of the phytonematode *Heterodera glycines. Mol. Plant Microbe Interact.* 16, 720-726.

Jefferson, R. A., Kavanagh, T. A. and Bevan, M. W. (1987) GUS fusions: β-glucuronidase as a sensitive and versatile gene fusion marker in higher plants. *EMBO J,* 6, 3901-3907.

Jeong, S., Trotochaud, A. E. and Clark, S. E. (1999) The *Arabidopsis* CLAVATA2 gene encodes a receptor-like protein required for the stability of the CLAVATA1 receptor-like kinase. *Plant Cell,* 11, 1925-1934.

Kayes, J. M. and Clark, S. E. (1998) CLAVATA2, a regulator of meristem and organ development in *Arabidopsis. Development,* 125, 3843-3851.

Koornneef, M., Van Eden, J., Hanhart, C. J., Stam, P., Braaksma, F. J. and Feenstra, W. J. (1983) Linkage Map of *Arabidopsis thaliana. J. Hered.* 74, 265-272.

Laux, T., Mayer, K. F. X., Berger, J. and Jurgens, G. (1996) The WUSCHEL gene is required for shoot and floral meristem integrity in *Arabidopsis. Development,* 122, 87-96.

Lu, S. W., Chen, S., Wang, J., Yu, H., Chronis, D., Mitchum, M. G. and Wang, X. (2009) Structural and functional diversity of CLAVATA3/ESR (CLE)-like genes from the potato cyst nematode *Globodera rostochiensis. Mol. Plant Microbe Interact.* 22, 1128-1142.

Meng, L., Ruth, K. C., Fletcher, J. C. and Feldman, L. (2010) The roles of different CLE domains in *Arabidopsis* CLE polypeptide activity and functional specificity. *Mol. Plant, doi:*10.1093/mp/ssq021

Mitchum, M. G., Sukno, S., Wang, X., Shani, Z., Tsabary, G., Shoseyov, O. and Davis, E. L. (2004) The promoter of the *Arabidopsis thaliana* Cell endo-1,4-beta glucanase gene is differentially expressed in plant feeding cells induced by root-knot and cyst nematodes. *Mol. Plant Pathol.* 5, 175-181.

Mitchum, M. G., Wang, X. H. and Davis, E. L. (2008) Diverse and conserved roles of CLE peptides. *Curr. Opin in Plant Biol.* 11, 75-81.

Miwa, H., Betsuyaku, S., Iwamoto, K., Kinoshita, A., Fukuda, H. and Sawa, S. (2008) The receptor-like kinase SOL2 mediates CLE signaling in *Arabidopsis. Plant Cell Physiol.* 49, 1752-1757.

Muller, R., Bleckmann, A. and Simon, R. (2008) The receptor kinase CORYNE of *Arabidopsis* transmits the stem cell-limiting signal CLAVATA3 independently of CLAVATA1. *Plant Cell,* 20, 934-946.

Ogawa, M., Shinohara, H., Sakagami, Y. and Matsubayashi, Y. (2008) *Arabidopsis* CLV3 peptide directly binds CLV1 ectodomain. *Science,* 319, 294.

Patel, N., Hamamouch, N., Chunying, L., Hussey, R., Mitchum, M., Baum, T., Wang, X. and Davis, E. L. (2008) Similarity and functional analyses of expressed parasitism genes in *Heterodera schachtii* and *Heterodera glycines. J. Nematol.* 40, 299-310.

Rojo, E., Sharma, V. K., Kovaleva, V., Raikhel, N. V. and Fletcher, J. C. (2002) CLV3 is localized to the extracellular space, where it activates the *Arabidopsis* CLAVATA stem cell signaling pathway. *Plant Cell,* 14, 969-977.

Sarkar, A. K., Luijten, M., Miyashima, S., Lenhard, M., Hashimoto, T., Nakajima, K., Scheres, B., Heidstra, R. and Laux, T. (2007) Conserved factors regulate signaling in *Arabidopsis thaliana* shoot and root stem cell organizers. *Nature,* 446, 811-814.

Sasser, J. N. and Freckman, D. W. (1987) A world perspective on Nematology: the role of the society. *Vistas on nematology*. Veech, J. A. and Dickson, D. W., Hyatssville, Md., USA: Society of Nematologists.

Sharma, V. K., Ramirez, J. and Fletcher, J. C. (2003) The *Arabidopsis* CLV3-like (CLE) genes are expressed in diverse tissues and encode secreted proteins. *Plant Mol. Biol.* 51, 415-425.

Shiu, S. H. and Bleecker, A. B. (2001) Plant receptor-like kinase gene family: diversity, function, and signaling. *Sci STKE,* 2001, re22.

Sijmons, P. C., Grundler, F. M. W., Von Mende, N., Burrows, P. R. and Wyss, U. (1991) *Arabidopsis thaliana* as a new model host for plant parasitic nematodes. *Plant J.* 1, 245-254.

Simon, R. and Stahl, T. (2006) Plant Cells CLEave Their Way to Differentiation. *Science,* 313, 773-774.

Stahl, Y., Wink, R. H., Ingram, G. C. and Simon, R. (2009) A signaling module controlling the stem cell niche in *Arabidopsis* root meristems. *Curr. Biol.* 19, 909-914.

Strabala, T. J., O'Donnell, P. J., Smit, A. M., Ampomah-Dwamena, C., Martin, E. J., Netzler, N., Nieuwenhuizen, N. J., Quinn, B. D., Foote, H. C. C. and Hudson, K. R. (2006) Gain-of-function phenotypes of many CLAVATA3/ESR genes, including four new family members, correlate with tandem variations in the conserved CLAVATA3/ESR domain. *Plant Physiol.* 140, 1331-1344.

Trotochaud, A. E., Hao, T., Wu, G., Yang, Z. and Clark, S. E. (1999) The CLAVATA1 receptor-like kinase requires CLAVATA3 for its assembly into a signaling complex that includes KAPP and a Rho-related protein. *Plant Cell,* 11, 393-406.

Wang, J., Lee, C., Replogle, A., Joshi, S., Korkin, D., Hussey, R., Baum, T. J., Davis, E. L., Wang, X. and Mitchum, M. G. (2010a) Dual roles for the variable domain in protein trafficking and host-specific recognition of *Heterodera glycines* CLE effector proteins. *New Phytol.* 10.1111/j.1469-8137.2010.03300.x Wang, J., Replogle, A., Hussey, R., Baum, T., Wang, X., Davis, E. L. and Mitchum, M. G. (2010b) Identification of potential host plant mimics of CLV3/ESR (CLE)-like peptides from the plant-parasitic nematode *Heterodera schachtii. Mol. Plant Pathol.* (under review).

Wang, X., Allen, R., Ding, X., Goellner, M., Maier, T., de Boer, J. M., Baum, T. J., Hussey, R. S. and Davis, E. L. (2001) Signal peptide-selection of cDNA cloned directly from the esophageal gland cells of the soybean cyst nematode *Heterodera glycines. Mol. Plant Microbe Interact.* 14, 536-544.

Wang, X., Mitchum, M. G., Gao, B., Li, C., Diab, H., Baum, T. J., Hussey, R. S. and Davis, E. L. (2005) A parasitism gene from a plant-parasitic nematode with function similar to CLAVATA3/ESR (CLE) of *Arabidopsis thaliana. Mol. Plant Pathol.* 6, 187-191.

Wang, X., Replogle, A., Davis, E. L. and Mitchum, M. G. (2007) The tobacco Cel7 gene promoter is auxin-responsive and locally induced in nematode feeding sites of heterologous plants. Mol. Plant Pathol. 8, 423-436.

Whitford, R., Fernandez, A., De Groodt, R., Ortega, E. and Hilson, P. (2008) Plant CLE peptides from two distinct functional classes synergistically induce division of vascular cells. *Proc. Natl. Acad. Sci. USA,* 105, 18625-18630.

Zhu, Y., Wang, Y., Li, R., Song, X., Wang, Q., Huang, S., Jin, J. B., Liu, C. M. and Lin, J. (2010) Analysis of interactions among the CLAVATA3 receptors reveals a direct interaction between CLAVATA2 and CORYNE in *Arabidopsis. Plant J.* 61, 223-233.

Example 2

Figure 8:
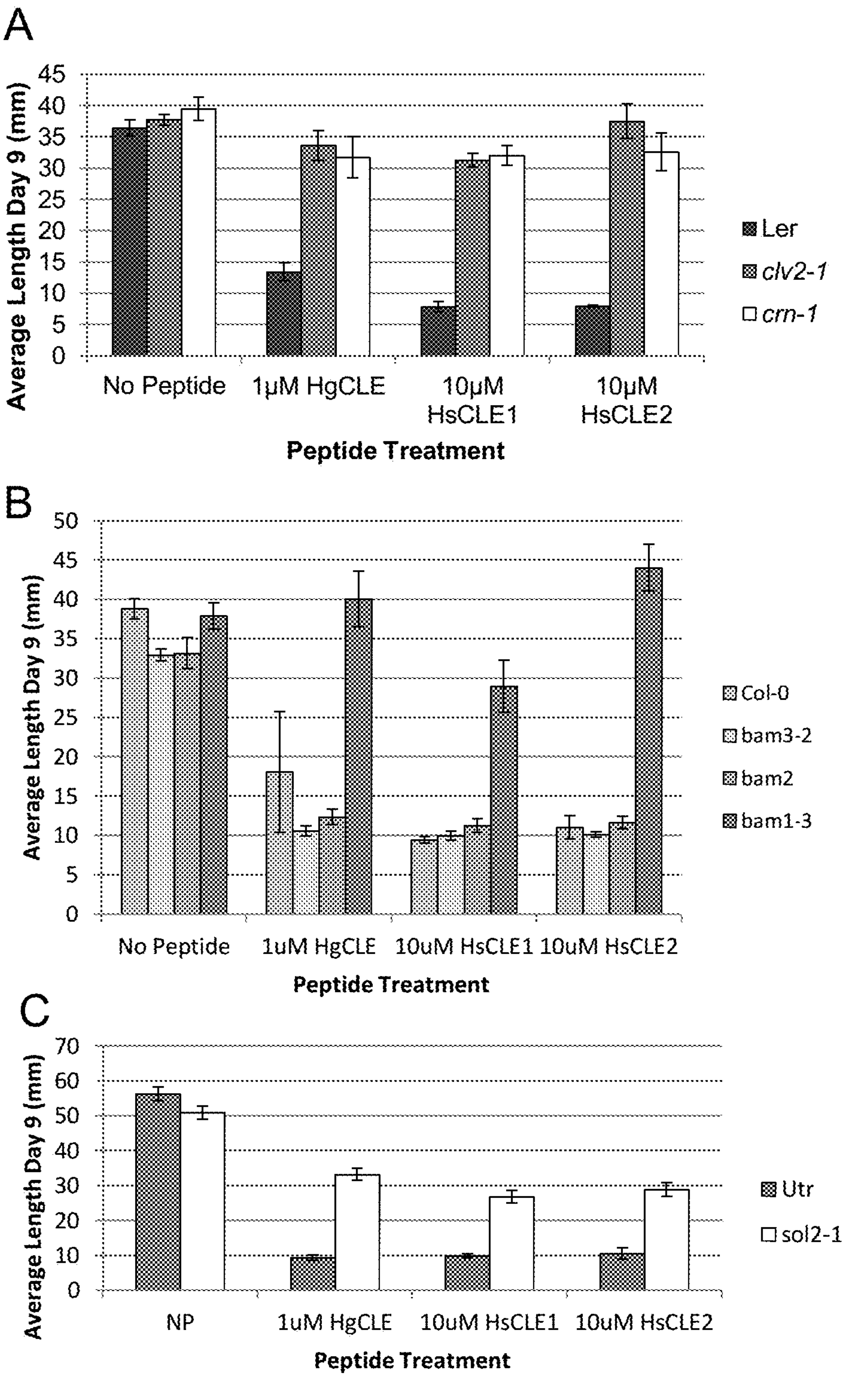
Figure 9:
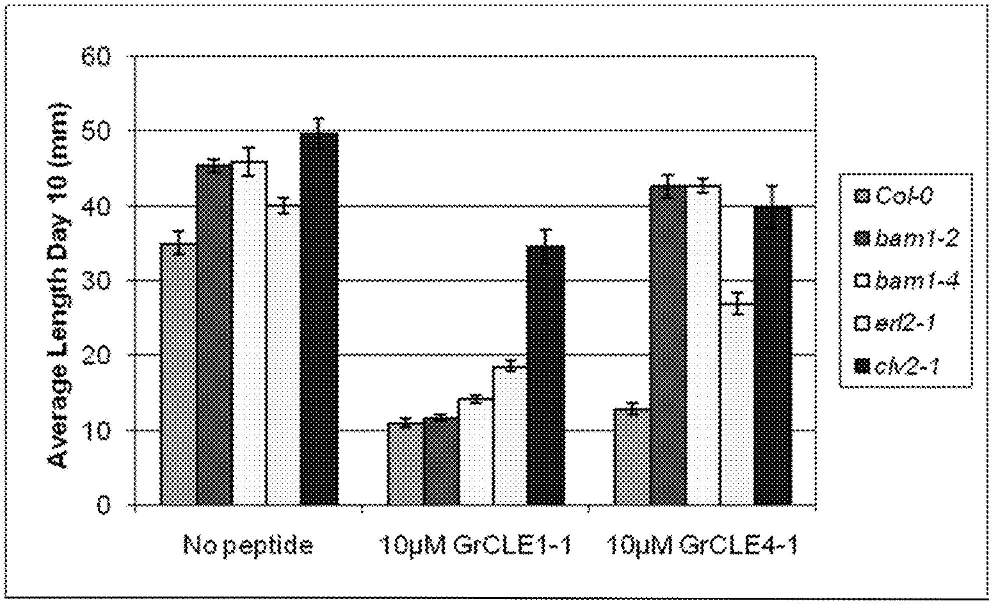
Figure 10:
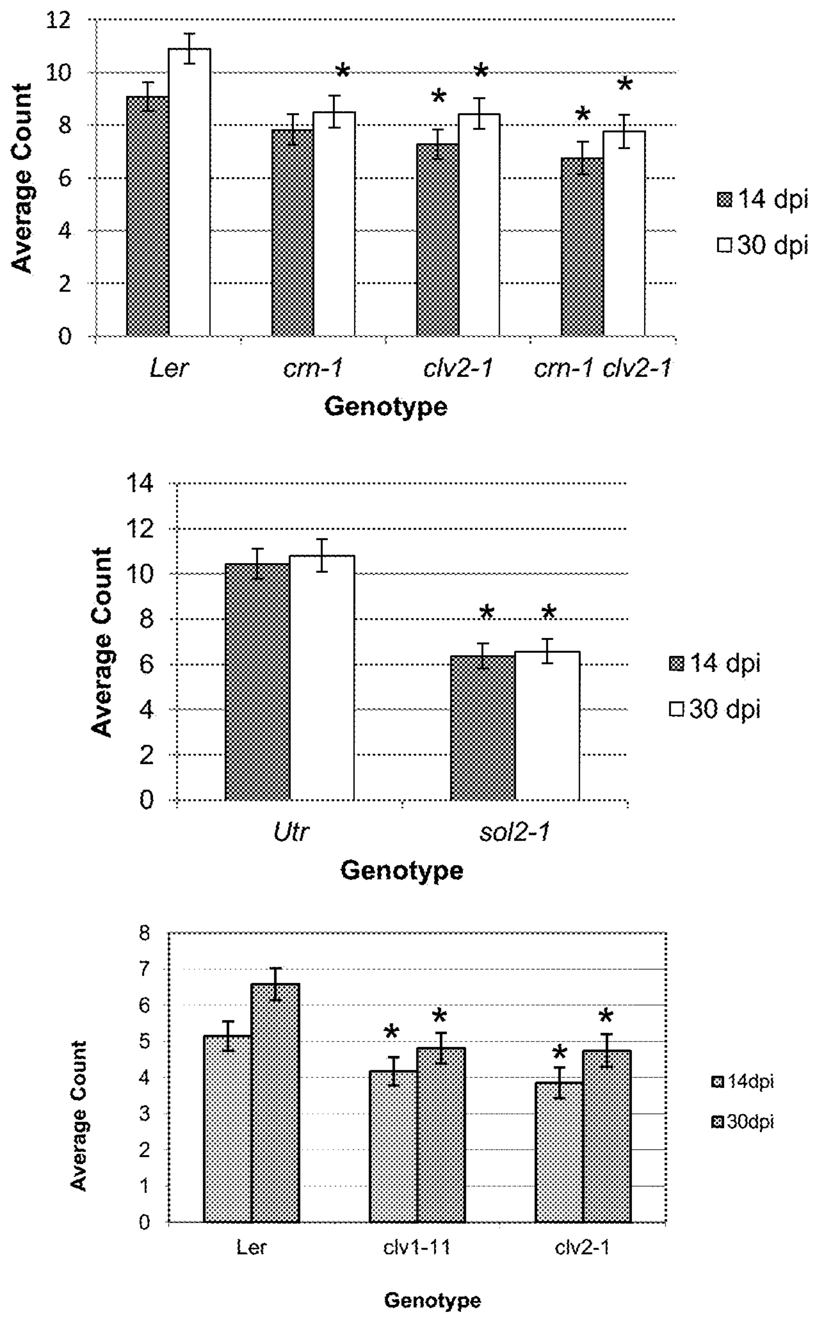
Figure 11:
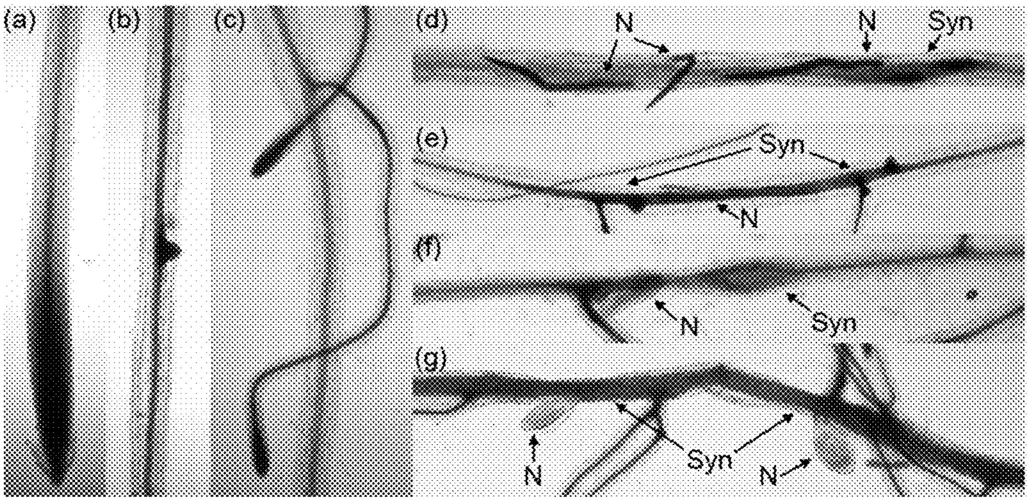
Figure 12:
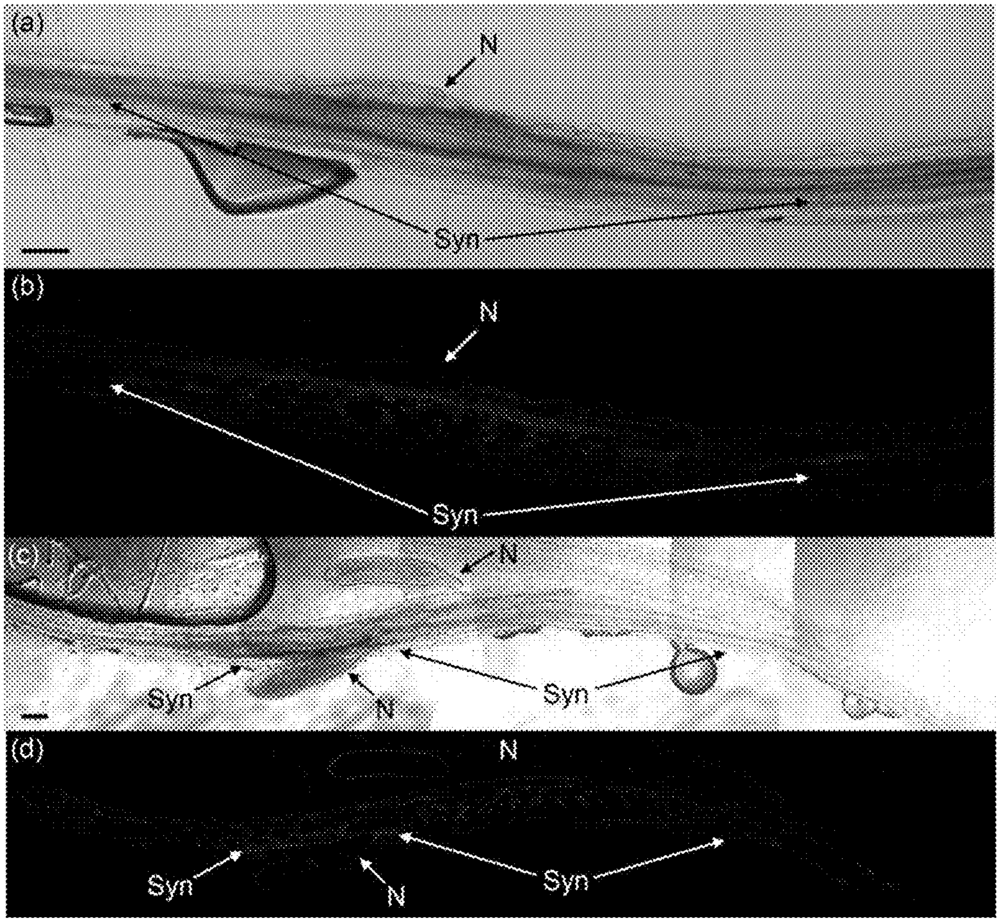
Figure 13:
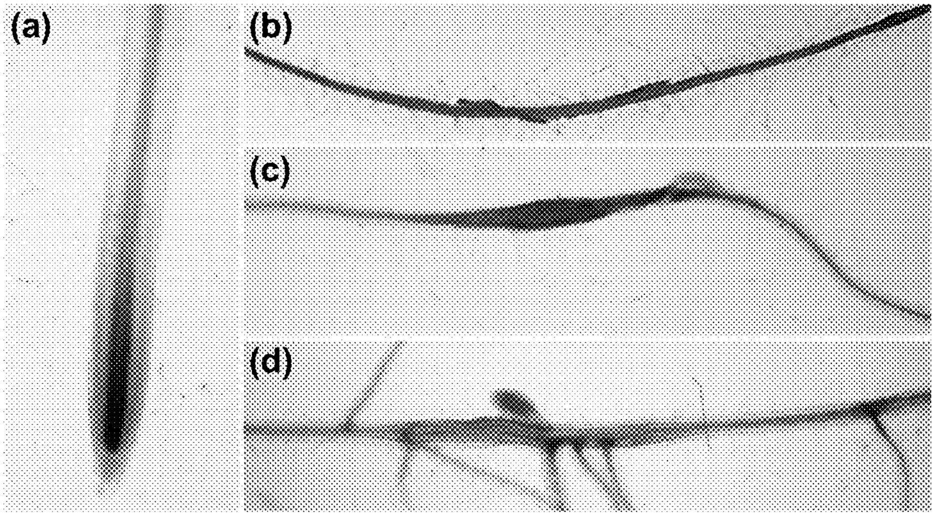
Figure 14:
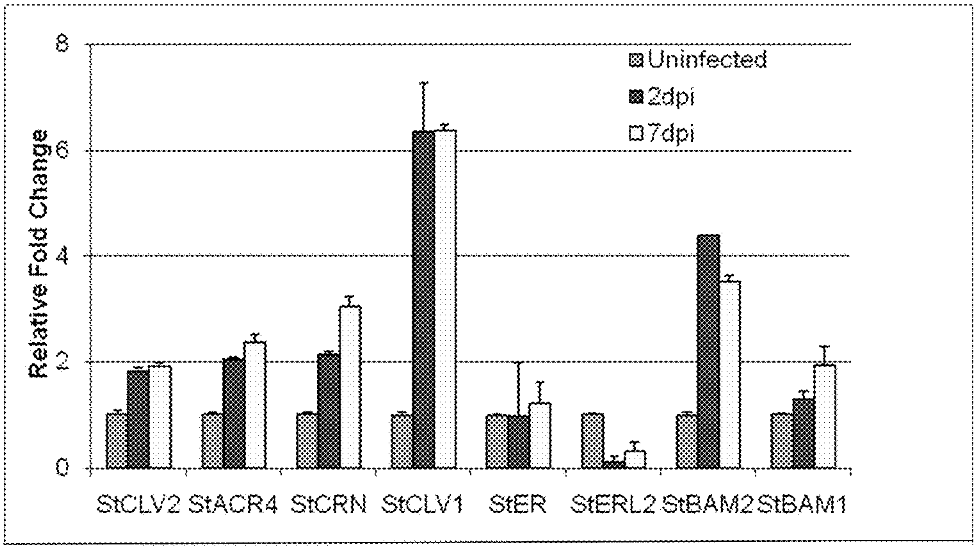

Screening of plant CLE receptor mutants for resistance to nematode CLE peptides, overexpression of the nematode CLEs in the receptor mutant background, and infection assays of plant receptor mutants, has identified several receptors involved in nematode CLE peptide signaling. Plant receptor mutants exhibiting resistance to exogenous treatment of nematode CLE peptides include CLAVATA2 (CLV2; At1g65380), CORYNE (CRN; At5g13290), BARELY ANY MERISTEM (BAM1; At5g65700), and ERECTA-LIKE2 (ERL2; (At5g07180) (FIGS. 8 and 9). Overexpression of nematode CLEs in the clv2 and crn mutant background abolished all phenotypes (Table 2) that are observed when nematode CLEs are overexpressed in wild type plants (Wang et al., 2005; 2010: Lu et al., 2009). Additionally, nematode infection is significantly reduced on several of the receptor mutants including clv1, clv2, and crn (FIG. 10). Expression of receptors in nematode feeding cells was confirmed by infection of transgenic plants containing promoter-reporter fusions (FIGS. 11-13) and upregulation of candidate soybean and potato receptor genes in *H. glycines*-induced syncytia and *G. rostochiensis*-infected potato roots were revealed by microarray analysis of laser-captured syncytia (Table 2, 5% FDR; Ithal et al., 2007) and qRT-PCR analysis (FIG. 14). Thus, the disruption or modulation of the host plant receptor proteins that perceive the nematode CLE peptides can be used to develop a novel management tactic to reduce cyst nematode parasitism in crop plants including, but not limited to potato or soybean. Nematode control can thus be obtained by inhibiting receptor proteins that interact with any nematode CLE peptide. Endogenous plant gene encoding a receptor for a nematode CLE peptide that can be inhibited to provide include functional or structural orthologs of the receptor proteins in any plant species, including but not limited to receptor genes from monocot or dicot plant, or receptor genes selected from the group consisting of a tobacco, cereal, sugar beet, cotton, fruit, fiber, oilseed, potato, rice, corn, soybean, vegetable, and wheat plant.

TABLE 2

| | | T1 Shoot Phenotypes | | | |
|---|---|---|---|---|---|
| Background | Construct | wus (%) | PNC (%) | WT (%) | Total (#) |
| Col-0 | HgCLE2$^{\Delta SP}$ | 78 | 6 | 15 | 80 |
| | HsCLE1 | 30 | 7 | 63 | 156 |
| | HsCLE2 | 6 | 5 | 89 | 158 |
| clv2-1 | HgCLE2$^{\Delta SP}$ | 0 | 0 | 100 | 96 |
| | HsCLE1 | 0 | 0 | 100 | 67 |
| | HsCLE2 | 0 | 0 | 100 | 28 |
| crn-1 | HgCLE2$^{\Delta SP}$ | 0 | 0 | 100 | 85 |
| | HsCLE1 | 0 | 0 | 100 | 41 |
| | HsCLE2 | 0 | 0 | 100 | 37 |

TABLE 3

Putative Soybean Receptors Upregulated in Soybean Cyst Nematode Induced Syncytia (5% FDR, LCM W82)

Sequences corresponding to the genes provided below can be obtained from the world wide web (internet) using the identifiers provided in Table 3 from the following internet locations:
1) "the world wide web at soybase.org" or the world wide web at soybase.org/gbrowse/cgi-bin/gbrowse/gmax1.01/
2) "the world wide web at phytozome.net" or the world wide web at phytozome.net/cgi-bin/gbrowse/soybean/?name=Gm09
3) "the world wide web at plantgdb.org" or the world wide web at plantgdb.org/GmGDB/(Assembly version Glyma1.170 (April 2009)
4) the world wide web at ncbi.nlm.nih.gov/sites/entrez

| Affymetrix Probset | Qvalue | FC dpl 2 | Soybean Gene | Best At Hit | E-value | PFAM Description(30) |
|---|---|---|---|---|---|---|
| Putative Soybean Leucine-Rich Repeat Receptor-Like Kinase (LRR-RLK) Upregulated | | | | | | |
| Gma.1778.1.S1_at | 0.000696 | 11.19428 | Glyma08g16220.1 | AT3G12610.1 | 1E−100 | Leucine Rich Repeat |
| GmaAffx.78459.1.S1_at | 0.000947 | 15.6836 | Glyma18g42700.1 | AT4G08850.1 | 0 | Leucine rich repeat N-terminal domain |
| Gma.17727.3.A1_at | 0.001475 | 1.696212 | Glyma13g37580.1 | AT4G03390.1 | 0 | Leucine rich repeat N-terminal domain |
| Gma.9956.1.S1_at | 0.001606 | 5.057105 | Glyma15g26790.1 | AT5G06860.1 | 1E−100 | Leucine rich repeat N-terminal domain |
| GmaAffx.3809.1_S1_at | 0.001904 | 1.789864 | Glyma18g00610.1 | AT3G23750.1 | 0 | Leucine rich repeat N-terminal domain |
| GmaAffx.50347.1.S1_at | 0.002786 | 26.80867 | Glyma16g06940.1 | AT4G08850.1 | 0 | Leucine rich repeat N-terminal domain |
| GmaAffx.91749.1.S1_s_at | 0.003961 | 12.73998 | Glyma15g26790.1 | AT5G06860.1 | 1E−100 | Leucine rich repeat N-terminal domain |
| GmaAffx.49400.1.S1_at | 0.006842 | 2.043868 | Glyma07g31970.1 | AT1G28340.1 | 0 | Leucine rich repeat N-terminal domain |
| Gma.17727.1.A1_at | 0.007366 | 2.014757 | Glyma13g37580.1 | AT4G03390.1 | 0 | Leucine rich repeat N-terminal domain |
| GmaAffx.47891.1.S1_s_at | 0.007905 | 8.874029 | Glyma19g32700.1 | AT5G06860.1 | 1E−112 | Leucine rich repeat N-terminal domain |
| GmaAffx.68769.1.S1_at | 0.008658 | 4.20926 | Glyma20g25570.1 | AT2G01210.1 | 0 | Leucine rich repeat N-terminal domain |
| GmaAffx.24529.1.S1_at | 0.008905 | 32.2986 | Glyma12g00960.1 | AT4G08850.1 | 0 | Leucine rich repeat N-terminal domain |
| GmaAffx.5435.1.A1_at | 0.009418 | 1.368383 | Glyma09g13540.1 | AT5G51350.1 | 0 | Leucine rich repeat N-terminal domain |
| GmaAffx.65770.1.S1_at | 0.012282 | 1.967988 | Glyma18g06670.1 | AT3G56050.2 | 1E−115 | Leucine Rich Repeat |
| Gma.9483.1.A1_at | 0.016684 | 2.107688 | Glyma19g29370.1 | AT3G03770.1 | 0 | Leucine Rich Repeat |
| Gma.16818.1.S1_s_at | 0.017963 | 2.874609 | Glyma11g04700.1 | AT5G65700.1 (BAM1) | 0 | Leucine rich repeat N-terminal domain |
| GmaAffx.6107.2.A1_at | 0.018015 | 14.17985 | Glyma06g13970.1 | AT3G47570.1 | 0 | Leucine rich repeat N-terminal domain |
| GmaAffx.51790.1.S1_at | 0.023845 | 3.00325 | Glyma17g18520.1 | AT5G67200.1 | 0 | Leucine rich repeat N-terminal domain |
| Gma.405.1.A1_at | 0.026584 | 16.80313 | Glyma11g13970.1 | AT3G20820.1 | 1E−125 | Leucine rich repeat N-terminal domain |
| GmaAffx.24583.1.S1_at | 0.02776 | 1.951831 | Glyma05g29150.1 | AT4G18640.1 | 1E−169 | Leucine rich repeat N-terminal domain |
| Gma.16642.1.S1_at | 0.034358 | 1.219904 | Glyma12g03370.1 | AT1G10850.1 | 0 | Leucine rich repeat N-terminal domain |
| Gma.4557.1.S1_at | 0.040772 | 1.199444 | Glyma08g01640.1 | AT1G63430.1 | 0 | Leucine Rich Repeat |
| Gma.5232.1.A1_at | 0.044053 | 1.576101 | Glyma06g36230.1 | AT5G53890.1 | 0 | Leucine rich repeat N-terminal domain |
| GmaAffx.18359.1.S1_at | 0.047925 | 4.386757 | Glyma03g32270.1 | AT1G35710.1 | 0 | Leucine rich repeat N-terminal domain |
| Gma.2806.1.S1_at | 0.047969 | 1.0518 | Glyma05g29530.1 | AT1G29750.2 | 0 | Leucine Rich Repeat |
| Gma.15907.1.A1_at | 0.048874 | 1.454241 | Glyma18g53970.1 | AT2G33490.1 | 1E−164 | Leucine rich repeat N-terminal domain |
| Other Putative Soybean Receptor-Like Kinases Upregulated | | | | | | |
| Gma.17579.1.S1_at | 0.001029 | 2.926118 | Glyma06g07170.1 | AT4G32300.1 | 0 | D-mannose binding lectin\|Protein kinase |
| Gma.10903.1.A1_at | 0.001984 | 3.921658 | Glyma06g06620.1 | AT5G54590.2 | 1E−101 | Protein kinase domain |
| GmaAffx.15130.1.A1_at | 0.002275 | 8.229938 | Glyma20g27740.1 | AT4G05200.1 | 0 | DUF26\|Protein kinase |
| GmaAffx.46387.1.S1_at | 0.002957 | 1.854171 | Glyma18g12830.1 | AT3G59110.1 | 0 | Protein kinase domain |
| Gma.11892.1.S1_at | 0.003085 | 2.491472 | Glyma18g47170.1 | AT1G01540.2 | 0 | Protein kinase domain |
| Gma.13100.2.A1_at | 0.003827 | 2.576388 | Glyma16g03650.1 | AT1G01540.2 | 0 | Protein kinase domain |
| GmaAffx.4463.1.A1_at | 0.004197 | 50.44552 | Glyma10g39910.1 | AT4G38830.1 | 0 | DUF26\|Protein kinase |
| GmaAffx.8689.1.S1_at | 0.004457 | 6.746447 | Glyma06g02000.1 | AT1G20650.1 | 1E−134 | Protein kinase domain |
| Gma.5637.1.S1_at | 0.005376 | 3.595321 | Glyma10g28610.1 | AT2G47180.1 | 1E−150 | Glycosyl transferase family 8 |
| GmaAffx.37615.1.S1_at | 0.006409 | 3.634731 | Glyma17g06430.1 | AT2G17220.2 | 1E−117 | Protein kinase domain |
| Gma.5416.1.S1_at | 0.00667 | 1.151061 | Glyma09g40650.1 | AT5G01020.1 | 0 | Protein kinase domain |
| GmaAffx.65711.1.S1_at | 0.007597 | 3.149387 | Glyma18g45000.1 | AT3G08600.1 | 5E−87 | Protein of unknown function (DUF1191) |
| Gma.8159.1.S1_at | 0.007785 | 2.089075 | Glyma14g03290.1 | AT3G59110.1 | 0 | Protein kinase domain |
| GmaAffx.83551.1.S1_at | 0.009487 | 36.43414 | Glyma06g41150.1 | AT4G21380.1 | 0 | D-mannose binding lectin\|Protein kinase |
| GmaAffx.22464.1.A1_at | 0.010743 | 2.290479 | Glyma12g16650.1 | AT5G54590.2 | 1E−176 | Protein tyrosine kinase |
| GmaAffx.56567.2.A1_at | 0.010919 | 8.11891 | Glyma10g05990.1 | AT1G16670.1 | 6E−90 | Protein kinase domain |
| GmaAffx.60687.1.S1_at | 0.014387 | 18.28579 | Glyma08g46630.1 | AT1G11300.1 | 1E−140 | D-mannose binding lectin\|PAN-like domain |
| GmaAffx.8293.1.S1_at | 0.015011 | 3.375224 | Glyma08g22770.1 | AT3G15890.1 | 1E−125 | Protein kinase domain |
| GmaAffx.76163.1.S1_at | 0.0178 | 1.444014 | Glyma09g32390.1 | AT3G24550.1 | 0 | Protein tyrosine kinase |
| GmaAffx.87698.1.S1_at | 0.020806 | 2.437942 | Glyma12g11840.1 | AT4G03390.1 | 1E−172 | Protein tyrosine kinase |
| GmaAffx.91247.1.S1_at | 0.024984 | 2.593136 | Glyma15g09490.1 | AT4G18950.1 | 0 | Ankyrin repeat\|Protein kinase domain |
| GmaAffx.10590.1.S1_s_at | 0.026872 | 4.633997 | Glyma06g40480.1 | AT4G27290.1 | 0 | D-mannose binding lectin\|Protein kinase |
| Gma.4931.1.S1_s_at | 0.030153 | 1.894182 | Glyma18g44830.1 | AT3G51550.1 | 0 | Protein tyrosine kinase |
| Gma.7158.1.A1_at | 0.032121 | 2.64156 | Glyma12g08210.1 | AT2G28250.2 | 1E−165 | Protein kinase domain |
| Gma.14610.1.A1_at | 0.039013 | 4.911538 | Glyma20g37470.1 | AT3G05140.1 | 1E−153 | Protein kinase domain |
| Gma.3334.1.S1_at | 0.042026 | 2.355478 | Glyma02g43710.1 | AT2G33580.1 | 1E−179 | LysM domain\|Protein kinase domain |
| GmaAffx.93403.1.S1_at | 0.042465 | 3.481746 | Glyma05g25370.1 | AT5G06870.1 | 7E−77 | Leucine rich repeat N-terminal domain |
| Gma.8195.2.S1_a_at | 0.042848 | 2.222809 | Glyma18g16060.1 | AT2G02800.2 | 1E−171 | Protein kinase domain |
| GmaAffx.4480.1.S1_at | 0.042861 | 6.312541 | Glyma18g06610.1 | AT5G58520.1 | 0 | Protein tyrosine kinase |

TABLE 3-continued

Putative Soybean Receptors Upregulated in Soybean Cyst Nematode Induced Syncytia (5% FDR, LCM W82)
Sequences corresponding to the genes provided below can be obtained from the world wide web (internet) using the identifiers provided in Table 3 from the following internet locations:
1) “the world wide web at soybase.org” or the world wide web at soybase.org/gbrowse/cgi-bin/gbrowse/gmax1.01/
2) “the world wide web at phytozome.net” or the world wide web at phytozome.net/cgi-bin/gbrowse/soybean/?name=Gm09
3) “the world wide web at plantgdb.org” or the world wide web at plantgdb.org/GmGDB/(Assembly version Glyma1.170 (April 2009)
4) the world wide web at ncbi.nlm.nih.gov/sites/entrez

| Affymetrix Probset | Qvalue | FC dpl 2 | Soybean Gene | Best At Hit | E-value | PFAM Description(30) |
|---|---|---|---|---|---|---|
| Gma.8195.2.S1_at | 0.045596 | 11.62797 | Glyma18g16060.1 | AT2G02800.2 | 1E−171 | Protein kinase domain |
| GmaAffx.19954.2.S1_at | 0.045643 | 4.577217 | Glyma10g43060.1 | AT4G38470.1 | 0 | ACT domain\|Protein tyrosine kinase |

REFERENCES

Gao, B. L., Allen, R., Maler, T., Davis, E. L., Baum, T. J., and Hussey, R. S. (2003) The parasitome of the phytonematode *Heterodera glycines*. *Mol. Plant-Microbe Interact*, 16, 720-726.

Ithal N, Recknor J. Nettleton D, Maier T, Baum TJ, Mitchum MG. (2007) Developmental transcript profiling of cyst nematode feeding cells in soybean roots. *Mol. Plant-Microbe Interact*, 20(5): 510-525.

Lu, S. W., Chen, S., Wang, J., Yu, H., Chronis, D., Mitchum, M. G., and Wang, X. (2009) Structural and functional diversity of CLAVATA3/ESR (CLE)-like genes from the potato cyst nematode *Globodera rostochiensis*. *Mol. Plant-Microbe Interact*, 22, 1128-1142.

Mitchum, M. G., Wang, X. and Davis, E. L. (2008) Diverse and conserved roles of CLE peptides. *Curr Opin Plant Biol*, 11, 75-81.

Patel, N., Hamamouch, N., Chunying, L., Hussey, R., Mitchum, M., Baum, T., Wang, X., and Davis, E. L. (2008) Similarity and functional analyses of expressed parasitism genes in *Heterodera schachtii* and *Heterodera glycines*. *J Nematol*, 40, 299-310.

Wang, J., Lee, C., Replogle, A, Joshi, S., Korkin, D., Hussey, R. S., Baum, T. J., Davis, E. L., Wang, X., and Mitchum, M. G. (2010) Dual roles for the variable domain in protein trafficking and host-specific recognition of *Heterodera glycines* CLE effector proteins. *New Phytol*, doi: 10.1111/j.1469-8137.2010.03300.x Wang, J., Replogle, A., Hussey, R. S., Baum, T. J., Wang, X., Davis, E. L., and Mitchum, M. G. (2010) Identification of potential host plant mimics of CLV3/ESR (CLE)-like peptides from the plant-parasitic nematode *Heterodera schachtil*, *Mol. Plant Pathol*. (submitted).

Wang, X. H., Allen, R., Ding, X. F., Goeliner, M., Maier, T., de Boer, J. M., Baum, T. J., Hussey, R. S., Davis, E. L. (2001) Signal peptide-selection of cDNA cloned directly from the esophageal gland cells of the soybean cyst nematode *Heterodera glycines*. *Mol Plant-Microbe Interact*, 14, 536-544.

Example 3

Promoter Sequences Useful in the Practice of the Invention

```
BARELY ANY MERISTEM (BAM1; At5g65700) - promoter sequence;
                                                     SEQ ID NO: 3
tctcattaagcacctacttcccacatctttcttaaagtttcttacataaagctcccttcacacgtgcttaccaaatc

agattgtcaataattcttgctcaataatttttcgaaatttatttgaatttatctaataaaaatacattgtttgagta

tgatattttgcttaagaaggttgattattctccctatcaaagtctaaaaagaagattacaaaacaattgtatggtta

aattcatataaatttgtgactagtattttaatatttacatatatacaaatacttatagatgaaacgagaatgcagaa

atgattatagatagatcagtgacagtgaactgtagcaaccggcaaagaaacctcgttagctggacacacgattacga

tcatgcccccagtctcctctgtccagacggctgcattaataacaacgagctagagggtgttttcgtcttttcgatac

ttatcccaaaaccgacaatctctggtttggactcgaaggctgatttggtcaattcatagcaaccgaacgagcagtcc

attcaagtccaaagagctccttagtggtaaaagatgtaattacgtagatgttccatggtcaagaatgtattcagtca

aaataaatatttgaccaaaactttcggttaatttcctaccaccagcaaaattataacttttttctaataattatcaat

cattttcaatctcttttaattttctttttcacttttttttattaattaaagtcaattcacactatacaaaaagaagg

aagtctaaatattttttttactttcatgttgcttttctaacttttatattttgctcttctcaacagattttgctggtt

tttgtattagaaatattattatgtttccagaaatgaatttttttatatgtcgtctggattcgtatatatatattggaa

agtgaaattaattcatttgattttttttctttgatatatcgaccaaatcaaataaatacgaccccattgtggcattgt

taatgcaaaaaggcacaagtacaaaaaaaaacataataattcactattttatttacagacacatgggcccaattcata

cggcccaattaccataaacctctcttttaaagagtgggttccacagtggtaaactttttgactatccattggaatga

ttgcatctggaccgttcatctacattaattattgggtttttttcgctttaaagcatcaattaacttattacgtatagg

attagattaccaataacgatctttttagcttttgtcgttttccgataaaaccatacgattaagaatatgacctcttg

tatcttttgagggattttagttaatctttctacatttattttgttggatgctcatacaattatcctgtgtctctcaa

aataaaacaaaaattactctatttattagtacattacacatgattatttagaaaatgtatattgtggtcatatgaaa

tgagaaattaaaggaaatttgtcaatacttgagaacatcaccattcaaatgtttcaagaacaacatgactccaaaac

aaaataaatgaacctttccctaataatagtatattctccatcgtacaaagttctaaataatacaatattcatttcgt
```

-continued caaagcatatgatgtgttggaatcagaattatctgcaaatgtttgaatttcaaatgttagtatcaggctatttttac tgttttatcaaatatcgtttcttctgcaatctatcacttgattgttttatcaaatcagcactagtattattgatttt gtaatttgtgtttgtctacctccaattactttttagtgttatgattagtaatgtaataaaatcacaaatctgacgtg gcacctatatacaattccaaaaacaagtggaacgaatataaaacaaattcacaccttcctcatcttcttcttcgtct tcacttaccttctctctacactcacaccatctcacaaccctaatctctcccacacaagagagatagagagaaaca CLAVATA2 (CLV2; At1g65380) - promoter sequence;

SEQ ID NO: 4

CACATACATagacacaaagccctttccattgtcctcttcgtttccttttgggtaaacaaccaatctcctgatttt tacaaaaaaggcaacatttcttagttatatatgcttgtagtgaagaaagatgtgaaagtctgacaagagaacaag acgaaggaggagtctttctccaagtcttcaacattgcagaatctgatgcatatgaacccattttctctacaaaat gttgcaaccctagagagcaaaacaaaacatacccataatcagaaatgatctgacgaaaatcgagttacaatacac aagagaacatttttttagaattctcagatattaaaaatgacacagaaagctttatgctttttcctcttaaaaga ctaaacaagttgaaatctagagaaagaactgaccaacctgagacaacgagagagacttgagagatttcttcggca cttactattagatctagggtttagataccatttatatagagaaagttttagagttgcacaaaacataaattaatg tgttagaatgggcctaaagctacaaagctggcctggttttgttttaaattgttggtttcatggacattttcgaca tcttcgaacatgttatttttgagactatgcaaacttgaagctctttactcgagttgaaatcgtatgacttatag tgaaattgtacatttggtttcgatttttcttttacactctttcttctttgagccggtaaatttggaatttttctt catagtggaatcatatgctgtttttttttttatagtaaacgttacaagaatgaatggtaactttatccaaaaaa aaagaatcatattattttgaaatgattttaagtaaattctaggttcaataacataagatttgagactaaatttaa aatttcttagtaaaatatatgatttttttataaatacctataaaattagtaattaacaatacggattacgtactg aatcaaaccctttgtattttgtttttcctagaaataagtgtagatttttggaattttgcattaattaatcacttc ttgggtctgaaaggctaaaacaaaaggaaccgaaagagaatgttctctctgtctttatcttccacttccacttcc aggtcgcgttgcttcactctccattgcaaagagaggtctctgcgatttctgcaactcacccctgaaaccttctta atttacttcaactgccgctatacctaaaaacttcatctttctcctctgagctATGATAAAG CORYNE (CRN; At5g13290) - promoter sequence;

SEQ ID NO: 5 aaagatgcataggcttgcggacataaaaattccggagctatg tttcatcgttgctttcacggtctgaagagccaatcaacactaaagaaggacctctaatgg tctctagcaagtttagccccccaattaagtattgtattgatgtttttgtgatggatggata taggctgcatattgggaaattatagtgtattgtattgtgtcgtgttgtgtgtatgtggga ctatagcatcctgagtttgtcatgtccagacgttgtaacttgtaagcaattacttatggt tttgttcacttcgtattaacgtatttaatttgtggctcgattttggttttgaatctgtgt caaaactaagataatttacgtgttaaaccaggcccaagtttgaaagttaattgtcaattt tcagaccagagtacatattggtccacttattcccattacattcatagttttgagtctttt gataatagtgttaccatttcaattaggctaatctttttttcaacccaagatatttttataa aaaggaatgtggttcaaatcggaaaacaagacctaactttgaataaaagcactacagcat aaagcttttacctttaacaaaaaaaaatataataatttttttacaaggaaaaagaagagaaa gcaattattctcagacaaacaaaggaaccacttttgtaggtgtagtagtaatctcacacg ctaagacaaaagtgcacaaattctcgagactctcttctatccaacggtccatatctcact aaccgcatctaaataacggacaagatcttcttttggcttcagctctctttagtctttacc ttccctcaagctcggtactcgatgtcttgctttcggccactcatgaaagcaacgagagct tccccttcatccgcctacgtggctatgggacccagtctaaccacgaccacctgacatcg -continued tgggccccactgtaaggcgggaaccccatttttttttggctgtaagtaacggattctcgg tcatgctttttttgtgaggatagagagagagactgagagagagagagagtgtgtcacggtc tcgcagatactgtgtattgaaaagagagttctagagagagagtgtgttatgtgtgtgtgt gtgtgtgtgtgtgtgtgtgtgtgtgtttggttactgggattaattgagctgaaacagttt ggatagttttgtttgttctgtttcatctttcaaccacagatatagtaatattgtgaaaac ccctcattgaagtttgttctctgctctctctttttgggtttagcactgagttttggggtt tatttcgagacatacccatacaaagtttgatacttttgtgtcccccccttatcaagaaaat tgtggggtttttttttttttaataagcttcctttaaattttcaatttttattttggag gaaaagagtgagaatttcagataagaatctatgagccaatgatattctaattcatcttct tcgtgaagatttgagttgaattccatttcctttttgtcttggtggtttctcattggtt ttctcgagaatatttgtggttttgggagaagaggcttcactgtagcattgaaaaagtctt aaacttttctgtgtcttttttatgtaagctttgaacagcttcacctttctgggtttctca gattgtgtctaatcttgaaaaaccttttattcgtagaagcagca Promoters associated with any of the potato genes provided below in Example 4 are also provided herewith. In particular, use of the promoter associated with the StCLV1 gene provided below in any of the methods of this invention is provided.

Example 4

Sequences of Various Candidate Potato Nematode CLE Receptor Genes are Provided Sequences correspond to potato genes analyzed in FIG. 14 and as described in the claims and Example 2. The ATG start codon and TGA stop codon are underlined.

>StCRN cDNA (From clone 4-3:

(SEQ ID NO: 6)

ATCGCATGGTTTCATGGAGCTCCTTGTTTTTTTGTTGGAATTTGATGATTTTCCAATTTGGTTATTATGTTGTTC

ATTGTTGTTGTTGAGTCTATTTTGTGGTGGTGCGGAGGTGTGAGCTTTAAATTGGAGTTGGGGTGATTGTTGTTT

TGTTCGCCGGAGAAGCCATCTCCAGTGAGGTTGGTTGGAGAAGGAGAGAGATGAGGAGAGCAATGAGTAATTTCA

ACTATTAAAGATTCGTTTCAGAAAGAGAAAAAAAGAAGAAAATGGTCACATTGTCGTCCTTGTGTAACATTCAGA

GGAGTGAACCCTAAACTTGCCGACCCACAGAGAAAAACAACCCTAGTTTCC<u>ATG</u>GGGACCTGCTGTAACAGTAGC

ACAGTTCTCAAGCTTTGTTTTTTGTGGCTACAACTAATCTGTGTGCAATGCCATGGAAGGATACTCAAGGATGAT

ACCTCCTCATCTGATCAGTTTAAGAACAGATTTCAAAGGATTTTTCTGAGTATACTTTTTGGTATGTTTACAGGA

TTGATTTGTGCACTTGTTTTTGCTTGGCTTGTTCGGAGTTTTGTTCGTTACATTAACAAAGCCCCAATTCTCAAA

GGCCCTGTTGTATTCTCTCCTAAAATTCCATCCAAAACTCTGCAATCAGCTCTTGCTAATGATACCCAGTTGATA

GGGTCAAGTAGTTCTGGAAAATACTACAGAACTGTTCTTGATAATGGGCTTACTGTTGCAGTTAAGAGAATGGAA

CCTGGTTCTCCACAGTTACATACCAAGTCATTTAAGAGAAGAATACAACACGAACTTGAACTTATTGCTAGTTTG

AGGCATAGGAATTTGATGAGTTTAAGGGCTTATGTTCGTGAATCGAATACGTTCTTTCTGGTTTACGATTATGTA

AACACTGGCAGTCTTGAAGATGTAATGAACAAAGTTAGGGAAAATCAATTGCAACTTACCTGGGAAGTCAGGCTC

CGAATTGCAGTTGGGATTGTTAAGGCTCTTCAGTATCTTCATTTCTCTTGTAACCCCACAGTTTTGCATCGGAAT

TTGAAACCCACAAATGTAATGTTGGATGCTGAGTTTGAGCCTAGGTTGGCTGATTGTGGTTTGGCTAAAATCATT

CCCACTTTAAATCTCCCTGCTGCATCAAACTATGGTCCTCCAGAATCATTCCAGAGTTGCAGCAGGTATACCGAT

AAAAGTGATGTATTTAGCTTTGGGGTTATATTGGGTGTTCTATTAACTGGAAAGTACCCAACAGATCCCTTCTTT

-continued

GGGGATACATCTACTGGAGGAAGTCTAGCACGTTGGCTTCAACGCTTGCAGGAAGCAGGCGATGCTCGAGAAGCA

TTGGATAAGAGTATTCTAGGGGAAGAGGTTGAGGAAGATGAGATGTTAATGGCAGTAAAAATAGCAGCGGTATGC

TTATCAGACATGCCTGCTGATCGACCTTCCAGTGATGAGCTCGTTTCCATGCTCACCCAATTAAATAGCTTCTGA

TTAATTACTTTGGTCGAGAGGGAAAGCAGTCAAGGATTCAAATAATCACAAGATCTTTAAGGTTGTTCTTTTGGC

TTTCTAAGGTGATAGTTTGCTGTGTGCTTTTGGTAGTTGAGCAATGCCTTTTGGTTATCGCAATGAGCACGAGTG

TAGTTGGC

>StBam1

(SEQ ID NO: 7)

TTCTCACTCTCACTGAGTGAATCTGCAAACCAAACAGTTGGTGGGCATTAGATTAAGGAAGGAAAAATGCGTCTT

CTTTTTCTTCTTCTTCTTGTTATGCATTTTACTGACTTTTCCGCCGGTAAACAACCTCGGTTACCGGAATATCAG

GCTTTGCTTGCCCTGAAAACTGCCATTACCGATGACCCACAGTTAACACTTGCCTCATGGAACATCTCCACCAGT

CACTGTACGTGGAATGGTGTCACGTGCGACACGCATCGTCACGTGACCTCTCTTGATATTTCTGGGTTTAATCTT

ACCGGTACTCTTCCGCCGGAAGTTGGGAATCTTCGTTTCTTACAAAATCTGTCTGTTGCTGTTAACCAGTTTACT

GGACCCATTCCTGTTGAAATCTCCTTTATTCCAAATCTCGGTTACCTTAATCTTTCTAATAACATATTCGGGATG

GAATTCCCTCCGCAGTTAACCCGTCTGCGTAACCTCCAAGTCCTTGACCTTTACAACAACAATATGACCGGTGAA

CTTCCCCTTGAGGTGTATCAGATGACTAACCTTCGACATCTACACCTCGGCGGGAACTTTTTCGGTGGCCGCATT

CCTCCGGAGTATGGAAGGTTCCCGTCTCTAGAGTACCTCGCAGTTTCAGGCAATGCACTGGTAGGAGAGATACCA

CCGGAGATTGGAAACATCACTACACTTCAGCAGTTGTATGTAGGATACTACAATACCTTCACCGGTGGGATTCCC

CCGGCAATAGGGAACTTATCGCAGCTCCTCCGGTTTGATGCTGCTAACTGTGGACTTTCGGGGGAGATTCCACCG

GAGATTGGGAAGCTTCAGAACCTTGACACTCTCTTCCTGCAAGTGAATTCTCTGTCTGGGTCATTAACTCCGGAG

ATAGGTTATCTGAAGAGCTTGAAATCTTTGGATCTGTCGAATAACATGTTCTCTGGCGAGATACCGCCAACATTT

GCGGAGCTTAAGAATATCACTCTTGTTAATCTTTTTCGGAATAAGCTTTATGGGTCAATACCAGAGTTCATAGAG

GACTTGCCGGAGCTAGAGGTGTTGCAACTTTGGGAAAATAACTTTACGGGAAGCATTCCACAGGGGTTAGGCACA

AAGAGCAAGCTCAAAAATGTTGATCTCAGTTCCAATAAATTGACTGGAAATTTACCCCCAAACATGTGTTCCGGT

AACAATCTGCAGACAATTATCACTCTAGGGAACTTCTTGTTTGGCCCAATTCCTGAATCTTTGGGTAGGTGTGAA

TCACTTAATCGGATTAGGATGGGAGAGAATTATCTGAATGGGTCAATTCCAAAGGGGCTCTTAAGCTTGCCACGT

CTGTCACAAATTGAACTTCAGAATAATATTCTCACTGGTACATTTCCTGATATTTCTTCCAAATCTAATAGTCTT

GGGCAGATTATCCTTTCAAATAATCGCCTAACTGGACCTTTGCCGCCAAGCATTGGAAACTTTGCTGTAGCCCAA

AAATTGCTTCTTGATGGGAACAAATTTTCGGGACGAATTCCAGCAGAAATAGGAAAGCTTCAACAGCTATCCAAA

ATTGATTTCAGTCACAACAACTTTTCTGGACCCATGGCTCCGGAGATTAGCCAGTGCAAGTTGCTGACTTATGTT

GATCTCAGCAGGAACCAACTTTCGGGTGAGATTCCTTCTGAGATCACAGGTATGAGGATACTCAACTACTTGAAC

TTATCGAGAAACCACTTAGTTGGGAGTATTCCTTCCCCTATTTCTAGTATGCAGAGTTTAACTTCTGTTGATTTC

TCATATAACAACTTTTCTGGTTTAGTTCCTGGAACCGGGCAATTTAGTTATTTCAACTACACCTCATTTCTGGGC

AATCCAGATCTTTGCGGACCCTATTTGGGCCCTTGCAAAGAGGGTGTTGTTGATGGGGTTAGTCAACCTCATCAA

CGAGGAGCCTTATCGCCTTCGATGAAGCTTTTACTTGTTATTGGTTTGCTTGTCTGTTCTATTGTGTTTGCTGTT

GCTGCAATTATAAAGGCCCGATCTTTAAAGAAGGCAAGTGAAGCTCGTGCCTGGAAGCTCACTGCTTTTCAGCGC

CTAGATTTTACTTGTGATGATATTTTGGACAGCTTGAAGGAGGATAACATTATTGGAAAAGGAGGTGCTGGTATA

GTCTACAAGGGGGTAATGCCGAGCGGGGAACATGTAGCAGTTAAGAGGTTGCCAGCTATGAGCAGGGGTTCCTCT

CATGATCATGGGTTCAATGCAGAGATACAGACTCTTGGGAGGATCCGACACAGGCACATTGTTAGATTATTAGGA

TTTTGCTCGAATCATGAGACAAATCTTTTGGTTTATGAGTACATGCCTAATGGAAGTCTTGGGGAAATGCTTCAT

GGCAAGAAAGGCGGTCATCTACATTGGGATACCAGGTATAAGATAGCCGTGGAGTCTGCAAAGGGTCTTTGCTAT

-continued

CTCCATCACGATTGCTCTCCTTTGATCCTCCATCGTGATGTGAAATCAAACAACATTCTGCTAGACTCCAGCTTT

GAAGCTCATGTTGCTGATTTTGGACTTGCTAAATTCTTGCAAGATTCAGGGACATCAGAATGCATGTCTGCTATT

GCTGGTTCTTATGGGTACATTGCTCCAGAATATGCTTACACGCTTAAGGTTGATGAGAAAAGTGATGTATATAGC

TTCGGTGTGGTGCTATTAGAACTGGTAAGTGGCAAAAAGCCAGTTGGAGAATTTGGTGATGGTGTTGACATAGTC

CAATGGGTTAGGAAAATGACTGATGGGAAAAAGGATGGAGTTCTCAAGATCCTTGACCCAAGACTCTCAACGGTT

CCCCTTAATGAGGTGATGCATGTCTTCTATGTCGCATTGTTGTGTGTTGAAGAGCAGGCTGTGGAACGCCCCACC

ATGCGA

> StBam2 (from clone 6-4;)

(SEQ ID NO: 8)

CCACCATTGAAGAAACATGCGTTTTCTTCTCCTCTTCTTCCTTTCCCTTATTCTCCATTTCCATCTCCTCCACTT

CACCACCGCAAAACCACCTTACGTGCCAGAATACCGGGCATTACTCTCCCTGAAAACTGCCATTACCGATGACCC

ACAATCTGCTCTTCTTTCATGGAATATCTCAACAAGTCATTGTACATGGAGAGGTGTCACGTGCGACCGGTATCG

TCACGTGACTTCTCTCGACATCTCTGGTTTTAATCTCACCGGTACTCTCACGCCGGAAGTTGGTCATCTCCGTTT

TTTGCTCAATCTTTCTGTAGCTGTTAACCAGTTCTCTGGACCCATTCCTATAGAGCTCTCGTTTATACCAAATCT

GAGTTACCTTAACCTCTCTAACAACATTTTCAATTTGAGTTTCCCTCCCCAGCTTACCCATCTCCGGTACTTGAA

AGTTCTCGATATTTATAATAACAATATGACCGGTGACCTTCCGGTTGGGGTTTACAATTTGACTAATCTTCGACA

TCTTCATTTGGGTGGCAATTTTTTTAGTGGCAGTATTCCACCGGAGTATGGTAGATTCCCATTCCTAGAATACCT

TGCAGTTTCTGGAAATGCGCTCGTCGGTATGATACCACCGGAGATCGGAAATATTACCACACTTCGTGAGCTTTA

CATTGGATACTACAACACGTTTTCCGGTGGGTTACCGGCGGAAATAGGGAACTTGTCGGAGCTCATTCGGTTAGA

TGCTGCAAACTGTGGACTTTCCGGTGGGATTCCGCCGGAGATAGGGAAGCTTCAGAAATTAGATACACTGTTCTT

GCAAGTGAATGGTCTTTCTGGGTCTGTTACACCGGAATTGGGGAATTTAAAAAGCTTGAAATCTTTAGATCTATC

AAACAATATGCTCTCCGGTGAAATACCGTTCACATTCACAGAGCTGAAGAATCTAACTCTGCTAAATCTTTTCCG

TAACAAGCTTTACGGGTCGATACCGGAGTTCATAGAAAATTTGCCGAAACTGGAAGTATTGCAGCTTTGGGAAAA

CAACTTTACCGGAAGTATTCCACAAGGTTTAGGCAAAAACAGTAAGTTAACAAACGTTGACATCAGTACCGACAA

ATTAACCGGAAATTTGCCCCCAAACATGTGTTCCGGCAACAAGTTACAGACGTTGATCACTCTTGGAAACTTCTT

GTTTGGCCCAATTCCAGAATCTTTAGGTGAGTGTCAATCACTTAATAGGATTAGAATGGGAGAAAATTTTCTAAA

TGGGTCTATTCCAAAAGGGCTATTCAGTTTGCCCAAGCTTTCACAAGTAGAACTTCAAGATAATCTTCTCACTGG

TACATTTCCAGTGACTGGTTCTGTTTCATCAAGTCTTGGACAGATTTGTCTGTCGAATAATCGTTTCACGGGGCC

TTTGCCATCGAGCATTGGAAATTTGACTGGTGTTCAAAAGTTGCTTCTTGATGGGAACAAGTTTTCTGGTCAAAT

TCCAGCTGAATTAGGGAAATTGCAGCAGCTGTCGAAAATGGATTTTAGTGGTAACAGTTTTTCAGGCCTGATTCC

ACCGGAGATAAGCCAGTGCAAGGCTTTAACTTATGTTGATCTTAGTAGGAATAAGCTATCTGGTGAAGTTCCTAC

TGAGATCACTGGTATGAGGATACTGAATTACTTGAATGTATCGCGGAATCAGTTAGTTGGGAGTATTCCTGCACC

TATTGCAGCAATGCAGAGTTTAACCTCGGTTGATTTTTCGTATAACAACTTATCTGGATTGGTTCCGGGTACTGG

TCAGTTCAGTTACTTCAATTACACATCATTTATTGGTAATCCAGATCTTTGCGGACCCTATTTGGGTCCTTGCAA

AGAAGGTATTGTTGATGGGGTTAGTCGACCTCATGAGAGAGGTGCATTTTCGCCTTCTATGAAGCTTTTACTTGT

TATCGGGTTGCTTGTTTGCTCGATTGTGTTTGCTATCGCTGCAATTATTAAGGCTAGATCGTTAAAGAAGGCGAG

TCAGGCTCGTGCCTGGAAGCTTACTGCTTTCCAACGCCTGGATTTCACTTGTGATGATGTATTGGAATGTTTGAA

AGAGGATAACATTATTGGTAAAGGAGGTGCTGGAATAGTATACAAGGGGGTAATGCCAAATGGTGAACTTGTTGC

TGTTAAAAGGTTGCCGGTTATGAGCCGTGGTTCTTCCCATGATCACGGGTTTAATGCCGAGATACAGACACTTGG

GAGTATTCGACATAGACATATTGTTAGATTATTAGGATTTTGCTCAAATCATGAAACAAATCTTTTGGTTTATGA

GTACATGCCTAATGGGAGCCTTGGTGAAATGCTTCATGGAAAGAAAGGAGGTCACTTGCATTGGGATACCAGGCA

TAAGATAGCATTGGAGGCTGCAAAGGGACTTTGTTATCTTCATCACGATTGCTCGCCTTTGATCCTCCATCGTGA

-continued

```
TGTAAAATCAAACAACATTCTTCTGGATTCCAGCTTCGAAGCTCACGTTGCTGATTTTGGGCTTGCCAAGTTTTT
GCAAGACTCGGGAACATCAGAATGCATGTCTGCAATTGCTGGTTCTTATGGCTACATTGCACCAGAATATGCATA
CACACTCAAGGTAGATGAGAAGAGTGATGTATACAGCTTTGGTGTGGTTCTGTTAGAATTGGTGAGCGGGAAAAA
GCCAGTTGGGGAATTTGGTGATGGCGTTGACATAGTCCAATGGGTAAGGAGGATGACCGATGGGAAAAAAGAAGG
AGTTCTAAAGATCCTTGATCCAAGACTCTCAACAGTTCCCCTTCATGAGGTGATGCATGTGTTCTATGTTGCAAT
GCTGTGTGTCGAAGAGCAAGCTGTTGAACGCCCCAAAATGCGTGAGGTTGTGCAAATGCTAACTGAGCTTCCCAA
GCCATCTGGTCCAAAAACAGAAGATTCAACAATCACCGAGTCGCCCCCATCATCAGGTCCTGCATTAGAGTCTCC
CACTTCGACTCCCGGAGACACGAAAGACCAGTACCACCATCAGCCATCACCTCAATCTCCTCCACCTGACCTACT
CAGCATATGACCTACAATGTTCCCTTCTAATAGAGGATG
```

>StER (From 8-16;
(SEQ ID NO: 9)

```
GTCGGTAAGTCCAAGAACTGGTTTTTCAATTCAAAGGAGCTGAGTTAGTGTAAACACTTTTGGTTTTGAGTTTTG
ACAGAGACTTGAGTCTCAGAGAAACTACCATGGCATCATTTTTACTTCAAAGATGTAATCTTTTCTTTGAGGTTC
TTCTTCTTTTGGGGTTCTTGATTTTCTTCAGCTTTGGTTCTGTGGTGTCTGATGATGGTTCTGCATTGTTGGAGA
TTAAGAAGTCAATTAGGGACATGGAGAATGTGTTGTATGACTGGACTGATTCTCCTTCATCTGATTACTGTGCCT
GGAGAGGTGTTACCTGTGATAATGTCACCTTCAATGTTGTTCAACTTAATCTTTCGAGTTTAAATCTTGATGGGG
AGTTGTCTCCTGCAATTGGACAGCTCAAAGGCCTTATATCTATTGATGTTAGGGGAAATCGCCTTTCTGGCCAGA
TACCAGATGAGATTGGTGACTGTTCAGCACTGAAAAACTTGGACCTATCCTTCAATGAGCTTTATGGTGATATTC
CGTTTTCCATATCAAAACTTAAGCAACTGGAATATCTGATTATAAAGAACAATCAGTTGATTGGACCAATTCCAT
CGACATTGTCACAGATCCCCAACTTGAAGGTCTTGGACCTGGCTCAAAATAGGTTAAGTGGAGAAATTCCTAGGC
TGATATACTGGAATGGAGTCCTGCAGTATTTGGGACTGCGTGGCAACAACTTGGGTGGATCACTTTCTCCTGATA
TGTGTCAGCTCACCGGCCTGTGGTACTTTGATGTTCGGAACAATAGTTTGACTGGTTCCATTCCTCAAAATATTG
GCAACTGTACTGCTTTCCAGGTTCTAGATTTGTCTTATAATGACTTGACTGGAGAGATTCCTTTCAACATTGGTT
TCCTGCAAGTAGCGACCTTGTCTTTGCAAGGTAATCGCCTTTCAGGGCAGATCCCTTCTGTCATTGGATTGATGC
AAGCTCTTGCAGTTTTGGACTTGAGCTGCAATATGTTGAGTGGAACAATTCCTTCAATTCTTGGGAATTTGACTT
ACACAGAAAAATTGTATCTACATGGGAACAAGCTATCTGGTTCCATTCCTCCAGAGCTGGGAAATATGACAAAGC
TTCACTACTTAGAATTGAATGATAACCAACTTACTGGACGCATACCACCAGAACTTGGAAAGCTGACGGAGTTGT
TTGACTTAAATGCTGCAAACAACCACCTTGATGGGCCCATTCCTTCCAATCTTAGCTCATGTACCAATTTGAATA
GTCTCAACGTTCATGGAAACAAATTGAATGGTACGATTCCACCTGCTTTTCAAAAGCTGGAAAGTATGACCTATC
TTAATCTCTCCTCCAACAACCTCAAAGGCCCAATTCCAATTGAGCTTTCTCGTATTGGGAATGTAGATACACTGG
ACTTGTCAAACAACAGGATCAGTGGTCCTATACCTTTGTCCCTCGGTGATTTGGAACATCTTCTTAAACTGAACT
TGAGCAAGAACGAAATAAATGGAAACTTGCCAGCTAAATTTGGCAATTTAAGGAGCATCATGGAGATTGATCTGT
CAAGCAATCACCTCTCTGGTCCCTTGCCTCAGGAACTTGGTCAGCTTCCAAATCTGTACTTGCTGAAACTGGAAA
ACAACAATTTATCAGGCGATGTGATGTCCTTAGCCAGTTGTCTCAGTCTAAATGTCCTAAATGTCTCGTACAATA
ATCTGGGAGGGAATATTCCAACAGGCAATAATTTCTCTAGATTTTCACCAGACAGCTTCATAGGAAATCCAGATC
TGTGTGGGTATTGGCTCACTTCTCCTTGTCATGCATCTCATCCAGCAGAGCGAGTTTCAATTTCTAAAGCTGCTA
TACTTGGTATTGCTCTGGGTGGCTCGGTGATTCTTCTGATGATACTAGTAGCAGCATGCCGGCCACAGAATCCTG
CACCTTTCATGGAAGGATCTATTGATAAACCAGTTTATTACTCATCTCCAAAGCTTGTGATCCTTCATATGAACA
TGGCACTTCATGTTTACGAGGACATTATGAGGATGACTGAGAACTTGAGTGAGAAGTATATAATTGGTTGTGGAG
CATCAAGTACGGTATATAAATGTGTTTTGAAAAATTGCAAGCCTGTAGCTATCAAGAAATTGTACTCTCACAACC
CGCAATACTTGAAGGAATTTGAGACTGAACTTGAGACAGTTGGGAGTATTAAGCATCGTAATCTTGTCTGCCTCC
```

-continued

AAGGATATTCTCTTTCTCCATCTGGCCATCTTCTTTTCTATGACTACATGGAAAATGGTAGCCTTTGGGATTTGC

TTCATGGTCCTACAACAAAGAAGAAAAAGCTTGATTGGGTTACTCGCCTTCGAATTGCATTGGGATCAGCTCAAG

GGCTTGCATATCTTCACCATGATTGTAGCCCTCGAATTATCCACCGTGATGTTAAATCATCAAATATCTTGTTGG

ACAAAGACTTTGAGGCTCATCTGACTGATTTTGGCATTGCCAAAAGCTTATGCATATCAAAGACCTATACGTCCA

CATACATTATGGGAACCATTGGTTACATTGATCCAGAGTATGCTCGCACTTCTCGCTTGACAGAGAAGTCTGATG

TTTACAGCTATGGAATTGTTCTATTGGAATTGCTCACTGGAAGGAAAGCTGTAGATAATGAGTCTAATCTACACC

ATATGATTCTAACTAAGGTAGCAAACAATGCTGTAATGGAAACAGTGGATCCTGAGATCACAGGCACATGCAAAG

ATCTTGCAGATGTGAAGAAGGTTTTTCAGCTTGCCCTTCTATGTTCCAAAAGACAGCCTGCTGAGAGACCAACAA

TGCATGAAGTGGCAAGAGTACTTGAAAGCCTAATACCCGTCACTGAAATGAAACAGCCAAATCCAACGCTCTCAC

TTGCATTACTTCCATCTGCTAAGGTACCTTGTTACATGGATGAATATGTCAACCTCAAGACACCCCATCTAGTGA

ATTGTTCATCCATGAGCATTTCAGATGCTCAACTTTTCCTGAAGTTTGGAGAGGTCATATCCCAGAATAGTGGCT

GAAAATAACATGAGTAGATTTCTTGGGATTGTGTAAAAAAATGTAGTGCCATTATAATATTATTATTGTAGGTAG

TTGTTGTAAGATGATGCATGCAATAGTGGTCCAGTCTACTTTTTCCACTACATAGGTCTAGTGTGTGTAAAAATA

TTTCACTTTTTACCATGATGAAATTGGAAGAGGTAGCACTTGGTAGAGTATTGTAATATTGGTTTTTGGGACTGA

TGCTGAGTATGGACTATACTGTCTGTAGGATTTTTGGCACACACTTTGAGGTGGCCTTAGCA

>StCLV1 (From clv1 clone 11-1 041710;

(SEQ ID NO: 10)

AGACTAAACTAACAGTGTAATAATGTCACTCCCCAAAAAAATATCCCTTTTCCTCCAAATTTTCATTTTTTTGT

TTTCTCCATTAATGCAAACTCTGATCTTGAAACCCTTTTGAAGCTCAAAGAATCCATGGTTGCTCCTGGAACTTC

TGCACTTCTTGATTGGAACAACAACACAAATTACCCTTTTTCCCATTGTTCTTTTTCTGGTGTTACATGTAACAA

TAACCCTCATGTTATATCTATAAACATCACTAATGTTCCTCTATTTGGTACTATTCCACCTGAAATTGGTCTTTT

ACAAAATCTTGAAAATCTTATTATTTTTGGTGATAATATTACTGGTACACTCCCTTTAGAAATGTCACAACTTTC

TTCTATTAAACATGTTAATCTTTCTTACAACAACTTTTCTGGTCCTTTTCCTAGAGAAATCTTGTTGGGGTTAAT

AAAGCTTGAATCTTTTGACATTTATAACAACAATTTCACTGGTGAACTTCCTACTGAGTTTGTAAAGTTGAAAAA

GTTGGAAACTTTACATCTTGGTGGAAACTATTTTCATGGTGAAATACCAGAAGTTTATTCTCATATTGTAAGTTT

AAAGTGGTTGGGTTTAGAGGGAAATTCACTAACTGGGAAAATACCAAAGAGTTTGGTTTTGTTACCAAATCTTGA

AGAACTTAGATTGGGCTATTATAATAGTTATGAAGGGGGTATTCCATCTGAGTTTGGTAATATTAGTACACTTAA

ACTTCTTGATCTTGGAAATTGTAATCTTGATGGTGAAGTTCCTCCAAGTCTTGGAAATTTGAAGAAGTTGCATAC

TTTGTTTCTACAAGTGAACAGACTTACAGGTCGCATACCTTCTGAACTATCTGGTTTAGAGAGTTTGATGTCGTT

TGATTTGTCTTTTAATCAACTGACCGGAGAAATACCAGAGAGTTTTGTGAAGTTGCAGAATTTGACATTGATTAA

CTTGTTTAGAAACAACTTGCATGGTCCAATTCCCCCTTTTATTGGTGACCTTCCAAATCTTGAAGTGTTGCAGAT

TTGGGGAAACAATTTTACTCTTGAATTGCCCGAAAATCTTGGGCGTAACGGGAGGTTTTTGTTTCTTGATATTTC

TATTAATCATTTTACTGGAAGGATACCACCTGATTTGTGTAGAGGAGGGAAGTTAAAGACACTGATTCTAATGGA

AAATTACTTCTTTGGTCCAATTCCTGAACAACTTGGTGAGTGCAAATCGCTTGCTCGAATTCGCGTTAGGAAGAA

TTACTTAAATGGTACTATTCCAGCTGGTTTTTTCAAGTTACCTGCATTGGATATGCTTGAACTTGACAACAACTA

TTTCACTGGTGAGCTGCCAACGGAGATAAACGCGAATAATCTCACTAAACTTGTACTTTCCAACAACTGGATCAC

GGGGAACATTCCTCCATCATTAGGGAACTTGAAGAATCTAGTCACTCTATCACTTGATATGAACAGGTTATCTGG

TGAAATTCCTCAAGAAATTGCGAGTTTGAATAAACTCGTGACCATCAACTTGAGTGGCAACAATTTAACAGGTGA

AATCCCAAGTTCAATTGCGCTTTGTTCAGAGCTAACATTGGTTGACTTGAGCAGAAACCAACTGGTTGGTGAAGT

GCCAAAAGAAATCACCAAGTTAAATAGCTTGAACGCTCTGAACTTGTCAAGAAACCAACTGAGTGGCGCCATTCC

TGGAGAAGTCGGAGTGATGAATGGCTTGACAGTTTTAGATCTTTCTTACAATGATCTTTCTGGAAGGAGACCGAC

CAACGGACAACTAAAGTTCTTCAATGACACTTATTTTGTAGGAAATCCAAAACTCTGTTCACCTCATGCTACTTT

-continued

TTGCCCGTCAGCCTCCAATTCACCACAAAACGCGCTCAAAATCCATGCTGGGAAGTTCACAACTATCCAATTGGT

GATTACAATAATCATCTTAGTCACTGTTGCATTGCTGTTGGCAGTTACCGTGTTGTTCATCAAGAAGGAAAAGTT

CAAGAATTCGAAACTTTGGAAGTTAACAGCATTCCAGAAACTTGATTTCAGAGCTGAGGATGTTTTGGAGTGTTT

AAAAGAGGAGAACATAATTGGGAAAGGTGGAGCTGGCGTTGTGTACCGAGGGTCTATGTCAAATGGCATCGACGT

TGCAATTAAGAAACTTGTAGGCCGAGGAACTGGACACCATGATCATGGATTCTCAGCTGAAATCCAAACACTAGG

AAGGATCAGGCACAGAAACATCGTACGATTACTAGGATATGTCTCAAACAAAGACACAAACTTGTTGTTGTACGA

ATACGTGTCGAATGGGAGCTTAGGTGAAATGTTACATGGTGCCAAAGGAGCACATTTGAAATGGGAGACGAGGTA

CCGTATTGCTGTGGAAGCTGCAAAGGGATTGTGTTATTTGCACCATGATTGTTCGCCTTCGATTATTCATAGAGA

TGTCAAGTCCAATAATATTCCGCTGGATTCCGATTACGAGGCTCATGTTGCTGATTTTGGCCTAGCCAAATTCTT

GCAGGATGCTGGTGCATCAGAGTGCATGTCCTCTATTGCTGGCTCATATGGTTACATTGCTCCAGAGTATGCATA

CACATTGAAAGTTGACCAAAAGAGTGATGTATACAGTTTTGGAGTTGTACTGTTGGAACTTATCACAGGTCACAA

GCCAGTTGGTGAATTCGGGGACGGTGTAGATATAGTCAGATGGGTAAATAAAACAATGTCCGAATTATCTCAGCC

GTCTGATGCAGCCTCAGTTTTAGCAGTCGTTGACTCGAGGCTACATAGTTACCCTCTTGCAAGTGTTGTAAATTT

GTTCAAGATTGCTATAATGTGTGTTGAAGAAGAGAGTTGTGCTAGGCCTACTATGAGGGAAGTTGTTCACATGCT

TACAAATCTTCCTCAGTCTACTACTACTACTACTACTACTCTCCTTGCCCTTTGAAATTGCACCGATATCAAGTG

TCTGGTTGAAAACTCGTGGAGTTTGAGGCCGGGAACACGAGTCTCATGAGTCTATTTGGGTACGGGGAACAA

>StCLV2 (From clv2-7;

(SEQ ID NO: 11)

ATGGCAGAATCAGTTCTTGAACCTTGTACAACCTCTTATTCCTTCAAAGTTTCAATCTTTATCCTATTCTTCTTG

ATTTTCCCTTTCTTGAACCCATTTTCATCTGCATTTCCTCTTTCTTTTGATACTAATGCAACTGAGGCTGTCAAT

CTTGAAACAGAAGAGGACATGGGTTTGCTTTTGTTCTTCAAGTTACAGTTTCGAGAAACCCCTTTACCAAGCTGG

GATGTCAATGTTCCTCTATCAAACTGGACTGGTGTTACCCGGTCTAACCAGACCGGACGGGTCACTGGACTTAAC

CTCACAAGGTTTAACTTGTCAGGACAGGTTCATCCTTGTTTGTGTAATCTTACTTTTCTTGAAACCCTTGTGTTG

TCTCATAATAGCTTTAACAATTCAATACCTTCTTGTTTATGGAAGTTGTGGAGCCTTAAGACCTTAGATCTTAGC

TATAATATGCTTACTCTTCTTATTCCTAGTACATTTGCAACAACTATGAGTAAGTTAATTGAGCTTGACCTTAGT

CATAACATGTTGAGTGATGAAATCCCAATGTGGATAGGGAATGTCTCAATGTCACTTGAAAAACTTAACTTAGGG

TTTAATAGTTTTCATGGGGATATACCTAAGAGCTTGTTGAATTTGATGTCTTTGAAGTATCTTGACTTGTCTCAC

AATAGTTTGATGGGAAATGTGGGTGATTTTAACCAAGAATTGGTCTCACTTAATCTTGAGTCTAATTTATTATCG

GGTACTTTGCCTTGTTTATATTCGTCAAGGGAATCACTTACACTTCTTAATTTAGCAAACAATTCGATTCTTGGA

GGTATACCAACGTGTATCTCGAGTCTTGGGGGTTTGACACAGCTCAACTTGTCACGTAATGAATTACGATATGGT

ATCTCGCCTAGACTGGTTTTTTCAGAGAGGTTATGTTTGTTGGACTTGAGTTATAATGAGCTATCAGGGAAGATT

CCAAGTAGGATTGTTGAGGCATCGGACAAGTCTGGACTTCTACTTCTTGACCTGTCTCACAATCAGTTCTCTGGT

AATATTCCTGTAACGATAACAGAATTGAAGAGCTTGCAAGCATTGTTTCTGTCTTATAATCTTCTTGTGGGCGAA

ATACCAGAAAGGATTGGTAATTTGACCTATCTACAGGTGATTGATCTCTCACATAACTTCCTCACCGGCTCGATT

CCTTTGAACATCGTAGGATGTTTCCAACTACTGGTGCTGATACTAAACAGTAATAATCTTTCTGGGGAAATTCAG

CCAGTGCTTGATGCGTTGGATAGTCTTAAGATATTTGATATAGGAAACAACAAGATTTCTGGTGAGATCCCACTG

ACATTGGCAGGCTGCAAGTCGTTGGAAGTTGTTGACTTGAGCTCTAACAATCTCTCAGGGTCTCTAAATGGTGCA

ATAACCAAATGGTCGAACCTCAAATTCCTCTCCCTTGCTCGGAACAAGTTCAGTGGATCTCTGCCAAGTTGGTTG

TTTACATTTCAGGCTATTCATACTCTGGATTTTTCTGGAAACAAGTTCTCGGGATATATACCAGATGGTAACTTT

AACACTAGTCCAAATTTCTACAACGGCGACATTAGGAAAACCATTCCTGCAGTACCATCAATTTCAGCTCGAAGC

CTGGATATCAAACTTTCACTCATTGCTGATGAAACTAGTTTGAGCTTCAACTATAACCTGACAACCACAATTGGA

-continued

ATTGATCTGTCTGACAATTTGCTTCATGGTGAAATTCCAGAGGGTCTGTTCGGATTACATGGTTTGGAGTACCTT

AATTTGTCATACAATTTTCTTAATGGTCCAGTTCCAGGGAGTTTAGGGAAGTTGCAGAAGCTAAAAGCACTTGAT

TTATCACATAATTCTTTATCTGGCCACATCCCTGAAAACATTACTGTCCTCAGAAATTTGACAGTTTTAAATCTG

TCTTATAATTGTTTCTCTGGTGTTATTCCGACAAAGCGAGGTTATTGGAAATTTCCTGGAGCATTTGCTGGGAAT

CCAGACTTATGTATGGAATCATCTGGTAATGTCTGTCAAAGAACTTTGCCTGTAGAGCCAGGGAAGAAATTTGAA

GAGGAAATGGAAGAGGGACCATTATCAGTTTGGATTTTCTGTATAAGTGCTTTAGTTAGCTTCTATGTTGGCATT

GTTGTTTTATTTTGTTCATCTCGAACAAGAAGCTGTATTCTGCAAACAAAAAGTTTAGCAGGTTGA

>StACR4 (From ACR4-3;)

SEQ ID NO: 12

ATGTCTTCAATTGCTATTTCATATGGTGAATATGGTTCTGTTTTTTGTGGGTTGAAGTCAGATGGATCTCATTTG

GTCAGCTGCTATGGCTCTACTTCTTCTATAATATATTCAACTCCAGCTCATTTCCCTTTTATTGGTCTTACTGCT

GGAAATGGCTTTGTATGTGGACTTTTGATGGATTCTTACCAGCCTTATTGTTGGGGGAAAAGTAATTTTGTACAA

ATGGGAGTGCCTCAGCCTATGATCAAAGGGTCTCAATACTTGGAAATATCTGCAGGTGAAAATCATTTGTGTGGA

CTAAGGCAACCTTTAATGGGGAAGCATAGGAACACTTCACTTGTTGATTGCTGGGGTTATAACATGACCACAAAT

AATGAGTTTGAAGGTCAGATCCACTCTATTTCAGCTGGTTCTGAGTTTAATTGTGCTTTGTTTTCTGTCAATAAA

AGTGTTTTATGTTGGGGGGATGAAACTAGTAGCCAGGTTATTACCCTAGCACCAAAAGATTTGAGATTTATTAAG

ATTGCAGCTGGGGGATATCATGTTTGTGGGATCCTAGAAGGGGTGAATTCTCAAGTGTATTGCTGGGGAAGGAGC

ATGAACCTTGAAGAAGAATTCTCTGTTGCTCAACTCAATGTTGAATTGGCAGCCCCTAGTGATCCAATTATATCT

GTTGTTGGTGGTAAGTTTCATGCTTGTGGGATTAGGAGCTATGACCGTCATGTCGTTTGCTGGGGTTACAGAGTT

GAGAAAAGCACACCACCTCCTAGTGGAGTTAGGCTTTATGAGATAGCAGCTGGTGACTACTTCACTTGTGGTATC

CTTGCGGAAATTTCACTTTTGCCTGTTTGTTGGGGGTTTGGTTTTCCCTCATCGCTACCACTCGCTGTTTCTCCT

GGAGTCTGCAAGCCTAGACCCTGTGCATCTGGCTTCTATGAGTTTAACAACGGAAGTGCAACTTGCAAGTCTCCT

GATTCTCGCATTTGCCTTCCCTGCACCAATGGCTGCCCCTGCTGAAATGTATCAACAGGTTCAATGCACTTCATCT

ACGGACAGTCAGTGCACGTATAATTGTTCAAGTTGTACCTCTGTTGACTGCCTAAACAGCTGTTCTACTGCTATT

TCTGGGAAGAAGAACGCTAAATTTTGGTCACTCCAGTTACCAGTAATTGTTGCTGAGGTTGCATTTGCAGTATTC

TTGGTGAGTGTTGTATCTCTAACTTCGATCGTATATGTTCGCTACAAATTAAGGAACTGTAGATGTTCAGGGAAA

GGTCCTAGTCCTAGGAAGAATGGTACTTTCCCAAAGGAAATTGCTAAAGATAGGGCTGATTTGGATGATCTTAAA

ATAAGGAGAGCTCAGATGTTTACTTATGAAGATCTTGAGAGAGCAACTGAGGGATTCAAAGAAGAATCACAAGTT

GGAAAGGGTAGCTTTTCGTGTGTTTTCAAGGGCGTTTTGAAGGACGGTACTGTGGTTGCTGTCAAGAGGGCTATA

ATGTCATCTGACATGAAGAAGAATTCAAAGGAGTTCCACAATGAGCTAGACTTGCTGTCCAGGTTGAATCATGCT

CATTTGCTCAATTTGCTAGGTTATTGTGAAGAAGGTGGAGAGAGACTTCTAGTTTATGAGTACATGGCTAATGAC

TCGTTGCATGAACATCTACATGGGAAAAAGAAGGAGCAATTGGATTGGATAAGAAGGGTAACCATTGCAGTCCAA

GCTGCTCGGGGAATCGAATATTTGCATGGTTATGCATGTCCACCTGTGATTCACAGAGACATCAAGTCCTCAAAC

ATCCTTATAGATGAAGAACACAATGCTCGAGTAGCTGATTTTGGGCTTTCCTTGCTTGGACCTGCTAATAGCAGT

TCCCCATTAGCTGAGTTACCAGCAGGGACACTTGGGTACCTTGATCCCGAGTACTACAGACTACATTATCTTACA

ACCAAATCTGATGTCTATAGCTTTGGTGTTTTGCTTTTGGAAATTCTCAGTGGTCGGAAAGCTATTGACATGCAA

TACGATGAAGGGAACATAGTGGAATGGGCAGTCCCATTAATCAAAGCTGGTGAAATAGAGGCAATACTGGATCCA

GTTTTGAAATCACCTTCTGATGCTGAAGCTCTTAGAAGAATCGCTAATATAGCCAGCAAATGCGTGAGGATGAGA

GGGAAAGAGAGGCCGTCAATGGATAAAGTAACAACAGCTTTGGAGAGAGCACTTGCTCAATTGATGGGTAGTCCA

AGCAATGACCAGCCTATCTTGCCAACAGAGGTTGTTCTAGGAAGCAGCAGAATGCACAAGAAGTCCTCATCAAAT

CGATCAACATCAGAAACAACAGATGTTGCAGAAACTGAGGATCAGTGGTATGTCGAATTCAGAGCTCCTTCGTGG

ATTACATTCCCAAGTGTAGCATCATCTCAGAGAAGAAAGTCTTCAGTATCGGACGCAGATGTTGAAGCAAAGAAT

-continued

TTAGAAAGTAGGAACTGTGGAAATGGAACTGATGGATTGAGAAGTTTGGAAGAAGAAATTGGACCAGCTTCTCCT

CATGAACATTTGTTCTTGAAACACAACTTCTAA

StERL2

(SEQ ID NO: 13)

ATGGAGGTGAGCGTGAAGATGAAATTCCCCTCACAAGCACTACTGTTGGCTCTATTGCTT

GTTTTACCGATCGTTTTAGCTCTCACCGAAGAAGGCAAAGCATTAATGTCGATCAAGGCA

TCGTTTAGCAACGTGGCAAACGTGTTGCTAGATTGGGATGATGTCCACGACGAGGATTTT

TGCTCATGGCGAGGCGTGTTGTGTGGAAATTTCTCCATTTCCGTCGTTGCCCTTGATTTG

TCTGATAACTTGCTCTATGGAGATATACCTTTCTCAATTTCTAAGCTCAAGCAGCTAGAG

TTATTGAACCTGAAAAACAACCAGTTGTCTGGCCCAATCCCATCCACATTAACTCAAATC

CCTAATCTAAAGACGCTTGGCTTAAGAGGCAACATGTTGACAGGAACATTGTCCCCTGAT

ATGTGCCAGTTGACTGGTTTGTGTGATGTGCGGGGCAATAACCTCAGTGGAATAGTTCCA

GATAATATTGGGAATTGTACAAGTTTTGAGATACTGGATATCTCATACAATCAGATAACT

GGAGAAATTCCCTACAATATTGGATTTTTACAAGTGGCTACCTTGTCTTTGCAAGGAAAT

AGGCTAACTGGGAAGATCCCAGAAGTGATTGGTCTAATGCAAGCTCTTGCTGTTCTGGAC

TTGAGTGAAAATGAGTTGGTGGGACCAATTCCTCCAATCTTTGGCAATTTATCCTACACT

GGGAAACTGTACCTGCACGGCAACAAACTTACAGGGCCAATACCACCGGAGCTAGGAAAT

ATGTCTAAACTTAGTTACTTGCAATTAAATGACAATCAGCTAATGGGGCGAATTCCCTCC

GAACTTGGCAAACTGGACCAGTTATTTGAATTGAATCTTGCAAATAACAAGTTGGAGGGA

CCAATTCCTGAAAATATCAGCTCCTGCTCGGCATTGAATCAACTTAATGTTCATGGCAAC

AACTTAAACGGGTCCATTCCTTCAGGGTTTAAGAATCTTGAGAGCCTGACATATCTGGAT

CTCTCTGGCAATGAATTTTCTGGGTCTATCCCTGGTTCTATTGGAGATTTGGAGCATCTC

CTCACACTGAATCTGAGCAGCAATCATCTTGATGGACAAATTCCTGTAGAATTTGGCAAT

CTGAAAAGTATACAGACCATTGATATGTCATGCAACAAGATTTCTGGTGCCATCCCAAAA

GAGCTGGGACAGCTGCAGACCATGATAACTCTGAATATATCCTACAACAATTTTAGTGGT

GTTGTTCCTCTTTCACGGAATTTCTCGCGGTTTGCACCTGACAGCTTTTTGGGGAACCCA

TTTCTTTGTGGCAACTGGAAAGGCTCAATATGTGACCCCTATGCACCAAGGTCTAACGCC

TTGTTCTCTAGAACAGCTGTTGTTTGCACAGCATTGGGTTTCATAGCACTCTTATCCATG

GTTATAGTGGCAGTGTACAAGTCCAACCAACCACACCAGTTTCTGAAGGGGCCTAAGACC

AATCAAGGTTCCCCCAAACTTGTGGTTCTTCACATGGATATGGCCATCCATACATATGAT

GACATTATGAGGATTACTGAGAACTTCAATGAGAAATTCATCATAGGATATGGTGCTTCC

AGCACTGTATATAAATGTGTTTTGAAAGATTCCCGACCGATTGCCGTTAAGCGACTTTAC

ACTACACATCCGCACAGCTTGCGAGAGTTTGAGACTGAACTGGAGACCATTGGAAGCATC

AGGCATAGAAACCTTGTTAGCTTGCATGGTTACTCCCTTTCCCCTCATGGGAATCTCCTT

TGTTACGACTACTTGGAGAATGGTTCACTCTGGGATCTACTTCATGGGCCTTCCAAAAAG

GTGAAGCTTGACTGGGAAACACGTCTGAGGATTGCTGTTGGTGCTGCTCAGGGTCTTGCT

TATCTTCACCACGATTGCAACCCAAGAATCATCCACAGAGATGTGAAATCTTCAAACATT

CTTGTTGATGAAAATTTTGAGGCTCATCTTTCTGATTTTGGGGTTGCAAAATGCATCCCT

TCTGCAAAAACTCATGCATCAACTTTGGTGTTGGGCACCATAGGTTACATTGACCCTGAG

TATGCCAGGACTTCCAGGTTAACTGAAAAATCAGACGTCTACAGCTTTGGCATTGTTCTC

CTAGAGCTTTTGACAGGAAAGAAACCGGTTGATAATGACTTGAACCTGCATCAGCTGATA

-continued

ATGTCAAAGGCGGATGATAACACCGTGATGGATGCTGTTGATCCTGAGGTATCTGTTACA

TGTATGGACTTAACACATGTGAGGAAAACTTTTCAGCTTGCGTTGCTGTGCACAAAAAGA

TTTCCATGTGAGAGGCCAACGATGCATGAGGTTGCTAGGGTACTTGTTTCCTTGCTTCCT

CCCCCGCCAACCAAACCTTGTTTAGACCCACCTCCCAAATCCATTGATTATACAAAGTTT

GTGATTGGGAAAGGACTACCGCAAGTTCAGCAGGGTGATGATTCCTCCGAAGCACAGTGG

CTTTTTCTTAGATATTTAGCTGCTGCACTGGTTCAATGGAACGAGTTTGAAGATGGTGAA

GAATTGCATCTATGTTGA

Example 5

Figure 15:
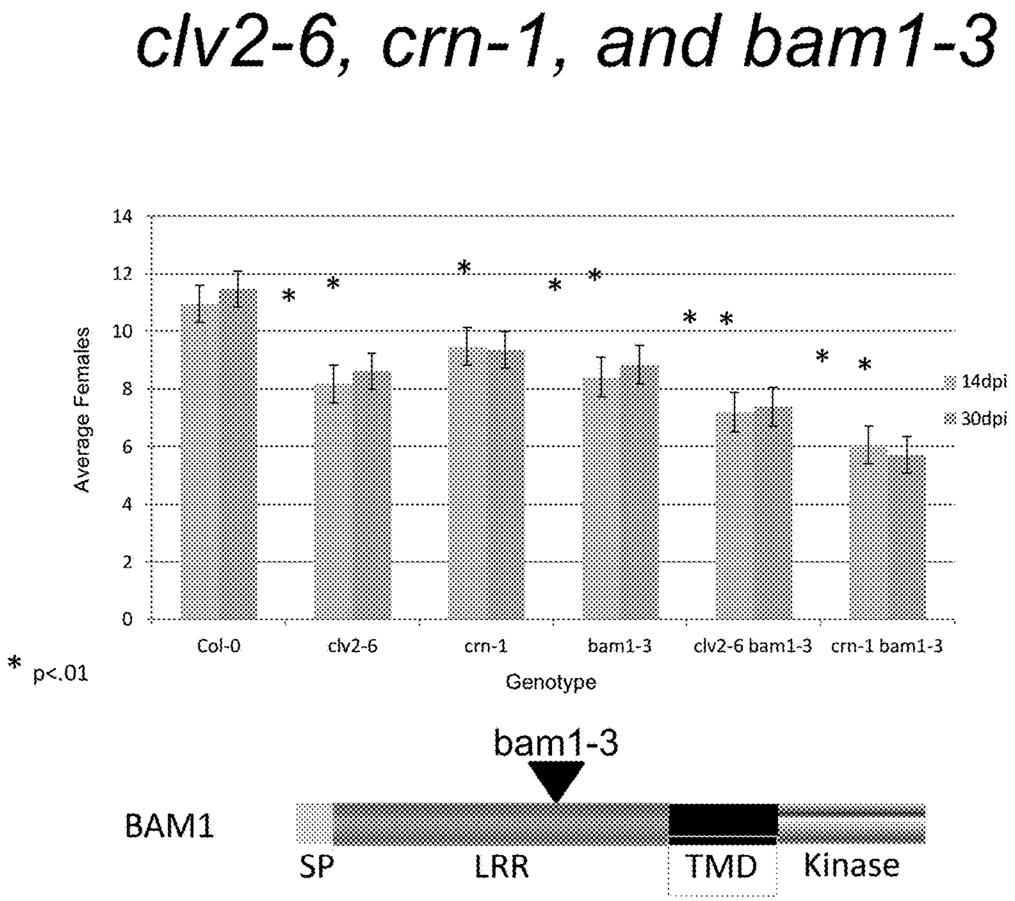

Inhibition of Plant Responses to Nematode CLE Peptides and Inhibition of Nematode Infections by Inhibition of a Plant CLV2, CRN1, and/or BAM1 Gene Mutant *Arabidopsis* plants i) homozygous for the recessive bam1-3 mutation; ii) homozygous for the recessive clv2-6 mutation; iii) homozygous for the recessive crn-1 mutation; iv) homozygous for both the recessive clv2-6 and bam1-3 mutations; and v) homozygous for both the recessive crn-1 and bam1-3 mutations were exposed to the cyst nematode *Heterodera schachtii* and assayed for a response as described in Example 1. More specifically, sterilized receptor mutants were plated in 12-well Falcon tissue culture plates (BD Biosciences) containing modified Knop's medium with 0.8% Daishin agar in a randomized block design. Plants were grown at 24° C. with a 12 hour photoperiod. Fourteen days after germination, seedlings were inoculated with 200 surface-sterilized BCN (Beet Cyst Nematodes; i.e. *Heterodera schachtii*) J2. J4 females were counted at 14 days post-inoculation (dpi) and adult females were counted at 30 dpi. The average values were calculated and significant differences were determined by using Student's t test ($P<0.05$). To measure syncytia size, receptor mutants were germinated on modified Knop's medium in vertical square plates and inoculated at 10 days after germination with 10 surface-sterilized BCN J2. At 14 dpi (days post infection) and 30 dpi, syncytia that were transparent and only fed upon by only one nematode were visualized with a Nikon Eclipse TS 100 inverted microscope. Area of syncytia was measured using Adobe Photoshop CS5 and significant differences were determined by using Student's t test ($P<0.05$). In these experiments, the bam1-3 mutant exhibited a 25% reduction in nematode infection that was similar to reductions obtained with clv2-6 mutants. The clv2-6, bam1-3 double mutant and the crn-1, bam1-3 double mutant showed a 35% and 50% reduction in nematode infection respectively (FIG. 15).

Example 6

Figure 16:
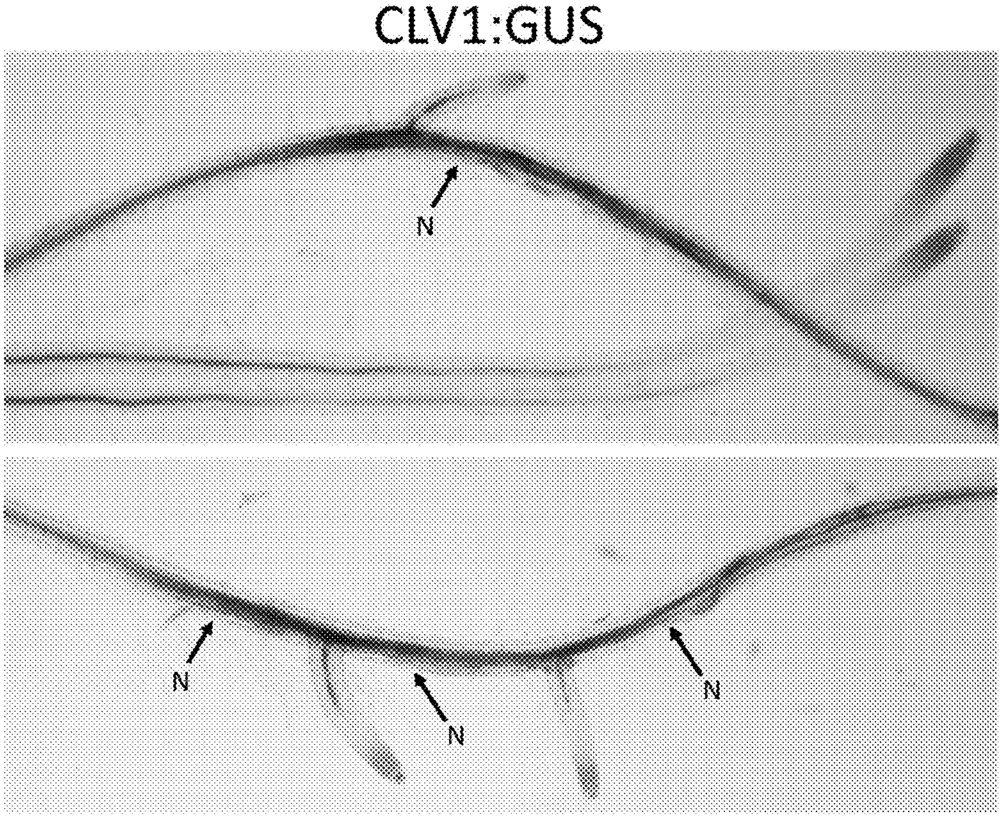
FIG. 16 shows the expression of a pCLV1 promoter fusion to a GUS gene in the vasculature of plants and upregulation at sites of *H. schachtii* in transgenic *Arabidopsis.*Abbreviations: nematode, N.

Use of a pCLV1 Promoter to Drive Expression of Heterologous Genes in Nematode Infected Roots The promoter for the *Arabidopsis* CLV1 gene was operably linked to a beta-glucuronidase gene (GUS) and introduced into transgenic *Arabidopsis* plants. The transgenic plants were then infected with BCN and expression of the GUS observed. It was determined that the pCLV1 promoter can provide for expression in the root vasculature uninfected plants as well as upregulation of expression at sites of BCN infection in plant roots (FIG. 16). The sequence of the pCLV1 promoter is provided in Table 4.

TABLE 4

| | |
|---|---|
| *Arabidopsis thaliana* Clv1 promoter and 5'UTR (SEQ ID NO: 14) | gaagacccaaggcccaacgacctactggtcca<br>ggttgactatgaacaaaagaactagatttttttttcc<br>cctacattttaaagaaaatacttgatgaagatgtg<br>gtgccttttcataagatctaaaaagtttcaaatcttta<br>cgatggaacaaaaagtgaaaggtgaagtaagg<br>gtcatttgggattgagaagtttcttcgtccaaaatca<br>ttgcatgagttgaatagatttgggattaaagctgcc<br>aatacaagaggattcggtaatgactgaagcaaa<br>agcccagcagggccattaggcaaacaccagttt<br>ccaagacggatttgtgtaagaccacttatgacac<br>aagtttgtcttcactatcatcatcttcttcttctacttcta<br>ctactacttttgtagccttgtcgtttttatcattaacatg<br>attgacaagactatgacctatatatcttattattatca<br>ttgctctctctatttgtttatattgattattactttttgagat<br>ttttcaatggttttatctctaactaaacattataattagt<br>gaaacaagcttagtagaagtaaaagtattattcta<br>tgctaaagtacattgattagtagagtgtgtaattgtg<br>tatacagataatctataaacaattggtgcatctgtat<br>ataaaactttatgatttatttattgtatttaataagtata<br>tgaattgggtacctaactttctaaacagttccaaatt<br>tattcttaaatcaaattgcatatgattttttaaatattttg<br>agacgattttattataacgcaaacaacagagtaa<br>aagaagcatatgttgcaaattgtactatggcaagt<br>tcaaatcgaaacatttttgtgaaaatcaaacatgtg<br>aaccaagcttctacagtttaattccctttcgtataatt<br>taatttcaacaaatttattgatatccatctagaaattg<br>gtccaaagttctttcacccttgagtcatttagtgata<br>aagatgacatgattttttggtgataaattttccatcgtt |

TABLE 4-continued

| |
|---|
| gctatatgtcgttatattattctcctatatgtatattata<br>ctatttacatcagaaaataatccaaagtttagagat<br>tctttttacaataataaaatttcccacttactaaaaa<br>gagctccttttctgctgaagagaacctaaaccttta<br>ttcccaaagttcattgagttagagcattttcagcga<br>atcacataagagatgctctcttcttcatcactaattg<br>acatctcattgttttaaaggttgcacttgtacctgttg<br>atctgattctcaatccacttaagttaaaccaaatag<br>acacgagaaaaaagcacatttatttgttgctaagt<br>atgcatatttttcagcgtttacttcttaatctaatgtata<br>tcataagataatatctaaaagagaatgcacaaa<br>agattattaatatgagaaattcgctgccatttagga<br>aggacctttataccaatataccgcaataataatag<br>aacattggtccccaagtgtatgtcaaccccaagtg<br>tatagatttctttaaagattaaaatcccttttttgttgcta<br>aagcacctgatatatttttctatcaaactaaaaaaa<br>ttgttagcgggatgaagatatattcgccaagaacc<br>atagtgcttgtataacggcagaccattaattcaca<br>actattattattttattgttagattgttgatagaatcgat<br>tttgattgtggcagaatcgatcttgtaaaaactgcttt<br>aaggtgcttacttataattaagaaagattcacttat<br>gtaagttaagcatattaatcatatcattcggcctaat<br>tcattaggaatattttgctattcgttttgccatcattaa<br>caacaaaattgacacgttttcagccaaaagtatta<br>acaactaaacctaaaacttcaaacattaaatagtt<br>tttagtatctttagtttcaaactagtgatttgtcctaata<br>tcaacactacgaacgaatttatatacattgaactttt<br>ttctgaatcaccgattacaaaacgaatataatttgg<br>tatcggcagttgctattaatttgatcggtttggactttg<br>gactaatcacgatcaaatcttaaatggaccgaag<br>tgaataaatccctaatgttttcaagagagtcacac<br>gaacgaaacaaaggtaaaatatgaacatagag<br>cgtggggaccttgaagcagaaggtctgtatggtg<br>acagaccggtgagtggagtgtatgaatgaacga<br>gaagtgagaagacaaaatacaagaaagagcg<br>ttgacttggaagttaaagccaaaaaaaccacaa<br>ggggcaaatttgtctctttaggaaaaggacacag<br>acagactttctatacgggccaattagaaaaatag<br>gccctacttctaattaaagcccatttacttctctcctt<br>gtcttcttattcctcttttctccccatcacgtgacgac<br>gatgctataaacgccgtcggattatataactggtg<br>ccgttgacaagacggcgacagaagaaagaaa<br>gaagaaaccacaggctctagggaacgtaacgtt<br>atgtcctgtctatagcatttataacggtcagatcaa<br>cgccgtttagataaagatctgtcaatgttaaagaa<br>gagatgcatctctacaccgttaaatttaaaacgcc<br>gtgaacctcttatctattgattttttgtttgatgaagcca<br>aaacaaatcgtgtcagaagacttatcagagaag<br>aagaaaacgacgacgttcccgtttctccatgtcta<br>ataagtgtagtagtggcggctactaaaaactctaa<br>agtttgactccagtaaaactgcctttctagtgtaatt<br>ccagtgattttagagtttgaatagtgtgtgaccaaa<br>tttgaaagtacaatctcagcaatattattgatcactc<br>gttataaaagaatcgaatgtaaaaatagccaatg<br>agagactgagacgtatgtgtttgaccataagtcgt<br>atagtttgtatctatctacctgcaagatcagcagat<br>ggttctctgatcaattgtaccttaattatcttttattttcg<br>taaaatttctctattcacaaatgataaatctacttaa<br>gacagtaaccataacaagatttacaagataatttg<br>aaaaatgaacacataaaagtattttggcgcattat<br>ttttaataataacaatatttatgtaaagtcacataaa<br>agtatatattcgctcacaaagtcttacggtatttaga<br>acagtagtaccacatcgattctcttcatcttcttcttc<br>ataatatgccattgttcatgtctctgtgtcctatcgca<br>taacactcacgctatcttattattttctctcgctctttct<br>cactgagaggacactaaaaaa |

Example 7

Nematode-Inducible Expression of the Potato CRN and CLV2 Promoters

Figure 17:
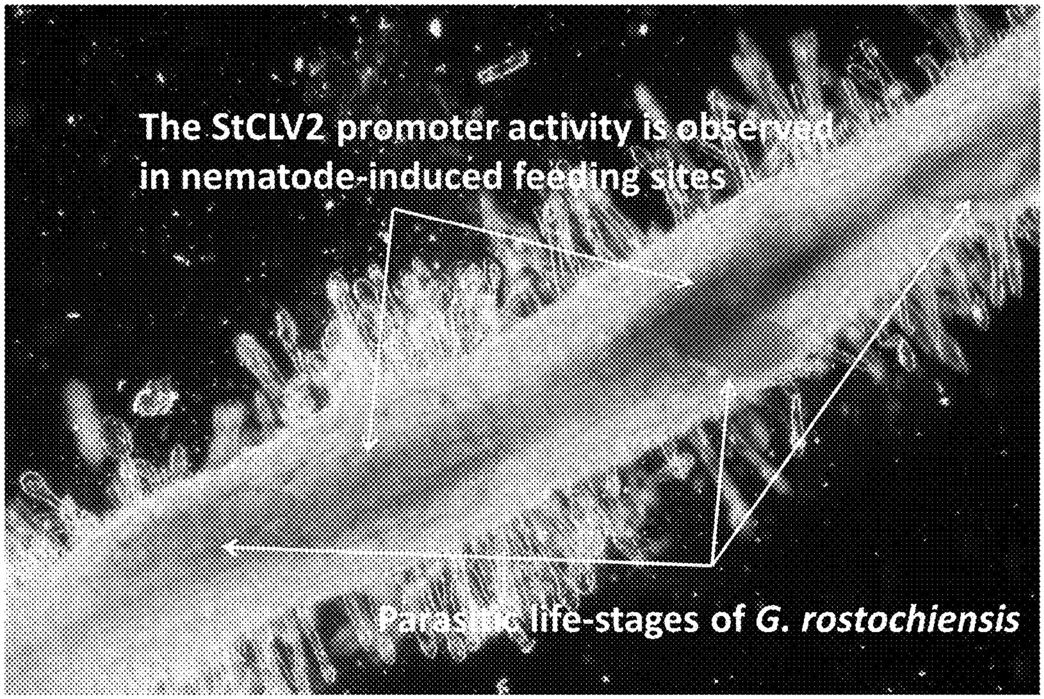
FIG. 17 shows a StCLV2 Potato Promoter:GUS transgenic plant line and activity of this promoter in *G. rostochiensis*-induced feeding sites.
Figure 18:
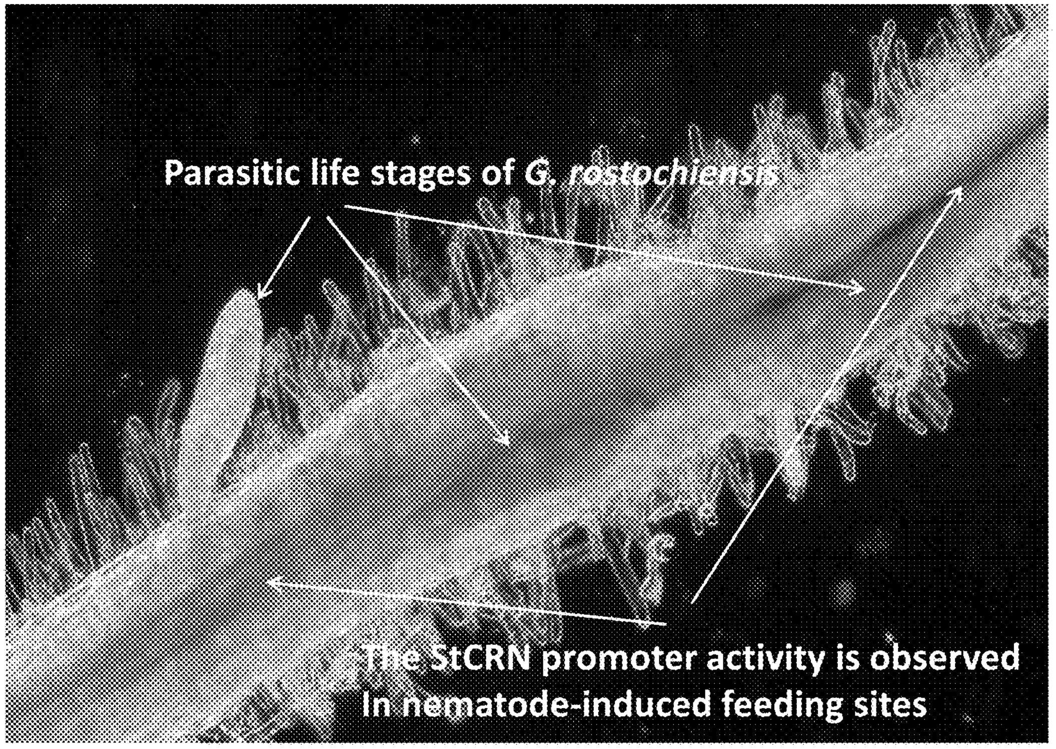
FIG. 18 shows a StCRN Potato Promoter:GUS transgenic plant line and activity of this promoter in *G. rostochiensis*-induced feeding sites.

The promoter for the *Solanum tuberosum* CRN and CLV2 genes was operably linked to a beta-glucuronidase gene (GUS) and introduced into transgenic *Arabidopsis* plants. The transgenic plants were then infected with BCN and expression of the GUS observed. It was determined that the StCRN and StCLV2 promoters can provide for expression in the root vasculature uninfected plants as well as upregulation of expression at sites of BCN infection in plant roots (FIGS. 17 and 18, respectively). The sequence of these and other nematode inducible potato promoters that can be used in the methods of this invention are provided in Table 5.

TABLE 5

| Promoter | Sequence |
|---|---|
| *Solanum tuberosum*<br>>StACR4 (clone 3)<br>promoter sequence; (SEQ<br>ID NO: 15) | CTCCGAGCGTGAAATGAAATTAATTCCTTTAGGAGAACATAAATGTCTGCA<br>GAACTATTCTTGAAACCTGGCGCAGAGGATAAAATAAATATTCAATCTATC<br>TAATAATAGTTGTTCACTCGCGCATTTCTTATGAAACTATAAATAGAATGA<br>TAATTTACTATATCACCTTTTGAATATACTCTCTCTGTCCCTAATTACTTG<br>TCCATTTTGATAAATCAAGAAAGAACAATTTTTTTTTTATCTATTATACCC<br>TCAATAAATTACTTTGAAACTGTAGAGCTTCTTGAAAATCTCAAGTTTTTA<br>ATTTATCCACTTCATAATTAATAGGGGTAAAATGGTAAACTACTATGCCAA<br>TAATTGTTTTCTTAATATGTGTGTCAATTCAAAAGTGGACAAATAATTAGG<br>GACATAGAAAGTAAGAGATACAATATCTTGAAAAATGTAATAGGGAAATAA<br>CTATAATTAATGATGAGTAAATTATGAACTAAGTGTAAAATTATTTATTGA<br>TGTCATAAAGTAGACAAATACTCTCTCTGTCCAATAATAGTTGTCCACTAT<br>TGACCTGACACACCCCTTAAAAAATAATAAATATTGTAATACTACTTTATT<br>ATCCTTTGACTTTATTAAATTTAATGTTTTGAAAAATGTTTTAGATGATAA<br>ATAATACCCTCTATCCCTAATTACTTGTCCACATTTTCTTTTTTAATTGTC<br>CCTAATTACTTGTTCATTTTAATAAATTAAGAAAGGACAATTTTTTTTTAC<br>CTATTATACCCTCAATTAATTATTTAAAAAAAAGTAGAACTTCTTGAAACT<br>ATTAAGTTTTTTAATTCATCCACTTCATAATTAATATGGGCAAAATGGTAA<br>ACTCATTATGTCAATTATTGATTTCTTAATAGGTGTGTCAATTCAAAAGTG<br>AACAAATAATTAGGAACAAAGAGAGTATTTAATAGCAAGAGTAAAACAAAC<br>ACAAAAGGTAAATTATATCTCTTAATTTTCTAGATTGGACAAATATTGATG<br>GACAACTATTTTTAGTATAGTGGATAACTATTGTTAGACAAATAAAGTATT<br>GTTGAATATCCCAAAATAATATAATGGACAACTATAATTAGGCGGAGGGAG<br>AATTATTGTTGGACGGAGGAAGTAGAAACAAAATTTTTAAAGCTAGCAATT<br>TTAGGATGATTAGGGGGGATTATGATAATGATTGTACTAAGTAGGTACAAT<br>TATAATGGAAATTTTAGTTAATTATGGTGTACTCTGTAAGAAGAGAGAAAA<br>TTTGAATAAAATTAAGTAGTAGTTATTTGTAGAAAGTAAGGGAGGACATGT<br>GTGCAGGTATCCAGGCATTGAAATATCAATTTTGCAATAAATTTTTCATTA<br>AATGCTTTCACCTACACTGCTCTTATTTTGAGAAGATGTAGTTTTGAAGCA<br>TTTAATGCTCACTTTTCTCTCTCTATTTCTCCTATGCTGTCTTTCACCACT<br>TCATTCTTGAGGGCACCGATAACTTTGACACAAAAGGGGCTAAAAAAAATG<br>TCATTATGTTCTCTTTTTTGTGTTTCTTGAACTGAAATATGCAGCTTCTTG<br>GCTACAAATTTTGTTTAATTGTATTGATAACGAGGGTATTATAATTATTTG<br>GGAGGAAGGAAAGTTGTGAATTTTGATCTCATCTACCCACCCATGGTATGT<br>TTGAACTATTTTTTTTCTCGTGTGTTTCATAAATTAAGTCAGCTACTATGG<br>AGAAGGAGGAGTGGTATTTTGGTTCTATCAAAAAGGATAAAGGTGAAAGAA<br>AGCACTGACTTTCTGTTTGTGTACTTTGTTTAATTTTTAATTTGTGTAATG<br>GACGTGTTTAATAAGTGGTGTGTGGTGATGTGGAAATGTAGATACTTTGTA<br>AGAGCTTTTATGCTTCTTGTAGTATTTTCAAAAGTATCAGGGTTTGGATCA<br>ATG |
| *Solanum tuberosum*<br>>StCLV1 (clone<br>5)promoter sequence;<br>(SEQ ID NO: 16) | CGATGAATAATGCTCCCTATCAATATTTTTTTTATACTGAGAATCCAAAAA<br>CAATTATAATGACCATGCTGAATTTCAGAAAATGGTGGGACAGTTATGAAA<br>AAGATGTTGAGATTGGTTGGATCGGAAGAAGAGAACAAAAAGAGTGGACTT<br>TTTACGCAATGCCAAAATTACAGAGTGTCTCTTACCCAAGGACACATACAG<br>ACTTTGCCAATGGGCCCCAGAACCACCCATTAACCCCCCCCCCCACAAAAT<br>ATGGGCCTTCCTACCATACCAAAGAAAAAAAAGAAAAAAAATTACGAAATA<br>ATTATAAGATCGATAATGTTATATGATAATGAATATTGGAGCGTAAAACTC<br>TAATAATTCATAATGGGAGGTTTGAAAGCAAAAATGAGTCTAATAATATAG<br>AAATACACACAAGATAGATGCGCAGAGATTCGACTGTTAAAATAATCATGT<br>GGTGAAATTATATACTAGATAAAATTAAAAATGACTAAATACATCAGTATA<br>TCAATCGTTGCATTGATCAATAGATACACTAATTATCATAGCTATAAAATT<br>ATAATAAGTAAAATACTGTAACAAAATAGCTCCTTCAAATCATATAAAAAT<br>CTACACTAACACAATAAATAGATTTAAAAAAAAATATAGCCTAAACAACAA<br>ATACCACACTCTAAATATGAGTTACGACCATTTTTTTTTTTATGGTTTTGT<br>AAGGAATTAGGGTGCAAATCATTAAAAACGAAGATAAGATGTAAGTAACCA<br>AAACGTGCATGCATTAGGATGCAAATCACAAACTACTCAAATTTACTATTA<br>GAAGTGCTCATTTTAATAAATTTAGAGGACCAAAGTGACAAAGAGTTATAC<br>TTAATAAACTAGTTTGAAATAACCCAAAGATAAAGATATTATTTTTGTTAT<br>TTTCTAGTATAAATCTTAGCTGACAGACTCAGAAGCGTCAATCATCAAAAG<br>AAGTTCACAAAAAGCCGTCAGTAATTTACTCTGTTTCTCATCTAACCATTG<br>CTTCTAAAGTCTGCTGCTACAATCATTTTACTTGCATCTATACATATCACC<br>ATGACTTTTTTTACCAATAAATATGAGATTTAACCGTAAGTTATTGAGTTC<br>GATTGAATCTTCACGTAACATAGTAATTAAATATGAAATTATACCATGATT<br>TAAAGCTAATTAAATATGAGATGGAATTATCGAAAATTATGATGAAGTAGT<br>CAATACTTTTTCATCTTAACAAGAGATTTTGAATTTAAATTTGAATTTTGG<br>ATGAAGTTACTTTTGATAAATAATGTTTTAACCTTAAACTAGAAAAGGTTG<br>ATTCGTTCATTAAAATATATTCTTTCAATCTCAATTTATGTAACACTGTTT<br>GACCTAATATAGATTTTAAGTAAGATAGAAAGGAAATTTTTATAAATTTAT<br>GATCTAACTCCTCATTTTGGTGATTATAAATCATTTGATTAGTAAAGAGTT<br>TTTGAAGTTACTCTTTTAAAATATTATAAAAATGATAATTTTTAATAAAAT<br>AAAAGAAAATTATATATTTTGTTGGGTCTTTTAGTATCCAATATCCATATT<br>TAAACTCGATTAGTTCTAAATTAGCGCTGAAAAGTGTTACAGTAGTTGTAC<br>AAAATTCTCTAATAAAAGTGATTCCGTATCGTATTTAAATTTGAAAGCTTT<br>GATTATGAATGATTAAGAATGGAGGAACAAAATTTGTTACCTTATTATTAT<br>TTGGTAGAGATGAAGTATTTACCACTCCCTGTGGTATCTTCACTTTGTTTC<br>CTNACACACATATATTCAAAGCCAAAAAGTTAATTTTGATTCTCCTTCCAC<br>TTTGGCCAAATGCAACAGTACTAAATACTCAACACTTCAAATACCCTTGAA<br>CCTATCCCAAAATTTGTACAAACCAGACTAAACTAACAGTGTAATA |

TABLE 5-continued

| Promoter | Sequence |
|---|---|
| *Solanum tuberosum*<br>>StCLV2 (clone 7)<br>promoter sequence; (SEQ<br>ID NO: 17) | CTCACTCGCCTCTCTCATCCCTCTCACCTTTTTCCTCCCTTTCCCATTCTC<br>ACTCGCCAGATATACAAATACATATGTATACTAGTTACATACAGAATGATA<br>TACATACACAATTCAACAAATATACAAATTCAATTTACCTCTCTTCACTCT<br>ATGTCCTCTCTCCTCCCTCTCCCAATCGCTCTCGTCTCTTTCCTCCCTTTA<br>AAATATAGCTACAAATCGTAATTATCAAATTATAGCTATGAAGCCTAATTA<br>AGTTATTTTTAATGGTTATTTGTGAAATTTCCTCTTTTTTAAAATAGTTTT<br>TAGAAAATCAAACTTCAGTAACTTTTAAGTTAAAAAATAAAAAGTAAGAGT<br>ACCTACTTTTAACTTTTTAAAAATCGTTTTTAAAATATTGAAATATTCTTG<br>GCGACTAAAAACTACTTTTAACCTAAGCGAAACACCCTCTGAATCTTAGTA<br>GAGTAAGTTCTCGAGTCATATCATGATTAATTTATTTTCACTCGTGTACTT<br>TAGCTTTTCATTTTTCCTTAATTTTGTTTTACACTACTATAAAATAGTGGG<br>ATGCATCTATATCTTATCGTTTTTTTATGTTACATTAATTCATCACTTTTA<br>AAATAATAAAAGTATTTAGATATATAGTTTTTGCCAAAGTTTTATGATATT<br>ATAAAACAAATTTGAAAATCAATCGAATCGAACTGACACTTAAATAATCGT<br>GATAATATTTAAATATTATAAAATAGAATAACTATAAAATTAATATTATGT<br>AAATTTAATAAAATAATCGATTGAAGCGTACCATTGAAAACTCGAAAGTGA<br>AAGGAAGAAGAGCATAATTGTTGATATGGGTTCACACGCTCACTTACATAC<br>ATATAATAAAGGCTCTCTTTAAAGAGAATTTGAAAAAGAAAAGAAAAGTGA<br>AGTTGTCTACTTTACTTTAGTTTTACACTTCTCCAGGCACGCCAAACACCT<br>TTTGCCTCTCTTTTTTTTTTTTTTTTTCATTGGGACTGTTTTTTTTTTTTA<br>GTTTGTTTTTCTTTTCTTTCATCAAAGAGGTATTTTTCGTTTCTATAATAT<br>TGGGAGTAGCAAAAATGCTACTAGTATATGAAATGGCAATTAGTACTTTTA<br>TTTATCATCAAATGATATATGGTGCAGTGTATACAATATTCAAATTCCGAA<br>TATGAAAAAATTCATAATAGAAAGTACTTTTCCATAAGAGATCATACAATG<br>AGAAAATATTCAAATTAATCAAACTCCAATACAGATACTATCAAAAATCAA<br>ATGAATGAGAAAATAATAAAAAAATATTACCCCCATTTGATCACTCAACTT<br>TTCTCTCCATTATTTAATACAAAAATATCAGGTGATTTTTCATATTTGTTC<br>TAACTTTAGTATATAGAGTTATCTAGTACTCCCTTCAATTACTTTTGATAC<br>TAATGCAACTAGGCTTGTCAATAAAATATTTCATTAGCTATTACTGATGAG<br>AGATAACAAATATTTCATAAAATTAGTTGAAGTGCGCAAAAGACCAACCTC<br>AAACACACAATCATAAAAAAAAAAAGTGAGGAAATATAGAGTGTGTGCCTCT<br>CAATAAAATAAGTACTAAAAAAGAAAACAAGAAACAAGAAAGAATGTTGGT<br>TCTTTAGTGGTGACTCTCAATGAAGTACCTACTTTCAGCTTACTCTCTCTA<br>TACTCACTACTACTGCTACTCAGTACTGATTCCTTTCACACATACTGTGCC<br>TGTAAACCCTGTCCAGGGACCCCCATTTCCCCTTTCCCCTTTCCCCTTTCT<br>CCTTCCTTCCTTAGCTATCTCTCACACAAACACTAATCTTTTTTCACCTCT<br>ACCTTACCTCC |
| >StCRN promoter<br>sequence; (SEQ ID NO: 18 | TCCGTTTGAGGGATTTCTGTAATTATAAACTTTTAAGGGATAGATTGTAAT<br>TTTGCCTTCAAAATATGTGATTTCTGTAATTTGCCTTATTATATAAACAAT<br>GTGTATTATCCGCATAATTACCACTTATAGTAATTGAATAGGTTTTACCAT<br>CTATAACATAACTTTTTTAACAATTTGTCTCCCTCTCCCATTCACTCCCCC<br>CCCCCCCCCCCTCTCTCCTTCTTCTCTTTTCTTTCTGCCCGTCTCTCTCT<br>ATAAATTTCAATTATCCTAATTTAAGACTTGATTTTGGATCGAGTATTATT<br>TCCAAACAATTGAGAACATCTTTGAAATTTATATCTTAATGTTTAAGGATT<br>GTTGATGAAGACTAATATTTATATAACTAATATATTTTTATTACAATAATA<br>AATCTAACAATGTTTAAAAGAGAAAAAATAATAAATAATTATCAGTATATT<br>ATACATATTTATGTTTCAATGCACATGGTGAATATAATTAAAATATTTTTA<br>AAACAAATGTATTATAAGTATTATGTGTGAATCTCAAACATTTCAGTACTA<br>TTTAAATTAGTTTACATTGTTAGAAATGTATTATATTTGTTGGAATAACAA<br>CAATCAAATTCATAACAATGTATAATATTGAATTTGAATGGTATTACAAGT<br>GTCTTCTATATTTAATACAATTGTAATACATAAACTAATTTGAATAACATT<br>TGAATATTTTAAATACAAGTACAATGCATTTTTAACACCATTAATAAGATA<br>GAAAATAACAATTGTAAAACATTATGAATCCAATATATTATACTTATTAGA<br>GGCATATTTCAAAACACGTGGTGAATATATAACTAAAACATCTTTAATAAA<br>AATGTATTATAAGAATTATATGTGAACTTCAAACATTCTACTACCATTTAA<br>ATTAGTTTACATTGTTAAAACTATATAGAGGTGGCAAATAGTTGGATTTGG<br>ATGGGTTTAAAATGATTTAAATAAAAATGGGTAATTATCCAATCCGTCCAT<br>ATTCTATATGGGTAAATATGGCTTGGATAATTAATGGACAGATTGGATATG<br>AGTTACCCATATTTCATCCACATTGATTGAAGAAATAAAAAATGAATTTAT<br>ATTTTTTAAGTTTCTAAAGTAATTTTTTATTCTACTCACTCCCATCCCTAC<br>CTCCAATTCACCCACCCCTAATTTTAGTTTGTTTTATTTTTTCTAACCCCC<br>GCCCAGTTTTTATCCCCCTCCACCTCACCCGTCTTCATCCCCTCTACCCCC<br>ACCTGCACCCACCCACCCCCACTTTTTTTTAAAAAAAAATTCTACGCCCCC<br>CTCCCTCAAGAATTTCCAATTTTTTTTTTGTTCTTCCATTAAAAAAATGAG<br>TTTCTTTTTAAAAATAAAAATTTACCCCCTCCGCTCCACTCCTATTTTTTT<br>TTTTTTTTGGTTTTTTTAAAAAAAGTAACATTTTCAGAAAAGAAAGTTACC<br>CCTGTTATAAACTAAAGTATAACAACTTACTCTTGCTTCTTTCTTTGTTAC<br>AAGAGGGGTATATATAGTTGTATACACTTGTGCCCAAAGTGTGATACACGG<br>ATAACTTCTTGCCATGTATACACTTTGGACACCAAGTATATCAAATGGCTA<br>ATTAGTATACACCACATAGCATTTTGTGTGTGTATTAATCTTACAACACTT<br>AACATATTAGTGTGGACATTCAATTTACAACAACCCTGAATTGTATTACAA<br>CTATCATTTATATTTCATACAACTTTTCAAAGTTGTAGCTCTTCTTTTCCG<br>ATGATTCACAATCACCGGATTATCAGTAGCTCAAATCAATCCCATTATTAC<br>AAATCACCACACAGTCCACCCACAGTCACCAAACTCTCTTTTCCCCATATT<br>TTTGGTCCAAACACCATGACCAAATTTGAATGCCGAAGAGAGTTTTTCAAT<br>TGGATCTAAACATCGATTTTCATGAAGCTCATCGGAGCAACGAACACCATC |

TABLE 5-continued

| Promoter | Sequence |
|---|---|
| | AAAATTATGTTCAGATCTAACAACACCACTGATTTATGTTCTACTCTTCTA<br>CTTAAACAATGAACATAGAAACTACAATCTTCTTTGGTTCTTATAATTACA<br>AATTAAAAAACAATAACGTAAAAGAAAAAAGATGCATAGAGATTGGGCATC<br>GCATGGTTTCATGGAGCTCCATGTTTTTTTGTTGGAATTTGATGATTTTCC<br>AATTTGGTTATTATGTTGTTCATTGTTGTTGTTGAGTCTATTTTGTGGTGG<br>TGCGGAGGTGAGAGCTTTAAATTGGAGTTGGGGTGATTGTTGTTTTGTTCG<br>CCGGAGAAGCCATCTCCAGTGAGGTTGGTTGGAGAAGGAGAGAGATGAGGA<br>GAGCAATGAGTAATTTCAACTATTAAAGGTAAATTGAATTAATATCTCATA<br>CGATCACTCGACTTTAAATAGTTTATTTAGAAAGTCACTTAACTTTGAATT<br>GTTCACTAAAAAAATCACTCAACCTTATTTTATAACTCAAAAGTCACTCAA<br>CTATTGATGTTTTACTTAAAAGTCACCTAAGTATTGATATATTGCTTAGA<br>AAGTCACTCAATCAATTTAAATAATTTTCCATTAAATTTTATTGTAAACTA<br>TTTTTTAAAGAAATAATAAGATTTCTATTTTAATTATCTTATTAATCCGCT<br>CCAATTATTTAATTATAATTTTCTGAAAAAACGTATAGCAATTGACCCAAA<br>AAAAAAACTTTTCCGTTCTAGTAGTTGTTTGATTGGAATTAAATATGTTTA<br>AAAATTATCAAAAAAAAATAGGATGTTGGAATTGATAAGAAGTAATAAAAA<br>AACGCACAGTAGCAATCTTTTACTATTTTAAAAAAAAAAAATAGTTAAAAAC<br>AAAAACTACATTTCAACGAAATTCAATAAAATAATTTAAATAATCATCTTA<br>TTATTTTTTAAAAACTAGTTTAATTATTTTTTGTATTTTTACAAATGAAAA<br>AATTATTTAAATTGATTGAGTGACTTTCTAAGTGAAACACTAATAACTGAG<br>TGAATTTTGAGTTATAAAAAAATTGAGTGACTTTCTAAGTGAACAACTCAA<br>AATTGAGTGATTTTTTAAGTGAACTATTCAAAATTGAATTACCATATGATA<br>TATTAACTCAAGGTAAATTAGGCTATGGACTATAATAGAAAAAAAACCCAAA<br>AAGGATAATAATTAATCTAAAAGAATTCATATATATATAAAACTATTTTGT<br>TTAATGATAAATTTTTGACCCATTGGGTCTTTAAAAAAAAAAGAGAATACT<br>CCATCTTGTTATTTTGTAGGTATAAAAAAAAAGTAGTTCTATCTTTAATAG<br>GTTCATTTCTTTAGTGGAGGAAAAAAGTGGATTTATTCACTAATCTTGTTT<br>TGTGAGAGGCAAAGTTGTTACATATTTGGAATTTGAACTTTGTAATGATTC<br>TATTCTTGTTCATTGTGAAGTTGTATATATTCCTCACTGTTCACTTTTATC<br>TTATTTTATTATTTATATAATTTTAAAATTAGCTTTTTCAGCAAAAGATTT<br>TTGTTCTTGAAGATTCGTTTCAGAAAGAGAAAAAAAGAAGAAAATGGTCAC<br>ATTGTCGTCCTTGTGTAACATTCAGAGGAGTGAACCCTAAACTTGCCGACC<br>CACAGAGAAAAACAACCCTAGTTTCC |
| >StBAM1 (clone 6) promoter sequence; (SEQ ID NO: 19 | GAAGGGCATAATTGCTACTTGGACAACACAGTATAATTAATAGGACAACGA<br>AAACTTCGTTTCATAAACTCATTCTCTAGCTTAAGTATAATTAATATGCCC<br>CTAAACTATTTGAAAAGGTCTAGATATACCCTCCGTTTAAAAGTTTGGCTC<br>ACTCATGCCCTCGCCGTTCAACTTTTTGTCTAAATATGCCCTTATGGGCAT<br>TAGTTGGCCTGCTGGACATATCTAGCTCATTTTCCATTTCTTTAAATGCCA<br>CATGGAATTGTCATGTCATTTTGACTTTACCACATGACATTTATATGAAAA<br>TGGAAAGGGATCAATTATGCCCGTAAAAAATTCGAACCCATAAACACCTAA<br>TCCGACCCATAAATCAACCCCCCCTCCTTTTAGATAAACTACCCGACCCAT<br>TTTCAATAATTTTGTTTAAATTTTTATTTTTTTCGGTAAATCCAGGAAATT<br>AGTAATTGATTAATAAAAAATAGAAAAAATATGGGGAAAAAAAATTAACGC<br>CAAAAATTCACAAATAAATATTGTAACCTTAAATTCAACAATTTTTTTATT<br>TTTTTCCGGTAAATCCCGAAAATGAGTAATTGATTAAAAAAATATATGAAA<br>AATATAAAATTAACGCCAAAAAATCACAAAAAAATCCATTTTTCATATAAA<br>TGTCATGTGGTAAAGTCAAAATGACATGGCAATTCCATGTGACATTTAAAG<br>AAATGAAAAATGAGTTGGATATGTCCAGCAGACCAACTAACTCCCATAAGG<br>GCATATTTAGACCAAAAGTTGGACGACGAGGACATGAGTGAGCCAAACTTT<br>AAACGGAGGATATATCTTAGACCTTTTCAAATAGTTTAGGAACATAATTGA<br>CCCTTTACCCATTGCACAAAATATCATTCATTTTGAAAGTAAAAGCAAATC<br>AAAATGACATGGAATTGGAATAGCACTTAAATGATACTCCCTCCTATCCAT<br>TTTAGTTGTCACTGTTTACTAAAAATAACTTGTCAAAAATATTGTCATAGA<br>AAACTATGAATACATACACATTATGTTATGATTGTTTAGATTGGCAGATCA<br>GTCTTGTTTTTATATACATTTCTTTATGTTCAACTTGAGCTAAAGGTATCA<br>GAAACGATATTTTTATTTTTTCAATGTAGGAGTAAATAAGAGTTTATTTTC<br>TTTGTCTCATATTAATCATTTTTATTTTTACACGCATATTAACAAATCATA<br>CGAAGATAATTTTACTAATTCACTTCTTAAAAACTTATTGAAATTTTAAAA<br>ATAAATGTGAACACTTTAATTTTTTTTTTGCAAGGGTAACAATATAAGAAA<br>ATTTTAATTAATGTTTTCTTGATTTAGTAAAATGGACAACTAATATAAGAC<br>AATTATTTTTAGTAAAATGATCAACTAATATGAGACGGAGAAAGTAATATA<br>TAAAATGTCATTCTTATTAATAATTTCTTAAGGAATGTGTAAAATAAAAAC<br>ACGATAACTAATCTCTCCTCTATTGTGGCTTTCTTTGTGCCATACTCTACT<br>GTCCAAAAAATATTACTACTCATCAAAAGAAGAAAGGGCTTTCCTTAAGAA<br>TGACATCTTATCAACTACAAAACTAACCTAAAGATGAAAAAACTACAGACG<br>TTAGTGGAGAATGTTTTAACACCCTAAATTAAAGGAGATAAAGATAAGTGA<br>AGTGCTTTTTGTGACAAACGAATTGAATGGAATTTTATGCCTCCCTCCCAA<br>ATACTCTTTTTAGCTAATGAAATCTCTTTAACTAGTAAGGACAACTATTCA<br>ACACGAGAAAAAGCAAGACCAATAGTTGTTTTTTTCTACTCTACTTTTTAT<br>CCGTGAAAAGATTGTGTAAATGTTAGCAACTTTATTATTTTTAAGGAACAA<br>AAAAGTTGGTTCCCCACGTTACAAAAAGAGTTGGGGCCTCCTCTACTTATC<br>TCACAATTCAAATTTATTCTTTATAATATAATAATCAATCCCCTCCTATTA<br>TATATATTTATTTACTCAAAACAAAAGAATATACACCAAACGGATTACCCA<br>CCCCCTCCTCACTTTTGCCTTTCTCACTCTCACTGAGTGAAACCGCAAACC<br>AAACAGTTGGTGGGCATTAGATTAAGGAAGGAAAA |

TABLE 5-continued

| Promoter | Sequence |
|---|---|
| >StBAM2 (clone 2) promoter sequence; (SEQ ID NO: 20 | GCGTCAAAGTATGAAGCAGACAACACATGAACACACAATAATGATCGACTC<br>CCACTTAAAAATATTATTATTTTTTTGTTAAAAGGGAACGAAAGCATTATT<br>TTTATTCGTTCACTATTTTAAAATTAATTCTTATTTGTACTTATCACTTTT<br>TAATATATTAAAAGAACTTTACTTTTAACATCAATTAAAATGATATTATGA<br>TAAAACATTCCTAATCAAATGTTATTTCTTAAATATGTACAAAGTTTAAAG<br>TGGATCAGTAAAAATGTTAATGAAGGTAGTAACTTTTATTTGTTGTTTATT<br>TACTTTGTTGATGTGTTTGTAATTTATAATCTTAAAGAATAATTATTAGAA<br>TAAAATGAAGAAAAAATAATTAATTCTATTTTAAATTAACAAATAATTTAT<br>AGTAATTATTTTTAAAAATGACGATAAATAATTTAAAACGGAGGAAGTATT<br>AACTGTATTAATAATTAATATTAATACCACTAATGATAATGAAAGTGTTAG<br>TATCCTACATGAAAAGGACATGATTGACTACTTTCGTATAATTTGACAATG<br>AATTGAATGGAATATTATTTTTTTCTACATATTTGTTTTTGTTGTTAATAA<br>TGTCTTAAATTATTAAACAGTTATATAATGCTGAAAAGAGAAAAACAAAAA<br>GTATTGAATTCTCCTCTTTCTTCTCTTCCACAAAAATTGNAAAAAAAAAAA<br>GCAGCTCTTTTATTAATATATATATTTTTTCTTTATTTCAAGTATAAAGTT<br>TATTTAATGAAAAAAAATACTTTTAAAATTTATTATTTTAAATATATCATA<br>ATATTTATGTTACTATTAAAATATTTATTATGAAAATTAAATTAATTTCAA<br>ATACATAAATGTATCATTCTTTTCAAATATCTTTTGACTATGGAAAGAAAT<br>TGTAAAGTAAACGATGACTTTTTTATTTTTTTGGTACTTAATTGATTTTTG<br>AGGAACAAAATAATTGTCCCAAAGTATAAAAATAAAAAAAGTTGGGACCTT<br>TTCTCTAGTCTCCATATGAAAAAGACAATTCAGTACTCAGTAGATTCAAAA<br>TATCCTTTAAAAGCTAGAGCTCTTTAATATACAATAAGAAACAAAATAATC<br>ACAAGACGATAATTATTTCAATTTTAAATGTAAAATTTTAAAAAATATACA<br>AGTTCTTTTTAAGGTTTCACTCATAGAGCTGTAAACATATTTTTAAGTCCA<br>CATACAACTTCTAACTTCTAAATATTCANTTTCAATCTAACTTCAAACACT<br>ACANTTTTTCAATAATAATCAATTTATGTCCGACGCTTATTTTGTTGATAA<br>TTAGGATAGAATATTACTAGTAGATAGTTGAGTGTTATCACATTTTACGTG<br>AATGTGAANNAGAGAGTGAGCTGACCTTCTTCTATCCTCTTGTTTTTTTAA<br>GTAGTATTATTTAGTTATCACGTAGTTTCTTACCTTCCACGTATATTGTTA<br>CCTATTGTTGTATTTATTTATTATCTTGCCATTTTGTTGTTTCTTTTCAAA<br>TAATTTTACACGACGTGTGATAAGTGTTTTCCTTTTGAGTCAATGGCCTTT<br>CAAAAACAATCGTTTTTACTTTATAATCGTGAGATTACATTCAATGTGTTA<br>TCATTACATTGGATATGTTTAACATTACATAAGGATGAAGAACGAATCAAT<br>CTATTCAAATATTAAATATTCATTAAAACAATACAATACGATATAACCATC<br>CAAACCAAACAGAGTGTCAATTTTTTTTAAAATTATTTTAGTTTCTAATGT<br>ATATATTCAAAAATTTCATATAAATACACATTTATAATATATCTGTTCGAT<br>AAAGACACGTGAACATTTCTTCTTCTTCTCCACCATTTCTGCTCTGCTCAC<br>TCTTTCCCCTCCACCATTGAAGAAAC |
| >StER(clone 2) promoter sequence; (SEQ ID NO: 21) | CCGAACATCTTTAGGGCATCTCCAACCGAATCCTCTATTTTACTCTTCAAA<br>TATAGAGTTTTCTATTTTTTTCAGACAACCAACTCCAACTCAATTCTCTAT<br>TTTACTCTCTAAAAATGAATTTTTTTTTCTCTCCTCGATATTATATTATTA<br>TTTCTATTTTATTCTTATTTTCTTATTTCATGATATAAATCCTTTATTTAT<br>TTTTTTCCAAATAATTACTTTATATAATTTTTAATGTGATATGAAATTATA<br>TTTTATTCTAAAATTTTAAATAACATAAATTGCAGGAAAATATAATATAAT<br>ACATAAATTAGGGGACAAATTCAAATAAAAGTGATATACAATTACATAAAT<br>ACTCAATTTTTAAAATTATTACGTTGCTCCCATAAATGCTCTATTAATGCA<br>TTACGGAGTTCAAAATGAACATTTTTGTCCTTAATTTTTTTATGTCTAGCT<br>AAAAATTGTTCAAACCGAAGATTTTCACTAGCTAAAAATTATTCAAATCGG<br>GGATTTTCATCTACCATCATTTCTATAGTTGGAGTTGGAGCCTCTACGGCA<br>TCTTGAATTGGTGCATTGAGATCACATTCATTCTCAATTTTCATGTTGTGC<br>AGTATAATACATGTAGTCATTATATCATGTAGCACCACTTCTTTTCTCCAA<br>AAATGTGACGGTCCTGCAATAATTGCAAAACGTGATTGCAAAAAGTTCGAG<br>GACAAGGCTCTACTTTGCAATCATCGGAGTCCAAGACGAAACTAAAATTTT<br>AACGAAAAATTTAGAAACTATTAGTGATCCAAATGTTCGTGGTTACCTGCA<br>ACGAGAACAACAACGAATACTTGAAAAAAGAAATCGACAATCACAACCGCA<br>ATCACAACCATAATCGCAACAATTCTCAGAATCATATCCTAATTTTTTTCC<br>GAATAGTGCTAAATTTGAAAACGACCTACCGAATTTCTAAATTATTGTTGT<br>GATCAATTAATTATTATGTCATGTATTGTATTTTATCTTGTATTTAAATTA<br>TTATGTTATGTATTATATTGTATTGTTATCTTGTATTTAAATTATTATGTT<br>ATGTATTATATTGTATTGTTATCTTGTATTTAAATTACCATATCATGTATT<br>GTATTTTTAAATTAATTTTTTTTGCGTATCCTTTATAATGAAAATTAATAA<br>TAAAATAATTTTATTATTCACGAAAATTAGAAAAAAAGTTAAAATACTATT<br>AATTTGAAATTAAAATAGTATATATTAAATAATTTTTTTAAAAAATATTAT<br>ATTACATTTAAAAAAGAATTATGAATATTAGATATTTAATTAATGGAATTA<br>TATGTAAAATAATATGTTAATTAGAAAGTAATAGAAATAATAATAAAATAA<br>TGAAAAAGTAGAAATAAAGAGCGTGAATAGTAGAATTTGGAGAACTATTCA<br>ACTCTCAAAATTTGAAAAATAGAGGGTGATTTGGAGGTGGGTTGGAGTGCC<br>CATTCTCTATTTTACTCTCCAAATATAGAGAATGAAGAGTAAAATAGAGGT<br>GGATTGGAGATGATCTTAGTGACATTTTTGATTCCGCCAATGCTCAGTTGG<br>CGTAGTCGCTGTCAAACTTGAGAAAGGATTACCCCTTTAGGCTTGCACAGA<br>CAGTGACTTATGATGAAATGAAGCCAGAGAAGGCACTCTGTTATCACACTT<br>AAATGAAAATACATGTGTATGGACTAGCAATAAAAGGGGCACTAGTAATTT<br>TAGTAATTGAAAAGCAAGTGTATAGAGAGAGATAATGAGAGAGAAAGAGTA<br>AGTACACTACTACTGCTACTATCCCATATAGCTGTAATGTTGCAGGTCTGA<br>TTTTTGCAGTTGCAGACCCCCTTCTTGGCACAAGCTCTTTTAACTTTTATC<br>TTCTCAAATAATTCTCTCTCTCTCTCTCTCTCTTTTTTCTCTTTTTACATT |

TABLE 5-continued

| Promoter | Sequence |
|---|---|
| | GTGAGGAAAGCTGAACACCCCATTGTATGTATTAGTGTGAGGCCTATCTGC<br>CACAAGGATGTGATGGAACACTATGCTTCCTCTGCTAAAACCCCCACAACC<br>CCAAAACTCTTTTTCACTTCACATTTAATCACAATTCCTCAGTGAAATTAT<br>TCTGTTGCTCTCTCTAATTTCAATTTCAATGTCGGTAAGTCCAAGACCTGG<br>TTTTTCAATTCAAAGGAGCTGAGTTAGTGCAAACACTTGAGGTTTTGAGTT<br>TTGACAGAGACTTGAGTCTCAGAGAAACTACC |
| >StERL2 (clone 1) promoter sequence; (SEQ ID NO: 22 | CCTGGGAGAAAATGAAAGCATGATCTCTTTCTTGTAAATTGTTTCTACCAT<br>ATTTTTTTTGGCACGATAAATAAATTTATATAAAATTGTATGAGTGACACT<br>AGATGACAAGTCACATAACATATATATTCAAATTGATTTGTATTATTTATA<br>GAACGAAAGTCTACTGTTTAACCTTATATAAGTTACAATTTAGTTATGTAT<br>ATAAGTTAAAATTAAATTAAAAGACATTTCGAAATAATATGATTATACCAT<br>TTCGAAATTAATTAGAGAGAGAAATAAGATCTCGCAAAATTAAGTGTCTTC<br>TTGAAATTAAGAACCATTTTTAGGAGATAATTATGTATTTTTTCATTTTTA<br>ATTTGACACGTATGCATATCCACTATTTTGTTTTATTCCAAAGTGACCCCT<br>ACTTCTTTTGGTAATTTCTTTGAGTATTTTAAACTCTAGTCCCCCTTTCTC<br>AAGCAAAAAGGCTCACTCGCGCACGCGCGAAGAGACATTGTGACGCGCTGG<br>ATGGAAAATCCAGAAGCGTAACTGTCAAAAAATAGAACAACTTTGGGAAAC<br>GGGGTGACGGCCGCTGCCACCACTTTTTTCATTTCCAAACACTCATTAACT<br>AACGTCGTTTCACCGCCGTTTACTGCTTAATGAGTATGAATTACACTCTAA<br>TAGTCTATTTTTACTTATTTTTAATGTGTTTATCAAATTATATTTTTAAAT<br>ATAATACTTTAAAAATATTATCATCAATAATAAGAGTAAATTAAAAAATAA<br>ATGACAAATTGTTTCTTAAATTGTTAAATTAAACAATTAAAACTGAATATT<br>TACAAAATACCTCTTAACTTGCTAAATTAAACAATTGAAACTATATTTATA<br>TTAATAAATTGAACTGACAAAAATAAATAAAGGAACTATATATTTTCTCAA<br>TTATATCTTTTTACTAAAATATTATTTTTCTAATACTAGTTAAACTTTTAA<br>AAAACATCTAATAAAGAAAAAGAATTTGTTCAATTATACTTTAGAAGCTTT<br>TATTATTATTATTATTATTAGTAGTAGTAGTAGTAGTAATAAATTAGATTA<br>AATTAAAGAGAGAAGTATTCAAAACTCCCAAAACTATTGTATTAGTTTTAT<br>TTCAGAACTATTGACAATCTTAATTTTTTTTTTTTTAATTTGACTAGGTGA<br>ACTTAAATATACTTCATTTTTTGCAAAACAAGTGAAGTACACTCTTAAATT<br>TTCATCAAGTTTAGAAATGTTTTCAACAATTTACTAGACTCTTTATTAAGA<br>ACTTCATGTTCTTTCAAGAGTTTATGAGCACTTGCTATGTCATGTTACAGA<br>TCAAGAATATCTACAGAGTGTATCTAAATTTAGTACTAGTAAAGTAGAAAA<br>TGTATTACTTATCTCTCAAACAATAGGTATTCATTATACTATTTTGAGATG<br>TCCAACAATTTTTTTTCACTTTATGAAATCAATGAATAATTTAACACTTAG<br>TTCCTAATTCCCAGTAAGCATTAATTATAGTTATTTACTTATTATATTTTT<br>CAACACATTATATTGAAAAAGTGATATAGTAAATCTATCTTTTTATTTTAT<br>TATTTCTTAAAATTTGTACAAACTTAATAATAGACAAATATTGTTGAATAG<br>GAATAATAATTTACATTAAATCCAATATATTTTTCAATAGTTGTCACTAAA<br>TGAAAATACTTCATCTGTTTCAATTTATGTGATAGTTTTCATTTTTCAAAA<br>GTCAGACAATTATATATTTATAAATTAAGTAAAAAATATTATAAGTCACAC<br>TAATTAACAATTCGAAATATTCGGTACGGAGGAACTAACACTTATGTTTTT<br>AGACCATATTAGTCTTTTCTCTCTATTTATTATATAATATTGAGAGGAGAG<br>TGCAACCACCATGGCAACTTTCTCTGTCTTCATAAAACGCAGCTGACATTA<br>AAAACACAGACACACACTTCGCATTTCATATCCCTCTCACTACACGCCAAA<br>TGCCTGCTCTTCCTATTTCTCTTCTTCTTCTTTTTCTTCTTCTCTCTCATT<br>CACATAACACACATTCTTGTACTAACTCTGCATCATAAACTCTACCCCACT<br>TTCTTCTTCTTCTCCGGTCATATTGCTCTGAAACTCCACTTATTGCTCTCT<br>CCCGGCATTTATTTTTAGTTTCTCAGAAATA |

Example 8

Inhibition of Nematode Infection in Transgenic Potato Plants Expressing miRNA Directed Against the StCLV2 Gene Transgenic potato plants that expressed an artificial miRNA (amiRNA) directed against the endogenous potato StCLV2 gene (SEQ ID NO:11) were generated and assayed for both expression of StCLV2 and for resistance to *G. rostochiensis* infection. Two independent transgenic potato lines tested exhibited both reductions in expression of the endogenous StCLV2 gene and reductions in the numbers of *G. rostochiensis* (FIGS. 19 A and B).

Example 9

Soybean Nematode CLE Receptor Genes

Sequences of various candidate soybean nematode CLE receptor genes are provided in Table 5. Inhibition of the expression of such genes is anticipated to be useful in the control of nematode infections in transgenic plants. It is further anticipated that promoter sequences associated with these soybean genes will be useful in providing nematode inducible expression of operably linked sequences. Start and stop codons are underlined in the genomic and cDNA sequences provided. The soybean PNCLEPRG promoters and 5'UT of Table 5 (SEQ ID NO: 23, 26, 29, 32, 35, 38, 41, 44, 47, and 50) thus comprise the nucleic acid sequences located 5' to the start codon of those genomic sequences.

TABLE 5

| Soybean Genomic DNA sequence, cDNA sequences, and protein sequences | |
|---|---|
| Sequence Description | DNA OR PROTEIN SEQUENCE |
| Glyma09g29840 gDNA and about 2.8 kb of promoter and 5'UT Sequence (SEQ ID NO: 23); Soybean BAM1-like gene: ATG start codon and TGA stop codon underlined | CAGTTCGAATCCAGGTTGCATGGAGATACAGGAAGAAACGTAAAAATTGTGTTGATACCTCAAAA<br>TTAGATCAATCATTTAACTCATAGGTTGTATAATCACCTGAATTGCTTGTAATTACCATGCACAA<br>TTCCTTTAAAAATTAAACAACAAGCAAATGTTACTGTTGGAGAGCAATTCAAATTTCAAAATAAA<br>TGGAACTTGTGAAAATTCAAGGAGATATTTTTAGGAATTTGTTATGTTAATTTCAAATCTTTAGA<br>ATTTTATCTAGATTTAAATATTTTATTAATTTGTTTAACTTATTTTAGGGATTTGTTTCCTTTTT<br>TAAAAGATTAGAATATGATAATATTTAAATTTTGTATTGTTATTTAGCTTTATATATAGAGCCAA<br>GAAATACAAATTTTATAATGTGTTCCATCTAAGATTTCTTGAACGTGTGATAATTTTGTTGTGTA<br>GAAAATTTTTTCCAACGGTTAACATTTTATTAGTAGTGCTTTGCTTATAATGCAAAGAGCCTTCT<br>CCTTTATTTTATGTCTACAATAAGTAATGAATTTATAAGGAATGAAAATAACTCTTAACTCTCAA<br>GAGAGGAAAGAACTTTGGTAAACAAGATTTCATATGTTACAGCCAGACTTACACAGAATATTTCA<br>TTTCACACAGCTCAGATGATTTTTAGAGAAAATGTACCCGATATATATTCTTCTTTTAAAGGCAG<br>AGTTGAAATCTAAATTATATGAGCAAAATATACAACCTATACAGTATAGACAGAATCAGAAATAA<br>AGTTCATATTTCTTAGATTACGGTATGAGAGTCACTGAGTCAATAACTTTTTACTACGAGAATAA<br>AGAAATGGAATGATTGAATGAGCAAAATATACCCCTGAATTCCATTTTCCTAGAAAGAGAAATAG<br>CATGCGATTGAATAAGAGAATGGCACCATCAAGATTGTGAATGAGAAAGAAGAAATGGAGGAAAC<br>TTGTGAATGGAAAGAGAGTGAGAATGGGAGAGAGCATAGTGTTGGACAATGACATTGTGACTGTA<br>AGGAAATTAATGAGTAACTAGAGAACGGAACGGAACTAACAAGCTTCTTGTTGTGTTTGTGATTT<br>AAGTGTTTGATGGAGTTTTAAGGATTCAATACAATGAAAGCTACGTGACAGTTAAATATATGATA<br>GATTCATCCTTTGAGTTCCAAGCAGTATACGTGAACGGAATCAACGTTGATCTTTAGGAAGATCA<br>TTCTCTCCGCTCGGAAGATCTTTTATCGTTTAATCGAATCATTTTTTAAAATTTTCAGTTTTCAT<br>TATCATGGTAAGTTTATTGATTTTTTATAATAATTTTTTTTGAAGTCATATAAAATATAATATTT<br>TATTGATTAGAAATGTAAAATAATTTACAATAAGGGAAAATATTTATTGAACATTTTTATAATAT<br>TAGAAATAGATTAAACTAATACAGTATTTCGGTATTGTATTGCATATATGTTTATCTATAACTAT<br>TATTTTTAAATTATCTTTTAATATATATAACGATTTTTTTTTTATAAACTTTCAAAATGTAGATG<br>TTACTATTTTTTCCTAAAACAATATTATCACTATTTTTTCATTTTTTTTCTTTTGAAAAAAAAAG<br>AAAATAAAGATAAATATATGAAGTGTCTTTCTTTCAACTGGTCTTATGTAAGAACAAATTACACT<br>CTATGCTCAGGACTTATTATACTTATACTTCCTACGTTAAAATGTATTTTTTTTATCTCTTCTAA<br>AGTAAATTATCATCGTTTAACTTTTGAGAAAAATGTCAAAAAAAAATCCATACACTTAACTCTCA<br>CAATCTGATTCTTCTCCATCTTTATTGGCCTCTTCTTTGTCATCCACCCTCCCGGTCAGCTAATT<br>TTTTTGTTATAATATTATTAATATGAAATATTCATCAACTTTATCGATAAATAATTTTTATTAAA<br>ATACTTAATTAAATATTTTTATGATGATATTTTTTTCTTTTAATTATATTTTTATTTTTCTTCAC<br>AAGATTAAAATTTAATATCTTTCTTAACGAGATTAAATAAATATTTCATCAACATATTTTATTTT<br>TATATATATATATTTTTTAACTCATCATATCACTTATCATATCTATATTTATTTTTATGTATCTT<br>AATACATCATTTTAGATGGGCAAATTAAATATATTTATCCAAAAGTAATGTCATGAGAATGAGAA<br>GAAAAGTTACATCACGCCTCCTTCTGGCCTTCTCCTAAATTATCGAGATTAATACCTTGTGCCTG<br>TAAATTTGGTAACCAGAAAAAAGAAAAATCATGTGAGGTAGAGGATTTTTTCGAATGTGTAAAAA<br>TAGATTTCTTGAGTGCCTAAGGTGTTTGCATTCAGCAATGGCACAACACGTGTCAAGTCCCAATC<br>TTACAAGAACCTTCCTTCCTACCGAAAGTCCCGTCACGACACGTGAGCAGTCACATCCGTCACGT<br>GTCACCTTTTCATCGACCATGGGAAGATCTTTCGGCACCGCACTTTCTGGTATCTTCACGCGCAA<br>TCCCCATCCCACCGTCCATTCTCTCACACGCTCGAGCCATCGTAGCCGTCGCCCCCTCACCCGTC<br>CCCAACTCCGCCACGCATCCAAATGACACGTGGCGCTAAAGTAACGGTCAAATCCACAATATTAC<br>TTATTGTAACCTTATCCTCTCCTCACCCCTCACCCCCCCCCTTCCCCCTATAAATCCCCCCTTTCC<br>CTCCCTCCAATTTCAACCTCACTCTGCATTCGCTAAACCCAAAACACTATTTTATTATCTTCTTC<br>GTCTGTTCTTTGCATTGAAGAAAATTTCTTTGAATTGAAGAAAACTTGAAATCGAATTGTGAAAC<br>AGAAAATAAACCAAAGGAAATTTTTACTGATTGAATTGTAGAGATTGGAAAAATGGCGTTGAGTA<br>TGACTCAACAGATCGGGACCCTAGCTGGTGCGACGGTGCCGGATTCCTCGGCCGGAGAATCGACC<br>GCGGCGGTGAGTGCTGCCGCGGTGTGGAAGTCACCGACGGCGAGTCTGAAGTGCAAGGTAATGAG<br>GACGGATGGCTGCGCGGAGGGGCTTTCGCCGCCGCTGAGTCCGTGCAGGTCGCCGGTGCTGCGGG<br>CGGATCTGTCGGCGGCGTGTCAGGCATTCACGGCGGAGGTGGCGGAGGAGGAGTACGTTGCCGGA<br>GGGAAGGAGGAGAAGGGGAAGGGGAAGGAGGGAGTGCCGGTGTTTGTGATGATGCCTTTGGACAG<br>CGTGACGGCGGGGAACGCGGTGAACCGGAAAAAGGCGATGAACGCGGCGATGGCTGCGCTGAAGA<br>GCGCGGGGGTGGAGGGGGTGATGATGGACGTGTGGTGGGGTTTGGTGGAGAGAGAGAAGCCTGGG<br>GAGTATAATTGGGGAGGGTACGTGGAACTCATGGAAATGGCGAAGAAGCATGGCCTCAAGGTGCA<br>GGCTGTTATGTCATTTCACCAATGTGGCGGTAACGTCGGAGACTCTTGCACGTGAGTCTTATGCA<br>ATCCCTTCTTCTTCCTTCTTTTTTTCTTTTTATTTGTCATTTGTGATTTTTATTTTTACTGGCGA<br>AATCTTATTAGATTCTAGATTAATTGGTTTTAACAATTAGAATTGTTACTAGTATTTTTTTTTAA<br>GTTTAATTTCTGCGAATTGGTTTTGAAATCTGAAAACTAATTGAGTGACACCATGAAAAGATTTT<br>ACGTTTTTGATACATTCTTGTTGGTTTTTTTTAACGTTAAGTTTTTGCTTTTAATTCAATTTACC<br>ATGAAATTCACATCTTTATCTTTATTGGTAAATATGTGGTGTTATTATTATATGGTGTTTTCGTT<br>GATTATGATTGAAAATGAGAGGCGTGCCCAGCACGGTGCAGCTCGTTTGTGAAAAATAAAATAAA<br>CGTTTTAAAAGGGGTTTTGTGATGGGAAATGAAGCCATGCCATGTGATGTTGGACTTGTATCACT<br>TTGATTCGAAGTATAGTATTTTTCTTTTCTATTGAATATTCAACTACGAACCTGGAATAATTGAA<br>TCTTGAGAATTGTGTATATGATATTGATAATTATTTAGCCATTTCTCTTTAACTGAAATTTTAAT<br>GTTTCATTTTTATTAGTACTTGAAGATTCTGAATTTAATTAAATTTTAATCCTTTTTTTACAGAA<br>ATTAATTTTTAATCTTTGTACTATACAGAATGAGTTAACATTCTTTTATAATTAGGGATAATGAC<br>AATTTTAATTTAGTATTTTAAACATGATGATTATATTTATTTTTATCATAATAACAACAATTTTC<br>CTGAAAAAAAAATAAAAATAATTTCATAAATCTTTATATTATGATTTAAAGAGGCGTAATGAGCA<br>CGGTGATGCTAGTCTTATTTTCTTTCATTTTTTGTGGTCCTTATGTAAAAAGTAAATACAAAATA<br>CATGAGAAAAGAGTGTGCTTTCGTGATGGGAAGTGCCAAAGTGGGACCACGTGAGGATGGACTTC<br>TAGTTCTACTGATTCACGTCGGCATCGCCACATACAGTAGACTAACTTTTAAGGACACCTTAAAT<br>TTAGTGGACCCGATATCTTAATTTATTTTTCGGTCCATTTTTTGAAAAAGTATTCCTCAAATTCT<br>CTCCATTTTTCTTAAAACATGTTATTCGAAACAAATAATCCAGGCATAGTTTCTGTTTATATATT<br>TTATGTAAATTATTTTTGACAGTTATAAGATTATCTAATGGTTTCGAATTCGAATCATGGACATG<br>TGGTAATGTTGATACTAAACAGTTGGAGGAGAGTTTAGCATCCATAATGATTCTATTCGGTTTCG<br>AGTAGAATTATCTCTTATTAGAGATACATCTGATCTACTAAAAAATATAAATAGTTAGTGTAATT |

TABLE 5-continued

Soybean Genomic DNA sequence, cDNA sequences, and protein sequences

| Sequence Description | DNA OR PROTEIN SEQUENCE |
|---|---|
| | TTAGATATTACTGCCATTAATTTTGCTATAAGTTAGCACTGTGTTGGAATACCAGTTGTCTTATT<br>GGTGGGCTTATCAGATAGTTTGTCCTGTGTTCAGTATTCCTTTGCCCAAATGGGTTGTGGAGGAG<br>ATTGATAATGACCACGATCTTGCATATACTGATCAATGGGGAAGAAGAAACTATGAATATATATC<br>ACTTGGATGTGATACTTTGCCGGTGCTCAAGGGACGATCCCCAGTTCAATGTTATGCTGATTTCA<br>TGCGTGCTTTCAGAGACACTTTCAAGCACCTCCTTGGTGATACCATTGTGGTAAATATCATTCTC<br>AGTGCACTTTTACATCATGCTGTGATTTGTTGTGCTATTTAAATATAACTTCTCATCTGAACTTC<br>TTTTACTGGCAATATTTCAGGAAATCCAAGTTGGGATGGGACCAGCAGGTGAGTTGCGTTACCCT<br>TCGTACCCAGAGCAAAATGGGACATGGAAATTCCCAGGAATTGGTGCTTTCCAATGCTATGACAA<br>GGTATATATATTTATGTTTTTTTTTCCTTCTCCTTGTTGTAGTCCTTTATATATAATTGTCTTA<br>GGATTTGTTTGGATAAATAAATTTCTTCATGAACAAAGAGGAGAAAACAAGGTAAAATGTGTTCT<br>AAACCTCTAATACTTAATTATGCTATGGTGCAGTATATGTTGAGTAGCTTAAAAGCTGCTGCTGA<br>AGCTCACGGTAAGCCTGAATGGGGAAGCACAGGCCCTACTGATGCTGGCCACTATAACAACTGGC<br>CAGAAGACACTCAATTTTTCCGCAAAGAAGGTGGTGGATGGGATGGTCCATATGGTGAGTTTTTC<br>CTCACTTGGTACTCTCAGATGCTGTTGGAACATGGTGACAGGATTCTCTCATCAGCCACGTCGAT<br>CTTTGACAACACTGGAGTTAAGATCTCAGTGAAGGTTGCCGGCATTCACTGGCACTATGGTACAA<br>GGTCTCACGCCCCAGAACTCACTGCAGGGTATTACAACACCCGATTCCGTGATGGCTACCTCCCC<br>ATTGCTCAAATGCTGGCGCGCCACGGTGCCATCTTTAACTTCACCTGTATCGAGATGCGCGATCA<br>CGAGCAGCCACAAGAGGCCCTTTGTGCACCTGAGAAGCTGGTGAAGCAAGTGGCTCTGGCAACGC<br>AGAAGGCACAGGTTCCACTTGCCGGCGAAAACGCGCTGCCACGGTACGACGAGTATGCACATGAG<br>CAGATCATAAGGGCATCACAATTGGATGTTGATGGTGAGTCTGGTGATAGAGAGATGTGTGCCTT<br>CACATACCTGAGGATGAATCCGCATTTGTTTGAACCAAATAACTGGAGGAAGTTTGTGGGGTTTG<br>TGAAGAAGATGAAAGAAGGGAAGAGTGCACACAAGTGTTGGGAAGAGGTGGAGAGGGAAGCTGAG<br>CATTTTGTGCATGTTACACAGCCTCTTGTGCAAGAGGCTGCAGTGCTGATGCACTGAGAATTGTT<br>GAACATCCTTGTGGTAATAGGGCTTAGGAATAAGTCACAAGGAGGCTGTGTGAAAGTTTTAGTGA<br>ACCAACAGCCCAGGTTTGTGGCTTTGAAGATGTAAAATTTTGTATTATATTGTTTTGTATTGTAT<br>GCACCTAAAACTTCTATTTGTGACCCTTTTACATTGTGTACGTAATCATAGACTTTGGGGTACTG<br>TTTCCTTAAAAGTTACTCTACTTTGTACAAGTAGTTACTTAATCTGGTTTAAAAAAATGTCATCC<br>CTTAATCTG |
| Glyma09g29840 cDNA SEQ ID NO: 24); Soybean BAM1-like gene; ATG start codon and TGA stop codon underlined | ATGGCGTTGAGTATGACTCAACAGATCGGGACCCTAGCTGGTGCGACGGTGCCGGATTCCTCGGC<br>CGGAGAATCGACCGCGGCGGTGAGTGCTGCCGCGGTGTGGAAGTCACCGACGGCGAGTCTGAAGT<br>GCAAGGTAATGAGGACGGATGGCTGCGCGGAGGGGCTTTCGCCGCCGCTGAGTCCGTGCAGGTCG<br>CCGGTGCTGCGGGCGGATCTGTCGGCGGCGTGTCAGGCATTCACGGCGGAGGTGGCGGAGGAGGA<br>GTACGTTGCCGGAGGGAAGGAGGAAGGGGAAGGGGAAGGAGGGAGTGCCGGTGTTTGTGATGA<br>TGCCTTTGGACAGCGTGACGGCGGGGAACGCGGTGAACCGGAAAAAGGCGATGAACGCGGCGATG<br>GCTGCGCTGAAGAGCGCGGGGGTGGAGGGGGTGATGATGGACGTGTGGTGGGGTTTGGTGGAGAG<br>AGAGAAGCCTGGGGAGTATAATTGGGGAGGGTACGTGGAACTCATGGAAATGGCGAAGAAGCATG<br>GCCTCAAGGTGCAGGCTGTTATGTCATTTCACCAATGTGGCGGTAACGTCGGAGACTCTTGCACT<br>ATTCCTTTGCCCAAATGGGTTGTGGAGGAGATTGATAATGACCACGATCTTGCATATACTGATCA<br>ATGGGGAAGAAGAAACTATGAATATATATCACTTGGATGTGATACTTTGCCGGTGCTCAAGGGAC<br>GATCCCCAGTTCAATGTTATGCTGATTTCATGCGTGCTTTCAGAGACACTTTCAAGCACCTCCTT<br>GGTGATACCATTGTGGAAATCCAAGTTGGGATGGGACCAGCAGGTGAGTTGCGTTACCCTTCGTA<br>CCCAGAGCAAAATGGGACATGGAAATTCCCAGGAATTGGTGCTTTCCAATGCTATGACAAGTATA<br>TGTTGAGTAGCTTAAAAGCTGCTGCTGAAGCTCACGGTAAGCCTGAATGGGGAAGCACAGGCCCT<br>ACTGATGCTGGCCACTATAACAACTGGCCAGAAGACACTCAATTTTTCCGCAAAGAAGGTGGTGG<br>ATGGGATGGTCCATATGGTGAGTTTTTCCTCACTTGGTACTCTCAGATGCTGTTGGAACATGGTG<br>ACAGGATTCTCTCATCAGCCACGTCGATCTTTGACAACACTGGAGTTAAGATCTCAGTGAAGGTT<br>GCCGGCATTCACTGGCACTATGGTACAAGGTCTCACGCCCCAGAACTCACTGCAGGGTATTACAA<br>CACCCGATTCCGTGATGGCTACCTCCCCATTGCTCAAATGCTGGCGCGCCACGGTGCCATCTTTA<br>ACTTCACCTGTATCGAGATGCGCGATCACGAGCAGCCACAAGAGGCCCTTTGTGCACCTGAGAAG<br>CTGGTGAAGCAAGTGGCTCTGGCAACGCAGAAGGCACAGGTTCCACTTGCCGGCGAAAACGCGCT<br>GCCACGGTACGACGAGTATGCACATGAGCAGATCATAAGGGCATCACAATTGGATGTTGATGGTG<br>AGTCTGGTGATAGAGAGATGTGTGCCTTCACATACCTGAGGATGAATCCGCATTTGTTTGAACCA<br>AATAACTGGAGGAAGTTTGTGGGGTTTGTGAAGAAGATGAAAGAAGGGAAGAGTGCACACAAGTG<br>TTGGGAAGAGGTGGAGAGGGAAGCTGAGCATTTTGTGCATGTTACACAGCCTCTTGTGCAAGAGG<br>CTGCAGTGCTGATGCACTGA |
| Glyma09g29840p protein SEQ ID NO: 25); Soybean BAM1-like gene; | MALSMTQQIGTLAGATVPDSSAGESTAAVSAAAVWKSPTASLKCKVMRTDGCAEGLSPPLSPCRS<br>PVLRADLSAACQAFTAEVAEEEYVAGGKEEKGKGKEGVPVFVMMPLDSVTAGNAVNRKKAMNAAM<br>AALKSAGVEGVMMDVWWGLVEREKPGEYNWGGYVELMEMAKKHGLKVQAVMSFHQCGGNVGDSCT<br>IPLPKWVVEEIDNDHDLAYTDQWGRRNYEYISLGCDTLPVLKGRSPVQCYADFMRAFRDTFKHLL<br>GDTIVEIQVGMGPAGELRYPSYPEQNGTWKFPGIGAFQCYDKYMLSSLKAAAEAHGKPEWGSTGP<br>TDAGHYNNWPEDTQFFRKEGGGWDGPYGEFFLTWYSQMLLEHGDRILSSATSIFDNTGVKISVKV<br>AGIHWHYGTRSHAPELTAGYYNTRFRDGYLPIAQMLARHGAIFNFTCIEMRDHEQPQEALCAPEK<br>LVKQVALATQKAQVPLAGENALPRYDEYAHEQIIRASQLDVDGESGDREMCAFTYLRMNPHLFEP<br>NNWRKFVGFVKKMKEGKSAHKCWEEVEREAEHFVHVTQPLVQEAAVLMH |
| Glyma16g34360 gDNA + about 2.7 kb promoter and 5' UT sequence(SEQ ID NO: 26) Soybean BAM1-like | TATTAGCTAAACTTTGTCATAGGTTGTACGATTATAAAATATCTTTGATAGTTTCACTTATTTCC<br>ATGTACAAATGTTCCTTCTAAAAGGCATGTATTAAGCGTCAAGAACTTAATTAAAAAATTGAGAA<br>TTGGATAACTCGCCAGAAGCAGCCATGAATTTTAACATGAATCAGATGAGCAAGTTCCATTTCTT<br>ACTTCCCCTACATAATTGGTCCAACAAAATACATAAGAACAATAAACATAGAACTATTGTTGAGG<br>AATCAGGAAGACAAACAATGACCATCTAATATCCTTTTAGAGTAGTAGTTGAAGATGCCAATGGC<br>AGTTGACAACTAGAAGAACATGTTGAAAAGCAAACGAATAGTTCTTAATTGAGAACAAGCATCAA<br>AGCACCCTCACATGATTTTTAGAGAAAATGTACCCGATATTTATTCTTCTTTTAAAGGAAGGGTT<br>AAAATTTAAATTATATGAGCAAAATATAACTGTTGTTTTTTTAATAAGAGTAGGCAGAAATATTA |

TABLE 5-continued

Soybean Genomic DNA sequence, cDNA sequences, and protein sequences

| Sequence Description | DNA OR PROTEIN SEQUENCE |
|---|---|
| gene; ATG start codon and TGA stop codon underlined | AACAATAAAAGGGAGCATAAAGAAAAAAAAAATTGAGATTGCAAAGGTTTATTTTAAAAGCAGAG<br>AAAAGATAGTAACTGCTAACAAAAAGATAACATCACTCACTAACAAATCATGCCTAGAGAATAGG<br>ATCAAAACTGTTTTATCCTATCAGTCAAATGACTTTTATTTTTCCTAAAAAAATAGCATAAAAGT<br>CTTATCTACTGTAGTTTCAACAGTCAAATCTTAACAATAACCTTAAATTTAAGGTGGATGATGAC<br>ATTCATCCTTTGAGCTCGCAGTATAATATACCTCAACACAAGTTATTATAGACTCATTCTATGCC<br>TTCGGAGTTCGCACTCCTAATAATTATACGCTAACGGATTCATTTATCCATCATATTTTTAAATT<br>TCAATTTTCTAATGAAAAAATACTATAACTACTCACTTTTTATTTACACTGTGATTTAATAATAA<br>ATTAAAAAAATATTTTTTAGATCATCATCCAATTATAATTTTTTAATGTATAATAAATTTGTTGA<br>CTTTCATGATACTTATTTTAAAAAAATTATTAATATTGAATTCTGATTAGATGATATTAAACTCA<br>AATAAATTATCATTTATGTTTAATTTATTGATTTTTATAATAATTATATTTAAAATTACATAAAA<br>TATAAATTTTTATTGATTAAAAAGTGTAAAAGCTTTTTACAGAAATGGTGGATATCTATTAAACT<br>CTTTTATAATAGAATCAAACTAATATTTTAGTACGTGAATTGAATAGAGTAAATGTTTATCTTAT<br>AAAACTATCCTTTATAATAATAATAATAAGGCATGCCCGATATTATTATTACTATTATTGAAGGA<br>ATATATAAGCATACGCATTTAAAAAAAATACCAAATATACTAGTTTAATTTGTAATCACAATTTT<br>TAATCTCTAATCATCTTCAATCTAGGAATAAGTCTCTAGCTATCATATTTAAACTGAGTTTAAAA<br>TATTTCACATATTTTGTTAATGTCAAATGACAATGTTTATTTGTTATGAAGTAATCAAAACCACG<br>AAACAACAAAACCAAATCTAGCTCTATATTAATCACAAAATAAGTATTATATTAAAAATATCTCA<br>AAATAAATATTATATTAATTTTTCAATGTAATATTAATTTTTCTATATTAACATCTTTGATAAGT<br>ATCACTTTAAATTTCAATGTAATACTAAAAGTTAGATTTATAAAATTATTATTCTCTTTTATTTG<br>TTTATTAACTTTTGTAAATAATTTATGTCAACATTTTTTAAACAAAAAAGAGTAGCTATTATATT<br>ATACTATTTTTAAAACATCTACTTTAAAAAAGTATATCATCTATTTATTACTGGTTTAATCATGA<br>TTGAATCACAATTGAATCATTAAAATTTAAATAAGTATCATCACTTTTTTTGTCCTACCTATTAT<br>AGTCTGCAACTCATATTAAGTTGAATAGCTAATTTTGGGATGTGAAAAAATAGATTTCATGACCA<br>TTGGCCGATGACATGACACTTGCCGTGTTCCCAATCTCACAAGATCCTTCTCCTCCCATATTTTC<br>TCTTGGCTCCTACATCGACACGTGACCACACATCTCTCACGTGTCACCTTTCCATGGACCATCAC<br>CTTCACGCGCAATCCCCATCCCACCGTCCATTCTCCCAAATGACACGTGGCGCAAAACTAACGGT<br>CATACCCAAAATATTAATATTACTTATTGTAACCTTATCCTCACCACCCCCTTCCCCCTATAAAT<br>ATCCTTCCCCCTCACTGCATTCGCTAAACCCAATAAATTGTTATTTTCTGTTCTTTGCATTTGAA<br>TCAAAGCAAATTTTGATTGATTGATTAGAAAATGGCGTTGAATATGACTCACCAGATCGGGACCC<br>TGGCTGCTGCGACGGTGCCGGTGCCGAATTCGTCTGCCGGAGAATCAACCGCGGCGATGAGTGCC<br>GCCACTCTGTGGAAGCCGCCGGCGGTGAGTCTGAAGTGCAAGGTCACGAGGACGGAGGGCGGCGC<br>TGAGGGGCTGTCGCCGCCGCTGAGCCCGTGCAGGTCGCCGGTGCTACGGGCGGATCTGTCGGCAG<br>CGTGTCAGGCGTTCACGGCGGAGGTGGCGGCGGAGGAGTACATTGCCGGAGGGAAGGAGAAAGGA<br>GAGGGGAAGGAGGGAGTGCCGCTGTTTGTGATGATGCCGTTGGACAGCGTAAAGACGGGAAACGC<br>GGTGAACCGGAAGAAGGCGATGAACGCGGCGATGGCGGCGCTGAAGAGTGCGGGGGTGGAGGGGG<br>TAATGATGGACGTGTGGTGGGGTTTGGTGGAGAGAGAGAAGCCTGGGGAGTATAATTGGGGAGGG<br>TACGTTGAACTCATGGAGATGGCGAAGAAGCATGGCCTGAAGGTGCAGGCCGTTATGTCATTTCA<br>CCAATGTGGCGGTAACGTCGGAGACTCTTGCACGTGAGTATTATTATGCAATCTCTCTCATTCTT<br>TTTTGTCATTGCTGATTGAATGTTATTAGATTCTGGATCAATTGGTTTTAACAATTAGAATTGTT<br>ACTATTAGATTCTGGAGTACTTTAAAGGTTTCTTTTAGGTTTAATTTCTGTGAATTCGTATTGAA<br>ATCTGAAAATCAATTGAGTGACACCATGAAATTTTTTTACGTTTTGGAAACATTCTTATTTAAAA<br>AAATTTTAACGTCGTGTTTTTGCTTTTAATTATATTTGTAGTTTTTTAAAATAAGCAATTATATT<br>TTATTAGTATTAAAATTGCTGGACACGTGAAACAAAACGGCTGGATACATTCTTATTAAAAAAAT<br>TTAACGTCAAGTTTAGATACCTAAATATTGTTATACGATATATATCTATAATGTTTGGATAATGA<br>AATTGGTCGGACAAGCAATTTGGATGAAAATTCATGCAGTGTGAAAATGTTAATTTTTTGTGAAA<br>GTAATTCGTTTAATTTATATTTTAATTTTTATAGTTTAAAATTAATATTTTTAGTTCTTATAATT<br>TACATTTTAAATATTAACATATATTTTAATTAATTTCATATATTTATCTTTATAGGAAAATATGT<br>GGTTATTAATTATATGGAGTTTTCGATGATTATGATTGAAAATGGGAGGCGTGCCCAGCACGATG<br>CAGCCTGTTTGTGAAAAATAAAATAAACGGATAAAAGGGGTTTTGTGATGGGAAATGAAGCCAAT<br>ACTGCCATGTGAATGATGTGATATTGGACTTGTATCACTTTGCTTCTAAGTGTAGTATTAGTTTT<br>CTCTATTGAATGAACTAGGAACCTGGAATAATTGAATCTTGAGAATTGTGTATATTCATAATTAT<br>TTAGCCATTTCCCTTTTACTGAAATTTTAGTGTTTCATTTTTATTACTACTATTTTGATCGAAGA<br>TTATGAAGTTAATTAAATTTTAATCCTTGTGCTATTACGAATGAGCTGGCATTCTCTTAAAATTA<br>GGGATAACAACAATATTAATTTAGTATTTTTAAGCATGATTATTATGCTTATTAAAAAAACATAA<br>TTATTATATCTATTTTAACATAATAACAATGATTAAAAATAATTTCATAAATGTTTATATTTTGA<br>TATGATTTAAAGAGGCGTAATGAGCACGGTGCAGAGTCTTATTTTCTTTCATCTTTCGTGGTCCT<br>TGTGTGTAGTAAATACAAAATACGTGAGAAAAGAGTGTGCTTTCGTGATGGAAAGTGCCAAAGTG<br>GGACCACGTGAGGTAGCACTTGTAGTTCTACTGATTCACGTCGGTATCGCCACAAACAGTAGACT<br>AACTTTTTAAGGATCTACTACCTTTAATCAAGTGGACCCGAGATCTTAATTTGTTTTTCAGTCTA<br>TTTTTTGAAAATGTATTTGTAAAATATTTTCATTTGTTTAAAATGTTATTTGAAACAAATAATCC<br>AGATATATTTTCTGTTTATATATTTCATGTAAATTATTTCAACGGCTATCAATTATAGTAAACTA<br>GTTTTCATTTATCAGTGATCGCATAAATCAACTATTGATTTCGAATTTGAGTCTTGGACATGCGG<br>TAGTTAAATAGTTGGAGGAGGGTTTAAAATTCACAGTGATTCTATCTGGTTCCAGTAAGAGATAA<br>TCCAGTAGAATTATCTCTTACAGGAGATAGCTGTGGTTTATTAAAAAAAAAAAAACTAGTTCATA<br>TTTTTATGATTTTAGATATTATTGCCATCAGTTTTGCTGTAAGTTAGCATAGTGTTGGAATACCA<br>GTTGTCTTATTGGTTGGCTTATCAGATTGTTTGTCTTGTGTGCAGTATTCCTTTACCCAAATGGG<br>TTGTGGAGGAGATTGATAATGACCCCGATCTTGCATATACTGATCAATGGGGAAGAAGAAACTAT<br>GAATATATATCACTTGGATGTGATACTTCGCCAGTGCTCAAGGGCCGAACCCCAGTTCAATGTTA<br>TGCTGATTTCATGCGTGCTTTCAGAGACACTTTCAAGCACCTCCTTGGTGACACCATTGTGGTAA<br>ATATCTTTCTCAGTGCACTTTTACATCATGGTGTGATTTTTGTTGCTATATAACTTCTCATCTAA<br>ACTCCTTTTACTGGCATATTTCAGGAAATTCAAGTTGGGATGGGACCGGCAGGTGAGCTGCGTTA<br>CCCTTCTTACCCAGAGCAAAATGGGACATGGAATTTCCCAGGAATTGGTGGTTTCCAATGCTATG<br>ACAAGGTATATATATTTACGTTTTTTTTTCCTTCTCCTTCTTGTACTCTTTTATATATAATTGTT<br>TTAGGATTTGTTTGGATAAATTTCTTGATGAACGAAGAGGAGAAAATTAGGTAAAATGTGTTCTA<br>ATACTTAAATTATGCTACGGTGCAGTATATGTTGAGTAGCTTAAAAGCTGCTGCTGAAGCTGAGG |

TABLE 5-continued

| Soybean Genomic DNA sequence, cDNA sequences, and protein sequences | |
|---|---|
| Sequence Description | DNA OR PROTEIN SEQUENCE |
| | GTAAGCCTGAATGGGGAAGCACAGGCCCTACTGATGCTGGACACTATAACAACTGGCCAGAAGAC<br>ACTCAATTTTTCCGCAAAGAAGGTGGAGGCTGGGATGGTCCATATGGTGAGTTTTTCCTCACCTG<br>GTACTCTCAGATGCTGTTGGACCACGGTGACAGGATTCTCTCATCAGCCACGTCAATCTTTGACA<br>ACACTGGAGTGAAGATCTCAGTGAAGGTTGCTGGCATTCACTGGCACTATGGCTCAAGGTCTCAC<br>GCCCCAGAACTCACAGCAGGGTATTACAACACCCGGTTCCGTGATGGCTACATCCCCATTGCTCA<br>AATGTTGGCACGCCACGGTGCCATCTTCAACTTCACCTGTATTGAGATGCGCGATCACGAGCAGC<br>CACAAGATGCCCTTTGTGCACCCGAGAAGCTTGTGAAGCAAGTGGCTCTGGCAACGCAGAAGGCA<br>CAGGTTCCACTTGCTGGTGAAAATGCGCTGCCACGGTACGATGAGTATGCTCATGAGCAGATCAT<br>AAGGGCATCACAGTTGGATGTTGATGGTGACTCTGGTGGAAGAGAGATGTGTGCATTCACTTACC<br>TGAGAATGAACCCGCATTTGTTTGAACCAAATAACTGGAGGAAGTTTGTGGGGTTTGTGAAGAAA<br>ATGAAAGAAGGGAAGAGTGCACACAAGTGTTGGGAAGAGGTGGAGAGGGAAGCTGAGCATTTTGT<br>GCATGTTACACAGCCTCTTGTGCAAGAAGCTGCAGTGCTGATGCACTGAGAATTGTTGAACAATC<br>TTGTGCTGATAGATGGCTTAGAAAAGGTCACAAGTAGGCTGTGTGAAAGTTTTAGTGAACCAGCA<br>GCCCAGGTTTGTGGCTTTGAAGATGTAAAATTTTGTATTATATTGTTGTTTTATATTCTATGCAC<br>CTAAAACTTCTATTTGTTACCCTTTTATATTGTGTACGTAATCATTGACTTTGGGGTACTATTTT<br>CTTAAAAGTTACTCTACTTTGTACAAGTAGTTACTTATTTCTGCATCATGAAACTGTTACATGGC<br>GTAACAGCAACAAGAGATGCTATTTTCTTCTATAGGGAAAAATGAATTTAAAATCAATGATTTTC<br>GTTGTGTTT |
| Glyma16g34360 cDNA (SEQ ID NO: 27) Soybean BAM1-like gene; ATG start codon and TGA stop codon underlined | ATGATGCCGTTGGACAGCGTAAAGACGGGAAACGCGGTGAACCGGAAGAAGGCGATGAACGCGGC<br>GATGGCGGCGCTGAAGAGTGCGGGGGTGGAGGGGGTAATGATGGACGTGTGGTGGGGTTTGGTGG<br>AGAGAGAGAAGCCTGGGGAGTATAATTGGGGAGGGTACGTTGAACTCATGGAGATGGCGAAGAAG<br>CATGGCCTGAAGGTGCAGGCCGTTATGTCATTTCACCAATGTGGCGGTAACGTCGGAGACTCTTG<br>CACTATTCCTTTACCCAAATGGGTTGTGGAGGAGATTGATAATGACCCCGATCTTGCATATACTG<br>ATCAATGGGGAAGAAGAAACTATGAATATATATCACTTGGATGTGATACTTCGCCAGTGCTCAAG<br>GGCCGAACCCCAGTTCAATGTTATGCTGATTTCATGCGTGCTTTCAGAGACACTTTCAAGCACCT<br>CCTTGGTGACACCATTGTGGAAATTCAAGTTGGGATGGGACCGGCAGGTGAGCTGCGTTACCCTT<br>CTTACCCAGAGCAAAATGGGACATGGAATTTCCCAGGAATTGGTGGTTTCCAATGCTATGACAAG<br>TATATGTTGAGTAGCTTAAAAGCTGCTGCTGAAGCTGAGGGTAAGCCTGAATGGGGAAGCACAGG<br>CCCTACTGATGCTGGACACTATAACAACTGGCCAGAAGACACTCAATTTTTCCGCAAAGAAGGTG<br>GAGGCTGGGATGGTCCATATGGTGAGTTTTTCCTCACCTGGTACTCTCAGATGCTGTTGGACCAC<br>GGTGACAGGATTCTCTCATCAGCCACGTCAATCTTTGACAACACTGGAGTGAAGATCTCAGTGAA<br>GGTTGCTGGCATTCACTGGCACTATGGCTCAAGGTCTCACGCCCCAGAACTCACAGCAGGGTATT<br>ACAACACCCGGTTCCGTGATGGCTACATCCCCATTGCTCAAATGTTGGCACGCCACGGTGCCATC<br>TTCAACTTCACCTGTATTGAGATGCGCGATCACGAGCAGCCACAAGATGCCCTTTGTGCACCCGA<br>GAAGCTTGTGAAGCAAGTGGCTCTGGCAACGCAGAAGGCACAGGTTCCACTTGCTGGTGAAAATG<br>CGCTGCCACGGTACGATGAGTATGCTCATGAGCAGATCATAAGGGCATCACAGTTGGATGTTGAT<br>GGTGACTCTGGTGGAAGAGAGATGTGTGCATTCACTTACCTGAGAATGAACCCGCATTTGTTTGA<br>ACCAAATAACTGGAGGAAGTTTGTGGGGTTTGTGAAGAAAATGAAAGAAGGGAAGAGTGCACACA<br>AGTGTTGGGAAGAGGTGGAGAGGGAAGCTGAGCATTTTGTGCATGTTACACAGCCTCTTGTGCAA<br>GAAGCTGCAGTGCTGATGCACTGA |
| Glyma16g34360 protein(SEQ ID NO: 28) Soybean BAM1-like gene | MMPLDSVKTGNAVNRKKAMNAAMAALKSAGVEGVMMDVWWGLVEREKPGEYNWGGYVELMEMAKK<br>HGLKVQAVMSFHQCGGNVGDSCTIPLPKWVVEEIDNDPDLAYTDQWGRRNYEYISLGCDTSPVLK<br>GRTPVQCYADFMRAFRDTFKHLLGDTIVEIQVGMGPAGELRYPSYPEQNGTWNFPGIGGFQCYDK<br>YMLSSLKAAAEAEGKPEWGSTGPTDAGHYNNWPEDTQFFRKEGGGWDGPYGEFFLTWYSQMLLDH<br>GDRILSSATSIFDNTGVKISVKVAGIHWHYGSRSHAPELTAGYYNTRFRDGYIPIAQMLARHGAI<br>FNFTCIEMRDHEQPQDALCAPEKLVKQVALATQKAQVPLAGENALPRYDEYAHEQIIRASQLDVD<br>GDSGGREMCAFTYLRMNPHLFEPNNWRKFVGFVKKMKEGKSAHKCWEEVEREAEHFVHVTQPLVQ<br>EAAVLMH |
| Glyma01g40590 gDNA + about 5 kb upstream promoter and 5'UT sequence (start and stop codons underlined; SEQ ID NO: 29); Soybean BAM2-like gene | TTGAGAACTTAACCTACTAAAATTATTCTTTGATGTAATGTTAATGATTTTTTTATTTATAATTA<br>TTCTAATTTAAATATGCATCTACTAGTATATTCTAATTTTACTCCCCAACATAAAAAAGTCTAAT<br>TTATCTATTTTCTCTCTCAAATCCCTTTACAAAACTAAAATAGTAAATTGCATTAAAAATATAGA<br>TGTATAACATGCTAAAGAAAAATTAATGTTTCCCCATGTTACCCCTAAAACTTATCATGCAAATG<br>GATGATCAAGTCATAAGAAATGTAATATTCATAAATAGATAAGAAGATAAATTACATCAAAAGTA<br>GTTGACGGTCAAATTTTCAACAAAAAAGGTTTAGCCTCTTATTGTCATGGAGATTTTATAATTGC<br>AAGAGTAAAATATTTAGTAAAGGGGAGAAAATAAAAAAGGGAATAAAGGAAATGAATGACTCTCA<br>ATATTTATTTCTCCTTCTTCTAGTCTTTGCCTTCTATAATGAAGTGTATTCTCTCTTAAAAATTT<br>TCCTTTGTTTTTTCTTATTCTCTCCTTTTCTTTTATAGATGCATATTAGTGGGCTTCTTGCATTA<br>AGTCTAAGTCTGTCTTTATTTTTCTTAATTAGTCATATTTTTCTTAATTAGTTCGCTTTCCTTAA<br>TTATTCCTCTCTTCTTGAATTATCCTACTTTTTTTTTACTCACTAAGCATAATAAATTCATCATT<br>TTTAATATTTGTTGCACAAAAAATAAAATAATGTTAATTTAACAATTATTTGCTTAAAAAAAATT<br>AGAAGAAAAAAATTACAAATTCTTATATATTTTAACCCTCAAAATATACTTATAATTAGTTGTTA<br>TTGATTTTAAAGTTAACCTATTTTTTCAAGATATCCATGGTAGGTATTTTCAAATTACACACTTC<br>ACATGTAAACTTTGAGGTTGCAAGGGTGAAAACAGGTAAAAAGAATAACAGCTAGCAAAGACATT<br>TAAAATAATTCTAGCAATATAAGTCCAATCTAAAGCGGATACGTCCAGCAATATTCATCCCTCAC<br>CAACTCCAACTTCACTCTCAATAAACTGGAAAATTATAACCAAACATGCTGAATCGTGAAGGCAT<br>CCCTACAATTCCTTCCTAGCCAACCAGCCCAACAATTTTCTTAGCTTTTAGAAATATTATCGTGT<br>GCAATGTGATACACTGCAGTAAGCATCAACAAGAATAGTAACCTGACCTTTCATGCCATATATGA<br>TCGAAGTGGTCAAGAATGGCAAGTAGAAGTGAGGTTCATGCTCTTTAATGATTAATCTAATGGGA<br>TAAAAAGGACAAAGACAAACAGAACTCTTAATAGAAAAGAAAAAAACTAAGTGGGTCAACAATGC<br>ATATTTTGGATTCAAAACCACCACTGTCCAATCGACAACATTGTTCTACAAAACCGGAATGATTG<br>TGATTCATCCGGAGGGTATTTGCTCATTCATGTTCCTTATTGTCGATATGGGCATGCCTAACTAG<br>CTAAGTACAATTTCCTTAATTTCTATTTTGGCACTTACAATCGTAATTAAAACTGAAATCAGGTT |

TABLE 5-continued

Soybean Genomic DNA sequence, cDNA sequences, and protein sequences

| Sequence Description | DNA OR PROTEIN SEQUENCE |
|---|---|
| | TATATATATATATATATATATATATATATATATATATATATATATATATATATATATAAATTAGCAT<br>GCATTATATATTTAAGGGGTACGGGTAACGTGTGTACAATATACTCCTTACAAAAGGTTTATATC<br>TCTGCTCGGCTTCTTATCCCAAAATTAGCAAGCATTAAATGAAGGGTAACGTGTGTTTTGTTCTT<br>ATTAAAAAAAAAACATAGTACAATTTTTTAAGTGGAAACATGGAAATATTTTTCACTCTTTTTAA<br>TGATTTTTTTATAACATAAAATTAAAATATTAATTCTAAAGTAGCCAATAATTATAAATTTTTCA<br>CTAACTATGTATTGTAATGAAAAAAAATATTTTTATATTTTACTTTTGGAAAATTTTAAATTTAT<br>TTGTTAGCAAATGATCTGTTCATGATATATTTTTATTAATTTTAAATATTATAATTTAAAACATA<br>TATATTTAAATTTAATTTTCTGATACAACATTGGAGGATTATATATATAACTGCTCAGATAGACC<br>CCTCCAATAGTCCAATTGTAATAAGAGTTTGAGAACATAAGAAAAAAAATCTTGTAATTACTAAT<br>CTATATTGTGGCTTTCCTCATACAATTGATCCATGGAGAGAAGGAGTAATTCACAATAATAATAG<br>TAATTATTAGTATTATAATAAATGTTAATGTTGGTGACTGCTTGGTCATTTTCTCTTCCAGAAAA<br>ACAGATAAGCTGTGACCTGTTAGTAAGGCCATGGTGGGAGGGACCACTGCATGGCATCTTTCTCA<br>GTGCTACTAGTGCTTCACTTATTACATGATTTTGAAGTTGTCAGTGAGCGGGTAGAAGATGGAGG<br>CCATGGTCCACACTTTGTTGCCGCATTGCAAGAAAATGGTAAAAATGATATTGAATCTGCAACCC<br>CCCAATGTAAGGGCCTCTTGTAATAATGGAAGCAGCACAGGGGCGAAGTCACACATTGATAATAG<br>GGTTTATCGAAAACACCACATCACACCATACCACTTCACTTACCACGCCCCCTCTCTTTTCGTGT<br>CAACAATCTTTGACCACCTTTATCCAACCTAACAAAATCATTACTGTTTATTAATTTTATACTCT<br>TGTTTTACTAGTAATTTTCTATATTGATTTCGTTCATTTGTTATGCAGGTGTGAAAATGAACACG<br>ATCAATAAAAGAAAGGAAGAAAAATCTAGCCTTTAGTGATGATATCGGACTTCTTTTTTGTTTTT<br>TCAAAAGGAGGGCTTGCAATTCGACAATAACTAAGCAAAATTAACAAAAATTAAAGAAACAATAA<br>TCCATTTTCTGTCATAATTTCGTGCTTTGATAAATTTAATACTGCAATATTATTGTAGAACCCGT<br>GATTATGAAGTATAAGAACATAAACTTCATGTGATAAATTTTCACTGCAAATAGAATGTCTATAT<br>GTTTTTCATTTAAGACACACTATTACAAAAAACAATCTTTGAACGACGATTCATTGACACATTTA<br>ATAATTGTTTTTAACCGTTATTGAAGTGAATGTAATGAGAAATATTATATTTTTTACGATAATTT<br>CTTAATCATCTTAGAAGATCTCATCTTTTAAGATAACTTTTATGTTAAAACCGTTGTAGAAGACC<br>CACCATCCTAAAAGAACACTAACTAGAAAAAGAATGGTGGAGAGGGTGAAATAGCTACGGGTTCC<br>TTGGCTTAGTGTACAGTTTGGCGGGACCTTACTCCTTGGGAAGGCTAGACAGTAGAAGGATACTC<br>CGAGATCACTTCAAAGAGAATACGACACCCATGATTATCAAAAGGTTAGACAAGTTGATGCGCAA<br>TTTCCTTGTTTTCAGTCATAATTTTGGACTAATTAAACTCCACACAGAACGACAAGCATGCTTAT<br>TTTCTAGGCTTTTGCTTTGCTGAATACTAGAAGATAAATCTCATAGCTTTAGCCCATTGCCAAAC<br>GCTGGATTTTACTCTCTTCCTCACAAGATGGTAACAAGTTAGATAATCTAAGATTTGTGACCTTA<br>TTCGTCTTATGTTTGGGTTAATATTCATGTTGTACCGAGTATCATGTGCTCTAAAACATGCAGTT<br>TTGGCTTGGCAATGAATTAGAAGTATTCCATCAAAGTAATTCATACCATACCCCATTTTTAAAGC<br>TCAAAATGAGCAAGATAAAAACTTTAAACGTATCTTAGGGCATTCATTATTATCAAAAGCCTTTA<br>TATTCATTAGAACTCTTTGCATGTATAGACCATTTTCTCTTTTTTAAATAAAAAACATATTAACA<br>TATGTATCTCAGGGAATTTATTAAACAATTAAAAATGAAAATATTTATATAAAAATATTATCGAC<br>ATAATATTATTATTATTATTATTATTATTATTATTATTATTATTATATATCGTGAGTTTTAATTA<br>AAAAAAATTCATTGATACTCTTTAAAGTAGAAACGCTTGTTAGTAAAAATGATATTTTTGAATTT<br>AAAAGGTTATACATTTTTATATTATTGTTAAAATTTAAAACTTAATAATGAAAATTAAAAATATT<br>TATTTTTATCCTCAAATGACTAGACACTACAACAAAATAAATAATAAATAAGACAAGGAAAACTA<br>ACAAAAGAACTAACCGTTGTCCTTGACCTTCCTTGGAAAATAAGGCAATAGCATAGGACCTACTT<br>CAAAAAAGACATTCGACTACAAAAACATGCAAAATGGACAAAGATGAACAGAAAAACTAAGAAGA<br>CGTTGCATTTATTTTTTCAATTTCACGTATTTTCATTGAAAATTATATTTTAACATTATTCATTT<br>ATTTGTTAACAGGCCTATTTTAAAATTCGAAACCTCGGTATTTTATTAAACTCATTAAAATATCT<br>ACACCATTTTTTATTAAAAATATAATAATAATAATTTTAATATAGTTTCTTAATAATAAAATCTC<br>TAATAACTGCGAAAAAAGTATTTTTCTAAAAATACCATAATTAAATACGTACAACAACGAAGTAT<br>TAAACATATAAAACTAAAGAACCACGACACATTTATGTCTTTCCTATCACAATCATAAGTAATGC<br>TTGATTTGTGAGCACACTCTCCATAACCAACAACACACACATAACATTCTTTTATTAAAATCATT<br>TTAAATTATGTCACATAATAACTACTGTAACAACACACATTAGCATGAAACTGGTATTAGTAGCA<br>CATACAATAAATAAATATTGATTATTATCTGATGTAATTATGTAAGTATTATGAGTGGTTGATTA<br>AAAAAACAAAATAGAGTTGGTAAGGGGGTGGATCCACATCCACCGCTTCTGCACCAAACTCAGCA<br>TAGCAGTGGGTCAATGATTGATTGGTAATTGTAATTCTATTCAAAAAGTGAAAAGAGTTGAATGA<br>GAATTCGTATATTCAGAAAATCCCCCCTCCTTTAAGATAAGAGAATAGGCCTCACTCTTTCTTTC<br>TCTTCCATTCCCAAAATGCGTGTCCTCTTTCTTTTTCTGTTTTTCCAGTTTCTCCATTTTCATTT<br>CCCCAAAACCCTTTCAGCCCCAATCTCAGAGTACCGTGCCCTTCTCTCTCTCCGTTCAGCCATTA<br>CCGACGCCACCCCACCTCTTCTCACTTCGTGGAACTCCTCCACCCCTTACTGTTCCTGGCTCGGC<br>GTCACCTGCGACAACCGCCGCCACGTCACCTCCCTAGACCTCACCGGCCTCGACCTCTCCGGCCC<br>CCTCTCCGCCGACGTCGCCCACCTCCCATTCCTCTCCAACCTCTCCCTCGCCTCGAATAAGTTCT<br>CCGGCCCCATTCCTCCCTCACTCTCCGCTCTCTCCGGCCTCCGCTTCCTCAACCTCTCCAACAAT<br>GTCTTCAACGAAACCTTCCCCTCGGAGCTCTCGCGCCTCCAGAACCTCGAGGTCCTCGACCTCTA<br>CAACAACAACATGACCGGCGTGCTTCCCCTCGCCGTCGCGCAGATGCAGAATCTTCGTCATTTGC<br>ATCTCGGCGGCAACTTCTTCTCCGGCCAGATCCCGCCGGAGTATGGACGCTGGCAGCGCCTCCAG<br>TACCTCGCCGTCTCCGGCAACGAGCTCGAGGGGACTATCCCTCCGGAGATCGGAAACTTGTCCAG<br>CCTCCGGGAGCTCTACATCGGCTACTACAACACCTACACCGGGGGCATTCCGCCGGAGATCGGAA<br>ATTTGTCGGAGCTGGTGAGGCTCGACGCCGCCTACTGTGGGTTGTCCGGCGAGATTCCGGCGGCG<br>CTGGGAAAGCTTCAGAAGCTGGACACGCTGTTCCTTCAGGTGAATGCATTGTCAGGGTCTTTGAC<br>TCCCGAGCTGGGGAACCTGAAGAGCCTGAAATCCATGGATTTGTCTAACAACATGCTCTCCGGTG<br>AGATTCCGGCGAGATTCGGCGAGCTGAAGAATATTACTCTTCTGAATCTGTTCAGGAACAAGCTT<br>CACGGAGCTATACCAGAGTTTATAGGGGAGCTTCCAGCGTTGGAAGTTGTGCAACTGTGGGAGAA<br>TAACTTCACAGGTAGCATTCCAGAGGGTTTGGGCAAAAACGGGAGACTCAACCTTGTTGATCTTT<br>CTTCTAACAAGTTAACTGGGACTTTGCCTACTTATCTCTGTTCTGGGAATACTCTTCAGACTCTG<br>ATAACTCTTGGGAATTTTCTTTTTGGTCCAATTCCTGAGTCGCTTGGTAGTTGTGAATCCCTTAC<br>ACGGATTAGAATGGGAGAGAACTTTTTGAATGGTTCCATTCCGAGAGGGCTTTTTGGACTTCCCA<br>AACTAACACAGGTTGAGCTTCAGGATAATTATCTCTCTGGAGAGTTTCCTGAGGTGGGTTCTGTT<br>GCTGTTAATCTTGGTCAGATTACTCTCTCTAACAACCAGCTTTCTGGGGTTCTACCTCCCTCCAT |

TABLE 5-continued

Soybean Genomic DNA sequence, cDNA sequences, and protein sequences

| Sequence Description | DNA OR PROTEIN SEQUENCE |
|---|---|
| | TGGTAACTTCTCCAGCGTGCAGAAGCTCCTTCTTGATGGCAACATGTTCACGGGTCGGATACCTC<br>CCCAGATTGGGAGGTTGCAACAGCTTTCTAAGATTGATTTTAGTGGCAACAAGTTCTCGGGTCCT<br>ATTGTGCCTGAGATCAGTCAGTGTAAGCTGTTAACTTTCCTTGACCTTAGCCGCAATGAGCTATC<br>TGGAGACATCCCAAATGAGATAACTGGCATGAGGATATTGAATTACTTGAATCTTTCTAGGAATC<br>ATTTAGTGGGTGGCATTCCCTCTTCGATATCATCTATGCAAAGCTTGACTTCTGTTGATTTTTCA<br>TACAACAACCTGTCTGGTTTGGTGCCTGGTACCGGTCAATTCAGCTACTTCAATTACACGTCTTT<br>CTTGGGAAACCCTGACCTCTGTGGCCCCTATTTGGGTGCTTGCAAGGATGGGGTTGCCAATGGCG<br>CACACCAACCTCATGTTAAAGGTCTCTCCTCTTCTTTTAAGCTGCTACTTGTTGTTGGGTTGCTA<br>CTATGTTCCATTGCTTTTGCTGTGGCTGCAATATTCAAGGCCCGGTCACTGAAGAAGGCCAGTGG<br>GGCTCGTGCATGGAAGTTGACTGCGTTCCAACGTTTGGACTTCACTGTCGATGATGTTTTGCATT<br>GCTTGAAGGAGGATAATATTATAGGGAAAGGAGGTGCTGGCATTGTCTACAAAGGGGCTATGCCT<br>AATGGGGATCATGTTGCTGTGAAAAGGCTTCCGGCTATGAGTAGAGGCTCTTCACATGATCATGG<br>CTTCAATGCTGAGATTCAAACATTGGGGCGAATCCGACACAGGCACATTGTTAGGTTGTTGGGCT<br>TCTGTTCAAATCATGAGACAAACCTTTTGGTCTATGAGTACATGCCCAATGGAAGTTTAGGCGAG<br>GTTCTTCATGGAAAGAAAGGGGGTCATTTGCATTGGGATACAAGGTATAAAATTGCGGTGGAGGC<br>TGCCAAGGGGCTTTGCTATCTGCACCATGATTGTTCGCCACTCATTGTCCATCGTGATGTGAAGT<br>CAAACAACATCCTTCTTGATTCTAATCATGAAGCCCATGTTGCTGATTTTGGGCTTGCTAAGTTC<br>CTGCAAGATTCTGGGACATCTGAATGCATGTCTGCTATTGCTGGTTCATATGGATACATAGCTCC<br>AGGTACCGTCCAATTTCGACATAATTAATGCATTATTTACATGGTTGTGGAAAATTTTCTTTTAC<br>CCGCCTGTTCATAATTGTACGTTTAATCATTGTTCAGAATTTGACTCTTTGACTTATCATCATGT<br>TTTAGGTGTAGACTGTTGATATTGAGGTGATGTCCCTAAATTAATTAACATTGCTATGTGGTTTT<br>TCTTGACTTTGGTTTTCTATCATACCCAAATGATCTCTTGATTTCGACCCCTTATTTAGTCTATT<br>TCAAGCCAAGTACTGAAAGTAAATGGTAGATAGCTCTGCAACGTTAGAGTCATTCACGACCGGAA<br>ACTGATGATTATGGGCAAAATATCGGATAAAAAGACCTATTATGTTACTTTACACTTATTGCCTT<br>TGTTTAACTTATAGTTTCAAATTCAAGTGTCTTGCTTTATTTTAGTTTATGATACATGTTCGATG<br>TTTGATTGCAGAGTATGCCTACACATTGAAAGTTGATGAGAAAAGCGATGTGTACAGTTTTGGTG<br>TGGTTCTCTTAGAACTTATAACAGGCAGGAAACCAGTTGGAGAATTTGGTGATGGCGTGGACATA<br>GTGCAATGGGTGAGGAAAATGACGGATTCTAACAAGGAAGGAGTTCTTAAAGTTCTTGATCCTAG<br>ACTTCCCTCAGTTCCCCTTCACGAAGTGATGCATGTTTTCTATGTAGCCATGCTGTGCGTTGAAG<br>AACAGGCTGTAGAGAGACCAACTATGCGTGAAGTTGTTCAAATACTGACAGAGCTTCCAAAGCCA<br>CCTGACTCTAAAGAGGGGAACTTAACAATAACGGAATCATCTTTGTCATCATCAAACGCTTTAGA<br>ATCTCCATCCTCAGCCTCTAAGGAAGATCAAAATCCTCCTCAATCCCCACCACCCGATCTTCTTA<br>GCATTTAAAGTGCTCTGTTGGGTGTTTCATCTTAGTTCCCTTGGGTTGTGATCGCTTATCCATTT<br>ACTTTCTTTTTCTGTCTCTCTTCTGGGATTGGTTTTTTTTTTTTTCCCTAACTGAAGGTGTTAAT<br>GTTTGGATTTTTTAATGGTTTTGTACAGTAGGATTGATGGGGGTATTTTCTTATAAAGTCACTGT<br>CTTCATCATGTAGTACTGCTTTTTAATTTTTATTTGCGACCGTTGTTGGGGAGGATTCAAGGGAT<br>ACAATTAAATTACTCGTTTGTTTCCTGAAATTTCATTATTCATACTTTTTTAGTTTATG |
| Glyma01g40590 cDNA (start and stop codons underlined; SEQ ID NO: 30); Soybean BAM2-like gene | ATGCGTGTCCTCTTTCTTTTTCTGTTTTTCCAGTTTCTCCATTTTCATTTCCCCAAAACCCTTTC<br>AGCCCCAATCTCAGAGTACCGTGCCCTTCTCTCTCTCCGTTCAGCCATTACCGACGCCACCCCAC<br>CTCTTCTCACTTCGTGGAACTCCTCCACCCCTTACTGTTCCTGGCTCGGCGTCACCTGCGACAAC<br>CGCCGCCACGTCACCTCCCTAGACCTCACCGGCCTCGACCTCTCCGGCCCCCTCTCCGCCGACGT<br>CGCCCACCTCCCATTCCTCTCCAACCTCTCCCTCGCCTCGAATAAGTTCTCCGGCCCCATTCCTC<br>CCTCACTCTCCGCTCTCTCCGGCCTCCGCTTCCTCAACCTCTCCAACAATGTCTTCAACGAAACC<br>TTCCCCTCGGAGCTCTCGCGCCTCCAGAACCTCGAGGTCCTCGACCTCTACAACAACAACATGAC<br>CGGCGTGCTTCCCCTCGCCGTCGCGCAGATGCAGAATCTTCGTCATTTGCATCTCGGCGGCAACT<br>TCTTCTCCGGCCAGATCCCGCCGGAGTATGGACGCTGGCAGCGCCTCCAGTACCTCGCCGTCTCC<br>GGCAACGAGCTCGAGGGGACTATCCCTCCGGAGATCGGAAACTTGTCCAGCCTCCGGGAGCTCTA<br>CATCGGCTACTACAACACCTACACCGGGGGCATTCCGCCGGAGATCGGAAATTTGTCGGAGCTGG<br>TGAGGCTCGACGCCGCCTACTGTGGGTTGTCCGGCGAGATTCCGGCGGCGCTGGGAAAGCTTCAG<br>AAGCTGGACACGCTGTTCCTTCAGGTGAATGCATTGTCAGGGTCTTTGACTCCCGAGCTGGGGAA<br>CCTGAAGAGCCTGAAATCCATGGATTTGTCTAACAACATGCTCTCCGGTGAGATTCCGGCGAGAT<br>TCGGCGAGCTGAAGAATATTACTCTTCTGAATCTGTTCAGGAACAAGCTTCACGGAGCTATACCA<br>GAGTTTATAGGGGAGCTTCCAGCGTTGGAAGTTGTGCAACTGTGGGAGAATAACTTCACAGGTAG<br>CATTCCAGAGGGTTTGGGCAAAAACGGGAGACTCAACCTTGTTGATCTTTCTTCTAACAAGTTAA<br>CTGGGACTTTGCCTACTTATCTCTGTTCTGGGAATACTCTTCAGACTCTGATAACTCTTGGGAAT<br>TTTCTTTTTGGTCCAATTCCTGAGTCGCTTGGTAGTTGTGAATCCCTTACACGGATTAGAATGGG<br>AGAGAACTTTTTGAATGGTTCCATTCCGAGAGGGCTTTTTGGACTTCCCAAACTAACACAGGTTG<br>AGCTTCAGGATAATTATCTCTCTGGAGAGTTTCCTGAGGTGGGTTCTGTTGCTGTTAATCTTGGT<br>CAGATTACTCTCTCTAACAACCAGCTTTCTGGGGTTCTACCTCCCTCCATTGGTAACTTCTCCAG<br>CGTGCAGAAGCTCCTTCTTGATGGCAACATGTTCACGGGTCGGATACCTCCCCAGATTGGGAGGT<br>TGCAACAGCTTTCTAAGATTGATTTTAGTGGCAACAAGTTCTCGGGTCCTATTGTGCCTGAGATC<br>AGTCAGTGTAAGCTGTTAACTTTCCTTGACCTTAGCCGCAATGAGCTATCTGGAGACATCCCAAA<br>TGAGATAACTGGCATGAGGATATTGAATTACTTGAATCTTTCTAGGAATCATTTAGTGGGTGGCA<br>TTCCCTCTTCGATATCATCTATGCAAAGCTTGACTTCTGTTGATTTTTCATACAACAACCTGTCT<br>GGTTTGGTGCCTGGTACCGGTCAATTCAGCTACTTCAATTACACGTCTTTCTTGGGAAACCCTGA<br>CCTCTGTGGCCCCTATTTGGGTGCTTGCAAGGATGGGGTTGCCAATGGCGCACACCAACCTCATG<br>TTAAAGGTCTCTCCTCTTCTTTTAAGCTGCTACTTGTTGTTGGGTTGCTACTATGTTCCATTGCT<br>TTTGCTGTGGCTGCAATATTCAAGGCCCGGTCACTGAAGAAGGCCAGTGGGGCTCGTGCATGGAA<br>GTTGACTGCGTTCCAACGTTTGGACTTCACTGTCGATGATGTTTTGCATTGCTTGAAGGAGGATA<br>ATATTATAGGGAAAGGAGGTGCTGGCATTGTCTACAAAGGGGCTATGCCTAATGGGGATCATGTT<br>GCTGTGAAAAGGCTTCCGGCTATGAGTAGAGGCTCTTCACATGATCATGGCTTCAATGCTGAGAT<br>TCAAACATTGGGGCGAATCCGACACAGGCACATTGTTAGGTTGTTGGGCTTCTGTTCAAATCATG<br>AGACAAACCTTTTGGTCTATGAGTACATGCCCAATGGAAGTTTAGGCGAGGTTCTTCATGGAAAG<br>AAAGGGGGTCATTTGCATTGGGATACAAGGTATAAAATTGCGGTGGAGGCTGCCAAGGGGCTTTG |

TABLE 5-continued

| Soybean Genomic DNA sequence, cDNA sequences, and protein sequences | |
|---|---|
| Sequence Description | DNA OR PROTEIN SEQUENCE |
| | CTATCTGCACCATGATTGTTCGCCACTCATTGTCCATCGTGATGTGAAGTCAAACAACATCCTTC TTGATTCTAATCATGAAGCCCATGTTGCTGATTTTGGGCTTGCTAAGTTCCTGCAAGATTCTGGG ACATCTGAATGCATGTCTGCTATTGCTGGTTCATATGGATACATAGCTCCAGAGTATGCCTACAC ATTGAAAGTTGATGAGAAAAGCGATGTGTACAGTTTTGGTGTGGTTCTCTTAGAACTTATAACAG GCAGGAAACCAGTTGGAGAATTTGGTGATGGCGTGGACATAGTGCAATGGGTGAGGAAAATGACG GATTCTAACAAGGAAGGAGTTCTTAAAGTTCTTGATCCTAGACTTCCCTCAGTTCCCCTTCACGA AGTGATGCATGTTTTCTATGTAGCCATGCTGTGCGTTGAAGAACAGGCTGTAGAGAGACCAACTA TGCGTGAAGTTGTTCAAATACTGACAGAGCTTCCAAAGCCACCTGACTCTAAAGAGGGGAACTTA ACAATAACGGAATCATCTTTGTCATCATCAAACGCTTTAGAATCTCCATCCTCAGCCTCTAAGGA AGATCAAAATCCTCCTCAATCCCCACCACCCGATCTTCTTAGCATTTAA |
| Glyma01g40590 protein (SEQ ID NO: 31); Soybean BAM2-like gene | MRVLFLFLFFQFLHFHFPKTLSAPISEYRALLSLRSAITDATPPLLTSWNSSTPYCSWLGVTCDN RRHVTSLDLTGLDLSGPLSADVAHLPFLSNLSLASNKFSGPIPPSLSALSGLRFLNLSNNVFNET FPSELSRLQNLEVLDLYNNNMTGVLPLAVAQMQNLRHLHLGGNFFSGQIPPEYGRWQRLQYLAVS GNELEGTIPPEIGNLSSLRELYIGYYNTYTGGIPPEIGNLSELVRLDAAYCGLSGEIPAALGKLQ KLDTLFLQVNALSGSLTPELGNLKSLKSMDLSNNMLSGEIPARFGELKNITLLNLFRNKLHGAIP EFIGELPALEVVQLWENNFTGSIPEGLGKNGRLNLVDLSSNKLTGTLPTYLCSGNTLQTLITLGN FLFGPIPESLGSCESLTRIRMGENFLNGSIPRGLFGLPKLTQVELQDNYLSGEFPEVGSVAVNLG QITLSNNQLSGVLPPSIGNFSSVQKLLLDGNMFTGRIPPQIGRLQQLSKIDFSGNKFSGPIVPEI SQCKLLTFLDLSRNELSGDIPNEITGMRILNYLNLSRNHLVGGIPSSISSMQSLTSVDFSYNNLS GLVPGTGQFSYFNYTSFLGNPDLCGPYLGACKDGVANGAHQPHVKGLSSSFKLLLVVGLLLCSIA FAVAAIFKARSLKKASGARAWKLTAFQRLDFTVDDVLHCLKEDNIIGKGGAGIVYKGAMPNGDHV AVKRLPAMSRGSSHDHGFNAEIQTLGRIRHRHIVRLLGFCSNHETNLLVYEYMPNGSLGEVLHGK KGGHLHWDTRYKIAVEAAKGLCYLHHDCSPLIVHRDVKSNNILLDSNHEAHVADFGLAKFLQDSG TSECMSAIAGSYGYIAPEYAYTLKVDEKSDVYSFGVVLLELITGRKPVGEFGDGVDIVQWVRKMT DSNKEGVLKVLDPRLPSVPLHEVMHVFYVAMLCVEEQAVERPTMREVVQILTELPKPPDSKEGNL TITESSLSSSNALESPSSASKEDQNPPQSPPPDLLSI |
| Glyma11g04700 gDNA + about 5 kb promoter and 5'UT sequence (SEQ ID NO: 32) Soybean BAM2-like gene | GTTGGAGTAAATCCAATAACATCAAATCCTTAATATATATTTATTAAATTTTATTGATAAAACTG ACTTACTAGTACATATTTTAGTTTGTAATAATATCATTTGTTTGGATCCAATATATAAGCCAATT TTTTTTATGGACAAAATATATGGAGCCAAAGCCGCAGCTCAAAAACCTATGTAACAAGAGACACT GAAGAGTGAAGAATCAGCAACATGATCAAAGCCTAAAATTGGGGCAAAAATTCAAACACTTGGCT ATAAATACACCAGATAGTCCATACTTAGCCGCTATTATGTCAAAATATAATAGTATTAATATTAC ATGGCAAAGTATAGGCTATATAATTTAATGTAATTTATTAAATTTTACAAGGTACTGATTCAACT TTAAACATGTATGCTAATTGGAGTTTAAAATTTGTGAACAAAAAGCAAGTGCATTTTGTTGCGTG ATCAAAATTGCTCAACCTTATCATGTAGGAAAACGGATAACCAGAATTTGTGTGGTCCCAAACGA CAACAAGACGCATTTATAAGCTTGACTAGTTCTCTTCGTCGTCAACTGACATTCTCATTTCTCAA TGATAGTTGCTACTTGATAATATTTTATTCGAATAATCTGTCGTTAACCTACCTATAATATATAG CTGGTGCTATTAATCGAATGTTTAATCTCATTTTAAGATTTACAGTGTGTGGATTGATGGTGAAG ATCCAAAAATCATAGTATCTGATTATGATTTAGTTTCCACCGCATCAGAGAGTATAGCTAGCTAG TTTTAAAGTTAGCATGATTTTTTCAAGATAACCCACCGTAGATTTTTTCAACATAATATAATATA ATTTTCACTTGTAAACTTTGAGGTTGCAAGGAAGAAAAGCAGGTAAAAAGAATAACAGGTAGCAA AGACATTTAAAAATTAAAATAGTTCTAACAATATAAGTCCAATCTAAAGGGGATACGTCCAGCAA TACTCATCCCTCACCAACTCCAACTTCACTCTCAATAAACTGGAATCGTGAAAGCATCATTACAA TTATCTCCTAGCTAACCAAACCCAACATTTTTTTTAGCTTTTAGAAATATTATCGCGTGCAATGT GATGCACTGCTGCAGTTAGCATCAACAAGAATAGTAACCTGACCCTTCATGCCATTATGATCGAG GTGGTAAAAAATGGCAAGTAGAAGTGAGGTTCATGCTCTTTAATGATTAATCTAATGGGATAACA AGAACCAGAACAAACAGAACTCTTGGTAGAAAAGAAAAAAAAAAGTGGGTCAATAATGCATATTT TGGATTCAAAACCACCACTGTCCAATTGACATCATTGTTCTACAAAACCGGAATGATTGTGATTC ATCCGGAGGGTATTTGCTCATTCATGTTCCTTATTATCGATATGGGCATACCTGACTAGCCAAGT ACAATTTCCTTAATTTCAATTTTGGCACTTACAATCGTGATTAAAACTGAGATCAGGTTTATATA TATGCTTGTCTTTTTATCCAAAAATTAGCATGCATTCTATATTTATGGGGTACGGGTCACGTGTG TACAATATACTCCTTACAAAAGGTTTATATATCTGCTTGGCTTTTAATCCCAAAATTAGCATGCA TTAAATGAAGGGTAACGTGTGTTTTATTCTTATTTAAATAAATAACATATAGTACAATTTTTAAG TAGCCAATAATTTTAAAATTTTCACTAACTCTGTATCTGTATTGTAATGAAAATATTTTTATATT TTACTTTTGGATCAATTTAAATTTATTTGTAAACAAATGGTTTTACATTTTATTAATTTCTTTTA TTAAATCTGTCCATAATATCTTTTTTTTTATAAGTTTTAAATTTTATAATTTTAATTTAAATTT CTAATACAACGTAAGAGGATTAATATACTTAGCTAGTTAAAGATTATAATAATTATTTTCAACTG CGTTGGAGTTAGCTGGGATGACCACGGATCTTCCCCCCCATAAATTACCACAAAGCACCCCATTT GTTACACAGAAAGGACTCTTGCAACAAGAGAATAAGGGACATTAAGTAATTTGCCTATTAATAA TGTTATAAGCTAATATAAAATTAGTTTGGCGGTTAAAATGAAAATTTAAAGATTGAAGGGAGAAA GAAGAAGAAAAGAGAGTTTTAAATTCAAATCTTCCACTGATCTTGGTTGATAAAAAAATGAAACC GCACACAAAAACGCTCTCCATCAATGCAATTGTACTAGTAATACTTAACTTGTGTCTTATATACA GCGTGGAAATATAAAATAAATAACATAATTATCATTTTTTGATAATATTATATATATATATATAT ATATATATAACTATTTTTTATATACGTTTGAGTACATAAGGAAACAATCTTGCTATTACCAATCT ATATTAGTTGTGGCTTTCCTCATAGAATTGATCCATGAAACGAAGGAGTAACACTGAATAATAAT AGTGCTAATGAAAAACCCATTATAATAGTAATTACTAATATTATTATGAAATATGAAATGTTAAT ATTCGGTGACTGCTTGGTCATTTTCTCTTCCAGAAAAACAGAGCTGTGACCTGTTAGTAAGGCCA TGGTGGGAGGGACCACTGCATGGCATCTTTCTCAGTGCTTCCCTTATTACATGATTTTGATGGCT TCAGTTGTCAGAGACCGGGTGGGTGGGTAGAAGATGGAGTATTGTATAGGAAGAAAATGGTAAAA TCATATTGAATCTTCTGCAATCCCCAATGTACTCTAGTTAGTAACTGTAATGTAAGGGCCTATTG TAATAATTGAAGCAGCACAGGGGCGAAGTCTCACATTCATAATAGGGTTTATCGAAAACACCACA CCATACCACTTGCCACGCCCCCTCTCTTTTCGTGACGGTCAACATTCTTTGACCACCTTTATCCA ACCTAACTAAATCATTACTACTGTTATTAATTTATACTCTTGTTTTAATTTTCTATATTGAATT TCATTCATTTGTAATATTAATATAGGTGTGAAAATGACCATGATCAATAAAAAGAAAGGAAGAGC |

TABLE 5-continued

Soybean Genomic DNA sequence, cDNA sequences, and protein sequences

| Sequence Description | DNA OR PROTEIN SEQUENCE |
| --- | --- |
| | AATATCTAGCTTTTAGTGATAACATTGGACTTCTTTTTTGTTTTAACAAAAATTAAAGAAACAAC<br>AGTCATTTTTCTGTCATAACTTGATGCCTTGACAAATTAATTTAATACTGTAAGATTATTGTAGA<br>ACCCGTGATTATGCAGTAGAAGAACATAAATTTGTATGTTTCTCATCTAAGAAAGGAAAAGTAGC<br>TAGAAAAAGAATGGTAGAGAGGGTGAAATAGCGAAATGCATGCTATGGCCAACGGGTTCCTTATT<br>CCTTGCGGAGGCTATACAGTAGAATGGTTGTCCTAGATCACTTCAAATAGAATACGACACCCATG<br>ATTGTCAAAAGGCTAAACAAGTTGATGCGCGCAATTTCCTTGTTTTCAGTCATAATTTTGGACTA<br>AACTCCACACAGAACGACATGTTCTTTTCTAGGCTTTTGCTTTGTTGAATACTAGCGTTGGATTT<br>TACTCTCTTCCTCACAAGATGGTAACAAGTTAGATAATCTATATAAGATTTCTGACCTTATTCGT<br>CTTAATATAATAAACATGTTATAGCGAGTATATATCATGTGCTCCAATACATGCAGTTTTGGCAA<br>TGGATTAGAAGTGTTAACGTTCCAGCAGAGTAATTCATACCATCCCCCATTTTTAATGCTCAAAA<br>TGAGCAAGATGAAAATTTTTTAAACGTATCTTAATTCTTAGGGCATTCATTATTATCAAAAAGCC<br>TTTATATTCATTAGAACTCTTTGCATGTATAGATCATTTTCTCTTTTTTTTTATTAAAAAAATTA<br>ACATATATATATATATATATATATATATATATATATATATATATATATATATATATATATATATATA<br>TATATATATCAGGCCATTCATTAAGCAATTAAACATGAAAATATTTTATACAAAATATTATTATA<br>TCTATTGTAAGTTTTAATTAAAAAATTCATTGATATTCTTAAAACGTTTGTTAGTAAAAAATATA<br>TTTTAAATTTAAAAGGTTATATATAGTTATACATTATTATATTATTCTTAAAATTTAAAACTTAA<br>TAATAATAAAATAAAAAATAGTATTCTTAATAACTAGACACGACAACAAAATAAATAAATAATTA<br>AGACAAGGAAAACTAACAGAAGAATTAGCCGTTTTCCTCGACCTTCCTTGGAAAATAAGGCAATA<br>GCATAGGACCTACTTAAAAAAAGTTAAAACATTCGACTACAAAAACATACAAAATGGACAAAGAT<br>AAACACGTAAGAAAAACTAAGAAAAACGTTACATTTTTTTCTTTTCAATTTCACGTATTGTTATT<br>GAAAATTTTATTTCAAACATTGTTCATTTATTTGTTTTTTTAAGAGAGTTCATTCATTTGTTATT<br>AATTTAACAAATTATTTGTTAACGATCTATTTTAAAATTCAAAACCTATTTTTATTAAACTCATT<br>AAATTATGTGCACCATTTTTTTTATTATAAATATAATAATAACTGTTATATAAATTTGATGAATG<br>ACATGATAAAAGACCGTATTATTTGCATAATTAAAGAAGCACGCCATATTTATGTCTTTCCTATC<br>ACAATCATAAGTAAAACTTGAGTTTACCACCATCCTCCGCTCAATAACCCAGCAACACACATAAC<br>ATTCTTTTATTAATGTCATTTTTAAGTGGCATAATAACTATATAACAACACACATGAGTGCCGCA<br>TCATAAATTACACATACGATAAATAAATCTTCATTATTATCTTATGCAATTATATATGTATTATG<br>AGTGGTTCATTAAAAAATAGTGCAGCAAAGTCACCATAGCCGTGGGTGAATGATTGATAGGTAAA<br>ATTGTATTTTTCTTTTTTTCCCGGGTATTTCAAAAAGTAAAAAGAGTTGAAGGGACGAATTCATA<br>TATTCAGAAAATTCCCTCTCCTTTAAGTATCGGTTTGTGTTTGGGGGCATCACTCGTTGTTTCTC<br>TCTTCCATGCCCAAAATGCGTGTCCTCTTTGTTTTTCTGTTTTTCCATTTTCATTTCCCTGAAAC<br>CCTTTCTGCCCCAATCTCAGAGTACCGCGCCCTTCTCTCTCTCCGTTCAGTCATTACCGACGCCA<br>CACCACCCGTTCTCTCTTCTTGGAACGCCTCCATCCCTTACTGTTCCTGGCTCGGCGTCACCTGC<br>GACAACCGCCGCCACGTCACCGCCCTCAACCTCACCGGCCTCGACCTCTCCGGCACGCTCTCTGC<br>CGACGTCGCCCACCTCCCTTTCCTCTCCAACCTCTCCCTCGCCGCAAACAAATTCTCCGGCCCCA<br>TTCCTCCCTCTCTCTCCGCCCTCTCCGGCCTCCGCTACCTCAACCTCTCCAACAATGTCTTCAAC<br>GAAACCTTCCCCTCGGAGCTTTGGCGCCTCCAGAGCCTCGAGGTCCTCGACCTCTACAACAACAA<br>CATGACCGGCGTGCTCCCTCTTGCCGTCGCGCAGATGCAGAATCTTCGTCATTTGCATCTCGGCG<br>GCAACTTCTTCTCCGGCCAGATCCCGCCGGAGTACGGACGCTGGCAGCGCCTCCAGTACCTCGCC<br>GTCTCCGGCAACGAACTCGACGGGACTATCCCGCCGGAGATCGGAAACTTGACCAGCCTCCGGGA<br>GCTCTACATCGGCTACTACAACACCTACACCGGCGGCATTCCGCCGGAGATCGGAAACTTGTCGG<br>AGCTGGTGAGGCTTGACGTAGCGTACTGTGCGTTGTCCGGGGAGATTCCGGCGGCGCTTGGGAAG<br>CTTCAGAAGCTGGACACGCTGTTCCTTCAGGTGAATGCATTGTCAGGATCACTGACGCCGGAGCT<br>GGGGAACCTGAAGAGCCTGAAATCCATGGATTTGTCTAACAACATGCTCTCCGGTGAGATTCCGG<br>CGAGTTTCGGCGAGCTGAAGAATATTACGCTTCTGAATCTGTTCAGGAACAAGCTTCATGGAGCT<br>ATACCGGAGTTTATAGGAGAGCTTCCAGCGTTGGAAGTTGTGCAACTGTGGGAAAATAACTTAAC<br>AGGTAGCATTCCTGAGGGTTTGGGCAAAAATGGGAGACTCAACCTTGTTGATCTTTCTTCTAACA<br>AGTTAACCGGGACTTTGCCTCCTTATCTCTGTTCTGGGAATACTCTTCAGACTCTGATAACTCTT<br>GGGAATTTTCTTTTCGGTCCAATTCCTGAGTCGCTCGGGACTTGTGAATCTCTTACACGGATTAG<br>AATGGGAGAAAACTTTTTGAATGGTTCCATTCCTAAAGGGCTTTTTGGACTTCCCAAACTCACCC<br>AGGTTGAACTTCAGGATAATTATCTCTCTGGAGAGTTTCCTGAGGTTGGTTCTGTTGCGGTTAAT<br>CTTGGTCAGATTACTCTCTCTAACAACCAGCTTTCTGGGGCTCTGTCTCCCTCCATTGGTAACTT<br>CTCCAGCGTGCAGAAGCTCCTTCTTGATGGCAACATGTTCACCGGTCGGATACCTACACAGATTG<br>GGAGGTTGCAACAGCTTTCTAAGATTGATTTTAGTGGCAACAAGTTCTCGGGTCCTATTGCGCCT<br>GAGATCAGTCAGTGTAAGCTGTTAACTTTCCTGGACCTTAGCCGCAATGAGCTATCTGGAGACAT<br>CCCTAATGAGATAACTGGCATGAGGATATTGAATTACTTGAATCTTTCTAAGAATCATTTAGTGG<br>GTAGCATTCCCTCTTCGATATCATCTATGCAAAGCTTGACTTCTGTTGATTTTTCATACAACAAC<br>CTGTCTGGTTTGGTGCCTGGTACCGGTCAATTCAGCTACTTCAACTACACGTCTTTCTTGGGAAA<br>CCCTGACCTGTGTGGCCCCTATTTGGGTGCTTGCAAGGGTGGGGTTGCCAATGGTGCACACCAAC<br>CTCATGTTAAAGGACTCTCCTCTTCTTTGAAGCTGCTACTTGTTGTTGGGTTGCTATTATGTTCC<br>ATTGCTTTTGCTGTGGCTGCAATATTCAAGGCCCGGTCATTAAAGAAGGCCAGTGAGGCTCGTGC<br>ATGGAAGTTGACTGCGTTCCAGCGTTTGGACTTCACTGTTGATGATGTTTTGCATTGCTTGAAAG<br>AGGATAATATTATTGGGAAAGGAGGTGCTGGAATTGTCTACAAAGGGGCTATGCCTAATGGGGAT<br>CATGTTGCTGTGAAAAGGCTTCCAGCTATGAGTAGAGGCTCTTCCCATGATCACGGATTCAATGC<br>TGAGATTCAGACATTGGGGCGAATCCGACACAGGCACATTGTTAGGTTGTTGGGTTTCTGTTCAA<br>ATCATGAGACAAACCTTTTGGTCTATGAGTACATGCCCAATGGAAGTTTAGGTGAGGTTCTTCAT<br>GGAAAAAAGGGGGGTCATTTGCATTGGGACACCAGGTATAAAATTGCGGTGGAGGCTGCCAAGGG<br>GCTTTGCTATCTGCACCATGATTGTTCGCCACTCATTGTCCATCGTGATGTGAAGTCAAACAACA<br>TCCTTCTTGATTCAAATCATGAAGCCCATGTTGCTGATTTTGGGCTTGCTAAGTTCCTGCAAGAT<br>TCTGGGACATCTGAATGCATGTCTGCTATTGCTGGTTCATATGGATACATAGCTCCAGGTACCGT<br>TGAATTTTGACATAATTAATGCATCATATGCATGGTTGTGGCAAATTTCCTTTTTCTCGCCTAAT<br>CATAATTGTACGTTTAAGCATTTTGTTCAGAATTTGACTCTTTGACTTATGCATGATATTGAGGT<br>GATGCCCCTAAATTTATTAACATTGCTATGTGGTTTTTCTTGACTTTGGTTTTCTATCATACCCA<br>ATTGATTCGCCCCCTTATTTGTTTTTTTTTCTAAGCCAAGTACTGAAGTAAATGGTAGGTATC<br>TCTGCACCGTTTGATTTTTTACCCTAACCCCCTCTCCCCACCTATGAAGTAGATAATGCTGTAGT |

TABLE 5-continued

| Soybean Genomic DNA sequence, cDNA sequences, and protein sequences | |
|---|---|
| Sequence Description | DNA OR PROTEIN SEQUENCE |
| | CGTAGGTTAAGAGTCATTCACAATCGGAAACTGATGGTTATGGGCAAAAACATCAGATAAAAAGA<br>CCTATTATGTTACTTTATACGTATTGCCTTTGTTTAACTTATTGTTTCAAATTAAAGTGTCTTGC<br>TTTATTATAGTGTATGATACCTGTTGGATGTTTGATTGCAGAGTATGCCTACACATTGAAAGTTG<br>ATGAGAAAAGCGATGTGTACAGTTTTGGTGTGGTTCTTTTAGAACTTATAACAGGCAGGAAACCA<br>GTTGGTGAATTTGGTGATGGCGTGGACATCGTGCAATGGGTGAGGAAAATGACGGACTCTAACAA<br>GGAAGGAGTTCTTAAAGTTCTTGATCCTAGGCTTCCCTCAGTTCCCCTTCACGAAGTGATGCATG<br>TTTTCTATGTGGCCATGCTGTGTGTTGAAGAACAGGCTGTAGAGAGACCAACAATGCGTGAAGTT<br>GTTCAAATACTGACCGAGCTTCCAAAGCCACCTGGCTCTAAAGAGGGAGACTTAACAATAACAGA<br>ATCCTCTTTGTCATCATCAAACGCTTTAGAATCTCCATCCTCAGCCTCCAAGGAAGATCAAAATC<br>CTCCTCAATCCCCACCACCCGACCTTCTTAGTATTTAAAGTGCTCTGTTGGGTGTTTCATCTTAT<br>TAGTTCCCTTGGTTGTGATAGCTTATCCATTTACTTTCTTTTTCTGTCTCTCTTCTGGGGTTGGG<br>GCTTTTCTTCTTCTTCTAACTGAAGGTATTAATGCTCTGATTTTTTAATGGTTTTGTACAGTAGG<br>ATTGGTGGGGGGGTTATTTTCTTATGAAGTCACTTTCTTCATCATGTAGTACTGCTTTTTAATT<br>TTTATGTTACGGCCGTTGTTGTGCTTCGCCTAAGCTGGGGAGTGGGGAGGGTTCAAGGGAATGGA<br>TACTCTTTTTTTATGCGATCACTGACAGGTAGACACAAAATGACGCAAACGGGTTGGGTATTAAA<br>CAGTGGGTATATTGTATGGTTTAGAATATTATTGATGAATCCTGAGTGGATTGGCACAGTGTGAA<br>CTGTGAGCCTGAGCTGTGACTGAGTCTATGAGTCAGGTTTGGATAAAAGCTTATTTGAAGAAGTT<br>AACCTGTTTCGAGAAAATCAGAGTGAATCAGGATTCAGGCGTGTTTTAGCTTT |
| Glyma11g04700 cDNA (SEQ ID NO: 33) Soybean BAM2-like gene | ATGCCCAAAATGCGTGTCCTCTTTGTTTTTCTGTTTTTCCATTTTCATTTCCCTGAAACCCTTTC<br>TGCCCCAATCTCAGAGTACCGCGCCCTTCTCTCTCTCCGTTCAGTCATTACCGACGCCACACCAC<br>CCGTTCTCTCTTCTTGGAACGCCTCCATCCCTTACTGTTCCTGGCTCGGCGTCACCTGCGACAAC<br>CGCCGCCACGTCACCGCCCTCAACCTCACCGGCCTCGACCTCTCCGGCACGCTCTCTGCCGACGT<br>CGCCCACCTCCCTTTCCTCTCCAACCTCTCCCTCGCCGCAAACAAATTCTCCGGCCCCATTCCTC<br>CCTCTCTCTCCGCCCTCTCCGGCCTCCGCTACCTCAACCTCTCCAACAATGTCTTCAACGAAACC<br>TTCCCCTCGGAGCTTTGGCGCCTCCAGAGCCTCGAGGTCCTCGACCTCTACAACAACAACATGAC<br>CGGCGTGCTCCCTCTTGCCGTCGCGCAGATGCAGAATCTTCGTCATTTGCATCTCGGCGGCAACT<br>TCTTCTCCGGCCAGATCCCGCCGGAGTACGGACGCTGGCAGCGCCTCCAGTACCTCGCCGTCTCC<br>GGCAACGAACTCGACGGGACTATCCCGCCGGAGATCGGAAACTTGACCAGCCTCCGGGAGCTCTA<br>CATCGGCTACTACAACACCTACACCGGCGGCATTCCGCCGGAGATCGGAAACTTGTCGGAGCTGG<br>TGAGGCTTGACGTAGCGTACTGTGCGTTGTCCGGGGAGATTCCGGCGGCGCTTGGGAAGCTTCAG<br>AAGCTGGACACGCTGTTCCTTCAGGTGAATGCATTGTCAGGATCACTGACGCCGGAGCTGGGGAA<br>CCTGAAGAGCCTGAAATCCATGGATTTGTCTAACAACATGCTCTCCGGTGAGATTCCGGCGAGTT<br>TCGGCGAGCTGAAGAATATTACGCTTCTGAATCTGTTCAGGAACAAGCTTCATGGAGCTATACCG<br>GAGTTTATAGGAGAGCTTCCAGCGTTGGAAGTTGTGCAACTGTGGGAAAATAACTTAACAGGTAG<br>CATTCCTGAGGGTTTGGGCAAAAATGGGAGACTCAACCTTGTTGATCTTTCTTCTAACAAGTTAA<br>CCGGGACTTTGCCTCCTTATCTCTGTTCTGGGAATACTCTTCAGACTCTGATAACTCTTGGGAAT<br>TTTCTTTTCGGTCCAATTCCTGAGTCGCTCGGGACTTGTGAATCTCTTACACGGATTAGAATGGG<br>AGAAAACTTTTTGAATGGTTCCATTCCTAAAGGGCTTTTTGGACTTCCCAAACTCACCCAGGTTG<br>AACTTCAGGATAATTATCTCTCTGGAGAGTTTCCTGAGGTTGGTTCTGTTGCGGTTAATCTTGGT<br>CAGATTACTCTCTCTAACAACCAGCTTTCTGGGGCTCTGTCTCCCTCCATTGGTAACTTCTCCAG<br>CGTGCAGAAGCTCCTTCTTGATGGCAACATGTTCACCGGTCGGATACCTACACAGATTGGGAGGT<br>TGCAACAGCTTTCTAAGATTGATTTTAGTGGCAACAAGTTCTCGGGTCCTATTGCGCCTGAGATC<br>AGTCAGTGTAAGCTGTTAACTTTCCTGGACCTTAGCCGCAATGAGCTATCTGGAGACATCCCTAA<br>TGAGATAACTGGCATGAGGATATTGAATTACTTGAATCTTTCTAAGAATCATTTAGTGGGTAGCA<br>TTCCCTCTTCGATATCATCTATGCAAAGCTTGACTTCTGTTGATTTTTCATACAACAACCTGTCT<br>GGTTTGGTGCCTGGTACCGGTCAATTCAGCTACTTCAACTACACGTCTTTCTTGGGAAACCCTGA<br>CCTGTGTGGCCCCTATTTGGGTGCTTGCAAGGGTGGGGTTGCCAATGGTGCACACCAACCTCATG<br>TTAAAGGACTCTCCTCTTCTTTGAAGCTGCTACTTGTTGTTGGGTTGCTATTATGTTCCATTGCT<br>TTTGCTGTGGCTGCAATATTCAAGGCCCGGTCATTAAAGAAGGCCAGTGAGGCTCGTGCATGGAA<br>GTTGACTGCGTTCCAGCGTTTGGACTTCACTGTTGATGATGTTTTGCATTGCTTGAAAGAGGATA<br>ATATTATTGGGAAAGGAGGTGCTGGAATTGTCTACAAAGGGGCTATGCCTAATGGGGATCATGTT<br>GCTGTGAAAAGGCTTCCAGCTATGAGTAGAGGCTCTTCCCATGATCACGGATTCAATGCTGAGAT<br>TCAGACATTGGGGCGAATCCGACACAGGCACATTGTTAGGTTGTTGGGTTTCTGTTCAAATCATG<br>AGACAAACCTTTTGGTCTATGAGTACATGCCCAATGGAAGTTTAGGTGAGGTTCTTCATGGAAAA<br>AAGGGGGGTCATTTGCATTGGGACACCAGGTATAAAATTGCGGTGGAGGCTGCCAAGGGGCTTTG<br>CTATCTGCACCATGATTGTTCGCCACTCATTGTCCATCGTGATGTGAAGTCAAACAACATCCTTC<br>TTGATTCAAATCATGAAGCCCATGTTGCTGATTTTGGGCTTGCTAAGTTCCTGCAAGATTCTGGG<br>ACATCTGAATGCATGTCTGCTATTGCTGGTTCATATGGATACATAGCTCCAGAGTATGCCTACAC<br>ATTGAAAGTTGATGAGAAAAGCGATGTGTACAGTTTTGGTGTGGTTCTTTTAGAACTTATAACAG<br>GCAGGAAACCAGTTGGTGAATTTGGTGATGGCGTGGACATCGTGCAATGGGTGAGGAAAATGACG<br>GACTCTAACAAGGAAGGAGTTCTTAAAGTTCTTGATCCTAGGCTTCCCTCAGTTCCCCTTCACGA<br>AGTGATGCATGTTTTCTATGTGGCCATGCTGTGTGTTGAAGAACAGGCTGTAGAGAGACCAACAA<br>TGCGTGAAGTTGTTCAAATACTGACCGAGCTTCCAAAGCCACCTGGCTCTAAAGAGGGAGACTTA<br>ACAATAACAGAATCCTCTTTGTCATCATCAAACGCTTTAGAATCTCCATCCTCAGCCTCCAAGGA<br>AGATCAAAATCCTCCTCAATCCCCACCACCCGACCTTCTTAGTATTTAA |
| Glyma11g04700 protein (SEQ ID NO: 34) Soybean BAM2-like gene | MPKMRVLFVFLFFHFHFPETLSAPISEYRALLSLRSVITDATPPVLSSWNASIPYCSWLGVTCDN<br>RRHVTALNLTGLDLSGTLSADVAHLPFLSNLSLAANKFSGPIPPSLSALSGLRYLNLSNNVFNET<br>FPSELWRLQSLEVLDLYNNNMTGVLPLAVAQMQNLRHLHLGGNFFSGQIPPEYGRWQRLQYLAVS<br>GNELDGTIPPEIGNLTSLRELYIGYYNTYTGGIPPEIGNLSELVRLDVAYCALSGEIPAALGKLQ<br>KLDTLFLQVNALSGSLTPELGNLKSLKSMDLSNNMLSGEIPASFGELKNITLLNLFRNKLHGAIP<br>EFIGELPALEVVQLWENNLTGSIPEGLGKNGRLNLVDLSSNKLTGTLPPYLCSGNTLQTLITLGN<br>FLFGPIPESLGTCESLTRIRMGENFLNGSIPKGLFGLPKLTQVELQDNYLSGEFPEVGSVAVNLG<br>QITLSNNQLSGALSPSIGNFSSVQKLLLDGNMFTGRIPTQIGRLQQLSKIDFSGNKFSGPTAPEI |

TABLE 5-continued

Soybean Genomic DNA sequence, cDNA sequences, and protein sequences

| Sequence Description | DNA OR PROTEIN SEQUENCE |
|---|---|
| | SQCKLLTFLDLSRNELSGDIPNEITGMRILNYLNLSKNHLVGSIPSSISSMQSLTSVDFSYNNLS<br>GLVPGTGQFSYFNYTSFLGNPDLCGPYLGACKGGVANGAHQPHVKGLSSSLKLLLVVGLLLCSIA<br>FAVAAIFKARSLKKASEARAWKLTAFQRLDFTVDDVLHCLKEDNIIGKGGAGIVYKGAMPNGDHV<br>AVKRLPAMSRGSSHDHGFNAEIQTLGRIRHRHIVRLLGFCSNHETNLLVYEYMPNGSLGEVLHGK<br>KGGHLHWDTRYKIAVEAAKGLCYLHHDCSPLIVHRDVKSNNILLDSNHEAHVADFGLAKFLQDSG<br>TSECMSATAGSYGYIAPEYAYTLKVDEKSDVYSFGVVLLELITGRKPVGEFGDGVDIVQWVRKMT<br>DSNKEGVLKVLDPRLPSVPLHEVMHVFYVAMLCVEEQAVERPTMREVVQILTELPKPPGSKEGDL<br>TITESSLSSSNALESPSSASKEDQNPPQSPPPDLLSI |
| Glyma09g38720 gDNA + about 1 kb of promoter and 5'UT sequence (SEQ ID NO: 35) Soybean CLV2-like gene | CACGTGGTACACGAACACCGACGCCATCAGAATCCAAAAGGGTATCAGGAATCACAATCAAAAAC<br>GAATTTTGTTCTAGTTTTTATATCCTTAAAAAATTCGAAACCAGAGAGAGAAAAAAAAATGGTTGG<br>GTTTTTTTACTCTTGTCGGGTGAGAGCTATAAGAGGGTGTGGAGGAAGATGAGGAGAAGATCGAG<br>GGCGGTGATGGGATGGCGGTGGAGGATCACAGCAGAGAAATAGTTTGCCATTGCCATGGAGGGAG<br>AGCGAAGAGGTTGAGGCCCATTCAATTGAATTGGATCAGAGAGAGTTAACTGAAGAATCGGTCAC<br>TGAGAAAAGGGCGCGTAGCTTAGCATTTGATATGTGGCGATTTGGTTTGGGTACGTCCTTTCGGG<br>GACAGAAGAAGATGGATCAAAGACGCTTAATGCGGTTGGGACCTGAGAATGAATGAGAGAGACAC<br>TCACTACACTCACAAAAGGAGGTTCAATTTATCAAATAAAAAAGAGAGACACAGGGGATGGATGT<br>GTCATGTGTGTGTCCATGTGTGGTGAGCTCCATCATATAGAGAATCTTTTCACCTTAATTATTTT<br>TTAAGGCTATTCTTAATCAGTAATCTTAGACATTGATTAAAAAATTAAAAAGAAAATATAAAATA<br>AGTTGTAGAGCACTATAATTTAATATTTTAATATAAAAAGTATTTAGAAGAATGATAAATATATC<br>TAGCTTTCTTAATATATAAAATTAATATAAATTAGTATAATATCACAAATATTTTATTAAACCAA<br>ACAATTAACATTTTAAAAATTTTATATTTGATTTTTACTGTGTCTAAAATTTTTTGGGTCGCTGA<br>TAACCACAAATTACAAACAAAATTAATCTCCCATTGAATTAAAAAATAACATAATCTATAACCTA<br>TCAAAAAGAAAAAGAAAAAAGAATCTGGACCTATTTCTACCCCGATGCACATGAGAAACTTAAAA<br>AGGGGGTGAAGTGTTATGTAGTATAGAGAGAAAGCGAGGGAAGGCAAAGCAAGCACAACAGAACA<br>AAGCCACTTTATTTTTTTGATCTAACCTAAACCATCCTTTCCCCCTGTTGCACTCTCACTTTATC<br>AACGTGACACAAGCAACTTATGACCAATGTGTAAGATGTTGTTCCTCTTTCCCTTCTCTTCTGTC<br>CATTTCATCAAGTTTCCATTCTAATCTCCAAATCTTTGCCACCCCAGTTCCTCTTTTGCTTCAAA<br>CTTCTCTTCCCCTCCCTAAAAATTGCACCTTTACTCTCATGGTGATGGGACACACCACACCCCTC<br>ACACTCCTCTGTATGATTCTTCTTTTTGCAACCCCTTCTCTCTCAATTGATGTTCACCCACAAGA<br>CAGAATCTCACTCTCACTGTTCAGGTCATCTCTGCCAAACCCCAACCAGAGTTTGCCCAGCTGGG<br>TAGGCTCCAACTGCACTTCATGGAGTGGAATCACCTGCGACAGCAGAACTGGGAGAGTGCTTTCC<br>ATCAACCTAACTAGCATGAACCTTTCAGGCAAAATCCACCCCAGTTTGTGCCACCTTTCATACCT<br>CAACAAGTTGGGGTTGTCACACAACAACTTCACAGCCCCACTTCCTGAGTGTTTTGGAAACTTGC<br>TTAACCTAAGAGCCATTGATCTCAGCCACAACAGGTTTCATGGTGGAATACCAGACTCTTTCATG<br>AGGCTCAGGCACCTCACTGAGCTTGTTTTCAGTGGGAACCCTGGTTTGGGGGGTCCACTTCCTGC<br>TTGGATTGGTAACTTCTCTGCAAATCTGGAAAAGTTACATCTTGGTTTCTGTTCATTCAGTGGTG<br>GCATACCTGAGAGCTTGCTTTACATGAAGTCCCTCAAGTATTTGGACCTTGAGAACAATCTCTTG<br>TTTGGTAATTTGGTTGATTTTCAACAGCCTTTGGTTTTGCTCAATCTTGCTTCCAATCAGTTTGC<br>TGGTACTTTGCCTTGCTTTGCAGCTTCAGTTCAGTCTCTAACTGTGTTGAATTTGTCCAACAATT<br>CTATTGCGGGGGGATTGCCTGCTTGTATTGCTTCTTTTCAAGCTTTGACTCATTTGAACCTTTCA<br>GGGAACCATTTGAAGTATAGAATATATCCTAGGCTTGTGTTCTCAGAGAAACTTCTTGTTTTGGA<br>CTTGAGTAATAATGCTTTTATCTGGTCCTATTCCCAGTAAAATTGCTGAGACTACTGACAAACTTG<br>GCCTTGTTCTTCTTGACCTTTCTCACAATCAGTTCTCTGGTGAAATACCTGTGAAAATTACTGAG<br>TTGAAAAGCTTGCAGGCCTTGTTTCTCTCTCACAATCTTCTCTCAGGAGAAATTCCTGCTAGAAT<br>TGGAAATTTGACTTATCTGCAGGTCATTGATCTCTCACACAACTCTTTGTCTGGAACCATTCCAT<br>TCAGTATTGTTGGGTGCTTTCAGCTGTATGCTCTGATACTTAACAACAACAATCTTTCTGGTGTA<br>ATTCAACCGGAGTTTGATGCGTTGGATATCTTGAGGATACTGGATATAAGCAACAACAGGTTTTC<br>CGGGGCTATCCCACTCACTTTGGCTGGATGCAAATCTTTGGAGATTGTAGACTTTAGTTCCAATG<br>AGCTTTCTGGATCGTTGAATGATGCAATAACCAAATGGACAAACCTCAGGTATTTGTCTCTTGCT<br>CAGAACAAGTTCAGTGAAAATCTGCCTAGTTGGTTGTTCACATTTAACGCAATAGAAATGATGGA<br>TTTCTCGCATAACAAGTTTACTGGCTTCATACCGGATATTAATTTTAAGGGTAGCTTAATATTTA<br>ACACTAGGAATGTCACTGTTAAAGAGCCATTGGTTGCAGCAAGAAAGGTTCAACTCAGAGTTTCG<br>GCGGTTGTTTCTGATAGCAATCAACTCAGTTTCACTTATGATCTTTCCTCAATGGTTGGAATTGA<br>TCTATCCAGCAACTCGCTTCATGGGGAAATTCCAAGGGGCTTATTTGGTCTATCTGGCCTAGAAT<br>ATCTGAATTTGTCATGCAACTTTCTTTACGGACAGCTTCCGGGGTTGCAGAAAATGCAGAGTTTG<br>AAAGCCTTGGATTTGTCACATAATTCCTTGTCAGGACATATCCCAGGAAACATCTCTATCCTTCA<br>AGATCTGTCTATTTTGAATCTTTCCTACAACTGCTTTTCTGGATGTGTTCCCCAGAAGCAAGGGT<br>ATGGGAGATTTCCTGGTGCATTTGCTGGAAATCCAGATCTGTGCATGGAATCTTCCAGTGGATTA<br>TGTGATGATGGAAGGACTCAATCTGCGCAAGGAAGTACTTTTAGGGAAGATAGGATGGATGACCC<br>AATTTCTGTGGGGATTTTCTTTATCAGTGCATTTGTTAGTTTTGATTTTGGTGTTGTGGTTCTCT<br>TCTGTTCCGCACGGGCAAGAAATTACATTCTCCAAACAAAAGTTTGATTTGATGCTTGTGACACA<br>TACAAATCTCCTGTAAATTCCATTTTGTAATGTGGTACCTGTCTTCTCAGTTTCAAGTAAACATA<br>CACTTACGTGACTGGGAATACTATCTGGCCATCAGCTTCACAAGTGTTTTCTCGTGATTACTGAA<br>CAAGTGTCTCGGAATTGCAGGATCAAAATGCCATGATATGAGTAACACAAGGTTTAAAGAACACT<br>CATAACGCTGGCTTTAACTATCTGAGTGAAGACTAGTCCTGCATCATTCAGCCAAGAAAAAAATG<br>GATGGTTATGATGAAAATTTGATCCAAGTAAAGACGAGTCCCTCATCATTCTGATGGTTGTTCTC<br>TTTTGCTGGAACTTGGTTGCATCAAGTTTATTATGCATCATCACATGCATTATTCATAATCAGGT<br>GGGTGAAGGGTCAGCAAGGAACATGCCTGATTGATATCTGGTCTAGTTATGGTGAAATTTTGATC<br>TTGGGACATCAAATTGCAGATTTGCAAGCATGTTTACGTGAAGAGAACTTGTATCATTCTAGATT<br>AACCCAGCTCTTTCTTGAGGTGGGGAACCAAGTTTTCCCTGTAAGTGTTTTACCTTAAGAATGTG<br>AGTTGATGAGTAGTGGGGAGTGGTAAGTGCAGACAAAATAAATGGAGTAGTTCTCATAAATCTAA<br>GATTTGTATTTGTATTACTGTCTTCATGCCTTCATCTTAGTGCTGTGATTTTAAATGAAATTCTC<br>ACGAAATCTTTTCATTGAGAACAGAAAAGAGGTAATTGAGCACCTTAGCTTTGTTATCAAATGCC<br>AAGCATGCTCAACAAAAATTAGAAAAATTATCTAGTTTACCAA |

TABLE 5-continued

Soybean Genomic DNA sequence, cDNA sequences, and protein sequences

| Sequence Description | DNA OR PROTEIN SEQUENCE |
|---|---|
| Glyma09g38720 cDNA (SEQ ID NO: 36) Soybean CLV2-like gene | ATGGTGATGGGACACACCACACCCCTCACACTCCTCTGTATGATTCTTCTTTTTGCAACCCCTTC<br>TCTCTCAATTGATGTTCACCCACAAGACAGAATCTCACTCTCACTGTTCAGGTCATCTCTGCCAA<br>ACCCCAACCAGAGTTTGCCCAGCTGGGTAGGCTCCAACTGCACTTCATGGAGTGGAATCACCTGC<br>GACAGCAGAACTGGGAGAGTGCTTTCCATCAACCTAACTAGCATGAACCTTTCAGGCAAAATCCA<br>CCCCAGTTTGTGCCACCTTTCATACCTCAACAAGTTGGGGTTGTCACACAACAACTTCACAGCCC<br>CACTTCCTGAGTGTTTTGGAAACTTGCTTAACCTAAGAGCCATTGATCTCAGCCACAACAGGTTT<br>CATGGTGGAATACCAGACTCTTTCATGAGGCTCAGGCACCTCACTGAGCTTGTTTTCAGTGGGAA<br>CCCTGGTTTGGGGGGTCCACTTCCTGCTTGGATTGGTAACTTCTCTGCAAATCTGGAAAAGTTAC<br>ATCTTGGTTTCTGTTCATTCAGTGGTGGCATACCTGAGAGCTTGCTTTACATGAAGTCCCTCAAG<br>TATTTGGACCTTGAGAACAATCTCTTGTTTGGTAATTTGGTTGATTTTCAACAGCCTTTGGTTTT<br>GCTCAATCTTGCTTCCAATCAGTTTGCTGGTACTTTGCCTTGCTTTGCAGCTTCAGTTCAGTCTC<br>TAACTGTGTTGAATTTGTCCAACAATTCTATTGCGGGGGGATTGCCTGCTTGTATTGCTTCTTTT<br>CAAGCTTTGACTCATTTGAACCTTTCAGGGAACCATTTGAAGTATAGAATATATCCTAGGCTTGT<br>GTTCTCAGAGAAACTTCTTGTTTTGGACTTGAGTAATAATGCTTTATCTGGTCCTATTCCCAGTA<br>AAATTGCTGAGACTACTGACAAACTTGGCCTTGTTCTTCTTGACCTTTCTCACAATCAGTTCTCT<br>GGTGAAATACCTGTGAAAATTACTGAGTTGAAAAGCTTGCAGGCCTTGTTTCTCTCTCACAATCT<br>TCTCTCAGGAGAAATTCCTGCTAGAATTGGAAATTTGACTTATCTGCAGGTCATTGATCTCTCAC<br>ACAACTCTTTGTCTGGAACCATTCCATTCAGTATTGTTGGGTGCTTTCAGCTGTATGCTCTGATA<br>CTTAACAACAACAATCTTTCTGGTGTAATTCAACCGGAGTTTGATGCGTTGGATATCTTGAGGAT<br>ACTGGATATAAGCAACAACAGGTTTTCCGGGGCTATCCCACTCACTTTGGCTGGATGCAAATCTT<br>TGGAGATTGTAGACTTTAGTTCCAATGAGCTTTCTGGATCGTTGAATGATGCAATAACCAAATGG<br>ACAAACCTCAGGTATTTGTCTCTTGCTCAGAACAAGTTCAGTGAAAATCTGCCTAGTTGGTTGTT<br>CACATTTAACGCAATAGAAATGATGGATTTCTCGCATAACAAGTTTACTGGCTTCATACCGGATA<br>TTAATTTTAAGGGTAGCTTAATATTTAACACTAGGAATGTCACTGTTAAAGAGCCATTGGTTGCA<br>GCAAGAAAGGTTCAACTCAGAGTTTCGGCGGTTGTTTCTGATAGCAATCAACTCAGTTTCACTTA<br>TGATCTTTCCTCAATGGTTGGAATTGATCTATCCAGCAACTCGCTTCATGGGGAAATTCCAAGGG<br>GCTTATTTGGTCTATCTGGCCTAGAATATCTGAATTTGTCATGCAACTTTCTTTACGGACAGCTT<br>CCGGGGTTGCAGAAAATGCAGAGTTTGAAAGCCTTGGATTTGTCACATAATTCCTTGTCAGGACA<br>TATCCCAGGAAACATCTCTATCCTTCAAGATCTGTCTATTTTGAATCTTTCCTACAACTGCTTTT<br>CTGGATGTGTTCCCCAGAAGCAAGGGTATGGGAGATTTCCTGGTGCATTTGCTGGAAATCCAGAT<br>CTGTGCATGGAATCTTCCAGTGGATTATGTGATGATGGAAGGACTCAATCTGCGCAAGGAAGTAC<br>TTTTAGGGAAGATAGGATGGATGACCCAATTTCTGTGGGGATTTTCTTTATCAGTGCATTTGTTA<br>GTTTTGATTTTGGTGTTGTGGTTCTCTTCTGTTCCGCACGGGCAAGAAATTACATTCTCCAAACA<br>AAAGTTTGA |
| Glyma09g38720 protein (SEQ ID NO: 37) Soybean CLV2-like gene | MVMGHTTPLTLLCMILLFATPSLSIDVHPQDRISLSLFRSSLPNPNQSLPSWVGSNCTSWSGITC<br>DSRTGRVLSINLTSMNLSGKIHPSLCHLSYLNKLGLSHNNFTAPLPECFGNLLNLRAIDLSHNRF<br>HGGIPDSFMRLRHLTELVFSGNPGLGGPLPAWIGNFSANLEKLHLGFCSFSGGIPESLLYMKSLK<br>YLDLENNLLFGNLVDFQQPLVLLNLASNQFAGTLPCFAASVQSLTVLNLSNNSIAGGLPACIASF<br>QALTHLNLSGNHLKYRIYPRLVFSEKLLVLDLSNNALSGPIPSKIAETTDKLGLVLLDLSHNQFS<br>GEIPVKITELKSLQALFLSHNLLSGEIPARIGNLTYLQVIDLSHNSLSGTIPFSIVGCFQLYALI<br>LNNNNLSGVIQPEFDALDILRILDISNNRFSGAIPLTLAGCKSLEIVDFSSNELSGSLNDAITKW<br>TNLRYLSLAQNKFSENLPSWLFTFNAIEMMDFSHNKFTGFIPDINFKGSLIFNTRNVTVKEPLVA<br>ARKVQLRVSAVVSDSNQLSFTYDLSSMVGIDLSSNSLHGEIPRGLFGLSGLEYLNLSCNFLYGQL<br>PGLQKMQSLKALDLSHNSLSGHIPGNISILQDLSILNLSYNCFSGCVPQKQGYGRFPGAFAGNPD<br>LCMESSSGLCDDGRTQSAQGSTFREDRMDDPISVGIFFISAFVSFDFGVVVLFCSARARNYILQT<br>KV |
| GmNARK: Glyma12g04390 gDNA + 5 kb promoter and 5'UT (SEQ ID NO: 38) Soybean CLV1-like gene | GCACCCACTGGGTAAGTTGGTAACTACTATGTATCTATATATCGTCAGGTCATTGTCTGTTTCAT<br>TCTCTTCTCACAAGAACAAAATGGTAATTTACATTTAACTTAGAAATGTTTGGGACAGAACCTCT<br>AGCTTGCGATGATTCTCTTCTCACAAGAACAAAATGGTAATTTACATTTAACTTTAGAAATGTTT<br>GGGACCGAACCTCTAGCTTGCGATGATTCTCTTCTCACAAGAACAAAATGGTAATTTACATTTAA<br>CTTTAGAAATGTTTGGGACCGAACCACTAGCTTGCGATGATTCCCTTCTCACAAGAACAAAATGG<br>TAATTTACATTTAACTTAGAAATGTTTGGGACAGAACCACTGGCTTGCGATGATTCTCTTCTCAC<br>AAGAACAAAATGGTAATTTGCATTTAACTTAGAAATGATTGGGACAGAACCACTAGCTTCGATGA<br>ATAATTTGCTTTAATTTTTATTAATGCATAATACCCTTTTATTGTCACACATAGAATCCGATTCT<br>GCAATAACTAGTGCTTGATCCTAATTGACAGAACAAATTAAAACAGAGAATTGATGCTTTGGCTT<br>TTCCATGGGCAATAATTATCCCAATGATATACTAAAGCATAGTAACTAGGAAGACTTCCATGTAA<br>AGAAACTTTCTTTTATTCTCCTTTTAAAATTTGGTGAATCACTTAAAACCACTTTTGTTTCATTC<br>CAAGGTTAGGCTCATGGAAAGCTTAAACCTACTTAACTGGTCACGAAGAGATTGCATCTTTGTTT<br>TCACAAAAGTCTAACTCCAAGTTCGTGTAGCTAGTATTGCATGCTACCATGGTGCAAGTGATGTA<br>CATGCATATATGATATTCAATTTAATTTGCTACTATAATATAAAGGTGTATATATAAATAGAGAG<br>TGCATGAGGTGTGTGGTGTCAACATATAAGGACGCAGCAAAGGTATAATAGCGACTACTGCGAAG<br>CAAGATCAGAGACTAGAGAGACATGATAAGAAGTTGTTAATTTGTTTTCTTCATATGGCTGCGCG<br>TGGCAACGTGCTCTTCGTTCACTGACATGGATGCGCTGCTGAAGCTGAAGGACTCCATGACTGGA<br>AGTTTTCCACGTCGCTTTCTGCACACTGTTTCTTTTCAGGCGTAAACTGCGACCAAGAACTTCGA<br>GTCGTTGCTATCAATGTCTCGTTTGTTCCTCTTTTCGGCTACCTTCCGCCGGAGATCGGACAATT<br>GGACAAACTCGAGAACCTCACTTCCCTCAAGCTCCTCGACATCTCTCACAACGTCTTCTCCGGCC<br>AAATTATTCTTCCGATGACGAAACTGGAGGTCCTCGACGTCTACGACAACAACTTCCGGCAGCAT<br>ACCGGAGATTTACTCGGAGTTTAAGAGCTTGGAGTTTTTAAGCTTAAGCACCAATAACTTATCGG<br>GGAAGATTCCGAAGAGTTTGTCTAAGTTGAAGACGCTGAGGTATCTCAAACTCGGATACAACAAC<br>GCTTACGAAGGTGAAATTCCACCGGAGTTTGGCAGCATAAAATCTGAGATACCTTGACCTCATCG<br>GCGAGATTCCACCTACTCTAAACAATAATAAGAAAAACTTATCACATTTCTTGAAACTTTAAAAG<br>ACCGATAAAAATAAAAGGAGGAAATGCCACTACAATATTTTTAATTTATTTTTTTTACTTATTTT |

TABLE 5-continued

Soybean Genomic DNA sequence, cDNA sequences, and protein sequences

| Sequence Description | DNA OR PROTEIN SEQUENCE |
|---|---|
| | ATTTGAATCTTTAATACATATGCTATTTTAGCATTATAAAAATACCTGGGCTATACAAAATATAC<br>TTGCTAGTAGTATTATGTGTGTGTGAAAGTTAAATGAGTCTTTAAGTATTTGTAAATGTTTAATA<br>AGTTTCGAGGTTTATCTTGATTCCAACAATGAATTCCTGAAATCTAATTTATCTAACTTTTTTT<br>AACCAAAATGTTAAATGGTCTAGTTAAGAGAACAAATCCTTATGTGTTCATTTTTTCACAAGACC<br>TAAAATCTAAAATTTCACTTTAAAAGAAACAAAATACTTGCTACTTGAACTAACAATCATTAGTA<br>CATTTTTTTAGTAATGATATACAAACATCTAAAACTCCTATACAACACAACACATAGAAGACAAT<br>AAAAAATATCAATATGATAAATAAAAATGAGAAATAGATGAATTATTTAAAATAATGAAATGTTT<br>ATTTATCATTACTTTTTTTTACTTTAACAGTTCATACATCTCCTACAAGGTAAGATGTGTAATGC<br>AAGTAAGTTGCAACATGGTTTTAAATTTTGACAATAAGAACCATGCATGTTAATTAGTCTAATCA<br>CAGAGCGTTCGGGATACGCCATTAGTGGTCTATAGTAGTCAACTGCCGGGATAAATCACGATCCA<br>CATTTCATAGGTGTTTCCACCATGTCAACATCGAACTAAAAGGAAAAATATGTGAATGGGTAAAA<br>ATGATTAAAAATATTTGTAAAAAATTATTTGAATTTATTTAAAACAATATGCAAGTTGTTTATAG<br>GTTGAGTATATTTCAATGGTTTTGAAAAATCTATGTAAATAAAAAAAATACAATTATTTATATA<br>AAATAAAATAATCTTTTTTTTATTATTATGACATTGATGAGAGTATCTAATAATTTGACCCATAA<br>CTAATTTGGATAAAAAAAAATCTGATTGACCACTTTTAATTTAATGTATCACTAAACTAAATACC<br>CTTTTTTAAAATAGTCTAAACATGAATTAAATATTCAAAAGAAATATTTTACTTGAGATTATTAC<br>CTAATATTAATGATAATTTCATTCAACTCCAATAAAATTAATTTTCATGTAAGATATATCTAAAA<br>GAAAAGATATATATAAATTTTATTTTCACTAGTAAAAAAAAGTTGATCTAGTTAGTGAAAAACCA<br>ACTCATATCCTATAAGAATATGAATTTGATTTTTTTTGTTAAGGTGAGAATTTTATTGATCAATA<br>ATTTATAAATATCTATATAAATAATCTTTAGCCTTATGAGTCCTTAGGTCAATTCAACTCACCTA<br>AATTTTTTATTATGAAAAAAAAAATTGTATCTTCACAAGATAAATGTGTTGGATTCAATCACTCC<br>TTATTAGCTTAATTAGATTATAATTGTAGTCCCCTATATATATATATGTATCATCTTGTCAAATA<br>ATAATGAAATATAGAATTTATTTAGACTTAGAGAATAAAATTAAAAACTGTCTGCCATGAAAAAA<br>GACGAAGTTAAGAAAAGGGCCAATCATAGAAGATTTTTATGGGCACTTCACGGACACTAACTCAC<br>TGTCACAATCATCACTGGGGTTGACAAAAGGACAATATGAAACACTTTTGAGAAGCATGTACCAC<br>TCATCCATTTATCAGTGGCTCCCAATTCCCAGAGGCCAGAACTATATATGAAAGAATTGTTGAAC<br>GCACGGGCATGAACCCATTCTTGAAGCATCATTGTGTGAGAATATCTTGACCTTGTAAGATGCAA<br>CACCTTTTTAAGCCTTAAATTTAAAAAAGGAAAAAAGAAAAATCTTGTCTCTACTTTCTTTTAGC<br>ACAAGTGTATAGAAATTCTTAAATATATACACTCTCCTTTATATTGTAGTATCAGTGGCGCAAAT<br>CATTATATTTCATTTTTAATAATAAAATTAAGAGCATTAATTTTATAGTTAAAATTGAAAATAAA<br>GATAATTTACAGAACTCATTTGACTTAAACTGACAAAATATATATATATATATATATATATATAT<br>ATATATATATTGTGAGATGAACATGTTACTTTTTTAACATGCAAAAAGGAGAATATATTTTACAT<br>GCATGCACCCATGATAACTTCTATGTATATATCCATACAATACATCGTTCGTATATCGTCTCGTT<br>TGTCTTTATTCTCCTCTCAAAATACGACAATAGCAATTTACATTTTTTTTTATAAGCAAATAGTA<br>ATTTACATTTAACTTAGTAATGTAGGGATCGAACATAACCACTTGCGATGAATAATTTGCTTTAA<br>ATTTTTGTTGATGCGTACCCTTTAACTGTCACTCATGGAATACGATTCTTCAATATCTAGTGCTT<br>GATCGTTGACAGAACAACTTAAAACAGAGAATTGATGTTTTGGCTTTTCCATGGATAATAATTAT<br>CCCAGTGACATACCAAAGCATAGTAGCTAAGAAGACTTTCACGTAAAAAAAAGTTTCTTTTATTC<br>CCTTTTTTAATTTGGTGAATCACAAAAAACCACTTTTGTTTGGTTCCAAAGTTAGGCTCATGGAA<br>AGTTTAAACCTCCATAGAATGGTCACGAAGAGATTGCATCTTTGTCTTCACAAAAGCTAACTCCA<br>CGTTGAGTAGACTTAACAGCCAGTGGCGAATAGCAAGGATATTTCATTAATTATACGCCACCGGC<br>CAAATGTTAACCAATCGTATTATAATTAAGTTCCATCATCATCAAACAATTTAGTAAAGTGCATG<br>ACCCAAATTTCTACGATACATATTTATTTATTAAAAATGTAAGAATATTTCAGTCATATTTAAAA<br>ATATATATATCAAGAATAATTAACTTTGTACACACGCACTGAATAAAAGATTTGTGACAGACAAG<br>GCTTGCATAAAAATTTCTCCTCTAAACTAATTGCTTGTAGGACCTCTCCCACCACTATAGAATCA<br>ATATAATTAATCCGCATTAGAAAGTTATATTGTATACAATTTTCTTGAAACATAATTATACTTCA<br>TGTTTCACAGACTTATAGTGGATCTTGTGTGGCTAGCTACTGATGAATATTGTTTTTTTTTTTC<br>CTAAGCATCCACTTTGAACAACTTTTCCCATTTCATACAAACAGAATTAATTAGTATTGCGTGCC<br>ACCATATGGTACAGTGTTGTACATGCATATAAGCTATTTAATTTAATAATATACAAACATAACGG<br>TGTATATAAATAGAGGCAGCATGTGGTGTGTGGTGTAAAAATAAGGACGCAGGCAAATGTATGCA<br>TTTGGCATAAGTATATAAGAGAGAGGGAGTAGTACTACTGCAAAGCAAAATCAGAGAGACATGAG<br>AAGCTGTGTGTGCTACACGCTATTATTGTTTATTTTCTTCATATGGCTGCGCGTGGCAACGTGCT<br>CTTCGTTCACTGACATGGAATCGCTTCTGAAGCTGAAGGACTCCATGAAAGGAGATAAAGCCAAA<br>GACGACGCTCTCCATGACTGGAAGTTTTTCCCCTCGCTTTCTGCACACTGTTTCTTTTCAGGCGT<br>AAAATGCGACCGAGAACTTCGAGTCGTTGCTATCAACGTCTCGTTTGTTCCTCTCTTCGGTCACC<br>TTCCGCCGGAGATCGGACAATTGGACAAACTCGAGAACCTCACCGTCTCGCAGAACAACCTCACC<br>GGCGTACTTCCCAAGGAGCTCGCCGCCCTCACTTCCCTCAAGCACCTCAACATCTCTCACAACGT<br>CTTCTCCGGCCATTTCCCCGGCCAAATTATCCTTCCGATGACGAAACTGGAGGTCCTCGACGTCT<br>ACGACAACAACTTCACCGGACCGCTTCCCGTAGAGTTGGTGAAACTGGAGAAATTAAAATACCTG<br>AAGCTCGACGGAAACTATTTCTCCGGCAGCATACCGGAGAGTTACTCGGAGTTTAAGAGCTTGGA<br>GTTTTTAAGCTTAAGCACCAATAGCTTATCGGGGAAGATTCCCAAGAGTTTGTCGAAGTTGAAGA<br>CGCTGAGGTACCTAAAACTCGGATACAACAACGCTTACGAAGGTGGAATTCCACCGGAGTTTGGC<br>AGCATGAAATCTCTGAGATACCTTGACCTCTCTAGCTGCAACCTCAGCGGCGAGATTCCACCGAG<br>CCTTGCAAATCTGACAAACCTTGACACGTTGTTCCTGCAAATTAACAACCTCACCGGAACCATTC<br>CGTCGGAGCTCTCCGCTATGGTGAGCCTCATGTCACTTGATCTCTCCATCAACGACCTCACCGGT<br>GAGATACCGATGAGCTTCTCACAGCTTAGAAACCTCACTCTCATGAACTTCTTCCAAAACAATCT<br>TCGCGGCTCAGTTCCGTCCTTCGTCGGCGAGCTTCCGAATCTGGAAACGCTGCAGCTCTGGGATA<br>ACAACTTCTCCTTCGTGCTACCTCCGAACCTTGGGCAAAACGGCAAGTTAAAGTTCTTCGACGTC<br>ATCAAGAATCACTTCACCGGGTTGATCCCTCGAGATTTGTGTAAGAGTGGGAGGTTACAAACGAT<br>CATGATCACAGATAACTTCTTCCGCGGTCCAATCCCTAACGAGATTGGTAACTGCAAGTCTCTCA<br>CCAAGATCCGAGCCTCCAATAACTACCTTAACGGCGTGGTTCCGTCAGGGATTTTCAAACTACCT<br>TCTGTCACGATAATCGAGCTGGCCAATAACCGTTTTAACGGCGAACTGCCTCCTGAGATTTCCGG<br>CGAATCCCTGGGGATTCTCACTCTTTCCAACAACTTATTCAGTGGGAAAATTCCCCCAGCGTTGA<br>AGAACTTGAGGGCACTGCAGACTCTCTCACTTGACGCAAACGAGTTCGTTGGAGAAATACCGGGA<br>GAGGTTTTTGACCTACCGATGCTGACTGTGGTCAACATAAGCGGCAACAATCTAACCGGACCAAT |

TABLE 5-continued

Soybean Genomic DNA sequence, cDNA sequences, and protein sequences

| Sequence Description | DNA OR PROTEIN SEQUENCE |
| --- | --- |
| | CCCAACGACGTTGACTCGCTGCGTTTCACTCACCGCCGTGGACCTCAGCCGGAACATGCTTGAAG<br>GGAAGATTCCGAAGGGAATCAAAAACCTCACGGACTTGAGCATTTTCAATGTGTCGATAAACCAA<br>ATTTCAGGGCCAGTCCCTGAGGAGATTCGCTTCATGTTGAGTCTCACCACATTGGATCTATCCAA<br>CAACAATTTCATCGGCAAGGTCCCAACCGGGGGTCAGTTCGCGGTCTTCAGCGAGAAATCCTTTG<br>CAGGGAACCCCAACCTCTGTACCTCCCACTCTTGCCCGAATTCCTCGTTGTACCCTGACGACGCC<br>TTGAAGAAGAGGCGCGGCCCTTGGAGTTTGAAATCCACGAGGGTGATAGTCATCGTGATTGCACT<br>GGGCACAGCCGCGCTGCTGGTGGCGGTGACGGTGTACATGATGAGGAGGAGGAAGATGAACCTTG<br>CGAAGACGTGGAAGCTGACGGCGTTCCAGCGGCTGAACTTCAAAGCCGAGGACGTGGTGGAGTGT<br>CTGAAGGAGGAGAACATAATAGGAAAAGGAGGGGCAGGGATCGTGTACCGCGGGTCCATGCCAAA<br>CGGAACAGACGTGGCGATAAAGCGGTTGGTTGGGGCGGGGAGTGGAAGGAACGATTACGGATTCA<br>AAGCGGAGATAGAAACGCTGGGGAAGATAAGGCACAGGAACATAATGAGGCTTTTAGGTTACGTG<br>TCGAACAAGGAGACGAACTTGCTGCTGTATGAGTACATGCCAAATGGGAGCTTAGGGGAATGGCT<br>GCATGGTGCCAAAGGAGGGCACTTGAAGTGGGAAATGAGGTACAAGATTGCGGTGGAAGCTGCTA<br>AGGGACTGTGCTATTTGCACCATGATTGTTCCCCTCTTATCATTCACAGGGATGTCAAGTCTAAT<br>AATATATTGCTGGATGGGGACTTGGAGGCCCATGTTGCTGATTTTGGCCTTGCCAAGTTCTTGTA<br>CGACCCTGGCGCCTCTCAGTCCATGTCCTCCATTGCTGGCTCCTACGGCTACATTGCTCCAGGTT<br>CCATTCATTATTATTTTCTCTTTTCCTTCTTCATAATCTTAATATACCATGCAGATAACGTACAA<br>CATGCATACTTATACATATAATTTTATCCTTTCAACATATAATCAAATATTTCATATCTAATAAT<br>ACCAACTTCATATTATAAACATCACCTAATATAATCAACATGACTTGATAAATAAGACATATAAG<br>TTCAATATTTAAACTCATGTGTCTGAAAAAACATTAATTGGAAAAGTCACTCTTAAAAATATTTG<br>ATAATATATCAATATGACCATATGATTCCAATTACGATCACAAACTCTGTTAAAAATTCTTGCTG<br>AAGATATTAGTCCTTGAATACTAATATAAGAATATCTTGGGTTAGAAAAGTTACTATTTTACTGT<br>TAATTCCCGTTTACTTTAGATGGGTTGGAAGTTGAAAAGTTGAGTGATTTAATTTGTTTCTGGTG<br>GTTGCGCAGAGTATGCATACACTTTGAAAGTGGACGAGAAAAGTGATGTGTACAGCTTTGGCGTT<br>GTGCTGCTGGAGCTGATAATAGGGAGGAAGCCAGTGGGAGAGTTTGGAGACGGGGTGGACATCGT<br>TGGATGGGTCAACAAAACGAGATTGGAGCTCGCTCAGCCGTCGGATGCAGCGTTGGTGTTGGCAG<br>TGGTGGACCCAAGGTTGAGTGGGTATCCATTGACAAGTGTCATTTACATGTTCAACATAGCTATG<br>ATGTGTGTTAAAGAAATGGGGCCCGCTAGGCCTACCATGAGGGAAGTCGTTCATATGCTCTCAGA<br>GCCTCCTCACTCTGCTACTCACACTCACAACCTAATTAATCTCTAGTTAATTAAGTTATTTGCTC<br>ATCGATCCAGAATCACTTCTTTTCAAAATAAATTAACACAGACGAAAACTGTAGGAATAACTTTC<br>ATCTGTTGTTTGTCGGAAGTGAAACAACGAATCAAATGTGAACTATGTATCAAATGTAAGATAGG<br>TTTTAATTAATTTTGTAATATTGGTGTCAACTGTCAAGTAATTCGAAGGATTTTCCCCATTGTGC<br>ATGTATCAAGA |
| GmNARK: Glyma12g04390 cDNA (SEQ ID NO: 39) Soybean CLV1-like gene | ATGAGAAGCTGTGTGTGCTACACGCTATTATTGTTTATTTTCTTCATATGGCTGCGCGTGGCAAC<br>GTGCTCTTCGTTCACTGACATGGAATCGCTTCTGAAGCTGAAGGACTCCATGAAAGGAGATAAAG<br>CCAAAGACGACGCTCTCCATGACTGGAAGTTTTTCCCCTCGCTTTCTGCACACTGTTTCTTTTCA<br>GGCGTAAAATGCGACCGAGAACTTCGAGTCGTTGCTATCAACGTCTCGTTTGTTCCTCTCTTCGG<br>TCACCTTCCGCCGGAGATCGGACAATTGGACAAACTCGAGAACCTCACCGTCTCGCAGAACAACC<br>TCACCGGCGTACTTCCCAAGGAGCTCGCCGCCCTCACTTCCCTCAAGCACCTCAACATCTCTCAC<br>AACGTCTTCTCCGGCCATTTCCCCGGCCAAATTATCCTTCCGATGACGAAACTGGAGGTCCTCGA<br>CGTCTACGACAACAACTTCACCGGACCGCTTCCCGTAGAGTTGGTGAAACTGGAGAAATTAAAAT<br>ACCTGAAGCTCGACGGAAACTATTTCTCCGGCAGCATACCGGAGAGTTACTCGGAGTTTAAGAGC<br>TTGGAGTTTTTAAGCTTAAGCACCAATAGCTTATCGGGGAAGATTCCCAAGAGTTTGTCGAAGTT<br>GAAGACGCTGAGGTACCTAAAACTCGGATACAACAACGCTTACGAAGGTGGAATTCCACCGGAGT<br>TTGGCAGCATGAAATCTCTGAGATACCTTGACCTCTCTAGCTGCAACCTCAGCGGCGAGATTCCA<br>CCGAGCCTTGCAAATCTGACAAACCTTGACACGTTGTTCCTGCAAATTAACAACCTCACCGGAAC<br>CATTCCGTCGGAGCTCTCCGCTATGGTGAGCCTCATGTCACTTGATCTCTCCATCAACGACCTCA<br>CCGGTGAGATACCGATGAGCTTCTCACAGCTTAGAAACCTCACTCTCATGAACTTCTTCCAAAAC<br>AATCTTCGCGGCTCAGTTCCGTCCTTCGTCGGCGAGCTTCCGAATCTGGAAACGCTGCAGCTCTG<br>GGATAACAACTTCTCCTTCGTGCTACCTCCGAACCTTGGGCAAAACGGCAAGTTAAAGTTCTTCG<br>ACGTCATCAAGAATCACTTCACCGGGTTGATCCCTCGAGATTTGTGTAAGAGTGGGAGGTTACAA<br>ACGATCATGATCACAGATAACTTCTTCCGCGGTCCAATCCCTAACGAGATTGGTAACTGCAAGTC<br>TCTCACCAAGATCCGAGCCTCCAATAACTACCTTAACGGCGTGGTTCCGTCAGGGATTTTCAAAC<br>TACCTTCTGTCACGATAATCGAGCTGGCCAATAACCGTTTTAACGGCGAACTGCCTCCTGAGATT<br>TCCGGCGAATCCCTGGGGATTCTCACTCTTTCCAACAACTTATTCAGTGGGAAAATTCCCCCAGC<br>GTTGAAGAACTTGAGGGCACTGCAGACTCTCTCACTTGACGCAAACGAGTTCGTTGGAGAAATAC<br>CGGGAGAGGTTTTTGACCTACCGATGCTGACTGTGGTCAACATAAGCGGCAACAATCTAACCGGA<br>CCAATCCCAACGACGTTGACTCGCTGCGTTTCACTCACCGCCGTGGACCTCAGCCGGAACATGCT<br>TGAAGGGAAGATTCCGAAGGGAATCAAAAACCTCACGGACTTGAGCATTTTCAATGTGTCGATAA<br>ACCAAATTTCAGGGCCAGTCCCTGAGGAGATTCGCTTCATGTTGAGTCTCACCACATTGGATCTA<br>TCCAACAACAATTTCATCGGCAAGGTCCCAACCGGGGGTCAGTTCGCGGTCTTCAGCGAGAAATC<br>CTTTGCAGGGAACCCCAACCTCTGTACCTCCCACTCTTGCCCGAATTCCTCGTTGTACCCTGACG<br>ACGCCTTGAAGAAGAGGCGCGGCCCTTGGAGTTTGAAATCCACGAGGGTGATAGTCATCGTGATT<br>GCACTGGGCACAGCCGCGCTGCTGGTGGCGGTGACGGTGTACATGATGAGGAGGAGGAAGATGAA<br>CCTTGCGAAGACGTGGAAGCTGACGGCGTTCCAGCGGCTGAACTTCAAAGCCGAGGACGTGGTGG<br>AGTGTCTGAAGGAGGAGAACATAATAGGAAAAGGAGGGGCAGGGATCGTGTACCGCGGGTCCATG<br>CCAAACGGAACAGACGTGGCGATAAAGCGGTTGGTTGGGGCGGGGAGTGGAAGGAACGATTACGG<br>ATTCAAAGCGGAGATAGAAACGCTGGGGAAGATAAGGCACAGGAACATAATGAGGCTTTTAGGTT<br>ACGTGTCGAACAAGGAGACGAACTTGCTGCTGTATGAGTACATGCCAAATGGGAGCTTAGGGGAA<br>TGGCTGCATGGTGCCAAAGGAGGGCACTTGAAGTGGGAAATGAGGTACAAGATTGCGGTGGAAGC<br>TGCTAAGGGACTGTGCTATTTGCACCATGATTGTTCCCCTCTTATCATTCACAGGGATGTCAAGT<br>CTAATAATATATTGCTGGATGGGGACTTGGAGGCCCATGTTGCTGATTTTGGCCTTGCCAAGTTC<br>TTGTACGACCCTGGCGCCTCTCAGTCCATGTCCTCCATTGCTGGCTCCTACGGCTACATTGCTCC<br>AGAGTATGCATACACTTTGAAAGTGGACGAGAAAAGTGATGTGTACAGCTTTGGCGTTGTGCTGC |

TABLE 5-continued

Soybean Genomic DNA sequence, cDNA sequences, and protein sequences

| Sequence Description | DNA OR PROTEIN SEQUENCE |
|---|---|
| | TGGAGCTGATAATAGGGAGGAAGCCAGTGGGAGAGTTTGGAGACGGGGTGGACATCGTTGGATGG<br>GTCAACAAAACGAGATTGGAGCTCGCTCAGCCGTCGGATGCAGCGTTGGTGTTGGCAGTGGTGGA<br>CCCAAGGTTGAGTGGGTATCCATTGACAAGTGTCATTTACATGTTCAACATAGCTATGATGTGTG<br>TTAAAGAAATGGGGCCCGCTAGGCCTACCATGAGGGAAGTCGTTCATATGCTCTCAGAGCCTCCT<br>CACTCTGCTACTCACACTCACAACCTAATTAATCTCTAG |
| GmNARK: Glyma12g04390 protein (SEQ ID NO: 40) Soybean CLV1-like gene | MRSCVCYTLLLFIFFIWLRVATCSSFTDMESLLKLKDSMKGDKAKDDALHDWKFFPSLSAHCFFS<br>GVKCDRELRVVAINVSFVPLFGHLPPEIGQLDKLENLTVSQNNLTGVLPKELAALTSLKHLNISH<br>NVFSGHFPGQIILPMTKLEVLDVYDNNFTGPLPVELVKLEKLKYLKLDGNYFSGSIPESYSEFKS<br>LEFLSLSTNSLSGKIPKSLSKLKTLRYLKLGYNNAYEGGIPPEFGSMKSLRYLDLSSCNLSGEIP<br>PSLANLTNLDTLFLQINNLTGTIPSELSAMVSLMSLDLSINDLTGEIPMSFSQLRNLTLMNFFQN<br>NLRGSVPSFVGELPNLETLQLWDNNFSFVLPPNLGQNGKLKFFDVIKNHFTGLIPRDLCKSGRLQ<br>TIMITDNFFRGPIPNEIGNCKSLTKIRASNNYLNGVVPSGIFKLPSVTIIELANNRFNGELPPEI<br>SGESLGILTLSNNLFSGKIPPALKNLRALQTLSLDANEFVGEIPGEVFDLPMLTVVNISGNNLTG<br>PIPTTLTRCVSLTAVDLSRNMLEGKIPKGIKNLTDLSIFNVSINQISGPVPEEIRFMLSLTTLDL<br>SNNNFIGKVPTGGQFAVFSEKSFAGNPNLCTSHSCPNSSLYPDDALKKRRGPWSLKSTRVIVIVI<br>ALGTAALLVAVTVYMMRRRKMNLAKTWKLTAFQRLNFKAEDVVECLKEENIIGKGGAGIVYRGSM<br>PNGTDVAIKRLVGAGSGRNDYGFKAEIETLGKIRHRNIMRLLGYVSNKETNLLLYEYMPNGSLGE<br>WLHGAKGGHLKWEMRYKIAVEAAKGLCYLHHDCSPLIIHRDVKSNNILLDGDLEAHVADFGLAKF<br>LYDPGASQSMSSIAGSYGYIAPEYAYTLKVDEKSDVYSFGVVLLELIIGRKPVGEFGDGVDIVGW<br>VNKTRLELAQPSDAALVLAVVDPRLSGYPLTSVIYMFNIAMMCVKEMGPARPTMREVVHMLSEPP<br>HSATHTHNLINL |
| GmCLV1A: Glyma11g12190 gDNA + about 1.6 kb promoter and 5'UT sequence (SEQ ID NO: 41) Soybean CLV1-like gene | AGCTTCGCATAAGTAACGTGAGTTTAGTTAAGTCGAGCTAGTCGCCTTTTTCTATGGTTGGTTAT<br>GTGCAGTAGTGAATGTTGTGTAGTATCTTGCGAGGCCATGTTTGGTGTGACAAGCCCGAAAGTGA<br>CTTGAGGGGAACAAAATAGCTTTTGTCCAAACATGCTAACTTGTCATCATGACATCTACTTCTCT<br>GGTCATGGCAGCTCTGATTAATAATTTAAGTGATCATAATATTAGAAGTTAAAAAATTATAACAT<br>CTTTAATTATTTTTATTATTTTATATAATCTTAAAAATTATTTCAAACTTCTTTAAACAATGTTG<br>AATAAGATCATGTATTTTTTTTTTTTTCCTTACGTAGTAGTATCCTGGCAGTCACCCAGGAGCAAA<br>TGATGTAGATAAATCCTTTTTACTAAAATAGTCTTGGAGCAATATTTAAGAGGGGACCATTTTAT<br>GATCTTTTCTATCTTAATAGTGGCGTTAGAATAACACTTTTTTAAGCTTTAAATAAAAAATAAAA<br>AAATATTATCTTTACTTTCTTTTAGCAATTATTCCTACGTGTAGAGAAACTGTTAAATACACTCT<br>CCTTTGTATTGTATAATGTTGCATTGTATCAGTTGTCCAAATTAATCACAGTATATTAGTAATAA<br>AATTATGAACATTAATTTTATTCTTAAAATTTAGTTAAATATTGATAATTCACATAACTCGTGAC<br>TTAATCTAATTATATATAGAAGATCATGTTAGTATGTTACCTTTTTAAAATGCAAAATGAAGAAT<br>CTGTTACATGCACCCACTGGGTAAGTTGATAACTATTATGTATCTATATATCGTCTGGATATTGT<br>CTGTTTCATTCTCTTCTCAAAAGAACAAAATGGTAATTTACATTTAACTTAGAAATGTTTGGGAC<br>AGAATCACTAGCTTGCAGATGAATAATTTGTTTTAAATTCTTATTGATGCATAATACCCTCTACT<br>TGTCACTCATAGAATACGATTCTGCAATAACTAGTGCTTGATCCTTGACAGAACAAATTAAAACA<br>GAGAATTGATGCATTGGCTTTTCCATGGACAATAATTATCCCATTGATGTACTAAAGCACAGTAA<br>CTAGGTAGGAAGACCTCCACCTAAAGAAACTTTCTTTTATTCTCCTTTAATTTTAAATTTGGTGA<br>ATCACTTAAAACAACTTTTGTTTCATTCCAAAGTTAGGCTCATGGAAAGCTTAAACCTAGTTAAA<br>TAGCCACGAAAGAGATTGCATCTTTGTTTTCACAAAAGCTAACTGCGCGTTTGTGAAGCTAGTGA<br>TGCATAGTATATATATATTTTTTTCTCGGCATCCACTTTGAGAACTACTTTTTTTTTCATTTTCA<br>TAGAAACAGAATTGAAGTAGTATAACATGCCACCATGAACAGTACAGTGATGTACATGAATAAAT<br>GCATGCTATTCAATATAATGTATAATATAACGGTGTATATATAAATAGAGACTGCATGAGGTGTG<br>TGGTGTCAACATATAATAAGGACGCAGCGTAGGTATAATAGTGAGTACCGCGAAGAAAGATAAGA<br>GCCAGAGCCATGAGAAGCTGTGTGCTTTACACGCTATTATTGTTTGTTTTCTGCATATGGGTTCC<br>CATGGCAACGTGCTCTTCGTTCAGTGACATGGATGCGTTACTAAAGCTGAAGGAGTCCATGAAAG<br>GAGACGAAGCCAAAGACGACGCACTCCATGACTGGAAGTTTTCCACATCGCATTCTGCACACTGT<br>TTCTTTTCAGGCGTAACATGTGACCAAGACCTTCGAGTCGTTGCTATCAACGTCTCCTTTGTTCC<br>TCTCTTCGGTCACATTCCGCCGGAGATCGGAAACTTGGACAAGCTGGAAAATCTCACAATCGTGA<br>ACAACAATCTAACCGGTGTACTCCCCATGGAGCTTGCCGCCCTCACTTCCCTCAAGCACCTCAAC<br>ATATCTCACAACCTCTTCACCGGCGATTTCCCCGGCCAAGCCACTCTTCCGATGACGGAACTTCA<br>AGTCCTCGACGTCTACGACAACAACTTCACCGGACCGCTTCCGGAAGAATTCGTGAAACTGGAGA<br>AACTAAAATACCTGAAACTCGACGGAAACTATTTTACCGGCAGCATACCGGAGAGTTACTCGGAG<br>TTTAAGAGCTTGGAGTTTTTGAGCTTAAACACCAACAGCTTATCGGGGAGGATTCCGAAGAGTTT<br>GTCCAAGTTGAAGACTCTGAGGATTCTCAAACTCGGATACAGCAACGCTTACGAAGGTGGAATTC<br>CTCCGGAGTTCGGCACCATGGAATCTCTGAGATTCCTCGACCTCTCAAGCTGCAACCTCAGCGGC<br>GAGATTCCACCGAGTCTTGCAAATCTGACAAACCTAGACACGTTGTTCTTGCAAATGAACTTCCT<br>CACCGGAAGCATTCCGTCTGAACTCTCTTCTTTGGTGAGGCTCATGGCACTGGATCTCTCCTGCA<br>ACAGCCTCACCGGGGAGATTCCAGAGAGCTTTTCTCAGCTGAGAAACCTCACTCTCATGAACTTG<br>TTCCGCAACAATCTTCACGGCCCTATTCCGTCCTTGCTGAGCGAGCTTCCCAATCTGAATACGCT<br>GCAGCTCTGGGAGAATAACTTCTCCTCTGAGCTCCCGCAGAACCTGGGGCAAAACGGGAGGCTGA<br>AGTTCTTCGACGTCACGAAGAATCACTTCAGCGGGTTGATCCCTCGGGATTTGTGCAAGAGTGGG<br>AGGTTACAAATCTTCATTATCACAGATAACTTCTTTCATGGCCCAATCCCTAACGAGATTGCTAA<br>CTGCAAGTCTCTAACCAAGATCCGAGCCTCCAATAACTACCTTAACGGCGCAGTTCCGTCGGGGA<br>TTTTCAAGCTACCTTCCGTCACGATAATCGAGTTGGCCAATAACCGTTTTAACGGAGAACTGCCT<br>CCCGAAATTTCCGGCGATTCACTCGGGATTCTCACTCTTTCCAACAACTTATTCACTGGGAAAAT<br>TCCCCCAGCGTTGAAGAACTTAAGGGCACTGCAGACTCTGTCACTTGACACGAACGAGTTCCTTG<br>GAGAAATCCCGGGGGAGGTTTTTGACCTACCAATGCTGACTGTGGTCAACATAAGCGGCAACAAT<br>CTCACCGGACCAATCCCAACGACGTTTACTCGCTGCGTTTCACTCGCCGCCGTTGATCTCAGCCG<br>GAACATGCTAGTTGAGGATATTCCTAAGGGGATTAAGAACCTCACGGTCTTGAGCTTTTTCAATG<br>TCTCGAGAAACCATTTAACAGGGCCAGTCCCTGACGAGATAAAATTCATGACGAGCCTCACCACG<br>CTGGATCTCTCCTACAACAATTTCACAGGCAAGGTCCCCAACGAGGGTCAGTTTTTGGTCTTCAA |

TABLE 5-continued

| Soybean Genomic DNA sequence, cDNA sequences, and protein sequences | |
|---|---|
| Sequence Description | DNA OR PROTEIN SEQUENCE |
| | CGACAACTCGTTTGCAGGGAACCCTAACCTCTGTTCCATTCACGGATGCACTTTAAGCATTGTGG<br>GGGCAGCTGCCCCTATCAACATTTTAACATTTGTAAATATAGTATGTACAATTATAGTAATTTAT<br>AAATTGCTTGTATAA |
| GmCLV1A: Glyma11g12190 cDNA (SEQ ID NO: 42) Soybean CLV1-like gene | ATGGCAACGTGCTCTTCGTTCAGTGACATGGATGCGTTACTAAAGCTGAAGGAGTCCATGAAAGG<br>AGACGAAGCCAAAGACGACGCACTCCATGACTGGAAGTTTTCCACATCGCATTCTGCACACTGTT<br>TCTTTTCAGGCGTAACATGTGACCAAGACCTTCGAGTCGTTGCTATCAACGTCTCCTTTGTTCCT<br>CTCTTCGGTCACATTCCGCCGGAGATCGGAAACTTGGACAAGCTGGAAAATCTCACAATCGTGAA<br>CAACAATCTAACCGGTGTACTCCCCATGGAGCTTGCCGCCCTCACTTCCCTCAAGCACCTCAACA<br>TATCTCACAACCTCTTCACCGGCGATTTCCCCGGCCAAGCCACTCTTCCGATGACGGAACTTCAA<br>GTCCTCGACGTCTACGACAACAACTTCACCGGACCGCTTCCGGAAGAATTCGTGAAACTGGAGAA<br>ACTAAAATACCTGAAACTCGACGGAAACTATTTTACCGGCAGCATACCGGAGAGTTACTCGGAGT<br>TTAAGAGCTTGGAGTTTTTGAGCTTAAACACCAACAGCTTATCGGGGAGGATTCCGAAGAGTTTG<br>TCCAAGTTGAAGACTCTGAGGATTCTCAAACTCGGATACAGCAACGCTTACGAAGGTGGAATTCC<br>TCCGGAGTTCGGCACCATGGAATCTCTGAGATTCCTCGACCTCTCAAGCTGCAACCTCAGCGGCG<br>AGATTCCACCGAGTCTTGCAAATCTGACAAACCTAGACACGTTGTTCTTGCAAATGAACTTCCTC<br>ACCGGAAGCATTCCGTCTGAACTCTCTTCTTTGGTGAGGCTCATGGCACTGGATCTCTCCTGCAA<br>CAGCCTCACCGGGGAGATTCCAGAGAGCTTTTCTCAGCTGAGAAACCTCACTCTCATGAACTTGT<br>TCCGCAACAATCTTCACGGCCCTATTCCGTCCTTGCTGAGCGAGCTTCCCAATCTGAATACGCTG<br>CAGCTCTGGGAGAATAACTTCTCCTCTGAGCTCCCGCAGAACCTGGGGCAAAACGGGAGGCTGAA<br>GTTCTTCGACGTCACGAAGAATCACTTCAGCGGGTTGATCCCTCGGGATTTGTGCAAGAGTGGGA<br>GGTTACAAATCTTCATTATCACAGATAACTTCTTTCATGGCCCAATCCCTAACGAGATTGCTAAC<br>TGCAAGTCTCTAACCAAGATCCGAGCCTCCAATAACTACCTTAACGGCGCAGTTCCGTCGGGGAT<br>TTTCAAGCTACCTTCCGTCACGATAATCGAGTTGGCCAATAACCGTTTTAACGGAGAACTGCCTC<br>CCGAAATTTCCGGCGATTCACTCGGGATTCTCACTCTTTCCAACAACTTATTCACTGGGAAAATT<br>CCCCCAGCGTTGAAGAACTTAAGGGCACTGCAGACTCTGTCACTTGACACGAACGAGTTCCTTGG<br>AGAAATCCCGGGGGAGGTTTTTGACCTACCAATGCTGACTGTGGTCAACATAAGCGGCAACAATC<br>TCACCGGACCAATCCCAACGACGTTTACTCGCTGCGTTTCACTCGCCGCCGTTGATCTCAGCCGG<br>AACATGCTAGTTGAGGATATTCCTAAGGGGATTAAGAACCTCACGGTCTTGAGCTTTTTCAATGT<br>CTCGAGAAACCATTTAACAGGGCCAGTCCCTGACGAGATAAAATTCATGACGAGCCTCACCACGC<br>TGGATCTCTCCTACAACAATTTCACAGGCAAGGTCCCCAACGAGGGTCAGTTTTTGGTCTTCAAC<br>GACAACTCGTTTGCAGGGAACCCTAACCTCTGTTCCATTCACGGATGCACTTTAAGCATTGTGGG<br>GGCAGCTGCCCCTATCAACATTTTAACATTTGTAAATATAGTATGTACAATTATAGTAATTTATA<br>AATTGCTTGTATAA |
| GmCLV1A: Glyma11g12190 protein (SEQ ID NO: 43) Soybean CLV1-like gene | MATCSSFSDMDALLKLKESMKGDEAKDDALHDWKFSTSHSAHCFFSGVTCDQDLRVVAINVSFVP<br>LFGHIPPEIGNLDKLENLTIVNNNLTGVLPMELAALTSLKHLNISHNLFTGDFPGQATLPMTELQ<br>VLDVYDNNFTGPLPEEFVKLEKLKYLKLDGNYFTGSIPESYSEFKSLEFLSLNTNSLSGRIPKSL<br>SKLKTLRILKLGYSNAYEGGIPPEFGTMESLRFLDLSSCNLSGEIPPSLANLTNLDTLFLQMNFL<br>TGSIPSELSSLVRLMALDLSCNSLTGEIPESFSQLRNLTLMNLFRNNLHGPIPSLLSELPNLNTL<br>QLWENNFSSELPQNLGQNGRLKFFDVTKNHFSGLIPRDLCKSGRLQIFIITDNFFHGPIPNEIAN<br>CKSLTKIRASNNYLNGAVPSGIFKLPSVTIIELANNRFNGELPPEISGDSLGILTLSNNLFTGKI<br>PPALKNLRALQTLSLDTNEFLGEVPGEVFDLPMLTVVNISGNNLTGPIPTTFTRCVSLAAVDLSR<br>NMLVEDIPKGIKNLTVLSFFNVSRNHLTGPVPDEIKFMTSLTTLDLSYNNFTGKVPNEGQFLVFN<br>DNSFAGNPNLCSIHGCTLSIVGAAAPINILTFVNIVCTIIVIYKLLV |
| Glyma18g51820 gDNA + about 3.7 kb promoter and 5'UT (SEQ ID NO: 44) Soybean CRN-like gene | GCCTGCCCCTTAGTCATGTGCAAAATAGTGCTAAGATCTGTATTGTAAAATGGCCACATTGGTCT<br>TAGTAAAAGAGTTATGCATATGCTGCACTGGTAGCACCCAGCCTGCACTTCGTAATATGATGATT<br>GTGTATTTTTGTTTACTTTTGAGGTGAAGCTGCGATGCATTAGGCTAGGGATTTGTGTATGTTGT<br>GTACATTGGTTTTTGTGAAGGTGTTGTTGTGGCTGTAATTTACATTTTTGTATTTTTGGGATTAC<br>TTGGTGGGACATGTGCTGAGGATGCCATGTCCCTAGTTCTCTAATGTTCTGATGTATTATTTATT<br>TATATTGATAAAAAAAATTATATACTTTCAAAGGCAAAAAGATAAAGAAAACTATCAATCACCTG<br>CTATTTTAGAAATACCCCCCTCCCAAAAGAAAAACCCAAATTATTGTAATCATATAAAGTTTCGG<br>TGTTGAAAAGACGGCGTGGGGCACCATGTTGAAGGCTTGAGAATTTTTTGGTCAATTGAATCAAA<br>AAGTGAAGTGGTCCATTTGACCCCCAGTTTGCAATGGTAAATTCAAGAATTGGGTGGAAGTGTCC<br>ATTGTATTTTTCGTATCCAACAATAAAGAATCACAGTTGTTGCACAGATACAACAATCAAAGGTC<br>TAGATATTTTGTAGTCTTATAATAGGAATTTTCACTGTTTTACACAAACATTTTTTTATCTACAA<br>AACAAACCGTGAGGAATCTTGTAGGTTATAGTGGCCAACACTCATGTTGCGTTAACACAGCTATC<br>AACTAAAACTCAACTTTTGTCACGGGTGACCTCAACATAATTATTGATATTACTGACAGAGTAAC<br>AACACCTGAAGTGGGCCCTGTTGAACTGGGTTATGACTAATGACGAGACCACAACTTAGAGGATA<br>GATACATTTCTAATCTTTCAAATAAATACAAGTGATATTAACTTGGTCTTTGAAAAATATGAACA<br>TCAATTCTGTTTTTTAATTATAAAAACAATAGTAATTTGATTTGATTTACTGAAAAAATTAGCGT<br>CAATTTAAAATTTCAGTATTAAAAAATGATACGATTTACCATCTTAAGTATTGCACGCAAAAGAT<br>TATTTTAATATCATTTTTCAATTATTAAGAGAAAAAAAGTGACGTTAATATCTTAGGACAAAATT<br>AATATCTCTGGCATTTTAAGAAAATAAAGAGAATACTTATAAAATAAGACCACAATTCACGAAAT<br>CTTATATTAAATATGGTCCTGATAATTCCAATTTGTATAAACTTATTAAAATAATACTTATAGGG<br>AAAAAATAGAGAGGCAAATAAATTAAAATCAAATTATGTATTTTTACTTTTGGAGAATTTAAATA<br>AGAGAATTTCTTAAAACTTGAGTTAGATAAGTTGATTTTAATTTGTGGGAGATTCTTTTTTATTA<br>TATGTCTTTATTTTTTTCTCAGTATTTTTTTTTTTTGGAAAATTTTACCTAAACTGAAATTAAGC<br>ATTGTGGAGAATACTTTCAGGGAAAATGACTCAATGATTTAGCGTGTGATTTAAGCATAAATTTT<br>GGTACAAGAGTTTGATTAACTATTAATTAAATTAATTTAGAAAGGTCAAGGTCATTTTCACACAA<br>TTCTATTCCCTTGCTCGAGACCACTTTTCAAGTATAAATTTATGACTAATGGGTCAAAACATACA<br>ATGCCTTGTGTAAATAGTTATGAACGATATTAATATTTTTATGAAAATGATAGTTGCACCAAATA<br>TGTGAAATTCGCAATCTGAATTATCTGTTGCATTTGGCTTGGTTTCATTTTGTTAGGTTATTATT<br>ATTATTTTTTTTTAAAAAGGAACTGACTGTATCCAATTATATGTCTGTTTTTAAAATTTGAAAGA |

TABLE 5-continued

| Soybean Genomic DNA sequence, cDNA sequences, and protein sequences | |
|---|---|
| Sequence Description | DNA OR PROTEIN SEQUENCE |
| | AATAGTTTTAAACCATTTAATATAGCTATAATATATATTTAAGTTAATCTTAGCTATATATTTTG<br>TATTAAAATGTATATTTGCTATAATAATTAACTCTAGTAATTTACCAAATGGATATTATTTGTAA<br>AGGCTTGATTTGGGTTATACTAGTAATTTAAAATCTACGTACTTACTATTTCTGATTTCAAAATG<br>TCTCATGCCACAAATGAACAAAACAATCATGATAATTTATTCATACTATTATTGCTTGCTCATTC<br>ACTCACCCCACAGTGCTAGATCCTCGGACTCGAATAAATCATTTATTATGCTTAGATAATTCGAT<br>TTATTTTTATTCAATGCAACACTCATTCAATTGCACTACCCTCCTATTCCTATATCACATTAATA<br>TGAAGAGTTAATCTTATCCTCTCGATTCATTTTCTTTTTAAATTTAAGGGGTATAATGAGAAATT<br>AATTTTGACTATTAAATTTTAAAAACAATCCAAAAATGTCATAAAGAATTTTTCCTATTCCACGA<br>GAGAACTTGAAAGTTAAAATTTGATTAAAATCTTATTAAAGGCGTTCCTAATCCTAGCAACTTCC<br>ACCTATCACAGAGAAAAAAAAAGGAAAAGAAAAGGTAAGATAGAAAGAAAGAAGGAAAAGTAAAA<br>GCATGCAAATATAGAATTATAAATACTAAAAAATATTGTTAAGATATTAGTTAAAAAATTATTAA<br>GATACACAAAATTACATTATACACAATTTTTTATAATCTTTAAAATAAATATTTTTTATTTTATT<br>AATATCCTAAAGATATTAGTTAATTAACATTCATGTATTATTATTTGAAATTGAAACGTAAGTAG<br>TAATTAAAAGCAAATTATTCTATCGAAAAAGAGATAACTTTATTAATGACACACACCAAACATAC<br>CAATCGCTAGAGTTGTTAACCACTCACTCATATAGCATATCACAAATTCCCATGCAACCTTAATT<br>CAACGGTCCAGATGCAGTCTGATGAGATCAGACGGTCGAGACGAACTGTACATTCTCCCTCTCAC<br>GGATTTCGATGTTTCTCTTTCGGACCAAATGTGGGGCCCACATAGTACTGTGTCCTGAGTGCTGG<br>CTACTCACAAAGGCGGGAACCAGTTTTTGTCGCAGAAGAGGTATGGCTCTTTGTTTGTTGTCATC<br>AGATGAGAGAGAAACAAAACAAAGAGACAATCACTGAATCACTCTCACTCACTCTGCATGCTGTG<br>TGCGTGACTCTGTCATTGTGTTTTGTGTTTTAAGCACTTTGCAGTTTAGTTTCTGAGGAGCGTTT<br>TTTTTTTTTCTTTCTTATGAGTGTGTGTCTGTTCTTAGTTGCTGTTATTGTTGTTCAAGTTTCG<br>GTTACTACTACTACTACCACATGTCCATGCCCCTTCAATTTCTGTTCAACTTTGTGACTTTTTGT<br>TTGGTTTCTAAGGAAAAAGATTGCAACTTGTTTCTGGGTCTAGTTTGCTTTTGGTTGGGTTTGTT<br>AGTCACCGCTGGCAACTCGGAATAGTGGGTTTTTTTTTGGAGGGTGTTTTTTTTTTCTTCTTTTG<br>GAGGTTCAAATTCTTGTTCTGATTCGTGTGAAGGTGGAAAATTTATGGGTGCTGAGAGGAGGAAA<br>AAGATGGGATTTGGTGGAATAAATGTAAAACTATTCGGCGACAACATGTCTGCTTGCTTTTTTGG<br>GACGGCTTTCTTGTGAAGATTTTGGGTTTAAAAGGTTGAGGAAGATGCTTATGCCTTATGCTTAT<br>GCTTGCAACTTTTTTTTTAAAACCCATTTTAGCATCAAGTATAAAAGTTTCTTCTTGGTCTTGTT<br>TCCAAGTGTTTGAGGTGATGGGGGTTTTGAGCATGTGAGTGATTCATGCCTCATTTTGGAGCTTC<br>TGAGATTGGTTTCTGGTTGTGGCTTTGTTTGTTTTGTGTTGTGCTTTCATGTTTAGGAAAAGGCA<br>CACCCTTTCTTCTCTTGCAAGGGAATTGTTGGCATTTCAGCCACTTTTTCTTCTCTTCTTGTTCA<br>GCTTGCACCACAACACTATGCAGTGTCAAGGAAGGTTGAGTAAACATGTTTCTTCTGAGCCTCCC<br>TCACCTTCTAGGTCAACACCATCACCACCATCTTCATCAGGATACAAGGATGACCCTAGGAAGAT<br>AATTTTGAGCATGGTTTTAGGAGCAGTCACTGGACTAGTTTCTTCTGCTCTCTTTGCACTTGTGG<br>TTCGTTGTGTTGTTCAGTATCTGAACCGCACACCAATCCTCAAGGGACCTGTCATATTCTCCCCC<br>AAAATTGCCCCCATGACACTCCAATCAGCTTTGGCAAAGGAAAACCACTTGCTCGGTTCGAGTCC<br>TAATGGGAAGTACTACAAAACTGTGCTTGACAATGGACTCACTATTGCAGTCAAAAGGCTAACAC<br>CCTTTGAGAGTAATTCCCCGGAGGCTAAGAGAAAATCAGTGAAGAGGCAGATACAAACTGAGCTT<br>GAGCTTCTTGCAAGCCTTAGGCATAGGAACTTGATGAGTTTAAGGGCCTATGTTCGTGAGCCTGA<br>TGGGTTCTCATTGGTTTATGATTATGTTTCCACTGGGAGTCTTGCTGATGTGTTGAGTAAAGTGA<br>GGGAGAATGAGTTGCCCTTTGGTTGGGAAGTTAGGCTCAGGATTGCTGTTGGTGTGGTGAAGGGT<br>CTTCAGTATCTTCATTTCACTTGTGTGCCTCAGATTCTGCACTACAACTTGAAGCCCACAAATGT<br>GATGTTGGATGCTGAGTTTGAACCTAGATTGGCAGATTATGGGTTGGCTAAACTTCTACCCAATT<br>TGGATGGAGGAAGTTCTCTCTACACTCCTCCTGAATGTTTCCATAATTGCAGGTAAGACAAATTT<br>CAATCATACTCATTCACTAGTGTTTTGAACTTGGTCTGTTTCTGTTCTTTCACTTTTTTACACCA<br>ATAGGGTAATTAGGTGGTTGATATTGGGAATTTGTTTGATTCGTTACCTTTTCAAAAGCTCCACA<br>CCTCATTGGTTTTTTGCCCCCTTTGTAGTACCCTAATGAAAGACTCTTGTTTTGAAACGAAATTA<br>CTATTCTGTAATCTGTATTGTCATTGTATCATTTGCTGATTGAATTTGGTATTATTTAATAAAGA<br>CTTTGCTATTTGTTTTTGTAACTACCCATTACTTCCTGATGTCAAGTTTTAGACCTTAGGCAGTT<br>GGCACTAAGTCTGGTCCAAATGAATAATATAGTTTATAGTTCACATGCTGCAAACTACTAAACCT<br>AGATTGGTGAGTGAGACCACAACTAAATTATAATAATAATTGACAAAGGTTTTTTTTCCTAATTT<br>AACTTGGAATACTTCTAGTTTTTCAGTGGTGTATATTTGGATGCATCAATATCAATAGCAATAAG<br>TAATAACAATAAAAGATTGCTTGATTGATGGCATTGCATATATGGGTATGGTATTGCCAATAAGA<br>TGTTTATTTTAACTTCATTCCATTCTTGTATATGTGGAGCTTCATGGTATTCAGATTGAATGGTG<br>TTTTTTGGCAATTTCAGCAGGTACACTGACAAAAGTGACATCTTTAGTTTTGGCATGATACTAGG<br>TGTTTTGTTAACTGGTAAGGATCCTACAGATCCATTCTTTGGAGAAGCAGCCAGTGGGGGAAGTT<br>TGGGATGTTGGCTGAGACACTTGCAGCAAGCGGGCGAGGCGCACGAAGCTCTAGATAAGAGCATG<br>TTAGGGGAAGAAGGTGAGGAAGATGAGATGCTAATGGCGGTTAGGATTGCTGCTGCATGCCTCTC<br>TGATATGCCTGCAGATAGGCCTTCTAGTGATGAGCTTGTTCACATGCTAACGCAACTGCACAGTT<br>TTTGA |
| Glyma18g51820 cDNA (SEQ ID NO: 45) Soybean CRN-like gene | ATGTTTAGGAAAAGGCACACCCTTTCTTCTCTTGCAAGGGAATTGTTGGCATTTCAGCCACTTTT<br>TCTTCTCTTCTTGTTCAGCTTGCACCACAACACTATGCAGTGTCAAGGAAGGTTGAGTAAACATG<br>TTTCTTCTGAGCCTCCCTCACCTTCTAGGTCAACACCATCACCACCATCTTCATCAGGATACAAG<br>GATGACCCTAGGAAGATAATTTTGAGCATGGTTTTAGGAGCAGTCACTGGACTAGTTTCTTCTGC<br>TCTCTTTGCACTTGTGGTTCGTTGTGTTGTTCAGTATCTGAACCGCACACCAATCCTCAAGGGAC<br>CTGTCATATTCTCCCCCAAAATTGCCCCCATGACACTCCAATCAGCTTTGGCAAAGGAAAACCAC<br>TTGCTCGGTTCGAGTCCTAATGGGAAGTACTACAAAACTGTGCTTGACAATGGACTCACTATTGC<br>AGTCAAAAGGCTAACACCCTTTGAGAGTAATTCCCCGGAGGCTAAGAGAAAATCAGTGAAGAGGC<br>AGATACAAACTGAGCTTGAGCTTCTTGCAAGCCTTAGGCATAGGAACTTGATGAGTTTAAGGGCC<br>TATGTTCGTGAGCCTGATGGGTTCTCATTGGTTTATGATTATGTTTCCACTGGGAGTCTTGCTGA<br>TGTGTTGAGTAAAGTGAGGGAGAATGAGTTGCCCTTTGGTTGGGAAGTTAGGCTCAGGATTGCTG<br>TTGGTGTGGTGAAGGGTCTTCAGTATCTTCATTTCACTTGTGTGCCTCAGATTCTGCACTACAAC<br>TTGAAGCCCACAAATGTGATGTTGGATGCTGAGTTTGAACCTAGATTGGCAGATTATGGGTTGGC<br>TAAACTTCTACCCAATTTGGATGGAGGAAGTTCTCTCTACACTCCTCCTGAATGTTTCCATAATT |

TABLE 5-continued

| Soybean Genomic DNA sequence, cDNA sequences, and protein sequences | |
|---|---|
| Sequence Description | DNA OR PROTEIN SEQUENCE |
| | GCAGCAGGTACACTGACAAAAGTGACATCTTTAGTTTTGGCATGATACTAGGTGTTTTGTTAACT<br>GGTAAGGATCCTACAGATCCATTCTTTGGAGAAGCAGCCAGTGGGGGAAGTTTGGGATGTTGGCT<br>GAGACACTTGCAGCAAGCGGGCGAGGCGCACGAAGCTCTAGATAAGAGCATGTTAGGGGAAGAAG<br>GTGAGGAAGATGAGATGCTAATGGCGGTTAGGATTGCTGCTGCATGCCTCTCTGATATGCCTGCA<br>GATAGGCCTTCTAGTGATGAGCTTGTTCACATGCTAACGCAACTGCACAGTTTTTGA |
| Glyma18g51820 protein (SEQ ID NO: 46) Soybean CRN-like gene | MFRKRHTLSSLARELLAFQPLFLLFLFSLHHNTMQCQGRLSKHVSSEPPSPSRSTPSPPSSSGYK<br>DDPRKIILSMVLGAVTGLVSSALFALVVRCVVQYLNRTPILKGPVIFSPKIAPMTLQSALAKENH<br>LLGSSPNGKYYKTVLDNGLTIAVKRLTPFESNSPEAKRKSVKRQIQTELELLASLRHRNLMSLRA<br>YVREPDGFSLVYDYVSTGSLADVLSKVRENELPFGWEVRLRIAVGVVKGLQYLHFTCVPQILHYN<br>LKPTNVMLDAEFEPRLADYGLAKLLPNLDGGSSLYTPPECFHNCSRYTDKSDIFSFGMILGVLLT<br>GKDPTDPFFGEAASGGSLGCWLRHLQQAGEAHEALDKSMLGEEGEEDEMLMAVRIAAACLSDMPA<br>DRPSSDELVHMLTQLHSF |
| Glyma08g28900 gDNA + about 2.8 kb promoter and 5'UT sequence (SEQ ID NO: 47) Soybean CRN-like gene | ATTATAAGAAAATAATGGTAATTTGATTTACTGAAAAAATTAGCGTCAATTCATCATTTCAATAT<br>TACAAAATGATACTACGATTTAGTATCTTAAGTATTGCACGCAAAAGATTATTTTCATATCATTT<br>TTCAATTATTTAGAGAAAAAAGTGACGTTAATATCTTAGGAAAAAATTAATATCTCTGGCATTTT<br>AAGAAAATAAAGAGTTACTTATAAAATATGACCACGATTCATGAAATCTTATATTAAATATAGTC<br>CCGATAATTCCAATTTGTATAAACTAAAAGAATACTTATAGGAAAAAAATAGTGAGGCAAATAAA<br>TTAAACTTCTTTCATAAATAAAAATCAAATTATGTATTTTTACTTTTGGAAAAGTTAAATAAGAG<br>AATTTCTTAAAATTGATTAGATAAGTTAATTTTAACTTGTGGGAGATTTTTATTTATTTATTTTT<br>CATTATACCTCTATTTTTTCTGAGTATTTTTTGAAAATTTTATCTAAATTTAAATTAAAAATTGT<br>GGAGAATACTTTCAAGGAAAATGGCCTAATGGTTTAGCGTGTGTTTTAAGCATAAATTTTGGTAC<br>CCATGTTTGATTAACTATTAATTAAAATTAATTTTAAAAGGCCAAGGTCATTTTCACACAATTCT<br>ATTCCCTTGCACTAGACCACTTTTTAAGTATAAATTTATGACTAATGGGTCAAAGCATACAATGC<br>CTTGTGTAAATAGTTGACTATCAACCAAAAATTTGACATTCAATAAGACACCACTGGTCTTTGAG<br>CGACATCAATATTTTTATGAAAACGATAGTTGCACCTAATATGTGAAATTCGCAATCTGAATTAT<br>TTATAAAACGTTGCATTTGCGTTCCAAATAAAAAACTCAACCCAACAAGGAAAAAAAAAACTGAA<br>CTTATGTCTTGGTTTTGTTTTGTTTGGTTATTAAAAAAAGTAAATGGAACTGACTGTATCCAATT<br>ATATGTCTGTTTTTAGATTTTGAAAGAAATAATTTTAAACCAATAAATATAGTTATGATATATAT<br>TTAAATTAATCTCAGCTATATATTAAAATGTATATCACGGTAAAAATAATTAACTCTAGTAAATT<br>ATCAAATGGATATTTGCTATAATAATTATTTGTAAATGCCTGATTTAGATTATAGTAATTTAAAA<br>TCTAAGTACTTGTCATTTTTCATTTCAAAATGCCTCATGCCATAAATTAACCAAACAAACATGAA<br>TTATATCCTTTGATAATTTATTCATACTATTATTGCTTGCACCTGTACATATATGTGTTGCTCAT<br>TCACTCACCCCAGACTGAGTGCTAGATCCTCGGACTCGAATAAATCATTTATTATGCTTAAATAA<br>TTCGATTTTATTTTTCCTACATCACAATAATCTAAAGAGTTAATCTCATACTCTCGATTCATCCT<br>TAAAAATTTAATGGGTGTAATGAGAAATTAATTTTAACTACTATTATATTTTAAAAAATAAATAG<br>TGAAAATAATGAGAAACTCTAATTAAAATTACTCTTTGAGTAACTAACTTGATTTTTCCTCGTAG<br>AACAACCCAATCAATGTCACAACGAATTTTTCCTATTTCACGAGAGAACTTGAAAGTTAAAATTT<br>GGTTAAAGTCGTTCCTAAACGTAGCAGAAGATAAGATAGAAAGATGGAAAAGTAAAAGCATGCAA<br>ATATATAATTGAAATTGAAATGTAAGTAGTAGTAATTAAAAACAATTATTTGATGGAAAAAGAGA<br>TAACTTTACTAATGACACACACCAAACATAAGATGTGTTCGCTAGAGTTGTTAACCACACTCACT<br>CATATACAGCATATCACAAATTCCCATGCACCCTCAATTCAACGGTCCAGATGCGGTCTGATGAA<br>ATCACACGGTCGATACGAACTGTACATTCTCCCTCTCTCTATCACGGATTTCGATGTTTCGCTTT<br>CGGACCAAATGTGGGGCCCACATAGTACTGTGTCCTGAGTGCTGGCTACTCACAAAGGCGGGAAC<br>CAGTTTTTGTCGCAGAGGTATGGCTCTTTGTTGTCATCGGATGAGAGAGAAAGAGTGTAGAGAGA<br>GAAACAAAACTAAGAGACAATCACTGAATCACTCTCACTCACTCTACATGCTGTGTGCGTGACTC<br>TGTCACTGTGTTTTGTGTTTAAGCACATTGCATTTTAGTTTCAGAGGAGTTTTTTTTTTTTTTT<br>TGCTGTTATTGTTATTCAAGTTTTGGTTACTACTACCGCCACATGTTCATGCCCCTTCAATTTTT<br>GTTCAACTTTTTGACTTTCTGCTTGGTTTCCAAGGAAAAAGATTGCAACTTGTTTCTGGGTCTAG<br>TTTGCTTTTGGTTGGGTTTGTTAGTCCCTGCTGGCACCTCGGAATAGTGGGTTTTTGTTTTTGTT<br>TTTGTTTTTTTTCTTCTTTTGGAGGTTCAAATTCTTGTTCTGATTCGTGTGAAGGTGGAAAATTT<br>ATGGGTGGTCACCGGAAGAGGAAAAAGATGGGATTCGTTGGAAAAAAGTAAGACTATTCGGTGAT<br>AACATGTCTGCTTGCTTTTTTGGGACGGCTTTTTTGTTAAGATTTTGGGTTGAAAAGGTTGAGGA<br>AGATGCTTATGCTTGCAACTTTTTTTTAAACCCATTTTAGCACCAAGTATAAAAAGTTGTTCTTG<br>GTCTTGTTTCCAAGTGTTGAGGTAGGTGATAGGGGTTTTGAGCATGTGAGTGATTCATGCCTCTC<br>ATTTTGGAGCTTCTGAGATTGGTTTCTGGTTGTGGCTTCGTTTGTTTGTTTGTTTGTTTGTTGTG<br>CTTTCATGTTTAGGAAAAGGCACATCCTTTCTTCTCTTGCAAGGGAATTGTTGGCACTCCAGCCA<br>CTTTTTCTTCTCTTCTTGTTCAGCTTGCACCACAACACTGTGCAGTGTCAAGGAAGGTTGAGTAA<br>GCATGTTTCTTCAGAGCCTCCCTCACCTTCTAGGCCATCGTCAGCAGCACCATCTTCATCAGGAT<br>ACAAGGATGACCCTAGGAAGATAATTTTGAGCATGGTTTTAGGAGCAGTCACTGGGCTAGTTTGT<br>TCTGTTCTGTTTGCACTTGTGGTTCGTTGTGTTGTTCAGTATCTGAACCGCACACCAATCCTCAA<br>GGGCCCTGTCATATTCTCCCCCAAAATTGCCTCCAAGACACTCCAATCAGCTTTGGCAAAGGAAA<br>ACCACTTGCTTGGCTCGAGTCCTAATGGGAAGTACTATAAAACTATGCTTGACAATGGACTCACT<br>ATTGCAGTCAAAAGGCTAACACCCTTTGAGAGCAATTCCCCGGAGGCCAAGAGGAAATCAGTGAA<br>GAGGCAGATACAAACTGAGCTTGAACTTCTTGCAAGCCTTAGGAATAGGAACCTGATGAGTTTGA<br>GAGCCTATGTTCGTGAGCCTGATGGATTCTCATTGGTTTATGATTATGCGTCCACTGGGAGTCTT<br>GCTGATGTGTTGAATAGAGTGAGGGAGAATGAGTTGCCCTTTGGTTGGGAAGTTAGGCTCAGGAT<br>TGCTGTTGGTGTGGTGAAGGGTCTTCAGTATCTTCACTTCACTTGTGTGCCTCAGATTCTGCACT<br>ACAACTTGAAGCCCACTAATGTGATGTTGGATGCTGAGTTTGAACCTAGATTAGCAGATTATGGC<br>TTGGCTAAACTTCTGCCTAACTTGGATAGAGGAAGTTCTCTCTACACCCCTCCTGAATGTTTCCA<br>CAATTGCAGGTAAGACAAATCAATTGCTTTCAATCATACTCACTCACTAGTGTTTTGAACTTGGT<br>TTGTTTCTGTTTTTTCACTTTTTACACCAAATGGGTAACTAGTTGGTTGATATTGGGCACTTGCT<br>TGATTCGTTACCTTTTTAAAAGCTCCACTCCTCATTGGTTTTTTCTCCTTCTTTGGAGTACCTTA<br>ATCAAAGACTCTTAGTGTGAAACGTGATTATTGTTCTGTATTGTCATGGTGTCATTTGCTATTGT |

TABLE 5-continued

Soybean Genomic DNA sequence, cDNA sequences, and protein sequences

| Sequence Description | DNA OR PROTEIN SEQUENCE |
|---|---|
| | TTAATAATTAAGACTTTGCAAAACTAATGTTTTTGTAACTACCCATTACTTGTATAGTTCACATG<br>CTGCAAACTACTAAACCTAGATTGGTGATTGAGACCCCAATTAAAAATTATAATAATAATTTACT<br>AAGGTTTTTCTTTTCCAATTTAACTTATTTCTAGTTTTTCATTGTTGTGTATATCTCTGGATACA<br>TCAATCTTAATAGTAATAACTTAAAATAAGTAATAACAATAAAAAGATTGCTTGATTGATGCAT<br>TTCATATATGGGTATGGTATTGCCAATAAGATGTTAATTTTAACTTCATTCCATTCTTGTATGTG<br>AAACTTCATGGTATTTAGATTGGATGGTGTTTTTTGCAATTTCAGCAGGTACACCGACAAAAGTG<br>ATATCTTCAGTTTTGGCATCATACTAGGTGTTTTATTAACCAGTAAGGACCCTACAGATCCATTC<br>TTTGGAGAAGCAGCCAGTGGGGGAAGTTTGGGATGTTGGTTGAGACACTTGCAGCAAGCCGGTGA<br>GTCACGTGAAGCTCTAGATAAGAGCATGTTAGGAGAAGAAGGTGAGGAAGATGAGATGCTAATGG<br>CTGTTAGGATTGCTGCTGCATGCCTTTCTGATATGCCTGCAGATAGGCCTTCTAGTGATGAGCTT<br>GTTCACATGCTAACGCAACTGCACAGTTTTTGAAACAAACCTTGATTCTTCAGTTCCTAGATATT<br>TTTTTCTTTCTCTTATCCCCTCTTTCTGTAATAAGATGATAGGGGAATTTGGTTAGTGCCCATGA<br>TTCTGGTGTAATTGATTGTTTTGGTGTAATTGATTGTTTTGCATGATCTTGGTTTTCATGGTGTG<br>GTTTCTAATATTCCATTTTCTCTTTCTCTATTCTATTTCCTTTTTCTTTTGGCTGATTTTGCAGG<br>TTGTGGTGGGTTTAGGTCACACTATTATATTTTGTTTGTAAATGACTAGTCATGTTAACAAGAGT<br>TTTCTTTTCTTGCT |
| Glyma08g28900 cDNA (SEQ ID NO: 48) Soybean CRN-like gene | ATGTTTAGGAAAAGGCACATCCTTTCTTCTCTTGCAAGGGAATTGTTGGCACTCCAGCCACTTTT<br>TCTTCTCTTCTTGTTCAGCTTGCACCACAACACTGTGCAGTGTCAAGGAAGGTTGAGTAAGCATG<br>TTTCTTCAGAGCCTCCCTCACCTTCTAGGCCATCGTCAGCAGCACCATCTTCATCAGGATACAAG<br>GATGACCCTAGGAAGATAATTTTGAGCATGGTTTTAGGAGCAGTCACTGGGCTAGTTTGTTCTGT<br>TCTGTTTGCACTTGTGGTTCGTTGTGTTGTTCAGTATCTGAACCGCACACCAATCCTCAAGGGCC<br>CTGTCATATTCTCCCCCAAAATTGCCTCCAAGACACTCCAATCAGCTTTGGCAAAGGAAAACCAC<br>TTGCTTGGCTCGAGTCCTAATGGGAAGTACTATAAAACTATGCTTGACAATGGACTCACTATTGC<br>AGTCAAAAGGCTAACACCCTTTGAGAGCAATTCCCCGGAGGCCAAGAGGAAATCAGTGAAGAGGC<br>AGATACAAACTGAGCTTGAACTTCTTGCAAGCCTTAGGAATAGGAACCTGATGAGTTTGAGAGCC<br>TATGTTCGTGAGCCTGATGGATTCTCATTGGTTTATGATTATGCGTCCACTGGGAGTCTTGCTGA<br>TGTGTTGAATAGAGTGAGGGAGAATGAGTTGCCCTTTGGTTGGGAAGTTAGGCTCAGGATTGCTG<br>TTGGTGTGGTGAAGGGTCTTCAGTATCTTCACTTCACTTGTGTGCCTCAGATTCTGCACTACAAC<br>TTGAAGCCCACTAATGTGATGTTGGATGCTGAGTTTGAACCTAGATTAGCAGATTATGGCTTGGC<br>TAAACTTCTGCCTAACTTGGATAGAGGAAGTTCTCTCTACACCCCTCCTGAATGTTTCCACAATT<br>GCAGCAGGTACACCGACAAAAGTGATATCTTCAGTTTTGGCATCATACTAGGTGTTTTATTAACC<br>AGTAAGGACCCTACAGATCCATTCTTTGGAGAAGCAGCCAGTGGGGGAAGTTTGGGATGTTGGTT<br>GAGACACTTGCAGCAAGCCGGTGAGTCACGTGAAGCTCTAGATAAGAGCATGTTAGGAGAAGAAG<br>GTGAGGAAGATGAGATGCTAATGGCTGTTAGGATTGCTGCTGCATGCCTTTCTGATATGCCTGCA<br>GATAGGCCTTCTAGTGATGAGCTTGTTCACATGCTAACGCAACTGCACAGTTTTTGA |
| Glyma08g28900 protein (SEQ ID NO: 49) Soybean CRN-like gene | MFRKRHILSSLARELLALQPLFLLFLFSLHHNTVQCQGRLSKHVSSEPPSPSRPSSAAPSSSGYK<br>DDPRKIILSMVLGAVTGLVCSVLFALVVRCVVQYLNRTPILKGPVIFSPKIASKTLQSALAKENH<br>LLGSSPNGKYYKTMLDNGLTIAVKRLTPFESNSPEAKRKSVKRQIQTELELLASLRNRNLMSLRA<br>YVREPDGFSLVYDYASTGSLADVLNRVRENELPFGWEVRLRIAVGVVKGLQYLHFTCVPQILHYN<br>LKPTNVMLDAEFEPRLADYGLAKLLPNLDRGSSLYTPPECFHNCSRYTDKSDIFSFGIILGVLLT<br>SKDPTDPFFGEAASGGSLGCWLRHLQQAGESREALDKSMLGEEGEEDEMLMAVRIAAACLSDMPA<br>DRPSSDELVHMLTQLHSF |
| Glyma18g47610 gDNA + about 4 kb of promoter and 5'UT sequence (SEQ ID NO: 50) Soybean CLV2-like sequence | CAAATGGGTATGCTCCCTTCAGGGGACTCCCCAATCGCCCTAATCGCAGACTCCACCGTCTCACT<br>CTCGTGAAACTCCGCCAGCTCCGGCTTCCCCACCGTCAGATCGCCCACCACGTGGTACACGAACA<br>CCGACGCCATCGGAATCCAAAAGGGTATCCGGAACCACAATCAAAATCGATTTTTGTTCTGCTTT<br>TTGTATCCTTAAAAAAAAAACCGAAAACAGAAAGAAAAAAAAAAGTTTGCTTTTTTTGCTTTGTC<br>GGGTGAGAGCTATAAGAGGGTATGGAGGAAGATGAGGAGAAGATCGAGGGCGGTGATGGGAGGGC<br>GGTGGAGGATCACGGCAGAGAAAGAGTTAGCCATTGCCATGGAGGGAGAACGAAAAGGTTAAGGC<br>CCATTCAATTGAATCAGATCAGAGAGAGAGAGAGGGCGTAGCTTTTGGGGAAGATATGATATGTAGA<br>GATTTGGATAAGGTACGTCCTTTCGGGGACAGCAAGAGATGCAACGACAGAAGAAGATGGATCAG<br>CGACGCTTGATGCGGTTGGGACCTGAGAATGAATGGGACACCAGACACACACTAAAAGGAGGTTC<br>AATTTATCAAATAAAAAAGAGAAAGGCACAGGGGATGTGTCATGTGTCATGTGTCATGTGTCATG<br>TGTATGGTGAGCTGCATCATATAGAGAATCTTTTCACCTTAATTAATTTGTTTAGTTTAATACGT<br>TTTTCTTTTCTTGTCATACTCATCTTTGATTTCAATTCTATAGACCTATATATAAGTTAATTTAT<br>TTAATAAGAGAGGATAAACAAAGAATGAAAATAGGTAAATGAGAAAAAAGGAGAAATAAATTAAA<br>AACAATGCTTGTTTGAATTTAAAGAAACGGAAGAAAAATAAGAAAAATAGATTACTAATATAAAA<br>TATCCTTTATATTACATAATTTTTTCATATAACATAGTACATACGGACAAAACTTAGATACATT<br>ATTTTGGGTGTTATTTTTTTATTAGAGTTAAAGTTTCATTTCAATGATATATATATAAGTTTTAA<br>ATGTAAAACTTTATTATGCAAATTACTCAAATAAAACTCCAATTTTCATTAGAGAATAATACAAA<br>CCGTGTAACGACTACAAGTTTATCTTAAATTTCCAATCTTTGAAATTATGTTATTTGTCTCCCTT<br>TCTTAAAAATATAAAATTGATTTAGTGATAAAGAAAAAAGAGGAGAAGGGATAAGTTTTAAATAT<br>AAATTCTTCAGGTTATAGTTCAATAGGTCACCTTTAATTAATGACGTTAATTAACAGATTAATAA<br>TGACTTCAGAAGCAGTGTCTATGAAGTTTATGCGAGATCACCAATGATATATGTAGTTAATAGCA<br>ACAAGTTGAGGAAAGAGGTTTGGATGAATGTGTGGCTGTTTAATGTTGGGTGGTGGTGTGGTGGC<br>TATGACTACGAGGTTGGTGTTGGAAAATGTTGTCAATTCAATTGGGATTCGGTTTGCAAAGTTGT<br>GATAACTTTGAGTTGAATGATGGAATATTGAAATTTTCTAGGCTTAGTTAGGAATGATTGCTACA<br>TGTAACAGTGATACCACAACAACAGGGATGAGGGATTGTTGGGGTTTACTTTTAAAAAATGAATG<br>AATTGAATTACAATGTAAAAGTATACATATAAAACACTATTCTTGCTTCTTAAAAAAAACGTGAG<br>ACAGAGAGAAAGTGAAGATGATAAGATTATAGCGCACGCGTTGGAGCGTGCATGAGTTTACTAGG<br>TCTTGTACCATGCAAAAAAATTTAGGACCCTTAGATATAACAACAAGACAAGAAGATCTTTAAGA<br>GTGTAACATATGGATAACATACTGTATACCAACTTTTCTTTTTAATAGTATTTCTTCTCTCTGGT<br>TATAACATCATTTTAACTAATCTATGTCTGTTAAAAAAATATTAATTTAATTAATTATATTAAAT |

TABLE 5-continued

Soybean Genomic DNA sequence, cDNA sequences, and protein sequences

| Sequence Description | DNA OR PROTEIN SEQUENCE |
| --- | --- |
| | ATATCAATTATTTATATTTTTTATTTTTCTATCCACTTAATTTTTTATTAATGTTTTAAAAAAT<br>AATTAAGAATAAAATAATTAATGTATTAAAAATTAAAAAAATCTTATAAATCAAGACAAATAAAT<br>TTATGAAAAACATCATATAATTAGTATGGGATTATGGGATGGAGTAGTATTTAACTTGTGGCTTT<br>TGAAAATTACACCATATTTTCTCTCTCTTGACAAAATGAATGCAACTTAAAAACGTGGGATCA<br>TTCTTCCTCCTGAGTCCAGAATGTTCGACCCCATTCGTACTCTGATCTATGTGTGTTTGTGGTAT<br>ATCTCCGTTGTCACTTCACCATTCTAGCTTCATCAGAGAAAGTAATATATATATATTTGTAAACCAA<br>TTATATATATATTTGAGAGGATTTTAATTCTTACTAAAATTGTAAACCAATTAGAAATCATTTTT<br>CTGTAATTTTTGTGATCTGAAATTTTCTGTTCGGGTTGGAAATGACACAAAATCGTTGGGTCTTT<br>AAATGGGTTGCAACCGGATGAGAATGACCCAACTCAAGGTAGGGGATGACCAAAGCATAGCCTTT<br>TAATGGGTAATGTTAAACATGATATAAATTTATAACAAATTATTTTTATGGTGTAGTGGTTAACT<br>CTTTCATTAATAATAATATAGCTGGTTGTTGGTTCCATCCCACAATAAGTCAGTTTAGCTTTTTA<br>TCTTCTAAAGATTTCCTGTTTTCATTTATTTTGGTTTTTTTAAAAAAATAAACAATTTCGCCTTGG<br>AATCGAACTCACGATATAGTGATTAGTTATAAAAAAATAATTATAAATTATTTGGTAATTTTTTT<br>CTTACATTCACTCTTGTTTTGAATACTCTTCTCTTTGTGAAGTTATGAACTTTGTTCTCTTACCA<br>CAAATATGATACATCTTCTTATGTTTTTAATTTTAGATTATATTTGATAAAACTAACCAAAAAG<br>ATGAAAAATATAGTCTGTTTAAAATATTTAAGATCTAAGCTTAACTCGTTACATGTGATAGACTT<br>TATTTGTAGATTATACTTGATTTATTTGAAAGTTTAGCTTAACCTATTAGTTTATTTAAAGACCT<br>ATTTCATATGAAAGTTTTTATATAAGTCTATTTTTTTATATTGGACAATAAATTTATAAATCGTT<br>GAGAAAATTCCATGTAAACAAACTATAATCTATAAAAAAAAAAAAATTTCTTTATTCAAAGCACAA<br>GATAGGTGAAAATAGATGAACTAAGTTTTATAAGTGAAATTTAACATGTCATTATGATGTAAGTT<br>TATCAACTTCAAGATAACTTAGTTAAAAATATAATTTTGTAATAAGTCCTCTAATTAAAACATAA<br>ATTTCGCACTCAATAATTTTTTTTTAATCGTGGATCAACACTCATAATATTTTAAAAAAGTAAAT<br>AATGTATTATTTTGATACATTACAATAATTTTAATATTACAAAATATTATAATTTATATTTATTT<br>AAATAGGTTGATCTATTAGGTTTAAAACACTTTTTAAATAACTTAAAACCTAATTTTTTAATCAA<br>ATAGACTTTTATTAAAACTTAGATATGATTTATTTTTATTTTTTTAAAAAAAACTAACCTGACTT<br>GAGTTTGATATAAATTAGGTGTCAGTTTGTTTAAATTTATTTATTAAAATAAATGTTTATTTTAA<br>TAAAATAAGTAATTTTATATTTGTTTAGTATATTTGTGTAAATTCTTTTTCCTTAAAAAATATTT<br>TTTTCTTTTTAAAAAAAATACTTATTTTAAAATTATTTTTTTTAAAAAGAGAAACTTGAAAAAGG<br>ATAAAGTGTAATGCAGTATAGAGAGAAAGAGGAGGAAGCAAAGCAAACCAAGCACAACACAACAA<br>AGCCACTTTATTTTTTTGATCTAACCTAAACCCTCTTTTTCCCCTGTTGCTCTCTCACTTTATCA<br>GCGTGATACAACCAACCCAAGACCAATGTGGAAGATCTTGTTCCTCTTTCCCTTCTCTTATGTCC<br>ATTTCATCATGTTTTCATTCTAATCTCCAAAATCCATGCCCACCCAGTTCCTCTTTTGCTTCAAA<br>CTCCTCTCCCCCTTCCTAAAAATTGCACCTTTACTCTCATGGTGATGGGACACACCACACCCCTC<br>ACACTTCTCTGTGTGATTCTTCTTTTTGCAACTCCTTCTCACTCAATTGATGTTCACCCCACAAGA<br>CAGAATCTCACTTTCAATGTTCAGGTCATCTCTGCCAAACCCCAACCAGAGTTTGCCCAGCTGGG<br>TGGGCTCCAACTGCACTTCATGGAGTGGAATCACCTGTGACAACAGAACTGGGAGGGTGCTTTCC<br>ATCAACCTAACCAGTATGAACCTTTCAGGCAAAATCCACCCCAGTTTGTGCTACCTTTCATATCT<br>GAACAAGTTGGGGTTGTCCCACAACAACTTCACATCCCCTCTTCCTGAATGTTTTGGCAACTTGC<br>TTAACCTAAGAGCCATTGATCTCAGCCACAACAGGCTTCATGGGGGAATACCAGACTCTTTCATG<br>AGGCTTAGGCACCTCACTGAGCTTGTTTTGAGTGGGAACCCTGATTTGGGGGGTCCACTGCCTGC<br>TTGGATTGGTAACTTCTCTGCAAATCTGGAAAGGTTACATCTTGGTTTCTGTTCATTCAGTGGTG<br>GCATACCGGAGAGCTTGCTTTACCTGAAGTCCCTCAAGTATTTGGACCTTGAGAACAACCTCTTG<br>TCTGGTAACTTGGTCAATTTTCAACAGCCTTTGGTTTTGCTCAATCTTGCTTCCAATCAGTTTGC<br>TGGTACTTTGCCTTGCTTTGCAGCTTCAGTTCAGTCTCTAACTGTGTTGAATTTATCTAACAATT<br>CTATTGTGGGGGGACTACCTGCTTGTATTGCTTCTTTTCAAGCTTTGACTCATTTGAACCTGTCA<br>GGGAACCACTTGAAGTATAGAATATATCCTAGGCTTGTGTTCTCGGAGAAACTTCTTGTTTTGGA<br>CTTGAGTAATAATGCTTTGTCTGGTCCTATTCCTTGTAAAATTGCTGAGACAACTGAGAAACTTG<br>GCCTTGTTCTTCTTGACCTTTCTCACAATCAGTTCTCTGGTGAAATTCCTGTGAAAATCACTGAG<br>TTGAAAAGCTTGCAGGCCTTGTTTCTCTCTCACAATCTTCTCTCTGGAGAAATTCCTGCTAGAAT<br>TGGAAATTTGACTTATCTGCAGGTCATTGATCTCTCACACAACTCTTTGTCTGGAACCATTCCAT<br>TCAGTATTGTTGGGTGCTTTCAGCTGTATGCTCTAATACTTACTAACAACAATCTTTCTGGTGTA<br>ATTCAACCGGAGTTTGATGCGTTGGATATCTTGAGGATTCTGGATATAAGCAACAACAGGTTTTC<br>CGGGGCTATCCCACTCACTCTGGCTGGATGCAAATCTCTGGAGATTGTAGATTTTAGTTCCAATG<br>AGCTTTCTGGATCCTTGAATGATGCAATAACCAAATGGACAAACCTCAGGTATTTGTCTCTTGCT<br>CAGAACAAGTTCAGTGGAAATCTGCCTAGTTGGTTGTTCACATTTAACGCAATAGAAATGATGGA<br>TTTCTCGCATAACAAGTTTACTGGCTTCATACCTGATATTAATTTTAAGGGTAGCTTAATATTTA<br>ACACCAGGAATGTCACTGTTAAAGAGCCATTGGTTGCAGCAAGAAAGGTTCAACTGAGAGTTTCG<br>GCGGTTGTTTCTGATAGCAATCAGCTCAGTTTCACTTATGATCTTTCCTCAATGGTTGGAATTGA<br>TCTATCCAGCAATTCGCTTCATGGGGAAATTCCAAGGGGCTTATTTGGTCTAGCTGGCCTAGAAT<br>ATCTGAACTTGTCATGCAACTTTCTTTACGGACAGCTTCCGGGGTTGCAGAAAATGCATAGTTTG<br>AAAGCCTTGGATTTGTCACATAATTCCTTGTCTGGACATATCCCAGGAAACATTTCTAGCCTTCA<br>AGATCTGTCCATTTTGAATCTTTCCTACAACTGTTTTTCTGGATATGTTCCCCAGAAGCAAGGGT<br>ATGGGAGATTTCCCGGTGCATTTGCTGGAAATCCAGATCTGTGCATGGAAACTTCCAGTGGAGTA<br>TGTGATGATGGAAGGACTCAATCTGCGCAAGGAAGTTCTTTCAGTGAAGATAGGATGGATGGCCC<br>AATTTCTGTGGGGATTTTCTTTATCAGTGCCTTTGTTAGTTTTGATTTTGGTGTTGTGGTTCTCT<br>TCTGTTCTGCCCGGGCAAGAAATTACATTCTCCAAACAAAAGTTTGATTTGATGCTTGTGACAGT<br>TACAAATCTCCTGTAAATTCCATTTTGTAATTTGGTACCTGTGTTCTCAGTTTCAAGTAAAACAT<br>ACACTTATGTGACTAGGAATACTATCCGGCCATCAACTTCACAAGTGTTTTCTTGTGATTCCTGA<br>TCAAGTGTCTCAGATTTACAGGATCAAAATGCCATGACATGAGTAACACAAGGTTTAAAGAACAC<br>TCAACACTGGCTTTATCTATCTGAGTGAAGACTAGCCTGGCATCATTCAGCCAAGAAAAGAATGG<br>ATGATTATGATGAAAATTTGATCCGAGTAAAGACGAGTCCCTCATCATTCTGATGGTTGTTCTCT<br>TTTGCTGGAATTTGGTTGCATCAAGTTTAGAATGCATCATCACATGTATTATTCATAATCAGTGG<br>TGGGCGAAGGGTCAGTAGGGAACATGTCTGATATCTGGTCTAGTTATGGTGAAATTTTGATCTTG<br>GGCATCAAATTGCAGATTTGCAAGCATGTTTACGTGAAGAGAACTTGTATAATTCTTGATTAACC<br>TAGTTCTTTCTTGAGGTGGGGAACCAAGTTTTCCCTGTAAGTGGGGAGTAGGTTCTCATAAGTCT |

TABLE 5-continued

Soybean Genomic DNA sequence, cDNA sequences, and protein sequences

| Sequence Description | DNA OR PROTEIN SEQUENCE |
|---|---|
| | AAGATTTGTATTTGTATTACTATCTTCACACCTTCATCATAGTGCTGTGATTTTAAATGATATTC<br>TCACGAAACCTTTTCATTGACAACAGAAAAGAGGTTAATTGA |
| Glyma18g47610 cDNA (SEQ ID NO: 51) Soybean CLV2-like sequence | ATGCCCACCCAGTTCCTCTTTTGCTTCAAACTCCTCTCCCCCTTCCTAAAAATTGCACCTTTACT<br>CTCATGGTCATCTCTGCCAAACCCCAACCAGAGTTTGCCCAGCTGGGTGGGCTCCAACTGCACTT<br>CATGGAGTGGAATCACCTGTGACAACAGAACTGGGAGGGTGCTTTCCATCAACCTAACCAGTATG<br>AACCTTTCAGGCAAAATCCACCCCAGTTTGTGCTACCTTTCATATCTGAACAAGTTGGGGTTGTC<br>CCACAACAACTTCACATCCCCTCTTCCTGAATGTTTTGGCAACTTGCTTAACCTAAGAGCCATTG<br>ATCTCAGCCACAACAGGCTTCATGGGGGAATACCAGACTCTTTCATGAGGCTTAGGCACCTCACT<br>GAGCTTGTTTTGAGTGGGAACCCTGATTTGGGGGGTCCACTGCCTGCTTGGATTGGTAACTTCTC<br>TGCAAATCTGGAAAGGTTACATCTTGGTTTCTGTTCATTCAGTGGTGGCATACCGGAGAGCTTGC<br>TTTACCTGAAGTCCCTCAAGTATTTGGACCTTGAGAACAACCTCTTGTCTGGTAACTTGGTCAAT<br>TTTCAACAGCCTTTGGTTTTGCTCAATCTTGCTTCCAATCAGTTTGCTGGTACTTTGCCTTGCTT<br>TGCAGCTTCAGTTCAGTCTCTAACTGTGTTGAATTTATCTAACAATTCTATTGTGGGGGGACTAC<br>CTGCTTGTATTGCTTCTTTTCAAGCTTTGACTCATTTGAACCTGTCAGGGAACCACTTGAAGTAT<br>AGAATATATCCTAGGCTTGTGTTCTCGGAGAAACTTCTTGTTTTGGACTTGAGTAATAATGCTTT<br>GTCTGGTCCTATTCCTTGTAAAATTGCTGAGACAACTGAGAAACTTGGCCTTGTTCTTCTTGACC<br>TTTCTCACAATCAGTTCTCTGGTGAAATTCCTGTGAAAATCACTGAGTTGAAAAGCTTGCAGGCC<br>TTGTTTCTCTCTCACAATCTTCTCTCTGGAGAAATTCCTGCTAGAATTGGAAATTTGACTTATCT<br>GCAGGTCATTGATCTCTCACACAACTCTTTGTCTGGAACCATTCCATTCAGTATTGTTGGGTGCT<br>TTCAGCTGTATGCTCTAATACTTACTAACAACAATCTTTCTGGTGTAATTCAACCGGAGTTTGAT<br>GCGTTGGATATCTTGAGGATTCTGGATATAAGCAACAACAGGTTTTCCGGGGCTATCCCACTCAC<br>TCTGGCTGGATGCAAATCTCTGGAGATTGTAGATTTTAGTTCCAATGAGCTTTCTGGATCCTTGA<br>ATGATGCAATAACCAAATGGACAAACCTCAGGTATTTGTCTCTTGCTCAGAACAAGTTCAGTGGA<br>AATCTGCCTAGTTGGTTGTTCACATTTAACGCAATAGAAATGATGGATTTCTCGCATAACAAGTT<br>TACTGGCTTCATACCTGATATTAATTTTAAGGGTAGCTTAATATTTAACACCAGGAATGTCACTG<br>TTAAAGAGCCATTGGTTGCAGCAAGAAAGGTTCAACTGAGAGTTTCGGCGGTTGTTTCTGATAGC<br>AATCAGCTCAGTTTCACTTATGATCTTTCCTCAATGGTTGGAATTGATCTATCCAGCAATTCGCT<br>TCATGGGGAAATTCCAAGGGGCTTATTTGGTCTAGCTGGCCTAGAATATCTGAACTTGTCATGCA<br>ACTTTCTTTACGGACAGCTTCCGGGGTTGCAGAAAATGCATAGTTTGAAAGCCTTGGATTTGTCA<br>CATAATTCCTTGTCTGGACATATCCCAGGAAACATTTCTAGCCTTCAAGATCTGTCCATTTTGAA<br>TCTTTCCTACAACTGTTTTTCTGGATATGTTCCCCAGAAGCAAGGGTATGGGAGATTTCCCGGTG<br>CATTTGCTGGAAATCCAGATCTGTGCATGGAAACTTCCAGTGGAGTATGTGATGATGGAAGGACT<br>CAATCTGCGCAAGGAAGTTCTTTCAGTGAAGATAGGATGGATGGCCCAATTTCTGTGGGGATTTT<br>CTTTATCAGTGCCTTTGTTAGTTTTGATTTTGGTGTTGTGGTTCTCTTCTGTTCTGCCCGGGCAA<br>GAAATTACATTCTCCAAACAAAAGTTTGA |
| Glyma18g47610 protein (SEQ ID NO: 52) Soybean CLV2-like sequence | MPTQFLFCFKLLSPFLKIAPLLSWSSLPNPNQSLPSWVGSNCTSWSGITCDNRTGRVLSINLTSM<br>NLSGKIHPSLCYLSYLNKLGLSHNNFTSPLPECFGNLLNLRAIDLSHNRLHGGIPDSFMRLRHLT<br>ELVLSGNPDLGGPLPAWIGNFSANLERLHLGFCSFSGGIPESLLYLKSLKYLDLENNLLSGNLVN<br>FQQPLVLLNLASNQFAGTLPCFAASVQSLTVLNLSNNSIVGGLPACIASFQALTHLNLSGNHLKY<br>RIYPRLVFSEKLLVLDLSNNALSGPIPCKIAETTEKLGLVLLDLSHNQFSGEIPVKITELKSLQA<br>LFLSHNLLSGEIPARIGNLTYLQVIDLSHNSLSGTIPFSIVGCFQLYALILTNNNLSGVIQPEFD<br>ALDILRILDISNNRFSGAIPLTLAGCKSLEIVDFSSNELSGSLNDAITKWTNLRYLSLAQNKFSG<br>NLPSWLFTFNAIEMMDFSHNKFTGFIPDINFKGSLIFNTRNVTVKEPLVAARKVQLRVSAVVSDS<br>NQLSFTYDLSSMVGIDLSSNSLHGEIPRGLFGLAGLEYLNLSCNFLYGQLPGLQKMHSLKALDLS<br>HNSLSGHIPGNISSLQDLSILNLSYNCFSGYVPQKQGYGRFPGAFAGNPDLCMETSSGVCDDGRT<br>QSAQGSSFSEDRMDGPISVGIFFISAFVSFDFGVVVLFCSARARNYILQTKV |

Having illustrated and described the principles of the present invention, it should be apparent to persons skilled in the art that the invention can be modified in arrangement and detail without departing from such principles. Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for inhibiting plant parasitic nematode damage to a potato plant, said method comprising:

(1) reducing the expression of an endogenous CLAVATA2-like (CLV2-like) gene by introducing into said potato plant one or more non-natural mutations in said CLV2-like gene, or by expressing in said potato plant RNAi to silence said CLV2-like gene, wherein said CLV2-like gene is set forth in SEQ ID NO: 11, and (2) growing said potato plant comprising said one or more non-natural mutations or expressing said RNAi, thereby inhibiting plant parasitic nematode damage to said potato plant.

2. The method of claim 1, further comprising the step of harvesting a product of said potato plant.

3. The method of claim 2, wherein said product is a leaf, stem, flower, seed, root, or tuber.

4. The method of claim 2, wherein the yield and/or quality of said product is increased relative to a control plant not comprising said one or more non-natural mutations or expressing said RNAi.

5. The method of claim 1, wherein said plant parasitic nematode is a cyst nematode.

6. The method of claim 5, wherein said cyst nematode is a *Globodera* spp.

7. The method of claim 1, wherein said plant parasitic nematode is *G.rostochiensis* or *G.pallida.*

8. A genetically modified nematode resistant potato plant produced by the method of claim 1, wherein said potato plant comprises said one or more non-natural mutations or expresses said RNAi.

9. A method for inhibiting plant parasitic nematode damage to a soybean plant, said method comprising:

(1) reducing the expression of an endogenous CLAVATA2-like (CLV2-like) gene by introducing into said soybean plant one or more non-natural mutations in said CLV2-like gene, or by expressing in said soybean plant RNAi to silence said CLV2-like gene, wherein said CLV2-like gene is set forth in SEQ ID NO: 35 or SEQ ID NO: 50; and (2) growing said soybean plant comprising said one or more non-natural mutations or expressing said RNAi, thereby inhibiting plant parasitic nematode damage to said soybean plant.

10. The method of claim 9, further comprising the step of harvesting a product of said soybean plant.

11. The method of claim 10, wherein said product is a leaf, stem, flower, seed, root, or tuber.

12. The method of claim 10, wherein the yield and/or quality of said product is increased relative to a control plant not comprising said one or more non-natural mutations or expressing said RNAi.

13. The method of claim 9, wherein said plant parasitic nematode is a cyst nematode.

14. The method of claim 13, wherein said cyst nematode is a *Heterodera* spp.

15. The method of claim 9, wherein said plant parasitic nematode is *H.glycines*.

16. A genetically modified nematode resistant soybean plant produced by the method of claim 9, wherein said soybean plant comprises said one or more non-natural mutations or expresses said RNAi.

* * * * *

SEQUENCE LISTING

<160> NUMBER OF SEQ ID NOS: 52

<210> SEQ ID NO 1
<211> LENGTH: 28
<212> TYPE: DNA
<213> ORGANISM: Artificial
<220> FEATURE:
<223> OTHER INFORMATION: synthetic

<400> SEQUENCE: 1
caccagacac aaagcccttt ccattgtc 28

<210> SEQ ID NO 2
<211> LENGTH: 20
<212> TYPE: DNA
<213> ORGANISM: Artificial
<220> FEATURE:
<223> OTHER INFORMATION: synthetic

<400> SEQUENCE: 2
ctttatcata gctcagagga 20

<210> SEQ ID NO 3
<211> LENGTH: 2000
<212> TYPE: DNA
<213> ORGANISM: Arabidopsis thaliana

<400> SEQUENCE: 3
tctcattaag cacctacttc ccacatcttt cttaaagttt cttacataaa gctcccttca 60
cacgtgctta ccaaatcaga ttgtcaataa ttcttgctca ataatttttc gaaatttatt 120
tgaatttatc taataaaaat acattgtttg agtatgatat tttgcttaag aaggttgatt 180
attctcccta tcaaagtcta aaaagaagat tacaaaacaa ttgtatggtt aaattcatat 240
aaatttgtga ctagtatttt aatatttaca tatatacaaa tacttataga tgaaacgaga 300
atgcagaaat gattatagat agatcagtga cagtgaactg tagcaaccgg caaagaaacc 360
tcgttagctg gacacacgat tacgatcatg cccccagtct cctctgtcca gacggctgca 420
ttaataacaa cgagctagag ggtgttttcg tcttttcgat acttatccca aaaccgacaa 480
tctctggttt ggactcgaag gctgatttgg tcaattcata gcaaccgaac gagcagtcca 540
ttcaagtcca aagagctcct tagtggtaaa agatgtaatt acgtagatgt tccatggtca 600
agaatgtatt cagtcaaaat aaatatttga ccaaaacttt cggttaattt cctaccacca 660
gcaaaattat aactttttct aataattatc aatcattttc aatctctttt aattttcttt 720
ttcacttttt tttattaatt aaagtcaatt cacactatac aaaaagaagg aagtctaaat 780 attttttttac tttcatgttg cttttctaac ttttatattt tgctcttctc aacagatttt 840
gctggttttt gtattagaaa tattattatg tttccagaaa tgaatttttt atatgtcgtc 900
tggattcgta tatatatatt ggaaagtgaa attaattcat ttgatttttt tctttgatat 960
atcgaccaaa tcaaataaat acgaccccat tgtggcattg ttaatgcaaa aaggcacaag 1020
tacaaaaaaa acataataat tcactatttt atttacagac acatgggccc aattcatacg 1080
gcccaattac cataaacctc tcttttaaag agtgggttcc acagtggtaa actttttgac 1140
tatccattgg aatgattgca tctggaccgt tcatctacat taattattgg gttttttcgc 1200
tttaaagcat caattaactt attacgtata ggattagatt accaataacg atctttttag 1260
cttttgtcgt tttccgataa aaccatacga ttaagaatat gacctcttgt atcttttgag 1320
ggattttagt taatctttct acatttattt tgttggatgc tcatacaatt atcctgtgtc 1380
tctcaaaata aaacaaaaat tactctattt attagtacat tacacatgat tatttagaaa 1440
atgtatattg tggtcatatg aaatgagaaa ttaaaggaaa tttgtcaata cttgagaaca 1500
tcaccattca aatgtttcaa gaacaacatg actccaaaac aaaataaatg aacctttccc 1560
taataatagt atattctcca tcgtacaaag ttctaaataa tacaatattc atttcgtcaa 1620
agcatatgat gtgttggaat cagaattatc tgcaaatgtt tgaatttcaa atgttagtat 1680

-continued caggctattt ttactgtttt atcaaatatc gtttcttctg caatctatca cttgattgtt 1740
ttatcaaatc agcactagta ttattgattt tgtaatttgt gtttgtctac ctccaattac 1800
tttttagtgt tatgattagt aatgtaataa aatcacaaat ctgacgtggc acctatatac 1860
aattccaaaa acaagtggaa cgaatataaa acaaattcac accttcctca tcttcttctt 1920
cgtcttcact taccttctct ctacactcac accatctcac aaccctaatc tctcccacac 1980
aagagagata gagagaaaca 2000

<210> SEQ ID NO 4
<211> LENGTH: 1261
<212> TYPE: DNA
<213> ORGANISM: Arabidopsis thaliana

<400> SEQUENCE: 4
cacatacata gacacaaagc cctttccatt gtcctcttcg tttccttttg ggtaaacaac 60
caatctcctg atttttacaa aaaaggcaac atttcttagt tatatatgct tgtagtgaag 120
aaagatgtga aagtctgaca agagaacaag acgaaggagg agtctttctc caagtcttca 180
acattgcaga atctgatgca tatgaaccca ttttctctac aaaatgttgc aaccctagag 240
agcaaaacaa aacataccca taatcagaaa tgatctgacg aaaatcgagt tacaatacac 300
aagagaacat ttttttaga attctcagat attaaaaatg acacagaaag ctttatgctt 360
tttcctctta aaagactaaa caagttgaaa tctagagaaa gaactgacca acctgagaca 420
acgagagaga cttgagagat ttcttcggca cttactatta gatctagggt ttagatacca 480
tttatataga gaaagtttta gagttgcaca aaacataaat taatgtgtta gaatgggcct 540
aaagctacaa agctggcctg gttttgtttt aaattgttgg tttcatggac attttcgaca 600
tcttcgaaca tgttattttt tgagactatg caaacttgaa gctctttact cgagttgaaa 660
tcgtatgact tatagtgaaa ttgtacattt ggtttcgatt tttcttttac actctttctt 720
ctttgagccg gtaaatttgg aatttttctt catagtggaa tcatatgctg tttttttttt 780
ttatagtaaa cgttacaaga atgaatggta actttatcca aaaaaaaaga atcatattat 840
tttgaaatga ttttaagtaa attctaggtt caataacata agatttgaga ctaaatttaa 900
aatttcttag taaaatatat gatttttta taaataccta taaaattagt aattaacaat 960
acggattacg tactgaatca aaccctttgt attttgtttt tcctagaaat aagtgtagat 1020
ttttggaatt ttgcattaat taatcacttc ttgggtctga aaggctaaaa caaaaggaac 1080
cgaaagagaa tgttctctct gtctttatct tccacttcca cttccaggtc gcgttgcttc 1140
actctccatt gcaaagagag gtctctgcga tttctgcaac tcacccctga aaccttctta 1200
atttacttca actgccgcta tacctaaaaa cttcatcttt ctcctctgag ctatgataaa 1260
g 1261

<210> SEQ ID NO 5
<211> LENGTH: 1706
<212> TYPE: DNA
<213> ORGANISM: Arabidopsis thaliana

<400> SEQUENCE: 5
aaagatgcat aggcttgcgg acataaaaat tccggagcta tgtttcatcg ttgctttcac 60
ggtctgaaga gccaatcaac actaaagaag gacctctaat ggtctctagc aagtttagcc 120
cccaattaag tattgtattg atgtttttgt gatggatgga tataggctgc atattgggaa 180
attatagtgt attgtattgt gtcgtgttgt gtgtatgtgg gactatagca tcctgagttt 240
gtcatgtcca gacgttgtaa cttgtaagca attacttatg gttttgttca cttcgtatta 300
acgtatttaa tttgtggctc gattttggtt ttgaatctgt gtcaaaacta agataattta 360
cgtgttaaac caggcccaag tttgaaagtt aattgtcaat tttcagacca gagtacatat 420
tggtccactt attcccatta cattcatagt tttgagtctt ttgataatag tgttaccatt 480
tcaattaggc taatcttttt tcaacccaag atatttttat aaaaaggaat gtggttcaaa 540
tcggaaaaca agacctaact ttgaataaaa gcactacagc ataaagcttt tacctttaac 600
aaaaaaaata taataatttt ttacaaggaa aaagaagaga aagcaattat tctcagacaa 660
acaaaggaac cacttttgta ggtgtagtag taatctcaca cgctaagaca aaagtgcaca 720
aattctcgag actctcttct atccaacggt ccatatctca ctaaccgcat ctaaataacg 780
gacaagatct tcttttggct tcagctctct ttagtcttta ccttccctca agctcggtac 840
tcgatgtctt gctttcggcc actcatgaaa gcaacgagag cttccccttt catccgccta 900
cgtggctatg ggacccagtc taaccacgac cacctgacat cgtgggcccc actgtaaggc 960
gggaacccca tttttttttg gctgtaagta acggattctc ggtcatgctt ttttgtgagg 1020
atagagagag agactgagag agagagagag tgtgtcacgg tctcgcagat actgtgtatt 1080
gaaaagagag ttctagagag agagtgtgtt atgtgtgtgt gtgtgtgtgt gtgtgtgtgt 1140
gtgtgtgttt ggttactggg attaattgag ctgaaacagt ttggatagtt ttgtttgttc 1200
tgtttcatct ttcaaccaca gatatagtaa tattgtgaaa acccctcatt gaagtttgtt 1260
ctctgctctc tctttttggg tttagcactg agttttgggg tttatttcga gacataccca 1320
tacaaagttt gatacttttg tgtccccccct tatcaagaaa attgtggggt tttttttttt 1380
ttttaataag cttcctttaa attttcaatt tttattttgg aggaaaagag tgagaatttc 1440
agataagaat ctatgagcca atgatattct aattcatctt cttcgtgaag attttgagtt 1500
gaattccatt ttccttttttg tcttggtggt ttctcattgg ttttctcgag aatatttgtg 1560
gttttgggag aagaggcttc actgtagcat tgaaaaagtc ttaaactttt ctgtgtcttt 1620
ttatgtaagc tttgaacagc ttcacctttc tgggttttct cagattgtgt ctaatcttga 1680
aaaacctttt attcgtagaa gcagca 1706

<210> SEQ ID NO 6
<211> LENGTH: 1658
<212> TYPE: DNA
<213> ORGANISM: Solanum tuberosum

<400> SEQUENCE: 6
atcgcatggt ttcatggagc tccttgtttt tttgttggaa tttgatgatt ttccaatttg 60
gttattatgt tgttcattgt tgttgttgag tctattttgt ggtggtgcgg aggtgtgagc 120
tttaaattgg agttggggtg attgttgttt tgttcgccgg agaagccatc tccagtgagg 180
ttggttggag aaggagagag atgaggagag caatgagtaa tttcaactat taaagattcg 240
tttcagaaag agaaaaaaag aagaaaatgg tcacattgtc gtccttgtgt aacattcaga 300
ggagtgaacc ctaaacttgc cgacccacag agaaaaacaa ccctagtttc catggggacc 360
tgctgtaaca gtagcacagt tctcaagctt tgttttttgt ggctacaact aatctgtgtg 420
caatgccatg gaaggatact caaggatgat acctcctcat ctgatcagtt taagaacaga 480
tttcaaagga tttttctgag tatacttttt ggtatgttta caggattgat ttgtgcactt 540
gtttttgctt ggcttgttcg gagttttgtt cgttacatta acaaagcccc aattctcaaa 600

```
ggccctgttg tattctctcc taaaattcca tccaaaactc tgcaatcagc tcttgctaat    660

gatacccagt tgatagggtc aagtagttct ggaaaatact acagaactgt tcttgataat    720

gggcttactg ttgcagttaa gagaatggaa cctggttctc cacagttaca taccaagtca    780

tttaagagaa gaatacaaca cgaacttgaa cttattgcta gtttgaggca taggaatttg    840

atgagtttaa gggcttatgt tcgtgaatcg aatacgttct ttctggttta cgattatgta    900

aacactggca gtcttgaaga tgtaatgaac aaagttaggg aaaatcaatt gcaacttacc    960

tgggaagtca ggctccgaat tgcagttggg attgttaagg ctcttcagta tcttcatttc   1020

tcttgtaacc ccacagtttt gcatcggaat ttgaaaccca caaatgtaat gttggatgct   1080

gagtttgagc ctaggttggc tgattgtggt ttggctaaaa tcattcccac tttaaatctc   1140

cctgctgcat caaactatgg tcctccagaa tcattccaga gttgcagcag gtataccgat   1200

aaaagtgatg tatttagctt tggggttata ttgggtgttc tattaactgg aaagtaccca   1260

acagatccct tctttgggga tacatctact ggaggaagtc tagcacgttg gcttcaacgc   1320

ttgcaggaag caggcgatgc tcgagaagca ttggataaga gtattctagg ggaagaggtt   1380

gaggaagatg agatgttaat ggcagtaaaa atagcagcgg tatgcttatc agacatgcct   1440

gctgatcgac cttccagtga tgagctcgtt tccatgctca cccaattaaa tagcttctga   1500

ttaattactt tggtcgagag ggaaagcagt caaggattca aataatcaca agatctttaa   1560

ggttgttctt ttggctttct aaggtgatag tttgctgtgt gcttttggta gttgagcaat   1620

gccttttggt tatcgcaatg agcacgagtg tagttggc                           1658
```

<210> SEQ ID NO 7
<211> LENGTH: 2931
<212> TYPE: DNA
<213> ORGANISM: Solanum tuberosum

<400> SEQUENCE: 7

```
ttctcactct cactgagtga atctgcaaac caaacagttg gtgggcatta gattaaggaa     60

ggaaaaatgc gtcttctttt tcttcttctt cttgttatgc attttactga cttttccgcc    120

ggtaaacaac ctcggttacc ggaatatcag gctttgcttg ccctgaaaac tgccattacc    180

gatgacccac agttaacact tgcctcatgg aacatctcca ccagtcactg tacgtggaat    240

ggtgtcacgt gcgacacgca tcgtcacgtg acctctcttg atatttctgg gtttaatctt    300

accggtactc ttccgccgga agttgggaat cttcgtttct tacaaaatct gtctgttgct    360

gttaaccagt ttactggacc cattcctgtt gaaatctcct ttattccaaa tctcggttac    420

cttaatcttt ctaataacat attcgggatg gaattccctc cgcagttaac ccgtctgcgt    480

aacctccaag tccttgacct ttacaacaac aatatgaccg gtgaacttcc ccttgaggtg    540

tatcagatga ctaaccttcg acatctacac ctcggcggga actttttcgg tggccgcatt    600

cctccggagt atggaaggtt cccgtctcta gagtacctcg cagtttcagg caatgcactg    660

gtaggagaga taccaccgga gattggaaac atcactacac ttcagcagtt gtatgtagga    720

tactacaata ccttcaccgg tgggattccc ccggcaatag ggaacttatc gcagctcctc    780

cggtttgatg ctgctaactg tggactttcg ggggagattc caccggagat tgggaagctt    840

cagaaccttg acactctctt cctgcaagtg aattctctgt ctgggtcatt aactccggag    900

ataggttatc tgaagagctt gaaatctttg gatctgtcga ataacatgtt ctctggcgag    960

ataccgccaa catttgcgga gcttaagaat atcactcttg ttaatctttt tcggaataag   1020

ctttatgggt caataccaga gttcatagag gacttgccgg agctagaggt gttgcaactt   1080
```

```
tgggaaaata actttacggg aagcattcca caggggttag gcacaaagag caagctcaaa   1140

aatgttgatc tcagttccaa taaattgact ggaaatttac ccccaaacat gtgttccggt   1200

aacaatctgc agacaattat cactctaggg aacttcttgt ttggcccaat tcctgaatct   1260

ttgggtaggt gtgaatcact taatcggatt aggatgggag agaattatct gaatgggtca   1320

attccaaagg ggctcttaag cttgccacgt ctgtcacaaa ttgaacttca gaataatatt   1380

ctcactggta catttcctga tatttcttcc aaatctaata gtcttgggca gattatcctt   1440

tcaaataatc gcctaactgg acctttgccg ccaagcattg gaaactttgc tgtagcccaa   1500

aaattgcttc ttgatgggaa caaattttcg ggacgaattc cagcagaaat aggaaagctt   1560

caacagctat ccaaaattga tttcagtcac aacaactttt ctggacccat ggctccggag   1620

attagccagt gcaagttgct gacttatgtt gatctcagca ggaaccaact ttcgggtgag   1680

attccttctg agatcacagg tatgaggata ctcaactact tgaacttatc gagaaaccac   1740

ttagttggga gtattccttc ccctatttct agtatgcaga gtttaacttc tgttgatttc   1800

tcatataaca acttttctgg tttagttcct ggaaccgggc aatttagtta tttcaactac   1860

acctcatttc tgggcaatcc agatctttgc ggaccctatt tgggcccttg caaagagggt   1920

gttgttgatg ggggttagtca acctcatcaa cgaggagcct tatcgccttc gatgaagctt   1980

ttacttgtta ttggtttgct tgtctgttct attgtgtttg ctgttgctgc aattataaag   2040

gcccgatctt taaagaaggc aagtgaagct cgtgcctgga agctcactgc ttttcagcgc   2100

ctagatttta cttgtgatga tattttggac agcttgaagg aggataacat tattggaaaa   2160

ggaggtgctg gtatagtcta caagggggta atgccgagcg gggaacatgt agcagttaag   2220

aggttgccag ctatgagcag gggttcctct catgatcatg ggttcaatgc agagatacag   2280

actcttggga ggatccgaca caggcacatt gttagattat taggattttg ctcgaatcat   2340

gagacaaatc ttttggttta tgagtacatg cctaatggaa gtcttgggga aatgcttcat   2400

ggcaagaaag gcggtcatct acattgggat accaggtata agatagccgt ggagtctgca   2460

aagggtcttt gctatctcca tcacgattgc tctcctttga tcctccatcg tgatgtgaaa   2520

tcaaacaaca ttctgctaga ctccagcttt gaagctcatg ttgctgattt tggacttgct   2580

aaattcttgc aagattcagg gacatcagaa tgcatgtctg ctattgctgg ttcttatggg   2640

tacattgctc cagaatatgc ttacacgctt aaggttgatg agaaaagtga tgtatatagc   2700

ttcggtgtgg tgctattaga actggtaagt ggcaaaaagc cagttggaga atttggtgat   2760

ggtgttgaca tagtccaatg ggttaggaaa atgactgatg ggaaaaagga tggagttctc   2820

aagatccttg acccaagact ctcaacggtt ccccttaatg aggtgatgca tgtcttctat   2880

gtcgcattgt tgtgtgttga agagcaggct gtggaacgcc ccaccatgcg a            2931
```

<210> SEQ ID NO 8
<211> LENGTH: 3114
<212> TYPE: DNA
<213> ORGANISM: Solanum tuberosum

<400> SEQUENCE: 8

```
ccaccattga agaaacatgc gttttcttct cctcttcttc ctttccctta ttctccattt     60

ccatctcctc cacttcacca ccgcaaaacc accttacgtg ccagaatacc gggcattact    120

ctccctgaaa actgccatta ccgatgaccc acaatctgct cttctttcat ggaatatctc    180

aacaagtcat tgtacatgga gaggtgtcac gtgcgaccgg tatcgtcacg tgacttctct    240
```

```
cgacatctct ggttttaatc tcaccggtac tctcacgccg gaagttggtc atctccgttt    300
tttgctcaat ctttctgtag ctgttaacca gttctctgga cccattccta tagagctctc    360
gtttatacca aatctgagtt accttaacct ctctaacaac attttcaatt tgagtttccc    420
tccccagctt acccatctcc ggtacttgaa agttctcgat atttataata acaatatgac    480
cggtgacctt ccggttgggg tttacaattt gactaatctt cgacatcttc atttgggtgg    540
caattttttt agtggcagta ttccaccgga gtatggtaga ttcccattcc tagaatacct    600
tgcagtttct ggaaatgcgc tcgtcggtat gataccaccg gagatcggaa atattaccac    660
acttcgtgag ctttacattg gatactacaa cacgttttcc ggtgggttac cggcggaaat    720
agggaacttg tcggagctca ttcggttaga tgctgcaaac tgtggacttt ccggtgggat    780
tccgccggag atagggaagc ttcagaaatt agatacactg ttcttgcaag tgaatggtct    840
ttctgggtct gttacaccgg aattggggaa tttaaaaagc ttgaaatctt tagatctatc    900
aaacaatatg ctctccggtg aaataccgtt cacattcaca gagctgaaga atctaactct    960
gctaaatctt ttccgtaaca agctttacgg gtcgataccg gagttcatag aaaatttgcc   1020
gaaactggaa gtattgcagc tttgggaaaa caactttacc ggaagtattc cacaaggttt   1080
aggcaaaaac agtaagttaa caaacgttga catcagtacc gacaaattaa ccggaaattt   1140
gcccccaaac atgtgttccg gcaacaagtt acagacgttg atcactcttg gaaacttctt   1200
gtttggccca attccagaat ctttaggtga gtgtcaatca cttaatagga ttagaatggg   1260
agaaaatttt ctaaatgggt ctattccaaa agggctattc agtttgccca agctttcaca   1320
agtagaactt caagataatc ttctcactgg tacatttcca gtgactggtt ctgtttcatc   1380
aagtcttgga cagatttgtc tgtcgaataa tcgtttcacg ggcctttgc catcgagcat    1440
tggaaatttg actggtgttc aaaagttgct tcttgatggg aacaagtttt ctggtcaaat   1500
tccagctgaa ttagggaaat tgcagcagct gtcgaaaatg gattttagtg gtaacagttt   1560
ttcaggcctg attccaccgg agataagcca gtgcaaggct ttaacttatg ttgatcttag   1620
taggaataag ctatctggtg aagttcctac tgagatcact ggtatgagga tactgaatta   1680
cttgaatgta tcgcggaatc agttagttgg gagtattcct gcacctattg cagcaatgca   1740
gagtttaacc tcggttgatt tttcgtataa caacttatct ggattggttc cgggtactgg   1800
tcagttcagt tacttcaatt acacatcatt tattggtaat ccagatcttt gcggacccta   1860
tttgggtcct tgcaaagaag gtattgttga tggggttagt cgacctcatg agagaggtgc   1920
attttcgcct tctatgaagc ttttacttgt tatcgggttg cttgtttgct cgattgtgtt   1980
tgctatcgct gcaattatta aggctagatc gttaaagaag gcgagtcagg ctcgtgcctg   2040
gaagcttact gctttccaac gcctggattt cacttgtgat gatgtattgg aatgtttgaa   2100
agaggataac attattggta aaggaggtgc tggaatagta tacaaggggg taatgccaaa   2160
tggtgaactt gttgctgtta aaaggttgcc ggttatgagc cgtggttctt cccatgatca   2220
cgggtttaat gccgagatac agacacttgg gagtattcga catagacata ttgttagatt   2280
attaggattt tgctcaaatc atgaaacaaa tcttttggtt tatgagtaca tgcctaatgg   2340
gagccttggt gaaatgcttc atggaaagaa aggaggtcac ttgcattggg ataccaggca   2400
taagatagca ttggaggctg caaagggact ttgttatctt catcacgatt gctcgccttt   2460
gatcctccat cgtgatgtaa aatcaaacaa cattcttctg gattccagct tcgaagctca   2520
cgttgctgat tttgggcttg ccaagttttt gcaagactcg ggaacatcag aatgcatgtc   2580
tgcaattgct ggttcttatg gctacattgc accagaatat gcatacacac tcaaggtaga   2640
```

```
tgagaagagt gatgtataca gctttggtgt ggttctgtta gaattggtga gcgggaaaaa   2700

gccagttggg gaatttggtg atggcgttga catagtccaa tgggtaagga ggatgaccga   2760

tgggaaaaaa gaaggagttc taaagatcct tgatccaaga ctctcaacag ttccccttca   2820

tgaggtgatg catgtgttct atgttgcaat gctgtgtgtc gaagagcaag ctgttgaacg   2880

ccccaaaatg cgtgaggttg tgcaaatgct aactgagctt cccaagccat ctggtccaaa   2940

aacagaagat tcaacaatca ccgagtcgcc cccatcatca ggtcctgcat tagagtctcc   3000

cacttcgact cccggagaca cgaaagacca gtaccaccat cagccatcac ctcaatctcc   3060

tccacctgac ctactcagca tatgacctac aatgttccct tctaatagag gatg         3114
```

<210> SEQ ID NO 9
<211> LENGTH: 3362
<212> TYPE: DNA
<213> ORGANISM: Solanum tuberosum

<400> SEQUENCE: 9

```
gtcggtaagt ccaagaactg gtttttcaat tcaaaggagc tgagttagtg taaacacttt     60

tggttttgag ttttgacaga gacttgagtc tcagagaaac taccatggca tcatttttac    120

ttcaaagatg taatcttttc tttgaggttc ttcttctttt ggggttcttg atttcttca     180

gctttggttc tgtggtgtct gatgatggtt ctgcattgtt ggagattaag aagtcaatta    240

gggacatgga gaatgtgttg tatgactgga ctgattctcc ttcatctgat tactgtgcct    300

ggagaggtgt tacctgtgat aatgtcacct tcaatgttgt tcaacttaat ctttcgagtt    360

taaatcttga tggggagttg tctcctgcaa ttggacagct caaaggcctt atatctattg    420

atgttagggg aaatcgcctt tctggccaga taccagatga gattggtgac tgttcagcac    480

tgaaaaactt ggacctatcc ttcaatgagc tttatggtga tattccgttt tccatatcaa    540

aacttaagca actggaatat ctgattataa agaacaatca gttgattgga ccaattccat    600

cgacattgtc acagatcccc aacttgaagg tcttggacct ggctcaaaat aggttaagtg    660

gagaaattcc taggctgata tactggaatg gagtcctgca gtatttggga ctgcgtggca    720

acaacttggg tggatcactt tctcctgata tgtgtcagct caccggcctg tggtactttg    780

atgttcggaa caatagtttg actggttcca ttcctcaaaa tattggcaac tgtactgctt    840

tccaggttct agatttgtct tataatgact tgactggaga gattcctttc aacattggtt    900

tcctgcaagt agcgaccttg tctttgcaag gtaatcgcct ttcagggcag atcccttctg    960

tcattggatt gatgcaagct cttgcagttt tggacttgag ctgcaatatg ttgagtggaa   1020

caattccttc aattcttggg aatttgactt acacagaaaa attgtatcta catgggaaca   1080

agctatctgg ttccattcct ccagagctgg gaaatatgac aaagcttcac tacttagaat   1140

tgaatgataa ccaacttact ggacgcatac caccagaact tggaaagctg acggagttgt   1200

ttgacttaaa tgctgcaaac aaccaccttg atgggcccat tccttccaat cttagctcat   1260

gtaccaattt gaatagtctc aacgttcatg gaaacaaatt gaatggtacg attccacctg   1320

cttttcaaaa gctggaaagt atgacctatc ttaatctctc ctccaacaac ctcaaaggcc   1380

caattccaat tgagctttct cgtattggga atgtagatac actggacttg tcaaacaaca   1440

ggatcagtgg tcctatacct ttgtccctcg gtgatttgga acatcttctt aaactgaact   1500

tgagcaagaa cgaaataaat ggaaacttgc cagctaaatt tggcaattta aggagcatca   1560

tggagattga tctgtcaagc aatcacctct ctggtccctt gcctcaggaa cttggtcagc   1620
```

```
ttccaaatct gtacttgctg aaactggaaa acaacaattt atcaggcgat gtgatgtcct   1680
tagccagttg tctcagtcta aatgtcctaa atgtctcgta caataatctg ggagggaata   1740
ttccaacagg caataatttc tctagatttt caccagacag cttcatagga aatccagatc   1800
tgtgtgggta ttggctcact tctccttgtc atgcatctca tccagcagag cgagtttcaa   1860
tttctaaagc tgctatactt ggtattgctc tgggtggctc ggtgattctt ctgatgatac   1920
tagtagcagc atgccggcca cagaatcctg cacctttcat ggaaggatct attgataaac   1980
cagtttatta ctcatctcca aagcttgtga tccttcatat gaacatggca cttcatgttt   2040
acgaggacat tatgaggatg actgagaact tgagtgagaa gtatataatt ggttgtggag   2100
catcaagtac ggtatataaa tgtgttttga aaaattgcaa gcctgtagct atcaagaaat   2160
tgtactctca caacccgcaa tacttgaagg aatttgagac tgaacttgag acagttggga   2220
gtattaagca tcgtaatctt gtctgcctcc aaggatattc tctttctcca tctggccatc   2280
ttcttttcta tgactacatg gaaaatggta gcctttggga tttgcttcat ggtcctacaa   2340
caaagaagaa aaagcttgat tgggttactc gccttcgaat tgcattggga tcagctcaag   2400
ggcttgcata tcttcaccat gattgtagcc ctcgaattat ccaccgtgat gttaaatcat   2460
caaatatctt gttggacaaa gactttgagg ctcatctgac tgattttggc attgccaaaa   2520
gcttatgcat atcaaagacc tatacgtcca catacattat gggaaccatt ggttacattg   2580
atccagagta tgctcgcact tctcgcttga cagagaagtc tgatgtttac agctatggaa   2640
ttgttctatt ggaattgctc actggaagga aagctgtaga taatgagtct aatctacacc   2700
atatgattct aactaaggta gcaaacaatg ctgtaatgga aacagtggat cctgagatca   2760
caggcacatg caaagatctt gcagatgtga agaaggtttt tcagcttgcc cttctatgtt   2820
ccaaaagaca gcctgctgag agaccaacaa tgcatgaagt ggcaagagta cttgaaagcc   2880
taatacccgt cactgaaatg aaacagccaa atccaacgct ctcacttgca ttacttccat   2940
ctgctaaggt accttgttac atggatgaat atgtcaacct caagacaccc catctagtga   3000
attgttcatc catgagcatt tcagatgctc aacttttcct gaagtttgga gaggtcatat   3060
cccagaatag tggctgaaaa taacatgagt agatttcttg ggattgtgta aaaaaatgta   3120
gtgccattat aatattatta ttgtaggtag ttgttgtaag atgatgcatg caatagtggt   3180
ccagtctact ttttccacta cataggtcta gtgtgtgtaa aaatatttca ctttttacca   3240
tgatgaaatt ggaagaggta gcacttggta gagtattgta atattggttt ttgggactga   3300
tgctgagtat ggactatact gtctgtagga tttttggcac acactttgag gtggccttag   3360
ca                                                                  3362
```

<210> SEQ ID NO 10
<211> LENGTH: 3072
<212> TYPE: DNA
<213> ORGANISM: Solanum tuberosum

<400> SEQUENCE: 10

```
agactaaact aacagtgtaa taatgtcact ccccaaaaaa atatcccttt tcctccaaat     60
tttcattttt tttgttttct ccattaatgc aaactctgat cttgaaaccc ttttgaagct    120
caaagaatcc atggttgctc ctggaacttc tgcacttctt gattggaaca acaacacaaa    180
ttaccctttt tcccattgtt ctttttctgg tgttacatgt aacaataacc ctcatgttat    240
atctataaac atcactaatg ttcctctatt tggtactatt ccacctgaaa ttggtctttt    300
acaaaatctt gaaaatctta ttatttttgg tgataatatt actggtacac tccctttaga    360
```

-continued

```
aatgtcacaa ctttcttcta ttaaacatgt taatctttct tacaacaact tttctggtcc    420
ttttcctaga gaaatcttgt tggggttaat aaagcttgaa tcttttgaca tttataacaa    480
caatttcact ggtgaacttc ctactgagtt tgtaaagttg aaaaagttgg aaactttaca    540
tcttggtgga aactattttc atggtgaaat accagaagtt tattctcata ttgtaagttt    600
aaagtggttg ggtttagagg gaaattcact aactgggaaa ataccaaaga gtttggtttt    660
gttaccaaat cttgaagaac ttagattggg ctattataat agttatgaag gggtattcc     720
atctgagttt ggtaatatta gtacacttaa acttcttgat cttggaaatt gtaatcttga    780
tggtgaagtt cctccaagtc ttggaaattt gaagaagttg catactttgt ttctacaagt    840
gaacagactt acaggtcgca taccttctga actatctggt ttagagagtt tgatgtcgtt    900
tgatttgtct tttaatcaac tgaccggaga aataccagag agttttgtga agttgcagaa    960
tttgacattg attaacttgt ttagaaacaa cttgcatggt ccaattcccc cttttattgg   1020
tgaccttcca aatcttgaag tgttgcagat ttggggaaac aattttactc ttgaattgcc   1080
cgaaaatctt gggcgtaacg ggaggttttt gtttcttgat atttctatta atcattttac   1140
tggaaggata ccacctgatt tgtgtagagg agggaagtta aagacactga ttctaatgga   1200
aaattacttc tttggtccaa ttcctgaaca acttggtgag tgcaaatcgc ttgctcgaat   1260
tcgcgttagg aagaattact taaatggtac tattccagct ggttttttca agttacctgc   1320
attggatatg cttgaacttg acaacaacta tttcactggt gagctgccaa cggagataaa   1380
cgcgaataat ctcactaaac ttgtactttc caacaactgg atcacgggga acattcctcc   1440
atcattaggg aacttgaaga atctagtcac tctatcactt gatatgaaca ggttatctgg   1500
tgaaattcct caagaaattg cgagtttgaa taaactcgtg accatcaact tgagtggcaa   1560
caatttaaca ggtgaaatcc caagttcaat tgcgctttgt tcagagctaa cattggttga   1620
cttgagcaga aaccaactgg ttggtgaagt gccaaaagaa atcaccaagt taaatagctt   1680
gaacgctctg aacttgtcaa gaaaccaact gagtggcgcc attcctggag aagtcggagt   1740
gatgaatggc ttgacagttt tagatctttc ttacaatgat ctttctggaa ggagaccgac   1800
caacggacaa ctaaagttct tcaatgacac ttattttgta ggaaatccaa aactctgttc   1860
acctcatgct actttttgcc cgtcagcctc caattcacca caaaacgcgc tcaaaatcca   1920
tgctgggaag ttcacaacta tccaattggt gattacaata atcatcttag tcactgttgc   1980
attgctgttg gcagttaccg tgttgttcat caagaaggaa aagttcaaga attcgaaact   2040
ttggaagtta acagcattcc agaaacttga tttcagagct gaggatgttt tggagtgttt   2100
aaaagaggag aacataattg ggaaaggtgg agctggcgtt gtgtaccgag ggtctatgtc   2160
aaatggcatc gacgttgcaa ttaagaaact tgtaggccga ggaactggac accatgatca   2220
tggattctca gctgaaatcc aaacactagg aaggatcagg cacagaaaca tcgtacgatt   2280
actaggatat gtctcaaaca aagacacaaa cttgttgttg tacgaatacg tgtcgaatgg   2340
gagcttaggt gaaatgttac atggtgccaa aggagcacat ttgaaatggg agacgaggta   2400
ccgtattgct gtggaagctg caaagggatt gtgttatttg caccatgatt gttcgccttc   2460
gattattcat agagatgtca agtccaataa tattccgctg gattccgatt acgaggctca   2520
tgttgctgat tttggcctag ccaaattctt gcaggatgct ggtgcatcag agtgcatgtc   2580
ctctattgct ggctcatatg gttacattgc tccagagtat gcatacacat tgaaagttga   2640
ccaaaagagt gatgtataca gttttggagt tgtactgttg gaacttatca caggtcacaa   2700
```

```
gccagttggt gaattcgggg acggtgtaga tatagtcaga tgggtaaata aaacaatgtc   2760
cgaattatct cagccgtctg atgcagcctc agttttagca gtcgttgact cgaggctaca   2820
tagttaccct cttgcaagtg ttgtaaattt gttcaagatt gctataatgt gtgttgaaga   2880
agagagttgt gctaggccta ctatgaggga agttgttcac atgcttacaa atcttcctca   2940
gtctactact actactacta ctactctcct tgccctttga aattgcaccg atatcaagtg   3000
tctggttgaa aactcgtgga gtttgaggcc gggaacacga gtctcatgag tctatttggg   3060
tacggggaac aa                                                       3072
```

<210> SEQ ID NO 11
<211> LENGTH: 2241
<212> TYPE: DNA
<213> ORGANISM: Solanum tuberosum

<400> SEQUENCE: 11

```
atggcagaat cagttcttga accttgtaca acctcttatt ccttcaaagt ttcaatcttt     60
atcctattct tcttgatttt ccctttcttg aacccatttt catctgcatt tcctctttct    120
tttgatacta atgcaactga ggctgtcaat cttgaaacag aagaggacat gggtttgctt    180
ttgttcttca agttacagtt tcgagaaacc cctttaccaa gctgggatgt caatgttcct    240
ctatcaaact ggactggtgt tacccggtct aaccagaccg gacgggtcac tggacttaac    300
ctcacaaggt ttaacttgtc aggacaggtt catccttgtt tgtgtaatct tacttttctt    360
gaaacccttg tgttgtctca taatagcttt aacaattcaa taccttcttg tttatggaag    420
ttgtggagcc ttaagacctt agatcttagc tataatatgc ttactcttct tattcctagt    480
acatttgcaa caactatgag taagttaatt gagcttgacc ttagtcataa catgttgagt    540
gatgaaatcc caatgtggat agggaatgtc tcaatgtcac ttgaaaaact taacttaggg    600
tttaatagtt ttcatgggga tatacctaag agcttgttga atttgatgtc tttgaagtat    660
cttgacttgt ctcacaatag tttgatggga aatgtgggtg attttaacca agaattggtc    720
tcacttaatc ttgagtctaa tttattatcg ggtactttgc cttgtttata ttcgtcaagg    780
gaatcactta cacttcttaa tttagcaaac aattcgattc ttggaggtat accaacgtgt    840
atctcgagtc ttgggggttt gacacagctc aacttgtcac gtaatgaatt acgatatggt    900
atctcgccta gactggtttt ttcagagagg ttatgtttgt tggacttgag ttataatgag    960
ctatcaggga agattccaag taggattgtt gaggcatcgg acaagtctgg acttctactt   1020
cttgacctgt ctcacaatca gttctctggt aatattcctg taacgataac agaattgaag   1080
agcttgcaag cattgtttct gtcttataat cttcttgtgg gcgaaatacc agaaaggatt   1140
ggtaatttga cctatctaca ggtgattgat ctctcacata acttcctcac cggctcgatt   1200
cctttgaaca tcgtaggatg tttccaacta ctggtgctga tactaaacag taataatctt   1260
tctggggaaa ttcagccagt gcttgatgcg ttggatagtc ttaagatatt tgatatagga   1320
aacaacaaga tttctggtga gatcccactg acattggcag gctgcaagtc gttggaagtt   1380
gttgacttga gctctaacaa tctctcaggg tctctaaatg gtgcaataac caaatggtcg   1440
aacctcaaat tcctctccct tgctcggaac aagttcagtg gatctctgcc aagttggttg   1500
tttacatttc aggctattca tactctggat ttttctggaa acaagttctc gggatatata   1560
ccagatggta actttaacac tagtccaaat ttctacaacg gcgacattag gaaaaccatt   1620
cctgcagtac catcaatttc agctcgaagc ctggatatca aactttcact cattgctgat   1680
gaaactagtt tgagcttcaa ctataacctg acaaccacaa ttggaattga tctgtctgac   1740
```

```
aatttgcttc atggtgaaat tccagagggt ctgttcggat tacatggttt ggagtacctt   1800

aatttgtcat acaattttct taatggtcca gttccaggga gtttagggaa gttgcagaag   1860

ctaaaagcac ttgatttatc acataattct ttatctggcc acatccctga aaacattact   1920

gtcctcagaa atttgacagt tttaaatctg tcttataatt gtttctctgg tgttattccg   1980

acaaagcgag gttattggaa atttcctgga gcatttgctg ggaatccaga cttatgtatg   2040

gaatcatctg gtaatgtctg tcaaagaact ttgcctgtag agccagggaa gaaatttgaa   2100

gaggaaatgg aagagggacc attatcagtt tggatttttct gtataagtgc tttagttagc   2160

ttctatgttg gcattgttgt tttattttgt tcatctcgaa caagaagctg tattctgcaa   2220

acaaaaagtt tagcaggttg a                                              2241
```

<210> SEQ ID NO 12
<211> LENGTH: 2583
<212> TYPE: DNA
<213> ORGANISM: Solanum tuberosum

<400> SEQUENCE: 12

```
atgtcttcaa ttgctatttc atatggtgaa tatggttctg ttttttgtgg gttgaagtca     60

gatggatctc atttggtcag ctgctatggc tctacttctt ctataaatata ttcaactcca    120

gctcatttcc cttttattgg tcttactgct ggaaatggct ttgtatgtgg acttttgatg    180

gattcttacc agccttattg ttgggggaaa agtaattttg tacaaatggg agtgcctcag    240

cctatgatca aagggtctca atacttggaa atatctgcag gtgaaaatca tttgtgtgga    300

ctaaggcaac ctttaatggg gaagcatagg aacacttcac ttgttgattg ctggggttat    360

aacatgacca caaataatga gtttgaaggt cagatccact ctatttcagc tggttctgag    420

tttaattgtg ctttgttttc tgtcaataaa agtgttttat gttgggggga tgaaactagt    480

agccaggtta ttaccctagc accaaaagat ttgagattta ttaagattgc agctggggga    540

tatcatgttt gtgggatcct agaaggggtg aattctcaag tgtattgctg gggaaggagc    600

atgaaccttg aagaagaatt ctctgttgct caactcaatg ttgaattggc agcccctagt    660

gatccaatta tatctgttgt tggtggtaag tttcatgctt gtgggattag gagctatgac    720

cgtcatgtcg tttgctgggg ttacagagtt gagaaaagca caccacctcc tagtggagtt    780

aggctttatg agatagcagc tggtgactac ttcacttgtg gtatccttgc ggaaatttca    840

cttttgcctg tttgttgggg gtttggtttt ccctcatcgc taccactcgc tgtttctcct    900

ggagtctgca agcctagacc ctgtgcatct ggcttctatg agtttaacaa cggaagtgca    960

acttgcaagt ctcctgattc tcgcatttgc cttccctgca ccaatggctg ccctgctgaa   1020

atgtatcaac aggttcaatg cacttcatct acggacagtc agtgcacgta taattgttca   1080

agttgtacct ctgttgactg cctaaacagc tgttctactg ctatttctgg gaagaagaac   1140

gctaaatttt ggtcactcca gttaccagta attgttgctg aggttgcatt tgcagtattc   1200

ttggtgagtg ttgtatctct aacttcgatc gtatatgttc gctacaaatt aaggaactgt   1260

agatgttcag ggaaaggtcc tagtcctagg aagaatggta ctttcccaaa ggaaattgct   1320

aaagataggg ctgatttgga tgatcttaaa ataaggagag ctcagatgtt tacttatgaa   1380

gatcttgaga gagcaactga gggattcaaa gaagaatcac aagttggaaa gggtagcttt   1440

tcgtgtgttt tcaagggcgt tttgaaggac ggtactgtgg ttgctgtcaa gagggctata   1500

atgtcatctg acatgaagaa gaattcaaag gagttccaca atgagctaga cttgctgtcc   1560
```

aggttgaatc atgctcattt gctcaatttg ctaggttatt gtgaagaagg tggagagaga 1620
cttctagttt atgagtacat ggctaatgac tcgttgcatg aacatctaca tgggaaaaag 1680
aaggagcaat tggattggat aagaagggta accattgcag tccaagctgc tcggggaatc 1740
gaatatttgc atggttatgc atgtccacct gtgattcaca gagacatcaa gtcctcaaac 1800
atccttatag atgaagaaca caatgctcga gtagctgatt ttgggctttc cttgcttgga 1860
cctgctaata gcagttcccc attagctgag ttaccagcag ggacacttgg gtaccttgat 1920
cccgagtact acagactaca ttatcttaca accaaatctg atgtctatag ctttggtgtt 1980
ttgcttttgg aaattctcag tggtcggaaa gctattgaca tgcaatacga tgaagggaac 2040
atagtggaat gggcagtccc attaatcaaa gctggtgaaa tagaggcaat actggatcca 2100
gttttgaaat caccttctga tgctgaagct cttagaagaa tcgctaatat agccagcaaa 2160
tgcgtgagga tgagagggaa agagaggccg tcaatggata aagtaacaac agctttggag 2220
agagcacttg ctcaattgat gggtagtcca agcaatgacc agcctatctt gccaacagag 2280
gttgttctag gaagcagcag aatgcacaag aagtcctcat caaatcgatc aacatcagaa 2340
acaacagatg ttgcagaaac tgaggatcag tggtatgtcg aattcagagc tccttcgtgg 2400
attacattcc caagtgtagc atcatctcag agaagaaagt cttcagtatc ggacgcagat 2460
gttgaagcaa agaatttaga aagtaggaac tgtggaaatg gaactgatgg attgagaagt 2520
ttggaagaag aaattggacc agcttctcct catgaacatt tgttcttgaa acacaacttc 2580
taa 2583

<210> SEQ ID NO 13
<211> LENGTH: 2598
<212> TYPE: DNA
<213> ORGANISM: Solanum tuberosum

<400> SEQUENCE: 13
atggaggtga gcgtgaagat gaaattcccc tcacaagcac tactgttggc tctattgctt 60
gttttaccga tcgttttagc tctcaccgaa gaaggcaaag cattaatgtc gatcaaggca 120
tcgtttagca acgtggcaaa cgtgttgcta gattgggatg atgtccacga cgaggatttt 180
tgctcatggc gaggcgtgtt gtgtggaaat ttctccattt ccgtcgttgc ccttgatttg 240
tctgataact tgctctatgg agatatacct ttctcaattt ctaagctcaa gcagctagag 300
ttattgaacc tgaaaaacaa ccagttgtct ggcccaatcc catccacatt aactcaaatc 360
cctaatctaa agacgcttgg cttaagaggc aacatgttga caggaacatt gtcccctgat 420
atgtgccagt tgactggttt gtgtgatgtg cggggcaata acctcagtgg aatagttcca 480
gataatattg ggaattgtac aagttttgag atactggata tctcatacaa tcagataact 540
ggagaaattc cctacaatat tggattttta caagtggcta ccttgtcttt gcaaggaaat 600
aggctaactg ggaagatccc agaagtgatt ggtctaatgc aagctcttgc tgttctggac 660
ttgagtgaaa atgagttggt gggaccaatt cctccaatct ttggcaattt atcctacact 720
gggaaactgt acctgcacgg caacaaactt acagggccaa taccaccgga gctaggaaat 780
atgtctaaac ttagttactt gcaattaaat gacaatcagc taatggggcg aattccctcc 840
gaacttggca aactggacca gttatttgaa ttgaatcttg caaataacaa gttggaggga 900
ccaattcctg aaaatatcag ctcctgctcg gcattgaatc aacttaatgt tcatggcaac 960
aacttaaacg ggtccattcc ttcagggttt aagaatcttg agagcctgac atatctggat 1020
ctctctggca atgaattttc tgggtctatc cctggttcta ttggagattt ggagcatctc 1080
ctcacactga atctgagcag caatcatctt gatggacaaa ttcctgtaga atttggcaat 1140
ctgaaaagta tacagaccat tgatatgtca tgcaacaaga tttctggtgc catcccaaaa 1200
gagctgggac agctgcagac catgataact ctgaatatat cctacaacaa ttttagtggt 1260
gttgttcctc tttcacggaa tttctcgcgg tttgcacctg acagcttttt ggggaaccca 1320
tttctttgtg gcaactggaa aggctcaata tgtgacccct atgcaccaag gtctaacgcc 1380
ttgttctcta gaacagctgt tgtttgcaca gcattgggtt tcatagcact cttatccatg 1440
gttatagtgg cagtgtacaa gtccaaccaa ccacaccagt ttctgaaggg gcctaagacc 1500
aatcaaggtt cccccaaact tgtggttctt cacatggata tggccatcca tacatatgat 1560
gacattatga ggattactga gaacttcaat gagaaattca tcataggata tggtgcttcc 1620
agcactgtat ataaatgtgt tttgaaagat tcccgaccga ttgccgttaa gcgactttac 1680
actacacatc cgcacagctt gcgagagttt gagactgaac tggagaccat tggaagcatc 1740
aggcatagaa accttgttag cttgcatggt tactcccttt cccctcatgg gaatctcctt 1800
tgttacgact acttggagaa tggttcactc tgggatctac ttcatgggcc ttccaaaaag 1860
gtgaagcttg actgggaaac acgtctgagg attgctgttg gtgctgctca gggtcttgct 1920
tatcttcacc acgattgcaa cccaagaatc atccacagag atgtgaaatc ttcaaacatt 1980
cttgttgatg aaaattttga ggctcatctt tctgattttg ggttgcaaa atgcatccct 2040 tctgcaaaaa ctcatgcatc aactttggtg ttgggcacca taggttacat tgaccctgag 2100
tatgccagga cttccaggtt aactgaaaaa tcagacgtct acagctttgg cattgttctc 2160
ctagagcttt tgacaggaaa gaaaccggtt gataatgact tgaacctgca tcagctgata 2220
atgtcaaagg cggatgataa caccgtgatg gatgctgttg atcctgaggt atctgttaca 2280
tgtatggact taacacatgt gaggaaaact tttcagcttg cgttgctgtg cacaaaaaga 2340
tttccatgtg agaggccaac gatgcatgag gttgctaggg tacttgtttc cttgcttcct 2400
cccccgccaa ccaaaccttg tttagaccca cctcccaaat ccattgatta tacaaagttt 2460
gtgattggga aaggactacc gcaagttcag cagggtgatg attcctccga agcacagtgg 2520
ctttttctta gatatttagc tgctgcactg gttcaatgga acgagtttga agatggtgaa 2580
gaattgcatc tatgttga 2598

<210> SEQ ID NO 14
<211> LENGTH: 3397
<212> TYPE: DNA
<213> ORGANISM: Arabidopsis thaliana

<400> SEQUENCE: 14
gaagacccaa ggcccaacga cctactggtc caggttgact atgaacaaaa gaactagatt 60
tttttttccc ctacatttta aagaaaatac ttgatgaaga tgtggtgcct tttcataaga 120
tctaaaaagt ttcaaatctt tacgatggaa caaaaagtga aaggtgaagt aagggtcatt 180
tgggattgag aagtttcttc gtccaaaatc attgcatgag ttgaatagat ttgggattaa 240
agctgccaat acaagaggat tcggtaatga ctgaagcaaa agcccagcag ggccattagg 300
caaacaccag tttccaagac ggatttgtgt aagaccactt atgacacaag tttgtcttca 360
ctatcatcat cttcttcttc tacttctact actacttttg tagccttgtc gtttttatca 420
ttaacatgat tgacaagact atgacctata tatcttatta ttatcattgc tctctctatt 480
tgtttatatt gattattact ttttgagatt tttcaatggt tttatctcta actaaacatt 540

-continued

```
ataattagtg aaacaagctt agtagaagta aaagtattat tctatgctaa agtacattga    600
ttagtagagt gtgtaattgt gtatacagat aatctataaa caattggtgc atctgtatat    660
aaaactttat gatttattta ttgtatttaa taagtatatg aattgggtac ctaactttct    720
aaacagttcc aaatttattc ttaaatcaaa ttgcatatga tttttaaata ttttgagacg    780
attttattat aacgcaaaca acagagtaaa agaagcatat gttgcaaatt gtactatggc    840
aagttcaaat cgaaacattt ttgtgaaaat caaacatgtg aaccaagctt ctacagttta    900
attccctttc gtataattta atttcaacaa atttattgat atccatctag aaattggtcc    960
aaagttcttt cacccttgag tcatttagtg ataaagatga catgattttt ggtgataaat   1020
tttccatcgt tgctatatgt cgttatatta ttctcctata tgtatattat actatttaca   1080
tcagaaaata atccaaagtt tagagattct tttttacaat aataaaattt cccacttact   1140
aaaaagagct ccttttctgc tgaagagaac ctaaaccttt attcccaaag ttcattgagt   1200
tagagcattt tcagcgaatc acataagaga tgctctcttc ttcatcacta attgacatct   1260
cattgtttta aaggttgcac ttgtacctgt tgatctgatt ctcaatccac ttaagttaaa   1320
ccaaatagac acgagaaaaa agcacattta tttgttgcta agtatgcata tttttcagcg   1380
tttacttctt aatctaatgt atatcataag ataatatcta aaagagaatg cacaaaagat   1440
tattaatatg agaaattcgc tgccatttag gaaggacctt tataccaata taccgcaata   1500
ataatagaac attggtcccc aagtgtatgt caaccccaag tgtatagatt tctttaaaga   1560
ttaaaatccc tttttgttgc taaagcacct gatatatttt tctatcaaac taaaaaaatt   1620
gttagcggga tgaagatata ttcgccaaga accatagtgc ttgtataacg gcagaccatt   1680
aattcacaac tattattatt ttattgttag attgttgata gaatcgattt tgattgtggc   1740
agaatcgatc ttgtaaaaac tgctttaagg tgcttactta taattaagaa agattcactt   1800
atgtaagtta agcatattaa tcatatcatt cggcctaatt cattaggaat attttgctat   1860
tcgttttgcc atcattaaca acaaaattga cacgttttca gccaaaagta ttaacaacta   1920
aacctaaaac ttcaaacatt aaatagtttt tagtatcttt agtttcaaac tagtgatttg   1980
tcctaatatc aacactacga acgaatttat atacattgaa cttttttctg aatcaccgat   2040
tacaaaacga atataatttg gtatcggcag ttgctattaa tttgatcggt ttggactttg   2100
gactaatcac gatcaaatct taaatggacc gaagtgaata aatccctaat gttttcaaga   2160
gagtcacacg aacgaaacaa aggtaaaata tgaacataga gcgtggggac cttgaagcag   2220
aaggtctgta tggtgacaga ccggtgagtg gagtgtatga atgaacgaga agtgagaaga   2280
caaaatacaa gaaagagcgt tgacttggaa gttaaagcca aaaaaaccac aaggggcaaa   2340
tttgtctctt taggaaaagg acacagacag actttctata cgggccaatt agaaaaatag   2400
gccctacttc taattaaagc ccatttactt ctctccttgt cttcttattc ctcttttctc   2460
cccatcacgt gacgacgatg ctataaacgc cgtcggatta tataactggt gccgttgaca   2520
agacggcgac agaagaaaga aagaagaaac cacaggctct agggaacgta acgttatgtc   2580
ctgtctatag catttataac ggtcagatca acgccgttta gataaagatc tgtcaatgtt   2640
aaagaagaga tgcatctcta caccgttaaa tttaaaacgc cgtgaacctc ttatctattg   2700
atttttgttt gatgaagcca aaacaaatcg tgtcagaaga cttatcagag aagaagaaaa   2760
cgacgacgtt cccgtttctc catgtctaat aagtgtagta gtggcggcta ctaaaaactc   2820
taaagtttga ctccagtaaa actgcctttc tagtgtaatt ccagtgattt tagagtttga   2880
atagtgtgtg accaaatttg aaagtacaat ctcagcaata ttattgatca ctcgttataa   2940
```

```
aagaatcgaa tgtaaaaata gccaatgaga gactgagacg tatgtgtttg accataagtc   3000

gtatagtttg tatctatcta cctgcaagat cagcagatgg ttctctgatc aattgtacct   3060

taattatctt ttattttcgt aaaatttctc tattcacaaa tgataaatct acttaagaca   3120

gtaaccataa caagatttac aagataattt gaaaaatgaa cacataaaag tattttggcg   3180

cattattttt aataataaca atatttatgt aaagtcacat aaaagtatat attcgctcac   3240

aaagtcttac ggtatttaga acagtagtac cacatcgatt ctcttcatct tcttcttcat   3300

aatatgccat tgttcatgtc tctgtgtcct atcgcataac actcacgcta tcttattatt   3360

ttctctcgct ctttctcact gagaggacac taaaaaa                            3397
```

<210> SEQ ID NO 15
<211> LENGTH: 1941
<212> TYPE: DNA
<213> ORGANISM: Solanum tuberosum

<400> SEQUENCE: 15

```
ctccgagcgt gaaatgaaat taattccttt aggagaacat aaatgtctgc agaactattc     60

ttgaaacctg gcgcagagga taaaataaat attcaatcta tctaataata gttgttcact    120

cgcgcatttc ttatgaaact ataaatagaa tgataattta ctatatcacc ttttgaatat    180

actctctctg tccctaatta cttgtccatt ttgataaatc aagaaagaac aatttttttt    240

ttatctatta taccctcaat aaattacttt gaaactgtag agcttcttga aaatctcaag    300

tttttaattt atccacttca taattaatag gggtaaaatg gtaaactact atgccaataa    360

ttgtttttctt aatatgtgtg tcaattcaaa agtggacaaa taattaggga catagaaagt    420

aagagataca atatcttgaa aaatgtaata gggaaataac tataattaat gatgagtaaa    480

ttatgaacta agtgtaaaat tatttattga tgtcataaag tagacaaata ctctctctgt    540

ccaataatag ttgtccacta ttgacctgac acacccctta aaaaataata aatattgtaa    600

tactacttta ttatcctttg actttattaa atttaatgtt ttgaaaaatg ttttagatga    660

taaataatac cctctatccc taattacttg tccacatttt cttttttaat tgtccctaat    720

tacttgttca ttttaataaa ttaagaaagg acaatttttt tttacctatt ataccctcaa    780

ttaattattt aaaaaaaagt agaacttctt gaaactatta agtttttaa ttcatccact    840

tcataattaa tatgggcaaa atggtaaact cattatgtca attattgatt tcttaatagg    900

tgtgtcaatt caaaagtgaa caaataatta ggaacaaaga gagtatttaa tagcaagagt    960

aaaacaaaca caaaaggtaa attatatctc ttaattttct agattggaca aatattgatg   1020

gacaactatt tttagtatag tggataacta ttgttagaca aataaagtat tgttgaatat   1080

cccaaaataa tataatggac aactataatt aggcggaggg agaattattg ttggacggag   1140

gaagtagaaa caaaattttt aaagctagca attttaggat gattaggggg gattatgata   1200

atgattgtac taagtaggta caattataat ggaaatttta gttaattatg gtgtactctg   1260

taagaagaga gaaaatttga ataaaattaa gtagtagtta tttgtagaaa gtaagggagg   1320

acatgtgtgc aggtatccag gcattgaaat atcaattttg caataaattt ttcattaaat   1380

gctttcacct acactgctct tattttgaga agatgtagtt ttgaagcatt taatgctcac   1440

ttttctctct ctatttctcc tatgctgtct ttcaccactt cattcttgag ggcaccgata   1500

actttgacac aaaaggggct aaaaaaaatg tcattatgtt ctctttttttg tgtttcttga   1560

actgaaatat gcagcttctt ggctacaaat tttgtttaat tgtattgata acgagggtat   1620
```

```
tataattatt tgggaggaag gaaagttgtg aattttgatc tcatctaccc acccatggta   1680

tgtttgaact atttttttc tcgtgtgttt cataaattaa gtcagctact atggagaagg   1740

aggagtggta ttttggttct atcaaaaagg ataaaggtga aagaaagcac tgactttctg   1800

tttgtgtact ttgtttaatt tttaatttgt gtaatggacg tgtttaataa gtggtgtgtg   1860

gtgatgtgga aatgtagata ctttgtaaga gcttttatgc ttcttgtagt attttcaaaa   1920

gtatcagggt ttggatcaat g                                              1941


<210> SEQ ID NO 16
<211> LENGTH: 1933
<212> TYPE: DNA
<213> ORGANISM: Solanum tuberosum
<220> FEATURE:
<221> NAME/KEY: misc_feature
<222> LOCATION: (1788)..(1788)
<223> OTHER INFORMATION: n is a, c, g, or t

<400> SEQUENCE: 16

cgatgaataa tgctccctat caatattttt tttatactga gaatccaaaa acaattataa     60

tgaccatgct gaatttcaga aaatggtggg acagttatga aaaagatgtt gagattggtt    120

ggatcggaag aagagaacaa aaagagtgga ctttttacgc aatgccaaaa ttacagagtg    180

tctcttaccc aaggacacat acagactttg ccaatgggcc ccagaaccac ccattaaccc    240

cccccccac aaaatatggg ccttcctacc ataccaaaga aaaaaaagaa aaaaaattac    300

gaaataatta taagatcgat aatgttatat gataatgaat attggagcgt aaaactctaa    360

taattcataa tgggaggttt gaaagcaaaa atgagtctaa taatatagaa atacacacaa    420

gatagatgcg cagagattcg actgttaaaa taatcatgtg gtgaaattat atactagata    480

aaattaaaaa tgactaaata catcagtata tcaatcgttg cattgatcaa tagatacact    540

aattatcata gctataaaat tataataagt aaaatactgt aacaaaatag ctccttcaaa    600

tcatataaaa atctacacta acacaataaa tagatttaaa aaaaaatata gcctaaacaa    660

caaataccac actctaaata tgagttacga ccattttttt ttttatggtt ttgtaaggaa    720

ttagggtgca aatcattaaa aacgaagata agatgtaagt aaccaaaacg tgcatgcatt    780

aggatgcaaa tcacaaacta ctcaaattta ctattagaag tgctcatttt aataaattta    840

gaggaccaaa gtgacaaaga gttatactta ataaactagt ttgaaataac ccaaagataa    900

agatattatt tttgttattt tctagtataa atcttagctg acagactcag aagcgtcaat    960

catcaaaaga agttcacaaa aagccgtcag taatttactc tgtttctcat ctaaccattg   1020

cttctaaagt ctgctgctac aatcatttta cttgcatcta tacatatcac catgactttt   1080

tttaccaata aatatgagat ttaaccgtaa gttattgagt tcgattgaat cttcacgtaa   1140

catagtaatt aaatatgaaa ttataccatg atttaaagct aattaaatat gagatggaat   1200

tatcgaaaat tatgatgaag tagtcaatac tttttcatct taacaagaga ttttgaattt   1260

aaatttgaat tttggatgaa gttacttttg ataaataatg ttttaacctt aaactagaaa   1320

aggttgattc gttcattaaa atatattctt tcaatctcaa tttatgtaac actgtttgac   1380

ctaatataga ttttaagtaa gatagaaagg aaatttttat aaatttatga tctaactcct   1440

cattttggtg attataaatc atttgattag taaagagttt ttgaagttac tcttttaaaa   1500

tattataaaa atgataattt ttaataaaat aaaagaaaat tatatatttt gttgggtctt   1560

ttagtatcca atatccatat ttaaactcga ttagttctaa attagcgctg aaaagtgtta   1620

cagtagttgt acaaaattct ctaataaaag tgattccgta tcgtatttaa atttgaaagc   1680
```

```
tttgattatg aatgattaag aatggaggaa caaaatttgt taccttatta ttatttggta   1740

gagatgaagt atttaccact ccctgtggta tcttcacttt gtttcctnac acacatatat   1800

tcaaagccaa aaagttaatt ttgattctcc ttccactttg gccaaatgca acagtactaa   1860

atactcaaca cttcaaatac ccttgaacct atcccaaaat ttgtacaaac cagactaaac   1920

taacagtgta ata                                                      1933
```

<210> SEQ ID NO 17
<211> LENGTH: 1847
<212> TYPE: DNA
<213> ORGANISM: Solanum tuberosum

<400> SEQUENCE: 17

```
ctcactcgcc tctctcatcc ctctcacctt tttcctccct ttcccattct cactcgccag     60

atatacaaat acatatgtat actagttaca tacagaatga tatacataca caattcaaca    120

aatatacaaa ttcaatttac ctctcttcac tctatgtcct ctctcctccc tctcccaatc    180

gctctcgtct ctttcctccc tttaaaatat agctacaaat cgtaattatc aaattatagc    240

tatgaagcct aattaagtta tttttaatgg ttatttgtga aatttcctct tttttaaaat    300

agtttttaga aaatcaaact tcagtaactt ttaagttaaa aaataaaaag taagagtacc    360

tacttttaac tttttaaaaa tcgtttttaa aatattgaaa tattcttggc gactaaaaac    420

tacttttaac ctaagcgaaa caccctctga atcttagtag agtaagttct cgagtcatat    480

catgattaat ttattttcac tcgtgtactt tagcttttca tttttcctta attttgtttt    540

acactactat aaaatagtgg gatgcatcta tatcttatcg ttttttttatg ttacattaat    600

tcatcacttt taaaataata aaagtattta gatatatagt ttttgccaaa gttttatgat    660

attataaaac aaatttgaaa atcaatcgaa tcgaactgac acttaaataa tcgtgataat    720

atttaaatat tataaaatag aataactata aaattaatat tatgtaaatt taataaaata    780

atcgattgaa gcgtaccatt gaaaactcga aagtgaaagg aagaagagca taattgttga    840

tatgggttca cacgctcact tacatacata taataaaggc tctctttaaa gagaatttga    900

aaaagaaaag aaaagtgaag ttgtctactt tactttagtt ttacacttct ccaggcacgc    960

caaacacctt ttgcctctct tttttttttt tttttcatt gggactgttt tttttttttta   1020

gtttgttttt cttttctttc atcaaagagg tatttttcgt ttctataata ttgggagtag   1080

caaaaatgct actagtatat gaaatggcaa ttagtacttt tatttatcat caaatgatat   1140

atggtgcagt gtatacaata ttcaaattcc gaatatgaaa aaattcataa tagaaagtac   1200

ttttccataa gagatcatac aatgagaaaa tattcaaatt aatcaaactc caatacagat   1260

actatcaaaa atcaaatgaa tgagaaaata ataaaaaaat attacccccca tttgatcact   1320

caacttttct ctccattatt taatacaaaa atatcaggtg atttttcata tttgttctaa   1380

ctttagtata tagagttatc tagtactccc ttcaattact tttgatacta atgcaactag   1440

gcttgtcaat aaaatatttc attagctatt actgatgaga gataacaaat atttcataaa   1500

attagttgaa gtgcgcaaaa gaccaacctc aaacacacaa tcataaaaaa aaaagtgagg   1560

aaatatagag tgtgtgcctc tcaataaaat aagtactaaa aaagaaaaca agaaacaaga   1620

aagaatgttg gttctttagt ggtgactctc aatgaagtac ctactttcag cttactctct   1680

ctatactcac tactactgct actcagtact gattcctttc acacatactg tgcctgtaaa   1740

ccctgtccag ggacccccat ttccccttttc cccttttcccc tttctccttc cttccttagc   1800
```

```
tatctctcac acaaacacta atcttttttc acctctacct tacctcc                1847


<210> SEQ ID NO 18
<211> LENGTH: 3647
<212> TYPE: DNA
<213> ORGANISM: Solanum tuberosum

<400> SEQUENCE: 18

tccgtttgag ggatttctgt aattataaac ttttaaggga tagattgtaa ttttgccttc     60

aaaatatgtg atttctgtaa tttgccttat tatataaaca atgtgtatta tccgcataat    120

taccacttat agtaattgaa taggttttac catctataac ataacttttt taacaatttg    180

tctccctctc ccattcactc cccccccccc ccccctctc tccttcttct cttttctttc    240

tgcccgtctc tctctataaa tttcaattat cctaatttaa gacttgattt tggatcgagt    300

attatttcca aacaattgag aacatctttg aaatttatat cttaatgttt aaggattgtt    360

gatgaagact aatatttata taactaatat atttttatta caataataaa tctaacaatg    420

tttaaaagag aaaaaataat aaataattat cagtatatta tacatattta tgtttcaatg    480

cacatggtga atataattaa aatattttta aaacaaatgt attataagta ttatgtgtga    540

atctcaaaca tttcagtact atttaaatta gtttacattg ttagaaatgt attatatttg    600

ttggaataac aacaatcaaa ttcataacaa tgtataatat tgaatttgaa tggtattaca    660

agtgtcttct atatttaata caattgtaat acataaacta atttgaataa catttgaata    720

ttttaaatac aagtacaatg catttttaac accattaata agatagaaaa taacaattgt    780

aaaacattat gaatccaata tattatactt attagaggca tatttcaaaa cacgtggtga    840

atatataact aaaacatctt taataaaaat gtattataag aattatatgt gaacttcaaa    900

cattctacta ccatttaaat tagtttacat tgttaaaact atatagaggt ggcaaatagt    960

tggatttgga tgggtttaaa atgatttaaa taaaaatggg taattatcca atccgtccat   1020

attctatatg ggtaaatatg gcttggataa ttaatggaca gattggatat gagttaccca   1080

tatttcatcc acattgattg aagaaataaa aaatgaattt atattttttta agtttctaaa   1140

gtaatttttt attctactca ctcccatccc tacctccaat tcacccaccc ctaattttag   1200

tttgttttat tttttctaac ccccgcccag tttttatccc cctccacctc acccgtcttc   1260

atcccctcta cccccacctg cacccaccca cccccacttt tttttaaaaa aaaattctac   1320

gcccccctcc ctcaagaatt tccaattttt tttttgttct tccattaaaa aaatgagttt   1380

ctttttaaaa ataaaaattt accccctccg ctccactcct attttttttt ttttttggtt   1440

tttttaaaaa aagtaacatt ttcagaaaag aaagttaccc ctgttataaa ctaaagtata   1500

acaacttact cttgcttctt tctttgttac aagaggggta tatatagttg tatacacttg   1560

tgcccaaagt gtgatacacg gataacttct tgccatgtat acactttgga caccaagtat   1620

atcaaatggc taattagtat acaccacata gcattttgtg tgtgtattaa tcttacaaca   1680

cttaacatat tagtgtggac attcaattta caacaaccct gaattgtatt acaactatca   1740

tttatatttc atacaacttt tcaaagttgt agctcttctt ttccgatgat tcacaatcac   1800

cggattatca gtagctcaaa tcaatcccat tattacaaat caccacacag tccacccaca   1860

gtcaccaaac tctcttttcc ccatattttt ggtccaaaca ccatgaccaa atttgaatgc   1920

cgaagagagt ttttcaattg gatctaaaca tcgattttca tgaagctcat cggagcaacg   1980

aacaccatca aaattatgtt cagatctaac aacaccactg atttatgttc tactcttcta   2040

cttaaacaat gaacatagaa actacaatct tctttggttc ttataattac aaattaaaaa   2100
```

```
acaataacgt aaaagaaaaa agatgcatag agattgggca tcgcatggtt tcatggagct   2160
ccatgttttt ttgttggaat ttgatgattt tccaatttgg ttattatgtt gttcattgtt   2220
gttgttgagt ctattttgtg gtggtgcgga ggtgagagct ttaaattgga gttggggtga   2280
ttgttgtttt gttcgccgga gaagccatct ccagtgaggt tggttggaga aggagagaga   2340
tgaggagagc aatgagtaat ttcaactatt aaaggtaaat tgaattaata tctcatacga   2400
tcactcgact ttaaatagtt tatttagaaa gtcacttaac tttgaattgt tcactaaaaa   2460
aatcactcaa ccttatttta taactcaaaa gtcactcaac tattgatgtt ttacttaaaa   2520
agtcacctaa gtattgatat attgcttaga aagtcactca atcaatttaa ataattttcc   2580
attaaatttt attgtaaact attttttaaa gaaataataa gatttctatt ttaattatct   2640
tattaatccg ctccaattat ttaattataa ttttctgaaa aaacgtatag caattgaccc   2700
aaaaaaaaaa cttttccgtt ctagtagttg tttgattgga attaaatatg tttaaaaatt   2760
atcaaaaaaa aataggatgt tggaattgat aagaagtaat aaaaaaacgc acagtagcaa   2820
tcttttacta ttttaaaaaa aaaaatagtt aaaaacaaaa actacatttc aacgaaattc   2880
aataaaataa tttaaataat catcttatta ttttttaaaa actagtttaa ttattttttg   2940
tatttttaca aatgaaaaaa ttatttaaat tgattgagtg actttctaag tgaaacacta   3000
ataactgagt gaattttgag ttataaaaaa attgagtgac tttctaagtg aacaactcaa   3060
aattgagtga ttttttaagt gaactattca aaattgaatt accatatgat atattaactc   3120
aaggtaaatt aggctatgga ctataataga aaaaaaccca aaaaggataa taattaatct   3180
aaaagaattc atatatatat aaaactattt tgtttaatga taaatttttg acccattggg   3240
tctttaaaaa aaaaagagaa tactccatct tgttattttg taggtataaa aaaaaagtag   3300
ttctatcttt aataggttca tttctttagt ggaggaaaaa agtggattta ttcactaatc   3360
ttgttttgtg agaggcaaag ttgttacata tttggaattt gaactttgta atgattctat   3420
tcttgttcat tgtgaagttg tatatattcc tcactgttca cttttatctt attttattat   3480
ttatataatt ttaaaattag ctttttcagc aaaagatttt tgttcttgaa gattcgtttc   3540
agaaagagaa aaaaagaaga aaatggtcac attgtcgtcc ttgtgtaaca ttcagaggag   3600
tgaaccctaa acttgccgac ccacagagaa aaacaaccct agtttcc                  3647
```

<210> SEQ ID NO 19
<211> LENGTH: 2126
<212> TYPE: DNA
<213> ORGANISM: Solanum tuberosum

<400> SEQUENCE: 19

```
gaagggcata attgctactt ggacaacaca gtataattaa taggacaacg aaaacttcgt     60
ttcataaact cattctctag cttaagtata attaatatgc ccctaaacta tttgaaaagg    120
tctagatata ccctccgttt aaaagtttgg ctcactcatg ccctcgccgt tcaacttttt    180
gtctaaatat gcccttatgg gcattagttg gcctgctgga catatctagc tcattttcca    240
tttctttaaa tgccacatgg aattgtcatg tcattttgac tttaccacat gacatttata    300
tgaaaatgga aagggatcaa ttatgcccgt aaaaaattcg aacccataaa cacctaatcc    360
gacccataaa tcaacccccc ctccttttag ataaactacc cgacccattt tcaataattt    420
tgtttaaatt tttattttt tcggtaaatc caggaaatta gtaattgatt aataaaaaat    480
agaaaaaata tggggaaaaa aaattaacgc caaaaattca caaataaata ttgtaacctt    540
```

```
aaattcaaca atttttttat ttttttccgg taaatcccga aaatgagtaa ttgattaaaa    600

aaatatatga aaaatataaa attaacgcca aaaaatcaca aaaaaatcca tttttcatat    660

aaatgtcatg tggtaaagtc aaaatgacat ggcaattcca tgtgacattt aaagaaatga    720

aaaatgagtt ggatatgtcc agcagaccaa ctaactccca taagggcata tttagaccaa    780

aagttggacg acgaggacat gagtgagcca aactttaaac ggaggatata tcttagacct    840

tttcaaatag tttaggaaca taattgaccc tttacccatt gcacaaaata tcattcattt    900

tgaaagtaaa agcaaatcaa aatgacatgg aattggaata gcacttaaat gatactccct    960

cctatccatt ttagttgtca ctgtttacta aaaataactt gtcaaaaata ttgtcataga   1020

aaactatgaa tacatacaca ttatgttatg attgtttaga ttggcagatc agtcttgttt   1080

ttatatacat ttctttatgt tcaacttgag ctaaaggtat cagaaacgat atttttattt   1140

tttcaatgta ggagtaaata agagtttatt ttctttgtct catattaatc atttttattt   1200

ttacacgcat attaacaaat catacgaaga taattttact aattcacttc ttaaaaactt   1260

attgaaattt taaaaataaa tgtgaacact ttaatttttt ttttgcaagg gtaacaatat   1320

aagaaaattt taattaatgt tttcttgatt tagtaaaatg gacaactaat ataagacaat   1380

tatttttagt aaaatgatca actaatatga gacggagaaa gtaatatata aaatgtcatt   1440

cttattaata atttcttaag gaatgtgtaa aataaaaaca cgataactaa tctctcctct   1500

attgtggctt tctttgtgcc atactctact gtccaaaaaa tattactact catcaaaaga   1560

agaaagggct ttccttaaga atgacatctt atcaactaca aaactaacct aaagatgaaa   1620

aaactacaga cgttagtgga gaatgtttta acaccctaaa ttaaaggaga taaagataag   1680

tgaagtgctt tttgtgacaa acgaattgaa tggaatttta tgcctccctc ccaaatactc   1740

tttttagcta atgaaatctc tttaactagt aaggacaact attcaacacg agaaaaagca   1800

agaccaatag ttgttttttt ctactctact ttttatccgt gaaaagattg tgtaaatgtt   1860

agcaacttta ttatttttaa ggaacaaaaa agttggttcc ccacgttaca aaaagagttg   1920

gggcctcctc tacttatctc acaattcaaa tttattcttt ataatataat aatcaatccc   1980

ctcctattat atatatttat ttactcaaaa caaaagaata tacaccaaac ggattaccca   2040

ccccctcctc acttttgcct ttctcactct cactgagtga aaccgcaaac caaacagttg   2100

gtgggcatta gattaaggaa ggaaaa                                        2126
```

<210> SEQ ID NO 20
<211> LENGTH: 1913
<212> TYPE: DNA
<213> ORGANISM: Solanum tuberosum
<220> FEATURE:
<221> NAME/KEY: misc_feature
<222> LOCATION: (703)..(703)
<223> OTHER INFORMATION: n is a, c, g, or t
<220> FEATURE:
<221> NAME/KEY: misc_feature
<222> LOCATION: (1253)..(1253)
<223> OTHER INFORMATION: n is a, c, g, or t
<220> FEATURE:
<221> NAME/KEY: misc_feature
<222> LOCATION: (1279)..(1279)
<223> OTHER INFORMATION: n is a, c, g, or t
<220> FEATURE:
<221> NAME/KEY: misc_feature
<222> LOCATION: (1386)..(1387)
<223> OTHER INFORMATION: n is a, c, g, or t

<400> SEQUENCE: 20

```
gcgtcaaagt atgaagcaga caacacatga acacacaata atgatcgact cccacttaaa     60
```

```
aatattatta ttttttgtt aaaagggaac gaaagcatta tttttattcg ttcactattt    120
taaaattaat tcttatttgt acttatcact ttttaatata ttaaaagaac tttactttta    180
acatcaatta aaatgatatt atgataaaac attcctaatc aaatgttatt tcttaaatat    240
gtacaaagtt taaagtggat cagtaaaaat gttaatgaag gtagtaactt ttatttgttg    300
tttatttact ttgttgatgt gtttgtaatt tataatctta aagaataatt attagaataa    360
aatgaagaaa aaataattaa ttctatttta aattaacaaa taatttatag taattatttt    420
taaaaatgac gataaataat ttaaaacgga ggaagtatta actgtattaa taattaatat    480
taataccact aatgataatg aaagtgttag tatcctacat gaaaaggaca tgattgacta    540
ctttcgtata atttgacaat gaattgaatg gaatattatt tttttctaca tatttgtttt    600
tgttgttaat aatgtcttaa attattaaac agttatataa tgctgaaaag agaaaaacaa    660
aaagtattga attctcctct ttcttctctt ccacaaaaat tgnaaaaaaa aaaagcagct    720
cttttattaa tatatatatt ttttctttat ttcaagtata aagtttattt aatgaaaaaa    780
aatactttta aaatttatta ttttaaatat atcataatat ttatgttact attaaaatat    840
ttattatgaa aattaaatta atttcaaata cataaatgta tcattctttt caaatatctt    900
ttgactatgg aaagaaattg taaagtaaac gatgactttt ttattttttt ggtacttaat    960
tgatttttga ggaacaaaat aattgtccca aagtataaaa ataaaaaaag ttgggacctt   1020
ttctctagtc tccatatgaa aaagacaatt cagtactcag tagattcaaa atatccttta   1080
aaagctagag ctctttaata tacaataaga aacaaaataa tcacaagacg ataattattt   1140
caattttaaa tgtaaaattt taaaaaatat acaagttctt tttaaggttt cactcataga   1200
gctgtaaaca tatttttaag tccacataca acttctaact tctaaatatt cantttcaat   1260
ctaacttcaa acactacant ttttcaataa taatcaattt atgtccgacg cttattttgt   1320
tgataattag gatagaatat tactagtaga tagttgagtg ttatcacatt ttacgtgaat   1380
gtgaannaga gagtgagctg accttcttct atcctcttgt ttttttaagt agtattattt   1440
agttatcacg tagtttctta ccttccacgt atattgttac ctattgttgt atttatttat   1500
tatcttgcca ttttgttgtt tcttttcaaa taattttaca cgacgtgtga taagtgtttt   1560
ccttttgagt caatggcctt tcaaaaacaa tcgtttttac tttataatcg tgagattaca   1620
ttcaatgtgt tatcattaca ttggatatgt ttaacattac ataaggatga agaacgaatc   1680
aatctattca aatattaaat attcattaaa acaatacaat acgatataac catccaaacc   1740
aaacagagtg tcaatttttt ttaaaattat tttagtttct aatgtatata ttcaaaaatt   1800
tcatataaat acacatttat aatatatctg ttcgataaag acacgtgaac atttcttctt   1860
cttctccacc atttctgctc tgctcactct ttcccctcca ccattgaaga aac          1913
```

<210> SEQ ID NO 21
<211> LENGTH: 2225
<212> TYPE: DNA
<213> ORGANISM: Solanum tuberosum

<400> SEQUENCE: 21

```
ccgaacatct ttagggcatc tccaaccgaa tcctctattt tactcttcaa atatagagtt     60
ttctattttt ttcagacaac caactccaac tcaattctct attttactct ctaaaaatga    120
attttttttt ctctcctcga tattatatta ttatttctat tttattctta ttttcttatt    180
tcatgatata aatcctttat ttatttttt ccaaataatt actttatata atttttaatg    240
```

```
tgatatgaaa ttatatttta ttctaaaatt ttaaataaca taaattgcag gaaaatataa    300
tataatacat aaattagggg acaaattcaa ataaaagtga tatacaatta cataaatact    360
caatttttaa aattattacg ttgctcccat aaatgctcta ttaatgcatt acggagttca    420
aaatgaacat ttttgtcctt aattttttta tgtctagcta aaaattgttc aaaccgaaga    480
ttttcactag ctaaaaatta ttcaaatcgg ggattttcat ctaccatcat ttctatagtt    540
ggagttggag cctctacggc atcttgaatt ggtgcattga gatcacattc attctcaatt    600
ttcatgttgt gcagtataat acatgtagtc attatatcat gtagcaccac ttcttttctc    660
caaaaatgtg acggtcctgc aataattgca aaacgtgatt gcaaaaagtt cgaggacaag    720
gctctacttt gcaatcatcg gagtccaaga cgaaactaaa attttaacga aaaatttaga    780
aactattagt gatccaaatg ttcgtggtta cctgcaacga gaacaacaac gaatacttga    840
aaaaagaaat cgacaatcac aaccgcaatc acaaccataa tcgcaacaat tctcagaatc    900
atatcctaat tttttccgga atagtgctaa atttgaaaac gacctaccga atttctaaat    960
tattgttgtg atcaattaat tattatgtca tgtattgtat tttatcttgt atttaaatta   1020
ttatgttatg tattatattg tattgttatc ttgtatttaa attattatgt tatgtattat   1080
attgtattgt tatcttgtat ttaaattacc atatcatgta ttgtattttt aaattaattt   1140
tttttgcgta tcctttataa tgaaaattaa taataaaata attttattat tcacgaaaat   1200
tagaaaaaaa gttaaaatac tattaatttg aaattaaaat agtatatatt aaataatttt   1260
tttaaaaaat attatattac atttaaaaaa gaattatgaa tattagatat ttaattaatg   1320
gaattatatg taaaataata tgttaattag aaagtaatag aaataataat aaaataatga   1380
aaaagtagaa ataaagagcg tgaatagtag aatttggaga actattcaac tctcaaaatt   1440
tgaaaaatag agggtgattt ggaggtgggt tggagtgccc attctctatt ttactctcca   1500
aatatagaga atgaagagta aaatagaggt ggattggaga tgatcttagt gacatttttg   1560
attccgccaa tgctcagttg gcgtagtcgc tgtcaaactt gagaaaggat taccccttta   1620
ggcttgcaca gacagtgact tatgatgaaa tgaagccaga gaaggcactc tgttatcaca   1680
cttaaatgaa aatacatgtg tatggactag caataaaagg ggcactagta attttagtaa   1740
ttgaaaagca agtgtataga gagagataat gagagagaaa gagtaagtac actactactg   1800
ctactatccc atatagctgt aatgttgcag gtctgatttt tgcagttgca gacccccttc   1860
ttggcacaag ctcttttaac ttttatcttc tcaaataatt ctctctctct ctctctctct   1920
tttttctctt tttacattgt gaggaaagct gaacacccca ttgtatgtat tagtgtgagg   1980
cctatctgcc acaaggatgt gatggaacac tatgcttcct ctgctaaaac ccccacaacc   2040
ccaaaactct ttttcacttc acatttaatc acaattcctc agtgaaatta ttctgttgct   2100
ctctctaatt tcaatttcaa tgtcggtaag tccaagacct ggtttttcaa ttcaaaggag   2160
ctgagttagt gcaaacactt gaggttttga gttttgacag agacttgagt ctcagagaaa   2220
ctacc                                                                2225
```

```
<210> SEQ ID NO 22
<211> LENGTH: 2173
<212> TYPE: DNA
<213> ORGANISM: Solanum tuberosum

<400> SEQUENCE: 22

cctgggagaa aatgaaagca tgatctcttt cttgtaaatt gtttctacca tattttttttt     60
ggcacgataa ataaatttat ataaaattgt atgagtgaca ctagatgaca agtcacataa    120
```

```
catatatatt caaattgatt tgtattattt atagaacgaa agtctactgt ttaaccttat    180

ataagttaca atttagttat gtatataagt taaaattaaa ttaaaagaca tttcgaaata    240

atatgattat accatttcga aattaattag agagagaaat aagatctcgc aaaattaagt    300

gtcttcttga aattaagaac catttttagg agataattat gtatttttc atttttaatt    360

tgacacgtat gcatatccac tattttgttt tattccaaag tgacccctac ttcttttggt    420

aatttctttg agtattttaa actctagtcc ccctttctca agcaaaaagg ctcactcgcg    480

cacgcgcgaa gagacattgt gacgcgctgg atggaaaatc cagaagcgta actgtcaaaa    540

aatagaacaa ctttgggaaa cggggtgacg gccgctgcca ccactttttt catttccaaa    600

cactcattaa ctaacgtcgt ttcaccgccg tttactgctt aatgagtatg aattacactc    660

taatagtcta tttttactta tttttaatgt gtttatcaaa ttatattttt aaatataata    720

ctttaaaaat attatcatca ataataagag taaattaaaa aataaatgac aaattgtttc    780

ttaaattgtt aaattaaaca attaaaactg aatatttaca aaatacctct taacttgcta    840

aattaaacaa ttgaaactat atttatatta ataaattgaa ctgacaaaaa taaataaagg    900

aactatatat tttctcaatt atatcttttt actaaaatat tatttttcta atactagtta    960

aacttttaaa aaacatctaa taaagaaaaa gaatttgttc aattatactt tagaagcttt   1020

tattattatt attattatta gtagtagtag tagtagtaat aaattagatt aaattaaaga   1080

gagaagtatt caaaactccc aaaactattg tattagtttt atttcagaac tattgacaat   1140

cttaattttt tttttttaa tttgactagg tgaacttaaa tatacttcat tttttgcaaa   1200

acaagtgaag tacactctta aattttcatc aagtttagaa atgttttcaa caatttacta   1260

gactctttat taagaacttc atgttctttc aagagtttat gagcacttgc tatgtcatgt   1320

tacagatcaa gaatatctac agagtgtatc taaatttagt actagtaaag tagaaaatgt   1380

attacttatc tctcaaacaa taggtattca ttatactatt ttgagatgtc caacaatttt   1440

ttttcacttt atgaaatcaa tgaataattt aacacttagt tcctaattcc cagtaagcat   1500

taattatagt tatttactta ttatattttt caacacatta tattgaaaaa gtgatatagt   1560

aaatctatct ttttatttta ttatttctta aaatttgtac aaacttaata atagacaaat   1620

attgttgaat aggaataata atttacatta aatccaatat atttttcaat agttgtcact   1680

aaatgaaaat acttcatctg tttcaattta tgtgatagtt ttcatttttc aaaagtcaga   1740

caattatata tttataaatt aagtaaaaaa tattataagt cacactaatt aacaattcga   1800

aatattcggt acggaggaac taacacttat gtttttagac catattagtc ttttctctct   1860

atttattata taatattgag aggagagtgc aaccaccatg gcaactttct ctgtcttcat   1920

aaaacgcagc tgacattaaa aacacagaca cacacttcgc atttcatatc cctctcacta   1980

cacgccaaat gcctgctctt cctatttctc ttcttcttct ttttcttctt ctctctcatt   2040

cacataacac acattcttgt actaactctg catcataaac tctaccccac tttcttcttc   2100

ttctccggtc atattgctct gaaactccac ttattgctct ctcccggcat ttatttttag   2160

tttctcagaa ata                                                     2173
```

<210> SEQ ID NO 23
<211> LENGTH: 6639
<212> TYPE: DNA
<213> ORGANISM: Glycine max

<400> SEQUENCE: 23

-continued

```
cagttcgaat ccaggttgca tggagataca ggaagaaacg taaaaattgt gttgatacct     60
caaaattaga tcaatcattt aactcatagg ttgtataatc acctgaattg cttgtaatta    120
ccatgcacaa ttcctttaaa aattaaacaa caagcaaatg ttactgttgg agagcaattc    180
aaatttcaaa ataaatggaa cttgtgaaaa ttcaaggaga tatttttagg aatttgttat    240
gttaatttca aatctttaga attttatcta gatttaaata ttttattaat ttgtttaact    300
tattttaggg atttgtttcc ttttttaaaa gattagaata tgataatatt taaattttgt    360
attgttattt agctttatat atagagccaa gaaatacaaa ttttataatg tgttccatct    420
aagatttctt gaacgtgtga taattttgtt gtgtagaaaa ttttttccaa cggttaacat    480
tttattagta gtgctttgct tataatgcaa agagccttct cctttatttt atgtctacaa    540
taagtaatga atttataagg aatgaaaata actcttaact ctcaagagag gaaagaactt    600
tggtaaacaa gatttcatat gttacagcca gacttacaca gaatatttca tttcacacag    660
ctcagatgat ttttagagaa aatgtacccg atatatattc ttcttttaaa ggcagagttg    720
aaatctaaat tatatgagca aaatatacaa cctatacagt atagacagaa tcagaaataa    780
agttcatatt tcttagatta cggtatgaga gtcactgagt caataacttt ttactacgag    840
aataaagaaa tggaatgatt gaatgagcaa aatataccc  tgaattccat tttcctagaa    900
agagaaatag catgcgattg aataagagaa tggcaccatc aagattgtga atgagaaaga    960
agaaatggag gaaacttgtg aatggaaaga gagtgagaat gggagagagc atagtgttgg   1020
acaatgacat tgtgactgta aggaaattaa tgagtaacta gagaacggaa cggaactaac   1080
aagcttcttg ttgtgtttgt gatttaagtg tttgatggag ttttaaggat tcaatacaat   1140
gaaagctacg tgacagttaa atatatgata gattcatcct ttgagttcca agcagtatac   1200
gtgaacggaa tcaacgttga tctttaggaa gatcattctc tccgctcgga agatctttta   1260
tcgtttaatc gaatcatttt ttaaaatttt cagttttcat tatcatggta agtttattga   1320
tttttataa  taattttttt tgaagtcata taaaatataa tattttattg attagaaatg   1380
taaaataatt tacaataagg gaaaatattt attgaacatt tttataatat tagaaataga   1440
ttaaactaat acagtatttc ggtattgtat tgcatatatg tttatctata actattattt   1500
ttaaattatc ttttaatata tataacgatt ttttttttat aaactttcaa aatgtagatg   1560
ttactatttt ttcctaaaac aatattatca ctatttttc  atttttttc  ttttgaaaaa   1620
aaaagaaaat aaagataaat atatgaagtg tctttctttc aactggtctt atgtaagaac   1680
aaattacact ctatgctcag gacttattat acttatactt cctacgttaa aatgtatttt   1740
ttttatctct tctaaagtaa attatcatcg tttaactttt gagaaaaatg tcaaaaaaaa   1800
atccatacac ttaactctca caatctgatt cttctccatc tttattggcc tcttctttgt   1860
catccaccct cccggtcagc taattttttt gttataatat tattaatatg aaatattcat   1920
caactttatc gataaataat ttttattaaa atacttaatt aaatattttt atgatgatat   1980
ttttttcttt taattatatt tttatttttc ttcacaagat taaaatttaa tatctttctt   2040
aacgagatta aataaatatt tcatcaacat attttatttt tatatatata tattttttaa   2100
ctcatcatat cacttatcat atctatattt atttttatgt atcttaatac atcattttag   2160
atgggcaaat taaatatatt tatccaaaag taatgtcatg agaatgagaa gaaaagttac   2220
atcacgcctc cttctggcct tctcctaaat tatcgagatt aataccttgt gcctgtaaat   2280
ttggtaacca gaaaaaagaa aaatcatgtg aggtagagga ttttttcgaa tgtgtaaaaa   2340
tagatttctt gagtgcctaa ggtgtttgca ttcagcaatg gcacaacacg tgtcaagtcc   2400
```

```
caatcttaca agaaccttcc ttcctaccga aagtcccgtc acgacacgtg agcagtcaca   2460
tccgtcacgt gtcacctttt catcgaccat gggaagatct ttcggcaccg cactttctgg   2520
tatcttcacg cgcaatcccc atcccaccgt ccattctctc acacgctcga gccatcgtag   2580
ccgtcgcccc ctcacccgtc cccaactccg ccacgcatcc aaatgacacg tggcgctaaa   2640
gtaacggtca aatccacaat attacttatt gtaaccttat cctctcctca cccctcaccc   2700
ccccccttcc ccctataaat ccccctttcc ctccctccaa tttcaacctc actctgcatt   2760
cgctaaaccc aaaacactat tttattatct tcttcgtctg ttctttgcat tgaagaaaat   2820
ttctttgaat tgaagaaaac ttgaaatcga attgtgaaac agaaaataaa ccaaaggaaa   2880
tttttactga ttgaattgta gagattggaa aaatggcgtt gagtatgact caacagatcg   2940
ggaccctagc tggtgcgacg gtgccggatt cctcggccgg agaatcgacc gcggcggtga   3000
gtgctgccgc ggtgtggaag tcaccgacgg cgagtctgaa gtgcaaggta atgaggacgg   3060
atggctgcgc ggaggggctt tcgccgccgc tgagtccgtg caggtcgccg gtgctgcggg   3120
cggatctgtc ggcggcgtgt caggcattca cggcggaggt ggcggaggag gagtacgttg   3180
ccggagggaa ggaggagaag gggaagggga aggagggagt gccggtgttt gtgatgatgc   3240
ctttggacag cgtgacggcg gggaacgcgg tgaaccggaa aaaggcgatg aacgcggcga   3300
tggctgcgct gaagagcgcg ggggtggagg gggtgatgat ggacgtgtgg tggggtttgg   3360
tggagagaga gaagcctggg gagtataatt ggggagggta cgtggaactc atggaaatgg   3420
cgaagaagca tggcctcaag gtgcaggctg ttatgtcatt tcaccaatgt ggcggtaacg   3480
tcggagactc ttgcacgtga gtcttatgca atcccttctt cttccttctt tttttctttt   3540
tatttgtcat ttgtgatttt tatttttact ggcgaaatct tattagattc tagattaatt   3600
ggttttaaca attagaattg ttactagtat tttttttaa gtttaatttc tgcgaattgg   3660
ttttgaaatc tgaaaactaa ttgagtgaca ccatgaaaag attttacgtt tttgatacat   3720
tcttgttggt ttttttaac gttaagtttt tgcttttaat tcaatttacc atgaaattca   3780
catctttatc tttattggta aatatgtggt gttattatta tatggtgttt tcgttgatta   3840
tgattgaaaa tgagaggcgt gcccagcacg gtgcagctcg tttgtgaaaa ataaaataaa   3900
cgttttaaaa ggggttttgt gatgggaaat gaagccatgc catgtgatgt tggacttgta   3960
tcactttgat tcgaagtata gtatttttct tttctattga atattcaact acgaacctgg   4020
aataattgaa tcttgagaat tgtgtatatg atattgataa ttatttagcc atttctcttt   4080
aactgaaatt ttaatgtttc atttttatta gtacttgaag attctgaatt taattaaatt   4140
ttaatccttt ttttacagaa attaattttt aatctttgta ctatacagaa tgagttaaca   4200
ttcttttata attagggata atgacaattt taatttagta ttttaaacat gatgattata   4260
tttattttta tcataataac aacaattttc ctgaaaaaaa aataaaaata atttcataaa   4320
tctttatatt atgatttaaa gaggcgtaat gagcacggtg atgctagtct tattttcttt   4380
catttttttgt ggtccttatg taaaaagtaa atacaaaata catgagaaaa gagtgtgctt   4440
tcgtgatggg aagtgccaaa gtgggaccac gtgaggatgg acttctagtt ctactgattc   4500
acgtcggcat cgccacatac agtagactaa cttttaagga caccttaaat ttagtggacc   4560
cgatatctta atttattttt cggtccattt tttgaaaaag tattcctcaa attctctcca   4620
tttttcttaa aacatgttat tcgaaacaaa taatccaggc atagtttctg tttatatatt   4680
ttatgtaaat tatttttgac agttataaga ttatctaatg gtttcgaatt cgaatcatgg   4740
```

```
acatgtggta atgttgatac taaacagttg gaggagagtt tagcatccat aatgattcta   4800
ttcggtttcg agtagaatta tctcttatta gagatacatc tgatctacta aaaaatataa   4860
atagttagtg taattttaga tattactgcc attaattttg ctataagtta gcactgtgtt   4920
ggaataccag ttgtcttatt ggtgggctta tcagatagtt tgtcctgtgt tcagtattcc   4980
tttgcccaaa tgggttgtgg aggagattga taatgaccac gatcttgcat atactgatca   5040
atggggaaga agaaactatg aatatatatc acttggatgt gatactttgc cggtgctcaa   5100
gggacgatcc ccagttcaat gttatgctga tttcatgcgt gctttcagag acactttcaa   5160
gcacctcctt ggtgatacca ttgtggtaaa tatcattctc agtgcacttt tacatcatgc   5220
tgtgatttgt tgtgctattt aaatataact tctcatctga acttctttta ctggcaatat   5280
ttcaggaaat ccaagttggg atgggaccag caggtgagtt gcgttaccct tcgtacccag   5340
agcaaaatgg gacatggaaa ttcccaggaa ttggtgcttt ccaatgctat gacaaggtat   5400
atatatttat gttttttttt tccttctcct tgttgtagtc ctttatatat aattgtctta   5460
ggatttgttt ggataaataa atttcttcat gaacaaagag gagaaaacaa ggtaaaatgt   5520
gttctaaacc tctaatactt aattatgcta tggtgcagta tatgttgagt agcttaaaag   5580
ctgctgctga agctcacggt aagcctgaat ggggaagcac aggccctact gatgctggcc   5640
actataacaa ctggccagaa gacactcaat ttttccgcaa agaaggtggt ggatgggatg   5700
gtccatatgg tgagttttc ctcacttggt actctcagat gctgttggaa catggtgaca   5760
ggattctctc atcagccacg tcgatctttg acaacactgg agttaagatc tcagtgaagg   5820
ttgccggcat tcactggcac tatggtacaa ggtctcacgc cccagaactc actgcagggt   5880
attacaacac ccgattccgt gatggctacc tccccattgc tcaaatgctg gcgcgccacg   5940
gtgccatctt taacttcacc tgtatcgaga tgcgcgatca cgagcagcca caagaggccc   6000
tttgtgcacc tgagaagctg gtgaagcaag tggctctggc aacgcagaag gcacaggttc   6060
cacttgccgg cgaaaacgcg ctgccacggt acgacgagta tgcacatgag cagatcataa   6120
gggcatcaca attggatgtt gatggtgagt ctggtgatag agagatgtgt gccttcacat   6180
acctgaggat gaatccgcat ttgtttgaac caaataactg gaggaagttt gtggggtttg   6240
tgaagaagat gaaagaaggg aagagtgcac acaagtgttg ggaagaggtg gagagggaag   6300
ctgagcattt tgtgcatgtt acacagcctc ttgtgcaaga ggctgcagtg ctgatgcact   6360
gagaattgtt gaacatcctt gtggtaatag ggcttaggaa taagtcacaa ggaggctgtg   6420
tgaaagtttt agtgaaccaa cagcccaggt ttgtggcttt gaagatgtaa aattttgtat   6480
tatattgttt tgtattgtat gcacctaaaa cttctatttg tgaccctttt acattgtgta   6540
cgtaatcata gactttgggg tactgtttcc ttaaaagtta ctctactttg tacaagtagt   6600
tacttaatct ggtttaaaaa aatgtcatcc cttaatctg                          6639
```

<210> SEQ ID NO 24
<211> LENGTH: 1710
<212> TYPE: DNA
<213> ORGANISM: Glycine max
<220> FEATURE:
<221> NAME/KEY: CDS
<222> LOCATION: (1)..(1710)

<400> SEQUENCE: 24

```
atg gcg ttg agt atg act caa cag atc ggg acc cta gct ggt gcg acg      48
Met Ala Leu Ser Met Thr Gln Gln Ile Gly Thr Leu Ala Gly Ala Thr
1               5                   10                  15
```

-continued

```
gtg ccg gat tcc tcg gcc gga gaa tcg acc gcg gcg gtg agt gct gcc      96
Val Pro Asp Ser Ser Ala Gly Glu Ser Thr Ala Ala Val Ser Ala Ala
            20                  25                  30

gcg gtg tgg aag tca ccg acg gcg agt ctg aag tgc aag gta atg agg     144
Ala Val Trp Lys Ser Pro Thr Ala Ser Leu Lys Cys Lys Val Met Arg
        35                  40                  45

acg gat ggc tgc gcg gag ggg ctt tcg ccg ccg ctg agt ccg tgc agg     192
Thr Asp Gly Cys Ala Glu Gly Leu Ser Pro Pro Leu Ser Pro Cys Arg
    50                  55                  60

tcg ccg gtg ctg cgg gcg gat ctg tcg gcg gcg tgt cag gca ttc acg     240
Ser Pro Val Leu Arg Ala Asp Leu Ser Ala Ala Cys Gln Ala Phe Thr
65                  70                  75                  80

gcg gag gtg gcg gag gag gag tac gtt gcc gga ggg aag gag gag aag     288
Ala Glu Val Ala Glu Glu Glu Tyr Val Ala Gly Gly Lys Glu Glu Lys
                85                  90                  95

ggg aag ggg aag gag gga gtg ccg gtg ttt gtg atg atg cct ttg gac     336
Gly Lys Gly Lys Glu Gly Val Pro Val Phe Val Met Met Pro Leu Asp
            100                 105                 110

agc gtg acg gcg ggg aac gcg gtg aac cgg aaa aag gcg atg aac gcg     384
Ser Val Thr Ala Gly Asn Ala Val Asn Arg Lys Lys Ala Met Asn Ala
        115                 120                 125

gcg atg gct gcg ctg aag agc gcg ggg gtg gag ggg gtg atg atg gac     432
Ala Met Ala Ala Leu Lys Ser Ala Gly Val Glu Gly Val Met Met Asp
    130                 135                 140

gtg tgg tgg ggt ttg gtg gag aga gag aag cct ggg gag tat aat tgg     480
Val Trp Trp Gly Leu Val Glu Arg Glu Lys Pro Gly Glu Tyr Asn Trp
145                 150                 155                 160

gga ggg tac gtg gaa ctc atg gaa atg gcg aag aag cat ggc ctc aag     528
Gly Gly Tyr Val Glu Leu Met Glu Met Ala Lys Lys His Gly Leu Lys
                165                 170                 175

gtg cag gct gtt atg tca ttt cac caa tgt ggc ggt aac gtc gga gac     576
Val Gln Ala Val Met Ser Phe His Gln Cys Gly Gly Asn Val Gly Asp
            180                 185                 190

tct tgc act att cct ttg ccc aaa tgg gtt gtg gag gag att gat aat     624
Ser Cys Thr Ile Pro Leu Pro Lys Trp Val Val Glu Glu Ile Asp Asn
        195                 200                 205

gac cac gat ctt gca tat act gat caa tgg gga aga aga aac tat gaa     672
Asp His Asp Leu Ala Tyr Thr Asp Gln Trp Gly Arg Arg Asn Tyr Glu
    210                 215                 220

tat ata tca ctt gga tgt gat act ttg ccg gtg ctc aag gga cga tcc     720
Tyr Ile Ser Leu Gly Cys Asp Thr Leu Pro Val Leu Lys Gly Arg Ser
225                 230                 235                 240

cca gtt caa tgt tat gct gat ttc atg cgt gct ttc aga gac act ttc     768
Pro Val Gln Cys Tyr Ala Asp Phe Met Arg Ala Phe Arg Asp Thr Phe
                245                 250                 255

aag cac ctc ctt ggt gat acc att gtg gaa atc caa gtt ggg atg gga     816
Lys His Leu Leu Gly Asp Thr Ile Val Glu Ile Gln Val Gly Met Gly
            260                 265                 270

cca gca ggt gag ttg cgt tac cct tcg tac cca gag caa aat ggg aca     864
Pro Ala Gly Glu Leu Arg Tyr Pro Ser Tyr Pro Glu Gln Asn Gly Thr
        275                 280                 285

tgg aaa ttc cca gga att ggt gct ttc caa tgc tat gac aag tat atg     912
Trp Lys Phe Pro Gly Ile Gly Ala Phe Gln Cys Tyr Asp Lys Tyr Met
    290                 295                 300

ttg agt agc tta aaa gct gct gct gaa gct cac ggt aag cct gaa tgg     960
Leu Ser Ser Leu Lys Ala Ala Ala Glu Ala His Gly Lys Pro Glu Trp
305                 310                 315                 320

gga agc aca ggc cct act gat gct ggc cac tat aac aac tgg cca gaa    1008
Gly Ser Thr Gly Pro Thr Asp Ala Gly His Tyr Asn Asn Trp Pro Glu
                325                 330                 335
```

```
gac act caa ttt ttc cgc aaa gaa ggt ggt gga tgg gat ggt cca tat      1056
Asp Thr Gln Phe Phe Arg Lys Glu Gly Gly Gly Trp Asp Gly Pro Tyr
            340                 345                 350

ggt gag ttt ttc ctc act tgg tac tct cag atg ctg ttg gaa cat ggt      1104
Gly Glu Phe Phe Leu Thr Trp Tyr Ser Gln Met Leu Leu Glu His Gly
        355                 360                 365

gac agg att ctc tca tca gcc acg tcg atc ttt gac aac act gga gtt      1152
Asp Arg Ile Leu Ser Ser Ala Thr Ser Ile Phe Asp Asn Thr Gly Val
    370                 375                 380

aag atc tca gtg aag gtt gcc ggc att cac tgg cac tat ggt aca agg      1200
Lys Ile Ser Val Lys Val Ala Gly Ile His Trp His Tyr Gly Thr Arg
385                 390                 395                 400

tct cac gcc cca gaa ctc act gca ggg tat tac aac acc cga ttc cgt      1248
Ser His Ala Pro Glu Leu Thr Ala Gly Tyr Tyr Asn Thr Arg Phe Arg
                405                 410                 415

gat ggc tac ctc ccc att gct caa atg ctg gcg cgc cac ggt gcc atc      1296
Asp Gly Tyr Leu Pro Ile Ala Gln Met Leu Ala Arg His Gly Ala Ile
            420                 425                 430

ttt aac ttc acc tgt atc gag atg cgc gat cac gag cag cca caa gag      1344
Phe Asn Phe Thr Cys Ile Glu Met Arg Asp His Glu Gln Pro Gln Glu
        435                 440                 445

gcc ctt tgt gca cct gag aag ctg gtg aag caa gtg gct ctg gca acg      1392
Ala Leu Cys Ala Pro Glu Lys Leu Val Lys Gln Val Ala Leu Ala Thr
    450                 455                 460

cag aag gca cag gtt cca ctt gcc ggc gaa aac gcg ctg cca cgg tac      1440
Gln Lys Ala Gln Val Pro Leu Ala Gly Glu Asn Ala Leu Pro Arg Tyr
465                 470                 475                 480

gac gag tat gca cat gag cag atc ata agg gca tca caa ttg gat gtt      1488
Asp Glu Tyr Ala His Glu Gln Ile Ile Arg Ala Ser Gln Leu Asp Val
                485                 490                 495

gat ggt gag tct ggt gat aga gag atg tgt gcc ttc aca tac ctg agg      1536
Asp Gly Glu Ser Gly Asp Arg Glu Met Cys Ala Phe Thr Tyr Leu Arg
            500                 505                 510

atg aat ccg cat ttg ttt gaa cca aat aac tgg agg aag ttt gtg ggg      1584
Met Asn Pro His Leu Phe Glu Pro Asn Asn Trp Arg Lys Phe Val Gly
        515                 520                 525

ttt gtg aag aag atg aaa gaa ggg aag agt gca cac aag tgt tgg gaa      1632
Phe Val Lys Lys Met Lys Glu Gly Lys Ser Ala His Lys Cys Trp Glu
    530                 535                 540

gag gtg gag agg gaa gct gag cat ttt gtg cat gtt aca cag cct ctt      1680
Glu Val Glu Arg Glu Ala Glu His Phe Val His Val Thr Gln Pro Leu
545                 550                 555                 560

gtg caa gag gct gca gtg ctg atg cac tga                              1710
Val Gln Glu Ala Ala Val Leu Met His
                565


<210> SEQ ID NO 25
<211> LENGTH: 569
<212> TYPE: PRT
<213> ORGANISM: Glycine max

<400> SEQUENCE: 25

Met Ala Leu Ser Met Thr Gln Gln Ile Gly Thr Leu Ala Gly Ala Thr
1               5                   10                  15

Val Pro Asp Ser Ser Ala Gly Glu Ser Thr Ala Ala Val Ser Ala Ala
            20                  25                  30

Ala Val Trp Lys Ser Pro Thr Ala Ser Leu Lys Cys Lys Val Met Arg
        35                  40                  45

Thr Asp Gly Cys Ala Glu Gly Leu Ser Pro Pro Leu Ser Pro Cys Arg
```

-continued

```
    50                  55                  60

Ser Pro Val Leu Arg Ala Asp Leu Ser Ala Ala Cys Gln Ala Phe Thr
65                  70                  75                  80

Ala Glu Val Ala Glu Glu Glu Tyr Val Ala Gly Gly Lys Glu Glu Lys
                85                  90                  95

Gly Lys Gly Lys Glu Gly Val Pro Val Phe Val Met Met Pro Leu Asp
            100                 105                 110

Ser Val Thr Ala Gly Asn Ala Val Asn Arg Lys Lys Ala Met Asn Ala
        115                 120                 125

Ala Met Ala Ala Leu Lys Ser Ala Gly Val Glu Gly Val Met Met Asp
    130                 135                 140

Val Trp Trp Gly Leu Val Glu Arg Glu Lys Pro Gly Glu Tyr Asn Trp
145                 150                 155                 160

Gly Gly Tyr Val Glu Leu Met Glu Met Ala Lys Lys His Gly Leu Lys
                165                 170                 175

Val Gln Ala Val Met Ser Phe His Gln Cys Gly Gly Asn Val Gly Asp
            180                 185                 190

Ser Cys Thr Ile Pro Leu Pro Lys Trp Val Val Glu Glu Ile Asp Asn
        195                 200                 205

Asp His Asp Leu Ala Tyr Thr Asp Gln Trp Gly Arg Arg Asn Tyr Glu
    210                 215                 220

Tyr Ile Ser Leu Gly Cys Asp Thr Leu Pro Val Leu Lys Gly Arg Ser
225                 230                 235                 240

Pro Val Gln Cys Tyr Ala Asp Phe Met Arg Ala Phe Arg Asp Thr Phe
                245                 250                 255

Lys His Leu Leu Gly Asp Thr Ile Val Glu Ile Gln Val Gly Met Gly
            260                 265                 270

Pro Ala Gly Glu Leu Arg Tyr Pro Ser Tyr Pro Glu Gln Asn Gly Thr
        275                 280                 285

Trp Lys Phe Pro Gly Ile Gly Ala Phe Gln Cys Tyr Asp Lys Tyr Met
    290                 295                 300

Leu Ser Ser Leu Lys Ala Ala Ala Glu Ala His Gly Lys Pro Glu Trp
305                 310                 315                 320

Gly Ser Thr Gly Pro Thr Asp Ala Gly His Tyr Asn Asn Trp Pro Glu
                325                 330                 335

Asp Thr Gln Phe Phe Arg Lys Glu Gly Gly Gly Trp Asp Gly Pro Tyr
            340                 345                 350

Gly Glu Phe Phe Leu Thr Trp Tyr Ser Gln Met Leu Leu Glu His Gly
        355                 360                 365

Asp Arg Ile Leu Ser Ser Ala Thr Ser Ile Phe Asp Asn Thr Gly Val
    370                 375                 380

Lys Ile Ser Val Lys Val Ala Gly Ile His Trp His Tyr Gly Thr Arg
385                 390                 395                 400

Ser His Ala Pro Glu Leu Thr Ala Gly Tyr Tyr Asn Thr Arg Phe Arg
                405                 410                 415

Asp Gly Tyr Leu Pro Ile Ala Gln Met Leu Ala Arg His Gly Ala Ile
            420                 425                 430

Phe Asn Phe Thr Cys Ile Glu Met Arg Asp His Glu Gln Pro Gln Glu
        435                 440                 445

Ala Leu Cys Ala Pro Glu Lys Leu Val Lys Gln Val Ala Leu Ala Thr
    450                 455                 460

Gln Lys Ala Gln Val Pro Leu Ala Gly Glu Asn Ala Leu Pro Arg Tyr
465                 470                 475                 480
```

```
Asp Glu Tyr Ala His Glu Gln Ile Ile Arg Ala Ser Gln Leu Asp Val
                485                 490                 495

Asp Gly Glu Ser Gly Asp Arg Glu Met Cys Ala Phe Thr Tyr Leu Arg
            500                 505                 510

Met Asn Pro His Leu Phe Glu Pro Asn Asn Trp Arg Lys Phe Val Gly
        515                 520                 525

Phe Val Lys Lys Met Lys Glu Gly Lys Ser Ala His Lys Cys Trp Glu
    530                 535                 540

Glu Val Glu Arg Glu Ala Glu His Phe Val His Val Thr Gln Pro Leu
545                 550                 555                 560

Val Gln Glu Ala Ala Val Leu Met His
                565
```

<210> SEQ ID NO 26
<211> LENGTH: 6509
<212> TYPE: DNA
<213> ORGANISM: Glycine max

<400> SEQUENCE: 26

```
tattagctaa actttgtcat aggttgtacg attataaaat atctttgata gtttcactta     60

tttccatgta caaatgttcc ttctaaaagg catgtattaa gcgtcaagaa cttaattaaa    120

aaattgagaa ttggataact cgccagaagc agccatgaat tttaacatga atcagatgag    180

caagttccat ttcttacttc ccctacataa ttggtccaac aaaatacata agaacaataa    240

acatagaact attgttgagg aatcaggaag acaaacaatg accatctaat atccttttag    300

agtagtagtt gaagatgcca atggcagttg acaactagaa gaacatgttg aaaagcaaac    360

gaatagttct taattgagaa caagcatcaa agcaccctca catgattttt agagaaaatg    420

tacccgatat ttattcttct tttaaaggaa gggttaaaat ttaaattata tgagcaaaat    480

ataactgttg tttttttaat aagagtaggc agaaatatta aacaataaaa gggagcataa    540

agaaaaaaaa aattgagatt gcaaaggttt attttaaaag cagagaaaag atagtaactg    600

ctaacaaaaa gataacatca ctcactaaca aatcatgcct agagaatagg atcaaaactg    660

ttttatccta tcagtcaaat gacttttatt tttcctaaaa aaatagcata aaagtcttat    720

ctactgtagt ttcaacagtc aaatcttaac aataacctta aatttaaggt ggatgatgac    780

attcatcctt tgagctcgca gtataatata cctcaacaca agttattata gactcattct    840

atgccttcgg agttcgcact cctaataatt atacgctaac ggattcattt atccatcata    900

tttttaaatt tcaattttct aatgaaaaaa tactataact actcactttt tatttacact    960

gtgatttaat aataaattaa aaaaatattt tttagatcat catccaatta taattttta    1020

atgtataata aatttgttga ctttcatgat acttatttta aaaaaattat taatattgaa   1080

ttctgattag atgatattaa actcaaataa attatcattt atgtttaatt tattgatttt   1140

tataataatt atatttaaaa ttacataaaa tataaatttt tattgattaa aaagtgtaaa   1200

agctttttac agaaatggtg gatatctatt aaactctttt ataatagaat caaactaata   1260

ttttagtacg tgaattgaat agagtaaatg tttatcttat aaaactatcc tttataataa   1320

taataataag gcatgcccga tattattatt actattattg aaggaatata taagcatacg   1380

catttaaaaa aaataccaaa tatactagtt taatttgtaa tcacaatttt taatctctaa   1440

tcatcttcaa tctaggaata agtctctagc tatcatattt aaactgagtt taaaatattt   1500

cacatatttt gttaatgtca aatgacaatg tttatttgtt atgaagtaat caaaaccacg   1560
```

-continued

```
aaacaacaaa accaaatcta gctctatatt aatcacaaaa taagtattat attaaaaata   1620
tctcaaaata aatattatat taatttttca atgtaatatt aatttttcta tattaacatc   1680
tttgataagt atcactttaa atttcaatgt aatactaaaa gttagattta taaaattatt   1740
attctctttt atttgtttat taacttttgt aaataattta tgtcaacatt ttttaaacaa   1800
aaaagagtag ctattatatt atactatttt taaaacatct actttaaaaa agtatatcat   1860
ctatttatta ctggtttaat catgattgaa tcacaattga atcattaaaa tttaaataag   1920
tatcatcact ttttttgtcc tacctattat agtctgcaac tcatattaag ttgaatagct   1980
aattttggga tgtgaaaaaa tagatttcat gaccattggc cgatgacatg acacttgccg   2040
tgttcccaat ctcacaagat ccttctcctc ccatattttc tcttggctcc tacatcgaca   2100
cgtgaccaca catctctcac gtgtcacctt tccatggacc atcaccttca cgcgcaatcc   2160
ccatcccacc gtccattctc ccaaatgaca cgtggcgcaa aactaacggt catacccaaa   2220
atattaatat tacttattgt aaccttatcc tcaccacccc cttcccccta taaatatcct   2280
tccccctcac tgcattcgct aaacccaata aattgttatt ttctgttctt tgcatttgaa   2340
tcaaagcaaa ttttgattga ttgattagaa aatggcgttg aatatgactc accagatcgg   2400
gaccctggct gctgcgacgg tgccggtgcc gaattcgtct gccggagaat caaccgcggc   2460
gatgagtgcc gccactctgt ggaagccgcc ggcggtgagt ctgaagtgca aggtcacgag   2520
gacggagggc ggcgctgagg ggctgtcgcc gccgctgagc ccgtgcaggt cgccggtgct   2580
acgggcggat ctgtcggcag cgtgtcaggc gttcacggcg gaggtggcgg cggaggagta   2640
cattgccgga gggaaggaga aaggagaggg gaaggaggga gtgccgctgt ttgtgatgat   2700
gccgttggac agcgtaaaga cggaaaacgc ggtgaaccgg aagaaggcga tgaacgcggc   2760
gatggcggcg ctgaagagtg cgggggtgga gggggtaatg atggacgtgt ggtggggttt   2820
ggtggagaga gagaagcctg gggagtataa ttggggaggg tacgttgaac tcatggagat   2880
ggcgaagaag catggcctga aggtgcaggc cgttatgtca tttcaccaat gtggcggtaa   2940
cgtcggagac tcttgcacgt gagtattatt atgcaatctc tctcattctt ttttgtcatt   3000
gctgattgaa tgttattaga ttctggatca attggtttta acaattagaa ttgttactat   3060
tagattctgg agtactttaa aggtttcttt taggtttaat ttctgtgaat tcgtattgaa   3120
atctgaaaat caattgagtg acaccatgaa attttttttac gttttggaaa cattcttatt   3180
taaaaaaatt ttaacgtcgt gtttttgctt ttaattatat ttgtagtttt ttaaaataag   3240
caattatatt ttattagtat taaaattgct ggacacgtga aacaaaacgg ctggatacat   3300
tcttattaaa aaaatttaac gtcaagttta gatacctaaa tattgttata cgatatatat   3360
ctataatgtt tggataatga aattggtcgg acaagcaatt tggatgaaaa ttcatgcagt   3420
gtgaaaatgt taattttttg tgaaagtaat tcgtttaatt tatattttaa tttttatagt   3480
ttaaaattaa tatttttagt tcttataatt tacattttaa atattaacat atattttaat   3540
taatttcata tatttatctt tataggaaaa tatgtggtta ttaattatat ggagttttcg   3600
atgattatga ttgaaaatgg gaggcgtgcc cagcacgatg cagcctgttt gtgaaaaata   3660
aaataaacgg ataaaagggg ttttgtgatg ggaaatgaag ccaatactgc catgtgaatg   3720
atgtgatatt ggacttgtat cactttgctt ctaagtgtag tattagtttt ctctattgaa   3780
tgaactagga acctggaata attgaatctt gagaattgtg tatattcata attatttagc   3840
catttccctt ttactgaaat tttagtgttt cattttttatt actactattt tgatcgaaga   3900
ttatgaagtt aattaaattt taatccttgt gctattacga atgagctggc attctcttaa   3960
```

```
aattagggat aacaacaata ttaatttagt atttttaagc atgattatta tgcttattaa   4020
aaaaacataa ttattatatc tattttaaca taataacaat gattaaaaat aatttcataa   4080
atgtttatat tttgatatga tttaaagagg cgtaatgagc acggtgcaga gtcttatttt   4140
ctttcatctt tcgtggtcct tgtgtgtagt aaatacaaaa tacgtgagaa aagagtgtgc   4200
tttcgtgatg gaaagtgcca aagtgggacc acgtgaggta gcacttgtag ttctactgat   4260
tcacgtcggt atcgccacaa acagtagact aactttttaa ggatctacta cctttaatca   4320
agtggacccg agatcttaat ttgtttttca gtctattttt tgaaaatgta tttgtaaaat   4380
atttcattt gtttaaaatg ttatttgaaa caaataatcc agatatattt tctgtttata   4440
tatttcatgt aaattatttc aacggctatc aattatagta aactagtttt catttatcag   4500
tgatcgcata aatcaactat tgatttcgaa tttgagtctt ggacatgcgg tagttaaata   4560
gttggaggag ggtttaaaat tcacagtgat tctatctggt tccagtaaga gataatccag   4620
tagaattatc tcttacagga gatagctgtg gtttattaaa aaaaaaaaaa ctagttcata   4680
tttttatgat tttagatatt attgccatca gttttgctgt aagttagcat agtgttggaa   4740
taccagttgt cttattggtt ggcttatcag attgtttgtc ttgtgtgcag tattccttta   4800
cccaaatggg ttgtggagga gattgataat gaccccgatc ttgcatatac tgatcaatgg   4860
ggaagaagaa actatgaata tatatcactt ggatgtgata cttcgccagt gctcaagggc   4920
cgaaccccag ttcaatgtta tgctgatttc atgcgtgctt tcagagacac tttcaagcac   4980
ctccttggtg acaccattgt ggtaaatatc tttctcagtg cacttttaca tcatggtgtg   5040
atttttgttg ctatataact tctcatctaa actcctttta ctggcatatt tcaggaaatt   5100
caagttggga tgggaccggc aggtgagctg cgttaccctt cttacccaga gcaaaatggg   5160
acatggaatt tcccaggaat tggtggtttc caatgctatg acaaggtata tatatttacg   5220
ttttttttc cttctccttc ttgtactctt ttatatataa ttgttttagg atttgtttgg   5280
ataaatttct tgatgaacga agaggagaaa attaggtaaa atgtgttcta atacttaaat   5340
tatgctacgg tgcagtatat gttgagtagc ttaaaagctg ctgctgaagc tgagggtaag   5400
cctgaatggg gaagcacagg ccctactgat gctggacact ataacaactg gccagaagac   5460
actcaatttt tccgcaaaga aggtggaggc tgggatggtc catatggtga gtttttcctc   5520
acctggtact ctcagatgct gttggaccac ggtgacagga ttctctcatc agccacgtca   5580
atctttgaca acactggagt gaagatctca gtgaaggttg ctggcattca ctggcactat   5640
ggctcaaggt ctcacgcccc agaactcaca gcagggtatt acaacacccg gttccgtgat   5700
ggctacatcc ccattgctca aatgttggca cgccacggtg ccatcttcaa cttcacctgt   5760
attgagatgc gcgatcacga gcagccacaa gatgcccttt gtgcacccga gaagcttgtg   5820
aagcaagtgg ctctggcaac gcagaaggca caggttccac ttgctggtga aaatgcgctg   5880
ccacggtacg atgagtatgc tcatgagcag atcataaggg catcacagtt ggatgttgat   5940
ggtgactctg gtggaagaga gatgtgtgca ttcacttacc tgagaatgaa cccgcatttg   6000
tttgaaccaa ataactggag gaagtttgtg gggtttgtga agaaaatgaa agaagggaag   6060
agtgcacaca agtgttggga agaggtggag agggaagctg agcattttgt gcatgttaca   6120
cagcctcttg tgcaagaagc tgcagtgctg atgcactgag aattgttgaa caatcttgtg   6180
ctgatagatg gcttagaaaa ggtcacaagt aggctgtgtg aaagttttag tgaaccagca   6240
gcccaggttt gtggctttga agatgtaaaa ttttgtatta tattgttgtt ttatattcta   6300
```

```
tgcacctaaa acttctattt gttacccttt tatattgtgt acgtaatcat tgactttggg   6360

gtactatttt cttaaaagtt actctacttt gtacaagtag ttacttattt ctgcatcatg   6420

aaactgttac atggcgtaac agcaacaaga gatgctattt tcttctatag ggaaaaatga   6480

atttaaaatc aatgattttc gttgtgttt                                      6509


<210> SEQ ID NO 27
<211> LENGTH: 1389
<212> TYPE: DNA
<213> ORGANISM: Glycine max
<220> FEATURE:
<221> NAME/KEY: CDS
<222> LOCATION: (1)..(1389)

<400> SEQUENCE: 27

atg atg ccg ttg gac agc gta aag acg gga aac gcg gtg aac cgg aag       48
Met Met Pro Leu Asp Ser Val Lys Thr Gly Asn Ala Val Asn Arg Lys
1               5                   10                  15

aag gcg atg aac gcg gcg atg gcg gcg ctg aag agt gcg ggg gtg gag       96
Lys Ala Met Asn Ala Ala Met Ala Ala Leu Lys Ser Ala Gly Val Glu
            20                  25                  30

ggg gta atg atg gac gtg tgg tgg ggt ttg gtg gag aga gag aag cct      144
Gly Val Met Met Asp Val Trp Trp Gly Leu Val Glu Arg Glu Lys Pro
        35                  40                  45

ggg gag tat aat tgg gga ggg tac gtt gaa ctc atg gag atg gcg aag      192
Gly Glu Tyr Asn Trp Gly Gly Tyr Val Glu Leu Met Glu Met Ala Lys
    50                  55                  60

aag cat ggc ctg aag gtg cag gcc gtt atg tca ttt cac caa tgt ggc      240
Lys His Gly Leu Lys Val Gln Ala Val Met Ser Phe His Gln Cys Gly
65                  70                  75                  80

ggt aac gtc gga gac tct tgc act att cct tta ccc aaa tgg gtt gtg      288
Gly Asn Val Gly Asp Ser Cys Thr Ile Pro Leu Pro Lys Trp Val Val
                85                  90                  95

gag gag att gat aat gac ccc gat ctt gca tat act gat caa tgg gga      336
Glu Glu Ile Asp Asn Asp Pro Asp Leu Ala Tyr Thr Asp Gln Trp Gly
            100                 105                 110

aga aga aac tat gaa tat ata tca ctt gga tgt gat act tcg cca gtg      384
Arg Arg Asn Tyr Glu Tyr Ile Ser Leu Gly Cys Asp Thr Ser Pro Val
        115                 120                 125

ctc aag ggc cga acc cca gtt caa tgt tat gct gat ttc atg cgt gct      432
Leu Lys Gly Arg Thr Pro Val Gln Cys Tyr Ala Asp Phe Met Arg Ala
    130                 135                 140

ttc aga gac act ttc aag cac ctc ctt ggt gac acc att gtg gaa att      480
Phe Arg Asp Thr Phe Lys His Leu Leu Gly Asp Thr Ile Val Glu Ile
145                 150                 155                 160

caa gtt ggg atg gga ccg gca ggt gag ctg cgt tac cct tct tac cca      528
Gln Val Gly Met Gly Pro Ala Gly Glu Leu Arg Tyr Pro Ser Tyr Pro
                165                 170                 175

gag caa aat ggg aca tgg aat ttc cca gga att ggt ggt ttc caa tgc      576
Glu Gln Asn Gly Thr Trp Asn Phe Pro Gly Ile Gly Gly Phe Gln Cys
            180                 185                 190

tat gac aag tat atg ttg agt agc tta aaa gct gct gct gaa gct gag      624
Tyr Asp Lys Tyr Met Leu Ser Ser Leu Lys Ala Ala Ala Glu Ala Glu
        195                 200                 205

ggt aag cct gaa tgg gga agc aca ggc cct act gat gct gga cac tat      672
Gly Lys Pro Glu Trp Gly Ser Thr Gly Pro Thr Asp Ala Gly His Tyr
    210                 215                 220

aac aac tgg cca gaa gac act caa ttt ttc cgc aaa gaa ggt gga ggc      720
Asn Asn Trp Pro Glu Asp Thr Gln Phe Phe Arg Lys Glu Gly Gly Gly
225                 230                 235                 240
```

```
tgg gat ggt cca tat ggt gag ttt ttc ctc acc tgg tac tct cag atg      768
Trp Asp Gly Pro Tyr Gly Glu Phe Phe Leu Thr Trp Tyr Ser Gln Met
                245                 250                 255

ctg ttg gac cac ggt gac agg att ctc tca tca gcc acg tca atc ttt      816
Leu Leu Asp His Gly Asp Arg Ile Leu Ser Ser Ala Thr Ser Ile Phe
            260                 265                 270

gac aac act gga gtg aag atc tca gtg aag gtt gct ggc att cac tgg      864
Asp Asn Thr Gly Val Lys Ile Ser Val Lys Val Ala Gly Ile His Trp
        275                 280                 285

cac tat ggc tca agg tct cac gcc cca gaa ctc aca gca ggg tat tac      912
His Tyr Gly Ser Arg Ser His Ala Pro Glu Leu Thr Ala Gly Tyr Tyr
    290                 295                 300

aac acc cgg ttc cgt gat ggc tac atc ccc att gct caa atg ttg gca      960
Asn Thr Arg Phe Arg Asp Gly Tyr Ile Pro Ile Ala Gln Met Leu Ala
305                 310                 315                 320

cgc cac ggt gcc atc ttc aac ttc acc tgt att gag atg cgc gat cac     1008
Arg His Gly Ala Ile Phe Asn Phe Thr Cys Ile Glu Met Arg Asp His
                325                 330                 335

gag cag cca caa gat gcc ctt tgt gca ccc gag aag ctt gtg aag caa     1056
Glu Gln Pro Gln Asp Ala Leu Cys Ala Pro Glu Lys Leu Val Lys Gln
            340                 345                 350

gtg gct ctg gca acg cag aag gca cag gtt cca ctt gct ggt gaa aat     1104
Val Ala Leu Ala Thr Gln Lys Ala Gln Val Pro Leu Ala Gly Glu Asn
        355                 360                 365

gcg ctg cca cgg tac gat gag tat gct cat gag cag atc ata agg gca     1152
Ala Leu Pro Arg Tyr Asp Glu Tyr Ala His Glu Gln Ile Ile Arg Ala
    370                 375                 380

tca cag ttg gat gtt gat ggt gac tct ggt gga aga gag atg tgt gca     1200
Ser Gln Leu Asp Val Asp Gly Asp Ser Gly Gly Arg Glu Met Cys Ala
385                 390                 395                 400

ttc act tac ctg aga atg aac ccg cat ttg ttt gaa cca aat aac tgg     1248
Phe Thr Tyr Leu Arg Met Asn Pro His Leu Phe Glu Pro Asn Asn Trp
                405                 410                 415

agg aag ttt gtg ggg ttt gtg aag aaa atg aaa gaa ggg aag agt gca     1296
Arg Lys Phe Val Gly Phe Val Lys Lys Met Lys Glu Gly Lys Ser Ala
            420                 425                 430

cac aag tgt tgg gaa gag gtg gag agg gaa gct gag cat ttt gtg cat     1344
His Lys Cys Trp Glu Glu Val Glu Arg Glu Ala Glu His Phe Val His
        435                 440                 445

gtt aca cag cct ctt gtg caa gaa gct gca gtg ctg atg cac tga         1389
Val Thr Gln Pro Leu Val Gln Glu Ala Ala Val Leu Met His
    450                 455                 460


<210> SEQ ID NO 28
<211> LENGTH: 462
<212> TYPE: PRT
<213> ORGANISM: Glycine max

<400> SEQUENCE: 28

Met Met Pro Leu Asp Ser Val Lys Thr Gly Asn Ala Val Asn Arg Lys
1               5                   10                  15

Lys Ala Met Asn Ala Ala Met Ala Ala Leu Lys Ser Ala Gly Val Glu
            20                  25                  30

Gly Val Met Met Asp Val Trp Trp Gly Leu Val Glu Arg Glu Lys Pro
        35                  40                  45

Gly Glu Tyr Asn Trp Gly Gly Tyr Val Glu Leu Met Glu Met Ala Lys
    50                  55                  60

Lys His Gly Leu Lys Val Gln Ala Val Met Ser Phe His Gln Cys Gly
65                  70                  75                  80
```

-continued

```
Gly Asn Val Gly Asp Ser Cys Thr Ile Pro Leu Pro Lys Trp Val Val
                85                  90                  95

Glu Glu Ile Asp Asn Asp Pro Asp Leu Ala Tyr Thr Asp Gln Trp Gly
            100                 105                 110

Arg Arg Asn Tyr Glu Tyr Ile Ser Leu Gly Cys Asp Thr Ser Pro Val
        115                 120                 125

Leu Lys Gly Arg Thr Pro Val Gln Cys Tyr Ala Asp Phe Met Arg Ala
    130                 135                 140

Phe Arg Asp Thr Phe Lys His Leu Leu Gly Asp Thr Ile Val Glu Ile
145                 150                 155                 160

Gln Val Gly Met Gly Pro Ala Gly Glu Leu Arg Tyr Pro Ser Tyr Pro
                165                 170                 175

Glu Gln Asn Gly Thr Trp Asn Phe Pro Gly Ile Gly Gly Phe Gln Cys
            180                 185                 190

Tyr Asp Lys Tyr Met Leu Ser Ser Leu Lys Ala Ala Ala Glu Ala Glu
        195                 200                 205

Gly Lys Pro Glu Trp Gly Ser Thr Gly Pro Thr Asp Ala Gly His Tyr
    210                 215                 220

Asn Asn Trp Pro Glu Asp Thr Gln Phe Phe Arg Lys Glu Gly Gly Gly
225                 230                 235                 240

Trp Asp Gly Pro Tyr Gly Glu Phe Phe Leu Thr Trp Tyr Ser Gln Met
                245                 250                 255

Leu Leu Asp His Gly Asp Arg Ile Leu Ser Ser Ala Thr Ser Ile Phe
            260                 265                 270

Asp Asn Thr Gly Val Lys Ile Ser Val Lys Val Ala Gly Ile His Trp
        275                 280                 285

His Tyr Gly Ser Arg Ser His Ala Pro Glu Leu Thr Ala Gly Tyr Tyr
    290                 295                 300

Asn Thr Arg Phe Arg Asp Gly Tyr Ile Pro Ile Ala Gln Met Leu Ala
305                 310                 315                 320

Arg His Gly Ala Ile Phe Asn Phe Thr Cys Ile Glu Met Arg Asp His
                325                 330                 335

Glu Gln Pro Gln Asp Ala Leu Cys Ala Pro Glu Lys Leu Val Lys Gln
            340                 345                 350

Val Ala Leu Ala Thr Gln Lys Ala Gln Val Pro Leu Ala Gly Glu Asn
        355                 360                 365

Ala Leu Pro Arg Tyr Asp Glu Tyr Ala His Glu Gln Ile Ile Arg Ala
    370                 375                 380

Ser Gln Leu Asp Val Asp Gly Asp Ser Gly Gly Arg Glu Met Cys Ala
385                 390                 395                 400

Phe Thr Tyr Leu Arg Met Asn Pro His Leu Phe Glu Pro Asn Asn Trp
                405                 410                 415

Arg Lys Phe Val Gly Phe Val Lys Lys Met Lys Glu Gly Lys Ser Ala
            420                 425                 430

His Lys Cys Trp Glu Glu Val Glu Arg Glu Ala Glu His Phe Val His
        435                 440                 445

Val Thr Gln Pro Leu Val Gln Glu Ala Ala Val Leu Met His
    450                 455                 460
```

<210> SEQ ID NO 29
<211> LENGTH: 8834
<212> TYPE: DNA
<213> ORGANISM: Glycine max

<400> SEQUENCE: 29

```
ttgagaactt aacctactaa aattattctt tgatgtaatg ttaatgattt ttttatttat     60
aattattcta atttaaatat gcatctacta gtatattcta attttactcc ccaacataaa    120
aaagtctaat ttatctattt tctctctcaa atccctttac aaaactaaaa tagtaaattg    180
cattaaaaat atagatgtat aacatgctaa agaaaaatta atgtttcccc atgttacccc    240
taaaacttat catgcaaatg gatgatcaag tcataagaaa tgtaatattc ataaatagat    300
aagaagataa attacatcaa aagtagttga cggtcaaatt ttcaacaaaa aaggtttagc    360
ctcttattgt catggagatt ttataattgc aagagtaaaa tatttagtaa aggggagaaa    420
ataaaaaagg gaataaagga aatgaatgac tctcaatatt tatttctcct tcttctagtc    480
tttgccttct ataatgaagt gtattctctc ttaaaaattt tcctttgttt tttcttattc    540
tctccttttc ttttatagat gcatattagt gggcttcttg cattaagtct aagtctgtct    600
ttatttttct taattagtca tatttttctt aattagttcg ctttccttaa ttattcctct    660
cttcttgaat tatcctactt ttttttact cactaagcat aataaattca tcatttttaa     720
tatttgttgc acaaaaaata aaataatgtt aatttaacaa ttatttgctt aaaaaaaatt    780
agaagaaaaa aattacaaat tcttatatat tttaaccctc aaaatatact tataattagt    840
tgttattgat tttaaagtta acctattttt tcaagatatc catggtaggt attttcaaat    900
tacacacttc acatgtaaac tttgaggttg caagggtgaa aacaggtaaa aagaataaca    960
gctagcaaag acatttaaaa taattctagc aatataagtc caatctaaag cggatacgtc   1020
cagcaatatt catccctcac caactccaac ttcactctca ataaactgga aaattataac   1080
caaacatgct gaatcgtgaa ggcatcccta caattccttc ctagccaacc agcccaacaa   1140
ttttcttagc ttttagaaat attatcgtgt gcaatgtgat acactgcagt aagcatcaac   1200
aagaatagta acctgacctt tcatgccata tatgatcgaa gtggtcaaga atggcaagta   1260
gaagtgaggt tcatgctctt taatgattaa tctaatggga taaaaaggac aaagacaaac   1320
agaactctta atagaaaaga aaaaaactaa gtgggtcaac aatgcatatt ttggattcaa   1380
aaccaccact gtccaatcga caacattgtt ctacaaaacc ggaatgattg tgattcatcc   1440
ggagggtatt tgctcattca tgttccttat tgtcgatatg ggcatgccta actagctaag   1500
tacaatttcc ttaatttcta ttttggcact tacaatcgta attaaaactg aaatcaggtt   1560
tatatatata tatatatata tatatatata tatatatata tatatatata tatataaatt   1620
agcatgcatt atatatttaa ggggtacggg taacgtgtgt acaatatact ccttacaaaa   1680
ggtttatatc tctgctcggc ttcttatccc aaaattagca agcattaaat gaagggtaac   1740
gtgtgttttg ttcttattaa aaaaaaaaca tagtacaatt ttttaagtgg aaacatggaa   1800
atatttttca ctctttttaa tgattttttt ataacataaa attaaaatat taattctaaa   1860
gtagccaata attataaatt tttcactaac tatgtattgt aatgaaaaaa aatattttta   1920
tattttactt ttggaaaatt ttaaatttat ttgttagcaa atgatctgtt catgatatat   1980
ttttattaat tttaaatatt ataatttaaa acatatatat ttaaatttaa ttttctgata   2040
caacattgga ggattatata tataactgct cagatagacc cctccaatag tccaattgta   2100
ataagagttt gagaacataa gaaaaaaaat cttgtaatta ctaatctata ttgtggcttt   2160
cctcatacaa ttgatccatg gagagaagga gtaattcaca ataataatag taattattag   2220
tattataata aatgttaatg ttggtgactg cttggtcatt ttctcttcca gaaaaacaga   2280
taagctgtga cctgttagta aggccatggt gggagggacc actgcatggc atctttctca   2340
```

-continued

```
gtgctactag tgcttcactt attacatgat tttgaagttg tcagtgagcg ggtagaagat   2400
ggaggccatg gtccacactt tgttgccgca ttgcaagaaa atggtaaaaa tgatattgaa   2460
tctgcaaccc cccaatgtaa gggcctcttg taataatgga agcagcacag gggcgaagtc   2520
acacattgat aatagggttt atcgaaaaca ccacatcaca ccataccact tcacttacca   2580
cgccccctct cttttcgtgt caacaatctt tgaccacctt tatccaacct aacaaaatca   2640
ttactgttta ttaattttat actcttgttt tactagtaat tttctatatt gatttcgttc   2700
atttgttatg caggtgtgaa aatgaacacg atcaataaaa gaaaggaaga aaaatctagc   2760
ctttagtgat gatatcggac ttcttttttg tttttcaaa aggagggctt gcaattcgac   2820
aataactaag caaaattaac aaaaattaaa gaaacaataa tccattttct gtcataattt   2880
cgtgctttga taaatttaat actgcaatat tattgtagaa cccgtgatta tgaagtataa   2940
gaacataaac ttcatgtgat aaattttcac tgcaaataga atgtctatat gtttttcatt   3000
taagacacac tattacaaaa aacaatcttt gaacgacgat tcattgacac atttaataat   3060
tgtttttaac cgttattgaa gtgaatgtaa tgagaaatat tatatttttt acgataattt   3120
cttaatcatc ttagaagatc tcatctttta agataacttt tatgttaaaa ccgttgtaga   3180
agacccacca tcctaaaaga acactaacta gaaaaagaat ggtggagagg gtgaaatagc   3240
tacgggttcc ttggcttagt gtacagtttg gcgggacctt actccttggg aaggctagac   3300
agtagaagga tactccgaga tcacttcaaa gagaatacga cacccatgat tatcaaaagg   3360
ttagacaagt tgatgcgcaa tttccttgtt ttcagtcata attttggact aattaaactc   3420
cacacagaac gacaagcatg cttattttct aggcttttgc tttgctgaat actagaagat   3480
aaatctcata gctttagccc attgccaaac gctggatttt actctcttcc tcacaagatg   3540
gtaacaagtt agataatcta agatttgtga ccttattcgt cttatgtttg ggttaatatt   3600
catgttgtac cgagtatcat gtgctctaaa acatgcagtt ttggcttggc aatgaattag   3660
aagtattcca tcaaagtaat tcataccata ccccattttt aaagctcaaa atgagcaaga   3720
taaaaacttt aaacgtatct tagggcattc attattatca aaagccttta tattcattag   3780
aactctttgc atgtatagac cattttctct tttttaaata aaaaacatat taacatatgt   3840
atctcaggga atttattaaa caattaaaaa tgaaaatatt tatataaaaa tattatcgac   3900
ataatattat tattattatt attattatta ttattattat tattatatat cgtgagtttt   3960
aattaaaaaa aattcattga tactctttaa agtagaaacg cttgttagta aaaatgatat   4020
ttttgaattt aaaaggttat acatttttat attattgtta aaatttaaaa cttaataatg   4080
aaaattaaaa atatttattt ttatcctcaa atgactagac actacaacaa aataaataat   4140
aaataagaca aggaaaacta acaaaagaac taaccgttgt ccttgacctt ccttggaaaa   4200
taaggcaata gcataggacc tacttcaaaa aagacattcg actacaaaaa catgcaaaat   4260
ggacaaagat gaacagaaaa actaagaaga cgttgcattt attttttcaa tttcacgtat   4320
tttcattgaa aattatattt taacattatt catttatttg ttaacaggcc tattttaaaa   4380
ttcgaaacct cggtatttta ttaaactcat taaaatatct acaccatttt ttattaaaaa   4440
tataataata ataattttaa tatagtttct taataataaa atctctaata actgcgaaaa   4500
aagtattttt ctaaaaatac cataattaaa tacgtacaac aacgaagtat taaacatata   4560
aaactaaaga accacgacac atttatgtct ttcctatcac aatcataagt aatgcttgat   4620
ttgtgagcac actctccata accaacaaca cacacataac attcttttat taaaatcatt   4680
ttaaattatg tcacataata actactgtaa caacacacat tagcatgaaa ctggtattag   4740
```

-continued

```
tagcacatac aataaataaa tattgattat tatctgatgt aattatgtaa gtattatgag   4800
tggttgatta aaaaaacaaa atagagttgg taagggggtg gatccacatc caccgcttct   4860
gcaccaaact cagcatagca gtgggtcaat gattgattgg taattgtaat tctattcaaa   4920
aagtgaaaag agttgaatga gaattcgtat attcagaaaa tccccccctcc tttaagataa   4980
gagaataggc ctcactcttt ctttctcttc cattcccaaa atgcgtgtcc tctttctttt   5040
tctgtttttc cagtttctcc attttcattt ccccaaaacc ctttcagccc caatctcaga   5100
gtaccgtgcc cttctctctc tccgttcagc cattaccgac gccaccccac ctcttctcac   5160
ttcgtggaac tcctccaccc cttactgttc ctggctcggc gtcacctgcg acaaccgccg   5220
ccacgtcacc tccctagacc tcaccggcct cgacctctcc ggccccctct ccgccgacgt   5280
cgcccacctc ccattcctct ccaacctctc cctcgcctcg aataagttct ccggccccat   5340
tcctccctca ctctccgctc tctccggcct ccgcttcctc aacctctcca acaatgtctt   5400
caacgaaacc ttcccctcgg agctctcgcg cctccagaac ctcgaggtcc tcgacctcta   5460
caacaacaac atgaccggcg tgcttcccct cgccgtcgcg cagatgcaga atcttcgtca   5520
tttgcatctc ggcggcaact tcttctccgg ccagatcccg ccggagtatg gacgctggca   5580
gcgcctccag tacctcgccg tctccggcaa cgagctcgag gggactatcc ctccggagat   5640
cggaaacttg tccagcctcc gggagctcta catcggctac tacaacacct acaccggggg   5700
cattccgccg gagatcggaa atttgtcgga gctggtgagg ctcgacgccg cctactgtgg   5760
gttgtccggc gagattccgg cggcgctggg aaagcttcag aagctggaca cgctgttcct   5820
tcaggtgaat gcattgtcag ggtctttgac tcccgagctg ggaacctga agagcctgaa   5880
atccatggat ttgtctaaca acatgctctc cggtgagatt ccggcgagat tcggcgagct   5940
gaagaatatt actcttctga atctgttcag gaacaagctt cacggagcta taccagagtt   6000
tataggggag cttccagcgt tggaagttgt gcaactgtgg gagaataact tcacaggtag   6060
cattccagag ggtttgggca aaaacgggag actcaacctt gttgatcttt cttctaacaa   6120
gttaactggg actttgccta cttatctctg ttctgggaat actcttcaga ctctgataac   6180
tcttgggaat ttctttttg gtccaattcc tgagtcgctt ggtagttgtg aatcccttac   6240
acggattaga atgggagaga actttttgaa tggttccatt ccgagagggc tttttggact   6300
tcccaaacta acacaggttg agcttcagga taattatctc tctggagagt ttcctgaggt   6360
gggttctgtt gctgttaatc ttggtcagat tactctctct aacaaccagc tttctggggt   6420
tctacctccc tccattggta acttctccag cgtgcagaag ctccttcttg atggcaacat   6480
gttcacgggt cggatacctc cccagattgg gaggttgcaa cagctttcta agattgattt   6540
tagtggcaac aagttctcgg gtcctattgt gcctgagatc agtcagtgta agctgttaac   6600
tttccttgac cttagccgca atgagctatc tggagacatc ccaaatgaga taactggcat   6660
gaggatattg aattacttga atctttctag gaatcattta gtgggtggca ttccctcttc   6720
gatatcatct atgcaaagct tgacttctgt tgatttttca tacaacaacc tgtctggttt   6780
ggtgcctggt accggtcaat tcagctactt caattacacg tctttcttgg gaaaccctga   6840
cctctgtggc ccctatttgg gtgcttgcaa ggatggggtt gccaatggcg cacaccaacc   6900
tcatgttaaa ggtctctcct cttcttttaa gctgctactt gttgttgggt tgctactatg   6960
ttccattgct tttgctgtgg ctgcaatatt caaggcccgg tcactgaaga aggccagtgg   7020
ggctcgtgca tggaagttga ctgcgttcca acgtttggac ttcactgtcg atgatgtttt   7080
```

```
gcattgcttg aaggaggata atattatagg gaaaggaggt gctggcattg tctacaaagg   7140

ggctatgcct aatggggatc atgttgctgt gaaaaggctt ccggctatga gtagaggctc   7200

ttcacatgat catggcttca atgctgagat tcaaacattg ggcgaatcc gacacaggca   7260

cattgttagg ttgttgggct tctgttcaaa tcatgagaca aacctttgg tctatgagta   7320

catgcccaat ggaagtttag gcgaggttct tcatggaaag aaagggggtc atttgcattg   7380

ggatacaagg tataaaattg cggtggaggc tgccaagggg ctttgctatc tgcaccatga   7440

ttgttcgcca ctcattgtcc atcgtgatgt gaagtcaaac aacatccttc ttgattctaa   7500

tcatgaagcc catgttgctg attttgggct tgctaagttc ctgcaagatt ctgggacatc   7560

tgaatgcatg tctgctattg ctggttcata tggatacata gctccaggta ccgtccaatt   7620

tcgacataat taatgcatta tttacatggt tgtggaaaat ttcttttac ccgcctgttc   7680

ataattgtac gtttaatcat tgttcagaat ttgactcttt gacttatcat catgttttag   7740

gtgtagactg ttgatattga ggtgatgtcc ctaaattaat taacattgct atgtggtttt   7800

tcttgacttt ggtttctat catacccaaa tgatctcttg atttcgaccc cttatttagt   7860

ctatttcaag ccaagtactg aaagtaaatg gtagatagct ctgcaacgtt agagtcattc   7920

acgaccggaa actgatgatt atgggcaaaa tatcggataa aaagacctat tatgttactt   7980

tacacttatt gcctttgttt aacttatagt ttcaaattca agtgtcttgc tttattttag   8040

tttatgatac atgttcgatg tttgattgca gagtatgcct acacattgaa agttgatgag   8100

aaaagcgatg tgtacagttt tggtgtggtt ctcttagaac ttataacagg caggaaacca   8160

gttggagaat ttggtgatgg cgtggacata gtgcaatggg tgaggaaaat gacggattct   8220

aacaaggaag gagttcttaa agttcttgat cctagacttc cctcagttcc ccttcacgaa   8280

gtgatgcatg ttttctatgt agccatgctg tgcgttgaag aacaggctgt agagagacca   8340

actatgcgtg aagttgttca aatactgaca gagcttccaa agccacctga ctctaaagag   8400

gggaacttaa caataacgga atcatctttg tcatcatcaa acgctttaga atctccatcc   8460

tcagcctcta aggaagatca aaatcctcct caatccccac cacccgatct tcttagcatt   8520

taaagtgctc tgttgggtgt ttcatcttag ttcccttggg ttgtgatcgc ttatccattt   8580

actttctttt tctgtctctc ttctgggatt ggtttttttt tttttcccta actgaaggtg   8640

ttaatgtttg gatttttttaa tggttttgta cagtaggatt gatgggggta ttttcttata   8700

aagtcactgt cttcatcatg tagtactgct ttttaatttt tatttgcgac cgttgttggg   8760

gaggattcaa gggatacaat taaattactc gtttgtttcc tgaaatttca ttattcatac   8820

tttttagtt tatg                                                      8834
```

<210> SEQ ID NO 30
<211> LENGTH: 3039
<212> TYPE: DNA
<213> ORGANISM: Glycine max
<220> FEATURE:
<221> NAME/KEY: CDS
<222> LOCATION: (1)..(3039)

<400> SEQUENCE: 30

```
atg cgt gtc ctc ttt ctt ttt ctg ttt ttc cag ttt ctc cat ttt cat       48
Met Arg Val Leu Phe Leu Phe Leu Phe Phe Gln Phe Leu His Phe His
1               5                   10                  15

ttc ccc aaa acc ctt tca gcc cca atc tca gag tac cgt gcc ctt ctc       96
Phe Pro Lys Thr Leu Ser Ala Pro Ile Ser Glu Tyr Arg Ala Leu Leu
            20                  25                  30
```

-continued

```
tct ctc cgt tca gcc att acc gac gcc acc cca cct ctt ctc act tcg      144
Ser Leu Arg Ser Ala Ile Thr Asp Ala Thr Pro Pro Leu Leu Thr Ser
        35                  40                  45

tgg aac tcc tcc acc cct tac tgt tcc tgg ctc ggc gtc acc tgc gac      192
Trp Asn Ser Ser Thr Pro Tyr Cys Ser Trp Leu Gly Val Thr Cys Asp
    50                  55                  60

aac cgc cgc cac gtc acc tcc cta gac ctc acc ggc ctc gac ctc tcc      240
Asn Arg Arg His Val Thr Ser Leu Asp Leu Thr Gly Leu Asp Leu Ser
65                  70                  75                  80

ggc ccc ctc tcc gcc gac gtc gcc cac ctc cca ttc ctc tcc aac ctc      288
Gly Pro Leu Ser Ala Asp Val Ala His Leu Pro Phe Leu Ser Asn Leu
                85                  90                  95

tcc ctc gcc tcg aat aag ttc tcc ggc ccc att cct ccc tca ctc tcc      336
Ser Leu Ala Ser Asn Lys Phe Ser Gly Pro Ile Pro Pro Ser Leu Ser
            100                 105                 110

gct ctc tcc ggc ctc cgc ttc ctc aac ctc tcc aac aat gtc ttc aac      384
Ala Leu Ser Gly Leu Arg Phe Leu Asn Leu Ser Asn Asn Val Phe Asn
        115                 120                 125

gaa acc ttc ccc tcg gag ctc tcg cgc ctc cag aac ctc gag gtc ctc      432
Glu Thr Phe Pro Ser Glu Leu Ser Arg Leu Gln Asn Leu Glu Val Leu
    130                 135                 140

gac ctc tac aac aac aac atg acc ggc gtg ctt ccc ctc gcc gtc gcg      480
Asp Leu Tyr Asn Asn Asn Met Thr Gly Val Leu Pro Leu Ala Val Ala
145                 150                 155                 160

cag atg cag aat ctt cgt cat ttg cat ctc ggc ggc aac ttc ttc tcc      528
Gln Met Gln Asn Leu Arg His Leu His Leu Gly Gly Asn Phe Phe Ser
                165                 170                 175

ggc cag atc ccg ccg gag tat gga cgc tgg cag cgc ctc cag tac ctc      576
Gly Gln Ile Pro Pro Glu Tyr Gly Arg Trp Gln Arg Leu Gln Tyr Leu
            180                 185                 190

gcc gtc tcc ggc aac gag ctc gag ggg act atc cct ccg gag atc gga      624
Ala Val Ser Gly Asn Glu Leu Glu Gly Thr Ile Pro Pro Glu Ile Gly
        195                 200                 205

aac ttg tcc agc ctc cgg gag ctc tac atc ggc tac tac aac acc tac      672
Asn Leu Ser Ser Leu Arg Glu Leu Tyr Ile Gly Tyr Tyr Asn Thr Tyr
    210                 215                 220

acc ggg ggc att ccg ccg gag atc gga aat ttg tcg gag ctg gtg agg      720
Thr Gly Gly Ile Pro Pro Glu Ile Gly Asn Leu Ser Glu Leu Val Arg
225                 230                 235                 240

ctc gac gcc gcc tac tgt ggg ttg tcc ggc gag att ccg gcg gcg ctg      768
Leu Asp Ala Ala Tyr Cys Gly Leu Ser Gly Glu Ile Pro Ala Ala Leu
                245                 250                 255

gga aag ctt cag aag ctg gac acg ctg ttc ctt cag gtg aat gca ttg      816
Gly Lys Leu Gln Lys Leu Asp Thr Leu Phe Leu Gln Val Asn Ala Leu
            260                 265                 270

tca ggg tct ttg act ccc gag ctg ggg aac ctg aag agc ctg aaa tcc      864
Ser Gly Ser Leu Thr Pro Glu Leu Gly Asn Leu Lys Ser Leu Lys Ser
        275                 280                 285

atg gat ttg tct aac aac atg ctc tcc ggt gag att ccg gcg aga ttc      912
Met Asp Leu Ser Asn Asn Met Leu Ser Gly Glu Ile Pro Ala Arg Phe
    290                 295                 300

ggc gag ctg aag aat att act ctt ctg aat ctg ttc agg aac aag ctt      960
Gly Glu Leu Lys Asn Ile Thr Leu Leu Asn Leu Phe Arg Asn Lys Leu
305                 310                 315                 320

cac gga gct ata cca gag ttt ata ggg gag ctt cca gcg ttg gaa gtt     1008
His Gly Ala Ile Pro Glu Phe Ile Gly Glu Leu Pro Ala Leu Glu Val
                325                 330                 335

gtg caa ctg tgg gag aat aac ttc aca ggt agc att cca gag ggt ttg     1056
Val Gln Leu Trp Glu Asn Asn Phe Thr Gly Ser Ile Pro Glu Gly Leu
            340                 345                 350
```

-continued

```
ggc aaa aac ggg aga ctc aac ctt gtt gat ctt tct tct aac aag tta      1104
Gly Lys Asn Gly Arg Leu Asn Leu Val Asp Leu Ser Ser Asn Lys Leu
        355                 360                 365

act ggg act ttg cct act tat ctc tgt tct ggg aat act ctt cag act      1152
Thr Gly Thr Leu Pro Thr Tyr Leu Cys Ser Gly Asn Thr Leu Gln Thr
    370                 375                 380

ctg ata act ctt ggg aat ttt ctt ttt ggt cca att cct gag tcg ctt      1200
Leu Ile Thr Leu Gly Asn Phe Leu Phe Gly Pro Ile Pro Glu Ser Leu
385                 390                 395                 400

ggt agt tgt gaa tcc ctt aca cgg att aga atg gga gag aac ttt ttg      1248
Gly Ser Cys Glu Ser Leu Thr Arg Ile Arg Met Gly Glu Asn Phe Leu
                405                 410                 415

aat ggt tcc att ccg aga ggg ctt ttt gga ctt ccc aaa cta aca cag      1296
Asn Gly Ser Ile Pro Arg Gly Leu Phe Gly Leu Pro Lys Leu Thr Gln
            420                 425                 430

gtt gag ctt cag gat aat tat ctc tct gga gag ttt cct gag gtg ggt      1344
Val Glu Leu Gln Asp Asn Tyr Leu Ser Gly Glu Phe Pro Glu Val Gly
        435                 440                 445

tct gtt gct gtt aat ctt ggt cag att act ctc tct aac aac cag ctt      1392
Ser Val Ala Val Asn Leu Gly Gln Ile Thr Leu Ser Asn Asn Gln Leu
    450                 455                 460

tct ggg gtt cta cct ccc tcc att ggt aac ttc tcc agc gtg cag aag      1440
Ser Gly Val Leu Pro Pro Ser Ile Gly Asn Phe Ser Ser Val Gln Lys
465                 470                 475                 480

ctc ctt ctt gat ggc aac atg ttc acg ggt cgg ata cct ccc cag att      1488
Leu Leu Leu Asp Gly Asn Met Phe Thr Gly Arg Ile Pro Pro Gln Ile
                485                 490                 495

ggg agg ttg caa cag ctt tct aag att gat ttt agt ggc aac aag ttc      1536
Gly Arg Leu Gln Gln Leu Ser Lys Ile Asp Phe Ser Gly Asn Lys Phe
            500                 505                 510

tcg ggt cct att gtg cct gag atc agt cag tgt aag ctg tta act ttc      1584
Ser Gly Pro Ile Val Pro Glu Ile Ser Gln Cys Lys Leu Leu Thr Phe
        515                 520                 525

ctt gac ctt agc cgc aat gag cta tct gga gac atc cca aat gag ata      1632
Leu Asp Leu Ser Arg Asn Glu Leu Ser Gly Asp Ile Pro Asn Glu Ile
    530                 535                 540

act ggc atg agg ata ttg aat tac ttg aat ctt tct agg aat cat tta      1680
Thr Gly Met Arg Ile Leu Asn Tyr Leu Asn Leu Ser Arg Asn His Leu
545                 550                 555                 560

gtg ggt ggc att ccc tct tcg ata tca tct atg caa agc ttg act tct      1728
Val Gly Gly Ile Pro Ser Ser Ile Ser Ser Met Gln Ser Leu Thr Ser
                565                 570                 575

gtt gat ttt tca tac aac aac ctg tct ggt ttg gtg cct ggt acc ggt      1776
Val Asp Phe Ser Tyr Asn Asn Leu Ser Gly Leu Val Pro Gly Thr Gly
            580                 585                 590

caa ttc agc tac ttc aat tac acg tct ttc ttg gga aac cct gac ctc      1824
Gln Phe Ser Tyr Phe Asn Tyr Thr Ser Phe Leu Gly Asn Pro Asp Leu
        595                 600                 605

tgt ggc ccc tat ttg ggt gct tgc aag gat ggg gtt gcc aat ggc gca      1872
Cys Gly Pro Tyr Leu Gly Ala Cys Lys Asp Gly Val Ala Asn Gly Ala
    610                 615                 620

cac caa cct cat gtt aaa ggt ctc tcc tct tct ttt aag ctg cta ctt      1920
His Gln Pro His Val Lys Gly Leu Ser Ser Ser Phe Lys Leu Leu Leu
625                 630                 635                 640

gtt gtt ggg ttg cta cta tgt tcc att gct ttt gct gtg gct gca ata      1968
Val Val Gly Leu Leu Leu Cys Ser Ile Ala Phe Ala Val Ala Ala Ile
                645                 650                 655

ttc aag gcc cgg tca ctg aag aag gcc agt ggg gct cgt gca tgg aag      2016
Phe Lys Ala Arg Ser Leu Lys Lys Ala Ser Gly Ala Arg Ala Trp Lys
```

```
            660                 665                 670

ttg act gcg ttc caa cgt ttg gac ttc act gtc gat gat gtt ttg cat      2064
Leu Thr Ala Phe Gln Arg Leu Asp Phe Thr Val Asp Asp Val Leu His
        675                 680                 685

tgc ttg aag gag gat aat att ata ggg aaa gga ggt gct ggc att gtc      2112
Cys Leu Lys Glu Asp Asn Ile Ile Gly Lys Gly Gly Ala Gly Ile Val
    690                 695                 700

tac aaa ggg gct atg cct aat ggg gat cat gtt gct gtg aaa agg ctt      2160
Tyr Lys Gly Ala Met Pro Asn Gly Asp His Val Ala Val Lys Arg Leu
705                 710                 715                 720

ccg gct atg agt aga ggc tct tca cat gat cat ggc ttc aat gct gag      2208
Pro Ala Met Ser Arg Gly Ser Ser His Asp His Gly Phe Asn Ala Glu
                725                 730                 735

att caa aca ttg ggg cga atc cga cac agg cac att gtt agg ttg ttg      2256
Ile Gln Thr Leu Gly Arg Ile Arg His Arg His Ile Val Arg Leu Leu
            740                 745                 750

ggc ttc tgt tca aat cat gag aca aac ctt ttg gtc tat gag tac atg      2304
Gly Phe Cys Ser Asn His Glu Thr Asn Leu Leu Val Tyr Glu Tyr Met
        755                 760                 765

ccc aat gga agt tta ggc gag gtt ctt cat gga aag aaa ggg ggt cat      2352
Pro Asn Gly Ser Leu Gly Glu Val Leu His Gly Lys Lys Gly Gly His
    770                 775                 780

ttg cat tgg gat aca agg tat aaa att gcg gtg gag gct gcc aag ggg      2400
Leu His Trp Asp Thr Arg Tyr Lys Ile Ala Val Glu Ala Ala Lys Gly
785                 790                 795                 800

ctt tgc tat ctg cac cat gat tgt tcg cca ctc att gtc cat cgt gat      2448
Leu Cys Tyr Leu His His Asp Cys Ser Pro Leu Ile Val His Arg Asp
                805                 810                 815

gtg aag tca aac aac atc ctt ctt gat tct aat cat gaa gcc cat gtt      2496
Val Lys Ser Asn Asn Ile Leu Leu Asp Ser Asn His Glu Ala His Val
            820                 825                 830

gct gat ttt ggg ctt gct aag ttc ctg caa gat tct ggg aca tct gaa      2544
Ala Asp Phe Gly Leu Ala Lys Phe Leu Gln Asp Ser Gly Thr Ser Glu
        835                 840                 845

tgc atg tct gct att gct ggt tca tat gga tac ata gct cca gag tat      2592
Cys Met Ser Ala Ile Ala Gly Ser Tyr Gly Tyr Ile Ala Pro Glu Tyr
    850                 855                 860

gcc tac aca ttg aaa gtt gat gag aaa agc gat gtg tac agt ttt ggt      2640
Ala Tyr Thr Leu Lys Val Asp Glu Lys Ser Asp Val Tyr Ser Phe Gly
865                 870                 875                 880

gtg gtt ctc tta gaa ctt ata aca ggc agg aaa cca gtt gga gaa ttt      2688
Val Val Leu Leu Glu Leu Ile Thr Gly Arg Lys Pro Val Gly Glu Phe
                885                 890                 895

ggt gat ggc gtg gac ata gtg caa tgg gtg agg aaa atg acg gat tct      2736
Gly Asp Gly Val Asp Ile Val Gln Trp Val Arg Lys Met Thr Asp Ser
            900                 905                 910

aac aag gaa gga gtt ctt aaa gtt ctt gat cct aga ctt ccc tca gtt      2784
Asn Lys Glu Gly Val Leu Lys Val Leu Asp Pro Arg Leu Pro Ser Val
        915                 920                 925

ccc ctt cac gaa gtg atg cat gtt ttc tat gta gcc atg ctg tgc gtt      2832
Pro Leu His Glu Val Met His Val Phe Tyr Val Ala Met Leu Cys Val
    930                 935                 940

gaa gaa cag gct gta gag aga cca act atg cgt gaa gtt gtt caa ata      2880
Glu Glu Gln Ala Val Glu Arg Pro Thr Met Arg Glu Val Val Gln Ile
945                 950                 955                 960

ctg aca gag ctt cca aag cca cct gac tct aaa gag ggg aac tta aca      2928
Leu Thr Glu Leu Pro Lys Pro Pro Asp Ser Lys Glu Gly Asn Leu Thr
                965                 970                 975

ata acg gaa tca tct ttg tca tca tca aac gct tta gaa tct cca tcc      2976
```

```
Ile Thr Glu Ser Ser Leu Ser Ser Ser Asn Ala Leu Glu Ser Pro Ser
            980                 985                 990

tca gcc tct aag gaa gat caa aat  cct cct caa tcc cca  cca ccc gat   3024
Ser Ala Ser Lys Glu Asp Gln Asn  Pro Pro Gln Ser Pro  Pro Pro Asp
        995                 1000                 1005

ctt ctt  agc att taa                                                3039
Leu Leu  Ser Ile
    1010


<210> SEQ ID NO 31
<211> LENGTH: 1012
<212> TYPE: PRT
<213> ORGANISM: Glycine max

<400> SEQUENCE: 31

Met Arg Val Leu Phe Leu Phe Leu Phe Phe Gln Phe Leu His Phe His
1               5                   10                  15

Phe Pro Lys Thr Leu Ser Ala Pro Ile Ser Glu Tyr Arg Ala Leu Leu
            20                  25                  30

Ser Leu Arg Ser Ala Ile Thr Asp Ala Thr Pro Pro Leu Leu Thr Ser
        35                  40                  45

Trp Asn Ser Ser Thr Pro Tyr Cys Ser Trp Leu Gly Val Thr Cys Asp
    50                  55                  60

Asn Arg Arg His Val Thr Ser Leu Asp Leu Thr Gly Leu Asp Leu Ser
65                  70                  75                  80

Gly Pro Leu Ser Ala Asp Val Ala His Leu Pro Phe Leu Ser Asn Leu
                85                  90                  95

Ser Leu Ala Ser Asn Lys Phe Ser Gly Pro Ile Pro Pro Ser Leu Ser
            100                 105                 110

Ala Leu Ser Gly Leu Arg Phe Leu Asn Leu Ser Asn Asn Val Phe Asn
        115                 120                 125

Glu Thr Phe Pro Ser Glu Leu Ser Arg Leu Gln Asn Leu Glu Val Leu
    130                 135                 140

Asp Leu Tyr Asn Asn Asn Met Thr Gly Val Leu Pro Leu Ala Val Ala
145                 150                 155                 160

Gln Met Gln Asn Leu Arg His Leu His Leu Gly Gly Asn Phe Phe Ser
                165                 170                 175

Gly Gln Ile Pro Pro Glu Tyr Gly Arg Trp Gln Arg Leu Gln Tyr Leu
            180                 185                 190

Ala Val Ser Gly Asn Glu Leu Glu Gly Thr Ile Pro Pro Glu Ile Gly
        195                 200                 205

Asn Leu Ser Ser Leu Arg Glu Leu Tyr Ile Gly Tyr Tyr Asn Thr Tyr
    210                 215                 220

Thr Gly Gly Ile Pro Pro Glu Ile Gly Asn Leu Ser Glu Leu Val Arg
225                 230                 235                 240

Leu Asp Ala Ala Tyr Cys Gly Leu Ser Gly Glu Ile Pro Ala Ala Leu
                245                 250                 255

Gly Lys Leu Gln Lys Leu Asp Thr Leu Phe Leu Gln Val Asn Ala Leu
            260                 265                 270

Ser Gly Ser Leu Thr Pro Glu Leu Gly Asn Leu Lys Ser Leu Lys Ser
        275                 280                 285

Met Asp Leu Ser Asn Asn Met Leu Ser Gly Glu Ile Pro Ala Arg Phe
    290                 295                 300

Gly Glu Leu Lys Asn Ile Thr Leu Leu Asn Leu Phe Arg Asn Lys Leu
305                 310                 315                 320
```

-continued

```
His Gly Ala Ile Pro Glu Phe Ile Gly Glu Leu Pro Ala Leu Glu Val
                325                 330                 335

Val Gln Leu Trp Glu Asn Asn Phe Thr Gly Ser Ile Pro Glu Gly Leu
            340                 345                 350

Gly Lys Asn Gly Arg Leu Asn Leu Val Asp Leu Ser Ser Asn Lys Leu
        355                 360                 365

Thr Gly Thr Leu Pro Thr Tyr Leu Cys Ser Gly Asn Thr Leu Gln Thr
    370                 375                 380

Leu Ile Thr Leu Gly Asn Phe Leu Phe Gly Pro Ile Pro Glu Ser Leu
385                 390                 395                 400

Gly Ser Cys Glu Ser Leu Thr Arg Ile Arg Met Gly Glu Asn Phe Leu
                405                 410                 415

Asn Gly Ser Ile Pro Arg Gly Leu Phe Gly Leu Pro Lys Leu Thr Gln
            420                 425                 430

Val Glu Leu Gln Asp Asn Tyr Leu Ser Gly Glu Phe Pro Glu Val Gly
        435                 440                 445

Ser Val Ala Val Asn Leu Gly Gln Ile Thr Leu Ser Asn Asn Gln Leu
    450                 455                 460

Ser Gly Val Leu Pro Pro Ser Ile Gly Asn Phe Ser Ser Val Gln Lys
465                 470                 475                 480

Leu Leu Leu Asp Gly Asn Met Phe Thr Gly Arg Ile Pro Pro Gln Ile
                485                 490                 495

Gly Arg Leu Gln Gln Leu Ser Lys Ile Asp Phe Ser Gly Asn Lys Phe
            500                 505                 510

Ser Gly Pro Ile Val Pro Glu Ile Ser Gln Cys Lys Leu Leu Thr Phe
        515                 520                 525

Leu Asp Leu Ser Arg Asn Glu Leu Ser Gly Asp Ile Pro Asn Glu Ile
    530                 535                 540

Thr Gly Met Arg Ile Leu Asn Tyr Leu Asn Leu Ser Arg Asn His Leu
545                 550                 555                 560

Val Gly Gly Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
        595                 600                 605

Cys Gly Pro Tyr Leu Gly Ala Cys Lys Asp Gly Val Ala Asn Gly Ala
    610                 615                 620

His Gln Pro His Val Lys Gly Leu Ser Ser Ser Phe Lys Leu Leu Leu
625                 630                 635                 640

Val Val Gly Leu Leu Leu Cys Ser Ile Ala Phe Ala Val Ala Ala Ile
                645                 650                 655

Phe Lys Ala Arg Ser Leu Lys Lys Ala Ser Gly Ala Arg Ala Trp Lys
            660                 665                 670

Leu Thr Ala Phe Gln Arg Leu Asp Phe Thr Val Asp Asp Val Leu His
        675                 680                 685

Cys Leu Lys Glu Asp Asn Ile Ile Gly Lys Gly Gly Ala Gly Ile Val
    690                 695                 700

Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
```

```
            740                 745                 750

Gly Phe Cys Ser Asn His Glu Thr Asn Leu Leu Val Tyr Glu Tyr Met
        755                 760                 765

Pro Asn Gly Ser Leu Gly Glu Val Leu His Gly Lys Lys Gly Gly His
    770                 775                 780

Leu His Trp Asp Thr Arg Tyr Lys Ile Ala Val Glu Ala Ala Lys Gly
785                 790                 795                 800

Leu Cys Tyr Leu His His Asp Cys Ser Pro Leu Ile Val His Arg Asp
                805                 810                 815

Val Lys Ser Asn Asn Ile Leu Leu Asp Ser Asn His Glu Ala His Val
            820                 825                 830

Ala Asp Phe Gly Leu Ala Lys Phe Leu Gln Asp Ser Gly Thr Ser Glu
        835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Ile Thr Gly Arg Lys Pro Val Gly Glu Phe
                885                 890                 895

Gly Asp Gly Val Asp Ile Val Gln Trp Val Arg Lys Met Thr Asp Ser
            900                 905                 910

Asn Lys Glu Gly Val Leu Lys Val Leu Asp Pro Arg Leu Pro Ser Val
        915                 920                 925

Pro Leu His Glu Val Met His Val Phe Tyr Val Ala Met Leu Cys Val
    930                 935                 940

Glu Glu Gln Ala Val Glu Arg Pro Thr Met Arg Glu Val Val Gln Ile
945                 950                 955                 960

Leu Thr Glu Leu Pro Lys Pro Pro Asp Ser Lys Glu Gly Asn Leu Thr
                965                 970                 975

Ile Thr Glu Ser Ser Leu Ser Ser Ser Asn Ala Leu Glu Ser Pro Ser
            980                 985                 990

Ser Ala Ser Lys Glu Asp Gln Asn  Pro Pro Gln Ser Pro  Pro Pro Asp
        995                 1000                 1005

Leu Leu  Ser Ile
    1010


<210> SEQ ID NO 32
<211> LENGTH: 9088
<212> TYPE: DNA
<213> ORGANISM: Glycine max

<400> SEQUENCE: 32

gttggagtaa atccaataac atcaaatcct taatatatat ttattaaatt ttattgataa      60

aactgactta ctagtacata ttttagtttg taataatatc atttgtttgg atccaatata     120

taagccaatt ttttttatgg acaaaatata tggagccaaa gccgcagctc aaaaacctat     180

gtaacaagag acactgaaga gtgaagaatc agcaacatga tcaaagccta aaattggggc     240

aaaaattcaa acacttggct ataaatacac cagatagtcc atacttagcc gctattatgt     300

caaaatataa tagtattaat attacatggc aaagtatagg ctatataatt taatgtaatt     360

tattaaattt tacaaggtac tgattcaact ttaaacatgt atgctaattg gagtttaaaa     420

tttgtgaaca aaaagcaagt gcattttgtt gcgtgatcaa aattgctcaa ccttatcatg     480

taggaaaacg gataaccaga atttgtgtgg tcccaaacga caacaagacg catttataag     540
```

-continued

```
cttgactagt tctcttcgtc gtcaactgac attctcattt ctcaatgata gttgctactt    600
gataatattt tattcgaata atctgtcgtt aacctaccta taatatatag ctggtgctat    660
taatcgaatg tttaatctca ttttaagatt tacagtgtgt ggattgatgg tgaagatcca    720
aaaatcatag tatctgatta tgatttagtt tccaccgcat cagagagtat agctagctag    780
ttttaaagtt agcatgattt tttcaagata acccaccgta gattttttca acataatata    840
atataatttt cacttgtaaa ctttgaggtt gcaaggaaga aaagcaggta aaaagaataa    900
caggtagcaa agacatttaa aaattaaaat agttctaaca atataagtcc aatctaaagg    960
ggatacgtcc agcaatactc atccctcacc aactccaact tcactctcaa taaactggaa   1020
tcgtgaaagc atcattacaa ttatctccta gctaaccaaa cccaacattt tttttagctt   1080
ttagaaatat tatcgcgtgc aatgtgatgc actgctgcag ttagcatcaa caagaatagt   1140
aacctgaccc ttcatgccat tatgatcgag gtggtaaaaa atggcaagta gaagtgaggt   1200
tcatgctctt taatgattaa tctaatggga taacaagaac cagaacaaac agaactcttg   1260
gtagaaaaga aaaaaaaaag tgggtcaata atgcatattt tggattcaaa accaccactg   1320
tccaattgac atcattgttc tacaaaaccg gaatgattgt gattcatccg gagggtattt   1380
gctcattcat gttccttatt atcgatatgg gcatacctga ctagccaagt acaatttcct   1440
taatttcaat tttggcactt acaatcgtga ttaaaactga gatcaggttt atatatatgc   1500
ttgtcttttt atccaaaaat tagcatgcat tctatattta tggggtacgg gtcacgtgtg   1560
tacaatatac tccttacaaa aggtttatat atctgcttgg cttttaatcc caaaattagc   1620
atgcattaaa tgaagggtaa cgtgtgtttt attcttattt aaataaataa catatagtac   1680
aatttttaag tagccaataa ttttaaaatt ttcactaact ctgtatctgt attgtaatga   1740
aaatattttt atattttact tttggatcaa tttaaattta tttgtaaaca aatggtttta   1800
cattttatta atttctttta ttaaatctgt ccataatatc tttttttttt ataagtttta   1860
aattttataa ttttaattta aatttctaat acaacgtaag aggattaata tacttagcta   1920
gttaaagatt ataataatta ttttcaactg cgttggagtt agctgggatg accacggatc   1980
ttcccccccca taaattacca caaagcaccc catttgttac acagaaaggg actcttgcaa   2040
caagagaata agggacatta agtaatttgc ctattaataa tgttataagc taatataaaa   2100
ttagtttggc ggttaaaatg aaaatttaaa gattgaaggg agaaagaaga agaaaagaga   2160
gttttaaatt caaatcttcc actgatcttg gttgataaaa aaatgaaacc gcacacaaaa   2220
acgctctcca tcaatgcaat tgtactagta atacttaact tgtgtcttat atacagcgtg   2280
gaaatataaa ataaataaca taattatcat tttttgataa tattatatat atatatatat   2340
atatatataa ctatttttta tatacgtttg agtacataag gaaacaatct tgctattacc   2400
aatctatatt agttgtggct ttcctcatag aattgatcca tgaaacgaag gagtaacact   2460
gaataataat agtgctaatg aaaaacccat tataatagta attactaata ttattatgaa   2520
atatgaaatg ttaatattcg gtgactgctt ggtcattttc tcttccagaa aaacagagct   2580
gtgacctgtt agtaaggcca tggtgggagg gaccactgca tggcatcttt ctcagtgctt   2640
cccttattac atgattttga tggcttcagt tgtcagagac cgggtgggtg ggtagaagat   2700
ggagtattgt ataggaagaa aatggtaaaa tcatattgaa tcttctgcaa tccccaatgt   2760
actctagtta gtaactgtaa tgtaagggcc tattgtaata attgaagcag cacaggggcg   2820
aagtctcaca ttcataatag ggtttatcga aaacaccaca ccataccact tgccacgccc   2880
cctctctttt cgtgacggtc aacattcttt gaccaccttt atccaaccta actaaatcat   2940
```

```
tactactgtt tattaattta tactcttgtt ttaattttct atattgaatt tcattcattt   3000
gtaatattaa tataggtgtg aaaatgacca tgatcaataa aaagaaagga agagcaatat   3060
ctagctttta gtgataacat tggacttctt ttttgtttta acaaaaatta aagaaacaac   3120
agtcattttt ctgtcataac ttgatgcctt gacaaattaa tttaatactg taagattatt   3180
gtagaacccg tgattatgca gtagaagaac ataaatttgt atgtttctca tctaagaaag   3240
gaaaagtagc tagaaaaaga atggtagaga gggtgaaata gcgaaatgca tgctatggcc   3300
aacgggttcc ttattccttg cggaggctat acagtagaat ggttgtccta gatcacttca   3360
aatagaatac gacacccatg attgtcaaaa ggctaaacaa gttgatgcgc gcaatttcct   3420
tgttttcagt cataattttg gactaaactc cacacagaac gacatgttct tttctaggct   3480
tttgctttgt tgaatactag cgttggattt tactctcttc ctcacaagat ggtaacaagt   3540
tagataatct atataagatt tctgacctta ttcgtcttaa tataataaac atgttatagc   3600
gagtatatat catgtgctcc aatacatgca gttttggcaa tggattagaa gtgttaacgt   3660
tccagcagag taattcatac catcccccat ttttaatgct caaaatgagc aagatgaaaa   3720
ttttttaaac gtatcttaat tcttagggca ttcattatta tcaaaaagcc tttatattca   3780
ttagaactct ttgcatgtat agatcatttt ctcttttttt ttattaaaaa aattaacata   3840
tatatatata tatatatata tatatatata tatatatata tatatatata tatatatata   3900
tatatatatc aggccattca ttaagcaatt aaacatgaaa atattttata caaaatatta   3960
ttatatctat tgtaagtttt aattaaaaaa ttcattgata ttcttaaaac gtttgttagt   4020
aaaaaatata ttttaaattt aaaaggttat atatagttat acattattat attattctta   4080
aaatttaaaa cttaataata ataaaataaa aaatagtatt cttaataact agacacgaca   4140
acaaaataaa taaataatta agacaaggaa aactaacaga agaattagcc gttttcctcg   4200
accttccttg gaaaataagg caatagcata ggacctactt aaaaaaagtt aaaacattcg   4260
actacaaaaa catacaaaat ggacaaagat aaacacgtaa gaaaaactaa gaaaaacgtt   4320
acattttttt cttttcaatt tcacgtattg ttattgaaaa ttttatttca aacattgttc   4380
atttatttgt ttttttaaga gagttcattc atttgttatt aatttaacaa attatttgtt   4440
aacgatctat tttaaaattc aaaacctatt tttattaaac tcattaaatt atgtgcacca   4500
ttttttttat tataaatata ataataactg ttatataaat ttgatgaatg acatgataaa   4560
agaccgtatt atttgcataa ttaaagaagc acgccatatt tatgtctttc ctatcacaat   4620
cataagtaaa acttgagttt accaccatcc tccgctcaat aacccagcaa cacacataac   4680
attcttttat taatgtcatt tttaagtggc ataataacta tataacaaca cacatgagtg   4740
ccgcatcata aattacacat acgataaata aatcttcatt attatcttat gcaattatat   4800
atgtattatg agtggttcat taaaaaatag tgcagcaaag tcaccatagc cgtgggtgaa   4860
tgattgatag gtaaaattgt atttttcttt ttttcccggg tatttcaaaa agtaaaaaga   4920
gttgaaggga cgaattcata tattcagaaa attccctctc ctttaagtat cggtttgtgt   4980
ttgggggcat cactcgttgt ttctctcttc catgcccaaa atgcgtgtcc tctttgtttt   5040
tctgtttttc cattttcatt tccctgaaac cctttctgcc ccaatctcag agtaccgcgc   5100
ccttctctct ctccgttcag tcattaccga cgccacacca cccgttctct cttcttggaa   5160
cgcctccatc ccttactgtt cctggctcgg cgtcacctgc gacaaccgcc gccacgtcac   5220
cgccctcaac ctcaccggcc tcgacctctc cggcacgctc tctgccgacg tcgcccacct   5280
```

-continued

```
ccctttcctc tccaacctct ccctcgccgc aaacaaattc tccggcccca ttcctccctc   5340
tctctccgcc ctctccggcc tccgctacct caacctctcc aacaatgtct tcaacgaaac   5400
cttcccctcg gagctttggc gcctccagag cctcgaggtc ctcgacctct acaacaacaa   5460
catgaccggc gtgctccctc ttgccgtcgc gcagatgcag aatcttcgtc atttgcatct   5520
cggcggcaac ttcttctccg gccagatccc gccggagtac ggacgctggc agcgcctcca   5580
gtacctcgcc gtctccggca acgaactcga cgggactatc ccgccggaga tcggaaactt   5640
gaccagcctc cgggagctct acatcggcta ctacaacacc tacaccggcg gcattccgcc   5700
ggagatcgga aacttgtcgg agctggtgag gcttgacgta gcgtactgtg cgttgtccgg   5760
ggagattccg gcggcgcttg ggaagcttca gaagctggac acgctgttcc ttcaggtgaa   5820
tgcattgtca ggatcactga cgccggagct ggggaacctg aagagcctga aatccatgga   5880
tttgtctaac aacatgctct ccggtgagat tccggcgagt ttcggcgagc tgaagaatat   5940
tacgcttctg aatctgttca ggaacaagct tcatggagct ataccggagt ttataggaga   6000
gcttccagcg ttggaagttg tgcaactgtg ggaaaataac ttaacaggta gcattcctga   6060
gggtttgggc aaaaatggga gactcaacct tgttgatctt tcttctaaca agttaaccgg   6120
gactttgcct ccttatctct gttctgggaa tactcttcag actctgataa ctcttgggaa   6180
ttttcttttc ggtccaattc ctgagtcgct cgggacttgt gaatctctta cacggattag   6240
aatgggagaa aactttttga atggttccat tcctaaaggg ctttttggac ttcccaaact   6300
cacccaggtt gaacttcagg ataattatct ctctggagag tttcctgagg ttggttctgt   6360
tgcggttaat cttggtcaga ttactctctc taacaaccag ctttctgggg ctctgtctcc   6420
ctccattggt aacttctcca gcgtgcagaa gctccttctt gatggcaaca tgttcaccgg   6480
tcggatacct acacagattg ggaggttgca acagctttct aagattgatt ttagtggcaa   6540
caagttctcg ggtcctattg cgcctgagat cagtcagtgt aagctgttaa ctttcctgga   6600
ccttagccgc aatgagctat ctggagacat ccctaatgag ataactggca tgaggatatt   6660
gaattacttg aatctttcta agaatcattt agtgggtagc attccctctt cgatatcatc   6720
tatgcaaagc ttgacttctg ttgatttttc atacaacaac ctgtctggtt tggtgcctgg   6780
taccggtcaa ttcagctact tcaactacac gtctttcttg ggaaaccctg acctgtgtgg   6840
cccctatttg ggtgcttgca agggtggggt tgccaatggt gcacaccaac ctcatgttaa   6900
aggactctcc tcttctttga agctgctact tgttgttggg ttgctattat gttccattgc   6960
ttttgctgtg gctgcaatat tcaaggcccg gtcattaaag aaggccagtg aggctcgtgc   7020
atggaagttg actgcgttcc agcgtttgga cttcactgtt gatgatgttt tgcattgctt   7080
gaaagaggat aatattattg ggaaaggagg tgctggaatt gtctacaaag ggggctatgcc   7140
taatggggat catgttgctg tgaaaaggct tccagctatg agtagaggct cttcccatga   7200
tcacggattc aatgctgaga ttcagacatt ggggcgaatc cgacacaggc acattgttag   7260
gttgttgggt ttctgttcaa atcatgagac aaacctttttg gtctatgagt acatgcccaa   7320
tggaagttta ggtgaggttc ttcatggaaa aaagggggggt catttgcatt gggacaccag   7380
gtataaaatt gcggtggagg ctgccaaggg gctttgctat ctgcaccatg attgttcgcc   7440
actcattgtc catcgtgatg tgaagtcaaa caacatcctt cttgattcaa atcatgaagc   7500
ccatgttgct gattttgggc ttgctaagtt cctgcaagat tctgggacat ctgaatgcat   7560
gtctgctatt gctggttcat atggatacat agctccaggt accgttgaat tttgacataa   7620
ttaatgcatc atatgcatgg ttgtggcaaa tttcctttttt ctcgcctaat cataattgta   7680
```

-continued

```
cgtttaagca ttttgttcag aatttgactc tttgacttat gcatgatatt gaggtgatgc   7740

ccctaaattt attaacattg ctatgtggtt tttcttgact ttggttttct atcataccca   7800

attgattcgc ccccttattt tgtttttttt tctaagccaa gtactgaaag taaatggtag   7860

gtatctctgc accgtttgat tttttaccct aaccccctct ccccacctat gaagtagata   7920

atgctgtagt cgtaggttaa gagtcattca caatcggaaa ctgatggtta tgggcaaaaa   7980

catcagataa aaagacctat tatgttactt tatacgtatt gcctttgttt aacttattgt   8040

ttcaaattaa agtgtcttgc tttattatag tgtatgatac ctgttggatg tttgattgca   8100

gagtatgcct acacattgaa agttgatgag aaaagcgatg tgtacagttt tggtgtggtt   8160

cttttagaac ttataacagg caggaaacca gttggtgaat ttggtgatgg cgtggacatc   8220

gtgcaatggg tgaggaaaat gacggactct aacaaggaag gagttcttaa agttcttgat   8280

cctaggcttc cctcagttcc ccttcacgaa gtgatgcatg ttttctatgt ggccatgctg   8340

tgtgttgaag aacaggctgt agagagacca acaatgcgtg aagttgttca aatactgacc   8400

gagcttccaa agccacctgg ctctaaagag ggagacttaa caataacaga atcctctttg   8460

tcatcatcaa acgctttaga atctccatcc tcagcctcca aggaagatca aaatcctcct   8520

caatccccac cacccgacct tcttagtatt taaagtgctc tgttgggtgt ttcatcttat   8580

tagttccctt ggttgtgata gcttatccat ttactttctt tttctgtctc tcttctgggg   8640

ttggggcttt tcttcttctt ctaactgaag gtattaatgc tctgattttt taatggtttt   8700

gtacagtagg attggtgggg ggggttattt tcttatgaag tcactttctt catcatgtag   8760

tactgctttt taatttttat gttacggccg ttgttgtgct tcgcctaagc tggggagtgg   8820

ggagggttca agggaatgga tactcttttt ttatgcgatc actgacaggt agacacaaaa   8880

tgacgcaaac gggttgggta ttaaacagtg ggtatattgt atggtttaga atattattga   8940

tgaatcctga gtggattggc acagtgtgaa ctgtgagcct gagctgtgac tgagtctatg   9000

agtcaggttt ggataaaagc ttatttgaag aagttaacct gtttcgagaa aatcagagtg   9060

aatcaggatt caggcgtgtt ttagcttt                                      9088
```

<210> SEQ ID NO 33
<211> LENGTH: 3039
<212> TYPE: DNA
<213> ORGANISM: Glycine max
<220> FEATURE:
<221> NAME/KEY: CDS
<222> LOCATION: (1)..(3039)

<400> SEQUENCE: 33

```
atg ccc aaa atg cgt gtc ctc ttt gtt ttt ctg ttt ttc cat ttt cat       48
Met Pro Lys Met Arg Val Leu Phe Val Phe Leu Phe Phe His Phe His
1               5                   10                  15

ttc cct gaa acc ctt tct gcc cca atc tca gag tac cgc gcc ctt ctc       96
Phe Pro Glu Thr Leu Ser Ala Pro Ile Ser Glu Tyr Arg Ala Leu Leu
            20                  25                  30

tct ctc cgt tca gtc att acc gac gcc aca cca ccc gtt ctc tct tct      144
Ser Leu Arg Ser Val Ile Thr Asp Ala Thr Pro Pro Val Leu Ser Ser
        35                  40                  45

tgg aac gcc tcc atc cct tac tgt tcc tgg ctc ggc gtc acc tgc gac      192
Trp Asn Ala Ser Ile Pro Tyr Cys Ser Trp Leu Gly Val Thr Cys Asp
    50                  55                  60

aac cgc cgc cac gtc acc gcc ctc aac ctc acc ggc ctc gac ctc tcc      240
Asn Arg Arg His Val Thr Ala Leu Asn Leu Thr Gly Leu Asp Leu Ser
65                  70                  75                  80
```

```
ggc acg ctc tct gcc gac gtc gcc cac ctc cct ttc ctc tcc aac ctc      288
Gly Thr Leu Ser Ala Asp Val Ala His Leu Pro Phe Leu Ser Asn Leu
                85                  90                  95

tcc ctc gcc gca aac aaa ttc tcc ggc ccc att cct ccc tct ctc tcc      336
Ser Leu Ala Ala Asn Lys Phe Ser Gly Pro Ile Pro Pro Ser Leu Ser
            100                 105                 110

gcc ctc tcc ggc ctc cgc tac ctc aac ctc tcc aac aat gtc ttc aac      384
Ala Leu Ser Gly Leu Arg Tyr Leu Asn Leu Ser Asn Asn Val Phe Asn
        115                 120                 125

gaa acc ttc ccc tcg gag ctt tgg cgc ctc cag agc ctc gag gtc ctc      432
Glu Thr Phe Pro Ser Glu Leu Trp Arg Leu Gln Ser Leu Glu Val Leu
    130                 135                 140

gac ctc tac aac aac aac atg acc ggc gtg ctc cct ctt gcc gtc gcg      480
Asp Leu Tyr Asn Asn Asn Met Thr Gly Val Leu Pro Leu Ala Val Ala
145                 150                 155                 160

cag atg cag aat ctt cgt cat ttg cat ctc ggc ggc aac ttc ttc tcc      528
Gln Met Gln Asn Leu Arg His Leu His Leu Gly Gly Asn Phe Phe Ser
                165                 170                 175

ggc cag atc ccg ccg gag tac gga cgc tgg cag cgc ctc cag tac ctc      576
Gly Gln Ile Pro Pro Glu Tyr Gly Arg Trp Gln Arg Leu Gln Tyr Leu
            180                 185                 190

gcc gtc tcc ggc aac gaa ctc gac ggg act atc ccg ccg gag atc gga      624
Ala Val Ser Gly Asn Glu Leu Asp Gly Thr Ile Pro Pro Glu Ile Gly
        195                 200                 205

aac ttg acc agc ctc cgg gag ctc tac atc ggc tac tac aac acc tac      672
Asn Leu Thr Ser Leu Arg Glu Leu Tyr Ile Gly Tyr Tyr Asn Thr Tyr
    210                 215                 220

acc ggc ggc att ccg ccg gag atc gga aac ttg tcg gag ctg gtg agg      720
Thr Gly Gly Ile Pro Pro Glu Ile Gly Asn Leu Ser Glu Leu Val Arg
225                 230                 235                 240

ctt gac gta gcg tac tgt gcg ttg tcc ggg gag att ccg gcg gcg ctt      768
Leu Asp Val Ala Tyr Cys Ala Leu Ser Gly Glu Ile Pro Ala Ala Leu
                245                 250                 255

ggg aag ctt cag aag ctg gac acg ctg ttc ctt cag gtg aat gca ttg      816
Gly Lys Leu Gln Lys Leu Asp Thr Leu Phe Leu Gln Val Asn Ala Leu
            260                 265                 270

tca gga tca ctg acg ccg gag ctg ggg aac ctg aag agc ctg aaa tcc      864
Ser Gly Ser Leu Thr Pro Glu Leu Gly Asn Leu Lys Ser Leu Lys Ser
        275                 280                 285

atg gat ttg tct aac aac atg ctc tcc ggt gag att ccg gcg agt ttc      912
Met Asp Leu Ser Asn Asn Met Leu Ser Gly Glu Ile Pro Ala Ser Phe
    290                 295                 300

ggc gag ctg aag aat att acg ctt ctg aat ctg ttc agg aac aag ctt      960
Gly Glu Leu Lys Asn Ile Thr Leu Leu Asn Leu Phe Arg Asn Lys Leu
305                 310                 315                 320

cat gga gct ata ccg gag ttt ata gga gag ctt cca gcg ttg gaa gtt     1008
His Gly Ala Ile Pro Glu Phe Ile Gly Glu Leu Pro Ala Leu Glu Val
                325                 330                 335

gtg caa ctg tgg gaa aat aac tta aca ggt agc att cct gag ggt ttg     1056
Val Gln Leu Trp Glu Asn Asn Leu Thr Gly Ser Ile Pro Glu Gly Leu
            340                 345                 350

ggc aaa aat ggg aga ctc aac ctt gtt gat ctt tct tct aac aag tta     1104
Gly Lys Asn Gly Arg Leu Asn Leu Val Asp Leu Ser Ser Asn Lys Leu
        355                 360                 365

acc ggg act ttg cct cct tat ctc tgt tct ggg aat act ctt cag act     1152
Thr Gly Thr Leu Pro Pro Tyr Leu Cys Ser Gly Asn Thr Leu Gln Thr
    370                 375                 380

ctg ata act ctt ggg aat ttt ctt ttc ggt cca att cct gag tcg ctc     1200
Leu Ile Thr Leu Gly Asn Phe Leu Phe Gly Pro Ile Pro Glu Ser Leu
```

```
385                 390                 395                 400

ggg act tgt gaa tct ctt aca cgg att aga atg gga gaa aac ttt ttg      1248
Gly Thr Cys Glu Ser Leu Thr Arg Ile Arg Met Gly Glu Asn Phe Leu
                405                 410                 415

aat ggt tcc att cct aaa ggg ctt ttt gga ctt ccc aaa ctc acc cag      1296
Asn Gly Ser Ile Pro Lys Gly Leu Phe Gly Leu Pro Lys Leu Thr Gln
            420                 425                 430

gtt gaa ctt cag gat aat tat ctc tct gga gag ttt cct gag gtt ggt      1344
Val Glu Leu Gln Asp Asn Tyr Leu Ser Gly Glu Phe Pro Glu Val Gly
        435                 440                 445

tct gtt gcg gtt aat ctt ggt cag att act ctc tct aac aac cag ctt      1392
Ser Val Ala Val Asn Leu Gly Gln Ile Thr Leu Ser Asn Asn Gln Leu
    450                 455                 460

tct ggg gct ctg tct ccc tcc att ggt aac ttc tcc agc gtg cag aag      1440
Ser Gly Ala Leu Ser Pro Ser Ile Gly Asn Phe Ser Ser Val Gln Lys
465                 470                 475                 480

ctc ctt ctt gat ggc aac atg ttc acc ggt cgg ata cct aca cag att      1488
Leu Leu Leu Asp Gly Asn Met Phe Thr Gly Arg Ile Pro Thr Gln Ile
                485                 490                 495

ggg agg ttg caa cag ctt tct aag att gat ttt agt ggc aac aag ttc      1536
Gly Arg Leu Gln Gln Leu Ser Lys Ile Asp Phe Ser Gly Asn Lys Phe
            500                 505                 510

tcg ggt cct att gcg cct gag atc agt cag tgt aag ctg tta act ttc      1584
Ser Gly Pro Ile Ala Pro Glu Ile Ser Gln Cys Lys Leu Leu Thr Phe
        515                 520                 525

ctg gac ctt agc cgc aat gag cta tct gga gac atc cct aat gag ata      1632
Leu Asp Leu Ser Arg Asn Glu Leu Ser Gly Asp Ile Pro Asn Glu Ile
    530                 535                 540

act ggc atg agg ata ttg aat tac ttg aat ctt tct aag aat cat tta      1680
Thr Gly Met Arg Ile Leu Asn Tyr Leu Asn Leu Ser Lys Asn His Leu
545                 550                 555                 560

gtg ggt agc att ccc tct tcg ata tca tct atg caa agc ttg act tct      1728
Val Gly Ser Ile Pro Ser Ser Ile Ser Ser Met Gln Ser Leu Thr Ser
                565                 570                 575

gtt gat ttt tca tac aac aac ctg tct ggt ttg gtg cct ggt acc ggt      1776
Val Asp Phe Ser Tyr Asn Asn Leu Ser Gly Leu Val Pro Gly Thr Gly
            580                 585                 590

caa ttc agc tac ttc aac tac acg tct ttc ttg gga aac cct gac ctg      1824
Gln Phe Ser Tyr Phe Asn Tyr Thr Ser Phe Leu Gly Asn Pro Asp Leu
        595                 600                 605

tgt ggc ccc tat ttg ggt gct tgc aag ggt ggg gtt gcc aat ggt gca      1872
Cys Gly Pro Tyr Leu Gly Ala Cys Lys Gly Gly Val Ala Asn Gly Ala
    610                 615                 620

cac caa cct cat gtt aaa gga ctc tcc tct tct ttg aag ctg cta ctt      1920
His Gln Pro His Val Lys Gly Leu Ser Ser Ser Leu Lys Leu Leu Leu
625                 630                 635                 640

gtt gtt ggg ttg cta tta tgt tcc att gct ttt gct gtg gct gca ata      1968
Val Val Gly Leu Leu Leu Cys Ser Ile Ala Phe Ala Val Ala Ala Ile
                645                 650                 655

ttc aag gcc cgg tca tta aag aag gcc agt gag gct cgt gca tgg aag      2016
Phe Lys Ala Arg Ser Leu Lys Lys Ala Ser Glu Ala Arg Ala Trp Lys
            660                 665                 670

ttg act gcg ttc cag cgt ttg gac ttc act gtt gat gat gtt ttg cat      2064
Leu Thr Ala Phe Gln Arg Leu Asp Phe Thr Val Asp Asp Val Leu His
        675                 680                 685

tgc ttg aaa gag gat aat att att ggg aaa gga ggt gct gga att gtc      2112
Cys Leu Lys Glu Asp Asn Ile Ile Gly Lys Gly Gly Ala Gly Ile Val
    690                 695                 700

tac aaa ggg gct atg cct aat ggg gat cat gtt gct gtg aaa agg ctt      2160
```

-continued

```
Tyr Lys Gly Ala Met Pro Asn Gly Asp His Val Ala Val Lys Arg Leu
705                 710                 715                 720

cca gct atg agt aga ggc tct tcc cat gat cac gga ttc aat gct gag      2208
Pro Ala Met Ser Arg Gly Ser Ser His Asp His Gly Phe Asn Ala Glu
                725                 730                 735

att cag aca ttg ggg cga atc cga cac agg cac att gtt agg ttg ttg      2256
Ile Gln Thr Leu Gly Arg Ile Arg His Arg His Ile Val Arg Leu Leu
            740                 745                 750

ggt ttc tgt tca aat cat gag aca aac ctt ttg gtc tat gag tac atg      2304
Gly Phe Cys Ser Asn His Glu Thr Asn Leu Leu Val Tyr Glu Tyr Met
        755                 760                 765

ccc aat gga agt tta ggt gag gtt ctt cat gga aaa aag ggg ggt cat      2352
Pro Asn Gly Ser Leu Gly Glu Val Leu His Gly Lys Lys Gly Gly His
    770                 775                 780

ttg cat tgg gac acc agg tat aaa att gcg gtg gag gct gcc aag ggg      2400
Leu His Trp Asp Thr Arg Tyr Lys Ile Ala Val Glu Ala Ala Lys Gly
785                 790                 795                 800

ctt tgc tat ctg cac cat gat tgt tcg cca ctc att gtc cat cgt gat      2448
Leu Cys Tyr Leu His His Asp Cys Ser Pro Leu Ile Val His Arg Asp
                805                 810                 815

gtg aag tca aac aac atc ctt ctt gat tca aat cat gaa gcc cat gtt      2496
Val Lys Ser Asn Asn Ile Leu Leu Asp Ser Asn His Glu Ala His Val
            820                 825                 830

gct gat ttt ggg ctt gct aag ttc ctg caa gat tct ggg aca tct gaa      2544
Ala Asp Phe Gly Leu Ala Lys Phe Leu Gln Asp Ser Gly Thr Ser Glu
        835                 840                 845

tgc atg tct gct att gct ggt tca tat gga tac ata gct cca gag tat      2592
Cys Met Ser Ala Ile Ala Gly Ser Tyr Gly Tyr Ile Ala Pro Glu Tyr
    850                 855                 860

gcc tac aca ttg aaa gtt gat gag aaa agc gat gtg tac agt ttt ggt      2640
Ala Tyr Thr Leu Lys Val Asp Glu Lys Ser Asp Val Tyr Ser Phe Gly
865                 870                 875                 880

gtg gtt ctt tta gaa ctt ata aca ggc agg aaa cca gtt ggt gaa ttt      2688
Val Val Leu Leu Glu Leu Ile Thr Gly Arg Lys Pro Val Gly Glu Phe
                885                 890                 895

ggt gat ggc gtg gac atc gtg caa tgg gtg agg aaa atg acg gac tct      2736
Gly Asp Gly Val Asp Ile Val Gln Trp Val Arg Lys Met Thr Asp Ser
            900                 905                 910

aac aag gaa gga gtt ctt aaa gtt ctt gat cct agg ctt ccc tca gtt      2784
Asn Lys Glu Gly Val Leu Lys Val Leu Asp Pro Arg Leu Pro Ser Val
        915                 920                 925

ccc ctt cac gaa gtg atg cat gtt ttc tat gtg gcc atg ctg tgt gtt      2832
Pro Leu His Glu Val Met His Val Phe Tyr Val Ala Met Leu Cys Val
    930                 935                 940

gaa gaa cag gct gta gag aga cca aca atg cgt gaa gtt gtt caa ata      2880
Glu Glu Gln Ala Val Glu Arg Pro Thr Met Arg Glu Val Val Gln Ile
945                 950                 955                 960

ctg acc gag ctt cca aag cca cct ggc tct aaa gag gga gac tta aca      2928
Leu Thr Glu Leu Pro Lys Pro Pro Gly Ser Lys Glu Gly Asp Leu Thr
                965                 970                 975

ata aca gaa tcc tct ttg tca tca tca aac gct tta gaa tct cca tcc      2976
Ile Thr Glu Ser Ser Leu Ser Ser Ser Asn Ala Leu Glu Ser Pro Ser
            980                 985                 990

tca gcc tcc aag gaa gat caa aat  cct cct caa tcc cca  cca ccc gac    3024
Ser Ala Ser Lys Glu Asp Gln Asn  Pro Pro Gln Ser Pro  Pro Pro Asp
        995                 1000                 1005

ctt ctt  agt att taa                                                 3039
Leu Leu  Ser Ile
    1010
```

<210> SEQ ID NO 34
<211> LENGTH: 1012
<212> TYPE: PRT
<213> ORGANISM: Glycine max

<400> SEQUENCE: 34

```
Met Pro Lys Met Arg Val Leu Phe Val Phe Leu Phe Phe His Phe His
1               5                   10                  15

Phe Pro Glu Thr Leu Ser Ala Pro Ile Ser Glu Tyr Arg Ala Leu Leu
            20                  25                  30

Ser Leu Arg Ser Val Ile Thr Asp Ala Thr Pro Pro Val Leu Ser Ser
        35                  40                  45

Trp Asn Ala Ser Ile Pro Tyr Cys Ser Trp Leu Gly Val Thr Cys Asp
    50                  55                  60

Asn Arg Arg His Val Thr Ala Leu Asn Leu Thr Gly Leu Asp Leu Ser
65                  70                  75                  80

Gly Thr Leu Ser Ala Asp Val Ala His Leu Pro Phe Leu Ser Asn Leu
                85                  90                  95

Ser Leu Ala Ala Asn Lys Phe Ser Gly Pro Ile Pro Pro Ser Leu Ser
            100                 105                 110

Ala Leu Ser Gly Leu Arg Tyr Leu Asn Leu Ser Asn Asn Val Phe Asn
        115                 120                 125

Glu Thr Phe Pro Ser Glu Leu Trp Arg Leu Gln Ser Leu Glu Val Leu
    130                 135                 140

Asp Leu Tyr Asn Asn Asn Met Thr Gly Val Leu Pro Leu Ala Val Ala
145                 150                 155                 160

Gln Met Gln Asn Leu Arg His Leu His Leu Gly Gly Asn Phe Phe Ser
                165                 170                 175

Gly Gln Ile Pro Pro Glu Tyr Gly Arg Trp Gln Arg Leu Gln Tyr Leu
            180                 185                 190

Ala Val Ser Gly Asn Glu Leu Asp Gly Thr Ile Pro Pro Glu Ile Gly
        195                 200                 205

Asn Leu Thr Ser Leu Arg Glu Leu Tyr Ile Gly Tyr Tyr Asn Thr Tyr
    210                 215                 220

Thr Gly Gly Ile Pro Pro Glu Ile Gly Asn Leu Ser Glu Leu Val Arg
225                 230                 235                 240

Leu Asp Val Ala Tyr Cys Ala Leu Ser Gly Glu Ile Pro Ala Ala Leu
                245                 250                 255

Gly Lys Leu Gln Lys Leu Asp Thr Leu Phe Leu Gln Val Asn Ala Leu
            260                 265                 270

Ser Gly Ser Leu Thr Pro Glu Leu Gly Asn Leu Lys Ser Leu Lys Ser
        275                 280                 285

Met Asp Leu Ser Asn Asn Met Leu Ser Gly Glu Ile Pro Ala Ser Phe
    290                 295                 300

Gly Glu Leu Lys Asn Ile Thr Leu Leu Asn Leu Phe Arg Asn Lys Leu
305                 310                 315                 320

His Gly Ala Ile Pro Glu Phe Ile Gly Glu Leu Pro Ala Leu Glu Val
                325                 330                 335

Val Gln Leu Trp Glu Asn Asn Leu Thr Gly Ser Ile Pro Glu Gly Leu
            340                 345                 350

Gly Lys Asn Gly Arg Leu Asn Leu Val Asp Leu Ser Ser Asn Lys Leu
        355                 360                 365

Thr Gly Thr Leu Pro Pro Tyr Leu Cys Ser Gly Asn Thr Leu Gln Thr
    370                 375                 380
```

```
Leu Ile Thr Leu Gly Asn Phe Leu Phe Gly Pro Ile Pro Glu Ser Leu
385                 390                 395                 400

Gly Thr Cys Glu Ser Leu Thr Arg Ile Arg Met Gly Glu Asn Phe Leu
                405                 410                 415

Asn Gly Ser Ile Pro Lys Gly Leu Phe Gly Leu Pro Lys Leu Thr Gln
            420                 425                 430

Val Glu Leu Gln Asp Asn Tyr Leu Ser Gly Glu Phe Pro Glu Val Gly
        435                 440                 445

Ser Val Ala Val Asn Leu Gly Gln Ile Thr Leu Ser Asn Asn Gln Leu
    450                 455                 460

Ser Gly Ala Leu Ser Pro Ser Ile Gly Asn Phe Ser Ser Val Gln Lys
465                 470                 475                 480

Leu Leu Leu Asp Gly Asn Met Phe Thr Gly Arg Ile Pro Thr Gln Ile
                485                 490                 495

Gly Arg Leu Gln Gln Leu Ser Lys Ile Asp Phe Ser Gly Asn Lys Phe
            500                 505                 510

Ser Gly Pro Ile Ala Pro Glu Ile Ser Gln Cys Lys Leu Leu Thr Phe
        515                 520                 525

Leu Asp Leu Ser Arg Asn Glu Leu Ser Gly Asp Ile Pro Asn Glu Ile
    530                 535                 540

Thr Gly Met Arg Ile Leu Asn Tyr Leu Asn Leu Ser Lys Asn His Leu
545                 550                 555                 560

Val Gly Ser Ile Pro Ser Ser Ile Ser Ser Met Gln Ser Leu Thr Ser
                565                 570                 575

Val Asp Phe Ser Tyr Asn Asn Leu Ser Gly Leu Val Pro Gly Thr Gly
            580                 585                 590

Gln Phe Ser Tyr Phe Asn Tyr Thr Ser Phe Leu Gly Asn Pro Asp Leu
        595                 600                 605

Cys Gly Pro Tyr Leu Gly Ala Cys Lys Gly Gly Val Ala Asn Gly Ala
    610                 615                 620

His Gln Pro His Val Lys Gly Leu Ser Ser Ser Leu Lys Leu Leu Leu
625                 630                 635                 640

Val Val Gly Leu Leu Leu Cys Ser Ile Ala Phe Ala Val Ala Ala Ile
                645                 650                 655

Phe Lys Ala Arg Ser Leu Lys Lys Ala Ser Glu Ala Arg Ala Trp Lys
            660                 665                 670

Leu Thr Ala Phe Gln Arg Leu Asp Phe Thr Val Asp Asp Val Leu His
        675                 680                 685

Cys Leu Lys Glu Asp Asn Ile Ile Gly Lys Gly Gly Ala Gly Ile Val
    690                 695                 700

Tyr Lys Gly Ala Met Pro Asn Gly Asp His Val Ala Val Lys Arg Leu
705                 710                 715                 720

Pro Ala Met Ser Arg Gly Ser Ser His Asp His Gly Phe Asn Ala Glu
                725                 730                 735

Ile Gln Thr Leu Gly Arg Ile Arg His Arg His Ile Val Arg Leu Leu
            740                 745                 750

Gly Phe Cys Ser Asn His Glu Thr Asn Leu Leu Val Tyr Glu Tyr Met
        755                 760                 765

Pro Asn Gly Ser Leu Gly Glu Val Leu His Gly Lys Lys Gly Gly His
    770                 775                 780

Leu His Trp Asp Thr Arg Tyr Lys Ile Ala Val Glu Ala Ala Lys Gly
785                 790                 795                 800
```

```
Leu Cys Tyr Leu His His Asp Cys Ser Pro Leu Ile Val His Arg Asp
                805                 810                 815

Val Lys Ser Asn Asn Ile Leu Leu Asp Ser Asn His Glu Ala His Val
            820                 825                 830

Ala Asp Phe Gly Leu Ala Lys Phe Leu Gln Asp Ser Gly Thr Ser Glu
        835                 840                 845

Cys Met Ser Ala Ile Ala Gly Ser Tyr Gly Tyr Ile Ala Pro Glu Tyr
    850                 855                 860

Ala Tyr Thr Leu Lys Val Asp Glu Lys Ser Asp Val Tyr Ser Phe Gly
865                 870                 875                 880

Val Val Leu Leu Glu Leu Ile Thr Gly Arg Lys Pro Val Gly Glu Phe
                885                 890                 895

Gly Asp Gly Val Asp Ile Val Gln Trp Val Arg Lys Met Thr Asp Ser
            900                 905                 910

Asn Lys Glu Gly Val Leu Lys Val Leu Asp Pro Arg Leu Pro Ser Val
        915                 920                 925

Pro Leu His Glu Val Met His Val Phe Tyr Val Ala Met Leu Cys Val
    930                 935                 940

Glu Glu Gln Ala Val Glu Arg Pro Thr Met Arg Glu Val Val Gln Ile
945                 950                 955                 960

Leu Thr Glu Leu Pro Lys Pro Pro Gly Ser Lys Glu Gly Asp Leu Thr
                965                 970                 975

Ile Thr Glu Ser Ser Leu Ser Ser Ser Asn Ala Leu Glu Ser Pro Ser
            980                 985                 990

Ser Ala Ser Lys Glu Asp Gln Asn  Pro Pro Gln Ser Pro  Pro Pro Asp
        995                 1000                1005

Leu Leu  Ser Ile
    1010
```

<210> SEQ ID NO 35
<211> LENGTH: 4268
<212> TYPE: DNA
<213> ORGANISM: Glycine max

<400> SEQUENCE: 35

```
cacgtggtac acgaacaccg acgccatcag aatccaaaag ggtatcagga atcacaatca     60

aaaacgaatt ttgttctagt ttttatatcc ttaaaaaatt cgaaaccaga gagagaaaaa    120

aaatggttgg gttttttttac tcttgtcggg tgagagctat aagagggtgt ggaggaagat    180

gaggagaaga tcgagggcgg tgatgggatg gcggtggagg atcacagcag agaaatagtt    240

tgccattgcc atggagggag agcgaagagg ttgaggccca ttcaattgaa ttggatcaga    300

gagagttaac tgaagaatcg gtcactgaga aaagggcgcg tagcttagca tttgatatgt    360

ggcgatttgg tttgggtacg tcctttcggg gacagaagaa gatggatcaa agacgcttaa    420

tgcggttggg acctgagaat gaatgagaga gacactcact acactcacaa aaggaggttc    480

aatttatcaa ataaaaaaga gagacacagg ggatggatgt gtcatgtgtg tgtccatgtg    540

tggtgagctc catcatatag agaatctttt caccttaatt attttttaag gctattctta    600

atcagtaatc ttagacattg attaaaaaat taaaaagaaa atataaaata agttgtagag    660

cactataatt taatatttta atataaaaag tatttagaag aatgataaat atatctagct    720

ttcttaatat ataaaattaa tataaattag tataatatca caaatatttt attaaaccaa    780

acaattaaca ttttaaaaat tttatatttg atttttactg tgtctaaaat tttttgggtc    840

gctgataacc acaaattaca aacaaaatta atctcccatt gaattaaaaa ataacataat    900
```

```
ctataaccta tcaaaaagaa aaagaaaaaa gaatctggac ctatttctac cccgatgcac    960
atgagaaact taaaaagggg gtgaagtgtt atgtagtata gagagaaagc gagggaaggc   1020
aaagcaagca caacagaaca aagccacttt attttttga tctaacctaa accatccttt   1080
ccccctgttg cactctcact ttatcaacgt gacacaagca acttatgacc aatgtgtaag   1140
atgttgttcc tctttccctt ctcttctgtc catttcatca agtttccatt ctaatctcca   1200
aatctttgcc accccagttc ctcttttgct tcaaacttct cttcccctcc ctaaaaattg   1260
cacctttact ctcatggtga tgggacacac cacacccctc acactcctct gtatgattct   1320
tctttttgca accccttctc tctcaattga tgttcaccca caagacagaa tctcactctc   1380
actgttcagg tcatctctgc caaaccccaa ccagagtttg cccagctggg taggctccaa   1440
ctgcacttca tggagtggaa tcacctgcga cagcagaact gggagagtgc tttccatcaa   1500
cctaactagc atgaaccttt caggcaaaat ccaccccagt ttgtgccacc tttcatacct   1560
caacaagttg gggttgtcac acaacaactt cacagcccca cttcctgagt gttttggaaa   1620
cttgcttaac ctaagagcca ttgatctcag ccacaacagg tttcatggtg gaataccaga   1680
ctctttcatg aggctcaggc acctcactga gcttgttttc agtgggaacc ctggtttggg   1740
gggtccactt cctgcttgga ttggtaactt ctctgcaaat ctggaaaagt tacatcttgg   1800
tttctgttca ttcagtggtg gcatacctga gagcttgctt tacatgaagt ccctcaagta   1860
tttggacctt gagaacaatc tcttgtttgg taatttggtt gattttcaac agcctttggt   1920
tttgctcaat cttgcttcca atcagtttgc tggtactttg ccttgctttg cagcttcagt   1980
tcagtctcta actgtgttga atttgtccaa caattctatt gcgggggat tgcctgcttg   2040
tattgcttct tttcaagctt tgactcattt gaacctttca gggaaccatt tgaagtatag   2100
aatatatcct aggcttgtgt tctcagagaa acttcttgtt ttggacttga gtaataatgc   2160
tttatctggt cctattccca gtaaaattgc tgagactact gacaaacttg gccttgttct   2220
tcttgacctt tctcacaatc agttctctgg tgaaatacct gtgaaaatta ctgagttgaa   2280
aagcttgcag gccttgtttc tctctcacaa tcttctctca ggagaaattc ctgctagaat   2340
tggaaatttg acttatctgc aggtcattga tctctcacac aactctttgt ctggaaccat   2400
tccattcagt attgttgggt gctttcagct gtatgctctg atacttaaca acaacaatct   2460
ttctggtgta attcaaccgg agtttgatgc gttggatatc ttgaggatac tggatataag   2520
caacaacagg ttttccgggg ctatcccact cactttggct ggatgcaaat ctttggagat   2580
tgtagacttt agttccaatg agctttctgg atcgttgaat gatgcaataa ccaaatggac   2640
aaacctcagg tatttgtctc ttgctcagaa caagttcagt gaaaatctgc ctagttggtt   2700
gttcacattt aacgcaatag aaatgatgga tttctcgcat aacaagttta ctggcttcat   2760
accggatatt aattttaagg gtagcttaat atttaacact aggaatgtca ctgttaaaga   2820
gccattggtt gcagcaagaa aggttcaact cagagtttcg gcggttgttt ctgatagcaa   2880
tcaactcagt ttcacttatg atctttcctc aatggttgga attgatctat ccagcaactc   2940
gcttcatggg gaaattccaa ggggcttatt tggtctatct ggcctagaat atctgaattt   3000
gtcatgcaac tttctttacg gacagcttcc ggggttgcag aaaatgcaga gtttgaaagc   3060
cttggatttg tcacataatt ccttgtcagg acatatccca ggaaacatct ctatccttca   3120
agatctgtct attttgaatc tttcctacaa ctgcttttct ggatgtgttc cccagaagca   3180
agggtatggg agatttcctg gtgcatttgc tggaaatcca gatctgtgca tggaatcttc   3240
```

-continued

```
cagtggatta tgtgatgatg gaaggactca atctgcgcaa ggaagtactt ttagggaaga   3300

taggatggat gacccaattt ctgtggggat tttctttatc agtgcatttg ttagttttga   3360

ttttggtgtt gtggttctct tctgttccgc acgggcaaga aattacattc tccaaacaaa   3420

agtttgattt gatgcttgtg acacatacaa atctcctgta aattccattt tgtaatgtgg   3480

tacctgtctt ctcagtttca agtaaacata cacttacgtg actgggaata ctatctggcc   3540

atcagcttca caagtgtttt ctcgtgatta ctgaacaagt gtctcggaat tgcaggatca   3600

aaatgccatg atatgagtaa cacaaggttt aaagaacact cataacgctg gctttaacta   3660

tctgagtgaa gactagtcct gcatcattca gccaagaaaa aaatggatgg ttatgatgaa   3720

aatttgatcc aagtaaagac gagtccctca tcattctgat ggttgttctc ttttgctgga   3780

acttggttgc atcaagttta ttatgcatca tcacatgcat tattcataat caggtgggtg   3840

aagggtcagc aaggaacatg cctgattgat atctggtcta gttatggtga aattttgatc   3900

ttgggacatc aaattgcaga tttgcaagca tgtttacgtg aagagaactt gtatcattct   3960

agattaaccc agctctttct tgaggtgggg aaccaagttt tccctgtaag tgttttacct   4020

taagaatgtg agttgatgag tagtggggag tggtaagtgc agacaaaata aatggagtag   4080

ttctcataaa tctaagattt gtatttgtat tactgtcttc atgccttcat cttagtgctg   4140

tgattttaaa tgaaattctc acgaaatctt ttcattgaga acagaaaaga ggtaattgag   4200

caccttagct ttgttatcaa atgccaagca tgctcaacaa aaattagaaa aattatctag   4260

tttaccaa                                                            4268
```

<210> SEQ ID NO 36
<211> LENGTH: 2154
<212> TYPE: DNA
<213> ORGANISM: Glycine max
<220> FEATURE:
<221> NAME/KEY: CDS
<222> LOCATION: (1)..(2154)

<400> SEQUENCE: 36

```
atg gtg atg gga cac acc aca ccc ctc aca ctc ctc tgt atg att ctt       48
Met Val Met Gly His Thr Thr Pro Leu Thr Leu Leu Cys Met Ile Leu
1               5                   10                  15

ctt ttt gca acc cct tct ctc tca att gat gtt cac cca caa gac aga       96
Leu Phe Ala Thr Pro Ser Leu Ser Ile Asp Val His Pro Gln Asp Arg
            20                  25                  30

atc tca ctc tca ctg ttc agg tca tct ctg cca aac ccc aac cag agt      144
Ile Ser Leu Ser Leu Phe Arg Ser Ser Leu Pro Asn Pro Asn Gln Ser
        35                  40                  45

ttg ccc agc tgg gta ggc tcc aac tgc act tca tgg agt gga atc acc      192
Leu Pro Ser Trp Val Gly Ser Asn Cys Thr Ser Trp Ser Gly Ile Thr
    50                  55                  60

tgc gac agc aga act ggg aga gtg ctt tcc atc aac cta act agc atg      240
Cys Asp Ser Arg Thr Gly Arg Val Leu Ser Ile Asn Leu Thr Ser Met
65                  70                  75                  80

aac ctt tca ggc aaa atc cac ccc agt ttg tgc cac ctt tca tac ctc      288
Asn Leu Ser Gly Lys Ile His Pro Ser Leu Cys His Leu Ser Tyr Leu
                85                  90                  95

aac aag ttg ggg ttg tca cac aac aac ttc aca gcc cca ctt cct gag      336
Asn Lys Leu Gly Leu Ser His Asn Asn Phe Thr Ala Pro Leu Pro Glu
            100                 105                 110

tgt ttt gga aac ttg ctt aac cta aga gcc att gat ctc agc cac aac      384
Cys Phe Gly Asn Leu Leu Asn Leu Arg Ala Ile Asp Leu Ser His Asn
        115                 120                 125
```

-continued

```
agg ttt cat ggt gga ata cca gac tct ttc atg agg ctc agg cac ctc      432
Arg Phe His Gly Gly Ile Pro Asp Ser Phe Met Arg Leu Arg His Leu
    130                 135                 140

act gag ctt gtt ttc agt ggg aac cct ggt ttg ggg ggt cca ctt cct      480
Thr Glu Leu Val Phe Ser Gly Asn Pro Gly Leu Gly Gly Pro Leu Pro
145                 150                 155                 160

gct tgg att ggt aac ttc tct gca aat ctg gaa aag tta cat ctt ggt      528
Ala Trp Ile Gly Asn Phe Ser Ala Asn Leu Glu Lys Leu His Leu Gly
                165                 170                 175

ttc tgt tca ttc agt ggt ggc ata cct gag agc ttg ctt tac atg aag      576
Phe Cys Ser Phe Ser Gly Gly Ile Pro Glu Ser Leu Leu Tyr Met Lys
            180                 185                 190

tcc ctc aag tat ttg gac ctt gag aac aat ctc ttg ttt ggt aat ttg      624
Ser Leu Lys Tyr Leu Asp Leu Glu Asn Asn Leu Leu Phe Gly Asn Leu
        195                 200                 205

gtt gat ttt caa cag cct ttg gtt ttg ctc aat ctt gct tcc aat cag      672
Val Asp Phe Gln Gln Pro Leu Val Leu Leu Asn Leu Ala Ser Asn Gln
    210                 215                 220

ttt gct ggt act ttg cct tgc ttt gca gct tca gtt cag tct cta act      720
Phe Ala Gly Thr Leu Pro Cys Phe Ala Ala Ser Val Gln Ser Leu Thr
225                 230                 235                 240

gtg ttg aat ttg tcc aac aat tct att gcg ggg gga ttg cct gct tgt      768
Val Leu Asn Leu Ser Asn Asn Ser Ile Ala Gly Gly Leu Pro Ala Cys
                245                 250                 255

att gct tct ttt caa gct ttg act cat ttg aac ctt tca ggg aac cat      816
Ile Ala Ser Phe Gln Ala Leu Thr His Leu Asn Leu Ser Gly Asn His
            260                 265                 270

ttg aag tat aga ata tat cct agg ctt gtg ttc tca gag aaa ctt ctt      864
Leu Lys Tyr Arg Ile Tyr Pro Arg Leu Val Phe Ser Glu Lys Leu Leu
        275                 280                 285

gtt ttg gac ttg agt aat aat gct tta tct ggt cct att ccc agt aaa      912
Val Leu Asp Leu Ser Asn Asn Ala Leu Ser Gly Pro Ile Pro Ser Lys
    290                 295                 300

att gct gag act act gac aaa ctt ggc ctt gtt ctt ctt gac ctt tct      960
Ile Ala Glu Thr Thr Asp Lys Leu Gly Leu Val Leu Leu Asp Leu Ser
305                 310                 315                 320

cac aat cag ttc tct ggt gaa ata cct gtg aaa att act gag ttg aaa     1008
His Asn Gln Phe Ser Gly Glu Ile Pro Val Lys Ile Thr Glu Leu Lys
                325                 330                 335

agc ttg cag gcc ttg ttt ctc tct cac aat ctt ctc tca gga gaa att     1056
Ser Leu Gln Ala Leu Phe Leu Ser His Asn Leu Leu Ser Gly Glu Ile
            340                 345                 350

cct gct aga att gga aat ttg act tat ctg cag gtc att gat ctc tca     1104
Pro Ala Arg Ile Gly Asn Leu Thr Tyr Leu Gln Val Ile Asp Leu Ser
        355                 360                 365

cac aac tct ttg tct gga acc att cca ttc agt att gtt ggg tgc ttt     1152
His Asn Ser Leu Ser Gly Thr Ile Pro Phe Ser Ile Val Gly Cys Phe
    370                 375                 380

cag ctg tat gct ctg ata ctt aac aac aac aat ctt tct ggt gta att     1200
Gln Leu Tyr Ala Leu Ile Leu Asn Asn Asn Asn Leu Ser Gly Val Ile
385                 390                 395                 400

caa ccg gag ttt gat gcg ttg gat atc ttg agg ata ctg gat ata agc     1248
Gln Pro Glu Phe Asp Ala Leu Asp Ile Leu Arg Ile Leu Asp Ile Ser
                405                 410                 415

aac aac agg ttt tcc ggg gct atc cca ctc act ttg gct gga tgc aaa     1296
Asn Asn Arg Phe Ser Gly Ala Ile Pro Leu Thr Leu Ala Gly Cys Lys
            420                 425                 430

tct ttg gag att gta gac ttt agt tcc aat gag ctt tct gga tcg ttg     1344
Ser Leu Glu Ile Val Asp Phe Ser Ser Asn Glu Leu Ser Gly Ser Leu
        435                 440                 445
```

```
aat gat gca ata acc aaa tgg aca aac ctc agg tat ttg tct ctt gct      1392
Asn Asp Ala Ile Thr Lys Trp Thr Asn Leu Arg Tyr Leu Ser Leu Ala
    450                 455                 460

cag aac aag ttc agt gaa aat ctg cct agt tgg ttg ttc aca ttt aac      1440
Gln Asn Lys Phe Ser Glu Asn Leu Pro Ser Trp Leu Phe Thr Phe Asn
465                 470                 475                 480

gca ata gaa atg atg gat ttc tcg cat aac aag ttt act ggc ttc ata      1488
Ala Ile Glu Met Met Asp Phe Ser His Asn Lys Phe Thr Gly Phe Ile
                485                 490                 495

ccg gat att aat ttt aag ggt agc tta ata ttt aac act agg aat gtc      1536
Pro Asp Ile Asn Phe Lys Gly Ser Leu Ile Phe Asn Thr Arg Asn Val
            500                 505                 510

act gtt aaa gag cca ttg gtt gca gca aga aag gtt caa ctc aga gtt      1584
Thr Val Lys Glu Pro Leu Val Ala Ala Arg Lys Val Gln Leu Arg Val
        515                 520                 525

tcg gcg gtt gtt tct gat agc aat caa ctc agt ttc act tat gat ctt      1632
Ser Ala Val Val Ser Asp Ser Asn Gln Leu Ser Phe Thr Tyr Asp Leu
    530                 535                 540

tcc tca atg gtt gga att gat cta tcc agc aac tcg ctt cat ggg gaa      1680
Ser Ser Met Val Gly Ile Asp Leu Ser Ser Asn Ser Leu His Gly Glu
545                 550                 555                 560

att cca agg ggc tta ttt ggt cta tct ggc cta gaa tat ctg aat ttg      1728
Ile Pro Arg Gly Leu Phe Gly Leu Ser Gly Leu Glu Tyr Leu Asn Leu
                565                 570                 575

tca tgc aac ttt ctt tac gga cag ctt ccg ggg ttg cag aaa atg cag      1776
Ser Cys Asn Phe Leu Tyr Gly Gln Leu Pro Gly Leu Gln Lys Met Gln
            580                 585                 590

agt ttg aaa gcc ttg gat ttg tca cat aat tcc ttg tca gga cat atc      1824
Ser Leu Lys Ala Leu Asp Leu Ser His Asn Ser Leu Ser Gly His Ile
        595                 600                 605

cca gga aac atc tct atc ctt caa gat ctg tct att ttg aat ctt tcc      1872
Pro Gly Asn Ile Ser Ile Leu Gln Asp Leu Ser Ile Leu Asn Leu Ser
    610                 615                 620

tac aac tgc ttt tct gga tgt gtt ccc cag aag caa ggg tat ggg aga      1920
Tyr Asn Cys Phe Ser Gly Cys Val Pro Gln Lys Gln Gly Tyr Gly Arg
625                 630                 635                 640

ttt cct ggt gca ttt gct gga aat cca gat ctg tgc atg gaa tct tcc      1968
Phe Pro Gly Ala Phe Ala Gly Asn Pro Asp Leu Cys Met Glu Ser Ser
                645                 650                 655

agt gga tta tgt gat gat gga agg act caa tct gcg caa gga agt act      2016
Ser Gly Leu Cys Asp Asp Gly Arg Thr Gln Ser Ala Gln Gly Ser Thr
            660                 665                 670

ttt agg gaa gat agg atg gat gac cca att tct gtg ggg att ttc ttt      2064
Phe Arg Glu Asp Arg Met Asp Asp Pro Ile Ser Val Gly Ile Phe Phe
        675                 680                 685

atc agt gca ttt gtt agt ttt gat ttt ggt gtt gtg gtt ctc ttc tgt      2112
Ile Ser Ala Phe Val Ser Phe Asp Phe Gly Val Val Val Leu Phe Cys
    690                 695                 700

tcc gca cgg gca aga aat tac att ctc caa aca aaa gtt tga              2154
Ser Ala Arg Ala Arg Asn Tyr Ile Leu Gln Thr Lys Val
705                 710                 715


<210> SEQ ID NO 37
<211> LENGTH: 717
<212> TYPE: PRT
<213> ORGANISM: Glycine max

<400> SEQUENCE: 37

Met Val Met Gly His Thr Thr Pro Leu Thr Leu Leu Cys Met Ile Leu
1               5                   10                  15
```

-continued

```
Leu Phe Ala Thr Pro Ser Leu Ser Ile Asp Val His Pro Gln Asp Arg
            20                  25                  30

Ile Ser Leu Ser Leu Phe Arg Ser Ser Leu Pro Asn Pro Asn Gln Ser
        35                  40                  45

Leu Pro Ser Trp Val Gly Ser Asn Cys Thr Ser Trp Ser Gly Ile Thr
    50                  55                  60

Cys Asp Ser Arg Thr Gly Arg Val Leu Ser Ile Asn Leu Thr Ser Met
65                  70                  75                  80

Asn Leu Ser Gly Lys Ile His Pro Ser Leu Cys His Leu Ser Tyr Leu
                85                  90                  95

Asn Lys Leu Gly Leu Ser His Asn Asn Phe Thr Ala Pro Leu Pro Glu
            100                 105                 110

Cys Phe Gly Asn Leu Leu Asn Leu Arg Ala Ile Asp Leu Ser His Asn
        115                 120                 125

Arg Phe His Gly Gly Ile Pro Asp Ser Phe Met Arg Leu Arg His Leu
    130                 135                 140

Thr Glu Leu Val Phe Ser Gly Asn Pro Gly Leu Gly Gly Pro Leu Pro
145                 150                 155                 160

Ala Trp Ile Gly Asn Phe Ser Ala Asn Leu Glu Lys Leu His Leu Gly
                165                 170                 175

Phe Cys Ser Phe Ser Gly Gly Ile Pro Glu Ser Leu Leu Tyr Met Lys
            180                 185                 190

Ser Leu Lys Tyr Leu Asp Leu Glu Asn Asn Leu Leu Phe Gly Asn Leu
        195                 200                 205

Val Asp Phe Gln Gln Pro Leu Val Leu Leu Asn Leu Ala Ser Asn Gln
    210                 215                 220

Phe Ala Gly Thr Leu Pro Cys Phe Ala Ala Ser Val Gln Ser Leu Thr
225                 230                 235                 240

Val Leu Asn Leu Ser Asn Asn Ser Ile Ala Gly Gly Leu Pro Ala Cys
                245                 250                 255

Ile Ala Ser Phe Gln Ala Leu Thr His Leu Asn Leu Ser Gly Asn His
            260                 265                 270

Leu Lys Tyr Arg Ile Tyr Pro Arg Leu Val Phe Ser Glu Lys Leu Leu
        275                 280                 285

Val Leu Asp Leu Ser Asn Asn Ala Leu Ser Gly Pro Ile Pro Ser Lys
    290                 295                 300

Ile Ala Glu Thr Thr Asp Lys Leu Gly Leu Val Leu Leu Asp Leu Ser
305                 310                 315                 320

His Asn Gln Phe Ser Gly Glu Ile Pro Val Lys Ile Thr Glu Leu Lys
                325                 330                 335

Ser Leu Gln Ala Leu Phe Leu Ser His Asn Leu Leu Ser Gly Glu Ile
            340                 345                 350

Pro Ala Arg Ile Gly Asn Leu Thr Tyr Leu Gln Val Ile Asp Leu Ser
        355                 360                 365

His Asn Ser Leu Ser Gly Thr Ile Pro Phe Ser Ile Val Gly Cys Phe
    370                 375                 380

Gln Leu Tyr Ala Leu Ile Leu Asn Asn Asn Asn Leu Ser Gly Val Ile
385                 390                 395                 400

Gln Pro Glu Phe Asp Ala Leu Asp Ile Leu Arg Ile Leu Asp Ile Ser
                405                 410                 415

Asn Asn Arg Phe Ser Gly Ala Ile Pro Leu Thr Leu Ala Gly Cys Lys
            420                 425                 430
```

-continued

```
Ser Leu Glu Ile Val Asp Phe Ser Ser Asn Glu Leu Ser Gly Ser Leu
        435                 440                 445

Asn Asp Ala Ile Thr Lys Trp Thr Asn Leu Arg Tyr Leu Ser Leu Ala
    450                 455                 460

Gln Asn Lys Phe Ser Glu Asn Leu Pro Ser Trp Leu Phe Thr Phe Asn
465                 470                 475                 480

Ala Ile Glu Met Met Asp Phe Ser His Asn Lys Phe Thr Gly Phe Ile
                485                 490                 495

Pro Asp Ile Asn Phe Lys Gly Ser Leu Ile Phe Asn Thr Arg Asn Val
            500                 505                 510

Thr Val Lys Glu Pro Leu Val Ala Ala Arg Lys Val Gln Leu Arg Val
        515                 520                 525

Ser Ala Val Val Ser Asp Ser Asn Gln Leu Ser Phe Thr Tyr Asp Leu
    530                 535                 540

Ser Ser Met Val Gly Ile Asp Leu Ser Ser Asn Ser Leu His Gly Glu
545                 550                 555                 560

Ile Pro Arg Gly Leu Phe Gly Leu Ser Gly Leu Glu Tyr Leu Asn Leu
                565                 570                 575

Ser Cys Asn Phe Leu Tyr Gly Gln Leu Pro Gly Leu Gln Lys Met Gln
            580                 585                 590

Ser Leu Lys Ala Leu Asp Leu Ser His Asn Ser Leu Ser Gly His Ile
        595                 600                 605

Pro Gly Asn Ile Ser Ile Leu Gln Asp Leu Ser Ile Leu Asn Leu Ser
    610                 615                 620

Tyr Asn Cys Phe Ser Gly Cys Val Pro Gln Lys Gln Gly Tyr Gly Arg
625                 630                 635                 640

Phe Pro Gly Ala Phe Ala Gly Asn Pro Asp Leu Cys Met Glu Ser Ser
                645                 650                 655

Ser Gly Leu Cys Asp Asp Gly Arg Thr Gln Ser Ala Gln Gly Ser Thr
            660                 665                 670

Phe Arg Glu Asp Arg Met Asp Asp Pro Ile Ser Val Gly Ile Phe Phe
        675                 680                 685

Ile Ser Ala Phe Val Ser Phe Asp Phe Gly Val Val Val Leu Phe Cys
    690                 695                 700

Ser Ala Arg Ala Arg Asn Tyr Ile Leu Gln Thr Lys Val
705                 710                 715
```

<210> SEQ ID NO 38
<211> LENGTH: 8656
<212> TYPE: DNA
<213> ORGANISM: Glycine max

<400> SEQUENCE: 38

```
gcacccactg ggtaagttgg taactactat gtatctatat atcgtcaggt cattgtctgt      60

ttcattctct tctcacaaga acaaaatggt aatttacatt taacttagaa atgtttggga     120

cagaacctct agcttgcgat gattctcttc tcacaagaac aaaatggtaa tttacattta     180

actttagaaa tgtttgggac cgaacctcta gcttgcgatg attctcttct cacaagaaca     240

aaatggtaat ttacatttaa ctttagaaat gtttgggacc gaaccactag cttgcgatga     300

ttcccttctc acaagaacaa aatggtaatt tacatttaac ttagaaatgt ttgggacaga     360

accactggct tgcgatgatt ctcttctcac aagaacaaaa tggtaatttg catttaactt     420

agaaatgatt gggacagaac cactagcttc gatgaataat ttgctttaat ttttattaat     480

gcataatacc cttttattgt cacacataga atccgattct gcaataacta gtgcttgatc     540
```

```
ctaattgaca gaacaaatta aaacagagaa ttgatgcttt ggcttttcca tgggcaataa    600
ttatcccaat gatatactaa agcatagtaa ctaggaagac ttccatgtaa agaaactttc    660
ttttattctc cttttaaaat ttggtgaatc acttaaaacc acttttgttt cattccaagg    720
ttaggctcat ggaaagctta aacctactta actggtcacg aagagattgc atctttgttt    780
tcacaaaagt ctaactccaa gttcgtgtag ctagtattgc atgctaccat ggtgcaagtg    840
atgtacatgc atatatgata ttcaatttaa tttgctacta taatataaag gtgtatatat    900
aaatagagag tgcatgaggt gtgtggtgtc aacatataag gacgcagcaa aggtataata    960
gcgactactg cgaagcaaga tcagagacta gagagacatg ataagaagtt gttaatttgt   1020
tttcttcata tggctgcgcg tggcaacgtg ctcttcgttc actgacatgg atgcgctgct   1080
gaagctgaag gactccatga ctggaagttt tccacgtcgc tttctgcaca ctgtttcttt   1140
tcaggcgtaa actgcgacca agaacttcga gtcgttgcta tcaatgtctc gtttgttcct   1200
cttttcggct accttccgcc ggagatcgga caattggaca aactcgagaa cctcacttcc   1260
ctcaagctcc tcgacatctc tcacaacgtc ttctccggcc aaattattct tccgatgacg   1320
aaactggagg tcctcgacgt ctacgacaac aacttccggc agcataccgg agatttactc   1380
ggagtttaag agcttggagt ttttaagctt aagcaccaat aacttatcgg ggaagattcc   1440
gaagagtttg tctaagttga agacgctgag gtatctcaaa ctcggataca acaacgctta   1500
cgaaggtgaa attccaccgg agtttggcag cataaaatct gagatacctt gacctcatcg   1560
gcgagattcc acctactcta aacaataata agaaaaactt atcacatttc ttgaaacttt   1620
aaaagaccga taaaaataaa aggaggaaat gccactacaa tatttttaat ttattttttt   1680
tacttatttt atttgaatct ttaatacata tgctatttta gcattataaa aatacctggg   1740
ctatacaaaa tatacttgct agtagtatta tgtgtgtgtg aaagttaaat gagtctttaa   1800
gtatttgtaa atgtttaata agtttcgagg tttatcttga ttccaacaat gaattcctga   1860
aatctaattt atctaacttt tttttaacca aaatgttaaa tggtctagtt aagagaacaa   1920
atccttatgt gttcattttt tcacaagacc taaaatctaa aatttcactt taaaagaaac   1980
aaaatacttg ctacttgaac taacaatcat tagtacattt ttttagtaat gatatacaaa   2040
catctaaaac tcctatacaa cacaacacat agaagacaat aaaaaatatc aatatgataa   2100
ataaaaatga gaaatagatg aattatttaa aataatgaaa tgtttattta tcattacttt   2160
tttttacttt aacagttcat acatctccta caaggtaaga tgtgtaatgc aagtaagttg   2220
caacatggtt ttaaatttttg acaataagaa ccatgcatgt taattagtct aatcacagag   2280
cgttcgggat acgccattag tggtctatag tagtcaactg ccgggataaa tcacgatcca   2340
catttcatag gtgtttccac catgtcaaca tcgaactaaa aggaaaaata tgtgaatggg   2400
taaaaatgat taaaaatatt tgtaaaaaat tatttgaatt tatttaaaac aatatgcaag   2460
ttgtttatag gttgagtata tttcaatggt ttttgaaaaa tctatgtaaa taaaaaaaat   2520
acaattattt atataaaata aaataatctt ttttttatta ttatgacatt gatgagagta   2580
tctaataatt tgacccataa ctaatttgga taaaaaaaaa tctgattgac cacttttaat   2640
ttaatgtatc actaaactaa atacccttttt ttaaaatagt ctaaacatga attaaatatt   2700
caaaagaaat attttacttg agattattac ctaatattaa tgataatttc attcaactcc   2760
aataaaatta attttcatgt aagatatatc taaaagaaaa gatatatata aattttattt   2820
tcactagtaa aaaaaagttg atctagttag tgaaaaacca actcatatcc tataagaata   2880
```

-continued

```
tgaatttgat ttttttgtt aaggtgagaa ttttattgat caataattta taaatatcta   2940

tataaataat ctttagcctt atgagtcctt aggtcaattc aactcaccta aattttttat   3000

tatgaaaaaa aaaattgtat cttcacaaga taaatgtgtt ggattcaatc actccttatt   3060

agcttaatta gattataatt gtagtcccct atatatatat atgtatcatc ttgtcaaata   3120

ataatgaaat atagaattta tttagactta gagaataaaa ttaaaaactg tctgccatga   3180

aaaaagacga agttaagaaa agggccaatc atagaagatt tttatgggca cttcacggac   3240

actaactcac tgtcacaatc atcactgggg ttgacaaaag gacaatatga aacacttttg   3300

agaagcatgt accactcatc catttatcag tggctcccaa ttcccagagg ccagaactat   3360

atatgaaaga attgttgaac gcacgggcat gaacccattc ttgaagcatc attgtgtgag   3420

aatatcttga ccttgtaaga tgcaacacct ttttaagcct taaatttaaa aaaggaaaaa   3480

agaaaaatct tgtctctact ttcttttagc acaagtgtat agaaattctt aaatatatac   3540

actctccttt atattgtagt atcagtggcg caaatcatta tatttcattt ttaataataa   3600

aattaagagc attaatttta tagttaaaat tgaaaataaa gataatttac agaactcatt   3660

tgacttaaac tgacaaaata tatatatata tatatatata tatatatata tatattgtga   3720

gatgaacatg ttactttttt aacatgcaaa aaggagaata tattttacat gcatgcaccc   3780

atgataactt ctatgtatat atccatacaa tacatcgttc gtatatcgtc tcgtttgtct   3840

ttattctcct ctcaaaatac gacaatagca atttacattt ttttttataa gcaaatagta   3900

atttacattt aacttagtaa tgtagggatc gaacataacc acttgcgatg aataatttgc   3960

tttaaatttt tgttgatgcg taccctttaa ctgtcactca tggaatacga ttcttcaata   4020

tctagtgctt gatcgttgac agaacaactt aaaacagaga attgatgttt tggcttttcc   4080

atggataata attatcccag tgacatacca aagcatagta gctaagaaga ctttcacgta   4140

aaaaaaagtt tcttttattc cctttttaa tttggtgaat cacaaaaaac cacttttgtt   4200

tggttccaaa gttaggctca tggaaagttt aaacctccat agaatggtca cgaagagatt   4260

gcatctttgt cttcacaaaa gctaactcca cgttgagtag acttaacagc cagtggcgaa   4320

tagcaaggat atttcattaa ttatacgcca ccggccaaat gttaaccaat cgtattataa   4380

ttaagttcca tcatcatcaa acaatttagt aaagtgcatg acccaaattt ctacgataca   4440

tatttattta ttaaaaatgt aagaatattt cagtcatatt taaaaatata tatatcaaga   4500

ataattaact ttgtacacac gcactgaata aaagatttgt gacagacaag gcttgcataa   4560

aaatttctcc tctaaactaa ttgcttgtag gacctctccc accactatag aatcaatata   4620

attaatccgc attagaaagt tatattgtat acaattttct tgaaacataa ttatacttca   4680

tgtttcacag acttatagtg gatcttgtgt ggctagctac tgatgaatat tgtttttttt   4740

ttttcctaag catccacttt gaacaacttt tcccatttca tacaaacaga attaattagt   4800

attgcgtgcc accatatggt acagtgttgt acatgcatat aagctattta atttaataat   4860

atacaaacat aacggtgtat ataaatagag gcagcatgtg gtgtgtggtg taaaaataag   4920

gacgcaggca aatgtatgca tttggcataa gtatataaga gagagggagt agtactactg   4980

caaagcaaaa tcagagagac atgagaagct gtgtgtgcta cacgctatta ttgtttattt   5040

tcttcatatg gctgcgcgtg gcaacgtgct cttcgttcac tgacatggaa tcgcttctga   5100

agctgaagga ctccatgaaa ggagataaag ccaaagacga cgctctccat gactggaagt   5160

ttttcccctc gctttctgca cactgtttct tttcaggcgt aaaatgcgac cgagaacttc   5220

gagtcgttgc tatcaacgtc tcgtttgttc ctctcttcgg tcaccttccg ccggagatcg   5280
```

-continued

```
gacaattgga caaactcgag aacctcaccg tctcgcagaa caacctcacc ggcgtacttc   5340
ccaaggagct cgccgccctc acttccctca agcacctcaa catctctcac aacgtcttct   5400
ccggccattt ccccggccaa attatccttc cgatgacgaa actggaggtc ctcgacgtct   5460
acgacaacaa cttcaccgga ccgcttcccg tagagttggt gaaactggag aaattaaaat   5520
acctgaagct cgacggaaac tatttctccg gcagcatacc ggagagttac tcggagttta   5580
agagcttgga gtttttaagc ttaagcacca atagcttatc ggggaagatt cccaagagtt   5640
tgtcgaagtt gaagacgctg aggtacctaa aactcggata caacaacgct tacgaaggtg   5700
gaattccacc ggagtttggc agcatgaaat ctctgagata ccttgacctc tctagctgca   5760
acctcagcgg cgagattcca ccgagccttg caaatctgac aaaccttgac acgttgttcc   5820
tgcaaattaa caacctcacc ggaaccattc cgtcggagct ctccgctatg gtgagcctca   5880
tgtcacttga tctctccatc aacgacctca ccggtgagat accgatgagc ttctcacagc   5940
ttagaaacct cactctcatg aacttcttcc aaaacaatct tcgcggctca gttccgtcct   6000
tcgtcggcga gcttccgaat ctggaaacgc tgcagctctg ggataacaac ttctccttcg   6060
tgctacctcc gaaccttggg caaaacggca agttaaagtt cttcgacgtc atcaagaatc   6120
acttcaccgg gttgatccct cgagatttgt gtaagagtgg gaggttacaa acgatcatga   6180
tcacagataa cttcttccgc ggtccaatcc ctaacgagat tggtaactgc aagtctctca   6240
ccaagatccg agcctccaat aactacctta acggcgtggt tccgtcaggg attttcaaac   6300
taccttctgt cacgataatc gagctggcca ataaccgttt taacggcgaa ctgcctcctg   6360
agatttccgg cgaatccctg ggattctca ctctttccaa caacttattc agtgggaaaa   6420
ttcccccagc gttgaagaac ttgagggcac tgcagactct ctcacttgac gcaaacgagt   6480
tcgttggaga aataccggga gaggtttttg acctaccgat gctgactgtg gtcaacataa   6540
gcggcaacaa tctaaccgga ccaatcccaa cgacgttgac tcgctgcgtt tcactcaccg   6600
ccgtggacct cagccggaac atgcttgaag ggaagattcc gaagggaatc aaaaacctca   6660
cggacttgag cattttcaat gtgtcgataa accaaatttc agggccagtc cctgaggaga   6720
ttcgcttcat gttgagtctc accacattgg atctatccaa caacaatttc atcggcaagg   6780
tcccaaccgg gggtcagttc gcggtcttca gcgagaaatc ctttgcaggg aaccccaacc   6840
tctgtacctc ccactcttgc ccgaattcct cgttgtaccc tgacgacgcc ttgaagaaga   6900
ggcgcggccc ttggagtttg aaatccacga gggtgatagt catcgtgatt gcactgggca   6960
cagccgcgct gctggtggcg gtgacggtgt acatgatgag gaggaggaag atgaaccttg   7020
cgaagacgtg gaagctgacg gcgttccagc ggctgaactt caaagccgag gacgtggtgg   7080
agtgtctgaa ggaggagaac ataataggaa aaggaggggc agggatcgtg taccgcgggt   7140
ccatgccaaa cggaacagac gtggcgataa agcggttggt tggggcgggg agtggaagga   7200
acgattacgg attcaaagcg gagatagaaa cgctggggaa gataaggcac aggaacataa   7260
tgaggctttt aggttacgtg tcgaacaagg agacgaactt gctgctgtat gagtacatgc   7320
caaatgggag cttaggggaa tggctgcatg gtgccaaagg agggcacttg aagtgggaaa   7380
tgaggtacaa gattgcggtg gaagctgcta agggactgtg ctatttgcac catgattgtt   7440
cccctcttat cattcacagg gatgtcaagt ctaataatat attgctggat ggggacttgg   7500
aggcccatgt tgctgatttt ggccttgcca agttcttgta cgaccctggc gcctctcagt   7560
ccatgtcctc cattgctggc tcctacggct acattgctcc aggttccatt cattattatt   7620
```

-continued

```
ttctcttttc cttcttcata atcttaatat accatgcaga taacgtacaa catgcatact   7680

tatacatata attttatcct ttcaacatat aatcaaatat ttcatatcta ataataccaa   7740

cttcatatta taaacatcac ctaatataat caacatgact tgataaataa gacatataag   7800

ttcaatattt aaactcatgt gtctgaaaaa acattaattg gaaaagtcac tcttaaaaat   7860

atttgataat atatcaatat gaccatatga ttccaattac gatcacaaac tctgttaaaa   7920

attcttgctg aagatattag tccttgaata ctaatataag aatatcttgg gttagaaaag   7980

ttactatttt actgttaatt cccgtttact ttagatgggt tggaagttga aaagttgagt   8040

gatttaattt gtttctggtg gttgcgcaga gtatgcatac actttgaaag tggacgagaa   8100

aagtgatgtg tacagctttg gcgttgtgct gctggagctg ataataggga ggaagccagt   8160

gggagagttt ggagacgggg tggacatcgt tggatgggtc aacaaaacga gattggagct   8220

cgctcagccg tcggatgcag cgttggtgtt ggcagtggtg gacccaaggt tgagtgggta   8280

tccattgaca agtgtcattt acatgttcaa catagctatg atgtgtgtta aagaaatggg   8340

gcccgctagg cctaccatga gggaagtcgt tcatatgctc tcagagcctc ctcactctgc   8400

tactcacact cacaacctaa ttaatctcta gttaattaag ttatttgctc atcgatccag   8460

aatcacttct tttcaaaata aattaacaca gacgaaaact gtaggaataa ctttcatctg   8520

ttgtttgtcg gaagtgaaac aacgaatcaa atgtgaacta tgtatcaaat gtaagatagg   8580

ttttaattaa ttttgtaata ttggtgtcaa ctgtcaagta attcgaagga ttttccccat   8640

tgtgcatgta tcaaga                                                    8656


<210> SEQ ID NO 39
<211> LENGTH: 2964
<212> TYPE: DNA
<213> ORGANISM: Glycine max
<220> FEATURE:
<221> NAME/KEY: CDS
<222> LOCATION: (1)..(2964)

<400> SEQUENCE: 39

atg aga agc tgt gtg tgc tac acg cta tta ttg ttt att ttc ttc ata       48
Met Arg Ser Cys Val Cys Tyr Thr Leu Leu Leu Phe Ile Phe Phe Ile
1               5                   10                  15

tgg ctg cgc gtg gca acg tgc tct tcg ttc act gac atg gaa tcg ctt       96
Trp Leu Arg Val Ala Thr Cys Ser Ser Phe Thr Asp Met Glu Ser Leu
            20                  25                  30

ctg aag ctg aag gac tcc atg aaa gga gat aaa gcc aaa gac gac gct      144
Leu Lys Leu Lys Asp Ser Met Lys Gly Asp Lys Ala Lys Asp Asp Ala
        35                  40                  45

ctc cat gac tgg aag ttt ttc ccc tcg ctt tct gca cac tgt ttc ttt      192
Leu His Asp Trp Lys Phe Phe Pro Ser Leu Ser Ala His Cys Phe Phe
    50                  55                  60

tca ggc gta aaa tgc gac cga gaa ctt cga gtc gtt gct atc aac gtc      240
Ser Gly Val Lys Cys Asp Arg Glu Leu Arg Val Val Ala Ile Asn Val
65                  70                  75                  80

tcg ttt gtt cct ctc ttc ggt cac ctt ccg ccg gag atc gga caa ttg      288
Ser Phe Val Pro Leu Phe Gly His Leu Pro Pro Glu Ile Gly Gln Leu
                85                  90                  95

gac aaa ctc gag aac ctc acc gtc tcg cag aac aac ctc acc ggc gta      336
Asp Lys Leu Glu Asn Leu Thr Val Ser Gln Asn Asn Leu Thr Gly Val
            100                 105                 110

ctt ccc aag gag ctc gcc gcc ctc act tcc ctc aag cac ctc aac atc      384
Leu Pro Lys Glu Leu Ala Ala Leu Thr Ser Leu Lys His Leu Asn Ile
        115                 120                 125
```

-continued

```
tct cac aac gtc ttc tcc ggc cat ttc ccc ggc caa att atc ctt ccg      432
Ser His Asn Val Phe Ser Gly His Phe Pro Gly Gln Ile Ile Leu Pro
    130                 135                 140

atg acg aaa ctg gag gtc ctc gac gtc tac gac aac aac ttc acc gga      480
Met Thr Lys Leu Glu Val Leu Asp Val Tyr Asp Asn Asn Phe Thr Gly
145                 150                 155                 160

ccg ctt ccc gta gag ttg gtg aaa ctg gag aaa tta aaa tac ctg aag      528
Pro Leu Pro Val Glu Leu Val Lys Leu Glu Lys Leu Lys Tyr Leu Lys
                165                 170                 175

ctc gac gga aac tat ttc tcc ggc agc ata ccg gag agt tac tcg gag      576
Leu Asp Gly Asn Tyr Phe Ser Gly Ser Ile Pro Glu Ser Tyr Ser Glu
            180                 185                 190

ttt aag agc ttg gag ttt tta agc tta agc acc aat agc tta tcg ggg      624
Phe Lys Ser Leu Glu Phe Leu Ser Leu Ser Thr Asn Ser Leu Ser Gly
        195                 200                 205

aag att ccc aag agt ttg tcg aag ttg aag acg ctg agg tac cta aaa      672
Lys Ile Pro Lys Ser Leu Ser Lys Leu Lys Thr Leu Arg Tyr Leu Lys
    210                 215                 220

ctc gga tac aac aac gct tac gaa ggt gga att cca ccg gag ttt ggc      720
Leu Gly Tyr Asn Asn Ala Tyr Glu Gly Gly Ile Pro Pro Glu Phe Gly
225                 230                 235                 240

agc atg aaa tct ctg aga tac ctt gac ctc tct agc tgc aac ctc agc      768
Ser Met Lys Ser Leu Arg Tyr Leu Asp Leu Ser Ser Cys Asn Leu Ser
                245                 250                 255

ggc gag att cca ccg agc ctt gca aat ctg aca aac ctt gac acg ttg      816
Gly Glu Ile Pro Pro Ser Leu Ala Asn Leu Thr Asn Leu Asp Thr Leu
            260                 265                 270

ttc ctg caa att aac aac ctc acc gga acc att ccg tcg gag ctc tcc      864
Phe Leu Gln Ile Asn Asn Leu Thr Gly Thr Ile Pro Ser Glu Leu Ser
        275                 280                 285

gct atg gtg agc ctc atg tca ctt gat ctc tcc atc aac gac ctc acc      912
Ala Met Val Ser Leu Met Ser Leu Asp Leu Ser Ile Asn Asp Leu Thr
    290                 295                 300

ggt gag ata ccg atg agc ttc tca cag ctt aga aac ctc act ctc atg      960
Gly Glu Ile Pro Met Ser Phe Ser Gln Leu Arg Asn Leu Thr Leu Met
305                 310                 315                 320

aac ttc ttc caa aac aat ctt cgc ggc tca gtt ccg tcc ttc gtc ggc     1008
Asn Phe Phe Gln Asn Asn Leu Arg Gly Ser Val Pro Ser Phe Val Gly
                325                 330                 335

gag ctt ccg aat ctg gaa acg ctg cag ctc tgg gat aac aac ttc tcc     1056
Glu Leu Pro Asn Leu Glu Thr Leu Gln Leu Trp Asp Asn Asn Phe Ser
            340                 345                 350

ttc gtg cta cct ccg aac ctt ggg caa aac ggc aag tta aag ttc ttc     1104
Phe Val Leu Pro Pro Asn Leu Gly Gln Asn Gly Lys Leu Lys Phe Phe
        355                 360                 365

gac gtc atc aag aat cac ttc acc ggg ttg atc cct cga gat ttg tgt     1152
Asp Val Ile Lys Asn His Phe Thr Gly Leu Ile Pro Arg Asp Leu Cys
    370                 375                 380

aag agt ggg agg tta caa acg atc atg atc aca gat aac ttc ttc cgc     1200
Lys Ser Gly Arg Leu Gln Thr Ile Met Ile Thr Asp Asn Phe Phe Arg
385                 390                 395                 400

ggt cca atc cct aac gag att ggt aac tgc aag tct ctc acc aag atc     1248
Gly Pro Ile Pro Asn Glu Ile Gly Asn Cys Lys Ser Leu Thr Lys Ile
                405                 410                 415

cga gcc tcc aat aac tac ctt aac ggc gtg gtt ccg tca ggg att ttc     1296
Arg Ala Ser Asn Asn Tyr Leu Asn Gly Val Val Pro Ser Gly Ile Phe
            420                 425                 430

aaa cta cct tct gtc acg ata atc gag ctg gcc aat aac cgt ttt aac     1344
Lys Leu Pro Ser Val Thr Ile Ile Glu Leu Ala Asn Asn Arg Phe Asn
        435                 440                 445
```

```
ggc gaa ctg cct cct gag att tcc ggc gaa tcc ctg ggg att ctc act      1392
Gly Glu Leu Pro Pro Glu Ile Ser Gly Glu Ser Leu Gly Ile Leu Thr
    450                 455                 460

ctt tcc aac aac tta ttc agt ggg aaa att ccc cca gcg ttg aag aac      1440
Leu Ser Asn Asn Leu Phe Ser Gly Lys Ile Pro Pro Ala Leu Lys Asn
465                 470                 475                 480

ttg agg gca ctg cag act ctc tca ctt gac gca aac gag ttc gtt gga      1488
Leu Arg Ala Leu Gln Thr Leu Ser Leu Asp Ala Asn Glu Phe Val Gly
                485                 490                 495

gaa ata ccg gga gag gtt ttt gac cta ccg atg ctg act gtg gtc aac      1536
Glu Ile Pro Gly Glu Val Phe Asp Leu Pro Met Leu Thr Val Val Asn
            500                 505                 510

ata agc ggc aac aat cta acc gga cca atc cca acg acg ttg act cgc      1584
Ile Ser Gly Asn Asn Leu Thr Gly Pro Ile Pro Thr Thr Leu Thr Arg
        515                 520                 525

tgc gtt tca ctc acc gcc gtg gac ctc agc cgg aac atg ctt gaa ggg      1632
Cys Val Ser Leu Thr Ala Val Asp Leu Ser Arg Asn Met Leu Glu Gly
    530                 535                 540

aag att ccg aag gga atc aaa aac ctc acg gac ttg agc att ttc aat      1680
Lys Ile Pro Lys Gly Ile Lys Asn Leu Thr Asp Leu Ser Ile Phe Asn
545                 550                 555                 560

gtg tcg ata aac caa att tca ggg cca gtc cct gag gag att cgc ttc      1728
Val Ser Ile Asn Gln Ile Ser Gly Pro Val Pro Glu Glu Ile Arg Phe
                565                 570                 575

atg ttg agt ctc acc aca ttg gat cta tcc aac aac aat ttc atc ggc      1776
Met Leu Ser Leu Thr Thr Leu Asp Leu Ser Asn Asn Asn Phe Ile Gly
            580                 585                 590

aag gtc cca acc ggg ggt cag ttc gcg gtc ttc agc gag aaa tcc ttt      1824
Lys Val Pro Thr Gly Gly Gln Phe Ala Val Phe Ser Glu Lys Ser Phe
        595                 600                 605

gca ggg aac ccc aac ctc tgt acc tcc cac tct tgc ccg aat tcc tcg      1872
Ala Gly Asn Pro Asn Leu Cys Thr Ser His Ser Cys Pro Asn Ser Ser
    610                 615                 620

ttg tac cct gac gac gcc ttg aag aag agg cgc ggc cct tgg agt ttg      1920
Leu Tyr Pro Asp Asp Ala Leu Lys Lys Arg Arg Gly Pro Trp Ser Leu
625                 630                 635                 640

aaa tcc acg agg gtg ata gtc atc gtg att gca ctg ggc aca gcc gcg      1968
Lys Ser Thr Arg Val Ile Val Ile Val Ile Ala Leu Gly Thr Ala Ala
                645                 650                 655

ctg ctg gtg gcg gtg acg gtg tac atg atg agg agg agg aag atg aac      2016
Leu Leu Val Ala Val Thr Val Tyr Met Met Arg Arg Arg Lys Met Asn
            660                 665                 670

ctt gcg aag acg tgg aag ctg acg gcg ttc cag cgg ctg aac ttc aaa      2064
Leu Ala Lys Thr Trp Lys Leu Thr Ala Phe Gln Arg Leu Asn Phe Lys
        675                 680                 685

gcc gag gac gtg gtg gag tgt ctg aag gag gag aac ata ata gga aaa      2112
Ala Glu Asp Val Val Glu Cys Leu Lys Glu Glu Asn Ile Ile Gly Lys
    690                 695                 700

gga ggg gca ggg atc gtg tac cgc ggg tcc atg cca aac gga aca gac      2160
Gly Gly Ala Gly Ile Val Tyr Arg Gly Ser Met Pro Asn Gly Thr Asp
705                 710                 715                 720

gtg gcg ata aag cgg ttg gtt ggg gcg ggg agt gga agg aac gat tac      2208
Val Ala Ile Lys Arg Leu Val Gly Ala Gly Ser Gly Arg Asn Asp Tyr
                725                 730                 735

gga ttc aaa gcg gag ata gaa acg ctg ggg aag ata agg cac agg aac      2256
Gly Phe Lys Ala Glu Ile Glu Thr Leu Gly Lys Ile Arg His Arg Asn
            740                 745                 750

ata atg agg ctt tta ggt tac gtg tcg aac aag gag acg aac ttg ctg      2304
Ile Met Arg Leu Leu Gly Tyr Val Ser Asn Lys Glu Thr Asn Leu Leu
```

```
        755                 760                 765

ctg tat gag tac atg cca aat ggg agc tta ggg gaa tgg ctg cat ggt      2352
Leu Tyr Glu Tyr Met Pro Asn Gly Ser Leu Gly Glu Trp Leu His Gly
    770                 775                 780

gcc aaa gga ggg cac ttg aag tgg gaa atg agg tac aag att gcg gtg      2400
Ala Lys Gly Gly His Leu Lys Trp Glu Met Arg Tyr Lys Ile Ala Val
785                 790                 795                 800

gaa gct gct aag gga ctg tgc tat ttg cac cat gat tgt tcc cct ctt      2448
Glu Ala Ala Lys Gly Leu Cys Tyr Leu His His Asp Cys Ser Pro Leu
                805                 810                 815

atc att cac agg gat gtc aag tct aat aat ata ttg ctg gat ggg gac      2496
Ile Ile His Arg Asp Val Lys Ser Asn Asn Ile Leu Leu Asp Gly Asp
            820                 825                 830

ttg gag gcc cat gtt gct gat ttt ggc ctt gcc aag ttc ttg tac gac      2544
Leu Glu Ala His Val Ala Asp Phe Gly Leu Ala Lys Phe Leu Tyr Asp
        835                 840                 845

cct ggc gcc tct cag tcc atg tcc tcc att gct ggc tcc tac ggc tac      2592
Pro Gly Ala Ser Gln Ser Met Ser Ser Ile Ala Gly Ser Tyr Gly Tyr
    850                 855                 860

att gct cca gag tat gca tac act ttg aaa gtg gac gag aaa agt gat      2640
Ile Ala Pro Glu Tyr Ala Tyr Thr Leu Lys Val Asp Glu Lys Ser Asp
865                 870                 875                 880

gtg tac agc ttt ggc gtt gtg ctg ctg gag ctg ata ata ggg agg aag      2688
Val Tyr Ser Phe Gly Val Val Leu Leu Glu Leu Ile Ile Gly Arg Lys
                885                 890                 895

cca gtg gga gag ttt gga gac ggg gtg gac atc gtt gga tgg gtc aac      2736
Pro Val Gly Glu Phe Gly Asp Gly Val Asp Ile Val Gly Trp Val Asn
            900                 905                 910

aaa acg aga ttg gag ctc gct cag ccg tcg gat gca gcg ttg gtg ttg      2784
Lys Thr Arg Leu Glu Leu Ala Gln Pro Ser Asp Ala Ala Leu Val Leu
        915                 920                 925

gca gtg gtg gac cca agg ttg agt ggg tat cca ttg aca agt gtc att      2832
Ala Val Val Asp Pro Arg Leu Ser Gly Tyr Pro Leu Thr Ser Val Ile
    930                 935                 940

tac atg ttc aac ata gct atg atg tgt gtt aaa gaa atg ggg ccc gct      2880
Tyr Met Phe Asn Ile Ala Met Met Cys Val Lys Glu Met Gly Pro Ala
945                 950                 955                 960

agg cct acc atg agg gaa gtc gtt cat atg ctc tca gag cct cct cac      2928
Arg Pro Thr Met Arg Glu Val Val His Met Leu Ser Glu Pro Pro His
                965                 970                 975

tct gct act cac act cac aac cta att aat ctc tag                      2964
Ser Ala Thr His Thr His Asn Leu Ile Asn Leu
            980                 985


<210> SEQ ID NO 40
<211> LENGTH: 987
<212> TYPE: PRT
<213> ORGANISM: Glycine max

<400> SEQUENCE: 40

Met Arg Ser Cys Val Cys Tyr Thr Leu Leu Leu Phe Ile Phe Phe Ile
1               5                   10                  15

Trp Leu Arg Val Ala Thr Cys Ser Ser Phe Thr Asp Met Glu Ser Leu
            20                  25                  30

Leu Lys Leu Lys Asp Ser Met Lys Gly Asp Lys Ala Lys Asp Asp Ala
        35                  40                  45

Leu His Asp Trp Lys Phe Phe Pro Ser Leu Ser Ala His Cys Phe Phe
    50                  55                  60

Ser Gly Val Lys Cys Asp Arg Glu Leu Arg Val Val Ala Ile Asn Val
```

-continued

```
65                  70                  75                  80

Ser Phe Val Pro Leu Phe Gly His Leu Pro Pro Glu Ile Gly Gln Leu
                85                  90                  95

Asp Lys Leu Glu Asn Leu Thr Val Ser Gln Asn Asn Leu Thr Gly Val
            100                 105                 110

Leu Pro Lys Glu Leu Ala Ala Leu Thr Ser Leu Lys His Leu Asn Ile
        115                 120                 125

Ser His Asn Val Phe Ser Gly His Phe Pro Gly Gln Ile Ile Leu Pro
    130                 135                 140

Met Thr Lys Leu Glu Val Leu Asp Val Tyr Asp Asn Asn Phe Thr Gly
145                 150                 155                 160

Pro Leu Pro Val Glu Leu Val Lys Leu Glu Lys Leu Lys Tyr Leu Lys
                165                 170                 175

Leu Asp Gly Asn Tyr Phe Ser Gly Ser Ile Pro Glu Ser Tyr Ser Glu
            180                 185                 190

Phe Lys Ser Leu Glu Phe Leu Ser Leu Ser Thr Asn Ser Leu Ser Gly
        195                 200                 205

Lys Ile Pro Lys Ser Leu Ser Lys Leu Lys Thr Leu Arg Tyr Leu Lys
    210                 215                 220

Leu Gly Tyr Asn Asn Ala Tyr Glu Gly Gly Ile Pro Pro Glu Phe Gly
225                 230                 235                 240

Ser Met Lys Ser Leu Arg Tyr Leu Asp Leu Ser Ser Cys Asn Leu Ser
                245                 250                 255

Gly Glu Ile Pro Pro Ser Leu Ala Asn Leu Thr Asn Leu Asp Thr Leu
            260                 265                 270

Phe Leu Gln Ile Asn Asn Leu Thr Gly Thr Ile Pro Ser Glu Leu Ser
        275                 280                 285

Ala Met Val Ser Leu Met Ser Leu Asp Leu Ser Ile Asn Asp Leu Thr
    290                 295                 300

Gly Glu Ile Pro Met Ser Phe Ser Gln Leu Arg Asn Leu Thr Leu Met
305                 310                 315                 320

Asn Phe Phe Gln Asn Asn Leu Arg Gly Ser Val Pro Ser Phe Val Gly
                325                 330                 335

Glu Leu Pro Asn Leu Glu Thr Leu Gln Leu Trp Asp Asn Asn Phe Ser
            340                 345                 350

Phe Val Leu Pro Pro Asn Leu Gly Gln Asn Gly Lys Leu Lys Phe Phe
        355                 360                 365

Asp Val Ile Lys Asn His Phe Thr Gly Leu Ile Pro Arg Asp Leu Cys
    370                 375                 380

Lys Ser Gly Arg Leu Gln Thr Ile Met Ile Thr Asp Asn Phe Phe Arg
385                 390                 395                 400

Gly Pro Ile Pro Asn Glu Ile Gly Asn Cys Lys Ser Leu Thr Lys Ile
                405                 410                 415

Arg Ala Ser Asn Asn Tyr Leu Asn Gly Val Val Pro Ser Gly Ile Phe
            420                 425                 430

Lys Leu Pro Ser Val Thr Ile Ile Glu Leu Ala Asn Asn Arg Phe Asn
        435                 440                 445

Gly Glu Leu Pro Pro Glu Ile Ser Gly Glu Ser Leu Gly Ile Leu Thr
    450                 455                 460

Leu Ser Asn Asn Leu Phe Ser Gly Lys Ile Pro Pro Ala Leu Lys Asn
465                 470                 475                 480

Leu Arg Ala Leu Gln Thr Leu Ser Leu Asp Ala Asn Glu Phe Val Gly
                485                 490                 495
```

```
Glu Ile Pro Gly Glu Val Phe Asp Leu Pro Met Leu Thr Val Val Asn
            500                 505                 510

Ile Ser Gly Asn Asn Leu Thr Gly Pro Ile Pro Thr Thr Leu Thr Arg
        515                 520                 525

Cys Val Ser Leu Thr Ala Val Asp Leu Ser Arg Asn Met Leu Glu Gly
    530                 535                 540

Lys Ile Pro Lys Gly Ile Lys Asn Leu Thr Asp Leu Ser Ile Phe Asn
545                 550                 555                 560

Val Ser Ile Asn Gln Ile Ser Gly Pro Val Pro Glu Glu Ile Arg Phe
                565                 570                 575

Met Leu Ser Leu Thr Thr Leu Asp Leu Ser Asn Asn Asn Phe Ile Gly
            580                 585                 590

Lys Val Pro Thr Gly Gly Gln Phe Ala Val Phe Ser Glu Lys Ser Phe
        595                 600                 605

Ala Gly Asn Pro Asn Leu Cys Thr Ser His Ser Cys Pro Asn Ser Ser
    610                 615                 620

Leu Tyr Pro Asp Asp Ala Leu Lys Lys Arg Arg Gly Pro Trp Ser Leu
625                 630                 635                 640

Lys Ser Thr Arg Val Ile Val Ile Val Ile Ala Leu Gly Thr Ala Ala
                645                 650                 655

Leu Leu Val Ala Val Thr Val Tyr Met Met Arg Arg Arg Lys Met Asn
            660                 665                 670

Leu Ala Lys Thr Trp Lys Leu Thr Ala Phe Gln Arg Leu Asn Phe Lys
        675                 680                 685

Ala Glu Asp Val Val Glu Cys Leu Lys Glu Glu Asn Ile Ile Gly Lys
    690                 695                 700

Gly Gly Ala Gly Ile Val Tyr Arg Gly Ser Met Pro Asn Gly Thr Asp
705                 710                 715                 720

Val Ala Ile Lys Arg Leu Val Gly Ala Gly Ser Gly Arg Asn Asp Tyr
                725                 730                 735

Gly Phe Lys Ala Glu Ile Glu Thr Leu Gly Lys Ile Arg His Arg Asn
            740                 745                 750

Ile Met Arg Leu Leu Gly Tyr Val Ser Asn Lys Glu Thr Asn Leu Leu
        755                 760                 765

Leu Tyr Glu Tyr Met Pro Asn Gly Ser Leu Gly Glu Trp Leu His Gly
    770                 775                 780

Ala Lys Gly Gly His Leu Lys Trp Glu Met Arg Tyr Lys Ile Ala Val
785                 790                 795                 800

Glu Ala Ala Lys Gly Leu Cys Tyr Leu His His Asp Cys Ser Pro Leu
                805                 810                 815

Ile Ile His Arg Asp Val Lys Ser Asn Asn Ile Leu Leu Asp Gly Asp
            820                 825                 830

Leu Glu Ala His Val Ala Asp Phe Gly Leu Ala Lys Phe Leu Tyr Asp
        835                 840                 845

Pro Gly Ala Ser Gln Ser Met Ser Ser Ile Ala Gly Ser Tyr Gly Tyr
    850                 855                 860

Ile Ala Pro Glu Tyr Ala Tyr Thr Leu Lys Val Asp Glu Lys Ser Asp
865                 870                 875                 880

Val Tyr Ser Phe Gly Val Val Leu Leu Glu Leu Ile Ile Gly Arg Lys
                885                 890                 895

Pro Val Gly Glu Phe Gly Asp Gly Val Asp Ile Val Gly Trp Val Asn
            900                 905                 910
```

```
Lys Thr Arg Leu Glu Leu Ala Gln Pro Ser Asp Ala Ala Leu Val Leu
        915                 920                 925

Ala Val Val Asp Pro Arg Leu Ser Gly Tyr Pro Leu Thr Ser Val Ile
    930                 935                 940

Tyr Met Phe Asn Ile Ala Met Met Cys Val Lys Glu Met Gly Pro Ala
945                 950                 955                 960

Arg Pro Thr Met Arg Glu Val Val His Met Leu Ser Glu Pro Pro His
                965                 970                 975

Ser Ala Thr His Thr His Asn Leu Ile Asn Leu
            980                 985


<210> SEQ ID NO 41
<211> LENGTH: 3525
<212> TYPE: DNA
<213> ORGANISM: Glycine max

<400> SEQUENCE: 41

agcttcgcat aagtaacgtg agtttagtta agtcgagcta gtcgcctttt tctatggttg     60

gttatgtgca gtagtgaatg ttgtgtagta tcttgcgagg ccatgtttgg tgtgacaagc    120

ccgaaagtga cttgagggga acaaaatagc ttttgtccaa acatgctaac ttgtcatcat    180

gacatctact tctctggtca tggcagctct gattaataat ttaagtgatc ataatattag    240

aagttaaaaa attataacat ctttaattat ttttattatt ttatataatc ttaaaaatta    300

tttcaaactt ctttaaacaa tgttgaataa gatcatgtat ttttttttt tccttacgta     360

gtagtatcct ggcagtcacc caggagcaaa tgatgtagat aaatcctttt tactaaaata    420

gtcttggagc aatatttaag aggggaccat tttatgatct tttctatctt aatagtggcg    480

ttagaataac actttttaa gctttaaata aaaaataaaa aaatattatc tttactttct     540

tttagcaatt attcctacgt gtagagaaac tgttaaatac actctccttt gtattgtata    600

atgttgcatt gtatcagttg tccaaattaa tcacagtata ttagtaataa aattatgaac    660

attaatttta ttcttaaaat ttagttaaat attgataatt cacataactc gtgacttaat    720

ctaattatat atagaagatc atgttagtat gttacctttt taaaatgcaa aatgaagaat    780

ctgttacatg cacccactgg gtaagttgat aactattatg tatctatata tcgtctggat    840

attgtctgtt tcattctctt ctcaaaagaa caaaatggta atttacattt aacttagaaa    900

tgtttgggac agaatcacta gcttgcagat gaataatttg ttttaaattc ttattgatgc    960

ataataccct ctacttgtca ctcatagaat acgattctgc aataactagt gcttgatcct   1020

tgacagaaca aattaaaaca gagaattgat gcattggctt ttccatggac aataattatc   1080

ccattgatgt actaaagcac agtaactagg taggaagacc tccacctaaa gaaactttct   1140

tttattctcc tttaatttta aatttggtga atcacttaaa acaacttttg tttcattcca   1200

aagttaggct catggaaagc ttaaacctag ttaaatagcc acgaaagaga ttgcatcttt   1260

gttttcacaa aagctaactg cgcgtttgtg aagctagtga tgcatagtat atatatattt   1320

ttttctcggc atccactttg agaactactt ttttttcat tttcatagaa acagaattga    1380

agtagtataa catgccacca tgaacagtac agtgatgtac atgaataaat gcatgctatt   1440

caatataatg tataatataa cggtgtatat ataaatagag actgcatgag gtgtgtggtg   1500

tcaacatata ataaggacgc agcgtaggta taatagtgag taccgcgaag aaagataaga   1560

gccagagcca tgagaagctg tgtgctttac acgctattat tgtttgtttt ctgcatatgg   1620

gttcccatgg caacgtgctc ttcgttcagt gacatggatg cgttactaaa gctgaaggag   1680
```

tccatgaaag gagacgaagc caaagacgac gcactccatg actggaagtt ttccacatcg 1740
cattctgcac actgtttctt ttcaggcgta acatgtgacc aagaccttcg agtcgttgct 1800
atcaacgtct cctttgttcc tctcttcggt cacattccgc cggagatcgg aaacttggac 1860
aagctggaaa atctcacaat cgtgaacaac aatctaaccg gtgtactccc catggagctt 1920
gccgccctca cttccctcaa gcacctcaac atatctcaca acctcttcac cggcgatttc 1980
cccggccaag ccactcttcc gatgacggaa cttcaagtcc tcgacgtcta cgacaacaac 2040
ttcaccggac cgcttccgga agaattcgtg aaactggaga aactaaaata cctgaaactc 2100
gacggaaact attttaccgg cagcataccg gagagttact cggagtttaa gagcttggag 2160
tttttgagct taaacaccaa cagcttatcg gggaggattc cgaagagttt gtccaagttg 2220
aagactctga ggattctcaa actcggatac agcaacgctt acgaaggtgg aattcctccg 2280
gagttcggca ccatggaatc tctgagattc ctcgacctct caagctgcaa cctcagcggc 2340
gagattccac cgagtcttgc aaatctgaca aacctagaca cgttgttctt gcaaatgaac 2400
ttcctcaccg gaagcattcc gtctgaactc tcttctttgg tgaggctcat ggcactggat 2460
ctctcctgca acagcctcac cggggagatt ccagagagct tttctcagct gagaaacctc 2520
actctcatga acttgttccg caacaatctt cacggcccta ttccgtcctt gctgagcgag 2580
cttcccaatc tgaatacgct gcagctctgg gagaataact tctcctctga gctcccgcag 2640
aacctggggc aaaacgggag gctgaagttc ttcgacgtca cgaagaatca cttcagcggg 2700
ttgatccctc gggatttgtg caagagtggg aggttacaaa tcttcattat cacagataac 2760
ttctttcatg gcccaatccc taacgagatt gctaactgca agtctctaac caagatccga 2820
gcctccaata actaccttaa cggcgcagtt ccgtcgggga ttttcaagct accttccgtc 2880
acgataatcg agttggccaa taaccgtttt aacggagaac tgcctcccga aatttccggc 2940
gattcactcg ggattctcac tctttccaac aacttattca ctgggaaaat tcccccagcg 3000
ttgaagaact taagggcact gcagactctg tcacttgaca cgaacgagtt ccttggagaa 3060
atcccggggg aggtttttga cctaccaatg ctgactgtgg tcaacataag cggcaacaat 3120
ctcaccggac caatcccaac gacgtttact cgctgcgttt cactcgccgc cgttgatctc 3180
agccggaaca tgctagttga ggatattcct aaggggatta agaacctcac ggtcttgagc 3240
tttttcaatg tctcgagaaa ccatttaaca gggccagtcc ctgacgagat aaaattcatg 3300
acgagcctca ccacgctgga tctctcctac aacaatttca caggcaaggt ccccaacgag 3360
ggtcagtttt tggtcttcaa cgacaactcg tttgcaggga accctaacct ctgttccatt 3420
cacggatgca ctttaagcat tgtgggggca gctgccccta tcaacatttt aacatttgta 3480
aatatagtat gtacaattat agtaatttat aaattgcttg tataa 3525

<210> SEQ ID NO 42
<211> LENGTH: 1899
<212> TYPE: DNA
<213> ORGANISM: Glycine max
<220> FEATURE:
<221> NAME/KEY: CDS
<222> LOCATION: (1)..(1899)

<400> SEQUENCE: 42 atg gca acg tgc tct tcg ttc agt gac atg gat gcg tta cta aag ctg 48
Met Ala Thr Cys Ser Ser Phe Ser Asp Met Asp Ala Leu Leu Lys Leu
1 5 10 15 aag gag tcc atg aaa gga gac gaa gcc aaa gac gac gca ctc cat gac 96
Lys Glu Ser Met Lys Gly Asp Glu Ala Lys Asp Asp Ala Leu His Asp

```
             20                  25                  30

tgg aag ttt tcc aca tcg cat tct gca cac tgt ttc ttt tca ggc gta      144
Trp Lys Phe Ser Thr Ser His Ser Ala His Cys Phe Phe Ser Gly Val
        35                  40                  45

aca tgt gac caa gac ctt cga gtc gtt gct atc aac gtc tcc ttt gtt      192
Thr Cys Asp Gln Asp Leu Arg Val Val Ala Ile Asn Val Ser Phe Val
    50                  55                  60

cct ctc ttc ggt cac att ccg ccg gag atc gga aac ttg gac aag ctg      240
Pro Leu Phe Gly His Ile Pro Pro Glu Ile Gly Asn Leu Asp Lys Leu
65                  70                  75                  80

gaa aat ctc aca atc gtg aac aac aat cta acc ggt gta ctc ccc atg      288
Glu Asn Leu Thr Ile Val Asn Asn Asn Leu Thr Gly Val Leu Pro Met
                85                  90                  95

gag ctt gcc gcc ctc act tcc ctc aag cac ctc aac ata tct cac aac      336
Glu Leu Ala Ala Leu Thr Ser Leu Lys His Leu Asn Ile Ser His Asn
            100                 105                 110

ctc ttc acc ggc gat ttc ccc ggc caa gcc act ctt ccg atg acg gaa      384
Leu Phe Thr Gly Asp Phe Pro Gly Gln Ala Thr Leu Pro Met Thr Glu
        115                 120                 125

ctt caa gtc ctc gac gtc tac gac aac aac ttc acc gga ccg ctt ccg      432
Leu Gln Val Leu Asp Val Tyr Asp Asn Asn Phe Thr Gly Pro Leu Pro
    130                 135                 140

gaa gaa ttc gtg aaa ctg gag aaa cta aaa tac ctg aaa ctc gac gga      480
Glu Glu Phe Val Lys Leu Glu Lys Leu Lys Tyr Leu Lys Leu Asp Gly
145                 150                 155                 160

aac tat ttt acc ggc agc ata ccg gag agt tac tcg gag ttt aag agc      528
Asn Tyr Phe Thr Gly Ser Ile Pro Glu Ser Tyr Ser Glu Phe Lys Ser
                165                 170                 175

ttg gag ttt ttg agc tta aac acc aac agc tta tcg ggg agg att ccg      576
Leu Glu Phe Leu Ser Leu Asn Thr Asn Ser Leu Ser Gly Arg Ile Pro
            180                 185                 190

aag agt ttg tcc aag ttg aag act ctg agg att ctc aaa ctc gga tac      624
Lys Ser Leu Ser Lys Leu Lys Thr Leu Arg Ile Leu Lys Leu Gly Tyr
        195                 200                 205

agc aac gct tac gaa ggt gga att cct ccg gag ttc ggc acc atg gaa      672
Ser Asn Ala Tyr Glu Gly Gly Ile Pro Pro Glu Phe Gly Thr Met Glu
    210                 215                 220

tct ctg aga ttc ctc gac ctc tca agc tgc aac ctc agc ggc gag att      720
Ser Leu Arg Phe Leu Asp Leu Ser Ser Cys Asn Leu Ser Gly Glu Ile
225                 230                 235                 240

cca ccg agt ctt gca aat ctg aca aac cta gac acg ttg ttc ttg caa      768
Pro Pro Ser Leu Ala Asn Leu Thr Asn Leu Asp Thr Leu Phe Leu Gln
                245                 250                 255

atg aac ttc ctc acc gga agc att ccg tct gaa ctc tct tct ttg gtg      816
Met Asn Phe Leu Thr Gly Ser Ile Pro Ser Glu Leu Ser Ser Leu Val
            260                 265                 270

agg ctc atg gca ctg gat ctc tcc tgc aac agc ctc acc ggg gag att      864
Arg Leu Met Ala Leu Asp Leu Ser Cys Asn Ser Leu Thr Gly Glu Ile
        275                 280                 285

cca gag agc ttt tct cag ctg aga aac ctc act ctc atg aac ttg ttc      912
Pro Glu Ser Phe Ser Gln Leu Arg Asn Leu Thr Leu Met Asn Leu Phe
    290                 295                 300

cgc aac aat ctt cac ggc cct att ccg tcc ttg ctg agc gag ctt ccc      960
Arg Asn Asn Leu His Gly Pro Ile Pro Ser Leu Leu Ser Glu Leu Pro
305                 310                 315                 320

aat ctg aat acg ctg cag ctc tgg gag aat aac ttc tcc tct gag ctc     1008
Asn Leu Asn Thr Leu Gln Leu Trp Glu Asn Asn Phe Ser Ser Glu Leu
                325                 330                 335

ccg cag aac ctg ggg caa aac ggg agg ctg aag ttc ttc gac gtc acg     1056
```

-continued

```
Pro Gln Asn Leu Gly Gln Asn Gly Arg Leu Lys Phe Phe Asp Val Thr
            340                 345                 350

aag aat cac ttc agc ggg ttg atc cct cgg gat ttg tgc aag agt ggg     1104
Lys Asn His Phe Ser Gly Leu Ile Pro Arg Asp Leu Cys Lys Ser Gly
        355                 360                 365

agg tta caa atc ttc att atc aca gat aac ttc ttt cat ggc cca atc     1152
Arg Leu Gln Ile Phe Ile Ile Thr Asp Asn Phe Phe His Gly Pro Ile
    370                 375                 380

cct aac gag att gct aac tgc aag tct cta acc aag atc cga gcc tcc     1200
Pro Asn Glu Ile Ala Asn Cys Lys Ser Leu Thr Lys Ile Arg Ala Ser
385                 390                 395                 400

aat aac tac ctt aac ggc gca gtt ccg tcg ggg att ttc aag cta cct     1248
Asn Asn Tyr Leu Asn Gly Ala Val Pro Ser Gly Ile Phe Lys Leu Pro
                405                 410                 415

tcc gtc acg ata atc gag ttg gcc aat aac cgt ttt aac gga gaa ctg     1296
Ser Val Thr Ile Ile Glu Leu Ala Asn Asn Arg Phe Asn Gly Glu Leu
            420                 425                 430

cct ccc gaa att tcc ggc gat tca ctc ggg att ctc act ctt tcc aac     1344
Pro Pro Glu Ile Ser Gly Asp Ser Leu Gly Ile Leu Thr Leu Ser Asn
        435                 440                 445

aac tta ttc act ggg aaa att ccc cca gcg ttg aag aac tta agg gca     1392
Asn Leu Phe Thr Gly Lys Ile Pro Pro Ala Leu Lys Asn Leu Arg Ala
    450                 455                 460

ctg cag act ctg tca ctt gac acg aac gag ttc ctt gga gaa atc ccg     1440
Leu Gln Thr Leu Ser Leu Asp Thr Asn Glu Phe Leu Gly Glu Ile Pro
465                 470                 475                 480

ggg gag gtt ttt gac cta cca atg ctg act gtg gtc aac ata agc ggc     1488
Gly Glu Val Phe Asp Leu Pro Met Leu Thr Val Val Asn Ile Ser Gly
                485                 490                 495

aac aat ctc acc gga cca atc cca acg acg ttt act cgc tgc gtt tca     1536
Asn Asn Leu Thr Gly Pro Ile Pro Thr Thr Phe Thr Arg Cys Val Ser
            500                 505                 510

ctc gcc gcc gtt gat ctc agc cgg aac atg cta gtt gag gat att cct     1584
Leu Ala Ala Val Asp Leu Ser Arg Asn Met Leu Val Glu Asp Ile Pro
        515                 520                 525

aag ggg att aag aac ctc acg gtc ttg agc ttt ttc aat gtc tcg aga     1632
Lys Gly Ile Lys Asn Leu Thr Val Leu Ser Phe Phe Asn Val Ser Arg
    530                 535                 540

aac cat tta aca ggg cca gtc cct gac gag ata aaa ttc atg acg agc     1680
Asn His Leu Thr Gly Pro Val Pro Asp Glu Ile Lys Phe Met Thr Ser
545                 550                 555                 560

ctc acc acg ctg gat ctc tcc tac aac aat ttc aca ggc aag gtc ccc     1728
Leu Thr Thr Leu Asp Leu Ser Tyr Asn Asn Phe Thr Gly Lys Val Pro
                565                 570                 575

aac gag ggt cag ttt ttg gtc ttc aac gac aac tcg ttt gca ggg aac     1776
Asn Glu Gly Gln Phe Leu Val Phe Asn Asp Asn Ser Phe Ala Gly Asn
            580                 585                 590

cct aac ctc tgt tcc att cac gga tgc act tta agc att gtg ggg gca     1824
Pro Asn Leu Cys Ser Ile His Gly Cys Thr Leu Ser Ile Val Gly Ala
        595                 600                 605

gct gcc cct atc aac att tta aca ttt gta aat ata gta tgt aca att     1872
Ala Ala Pro Ile Asn Ile Leu Thr Phe Val Asn Ile Val Cys Thr Ile
    610                 615                 620

ata gta att tat aaa ttg ctt gta taa                                 1899
Ile Val Ile Tyr Lys Leu Leu Val
625                 630
```

<210> SEQ ID NO 43
<211> LENGTH: 632
<212> TYPE: PRT

<213> ORGANISM: Glycine max

<400> SEQUENCE: 43

Met Ala Thr Cys Ser Ser Phe Ser Asp Met Asp Ala Leu Leu Lys Leu
1 5 10 15

Lys Glu Ser Met Lys Gly Asp Glu Ala Lys Asp Asp Ala Leu His Asp
20 25 30

Trp Lys Phe Ser Thr Ser His Ser Ala His Cys Phe Phe Ser Gly Val
35 40 45

Thr Cys Asp Gln Asp Leu Arg Val Val Ala Ile Asn Val Ser Phe Val
50 55 60

Pro Leu Phe Gly His Ile Pro Pro Glu Ile Gly Asn Leu Asp Lys Leu
65 70 75 80

Glu Asn Leu Thr Ile Val Asn Asn Asn Leu Thr Gly Val Leu Pro Met
85 90 95

Glu Leu Ala Ala Leu Thr Ser Leu Lys His Leu Asn Ile Ser His Asn
100 105 110

Leu Phe Thr Gly Asp Phe Pro Gly Gln Ala Thr Leu Pro Met Thr Glu
115 120 125

Leu Gln Val Leu Asp Val Tyr Asp Asn Asn Phe Thr Gly Pro Leu Pro
130 135 140

Glu Glu Phe Val Lys Leu Glu Lys Leu Lys Tyr Leu Lys Leu Asp Gly
145 150 155 160

Asn Tyr Phe Thr Gly Ser Ile Pro Glu Ser Tyr Ser Glu Phe Lys Ser
165 170 175

Leu Glu Phe Leu Ser Leu Asn Thr Asn Ser Leu Ser Gly Arg Ile Pro
180 185 190

Lys Ser Leu Ser Lys Leu Lys Thr Leu Arg Ile Leu Lys Leu Gly Tyr
195 200 205

Ser Asn Ala Tyr Glu Gly Gly Ile Pro Pro Glu Phe Gly Thr Met Glu
210 215 220

Ser Leu Arg Phe Leu Asp Leu Ser Ser Cys Asn Leu Ser Gly Glu Ile
225 230 235 240

Pro Pro Ser Leu Ala Asn Leu Thr Asn Leu Asp Thr Leu Phe Leu Gln
245 250 255

Met Asn Phe Leu Thr Gly Ser Ile Pro Ser Glu Leu Ser Ser Leu Val
260 265 270

Arg Leu Met Ala Leu Asp Leu Ser Cys Asn Ser Leu Thr Gly Glu Ile
275 280 285

Pro Glu Ser Phe Ser Gln Leu Arg Asn Leu Thr Leu Met Asn Leu Phe
290 295 300

Arg Asn Asn Leu His Gly Pro Ile Pro Ser Leu Leu Ser Glu Leu Pro
305 310 315 320

Asn Leu Asn Thr Leu Gln Leu Trp Glu Asn Asn Phe Ser Ser Glu Leu
325 330 335

Pro Gln Asn Leu Gly Gln Asn Gly Arg Leu Lys Phe Phe Asp Val Thr
340 345 350

Lys Asn His Phe Ser Gly Leu Ile Pro Arg Asp Leu Cys Lys Ser Gly
355 360 365

Arg Leu Gln Ile Phe Ile Ile Thr Asp Asn Phe Phe His Gly Pro Ile
370 375 380

Pro Asn Glu Ile Ala Asn Cys Lys Ser Leu Thr Lys Ile Arg Ala Ser
385 390 395 400

```
Asn Asn Tyr Leu Asn Gly Ala Val Pro Ser Gly Ile Phe Lys Leu Pro
                405                 410                 415

Ser Val Thr Ile Ile Glu Leu Ala Asn Asn Arg Phe Asn Gly Glu Leu
            420                 425                 430

Pro Pro Glu Ile Ser Gly Asp Ser Leu Gly Ile Leu Thr Leu Ser Asn
        435                 440                 445

Asn Leu Phe Thr Gly Lys Ile Pro Pro Ala Leu Lys Asn Leu Arg Ala
    450                 455                 460

Leu Gln Thr Leu Ser Leu Asp Thr Asn Glu Phe Leu Gly Glu Ile Pro
465                 470                 475                 480

Gly Glu Val Phe Asp Leu Pro Met Leu Thr Val Val Asn Ile Ser Gly
                485                 490                 495

Asn Asn Leu Thr Gly Pro Ile Pro Thr Thr Phe Thr Arg Cys Val Ser
            500                 505                 510

Leu Ala Ala Val Asp Leu Ser Arg Asn Met Leu Val Glu Asp Ile Pro
        515                 520                 525

Lys Gly Ile Lys Asn Leu Thr Val Leu Ser Phe Phe Asn Val Ser Arg
    530                 535                 540

Asn His Leu Thr Gly Pro Val Pro Asp Glu Ile Lys Phe Met Thr Ser
545                 550                 555                 560

Leu Thr Thr Leu Asp Leu Ser Tyr Asn Asn Phe Thr Gly Lys Val Pro
                565                 570                 575

Asn Glu Gly Gln Phe Leu Val Phe Asn Asp Asn Ser Phe Ala Gly Asn
            580                 585                 590

Pro Asn Leu Cys Ser Ile His Gly Cys Thr Leu Ser Ile Val Gly Ala
        595                 600                 605

Ala Ala Pro Ile Asn Ile Leu Thr Phe Val Asn Ile Val Cys Thr Ile
    610                 615                 620

Ile Val Ile Tyr Lys Leu Leu Val
625                 630
```

<210> SEQ ID NO 44
<211> LENGTH: 5725
<212> TYPE: DNA
<213> ORGANISM: Glycine max

<400> SEQUENCE: 44

```
gcctgcccct tagtcatgtg caaaatagtg ctaagatctg tattgtaaaa tggccacatt      60

ggtcttagta aaagagttat gcatatgctg cactggtagc acccagcctg cacttcgtaa     120

tatgatgatt gtgtattttt gtttactttt gaggtgaagc tgcgatgcat taggctaggg     180

atttgtgtat gttgtgtaca ttggtttttg tgaaggtgtt gttgtggctg taatttacat     240

ttttgtattt ttgggattac ttggtgggac atgtgctgag gatgccatgt ccctagttct     300

ctaatgttct gatgtattat ttatttatat tgataaaaaa aattatatac tttcaaaggc     360

aaaaagataa agaaaactat caatcacctg ctattttaga aatacccccc tcccaaaaga     420

aaaacccaaa ttattgtaat catataaagt ttcggtgttg aaaagacggc gtggggcacc     480

atgttgaagg cttgagaatt ttttggtcaa ttgaatcaaa aagtgaagtg gtccatttga     540

cccccagttt gcaatggtaa attcaagaat tgggtggaag tgtccattgt atttttcgta     600

tccaacaata aagaatcaca gttgttgcac agatacaaca atcaaaggtc tagatatttt     660

gtagtcttat aataggaatt ttcactgttt tacacaaaca ttttttttatc tacaaaacaa     720

accgtgagga atcttgtagg ttatagtggc caacactcat gttgcgttaa cacagctatc     780
```

-continued

```
aactaaaact caacttttgt cacgggtgac ctcaacataa ttattgatat tactgacaga    840
gtaacaacac ctgaagtggg ccctgttgaa ctgggttatg actaatgacg agaccacaac    900
ttagaggata gatacatttc taatctttca aataaataca agtgatatta acttggtctt    960
tgaaaaatat gaacatcaat tctgtttttt aattataaaa acaatagtaa tttgatttga   1020
tttactgaaa aaattagcgt caatttaaaa tttcagtatt aaaaaatgat acgatttacc   1080
atcttaagta ttgcacgcaa aagattattt taatatcatt tttcaattat taagagaaaa   1140
aaagtgacgt taatatctta ggacaaaatt aatatctctg gcattttaag aaaataaaga   1200
gaatacttat aaaataagac cacaattcac gaaatcttat attaaatatg gtcctgataa   1260
ttccaatttg tataaactta ttaaaataat acttataggg aaaaaataga gaggcaaata   1320
aattaaaatc aaattatgta tttttacttt tggagaattt aaataagaga atttcttaaa   1380
acttgagtta gataagttga ttttaatttg tgggagattc tttttttatta tatgtcttta   1440
ttttttctc agtatttttt ttttttggaa aattttacct aaactgaaat taagcattgt   1500
ggagaatact ttcagggaaa atgactcaat gatttagcgt gtgatttaag cataaatttt   1560
ggtacaagag tttgattaac tattaattaa attaatttag aaaggtcaag gtcattttca   1620
cacaattcta ttcccttgct cgagaccact tttcaagtat aaatttatga ctaatgggtc   1680
aaaacataca atgccttgtg taaatagtta tgaacgatat taatattttt atgaaaatga   1740
tagttgcacc aaatatgtga aattcgcaat ctgaattatc tgttgcattt ggcttggttt   1800
cattttgtta ggttattatt attatttttt tttaaaaagg aactgactgt atccaattat   1860
atgtctgttt ttaaaatttg aaagaaatag ttttaaacca tttaatatag ctataatata   1920
tatttaagtt aatcttagct atatattttg tattaaaatg tatatttgct ataataatta   1980
actctagtaa tttaccaaat ggatattatt tgtaaaggct tgatttgggt tatactagta   2040
atttaaaatc tacgtactta ctatttctga tttcaaaatg tctcatgcca caaatgaaca   2100
aaacaatcat gataatttat tcatactatt attgcttgct cattcactca ccccacagtg   2160
ctagatcctc ggactcgaat aaatcattta ttatgcttag ataattcgat ttatttttat   2220
tcaatgcaac actcattcaa ttgcactacc ctcctattcc tatatcacat taatatgaag   2280
agttaatctt atcctctcga ttcattttct ttttaaattt aaggggtata atgagaaatt   2340
aattttgact attaaatttt aaaaacaatc caaaaatgtc ataaagaatt tttcctattc   2400
cacgagagaa cttgaaagtt aaaatttgat taaaatctta ttaaaggcgt tcctaatcct   2460
agcaacttcc acctatcaca gagaaaaaaa aaggaaaaga aaaggtaaga tagaaagaaa   2520
gaaggaaaag taaaagcatg caaatataga attataaata ctaaaaaata ttgttaagat   2580
attagttaaa aaattattaa gatacacaaa attacattat acacaatttt ttataatctt   2640
taaaataaat attttttatt ttattaatat cctaaagata ttagttaatt aacattcatg   2700
tattattatt tgaaattgaa acgtaagtag taattaaaag caaattattc tatcgaaaaa   2760
gagataactt tattaatgac acacaccaaa cataccaatc gctagagttg ttaaccactc   2820
actcatatag catatcacaa attcccatgc aaccttaatt caacggtcca gatgcagtct   2880
gatgagatca gacggtcgag acgaactgta cattctccct ctcacggatt tcgatgtttc   2940
tctttcggac caaatgtggg gcccacatag tactgtgtcc tgagtgctgg ctactcacaa   3000
aggcgggaac cagtttttgt cgcagaagag gtatggctct ttgtttgttg tcatcagatg   3060
agagagaaac aaaacaaaga gacaatcact gaatcactct cactcactct gcatgctgtg   3120
tgcgtgactc tgtcattgtg ttttgtgttt taagcacttt gcagtttagt ttctgaggag   3180
```

```
cgttttttttt tttttctttc ttatgagtgt gtgtctgttc ttagttgctg ttattgttgt   3240
tcaagtttcg gttactacta ctactaccac atgtccatgc cccttcaatt tctgttcaac   3300
tttgtgactt tttgtttggt ttctaaggaa aaagattgca acttgtttct gggtctagtt   3360
tgcttttggt tgggtttgtt agtcaccgct ggcaactcgg aatagtgggt tttttttgg   3420
agggtgtttt ttttttcttc ttttggaggt tcaaattctt gttctgattc gtgtgaaggt   3480
ggaaaattta tgggtgctga gaggaggaaa aagatgggat ttggtggaat aaatgtaaaa   3540
ctattcggcg acaacatgtc tgcttgcttt tttgggacgg ctttcttgtg aagattttgg   3600
gtttaaaagg ttgaggaaga tgcttatgcc ttatgcttat gcttgcaact ttttttttaa   3660
aacccatttt agcatcaagt ataaaagttt cttcttggtc ttgtttccaa gtgtttgagg   3720
tgatgggggt tttgagcatg tgagtgattc atgcctcatt ttggagcttc tgagattggt   3780
ttctggttgt ggctttgttt gttttgtgtt gtgctttcat gtttaggaaa aggcacaccc   3840
tttcttctct tgcaagggaa ttgttggcat ttcagccact ttttcttctc ttcttgttca   3900
gcttgcacca caacactatg cagtgtcaag gaaggttgag taaacatgtt tcttctgagc   3960
ctccctcacc ttctaggtca acaccatcac caccatcttc atcaggatac aaggatgacc   4020
ctaggaagat aattttgagc atggttttag gagcagtcac tggactagtt tcttctgctc   4080
tctttgcact tgtggttcgt tgtgttgttc agtatctgaa ccgcacacca atcctcaagg   4140
gacctgtcat attctccccc aaaattgccc ccatgacact ccaatcagct ttggcaaagg   4200
aaaaccactt gctcggttcg agtcctaatg ggaagtacta caaaactgtg cttgacaatg   4260
gactcactat tgcagtcaaa aggctaacac cctttgagag taattccccg gaggctaaga   4320
gaaaatcagt gaagaggcag atacaaactg agcttgagct tcttgcaagc cttaggcata   4380
ggaacttgat gagtttaagg gcctatgttc gtgagcctga tgggttctca ttggtttatg   4440
attatgtttc cactgggagt cttgctgatg tgttgagtaa agtgagggag aatgagttgc   4500
cctttggttg ggaagttagg ctcaggattg ctgttggtgt ggtgaagggt cttcagtatc   4560
ttcatttcac ttgtgtgcct cagattctgc actacaactt gaagcccaca aatgtgatgt   4620
tggatgctga gtttgaacct agattggcag attatgggtt ggctaaactt ctacccaatt   4680
tggatggagg aagttctctc tacactcctc ctgaatgttt ccataattgc aggtaagaca   4740
aatttcaatc atactcattc actagtgttt tgaacttggt ctgtttctgt tctttcactt   4800
ttttacacca atagggtaat taggtggttg atattgggaa tttgtttgat tcgttacctt   4860
ttcaaaagct ccacacctca ttggtttttt gccccctttg tagtacccta atgaaagact   4920
cttgttttga aacgaaatta ctattctgta atctgtattg tcattgtatc atttgctgat   4980
tgaatttggt attatttaat aaagactttg ctatttgttt ttgtaactac ccattacttc   5040
ctgatgtcaa gttttagacc ttaggcagtt ggcactaagt ctggtccaaa tgaataatat   5100
agtttatagt tcacatgctg caaactacta aacctagatt ggtgagtgag accacaacta   5160
aattataata ataattgaca aaggtttttt ttcctaattt aacttggaat acttctagtt   5220
tttcagtggt gtatatttgg atgcatcaat atcaatagca ataagtaata acaataaaag   5280
attgcttgat tgatggcatt gcatatatgg gtatggtatt gccaataaga tgtttatttt   5340
aacttcattc cattcttgta tatgtggagc ttcatggtat tcagattgaa tggtgttttt   5400
tggcaatttc agcaggtaca ctgacaaaag tgacatcttt agttttggca tgatactagg   5460
tgttttgtta actggtaagg atcctacaga tccattcttt ggagaagcag ccagtggggg   5520
```

```
aagtttggga tgttggctga gacacttgca gcaagcgggc gaggcgcacg aagctctaga   5580

taagagcatg ttaggggaag aaggtgagga agatgagatg ctaatggcgg ttaggattgc   5640

tgctgcatgc ctctctgata tgcctgcaga taggccttct agtgatgagc ttgttcacat   5700

gctaacgcaa ctgcacagtt tttga                                         5725
```

<210> SEQ ID NO 45
<211> LENGTH: 1227
<212> TYPE: DNA
<213> ORGANISM: Glycine max
<220> FEATURE:
<221> NAME/KEY: CDS
<222> LOCATION: (1)..(1227)

<400> SEQUENCE: 45

```
atg ttt agg aaa agg cac acc ctt tct tct ctt gca agg gaa ttg ttg       48
Met Phe Arg Lys Arg His Thr Leu Ser Ser Leu Ala Arg Glu Leu Leu
1               5                   10                  15

gca ttt cag cca ctt ttt ctt ctc ttc ttg ttc agc ttg cac cac aac       96
Ala Phe Gln Pro Leu Phe Leu Leu Phe Leu Phe Ser Leu His His Asn
            20                  25                  30

act atg cag tgt caa gga agg ttg agt aaa cat gtt tct tct gag cct      144
Thr Met Gln Cys Gln Gly Arg Leu Ser Lys His Val Ser Ser Glu Pro
        35                  40                  45

ccc tca cct tct agg tca aca cca tca cca cca tct tca tca gga tac      192
Pro Ser Pro Ser Arg Ser Thr Pro Ser Pro Pro Ser Ser Ser Gly Tyr
    50                  55                  60

aag gat gac cct agg aag ata att ttg agc atg gtt tta gga gca gtc      240
Lys Asp Asp Pro Arg Lys Ile Ile Leu Ser Met Val Leu Gly Ala Val
65                  70                  75                  80

act gga cta gtt tct tct gct ctc ttt gca ctt gtg gtt cgt tgt gtt      288
Thr Gly Leu Val Ser Ser Ala Leu Phe Ala Leu Val Val Arg Cys Val
                85                  90                  95

gtt cag tat ctg aac cgc aca cca atc ctc aag gga cct gtc ata ttc      336
Val Gln Tyr Leu Asn Arg Thr Pro Ile Leu Lys Gly Pro Val Ile Phe
            100                 105                 110

tcc ccc aaa att gcc ccc atg aca ctc caa tca gct ttg gca aag gaa      384
Ser Pro Lys Ile Ala Pro Met Thr Leu Gln Ser Ala Leu Ala Lys Glu
        115                 120                 125

aac cac ttg ctc ggt tcg agt cct aat ggg aag tac tac aaa act gtg      432
Asn His Leu Leu Gly Ser Ser Pro Asn Gly Lys Tyr Tyr Lys Thr Val
    130                 135                 140

ctt gac aat gga ctc act att gca gtc aaa agg cta aca ccc ttt gag      480
Leu Asp Asn Gly Leu Thr Ile Ala Val Lys Arg Leu Thr Pro Phe Glu
145                 150                 155                 160

agt aat tcc ccg gag gct aag aga aaa tca gtg aag agg cag ata caa      528
Ser Asn Ser Pro Glu Ala Lys Arg Lys Ser Val Lys Arg Gln Ile Gln
                165                 170                 175

act gag ctt gag ctt ctt gca agc ctt agg cat agg aac ttg atg agt      576
Thr Glu Leu Glu Leu Leu Ala Ser Leu Arg His Arg Asn Leu Met Ser
            180                 185                 190

tta agg gcc tat gtt cgt gag cct gat ggg ttc tca ttg gtt tat gat      624
Leu Arg Ala Tyr Val Arg Glu Pro Asp Gly Phe Ser Leu Val Tyr Asp
        195                 200                 205

tat gtt tcc act ggg agt ctt gct gat gtg ttg agt aaa gtg agg gag      672
Tyr Val Ser Thr Gly Ser Leu Ala Asp Val Leu Ser Lys Val Arg Glu
    210                 215                 220

aat gag ttg ccc ttt ggt tgg gaa gtt agg ctc agg att gct gtt ggt      720
Asn Glu Leu Pro Phe Gly Trp Glu Val Arg Leu Arg Ile Ala Val Gly
225                 230                 235                 240
```

```
gtg gtg aag ggt ctt cag tat ctt cat ttc act tgt gtg cct cag att      768
Val Val Lys Gly Leu Gln Tyr Leu His Phe Thr Cys Val Pro Gln Ile
                245                 250                 255

ctg cac tac aac ttg aag ccc aca aat gtg atg ttg gat gct gag ttt      816
Leu His Tyr Asn Leu Lys Pro Thr Asn Val Met Leu Asp Ala Glu Phe
            260                 265                 270

gaa cct aga ttg gca gat tat ggg ttg gct aaa ctt cta ccc aat ttg      864
Glu Pro Arg Leu Ala Asp Tyr Gly Leu Ala Lys Leu Leu Pro Asn Leu
        275                 280                 285

gat gga gga agt tct ctc tac act cct cct gaa tgt ttc cat aat tgc      912
Asp Gly Gly Ser Ser Leu Tyr Thr Pro Pro Glu Cys Phe His Asn Cys
    290                 295                 300

agc agg tac act gac aaa agt gac atc ttt agt ttt ggc atg ata cta      960
Ser Arg Tyr Thr Asp Lys Ser Asp Ile Phe Ser Phe Gly Met Ile Leu
305                 310                 315                 320

ggt gtt ttg tta act ggt aag gat cct aca gat cca ttc ttt gga gaa     1008
Gly Val Leu Leu Thr Gly Lys Asp Pro Thr Asp Pro Phe Phe Gly Glu
                325                 330                 335

gca gcc agt ggg gga agt ttg gga tgt tgg ctg aga cac ttg cag caa     1056
Ala Ala Ser Gly Gly Ser Leu Gly Cys Trp Leu Arg His Leu Gln Gln
            340                 345                 350

gcg ggc gag gcg cac gaa gct cta gat aag agc atg tta ggg gaa gaa     1104
Ala Gly Glu Ala His Glu Ala Leu Asp Lys Ser Met Leu Gly Glu Glu
        355                 360                 365

ggt gag gaa gat gag atg cta atg gcg gtt agg att gct gct gca tgc     1152
Gly Glu Glu Asp Glu Met Leu Met Ala Val Arg Ile Ala Ala Ala Cys
    370                 375                 380

ctc tct gat atg cct gca gat agg cct tct agt gat gag ctt gtt cac     1200
Leu Ser Asp Met Pro Ala Asp Arg Pro Ser Ser Asp Glu Leu Val His
385                 390                 395                 400

atg cta acg caa ctg cac agt ttt tga                                 1227
Met Leu Thr Gln Leu His Ser Phe
                405
```

<210> SEQ ID NO 46
<211> LENGTH: 408
<212> TYPE: PRT
<213> ORGANISM: Glycine max

<400> SEQUENCE: 46

```
Met Phe Arg Lys Arg His Thr Leu Ser Ser Leu Ala Arg Glu Leu Leu
1               5                   10                  15

Ala Phe Gln Pro Leu Phe Leu Leu Phe Leu Phe Ser Leu His His Asn
            20                  25                  30

Thr Met Gln Cys Gln Gly Arg Leu Ser Lys His Val Ser Ser Glu Pro
        35                  40                  45

Pro Ser Pro Ser Arg Ser Thr Pro Ser Pro Pro Ser Ser Ser Gly Tyr
    50                  55                  60

Lys Asp Asp Pro Arg Lys Ile Ile Leu Ser Met Val Leu Gly Ala Val
65                  70                  75                  80

Thr Gly Leu Val Ser Ser Ala Leu Phe Ala Leu Val Val Arg Cys Val
                85                  90                  95

Val Gln Tyr Leu Asn Arg Thr Pro Ile Leu Lys Gly Pro Val Ile Phe
            100                 105                 110

Ser Pro Lys Ile Ala Pro Met Thr Leu Gln Ser Ala Leu Ala Lys Glu
        115                 120                 125

Asn His Leu Leu Gly Ser Ser Pro Asn Gly Lys Tyr Tyr Lys Thr Val
    130                 135                 140
```

-continued

```
Leu Asp Asn Gly Leu Thr Ile Ala Val Lys Arg Leu Thr Pro Phe Glu
145                 150                 155                 160

Ser Asn Ser Pro Glu Ala Lys Arg Lys Ser Val Lys Arg Gln Ile Gln
                165                 170                 175

Thr Glu Leu Glu Leu Leu Ala Ser Leu Arg His Arg Asn Leu Met Ser
            180                 185                 190

Leu Arg Ala Tyr Val Arg Glu Pro Asp Gly Phe Ser Leu Val Tyr Asp
        195                 200                 205

Tyr Val Ser Thr Gly Ser Leu Ala Asp Val Leu Ser Lys Val Arg Glu
    210                 215                 220

Asn Glu Leu Pro Phe Gly Trp Glu Val Arg Leu Arg Ile Ala Val Gly
225                 230                 235                 240

Val Val Lys Gly Leu Gln Tyr Leu His Phe Thr Cys Val Pro Gln Ile
                245                 250                 255

Leu His Tyr Asn Leu Lys Pro Thr Asn Val Met Leu Asp Ala Glu Phe
            260                 265                 270

Glu Pro Arg Leu Ala Asp Tyr Gly Leu Ala Lys Leu Leu Pro Asn Leu
        275                 280                 285

Asp Gly Gly Ser Ser Leu Tyr Thr Pro Pro Glu Cys Phe His Asn Cys
    290                 295                 300

Ser Arg Tyr Thr Asp Lys Ser Asp Ile Phe Ser Phe Gly Met Ile Leu
305                 310                 315                 320

Gly Val Leu Leu Thr Gly Lys Asp Pro Thr Asp Pro Phe Phe Gly Glu
                325                 330                 335

Ala Ala Ser Gly Gly Ser Leu Gly Cys Trp Leu Arg His Leu Gln Gln
            340                 345                 350

Ala Gly Glu Ala His Glu Ala Leu Asp Lys Ser Met Leu Gly Glu Glu
        355                 360                 365

Gly Glu Glu Asp Glu Met Leu Met Ala Val Arg Ile Ala Ala Ala Cys
    370                 375                 380

Leu Ser Asp Met Pro Ala Asp Arg Pro Ser Ser Asp Glu Leu Val His
385                 390                 395                 400

Met Leu Thr Gln Leu His Ser Phe
                405
```

<210> SEQ ID NO 47
<211> LENGTH: 4954
<212> TYPE: DNA
<213> ORGANISM: Glycine max

<400> SEQUENCE: 47

```
attataagaa aataatggta atttgattta ctgaaaaaat tagcgtcaat tcatcatttc      60

aatattacaa aatgatacta cgatttagta tcttaagtat tgcacgcaaa agattatttt     120

catatcattt ttcaattatt tagagaaaaa agtgacgtta atatcttagg aaaaaattaa     180

tatctctggc attttaagaa aataaagagt tacttataaa atatgaccac gattcatgaa     240

atcttatatt aaatatagtc ccgataattc caatttgtat aaactaaaag aatacttata     300

ggaaaaaaat agtgaggcaa ataaattaaa cttctttcat aaataaaaat caaattatgt     360

atttttactt ttggaaaagt taaataagag aatttcttaa aattgattag ataagttaat     420

tttaacttgt gggagatttt tatttattta tttttcatta tacctctatt ttttctgagt     480

attttttgaa aattttatct aaatttaaat taaaaattgt ggagaatact ttcaaggaaa     540

atggcctaat ggtttagcgt gtgttttaag cataaatttt ggtacccatg tttgattaac     600
```

-continued

```
tattaattaa aattaatttt aaaaggccaa ggtcattttc acacaattct attcccttgc    660
actagaccac tttttaagta taaatttatg actaatgggt caaagcatac aatgccttgt    720
gtaaatagtt gactatcaac caaaaatttg acattcaata agacaccact ggtctttgag    780
cgacatcaat atttttatga aaacgatagt tgcacctaat atgtgaaatt cgcaatctga    840
attatttata aaacgttgca tttgcgttcc aaataaaaaa ctcaacccaa caaggaaaaa    900
aaaaactgaa cttatgtctt ggttttgttt tgtttggtta ttaaaaaaag taaatggaac    960
tgactgtatc caattatatg tctgttttta gattttgaaa gaaataattt taaaccaata   1020
aatatagtta tgatatatat ttaaattaat ctcagctata tattaaaatg tatatcacgg   1080
taaaaataat taactctagt aaattatcaa atggatattt gctataataa ttatttgtaa   1140
atgcctgatt tagattatag taatttaaaa tctaagtact tgtcattttt catttcaaaa   1200
tgcctcatgc cataaattaa ccaaacaaac atgaattata tcctttgata atttattcat   1260
actattattg cttgcacctg tacatatatg tgttgctcat tcactcaccc cagactgagt   1320
gctagatcct cggactcgaa taaatcattt attatgctta aataattcga ttttattttt   1380
cctacatcac aataatctaa agagttaatc tcatactctc gattcatcct taaaaattta   1440
atgggtgtaa tgagaaatta attttaacta ctattatatt ttaaaaaata aatagtgaaa   1500
ataatgagaa actctaatta aaattactct ttgagtaact aacttgattt ttcctcgtag   1560
aacaacccaa tcaatgtcac aacgaatttt tcctatttca cgagagaact tgaaagttaa   1620
aatttggtta aagtcgttcc taaacgtagc agaagataag atagaaagat ggaaaagtaa   1680
aagcatgcaa atatataatt gaaattgaaa tgtaagtagt agtaattaaa aacaattatt   1740
tgatggaaaa agagataact ttactaatga cacacaccaa acataagatg tgttcgctag   1800
agttgttaac cacactcact catatacagc atatcacaaa ttcccatgca ccctcaattc   1860
aacggtccag atgcggtctg atgaaatcac acggtcgata cgaactgtac attctccctc   1920
tctctatcac ggatttcgat gtttcgcttt cggaccaaat gtggggccca catagtactg   1980
tgtcctgagt gctggctact cacaaaggcg ggaaccagtt tttgtcgcag aggtatggct   2040
ctttgttgtc atcggatgag agagaaagag tgtagagaga gaaacaaaac taagagacaa   2100
tcactgaatc actctcactc actctacatg ctgtgtgcgt gactctgtca ctgtgttttg   2160
tgtttaagca cattgcattt tagtttcaga ggagtttttt tttttttttt tgctgttatt   2220
gttattcaag ttttggttac tactaccgcc acatgttcat gccccttcaa tttttgttca   2280
actttttgac tttctgcttg gtttccaagg aaaaagattg caacttgttt ctgggtctag   2340
tttgcttttg gttgggtttg ttagtccctg ctggcacctc ggaatagtgg gtttttgttt   2400
ttgtttttgt tttttttctt cttttggagg ttcaaattct tgttctgatt cgtgtgaagg   2460
tggaaaattt atgggtggtc accggaagag gaaaaagatg ggattcgttg gaaaaaagta   2520
agactattcg gtgataacat gtctgcttgc ttttttggga cggctttttt gttaagattt   2580
tgggttgaaa aggttgagga agatgcttat gcttgcaact ttttttttaaa cccattttag   2640
caccaagtat aaaaagttgt tcttggtctt gtttccaagt gttgaggtag gtgatagggg   2700
ttttgagcat gtgagtgatt catgcctctc attttggagc ttctgagatt ggtttctggt   2760
tgtggcttcg tttgtttgtt tgtttgtttg ttgtgctttc atgtttagga aaaggcacat   2820
cctttcttct cttgcaaggg aattgttggc actccagcca ctttttcttc tcttcttgtt   2880
cagcttgcac cacaacactg tgcagtgtca aggaaggttg agtaagcatg tttcttcaga   2940
gcctccctca ccttctaggc catcgtcagc agcaccatct tcatcaggat acaaggatga   3000
```

```
ccctaggaag ataattttga gcatggtttt aggagcagtc actgggctag tttgttctgt   3060

tctgtttgca cttgtggttc gttgtgttgt tcagtatctg aaccgcacac caatcctcaa   3120

gggccctgtc atattctccc ccaaaattgc ctccaagaca ctccaatcag ctttggcaaa   3180

ggaaaaccac ttgcttggct cgagtcctaa tgggaagtac tataaaacta tgcttgacaa   3240

tggactcact attgcagtca aaaggctaac accctttgag agcaattccc cggaggccaa   3300

gaggaaatca gtgaagaggc agatacaaac tgagcttgaa cttcttgcaa gccttaggaa   3360

taggaacctg atgagtttga gagcctatgt tcgtgagcct gatggattct cattggttta   3420

tgattatgcg tccactggga gtcttgctga tgtgttgaat agagtgaggg agaatgagtt   3480

gccctttggt tgggaagtta ggctcaggat tgctgttggt gtggtgaagg gtcttcagta   3540

tcttcacttc acttgtgtgc ctcagattct gcactacaac ttgaagccca ctaatgtgat   3600

gttggatgct gagtttgaac ctagattagc agattatggc ttggctaaac ttctgcctaa   3660

cttggataga ggaagttctc tctacacccc tcctgaatgt ttccacaatt gcaggtaaga   3720

caaatcaatt gctttcaatc atactcactc actagtgttt tgaacttggt ttgtttctgt   3780

tttttcactt tttacaccaa atgggtaact agttggttga tattgggcac ttgcttgatt   3840

cgttaccttt ttaaaagctc cactcctcat tggtttttc tccttctttg gagtacctta   3900

atcaaagact cttagtgtga aacgtgatta ttgttctgta ttgtcatggt gtcatttgct   3960

attgtttaat aattaagact ttgcaaaact aatgtttttg taactaccca ttacttgtat   4020

agttcacatg ctgcaaacta ctaaacctag attggtgatt gagaccccaa ttaaaaatta   4080

taataataat ttactaaggt ttttctttc caatttaact tatttctagt ttttcattgt   4140

tgtgtatatc tctggataca tcaatcttaa tagtaataac ttaaaaataa gtaataacaa   4200

taaaaagatt gcttgattga tgcatttcat atatgggtat ggtattgcca ataagatgtt   4260

aattttaact tcattccatt cttgtatgtg aaacttcatg gtatttagat tggatggtgt   4320

tttttgcaat ttcagcaggt acaccgacaa aagtgatatc ttcagttttg gcatcatact   4380

aggtgtttta ttaaccagta aggaccctac agatccattc tttggagaag cagccagtgg   4440

gggaagtttg ggatgttggt tgagacactt gcagcaagcc ggtgagtcac gtgaagctct   4500

agataagagc atgttaggag aagaaggtga ggaagatgag atgctaatgg ctgttaggat   4560

tgctgctgca tgcctttctg atatgcctgc agataggcct tctagtgatg agcttgttca   4620

catgctaacg caactgcaca gtttttgaaa caaaccttga ttcttcagtt cctagatatt   4680

tttttctttc tcttatcccc tctttctgta ataagatgat aggggaattt ggttagtgcc   4740

catgattctg gtgtaattga ttgttttggt gtaattgatt gttttgcatg atcttggttt   4800

tcatggtgtg gtttctaata ttccattttc tctttctcta ttctatttcc tttttctttt   4860

ggctgatttt gcaggttgtg gtgggtttag gtcacactat tatattttgt ttgtaaatga   4920

ctagtcatgt taacaagagt tttcttttct tgct                               4954
```

<210> SEQ ID NO 48
<211> LENGTH: 1227
<212> TYPE: DNA
<213> ORGANISM: Glycine max
<220> FEATURE:
<221> NAME/KEY: CDS
<222> LOCATION: (1)..(1227)

<400> SEQUENCE: 48

```
atg ttt agg aaa agg cac atc ctt tct tct ctt gca agg gaa ttg ttg       48
```

```
Met Phe Arg Lys Arg His Ile Leu Ser Ser Leu Ala Arg Glu Leu Leu
1               5                   10                  15

gca ctc cag cca ctt ttt ctt ctc ttc ttg ttc agc ttg cac cac aac       96
Ala Leu Gln Pro Leu Phe Leu Leu Phe Leu Phe Ser Leu His His Asn
            20                  25                  30

act gtg cag tgt caa gga agg ttg agt aag cat gtt tct tca gag cct      144
Thr Val Gln Cys Gln Gly Arg Leu Ser Lys His Val Ser Ser Glu Pro
        35                  40                  45

ccc tca cct tct agg cca tcg tca gca gca cca tct tca tca gga tac      192
Pro Ser Pro Ser Arg Pro Ser Ser Ala Ala Pro Ser Ser Ser Gly Tyr
    50                  55                  60

aag gat gac cct agg aag ata att ttg agc atg gtt tta gga gca gtc      240
Lys Asp Asp Pro Arg Lys Ile Ile Leu Ser Met Val Leu Gly Ala Val
65                  70                  75                  80

act ggg cta gtt tgt tct gtt ctg ttt gca ctt gtg gtt cgt tgt gtt      288
Thr Gly Leu Val Cys Ser Val Leu Phe Ala Leu Val Val Arg Cys Val
                85                  90                  95

gtt cag tat ctg aac cgc aca cca atc ctc aag ggc cct gtc ata ttc      336
Val Gln Tyr Leu Asn Arg Thr Pro Ile Leu Lys Gly Pro Val Ile Phe
            100                 105                 110

tcc ccc aaa att gcc tcc aag aca ctc caa tca gct ttg gca aag gaa      384
Ser Pro Lys Ile Ala Ser Lys Thr Leu Gln Ser Ala Leu Ala Lys Glu
        115                 120                 125

aac cac ttg ctt ggc tcg agt cct aat ggg aag tac tat aaa act atg      432
Asn His Leu Leu Gly Ser Ser Pro Asn Gly Lys Tyr Tyr Lys Thr Met
    130                 135                 140

ctt gac aat gga ctc act att gca gtc aaa agg cta aca ccc ttt gag      480
Leu Asp Asn Gly Leu Thr Ile Ala Val Lys Arg Leu Thr Pro Phe Glu
145                 150                 155                 160

agc aat tcc ccg gag gcc aag agg aaa tca gtg aag agg cag ata caa      528
Ser Asn Ser Pro Glu Ala Lys Arg Lys Ser Val Lys Arg Gln Ile Gln
                165                 170                 175

act gag ctt gaa ctt ctt gca agc ctt agg aat agg aac ctg atg agt      576
Thr Glu Leu Glu Leu Leu Ala Ser Leu Arg Asn Arg Asn Leu Met Ser
            180                 185                 190

ttg aga gcc tat gtt cgt gag cct gat gga ttc tca ttg gtt tat gat      624
Leu Arg Ala Tyr Val Arg Glu Pro Asp Gly Phe Ser Leu Val Tyr Asp
        195                 200                 205

tat gcg tcc act ggg agt ctt gct gat gtg ttg aat aga gtg agg gag      672
Tyr Ala Ser Thr Gly Ser Leu Ala Asp Val Leu Asn Arg Val Arg Glu
    210                 215                 220

aat gag ttg ccc ttt ggt tgg gaa gtt agg ctc agg att gct gtt ggt      720
Asn Glu Leu Pro Phe Gly Trp Glu Val Arg Leu Arg Ile Ala Val Gly
225                 230                 235                 240

gtg gtg aag ggt ctt cag tat ctt cac ttc act tgt gtg cct cag att      768
Val Val Lys Gly Leu Gln Tyr Leu His Phe Thr Cys Val Pro Gln Ile
                245                 250                 255

ctg cac tac aac ttg aag ccc act aat gtg atg ttg gat gct gag ttt      816
Leu His Tyr Asn Leu Lys Pro Thr Asn Val Met Leu Asp Ala Glu Phe
            260                 265                 270

gaa cct aga tta gca gat tat ggc ttg gct aaa ctt ctg cct aac ttg      864
Glu Pro Arg Leu Ala Asp Tyr Gly Leu Ala Lys Leu Leu Pro Asn Leu
        275                 280                 285

gat aga gga agt tct ctc tac acc cct cct gaa tgt ttc cac aat tgc      912
Asp Arg Gly Ser Ser Leu Tyr Thr Pro Pro Glu Cys Phe His Asn Cys
    290                 295                 300

agc agg tac acc gac aaa agt gat atc ttc agt ttt ggc atc ata cta      960
Ser Arg Tyr Thr Asp Lys Ser Asp Ile Phe Ser Phe Gly Ile Ile Leu
305                 310                 315                 320
```

```
ggt gtt tta tta acc agt aag gac cct aca gat cca ttc ttt gga gaa      1008
Gly Val Leu Leu Thr Ser Lys Asp Pro Thr Asp Pro Phe Phe Gly Glu
                325                 330                 335

gca gcc agt ggg gga agt ttg gga tgt tgg ttg aga cac ttg cag caa      1056
Ala Ala Ser Gly Gly Ser Leu Gly Cys Trp Leu Arg His Leu Gln Gln
            340                 345                 350

gcc ggt gag tca cgt gaa gct cta gat aag agc atg tta gga gaa gaa      1104
Ala Gly Glu Ser Arg Glu Ala Leu Asp Lys Ser Met Leu Gly Glu Glu
        355                 360                 365

ggt gag gaa gat gag atg cta atg gct gtt agg att gct gct gca tgc      1152
Gly Glu Glu Asp Glu Met Leu Met Ala Val Arg Ile Ala Ala Ala Cys
    370                 375                 380

ctt tct gat atg cct gca gat agg cct tct agt gat gag ctt gtt cac      1200
Leu Ser Asp Met Pro Ala Asp Arg Pro Ser Ser Asp Glu Leu Val His
385                 390                 395                 400

atg cta acg caa ctg cac agt ttt tga                                  1227
Met Leu Thr Gln Leu His Ser Phe
                405


<210> SEQ ID NO 49
<211> LENGTH: 408
<212> TYPE: PRT
<213> ORGANISM: Glycine max

<400> SEQUENCE: 49

Met Phe Arg Lys Arg His Ile Leu Ser Ser Leu Ala Arg Glu Leu Leu
1               5                   10                  15

Ala Leu Gln Pro Leu Phe Leu Leu Phe Leu Phe Ser Leu His His Asn
            20                  25                  30

Thr Val Gln Cys Gln Gly Arg Leu Ser Lys His Val Ser Ser Glu Pro
        35                  40                  45

Pro Ser Pro Ser Arg Pro Ser Ser Ala Ala Pro Ser Ser Ser Gly Tyr
    50                  55                  60

Lys Asp Asp Pro Arg Lys Ile Ile Leu Ser Met Val Leu Gly Ala Val
65                  70                  75                  80

Thr Gly Leu Val Cys Ser Val Leu Phe Ala Leu Val Val Arg Cys Val
                85                  90                  95

Val Gln Tyr Leu Asn Arg Thr Pro Ile Leu Lys Gly Pro Val Ile Phe
            100                 105                 110

Ser Pro Lys Ile Ala Ser Lys Thr Leu Gln Ser Ala Leu Ala Lys Glu
        115                 120                 125

Asn His Leu Leu Gly Ser Ser Pro Asn Gly Lys Tyr Tyr Lys Thr Met
    130                 135                 140

Leu Asp Asn Gly Leu Thr Ile Ala Val Lys Arg Leu Thr Pro Phe Glu
145                 150                 155                 160

Ser Asn Ser Pro Glu Ala Lys Arg Lys Ser Val Lys Arg Gln Ile Gln
                165                 170                 175

Thr Glu Leu Glu Leu Leu Ala Ser Leu Arg Asn Arg Asn Leu Met Ser
            180                 185                 190

Leu Arg Ala Tyr Val Arg Glu Pro Asp Gly Phe Ser Leu Val Tyr Asp
        195                 200                 205

Tyr Ala Ser Thr Gly Ser Leu Ala Asp Val Leu Asn Arg Val Arg Glu
    210                 215                 220

Asn Glu Leu Pro Phe Gly Trp Glu Val Arg Leu Arg Ile Ala Val Gly
225                 230                 235                 240

Val Val Lys Gly Leu Gln Tyr Leu His Phe Thr Cys Val Pro Gln Ile
                245                 250                 255
```

```
Leu His Tyr Asn Leu Lys Pro Thr Asn Val Met Leu Asp Ala Glu Phe
            260                 265                 270

Glu Pro Arg Leu Ala Asp Tyr Gly Leu Ala Lys Leu Leu Pro Asn Leu
        275                 280                 285

Asp Arg Gly Ser Ser Leu Tyr Thr Pro Pro Glu Cys Phe His Asn Cys
    290                 295                 300

Ser Arg Tyr Thr Asp Lys Ser Asp Ile Phe Ser Phe Gly Ile Ile Leu
305                 310                 315                 320

Gly Val Leu Leu Thr Ser Lys Asp Pro Thr Asp Pro Phe Phe Gly Glu
                325                 330                 335

Ala Ala Ser Gly Gly Ser Leu Gly Cys Trp Leu Arg His Leu Gln Gln
            340                 345                 350

Ala Gly Glu Ser Arg Glu Ala Leu Asp Lys Ser Met Leu Gly Glu Glu
        355                 360                 365

Gly Glu Glu Asp Glu Met Leu Met Ala Val Arg Ile Ala Ala Ala Cys
    370                 375                 380

Leu Ser Asp Met Pro Ala Asp Arg Pro Ser Ser Asp Glu Leu Val His
385                 390                 395                 400

Met Leu Thr Gln Leu His Ser Phe
                405
```

<210> SEQ ID NO 50
<211> LENGTH: 6932
<212> TYPE: DNA
<213> ORGANISM: Glycine max

<400> SEQUENCE: 50

```
caaatgggta tgctcccttc aggggactcc ccaatcgccc taatcgcaga ctccaccgtc      60

tcactctcgt gaaactccgc cagctccggc ttccccaccg tcagatcgcc caccacgtgg     120

tacacgaaca ccgacgccat cggaatccaa aagggtatcc ggaaccacaa tcaaaatcga     180

tttttgttct gctttttgta tccttaaaaa aaaaaccgaa aacagaaaga aaaaaaaaag     240

tttgcttttt ttgctttgtc gggtgagagc tataagaggg tatggaggaa gatgaggaga     300

agatcgaggg cggtgatggg agggcggtgg aggatcacgg cagagaaaga gttagccatt     360

gccatggagg gagaacgaaa aggttaaggc ccattcaatt gaatcagatc agagagagag     420

agggcgtagc ttttggggaa gatatgatat gtagagattt ggataaggta cgtcctttcg     480

gggacagcaa gagatgcaac gacagaagaa gatggatcag cgacgcttga tgcggttggg     540

acctgagaat gaatgggaca ccagacacac actaaaagga ggttcaattt atcaaataaa     600

aaagagaaag gcacagggga tgtgtcatgt gtcatgtgtc atgtgtcatg tgtatggtga     660

gctgcatcat atagagaatc ttttcacctt aattaatttg tttagtttaa tacgtttttc     720

ttttcttgtc atactcatct ttgatttcaa ttctatagac ctatatataa gttaatttat     780

ttaataagag aggataaaca aagaatgaaa ataggtaaat gagaaaaaag gagaaataaa     840

ttaaaaacaa tgcttgtttg aatttaaaga aacggaagaa aaataagaaa aatagattac     900

taatataaaa tatcctttat attacataat ttttttcata taacatagta catacggaca     960

aaacttagat acattatttt gggtgttatt tttttattag agttaaagtt tcatttcaat    1020

gatatatata taagttttaa atgtaaaact ttattatgca aattactcaa ataaaactcc    1080

aattttcatt agagaataat acaaaccgtg taacgactac aagtttatct taaatttcca    1140

atctttgaaa ttatgttatt tgtctccctt tcttaaaaat ataaaattga tttagtgata    1200
```

-continued

```
aagaaaaaag aggagaaggg ataagtttta aatataaatt cttcaggtta tagttcaata   1260
ggtcaccttt aattaatgac gttaattaac agattaataa tgacttcaga agcagtgtct   1320
atgaagttta tgcgagatca ccaatgatat atgtagttaa tagcaacaag ttgaggaaag   1380
aggtttggat gaatgtgtgg ctgtttaatg ttgggtggtg gtgtggtggc tatgactacg   1440
aggttggtgt tggaaaatgt tgtcaattca attgggattc ggtttgcaaa gttgtgataa   1500
ctttgagttg aatgatggaa tattgaaatt ttctaggctt agttaggaat gattgctaca   1560
tgtaacagtg ataccacaac aacagggatg agggattgtt ggggtttact tttaaaaaat   1620
gaatgaattg aattacaatg taaaagtata catataaaac actattcttg cttcttaaaa   1680
aaaacgtgag acagagagaa agtgaagatg ataagattat agcgcacgcg ttggagcgtg   1740
catgagttta ctaggtcttg taccatgcaa aaaaatttag gacccttaga tataacaaca   1800
agacaagaag atctttaaga gtgtaacata tggataacat actgtatacc aacttttctt   1860
tttaatagta tttcttctct ctggttataa catcatttta actaatctat gtctgttaaa   1920
aaaatattaa tttaattaat tatattaaat atatcaatta tttatatttt ttatttttct   1980
atccacttaa tttttattta atgttttaaa aaaataatta agaataaaat aattaatgta   2040
ttaaaaatta aaaaaatctt ataaatcaag acaaataaat ttatgaaaaa catcatataa   2100
ttagtatggg attatgggat ggagtagtat ttaacttgtg gcttttgaaa attacaccat   2160
attttctctc tctcttgaca aaatgaatgc aacttaaaaa cgtgggatca ttcttcctcc   2220
tgagtccaga atgttcgacc ccattcgtac tctgatctat gtgtgtttgt ggtatatctc   2280
cgttgtcact tcaccattct agcttcatca gagaaagtaa tatatatatt tgtaaaccaa   2340
ttatatatat atttgagagg attttaattc ttactaaaat tgtaaaccaa ttagaaatca   2400
tttttctgta atttttgtga tctgaaattt tctgttcggg ttggaaatga cacaaaatcg   2460
ttgggtcttt aaatgggttg caaccggatg agaatgaccc aactcaaggt aggggatgac   2520
caaagcatag ccttttaatg ggtaatgtta aacatgatat aaatttataa caaattattt   2580
ttatggtgta gtggttaact ctttcattaa taataatata gctggttgtt ggttccatcc   2640
cacaataagt cagtttagct ttttatcttc taaagatttc ctgttttcat ttattttggt   2700
tttttaaaa aataaacaat ttcgccttgg aatcgaactc acgatatagt gattagttat   2760
aaaaaaataa ttataaatta tttggtaatt tttttcttac attcactctt gttttgaata   2820
ctcttctctt tgtgaagtta tgaactttgt tctcttacca caaatatgat acatcttctt   2880
atgtttttta attttagatt atatttgata aaactaacca aaaagatgaa aaatatagtc   2940
tgtttaaaat atttaagatc taagcttaac tcgttacatg tgatagactt tatttgtaga   3000
ttatacttga tttatttgaa agtttagctt aacctattag tttatttaaa gacctatttc   3060
atatgaaagt ttttatataa gtctattttt ttatattgga caataaattt ataaatcgtt   3120
gagaaaattc catgtaaaca aactataatc tataaaaaaa aaaaatttct ttattcaaag   3180
cacaagatag gtgaaaatag atgaactaag ttttataagt gaaatttaac atgtcattat   3240
gatgtaagtt tatcaacttc aagataactt agttaaaaat ataattttgt aataagtcct   3300
ctaattaaaa cataaatttc gcactcaata attttttttt aatcgtggat caacactcat   3360
aatattttaa aaaagtaaat aatgtattat tttgatacat tacaataatt ttaatattac   3420
aaaatattat aatttatatt tatttaaata ggttgatcta ttaggtttaa aacacttttt   3480
aaataactta aaacctaatt ttttaatcaa atagactttt attaaaactt agatatgatt   3540
tatttttatt tttttaaaaa aaactaacct gacttgagtt tgatataaat taggtgtcag   3600
```

-continued

```
tttgtttaaa tttatttatt aaaataaatg tttattttaa taaaataagt aattttatat   3660
ttgtttagta tatttgtgta aattcttttt ccttaaaaaa tattttttttc tttttaaaaa   3720
aaatacttat tttaaaatta tttttttttaa aaagagaaac ttgaaaaagg ataaagtgta   3780
atgcagtata gagagaaaga ggaggaagca aagcaaacca agcacaacac aacaaagcca   3840
ctttattttt ttgatctaac ctaaaccctc tttttcccct gttgctctct cactttatca   3900
gcgtgataca accaacccaa gaccaatgtg gaagatcttg ttcctctttc ccttctctta   3960
tgtccatttc atcatgtttt cattctaatc tccaaaatcc atgcccaccc agttcctctt   4020
ttgcttcaaa ctcctctccc ccttcctaaa aattgcacct ttactctcat ggtgatggga   4080
cacaccacac ccctcacact tctctgtgtg attcttcttt ttgcaactcc ttctcactca   4140
attgatgttc acccacaaga cagaatctca ctttcaatgt tcaggtcatc tctgccaaac   4200
cccaaccaga gtttgcccag ctgggtgggc tccaactgca cttcatggag tggaatcacc   4260
tgtgacaaca gaactgggag ggtgctttcc atcaacctaa ccagtatgaa cctttcaggc   4320
aaaatccacc ccagtttgtg ctacctttca tatctgaaca agttggggtt gtcccacaac   4380
aacttcacat cccctcttcc tgaatgtttt ggcaacttgc ttaacctaag agccattgat   4440
ctcagccaca acaggcttca tgggggaata ccagactctt tcatgaggct taggcacctc   4500
actgagcttg ttttgagtgg gaaccctgat ttggggggtc cactgcctgc ttggattggt   4560
aacttctctg caaatctgga aaggttacat cttggtttct gttcattcag tggtggcata   4620
ccggagagct tgctttacct gaagtccctc aagtatttgg accttgagaa caacctcttg   4680
tctggtaact tggtcaattt tcaacagcct ttggttttgc tcaatcttgc ttccaatcag   4740
tttgctggta ctttgccttg ctttgcagct tcagttcagt ctctaactgt gttgaattta   4800
tctaacaatt ctattgtggg gggactacct gcttgtattg cttcttttca agctttgact   4860
catttgaacc tgtcagggaa ccacttgaag tatagaatat atcctaggct tgtgttctcg   4920
gagaaacttc ttgttttgga cttgagtaat aatgctttgt ctggtcctat tccttgtaaa   4980
attgctgaga caactgagaa acttggcctt gttcttcttg acctttctca caatcagttc   5040
tctggtgaaa ttcctgtgaa aatcactgag ttgaaaagct tgcaggcctt gtttctctct   5100
cacaatcttc tctctggaga aattcctgct agaattggaa atttgactta tctgcaggtc   5160
attgatctct cacacaactc tttgtctgga accattccat tcagtattgt tgggtgcttt   5220
cagctgtatg ctctaatact tactaacaac aatctttctg gtgtaattca accggagttt   5280
gatgcgttgg atatcttgag gattctggat ataagcaaca acaggttttc cggggctatc   5340
ccactcactc tggctggatg caaatctctg gagattgtag attttagttc caatgagctt   5400
tctggatcct tgaatgatgc aataaccaaa tggacaaacc tcaggtattt gtctcttgct   5460
cagaacaagt tcagtggaaa tctgcctagt tggttgttca catttaacgc aatagaaatg   5520
atggatttct cgcataacaa gtttactggc ttcatacctg atattaattt taagggtagc   5580
ttaatattta acaccaggaa tgtcactgtt aaagagccat tggttgcagc aagaaaggtt   5640
caactgagag tttcggcggt tgtttctgat agcaatcagc tcagtttcac ttatgatctt   5700
tcctcaatgg ttggaattga tctatccagc aattcgcttc atggggaaat tccaaggggc   5760
ttatttggtc tagctggcct agaatatctg aacttgtcat gcaactttct ttacggacag   5820
cttccggggt tgcagaaaat gcatagtttg aaagccttgg atttgtcaca taattccttg   5880
tctggacata tcccaggaaa catttctagc cttcaagatc tgtccatttt gaatctttcc   5940
```

```
tacaactgtt tttctggata tgttccccag aagcaagggt atgggagatt tcccggtgca   6000

tttgctggaa atccagatct gtgcatggaa acttccagtg gagtatgtga tgatggaagg   6060

actcaatctg cgcaaggaag ttctttcagt gaagatagga tggatggccc aatttctgtg   6120

gggattttct ttatcagtgc ctttgttagt tttgattttg gtgttgtggt tctcttctgt   6180

tctgcccggg caagaaatta cattctccaa acaaaagttt gatttgatgc ttgtgacagt   6240

tacaaatctc ctgtaaattc cattttgtaa tttggtacct gtgttctcag tttcaagtaa   6300

aacatacact tatgtgacta ggaatactat ccggccatca acttcacaag tgttttcttg   6360

tgattcctga tcaagtgtct cagatttaca ggatcaaaat gccatgacat gagtaacaca   6420

aggtttaaag aacactcaac actggcttta tctatctgag tgaagactag cctggcatca   6480

ttcagccaag aaaagaatgg atgattatga tgaaaatttg atccgagtaa agacgagtcc   6540

ctcatcattc tgatggttgt tctcttttgc tggaatttgg ttgcatcaag tttagaatgc   6600

atcatcacat gtattattca taatcagtgg tgggcgaagg gtcagtaggg aacatgtctg   6660

atatctggtc tagttatggt gaaattttga tcttgggcat caaattgcag atttgcaagc   6720

atgtttacgt gaagagaact tgtataattc ttgattaacc tagttctttc ttgaggtggg   6780

gaaccaagtt ttccctgtaa gtggggagta ggttctcata agtctaagat ttgtatttgt   6840

attactatct tcacaccttc atcatagtgc tgtgatttta aatgatattc tcacgaaacc   6900

ttttcattga caacagaaaa gaggttaatt ga                                 6932
```

<210> SEQ ID NO 51
<211> LENGTH: 2109
<212> TYPE: DNA
<213> ORGANISM: Glycine max
<220> FEATURE:
<221> NAME/KEY: CDS
<222> LOCATION: (1)..(2109)

<400> SEQUENCE: 51

```
atg ccc acc cag ttc ctc ttt tgc ttc aaa ctc ctc tcc ccc ttc cta       48
Met Pro Thr Gln Phe Leu Phe Cys Phe Lys Leu Leu Ser Pro Phe Leu
1               5                   10                  15

aaa att gca cct tta ctc tca tgg tca tct ctg cca aac ccc aac cag       96
Lys Ile Ala Pro Leu Leu Ser Trp Ser Ser Leu Pro Asn Pro Asn Gln
            20                  25                  30

agt ttg ccc agc tgg gtg ggc tcc aac tgc act tca tgg agt gga atc      144
Ser Leu Pro Ser Trp Val Gly Ser Asn Cys Thr Ser Trp Ser Gly Ile
        35                  40                  45

acc tgt gac aac aga act ggg agg gtg ctt tcc atc aac cta acc agt      192
Thr Cys Asp Asn Arg Thr Gly Arg Val Leu Ser Ile Asn Leu Thr Ser
    50                  55                  60

atg aac ctt tca ggc aaa atc cac ccc agt ttg tgc tac ctt tca tat      240
Met Asn Leu Ser Gly Lys Ile His Pro Ser Leu Cys Tyr Leu Ser Tyr
65                  70                  75                  80

ctg aac aag ttg ggg ttg tcc cac aac aac ttc aca tcc cct ctt cct      288
Leu Asn Lys Leu Gly Leu Ser His Asn Asn Phe Thr Ser Pro Leu Pro
                85                  90                  95

gaa tgt ttt ggc aac ttg ctt aac cta aga gcc att gat ctc agc cac      336
Glu Cys Phe Gly Asn Leu Leu Asn Leu Arg Ala Ile Asp Leu Ser His
            100                 105                 110

aac agg ctt cat ggg gga ata cca gac tct ttc atg agg ctt agg cac      384
Asn Arg Leu His Gly Gly Ile Pro Asp Ser Phe Met Arg Leu Arg His
        115                 120                 125

ctc act gag ctt gtt ttg agt ggg aac cct gat ttg ggg ggt cca ctg      432
Leu Thr Glu Leu Val Leu Ser Gly Asn Pro Asp Leu Gly Gly Pro Leu
```

-continued

```
    130                 135                 140

cct gct tgg att ggt aac ttc tct gca aat ctg gaa agg tta cat ctt      480
Pro Ala Trp Ile Gly Asn Phe Ser Ala Asn Leu Glu Arg Leu His Leu
145                 150                 155                 160

ggt ttc tgt tca ttc agt ggt ggc ata ccg gag agc ttg ctt tac ctg      528
Gly Phe Cys Ser Phe Ser Gly Gly Ile Pro Glu Ser Leu Leu Tyr Leu
                165                 170                 175

aag tcc ctc aag tat ttg gac ctt gag aac aac ctc ttg tct ggt aac      576
Lys Ser Leu Lys Tyr Leu Asp Leu Glu Asn Asn Leu Leu Ser Gly Asn
            180                 185                 190

ttg gtc aat ttt caa cag cct ttg gtt ttg ctc aat ctt gct tcc aat      624
Leu Val Asn Phe Gln Gln Pro Leu Val Leu Leu Asn Leu Ala Ser Asn
        195                 200                 205

cag ttt gct ggt act ttg cct tgc ttt gca gct tca gtt cag tct cta      672
Gln Phe Ala Gly Thr Leu Pro Cys Phe Ala Ala Ser Val Gln Ser Leu
    210                 215                 220

act gtg ttg aat tta tct aac aat tct att gtg ggg gga cta cct gct      720
Thr Val Leu Asn Leu Ser Asn Asn Ser Ile Val Gly Gly Leu Pro Ala
225                 230                 235                 240

tgt att gct tct ttt caa gct ttg act cat ttg aac ctg tca ggg aac      768
Cys Ile Ala Ser Phe Gln Ala Leu Thr His Leu Asn Leu Ser Gly Asn
                245                 250                 255

cac ttg aag tat aga ata tat cct agg ctt gtg ttc tcg gag aaa ctt      816
His Leu Lys Tyr Arg Ile Tyr Pro Arg Leu Val Phe Ser Glu Lys Leu
            260                 265                 270

ctt gtt ttg gac ttg agt aat aat gct ttg tct ggt cct att cct tgt      864
Leu Val Leu Asp Leu Ser Asn Asn Ala Leu Ser Gly Pro Ile Pro Cys
        275                 280                 285

aaa att gct gag aca act gag aaa ctt ggc ctt gtt ctt ctt gac ctt      912
Lys Ile Ala Glu Thr Thr Glu Lys Leu Gly Leu Val Leu Leu Asp Leu
    290                 295                 300

tct cac aat cag ttc tct ggt gaa att cct gtg aaa atc act gag ttg      960
Ser His Asn Gln Phe Ser Gly Glu Ile Pro Val Lys Ile Thr Glu Leu
305                 310                 315                 320

aaa agc ttg cag gcc ttg ttt ctc tct cac aat ctt ctc tct gga gaa     1008
Lys Ser Leu Gln Ala Leu Phe Leu Ser His Asn Leu Leu Ser Gly Glu
                325                 330                 335

att cct gct aga att gga aat ttg act tat ctg cag gtc att gat ctc     1056
Ile Pro Ala Arg Ile Gly Asn Leu Thr Tyr Leu Gln Val Ile Asp Leu
            340                 345                 350

tca cac aac tct ttg tct gga acc att cca ttc agt att gtt ggg tgc     1104
Ser His Asn Ser Leu Ser Gly Thr Ile Pro Phe Ser Ile Val Gly Cys
        355                 360                 365

ttt cag ctg tat gct cta ata ctt act aac aac aat ctt tct ggt gta     1152
Phe Gln Leu Tyr Ala Leu Ile Leu Thr Asn Asn Asn Leu Ser Gly Val
    370                 375                 380

att caa ccg gag ttt gat gcg ttg gat atc ttg agg att ctg gat ata     1200
Ile Gln Pro Glu Phe Asp Ala Leu Asp Ile Leu Arg Ile Leu Asp Ile
385                 390                 395                 400

agc aac aac agg ttt tcc ggg gct atc cca ctc act ctg gct gga tgc     1248
Ser Asn Asn Arg Phe Ser Gly Ala Ile Pro Leu Thr Leu Ala Gly Cys
                405                 410                 415

aaa tct ctg gag att gta gat ttt agt tcc aat gag ctt tct gga tcc     1296
Lys Ser Leu Glu Ile Val Asp Phe Ser Ser Asn Glu Leu Ser Gly Ser
            420                 425                 430

ttg aat gat gca ata acc aaa tgg aca aac ctc agg tat ttg tct ctt     1344
Leu Asn Asp Ala Ile Thr Lys Trp Thr Asn Leu Arg Tyr Leu Ser Leu
        435                 440                 445

gct cag aac aag ttc agt gga aat ctg cct agt tgg ttg ttc aca ttt     1392
```

```
Ala Gln Asn Lys Phe Ser Gly Asn Leu Pro Ser Trp Leu Phe Thr Phe
    450                 455                 460

aac gca ata gaa atg atg gat ttc tcg cat aac aag ttt act ggc ttc      1440
Asn Ala Ile Glu Met Met Asp Phe Ser His Asn Lys Phe Thr Gly Phe
465                 470                 475                 480

ata cct gat att aat ttt aag ggt agc tta ata ttt aac acc agg aat      1488
Ile Pro Asp Ile Asn Phe Lys Gly Ser Leu Ile Phe Asn Thr Arg Asn
                485                 490                 495

gtc act gtt aaa gag cca ttg gtt gca gca aga aag gtt caa ctg aga      1536
Val Thr Val Lys Glu Pro Leu Val Ala Ala Arg Lys Val Gln Leu Arg
            500                 505                 510

gtt tcg gcg gtt gtt tct gat agc aat cag ctc agt ttc act tat gat      1584
Val Ser Ala Val Val Ser Asp Ser Asn Gln Leu Ser Phe Thr Tyr Asp
        515                 520                 525

ctt tcc tca atg gtt gga att gat cta tcc agc aat tcg ctt cat ggg      1632
Leu Ser Ser Met Val Gly Ile Asp Leu Ser Ser Asn Ser Leu His Gly
    530                 535                 540

gaa att cca agg ggc tta ttt ggt cta gct ggc cta gaa tat ctg aac      1680
Glu Ile Pro Arg Gly Leu Phe Gly Leu Ala Gly Leu Glu Tyr Leu Asn
545                 550                 555                 560

ttg tca tgc aac ttt ctt tac gga cag ctt ccg ggg ttg cag aaa atg      1728
Leu Ser Cys Asn Phe Leu Tyr Gly Gln Leu Pro Gly Leu Gln Lys Met
                565                 570                 575

cat agt ttg aaa gcc ttg gat ttg tca cat aat tcc ttg tct gga cat      1776
His Ser Leu Lys Ala Leu Asp Leu Ser His Asn Ser Leu Ser Gly His
            580                 585                 590

atc cca gga aac att tct agc ctt caa gat ctg tcc att ttg aat ctt      1824
Ile Pro Gly Asn Ile Ser Ser Leu Gln Asp Leu Ser Ile Leu Asn Leu
        595                 600                 605

tcc tac aac tgt ttt tct gga tat gtt ccc cag aag caa ggg tat ggg      1872
Ser Tyr Asn Cys Phe Ser Gly Tyr Val Pro Gln Lys Gln Gly Tyr Gly
    610                 615                 620

aga ttt ccc ggt gca ttt gct gga aat cca gat ctg tgc atg gaa act      1920
Arg Phe Pro Gly Ala Phe Ala Gly Asn Pro Asp Leu Cys Met Glu Thr
625                 630                 635                 640

tcc agt gga gta tgt gat gat gga agg act caa tct gcg caa gga agt      1968
Ser Ser Gly Val Cys Asp Asp Gly Arg Thr Gln Ser Ala Gln Gly Ser
                645                 650                 655

tct ttc agt gaa gat agg atg gat ggc cca att tct gtg ggg att ttc      2016
Ser Phe Ser Glu Asp Arg Met Asp Gly Pro Ile Ser Val Gly Ile Phe
            660                 665                 670

ttt atc agt gcc ttt gtt agt ttt gat ttt ggt gtt gtg gtt ctc ttc      2064
Phe Ile Ser Ala Phe Val Ser Phe Asp Phe Gly Val Val Val Leu Phe
        675                 680                 685

tgt tct gcc cgg gca aga aat tac att ctc caa aca aaa gtt tga          2109
Cys Ser Ala Arg Ala Arg Asn Tyr Ile Leu Gln Thr Lys Val
    690                 695                 700


<210> SEQ ID NO 52
<211> LENGTH: 702
<212> TYPE: PRT
<213> ORGANISM: Glycine max

<400> SEQUENCE: 52

Met Pro Thr Gln Phe Leu Phe Cys Phe Lys Leu Leu Ser Pro Phe Leu
1               5                   10                  15

Lys Ile Ala Pro Leu Leu Ser Trp Ser Ser Leu Pro Asn Pro Asn Gln
            20                  25                  30

Ser Leu Pro Ser Trp Val Gly Ser Asn Cys Thr Ser Trp Ser Gly Ile
        35                  40                  45
```

-continued

```
Thr Cys Asp Asn Arg Thr Gly Arg Val Leu Ser Ile Asn Leu Thr Ser
    50                  55                  60

Met Asn Leu Ser Gly Lys Ile His Pro Ser Leu Cys Tyr Leu Ser Tyr
65                  70                  75                  80

Leu Asn Lys Leu Gly Leu Ser His Asn Asn Phe Thr Ser Pro Leu Pro
                85                  90                  95

Glu Cys Phe Gly Asn Leu Leu Asn Leu Arg Ala Ile Asp Leu Ser His
            100                 105                 110

Asn Arg Leu His Gly Gly Ile Pro Asp Ser Phe Met Arg Leu Arg His
        115                 120                 125

Leu Thr Glu Leu Val Leu Ser Gly Asn Pro Asp Leu Gly Gly Pro Leu
    130                 135                 140

Pro Ala Trp Ile Gly Asn Phe Ser Ala Asn Leu Glu Arg Leu His Leu
145                 150                 155                 160

Gly Phe Cys Ser Phe Ser Gly Gly Ile Pro Glu Ser Leu Leu Tyr Leu
                165                 170                 175

Lys Ser Leu Lys Tyr Leu Asp Leu Glu Asn Asn Leu Leu Ser Gly Asn
            180                 185                 190

Leu Val Asn Phe Gln Gln Pro Leu Val Leu Leu Asn Leu Ala Ser Asn
        195                 200                 205

Gln Phe Ala Gly Thr Leu Pro Cys Phe Ala Ala Ser Val Gln Ser Leu
    210                 215                 220

Thr Val Leu Asn Leu Ser Asn Asn Ser Ile Val Gly Gly Leu Pro Ala
225                 230                 235                 240

Cys Ile Ala Ser Phe Gln Ala Leu Thr His Leu Asn Leu Ser Gly Asn
                245                 250                 255

His Leu Lys Tyr Arg Ile Tyr Pro Arg Leu Val Phe Ser Glu Lys Leu
            260                 265                 270

Leu Val Leu Asp Leu Ser Asn Asn Ala Leu Ser Gly Pro Ile Pro Cys
        275                 280                 285

Lys Ile Ala Glu Thr Thr Glu Lys Leu Gly Leu Val Leu Leu Asp Leu
    290                 295                 300

Ser His Asn Gln Phe Ser Gly Glu Ile Pro Val Lys Ile Thr Glu Leu
305                 310                 315                 320

Lys Ser Leu Gln Ala Leu Phe Leu Ser His Asn Leu Leu Ser Gly Glu
                325                 330                 335

Ile Pro Ala Arg Ile Gly Asn Leu Thr Tyr Leu Gln Val Ile Asp Leu
            340                 345                 350

Ser His Asn Ser Leu Ser Gly Thr Ile Pro Phe Ser Ile Val Gly Cys
        355                 360                 365

Phe Gln Leu Tyr Ala Leu Ile Leu Thr Asn Asn Asn Leu Ser Gly Val
    370                 375                 380

Ile Gln Pro Glu Phe Asp Ala Leu Asp Ile Leu Arg Ile Leu Asp Ile
385                 390                 395                 400

Ser Asn Asn Arg Phe Ser Gly Ala Ile Pro Leu Thr Leu Ala Gly Cys
                405                 410                 415

Lys Ser Leu Glu Ile Val Asp Phe Ser Ser Asn Glu Leu Ser Gly Ser
            420                 425                 430

Leu Asn Asp Ala Ile Thr Lys Trp Thr Asn Leu Arg Tyr Leu Ser Leu
        435                 440                 445

Ala Gln Asn Lys Phe Ser Gly Asn Leu Pro Ser Trp Leu Phe Thr Phe
    450                 455                 460
```

-continued

```
Asn Ala Ile Glu Met Met Asp Phe Ser His Asn Lys Phe Thr Gly Phe
465                 470                 475                 480

Ile Pro Asp Ile Asn Phe Lys Gly Ser Leu Ile Phe Asn Thr Arg Asn
                485                 490                 495

Val Thr Val Lys Glu Pro Leu Val Ala Ala Arg Lys Val Gln Leu Arg
            500                 505                 510

Val Ser Ala Val Val Ser Asp Ser Asn Gln Leu Ser Phe Thr Tyr Asp
        515                 520                 525

Leu Ser Ser Met Val Gly Ile Asp Leu Ser Ser Asn Ser Leu His Gly
    530                 535                 540

Glu Ile Pro Arg Gly Leu Phe Gly Leu Ala Gly Leu Glu Tyr Leu Asn
545                 550                 555                 560

Leu Ser Cys Asn Phe Leu Tyr Gly Gln Leu Pro Gly Leu Gln Lys Met
                565                 570                 575

His Ser Leu Lys Ala Leu Asp Leu Ser His Asn Ser Leu Ser Gly His
            580                 585                 590

Ile Pro Gly Asn Ile Ser Ser Leu Gln Asp Leu Ser Ile Leu Asn Leu
        595                 600                 605

Ser Tyr Asn Cys Phe Ser Gly Tyr Val Pro Gln Lys Gln Gly Tyr Gly
    610                 615                 620

Arg Phe Pro Gly Ala Phe Ala Gly Asn Pro Asp Leu Cys Met Glu Thr
625                 630                 635                 640

Ser Ser Gly Val Cys Asp Asp Gly Arg Thr Gln Ser Ala Gln Gly Ser
                645                 650                 655

Ser Phe Ser Glu Asp Arg Met Asp Gly Pro Ile Ser Val Gly Ile Phe
            660                 665                 670

Phe Ile Ser Ala Phe Val Ser Phe Asp Phe Gly Val Val Val Leu Phe
        675                 680                 685

Cys Ser Ala Arg Ala Arg Asn Tyr Ile Leu Gln Thr Lys Val
    690                 695                 700
```